(12) United States Patent
Shelton, IV et al.

(10) Patent No.: US 11,129,636 B2
(45) Date of Patent: Sep. 28, 2021

(54) SURGICAL INSTRUMENTS COMPRISING AN ARTICULATION DRIVE THAT PROVIDES FOR HIGH ARTICULATION ANGLES

(71) Applicant: Ethicon LLC, Guaynabo, PR (US)

(72) Inventors: Frederick E. Shelton, IV, Hillsboro, OH (US); Chester O. Baxter, III, Loveland, OH (US); Jason L. Harris, Lebanon, OH (US)

(73) Assignee: Cilag GmbH International, Zug (CH)

( * ) Notice: Subject to any disclaimer, the term of this patent is extended or adjusted under 35 U.S.C. 154(b) by 112 days.

(21) Appl. No.: 16/112,226

(22) Filed: Aug. 24, 2018

(65) Prior Publication Data

US 2019/0125379 A1    May 2, 2019

Related U.S. Application Data

(60) Provisional application No. 62/578,793, filed on Oct. 30, 2017, provisional application No. 62/578,804, (Continued)

(51) Int. Cl.
*A61B 17/29* (2006.01)
*A61B 17/28* (2006.01)
(Continued)

(52) U.S. Cl.
CPC .......... *A61B 17/2909* (2013.01); *A61B 17/00* (2013.01); *A61B 17/0469* (2013.01); (Continued)

(58) Field of Classification Search
CPC . A61B 17/00; A61B 17/0469; A61B 17/0482; A61B 17/0483; A61B 17/0491; A61B 17/06004; A61B 17/06066; A61B 17/06114; A61B 17/06133; A61B 17/062; A61B 17/0625; A61B 17/068; A61B 17/105; A61B 17/128; A61B 17/1285; A61B 17/282; A61B 17/2841; A61B 17/285; A61B 17/29; A61B 17/2909; A61B 17/295; A61B 17/3421; A61B 17/3468; (Continued)

(56) References Cited

U.S. PATENT DOCUMENTS 1,853,416 A    4/1932    Hall
2,222,125 A    11/1940   Stehlik
(Continued)

FOREIGN PATENT DOCUMENTS

AU    2015201140 A1    3/2015
CA       2795323 A1    5/2014
(Continued)

OTHER PUBLICATIONS

US 10,504,709, 12/2019, Karancsi et al. (withdrawn).
(Continued)

*Primary Examiner* — George J Ulsh

(57) ABSTRACT

A surgical instrument is disclosed comprising a shaft, an end effector, and an articulation joint rotatably connecting the end effector to the shaft. The surgical instrument further comprises an articulation drive system configured to permit high degrees of articulation.

19 Claims, 111 Drawing Sheets

Related U.S. Application Data filed on Oct. 30, 2017, provisional application No. 62/578,817, filed on Oct. 30, 2017, provisional application No. 62/578,835, filed on Oct. 30, 2017, provisional application No. 62/578,844, filed on Oct. 30, 2017, provisional application No. 62/578,855, filed on Oct. 30, 2017, provisional application No. 62/665,129, filed on May 1, 2018, provisional application No. 62/665,139, filed on May 1, 2018, provisional application No. 62/665,177, filed on May 1, 2018, provisional application No. 62/665,128, filed on May 1, 2018, provisional application No. 62/665,192, filed on May 1, 2018, provisional application No. 62/665,134, filed on May 1, 2018.

(51) Int. Cl.

| | | |
|---|---|---|
| *A61B 17/285* | (2006.01) | |
| *A61B 17/295* | (2006.01) | |
| *A61B 17/34* | (2006.01) | |
| *A61B 18/14* | (2006.01) | |
| *A61B 17/04* | (2006.01) | |
| *A61B 17/06* | (2006.01) | |
| *A61B 18/12* | (2006.01) | |
| *A61B 34/30* | (2016.01) | |
| *A61B 17/00* | (2006.01) | |
| *A61B 17/128* | (2006.01) | |
| *A61B 90/98* | (2016.01) | |
| *A61B 17/062* | (2006.01) | |
| *A61B 17/068* | (2006.01) | |
| *A61B 90/00* | (2016.01) | |
| *A61B 17/10* | (2006.01) | |
| *G06F 3/147* | (2006.01) | |
| *A61B 34/00* | (2016.01) | |
| *A61B 18/00* | (2006.01) | |
| *A61B 17/32* | (2006.01) | |
| *B33Y 80/00* | (2015.01) | |
| *A61B 17/3201* | (2006.01) | |
| *F16D 27/108* | (2006.01) | |
| *F16D 27/12* | (2006.01) | |
| *G09G 3/34* | (2006.01) | |
| *G09G 3/36* | (2006.01) | |
| *G09G 3/38* | (2006.01) | |
| *F16D 27/00* | (2006.01) | |

(52) U.S. Cl.
CPC ...... *A61B 17/0482* (2013.01); *A61B 17/0483* (2013.01); *A61B 17/0491* (2013.01); *A61B 17/062* (2013.01); *A61B 17/06004* (2013.01); *A61B 17/068* (2013.01); *A61B 17/0625* (2013.01); *A61B 17/06066* (2013.01); *A61B 17/06114* (2013.01); *A61B 17/06133* (2013.01); *A61B 17/105* (2013.01); *A61B 17/128* (2013.01); *A61B 17/1285* (2013.01); *A61B 17/282* (2013.01); *A61B 17/285* (2013.01); *A61B 17/2841* (2013.01); *A61B 17/29* (2013.01); *A61B 17/295* (2013.01); *A61B 17/3421* (2013.01); *A61B 17/3468* (2013.01); *A61B 18/1206* (2013.01); *A61B 18/1445* (2013.01); *A61B 34/30* (2016.02); *A61B 34/76* (2016.02); *A61B 90/03* (2016.02); *A61B 90/98* (2016.02); *G06F 3/147* (2013.01); *A61B 17/2833* (2013.01); *A61B 17/3201* (2013.01); *A61B 2017/0003* (2013.01); *A61B 2017/00017* (2013.01); *A61B 2017/00026* (2013.01); *A61B 2017/00039* (2013.01); *A61B 2017/0046* (2013.01); *A61B 2017/00057* (2013.01); *A61B 2017/00061* (2013.01); *A61B 2017/00075* (2013.01); *A61B 2017/00115* (2013.01); *A61B 2017/00119* (2013.01); *A61B 2017/00128* (2013.01); *A61B 2017/00212* (2013.01); *A61B 2017/00221* (2013.01); *A61B 2017/00327* (2013.01); *A61B 2017/00367* (2013.01); *A61B 2017/00393* (2013.01); *A61B 2017/00398* (2013.01); *A61B 2017/00407* (2013.01); *A61B 2017/00424* (2013.01); *A61B 2017/00438* (2013.01); *A61B 2017/00464* (2013.01); *A61B 2017/00473* (2013.01); *A61B 2017/00477* (2013.01); *A61B 2017/00526* (2013.01); *A61B 2017/00734* (2013.01); *A61B 2017/06052* (2013.01); *A61B 2017/06076* (2013.01); *A61B 2017/2825* (2013.01); *A61B 2017/2845* (2013.01); *A61B 2017/2902* (2013.01); *A61B 2017/2903* (2013.01); *A61B 2017/2911* (2013.01); *A61B 2017/2923* (2013.01); *A61B 2017/2925* (2013.01); *A61B 2017/2926* (2013.01); *A61B 2017/2927* (2013.01); *A61B 2017/2929* (2013.01); *A61B 2017/2931* (2013.01); *A61B 2017/2943* (2013.01); *A61B 2017/2945* (2013.01); *A61B 2017/320044* (2013.01); *A61B 2018/0063* (2013.01); *A61B 2018/0072* (2013.01); *A61B 2018/00077* (2013.01); *A61B 2018/00083* (2013.01); *A61B 2018/00136* (2013.01); *A61B 2018/00178* (2013.01); *A61B 2018/00208* (2013.01); *A61B 2018/00404* (2013.01); *A61B 2018/00577* (2013.01); *A61B 2018/00595* (2013.01); *A61B 2018/00601* (2013.01); *A61B 2018/00642* (2013.01); *A61B 2018/00672* (2013.01); *A61B 2018/00678* (2013.01); *A61B 2018/00696* (2013.01); *A61B 2018/00702* (2013.01); *A61B 2018/00708* (2013.01); *A61B 2018/00767* (2013.01); *A61B 2018/00827* (2013.01); *A61B 2018/00875* (2013.01); *A61B 2018/00892* (2013.01); *A61B 2018/126* (2013.01); *A61B 2018/1253* (2013.01); *A61B 2018/1266* (2013.01); *A61B 2018/146* (2013.01); *A61B 2018/1452* (2013.01); *A61B 2018/1457* (2013.01); *A61B 2090/035* (2016.02); *A61B 2090/0811* (2016.02); *B33Y 80/00* (2014.12); *F16D 27/004* (2013.01); *F16D 27/108* (2013.01); *F16D 27/12* (2013.01); *G09G 3/344* (2013.01); *G09G 3/3648* (2013.01); *G09G 3/38* (2013.01); *G09G 2380/08* (2013.01)

(58) Field of Classification Search
CPC . A61B 18/1206; A61B 18/1445; A61B 34/30; A61B 34/76; A61B 90/03; A61B 90/98; A61B 17/2833; F16D 27/09; F16D 11/16; F16D 27/12

See application file for complete search history.

(56) References Cited

U.S. PATENT DOCUMENTS

| | | |
|---|---|---|
| 3,082,426 A | 3/1963 | Miles |
| 3,503,396 A | 3/1970 | Pierie et al. |
| 3,584,628 A | 6/1971 | Green |
| 3,626,457 A | 12/1971 | Duerr et al. |
| 3,633,584 A | 1/1972 | Farrell |
| 3,759,017 A | 9/1973 | Young |
| 3,863,118 A | 1/1975 | Lander et al. |
| 3,898,545 A | 8/1975 | Coppa et al. |

(56) References Cited

U.S. PATENT DOCUMENTS

| | | |
|---|---|---|
| 3,912,121 A | 10/1975 | Steffen |
| 3,915,271 A | 10/1975 | Harper |
| 3,932,812 A | 1/1976 | Milligan |
| 4,041,362 A | 8/1977 | Ichiyanagi |
| 4,052,649 A | 10/1977 | Greenwell et al. |
| 4,087,730 A | 5/1978 | Goles |
| 4,157,859 A | 6/1979 | Terry |
| 4,412,539 A | 11/1983 | Jarvik |
| 4,448,193 A | 5/1984 | Ivanov |
| 4,523,695 A | 6/1985 | Braun et al. |
| 4,608,160 A | 8/1986 | Zoch |
| 4,614,366 A | 9/1986 | North et al. |
| 4,701,193 A | 10/1987 | Robertson et al. |
| 4,735,603 A | 4/1988 | Goodson et al. |
| 4,788,977 A | 12/1988 | Farin et al. |
| 4,892,244 A | 1/1990 | Fox et al. |
| 5,010,341 A | 4/1991 | Huntley et al. |
| 5,026,387 A | 6/1991 | Thomas |
| 5,035,692 A | 7/1991 | Lyon et al. |
| 5,042,460 A | 8/1991 | Sakurai et al. |
| 5,084,057 A | 1/1992 | Green et al. |
| 5,100,402 A | 3/1992 | Fan |
| 5,129,570 A | 7/1992 | Schulze et al. |
| 5,151,102 A | 9/1992 | Kamiyama et al. |
| 5,156,315 A | 10/1992 | Green et al. |
| 5,158,585 A | 10/1992 | Saho et al. |
| 5,171,247 A | 12/1992 | Hughett et al. |
| 5,197,962 A | 3/1993 | Sansom et al. |
| 5,242,474 A | 9/1993 | Herbst et al. |
| 5,253,793 A | 10/1993 | Green et al. |
| 5,271,543 A | 12/1993 | Grant et al. |
| RE34,519 E | 1/1994 | Fox et al. |
| 5,318,516 A | 6/1994 | Cosmescu |
| 5,322,055 A | 6/1994 | Davison et al. |
| 5,342,349 A | 8/1994 | Kaufman |
| 5,383,880 A | 1/1995 | Hooven |
| 5,396,900 A | 3/1995 | Slater et al. |
| 5,397,046 A | 3/1995 | Savage et al. |
| 5,403,312 A | 4/1995 | Yates et al. |
| 5,403,327 A | 4/1995 | Thornton et al. |
| 5,413,267 A | 5/1995 | Solyntjes et al. |
| 5,415,335 A | 5/1995 | Knodell, Jr. |
| 5,417,699 A | 5/1995 | Klein et al. |
| 5,439,468 A | 8/1995 | Schulze et al. |
| 5,445,304 A | 8/1995 | Plyley et al. |
| 5,462,545 A | 10/1995 | Wang et al. |
| 5,465,895 A | 11/1995 | Knodel et al. |
| 5,467,911 A | 11/1995 | Tsuruta et al. |
| 5,474,566 A | 12/1995 | Alesi et al. |
| 5,485,947 A | 1/1996 | Olson et al. |
| 5,496,315 A | 3/1996 | Weaver et al. |
| 5,503,320 A | 4/1996 | Webster et al. |
| 5,531,743 A | 7/1996 | Nettekoven et al. |
| 5,545,148 A | 8/1996 | Wurster |
| 5,552,685 A | 9/1996 | Young et al. |
| 5,560,372 A | 10/1996 | Cory |
| 5,584,425 A | 12/1996 | Savage et al. |
| 5,610,379 A | 3/1997 | Muz et al. |
| 5,610,811 A | 3/1997 | Honda |
| 5,613,966 A | 3/1997 | Makower et al. |
| 5,624,452 A | 4/1997 | Yates |
| 5,626,587 A | 5/1997 | Bishop et al. |
| 5,643,291 A | 7/1997 | Pier et al. |
| 5,654,750 A | 8/1997 | Weil et al. |
| 5,673,841 A | 10/1997 | Schulze et al. |
| 5,673,842 A | 10/1997 | Bittner et al. |
| 5,675,227 A | 10/1997 | Roos et al. |
| 5,693,052 A | 12/1997 | Weaver |
| 5,695,502 A | 12/1997 | Pier et al. |
| 5,697,926 A | 12/1997 | Weaver |
| 5,706,998 A | 1/1998 | Plyley et al. |
| 5,718,359 A | 2/1998 | Palmer et al. |
| 5,725,536 A | 3/1998 | Oberlin et al. |
| 5,725,542 A | 3/1998 | Yoon |
| 5,735,445 A | 4/1998 | Vidal et al. |
| 5,735,848 A | 4/1998 | Yates et al. |
| 5,746,209 A | 5/1998 | Yost et al. |
| 5,749,362 A | 5/1998 | Funda et al. |
| 5,749,893 A | 5/1998 | Vidal et al. |
| 5,752,644 A | 5/1998 | Bolanos et al. |
| 5,762,255 A | 6/1998 | Chrisman et al. |
| 5,766,186 A | 6/1998 | Faraz et al. |
| 5,769,791 A | 6/1998 | Benaron et al. |
| 5,775,331 A | 7/1998 | Raymond et al. |
| 5,797,537 A | 8/1998 | Oberlin et al. |
| 5,800,350 A | 9/1998 | Coppleson et al. |
| D399,561 S | 10/1998 | Ellingson |
| 5,817,093 A | 10/1998 | Williamson, IV et al. |
| 5,820,009 A | 10/1998 | Melling et al. |
| 5,833,690 A | 11/1998 | Yates et al. |
| 5,836,849 A | 11/1998 | Mathiak et al. |
| 5,836,909 A | 11/1998 | Cosmescu |
| 5,843,080 A | 12/1998 | Fleenor et al. |
| 5,846,237 A | 12/1998 | Nettekoven |
| 5,849,022 A | 12/1998 | Sakashita et al. |
| 5,873,873 A | 2/1999 | Smith et al. |
| 5,878,938 A | 3/1999 | Bittner et al. |
| 5,893,849 A | 4/1999 | Weaver |
| 5,906,625 A | 5/1999 | Bito et al. |
| 5,942,333 A | 8/1999 | Arnett et al. |
| 5,947,996 A | 9/1999 | Logeman |
| 5,968,032 A | 10/1999 | Sleister |
| 5,980,510 A | 11/1999 | Tsonton et al. |
| 5,987,346 A | 11/1999 | Benaron et al. |
| 5,997,528 A | 12/1999 | Bisch et al. |
| 6,010,054 A | 1/2000 | Johnson et al. |
| 6,030,437 A | 2/2000 | Gourrier et al. |
| 6,036,637 A | 3/2000 | Kudo |
| 6,039,734 A | 3/2000 | Goble |
| 6,039,735 A | 3/2000 | Greep |
| 6,059,799 A | 5/2000 | Aranyi et al. |
| 6,066,137 A | 5/2000 | Greep |
| 6,079,606 A | 6/2000 | Milliman et al. |
| 6,090,107 A | 7/2000 | Borgmeier et al. |
| 6,099,537 A | 8/2000 | Sugai et al. |
| 6,109,500 A | 8/2000 | Alli et al. |
| 6,113,598 A | 9/2000 | Baker |
| 6,126,592 A | 10/2000 | Proch et al. |
| 6,126,658 A | 10/2000 | Baker |
| 6,155,473 A | 12/2000 | Tompkins et al. |
| 6,214,000 B1 | 4/2001 | Fleenor et al. |
| 6,258,105 B1 | 7/2001 | Hart et al. |
| 6,273,887 B1 | 8/2001 | Yamauchi et al. |
| 6,301,495 B1 | 10/2001 | Gueziec et al. |
| 6,302,881 B1 | 10/2001 | Farin |
| 6,308,089 B1 | 10/2001 | von der Ruhr et al. |
| 6,325,808 B1 | 12/2001 | Bernard et al. |
| 6,325,811 B1 | 12/2001 | Messerly |
| 6,341,164 B1 | 1/2002 | Dilkie et al. |
| 6,391,102 B1 | 5/2002 | Bodden et al. |
| 6,434,416 B1 | 8/2002 | Mizoguchi et al. |
| 6,443,973 B1 | 9/2002 | Whitman |
| 6,451,015 B1 | 9/2002 | Rittman, III et al. |
| 6,454,781 B1 | 9/2002 | Witt et al. |
| 6,457,625 B1 | 10/2002 | Tormala et al. |
| 6,461,352 B2 | 10/2002 | Morgan et al. |
| 6,466,817 B1 | 10/2002 | Kaula et al. |
| 6,480,796 B2 | 11/2002 | Wiener |
| 6,524,307 B1 | 2/2003 | Palmerton et al. |
| 6,530,933 B1 | 3/2003 | Yeung et al. |
| 6,551,243 B2 | 4/2003 | Bocionek et al. |
| 6,569,109 B2 | 5/2003 | Sakurai et al. |
| 6,582,424 B2 | 6/2003 | Fleenor et al. |
| 6,585,791 B1 | 7/2003 | Garito et al. |
| 6,618,626 B2 | 9/2003 | West, Jr. et al. |
| 6,648,223 B2 | 11/2003 | Boukhny et al. |
| 6,678,552 B2 | 1/2004 | Pearlman |
| 6,679,899 B2 | 1/2004 | Wiener et al. |
| 6,685,704 B2 | 2/2004 | Greep |
| 6,699,187 B2 | 3/2004 | Webb et al. |
| 6,742,895 B2 | 6/2004 | Robin |
| 6,752,816 B2 | 6/2004 | Culp et al. |
| 6,760,616 B2 | 7/2004 | Hoey et al. |
| 6,770,072 B1 | 8/2004 | Truckai et al. |

(56) References Cited

U.S. PATENT DOCUMENTS

| | | |
|---|---|---|
| 6,773,444 B2 | 8/2004 | Messerly |
| 6,775,575 B2 | 8/2004 | Bommannan et al. |
| 6,778,846 B1 | 8/2004 | Martinez et al. |
| 6,781,683 B2 | 8/2004 | Kacyra et al. |
| 6,783,524 B2 | 8/2004 | Anderson et al. |
| 6,783,525 B2 | 8/2004 | Greep et al. |
| 6,793,663 B2 | 9/2004 | Kneifel et al. |
| 6,824,539 B2 | 11/2004 | Novak |
| 6,846,308 B2 | 1/2005 | Whitman et al. |
| 6,852,219 B2 | 2/2005 | Hammond |
| 6,863,650 B1 | 3/2005 | Irion |
| 6,869,430 B2 | 3/2005 | Balbierz et al. |
| 6,869,435 B2 | 3/2005 | Blake, III |
| 6,911,033 B2 | 6/2005 | de Guillebon et al. |
| 6,937,892 B2 | 8/2005 | Leyde et al. |
| 6,945,981 B2 | 9/2005 | Donofrio et al. |
| 6,951,559 B1 | 10/2005 | Greep |
| 6,962,587 B2 | 11/2005 | Johnson et al. |
| 6,978,921 B2 | 12/2005 | Shelton, IV et al. |
| 6,988,649 B2 | 1/2006 | Shelton, IV et al. |
| 7,000,818 B2 | 2/2006 | Shelton, IV et al. |
| 7,030,146 B2 | 4/2006 | Baynes et al. |
| 7,032,798 B2 | 4/2006 | Whitman et al. |
| 7,041,941 B2 | 5/2006 | Faries, Jr. et al. |
| 7,044,352 B2 | 5/2006 | Shelton, IV et al. |
| 7,044,911 B2 | 5/2006 | Drinan et al. |
| 7,048,775 B2 | 5/2006 | Jornitz et al. |
| 7,053,752 B2 | 5/2006 | Wang et al. |
| 7,055,730 B2 | 6/2006 | Ehrenfels et al. |
| 7,073,765 B2 | 7/2006 | Newkirk |
| 7,077,853 B2 | 7/2006 | Kramer et al. |
| 7,077,856 B2 | 7/2006 | Whitman |
| 7,081,096 B2 | 7/2006 | Brister et al. |
| 7,097,640 B2 | 8/2006 | Wang et al. |
| 7,103,688 B2 | 9/2006 | Strong |
| 7,104,949 B2 | 9/2006 | Anderson et al. |
| 7,118,564 B2 | 10/2006 | Ritchie et al. |
| 7,121,460 B1 | 10/2006 | Parsons et al. |
| 7,137,980 B2 | 11/2006 | Buysse et al. |
| 7,140,528 B2 | 11/2006 | Shelton, IV |
| 7,143,923 B2 | 12/2006 | Shelton, IV et al. |
| 7,143,925 B2 | 12/2006 | Shelton, IV et al. |
| 7,147,139 B2 | 12/2006 | Schwemberger et al. |
| 7,155,316 B2 | 12/2006 | Sutherland et al. |
| 7,164,940 B2 | 1/2007 | Hareyama et al. |
| 7,169,145 B2 | 1/2007 | Isaacson et al. |
| 7,177,533 B2 | 2/2007 | McFarlin et al. |
| 7,182,775 B2 | 2/2007 | de Guillebon et al. |
| 7,208,005 B2 | 4/2007 | Frecker et al. |
| 7,230,529 B2 | 6/2007 | Ketcherside, Jr. et al. |
| 7,232,447 B2 | 6/2007 | Gellman et al. |
| 7,236,817 B2 | 6/2007 | Papas et al. |
| 7,246,734 B2 | 7/2007 | Shelton, IV |
| 7,278,563 B1 | 10/2007 | Green |
| 7,294,106 B2 | 11/2007 | Birkenbach et al. |
| 7,294,116 B1 | 11/2007 | Ellman et al. |
| 7,296,724 B2 | 11/2007 | Green et al. |
| 7,317,955 B2 | 1/2008 | McGreevy |
| 7,328,828 B2 | 2/2008 | Ortiz et al. |
| 7,334,717 B2 | 2/2008 | Rethy et al. |
| 7,343,565 B2 | 3/2008 | Ying et al. |
| 7,362,228 B2 | 4/2008 | Nycz et al. |
| 7,371,227 B2 | 5/2008 | Zeiner |
| 7,380,695 B2 | 6/2008 | Doll et al. |
| 7,383,088 B2 | 6/2008 | Spinelli et al. |
| 7,391,173 B2 | 6/2008 | Schena |
| 7,407,074 B2 | 8/2008 | Ortiz et al. |
| 7,422,139 B2 | 9/2008 | Shelton, IV et al. |
| 7,423,972 B2 | 9/2008 | Shaham et al. |
| 7,457,804 B2 | 11/2008 | Uber, III et al. |
| 7,464,847 B2 | 12/2008 | Viola et al. |
| 7,464,849 B2 | 12/2008 | Shelton, IV et al. |
| 7,515,961 B2 | 4/2009 | Germanson et al. |
| 7,568,604 B2 | 8/2009 | Ehrenfels et al. |
| 7,575,144 B2 | 8/2009 | Ortiz et al. |
| 7,597,731 B2 | 10/2009 | Palmerton et al. |
| 7,617,137 B2 | 11/2009 | Kreiner et al. |
| 7,621,192 B2 | 11/2009 | Conti et al. |
| 7,621,898 B2 | 11/2009 | Lalomia et al. |
| 7,631,793 B2 | 12/2009 | Rethy et al. |
| 7,637,410 B2 | 12/2009 | Marczyk |
| 7,641,092 B2 | 1/2010 | Kruszynski et al. |
| 7,644,848 B2 | 1/2010 | Swayze et al. |
| 7,667,592 B2 | 2/2010 | Ohyama et al. |
| 7,667,839 B2 | 2/2010 | Bates |
| 7,670,334 B2 | 3/2010 | Hueil et al. |
| 7,694,865 B2 | 4/2010 | Scirica |
| 7,699,860 B2 | 4/2010 | Huitema et al. |
| 7,720,306 B2 | 5/2010 | Gardiner et al. |
| 7,721,934 B2 | 5/2010 | Shelton, IV et al. |
| 7,721,936 B2 | 5/2010 | Shalton, IV et al. |
| 7,736,357 B2 | 6/2010 | Lee, Jr. et al. |
| 7,742,176 B2 | 6/2010 | Braunecker et al. |
| 7,743,960 B2 | 6/2010 | Whitman et al. |
| 7,753,245 B2 | 7/2010 | Boudreaux et al. |
| 7,766,207 B2 | 8/2010 | Mather et al. |
| 7,766,905 B2 | 8/2010 | Paterson et al. |
| 7,770,773 B2 | 8/2010 | Whitman et al. |
| 7,771,429 B2 | 8/2010 | Ballard et al. |
| 7,776,037 B2 | 8/2010 | Odom |
| 7,782,789 B2 | 8/2010 | Stultz et al. |
| 7,784,663 B2 | 8/2010 | Shelton, IV |
| 7,803,151 B2 | 9/2010 | Whitman |
| 7,810,692 B2 | 10/2010 | Hall et al. |
| 7,818,041 B2 | 10/2010 | Kim et al. |
| 7,819,298 B2 | 10/2010 | Hall et al. |
| 7,832,612 B2 | 11/2010 | Baxter, III et al. |
| 7,833,219 B2 | 11/2010 | Tashiro et al. |
| 7,836,085 B2 | 11/2010 | Petakov et al. |
| 7,837,079 B2 | 11/2010 | Holsten et al. |
| 7,837,680 B2 | 11/2010 | Isaacson et al. |
| 7,841,980 B2 | 11/2010 | Minosawa et al. |
| 7,845,537 B2 | 12/2010 | Shelton, IV et al. |
| 7,857,185 B2 | 12/2010 | Swayze et al. |
| 7,862,560 B2 | 1/2011 | Marion |
| 7,862,579 B2 | 1/2011 | Ortiz et al. |
| 7,865,236 B2 | 1/2011 | Cory et al. |
| 7,884,735 B2 | 2/2011 | Newkirk |
| 7,887,530 B2 | 2/2011 | Zemlok et al. |
| 7,892,337 B2 | 2/2011 | Palmerton et al. |
| 7,907,166 B2 | 3/2011 | Lamprecht et al. |
| 7,913,891 B2 | 3/2011 | Doll et al. |
| 7,918,230 B2 | 4/2011 | Whitman et al. |
| 7,918,377 B2 | 4/2011 | Measamer et al. |
| 7,920,706 B2 | 4/2011 | Asokan et al. |
| 7,927,014 B2 | 4/2011 | Dehler |
| 7,942,300 B2 | 5/2011 | Rethy et al. |
| 7,954,682 B2 | 6/2011 | Giordano et al. |
| 7,955,322 B2 | 6/2011 | Devengenzo et al. |
| 7,956,620 B2 | 6/2011 | Gilbert |
| 7,963,433 B2 | 6/2011 | Whitman et al. |
| 7,966,269 B2 | 6/2011 | Bauer et al. |
| 7,967,180 B2 | 6/2011 | Scirica |
| 7,976,553 B2 | 7/2011 | Shelton, IV et al. |
| 7,979,157 B2 | 7/2011 | Anvari |
| 7,980,443 B2 | 7/2011 | Scheib et al. |
| 7,982,776 B2 | 7/2011 | Dunki-Jacobs et al. |
| 7,988,028 B2 | 8/2011 | Farascioni et al. |
| 7,993,140 B2 | 8/2011 | Sakezles |
| 7,995,045 B2 | 8/2011 | Dunki-Jacobs |
| 8,005,947 B2 | 8/2011 | Morris et al. |
| 8,007,494 B1 | 8/2011 | Taylor et al. |
| 8,007,513 B2 | 8/2011 | Nalagatla et al. |
| 8,010,180 B2 | 8/2011 | Quaid et al. |
| 8,012,170 B2 | 9/2011 | Whitman et al. |
| 8,015,976 B2 | 9/2011 | Shah |
| 8,016,855 B2 | 9/2011 | Whitman et al. |
| 8,025,199 B2 | 9/2011 | Whitman et al. |
| 8,027,710 B1 | 9/2011 | Dannan |
| 8,035,685 B2 | 10/2011 | Jensen |
| 8,038,686 B2 | 10/2011 | Huitema et al. |
| 8,038,693 B2 | 10/2011 | Allen |
| 8,043,560 B2 | 10/2011 | Okumoto et al. |
| 8,054,184 B2 | 11/2011 | Cline et al. |

(56) References Cited

U.S. PATENT DOCUMENTS

| | | |
|---|---|---|
| 8,054,752 B2 | 11/2011 | Druke et al. |
| 8,062,306 B2 | 11/2011 | Nobis et al. |
| 8,062,330 B2 | 11/2011 | Prommersberger et al. |
| 8,066,721 B2 | 11/2011 | Kortenbach et al. |
| 8,074,861 B2 | 12/2011 | Ehrenfels et al. |
| 8,075,571 B2 | 12/2011 | Vitali et al. |
| 8,096,459 B2 | 1/2012 | Ortiz et al. |
| 8,118,206 B2 | 2/2012 | Zand et al. |
| 8,120,301 B2 | 2/2012 | Goldberg et al. |
| 8,123,764 B2 | 2/2012 | Meade et al. |
| 8,128,625 B2 | 3/2012 | Odom |
| 8,131,565 B2 | 3/2012 | Dicks et al. |
| 8,136,712 B2 | 3/2012 | Zingman |
| 8,147,486 B2 | 4/2012 | Honour et al. |
| 8,155,479 B2 | 4/2012 | Hoffman et al. |
| 8,157,145 B2 | 4/2012 | Shelton, IV et al. |
| 8,157,150 B2 | 4/2012 | Viola et al. |
| 8,157,151 B2 | 4/2012 | Ingmanson et al. |
| 8,160,098 B1 | 4/2012 | Yan et al. |
| 8,160,690 B2 | 4/2012 | Wilfley et al. |
| 8,161,977 B2 | 4/2012 | Shelton, IV et al. |
| 8,170,396 B2 | 5/2012 | Kuspa et al. |
| 8,172,836 B2 | 5/2012 | Ward |
| 8,181,839 B2 | 5/2012 | Beetel |
| 8,185,409 B2 | 5/2012 | Putnam et al. |
| 8,206,345 B2 | 6/2012 | Abboud et al. |
| 8,208,707 B2 | 6/2012 | Mendonca et al. |
| 8,210,411 B2 | 7/2012 | Yates et al. |
| 8,214,007 B2 | 7/2012 | Baker et al. |
| 8,216,849 B2 | 7/2012 | Petty |
| 8,220,688 B2 | 7/2012 | Laurent et al. |
| 8,225,643 B2 | 7/2012 | Abboud et al. |
| 8,225,979 B2 | 7/2012 | Farascioni et al. |
| 8,229,549 B2 | 7/2012 | Whitman et al. |
| 8,231,042 B2 | 7/2012 | Hessler et al. |
| 8,241,322 B2 | 8/2012 | Whitman et al. |
| 8,255,045 B2 | 8/2012 | Gharib et al. |
| 8,257,387 B2 | 9/2012 | Cunningham |
| 8,260,016 B2 | 9/2012 | Maeda et al. |
| 8,262,560 B2 | 9/2012 | Whitman |
| 8,292,888 B2 | 10/2012 | Whitman |
| 8,295,902 B2 | 10/2012 | Salahieh et al. |
| 8,308,040 B2 | 11/2012 | Huang et al. |
| 8,321,581 B2 | 11/2012 | Katis et al. |
| 8,322,590 B2 | 12/2012 | Patel et al. |
| 8,328,065 B2 | 12/2012 | Shah |
| 8,335,590 B2 | 12/2012 | Costa et al. |
| 8,343,065 B2 | 1/2013 | Bartol et al. |
| 8,346,392 B2 | 1/2013 | Walser et al. |
| 8,360,299 B2 | 1/2013 | Zemlok et al. |
| 8,364,222 B2 | 1/2013 | Cook et al. |
| 8,365,975 B1 | 2/2013 | Manoux et al. |
| 8,388,652 B2 | 3/2013 | Viola |
| 8,393,514 B2 | 3/2013 | Shelton, IV et al. |
| 8,397,972 B2 | 3/2013 | Kostrzewski |
| 8,398,541 B2 | 3/2013 | DiMaio et al. |
| 8,403,944 B2 | 3/2013 | Pain et al. |
| 8,403,945 B2 | 3/2013 | Whitfield et al. |
| 8,403,946 B2 | 3/2013 | Whitfield et al. |
| 8,406,859 B2 | 3/2013 | Zuzak et al. |
| 8,411,034 B2 | 4/2013 | Boillot et al. |
| 8,413,871 B2 | 4/2013 | Racenet et al. |
| 8,422,035 B2 | 4/2013 | Hinderling et al. |
| 8,423,182 B2 | 4/2013 | Robinson et al. |
| 8,428,722 B2 | 4/2013 | Verhoef et al. |
| 8,439,910 B2 | 5/2013 | Greep et al. |
| 8,444,663 B2 | 5/2013 | Houser et al. |
| 8,452,615 B2 | 5/2013 | Abri |
| 8,454,506 B2 | 6/2013 | Rothman et al. |
| 8,461,744 B2 | 6/2013 | Wiener et al. |
| 8,468,030 B2 | 6/2013 | Stroup et al. |
| 8,469,973 B2 | 6/2013 | Meade et al. |
| 8,472,630 B2 | 6/2013 | Konrad et al. |
| 8,476,227 B2 | 7/2013 | Kaplan et al. |
| 8,489,235 B2 | 7/2013 | Moll et al. |
| 8,499,992 B2 | 8/2013 | Whitman et al. |
| 8,500,756 B2 | 8/2013 | Papa et al. |
| 8,503,759 B2 | 8/2013 | Greer et al. |
| 8,505,801 B2 | 8/2013 | Ehrenfels et al. |
| 8,506,478 B2 | 8/2013 | Mizuyoshi |
| 8,512,325 B2 | 8/2013 | Mathonnet |
| 8,512,365 B2 | 8/2013 | Wiener et al. |
| 8,515,520 B2 | 8/2013 | Brunnett et al. |
| 8,521,331 B2 | 8/2013 | Itkowitz |
| 8,523,043 B2 | 9/2013 | Ullrich et al. |
| 8,546,996 B2 | 10/2013 | Messerly et al. |
| 8,554,697 B2 | 10/2013 | Claus et al. |
| 8,560,047 B2 | 10/2013 | Haider et al. |
| 8,561,870 B2 | 10/2013 | Baxter, III et al. |
| 8,562,598 B2 | 10/2013 | Falkenstein et al. |
| 8,566,115 B2 | 10/2013 | Moore |
| 8,571,598 B2 | 10/2013 | Valavi |
| 8,573,459 B2 | 11/2013 | Smith et al. |
| 8,573,465 B2 | 11/2013 | Shelton, IV |
| 8,590,762 B2 | 11/2013 | Hess et al. |
| 8,591,536 B2 | 11/2013 | Robertson |
| 8,595,607 B2 | 11/2013 | Nekoomaram et al. |
| 8,596,513 B2 | 12/2013 | Olson et al. |
| 8,596,515 B2 | 12/2013 | Okoniewski |
| 8,604,709 B2 | 12/2013 | Jalbout et al. |
| 8,608,044 B2 | 12/2013 | Hueil et al. |
| 8,608,045 B2 | 12/2013 | Smith et al. |
| 8,616,431 B2 | 12/2013 | Timm et al. |
| 8,620,055 B2 | 12/2013 | Barratt et al. |
| 8,620,473 B2 | 12/2013 | Diolaiti et al. |
| 8,623,027 B2 | 1/2014 | Price et al. |
| 8,627,483 B2 | 1/2014 | Rachlin et al. |
| 8,627,993 B2 | 1/2014 | Smith et al. |
| 8,627,995 B2 | 1/2014 | Smith et al. |
| 8,628,518 B2 | 1/2014 | Blumenkranz et al. |
| 8,628,545 B2 | 1/2014 | Cabrera et al. |
| 8,631,987 B2 | 1/2014 | Shelton, IV et al. |
| 8,632,525 B2 | 1/2014 | Kerr et al. |
| 8,636,190 B2 | 1/2014 | Zemlok et al. |
| 8,636,736 B2 | 1/2014 | Yates et al. |
| 8,641,621 B2 | 2/2014 | Razzaque et al. |
| 8,652,086 B2 | 2/2014 | Gerg et al. |
| 8,652,121 B2 | 2/2014 | Quick et al. |
| 8,652,128 B2 | 2/2014 | Ward |
| 8,657,176 B2 | 2/2014 | Shelton, IV et al. |
| 8,657,177 B2 | 2/2014 | Scirica et al. |
| 8,663,220 B2 | 3/2014 | Wiener et al. |
| 8,666,544 B2 | 3/2014 | Moll et al. |
| 8,679,114 B2 | 3/2014 | Chapman et al. |
| 8,682,049 B2 | 3/2014 | Zhao et al. |
| 8,682,489 B2 | 3/2014 | Itkowitz et al. |
| 8,685,056 B2 | 4/2014 | Evans et al. |
| 8,688,188 B2 | 4/2014 | Heller et al. |
| 8,690,864 B2 | 4/2014 | Hoarau |
| 8,701,962 B2 | 4/2014 | Kostrzewski |
| 8,719,061 B2 | 5/2014 | Birchall |
| 8,720,766 B2 | 5/2014 | Hess et al. |
| 8,733,613 B2 | 5/2014 | Huitema et al. |
| 8,740,840 B2 | 6/2014 | Foley et al. |
| 8,740,866 B2 | 6/2014 | Reasoner et al. |
| 8,747,238 B2 | 6/2014 | Shelton, IV et al. |
| 8,752,749 B2 | 6/2014 | Moore et al. |
| 8,757,465 B2 | 6/2014 | Woodard, Jr. et al. |
| 8,761,717 B1 | 6/2014 | Buchheit |
| 8,763,879 B2 | 7/2014 | Shelton, IV et al. |
| 8,768,251 B2 | 7/2014 | Claus et al. |
| 8,771,270 B2 | 7/2014 | Burbank |
| 8,775,196 B2 | 7/2014 | Simpson et al. |
| 8,779,648 B2 | 7/2014 | Giordano et al. |
| 8,790,253 B2 | 7/2014 | Sunagawa et al. |
| 8,794,497 B2 | 8/2014 | Zingman |
| 8,799,008 B2 | 8/2014 | Johnson et al. |
| 8,799,009 B2 | 8/2014 | Mellin et al. |
| 8,800,838 B2 | 8/2014 | Shelton, IV |
| 8,801,703 B2 | 8/2014 | Gregg et al. |
| 8,814,996 B2 | 8/2014 | Giurgiutiu et al. |
| 8,818,556 B2 | 8/2014 | Sanchez et al. |
| 8,820,603 B2 | 9/2014 | Shelton, IV et al. |
| 8,820,608 B2 | 9/2014 | Miyamoto |

(56) References Cited

U.S. PATENT DOCUMENTS

| | | |
|---|---|---|
| 8,827,134 B2 | 9/2014 | Viola et al. |
| 8,840,003 B2 | 9/2014 | Morgan et al. |
| 8,851,354 B2 | 10/2014 | Swensgard et al. |
| 8,852,174 B2 | 10/2014 | Burbank |
| 8,875,973 B2 | 11/2014 | Whitman |
| 8,882,662 B2 | 11/2014 | Charles |
| 8,886,790 B2 | 11/2014 | Harrang et al. |
| 8,893,949 B2 | 11/2014 | Shelton, IV et al. |
| 8,899,479 B2 | 12/2014 | Cappuzzo et al. |
| 8,905,977 B2 | 12/2014 | Shelton et al. |
| 8,912,746 B2 | 12/2014 | Reid et al. |
| 8,914,098 B2 | 12/2014 | Brennan et al. |
| 8,918,207 B2 | 12/2014 | Prisco |
| 8,920,414 B2 | 12/2014 | Stone et al. |
| 8,920,433 B2 | 12/2014 | Barrier et al. |
| 8,930,203 B2 | 1/2015 | Kiaie et al. |
| 8,930,214 B2 | 1/2015 | Woolford |
| 8,931,679 B2 | 1/2015 | Kostrzewski |
| 8,945,095 B2 | 2/2015 | Blumenkranz et al. |
| 8,945,163 B2 | 2/2015 | Voegele et al. |
| 8,955,732 B2 | 2/2015 | Zemlok et al. |
| 8,956,581 B2 | 2/2015 | Rosenbaum et al. |
| 8,960,519 B2 | 2/2015 | Whitman et al. |
| 8,960,520 B2 | 2/2015 | McCuen |
| 8,962,062 B2 | 2/2015 | Podhajsky et al. |
| 8,967,443 B2 | 3/2015 | McCuen |
| 8,967,455 B2 | 3/2015 | Zhou |
| 8,968,276 B2 | 3/2015 | Zemlok et al. |
| 8,968,309 B2 | 3/2015 | Roy et al. |
| 8,968,337 B2 | 3/2015 | Whitfield et al. |
| 8,968,358 B2 | 3/2015 | Reschke |
| 8,974,429 B2 | 3/2015 | Gordon et al. |
| 8,979,890 B2 | 3/2015 | Boudreaux |
| 8,986,302 B2 | 3/2015 | Aldridge et al. |
| 8,989,903 B2 | 3/2015 | Weir et al. |
| 8,991,678 B2 | 3/2015 | Wellman et al. |
| 8,992,565 B2 | 3/2015 | Brisson et al. |
| 8,998,797 B2 | 4/2015 | Omori |
| 9,002,518 B2 | 4/2015 | Manzo et al. |
| 9,010,611 B2 | 4/2015 | Ross et al. |
| 9,011,366 B2 | 4/2015 | Dean et al. |
| 9,011,427 B2 | 4/2015 | Price et al. |
| 9,016,539 B2 | 4/2015 | Kostrzewski et al. |
| 9,017,326 B2 | 4/2015 | DiNardo et al. |
| 9,020,240 B2 | 4/2015 | Pettersson et al. |
| 9,023,071 B2 | 5/2015 | Miller et al. |
| 9,027,431 B2 | 5/2015 | Tang et al. |
| 9,028,494 B2 | 5/2015 | Shelton, IV et al. |
| 9,035,568 B2 | 5/2015 | Ganton et al. |
| 9,038,882 B2 | 5/2015 | Racenet et al. |
| 9,043,027 B2 | 5/2015 | Durant et al. |
| 9,044,227 B2 | 6/2015 | Shelton, IV et al. |
| 9,044,244 B2 | 6/2015 | Ludwin et al. |
| 9,044,261 B2 | 6/2015 | Houser |
| 9,050,063 B2 | 6/2015 | Roe et al. |
| 9,050,083 B2 | 6/2015 | Yates et al. |
| 9,050,120 B2 | 6/2015 | Swarup et al. |
| 9,052,809 B2 | 6/2015 | Vesto |
| 9,055,035 B2 | 6/2015 | Porsch et al. |
| 9,060,770 B2 | 6/2015 | Shelton, IV et al. |
| 9,060,775 B2 | 6/2015 | Wiener et al. |
| 9,066,650 B2 | 6/2015 | Sekiguchi |
| 9,072,523 B2 | 7/2015 | Houser et al. |
| 9,072,535 B2 | 7/2015 | Shelton, IV et al. |
| 9,072,536 B2 | 7/2015 | Shelton, IV et al. |
| 9,078,653 B2 | 7/2015 | Leimbach et al. |
| 9,078,727 B2 | 7/2015 | Miller |
| 9,084,606 B2 | 7/2015 | Greep |
| 9,089,360 B2 | 7/2015 | Messerly et al. |
| 9,095,362 B2 | 8/2015 | Dachs, II et al. |
| 9,095,367 B2 | 8/2015 | Olson et al. |
| 9,099,863 B2 | 8/2015 | Smith et al. |
| 9,101,358 B2 | 8/2015 | Kerr et al. |
| 9,101,359 B2 | 8/2015 | Smith et al. |
| 9,101,374 B1 | 8/2015 | Hoch et al. |
| 9,106,270 B2 | 8/2015 | Puterbaugh et al. |
| 9,107,573 B2 | 8/2015 | Birnkrant |
| 9,107,662 B2 | 8/2015 | Kostrzewski |
| 9,107,684 B2 | 8/2015 | Ma |
| 9,107,688 B2 | 8/2015 | Kimball et al. |
| 9,107,689 B2 | 8/2015 | Robertson et al. |
| 9,107,694 B2 | 8/2015 | Hendriks et al. |
| 9,111,548 B2 | 8/2015 | Nandy et al. |
| 9,113,880 B2 | 8/2015 | Zemlok et al. |
| 9,114,494 B1 | 8/2015 | Mah |
| 9,116,597 B1 | 8/2015 | Gulasky |
| 9,119,617 B2 | 9/2015 | Souls et al. |
| 9,119,655 B2 | 9/2015 | Bowling et al. |
| 9,119,657 B2 | 9/2015 | Shelton, IV et al. |
| 9,123,155 B2 | 9/2015 | Cunningham et al. |
| 9,125,644 B2 | 9/2015 | Lane et al. |
| 9,129,054 B2 | 9/2015 | Nawana et al. |
| 9,137,254 B2 | 9/2015 | Bilbrey et al. |
| 9,138,129 B2 | 9/2015 | Diolaiti |
| 9,138,225 B2 | 9/2015 | Huang et al. |
| 9,149,322 B2 | 10/2015 | Knowlton |
| 9,155,503 B2 | 10/2015 | Cadwell |
| 9,161,803 B2 | 10/2015 | Yates et al. |
| 9,168,054 B2 | 10/2015 | Turner et al. |
| 9,168,104 B2 | 10/2015 | Dein |
| 9,179,912 B2 | 11/2015 | Yates et al. |
| 9,183,723 B2 | 11/2015 | Sherman et al. |
| 9,186,143 B2 | 11/2015 | Timm et al. |
| 9,192,375 B2 | 11/2015 | Skinlo et al. |
| 9,192,447 B2 | 11/2015 | Choi et al. |
| 9,192,707 B2 | 11/2015 | Gerber et al. |
| 9,202,078 B2 | 12/2015 | Abuelsaad et al. |
| 9,204,830 B2 | 12/2015 | Zand et al. |
| 9,204,879 B2 | 12/2015 | Shelton, IV |
| 9,204,995 B2 | 12/2015 | Scheller et al. |
| 9,216,062 B2 | 12/2015 | Duque et al. |
| 9,218,053 B2 | 12/2015 | Komuro et al. |
| 9,220,502 B2 | 12/2015 | Zemlok et al. |
| 9,226,689 B2 | 1/2016 | Jacobsen et al. |
| 9,226,751 B2 | 1/2016 | Shelton, IV et al. |
| 9,226,766 B2 | 1/2016 | Aldridge et al. |
| 9,226,767 B2 | 1/2016 | Stulen et al. |
| 9,232,883 B2 | 1/2016 | Ozawa et al. |
| 9,237,891 B2 | 1/2016 | Shelton, IV |
| 9,237,921 B2 | 1/2016 | Messerly et al. |
| 9,241,728 B2 | 1/2016 | Price et al. |
| 9,241,730 B2 | 1/2016 | Babaev |
| 9,241,731 B2 | 1/2016 | Boudreaux et al. |
| 9,247,996 B1 | 2/2016 | Merana et al. |
| 9,250,172 B2 | 2/2016 | Harris et al. |
| 9,255,907 B2 | 2/2016 | Heanue et al. |
| 9,265,585 B2 | 2/2016 | Wingardner et al. |
| 9,272,406 B2 | 3/2016 | Aronhalt et al. |
| 9,277,956 B2 | 3/2016 | Zhang |
| 9,280,884 B1 | 3/2016 | Schultz et al. |
| 9,282,962 B2 | 3/2016 | Schmid et al. |
| 9,282,974 B2 | 3/2016 | Shelton, IV |
| 9,283,045 B2 | 3/2016 | Rhee et al. |
| 9,283,054 B2 | 3/2016 | Morgan et al. |
| 9,289,211 B2 | 3/2016 | Williams et al. |
| 9,289,212 B2 | 3/2016 | Shelton, IV et al. |
| 9,295,514 B2 | 3/2016 | Shelton, IV et al. |
| 9,301,691 B2 | 4/2016 | Hufnagel et al. |
| 9,301,753 B2 | 4/2016 | Aldridge et al. |
| 9,301,759 B2 | 4/2016 | Spivey et al. |
| 9,301,810 B2 | 4/2016 | Amiri et al. |
| 9,302,213 B2 | 4/2016 | Manahan et al. |
| 9,307,894 B2 | 4/2016 | von Grunberg et al. |
| 9,307,914 B2 | 4/2016 | Fahey |
| 9,307,986 B2 | 4/2016 | Hall et al. |
| 9,314,246 B2 | 4/2016 | Shelton, IV et al. |
| 9,314,308 B2 | 4/2016 | Parihar et al. |
| 9,320,563 B2 | 4/2016 | Brustad et al. |
| 9,325,732 B1 | 4/2016 | Stickle et al. |
| 9,326,767 B2 | 5/2016 | Koch et al. |
| 9,331,422 B2 | 5/2016 | Nazzaro et al. |
| 9,332,987 B2 | 5/2016 | Leimbach et al. |
| 9,333,042 B2 | 5/2016 | Diolaiti et al. |
| 9,336,385 B1 | 5/2016 | Spencer et al. |

(56) References Cited

U.S. PATENT DOCUMENTS

| | | |
|---|---|---|
| 9,341,704 B2 | 5/2016 | Picard et al. |
| 9,345,481 B2 | 5/2016 | Hall et al. |
| 9,345,490 B2 | 5/2016 | Ippisch |
| 9,345,546 B2 | 5/2016 | Toth et al. |
| 9,351,726 B2 | 5/2016 | Leimbach et al. |
| 9,351,727 B2 | 5/2016 | Leimbach et al. |
| 9,358,003 B2 | 6/2016 | Hall et al. |
| 9,358,685 B2 | 6/2016 | Meier et al. |
| 9,360,449 B2 | 6/2016 | Duric |
| 9,364,231 B2 | 6/2016 | Wenchell |
| 9,364,249 B2 | 6/2016 | Kimball et al. |
| 9,364,294 B2 | 6/2016 | Razzaque et al. |
| 9,370,400 B2 | 6/2016 | Parihar |
| 9,375,282 B2 | 6/2016 | Nau, Jr. et al. |
| 9,375,539 B2 | 6/2016 | Stearns et al. |
| 9,381,003 B2 | 7/2016 | Todor et al. |
| 9,381,058 B2 | 7/2016 | Houser et al. |
| 9,386,984 B2 | 7/2016 | Aronhalt et al. |
| 9,386,988 B2 | 7/2016 | Baxter, III et al. |
| 9,387,295 B1 | 7/2016 | Mastri et al. |
| 9,393,017 B2 | 7/2016 | Flanagan et al. |
| 9,393,037 B2 | 7/2016 | Olson et al. |
| 9,398,905 B2 | 7/2016 | Martin |
| 9,398,911 B2 | 7/2016 | Auld |
| 9,402,629 B2 | 8/2016 | Ehrenfels et al. |
| 9,414,776 B2 | 8/2016 | Sillay et al. |
| 9,419,018 B2 | 8/2016 | Sasagawa et al. |
| 9,421,014 B2 | 8/2016 | Ingmanson et al. |
| 9,433,470 B2 | 9/2016 | Choi |
| 9,439,622 B2 | 9/2016 | Case et al. |
| 9,439,668 B2 | 9/2016 | Timm et al. |
| 9,439,736 B2 | 9/2016 | Olson |
| 9,445,764 B2 | 9/2016 | Gross et al. |
| 9,445,813 B2 | 9/2016 | Shelton, IV et al. |
| 9,450,701 B2 | 9/2016 | Do et al. |
| 9,451,949 B2 | 9/2016 | Gorek et al. |
| 9,451,958 B2 | 9/2016 | Shelton, IV et al. |
| 9,463,022 B2 | 10/2016 | Swayze et al. |
| 9,468,438 B2 | 10/2016 | Baber et al. |
| 9,480,492 B2 | 11/2016 | Aranyi et al. |
| 9,485,475 B2 | 11/2016 | Speier et al. |
| 9,492,146 B2 | 11/2016 | Kostrzewski et al. |
| 9,492,237 B2 | 11/2016 | Kang et al. |
| 9,493,807 B2 | 11/2016 | Little et al. |
| 9,498,182 B2 | 11/2016 | Case et al. |
| 9,498,215 B2 | 11/2016 | Duque et al. |
| 9,498,231 B2 | 11/2016 | Haider et al. |
| 9,516,239 B2 | 12/2016 | Blanquart et al. |
| 9,519,753 B1 | 12/2016 | Gerdeman et al. |
| 9,522,003 B2 | 12/2016 | Weir et al. |
| 9,526,407 B2 | 12/2016 | Hoeg et al. |
| 9,526,499 B2 | 12/2016 | Kostrzewski et al. |
| 9,526,587 B2 | 12/2016 | Zhao et al. |
| 9,532,845 B1 | 1/2017 | Dossett et al. |
| 9,539,007 B2 | 1/2017 | Dhakad et al. |
| 9,539,020 B2 | 1/2017 | Conlon et al. |
| 9,542,481 B2 | 1/2017 | Halter et al. |
| 9,546,662 B2 | 1/2017 | Shener-Irmakoglu et al. |
| 9,554,692 B2 | 1/2017 | Levy |
| 9,554,794 B2 | 1/2017 | Baber et al. |
| 9,554,854 B2 | 1/2017 | Yates et al. |
| 9,561,038 B2 | 2/2017 | Shelton, IV et al. |
| 9,561,045 B2 | 2/2017 | Hinman et al. |
| 9,566,708 B2 | 2/2017 | Kurnianto |
| 9,572,592 B2 | 2/2017 | Price et al. |
| 9,579,503 B2 | 2/2017 | McKinney et al. |
| 9,585,657 B2 | 3/2017 | Shelton, IV et al. |
| 9,592,095 B2 | 3/2017 | Panescu et al. |
| 9,597,081 B2 | 3/2017 | Swayze et al. |
| 9,600,138 B2 | 3/2017 | Thomas et al. |
| 9,603,024 B2 | 3/2017 | Wang et al. |
| 9,610,114 B2 | 4/2017 | Baxter, III et al. |
| 9,622,684 B2 | 4/2017 | Wybo |
| 9,622,808 B2 | 4/2017 | Beller et al. |
| 9,628,501 B2 | 4/2017 | Datta Ray et al. |
| 9,629,560 B2 | 4/2017 | Joseph |
| 9,629,623 B2 | 4/2017 | Lytle, IV et al. |
| 9,629,628 B2 | 4/2017 | Aranyi |
| 9,629,629 B2 | 4/2017 | Leimbach et al. |
| 9,630,318 B2 | 4/2017 | Ibarz Gabardos et al. |
| 9,636,188 B2 | 5/2017 | Gattani et al. |
| 9,636,239 B2 | 5/2017 | Durand et al. |
| 9,636,825 B2 | 5/2017 | Penn et al. |
| 9,641,596 B2 | 5/2017 | Unagami et al. |
| 9,641,815 B2 | 5/2017 | Richardson et al. |
| 9,642,620 B2 | 5/2017 | Baxter, III et al. |
| 9,643,022 B2 | 5/2017 | Mashiach et al. |
| 9,649,110 B2 | 5/2017 | Parihar et al. |
| 9,649,111 B2 | 5/2017 | Shelton, IV et al. |
| 9,649,126 B2 | 5/2017 | Robertson et al. |
| 9,649,169 B2 | 5/2017 | Cinquin et al. |
| 9,652,655 B2 | 5/2017 | Satish et al. |
| 9,655,616 B2 | 5/2017 | Aranyi |
| 9,656,092 B2 | 5/2017 | Golden |
| 9,662,116 B2 | 5/2017 | Smith et al. |
| 9,662,177 B2 | 5/2017 | Weir et al. |
| 9,668,729 B2 | 6/2017 | Williams et al. |
| 9,668,732 B2 | 6/2017 | Patel et al. |
| 9,668,765 B2 | 6/2017 | Grace et al. |
| 9,671,860 B2 | 6/2017 | Ogawa et al. |
| 9,675,264 B2 | 6/2017 | Acquista et al. |
| 9,675,354 B2 | 6/2017 | Weir et al. |
| 9,681,870 B2 | 6/2017 | Baxter, III et al. |
| 9,686,306 B2 | 6/2017 | Chizeck et al. |
| 9,687,230 B2 | 6/2017 | Leimbach et al. |
| 9,690,362 B2 | 6/2017 | Leimbach et al. |
| 9,700,292 B2 | 7/2017 | Nawana et al. |
| 9,700,309 B2 | 7/2017 | Jaworek et al. |
| 9,700,312 B2 | 7/2017 | Kostrzewski et al. |
| 9,700,320 B2 | 7/2017 | Dinardo et al. |
| 9,706,993 B2 | 7/2017 | Hessler et al. |
| 9,710,214 B2 | 7/2017 | Lin et al. |
| 9,710,644 B2 | 7/2017 | Reybok et al. |
| 9,713,424 B2 | 7/2017 | Spaide |
| 9,717,141 B1 | 7/2017 | Tegg |
| 9,717,498 B2 | 8/2017 | Aranyi et al. |
| 9,717,525 B2 | 8/2017 | Ahluwalia et al. |
| 9,717,548 B2 | 8/2017 | Couture |
| 9,724,094 B2 | 8/2017 | Baber et al. |
| 9,724,100 B2 | 8/2017 | Scheib et al. |
| 9,724,118 B2 | 8/2017 | Schulte et al. |
| 9,733,663 B2 | 8/2017 | Leimbach et al. |
| 9,737,301 B2 | 8/2017 | Baber et al. |
| 9,737,310 B2 | 8/2017 | Whitfield et al. |
| 9,737,335 B2 | 8/2017 | Butler et al. |
| 9,737,355 B2 | 8/2017 | Yates et al. |
| 9,740,826 B2 | 8/2017 | Raghavan et al. |
| 9,743,016 B2 | 8/2017 | Nestares et al. |
| 9,743,929 B2 | 8/2017 | Leimbach et al. |
| 9,743,946 B2 | 8/2017 | Faller et al. |
| 9,743,947 B2 | 8/2017 | Price et al. |
| 9,750,499 B2 | 9/2017 | Leimbach et al. |
| 9,750,500 B2 | 9/2017 | Malkowski |
| 9,750,522 B2 | 9/2017 | Scheib et al. |
| 9,750,523 B2 | 9/2017 | Tsubuku |
| 9,753,135 B2 | 9/2017 | Bosch |
| 9,753,568 B2 | 9/2017 | McMillen |
| 9,757,126 B2 | 9/2017 | Cappola |
| 9,757,128 B2 | 9/2017 | Baber et al. |
| 9,757,142 B2 | 9/2017 | Shimizu |
| 9,757,152 B2 | 9/2017 | Ogilvie et al. |
| 9,763,741 B2 | 9/2017 | Alvarez et al. |
| 9,764,164 B2 | 9/2017 | Wiener et al. |
| 9,770,541 B2 | 9/2017 | Carr et al. |
| 9,775,611 B2 | 10/2017 | Kostrzewski |
| 9,777,913 B2 | 10/2017 | Talbert et al. |
| 9,782,164 B2 | 10/2017 | Mumaw et al. |
| 9,782,169 B2 | 10/2017 | Kimsey et al. |
| 9,782,212 B2 | 10/2017 | Wham et al. |
| 9,782,214 B2 | 10/2017 | Houser et al. |
| 9,788,836 B2 | 10/2017 | Overmyer et al. |
| 9,788,851 B2 | 10/2017 | Dannaher et al. |
| 9,788,902 B2 | 10/2017 | Inoue et al. |
| 9,788,907 B1 | 10/2017 | Alvi et al. |

(56) References Cited

U.S. PATENT DOCUMENTS

| | | |
|---|---|---|
| 9,795,436 B2 | 10/2017 | Yates et al. |
| 9,797,486 B2 | 10/2017 | Zergiebel et al. |
| 9,801,531 B2 | 10/2017 | Morita et al. |
| 9,801,626 B2 | 10/2017 | Parihar et al. |
| 9,801,627 B2 | 10/2017 | Harris et al. |
| 9,801,679 B2 | 10/2017 | Trees et al. |
| 9,802,033 B2 | 10/2017 | Hibner et al. |
| 9,804,618 B2 | 10/2017 | Leimbach et al. |
| 9,805,472 B2 | 10/2017 | Chou et al. |
| 9,808,244 B2 | 11/2017 | Leimbach et al. |
| 9,808,245 B2 | 11/2017 | Richard et al. |
| 9,808,246 B2 | 11/2017 | Shelton, IV et al. |
| 9,808,248 B2 | 11/2017 | Hoffman |
| 9,808,249 B2 | 11/2017 | Shelton, IV |
| 9,814,457 B2 | 11/2017 | Martin et al. |
| 9,814,460 B2 | 11/2017 | Kimsey et al. |
| 9,814,462 B2 | 11/2017 | Woodard, Jr. et al. |
| 9,814,463 B2 | 11/2017 | Williams et al. |
| 9,820,699 B2 | 11/2017 | Bingley et al. |
| 9,820,738 B2 | 11/2017 | Lytle, IV et al. |
| 9,820,741 B2 | 11/2017 | Kostrzewski |
| 9,826,976 B2 | 11/2017 | Parihar et al. |
| 9,826,977 B2 | 11/2017 | Leimbach et al. |
| 9,827,054 B2 | 11/2017 | Richmond et al. |
| 9,827,059 B2 | 11/2017 | Robinson et al. |
| 9,830,424 B2 | 11/2017 | Dixon et al. |
| 9,833,241 B2 | 12/2017 | Huitema et al. |
| 9,839,419 B2 | 12/2017 | Deck et al. |
| 9,839,424 B2 | 12/2017 | Zergiebel et al. |
| 9,839,428 B2 | 12/2017 | Baxter, III et al. |
| 9,839,470 B2 | 12/2017 | Gilbert et al. |
| 9,839,487 B2 | 12/2017 | Dachs, II |
| 9,844,368 B2 | 12/2017 | Boudreaux et al. |
| 9,844,369 B2 | 12/2017 | Huitema et al. |
| 9,844,374 B2 | 12/2017 | Lytle, IV et al. |
| 9,844,379 B2 | 12/2017 | Shelton, IV et al. |
| 9,848,058 B2 | 12/2017 | Johnson et al. |
| 9,848,877 B2 | 12/2017 | Shelton, IV et al. |
| 9,861,354 B2 | 1/2018 | Saliman et al. |
| 9,861,363 B2 | 1/2018 | Chen et al. |
| 9,861,428 B2 | 1/2018 | Trees et al. |
| 9,864,839 B2 | 1/2018 | Baym et al. |
| 9,867,612 B2 | 1/2018 | Parihar et al. |
| 9,867,651 B2 | 1/2018 | Wham |
| 9,867,914 B2 | 1/2018 | Bonano et al. |
| 9,872,609 B2 | 1/2018 | Levy |
| 9,872,683 B2 | 1/2018 | Hopkins et al. |
| 9,877,718 B2 | 1/2018 | Weir et al. |
| 9,877,721 B2 | 1/2018 | Schellin et al. |
| 9,883,860 B2 | 2/2018 | Leimbach |
| 9,888,864 B2 | 2/2018 | Rondoni et al. |
| 9,888,914 B2 | 2/2018 | Martin et al. |
| 9,888,919 B2 | 2/2018 | Leimbach et al. |
| 9,888,921 B2 | 2/2018 | Williams et al. |
| 9,888,975 B2 | 2/2018 | Auld |
| 9,895,148 B2 | 2/2018 | Shelton, IV et al. |
| 9,900,787 B2 | 2/2018 | Ou |
| 9,901,342 B2 | 2/2018 | Shelton, IV et al. |
| 9,901,406 B2 | 2/2018 | State et al. |
| 9,905,000 B2 | 2/2018 | Chou et al. |
| 9,907,550 B2 | 3/2018 | Sniffin et al. |
| 9,913,642 B2 | 3/2018 | Leimbach et al. |
| 9,913,645 B2 | 3/2018 | Zerkle et al. |
| 9,918,730 B2 | 3/2018 | Trees et al. |
| 9,918,778 B2 | 3/2018 | Walberg et al. |
| 9,918,788 B2 | 3/2018 | Paul et al. |
| 9,922,304 B2 | 3/2018 | DeBusk et al. |
| 9,924,941 B2 | 3/2018 | Burbank |
| 9,924,944 B2 | 3/2018 | Shelton, IV et al. |
| 9,924,961 B2 | 3/2018 | Shelton, IV et al. |
| 9,931,040 B2 | 4/2018 | Homyk et al. |
| 9,931,118 B2 | 4/2018 | Shelton, IV et al. |
| 9,931,124 B2 | 4/2018 | Gokharu |
| 9,936,863 B2 | 4/2018 | Tesar |
| 9,936,942 B2 | 4/2018 | Chin et al. |
| 9,936,955 B2 | 4/2018 | Miller et al. |
| 9,936,961 B2 | 4/2018 | Chien et al. |
| 9,937,012 B2 | 4/2018 | Hares et al. |
| 9,937,014 B2 | 4/2018 | Bowling et al. |
| 9,937,626 B2 | 4/2018 | Rockrohr |
| 9,938,972 B2 | 4/2018 | Walley |
| 9,943,230 B2 | 4/2018 | Kaku et al. |
| 9,943,309 B2 | 4/2018 | Shelton, IV et al. |
| 9,943,312 B2 | 4/2018 | Posada et al. |
| 9,943,377 B2 | 4/2018 | Yates et al. |
| 9,943,379 B2 | 4/2018 | Gregg, II et al. |
| 9,943,918 B2 | 4/2018 | Grogan et al. |
| 9,949,785 B2 | 4/2018 | Price et al. |
| 9,962,157 B2 | 5/2018 | Sapre |
| 9,968,355 B2 | 5/2018 | Shelton, IV et al. |
| 9,980,140 B1 | 5/2018 | Spencer et al. |
| 9,980,769 B2 | 5/2018 | Trees et al. |
| 9,980,778 B2 | 5/2018 | Ohline et al. |
| 9,987,000 B2 | 6/2018 | Shelton, IV et al. |
| 9,990,856 B2 | 6/2018 | Kuchenbecker et al. |
| 9,993,248 B2 | 6/2018 | Shelton, IV et al. |
| 9,993,258 B2 | 6/2018 | Shelton, IV et al. |
| 9,993,305 B2 | 6/2018 | Andersson |
| 10,004,491 B2 | 6/2018 | Martin et al. |
| 10,004,497 B2 | 6/2018 | Overmyer et al. |
| 10,004,500 B2 | 6/2018 | Shelton, IV et al. |
| 10,004,501 B2 | 6/2018 | Shelton, IV et al. |
| 10,004,527 B2 | 6/2018 | Gee et al. |
| 10,004,557 B2 | 6/2018 | Gross |
| D822,206 S | 7/2018 | Shelton, IV et al. |
| 10,010,322 B2 | 7/2018 | Shelton, IV et al. |
| 10,010,324 B2 | 7/2018 | Huitema et al. |
| 10,013,049 B2 | 7/2018 | Leimbach et al. |
| 10,016,199 B2 | 7/2018 | Baber et al. |
| 10,021,318 B2 | 7/2018 | Hugosson et al. |
| 10,022,090 B2 | 7/2018 | Whitman |
| 10,022,120 B2 | 7/2018 | Martin et al. |
| 10,022,391 B2 | 7/2018 | Ruderman Chen et al. |
| 10,022,568 B2 | 7/2018 | Messerly et al. |
| 10,028,744 B2 | 7/2018 | Shelton, IV et al. |
| 10,028,761 B2 | 7/2018 | Leimbach et al. |
| 10,028,788 B2 | 7/2018 | Kang |
| 10,034,704 B2 | 7/2018 | Asher et al. |
| 10,037,641 B2 | 7/2018 | Hyde et al. |
| 10,037,715 B2 | 7/2018 | Toly et al. |
| D826,405 S | 8/2018 | Shelton, IV et al. |
| 10,039,546 B2 | 8/2018 | Williams et al. |
| 10,039,564 B2 | 8/2018 | Hibner et al. |
| 10,039,565 B2 | 8/2018 | Vezzu |
| 10,041,822 B2 | 8/2018 | Zemlok |
| 10,044,791 B2 | 8/2018 | Kamen et al. |
| 10,045,704 B2 | 8/2018 | Fagin et al. |
| 10,045,776 B2 | 8/2018 | Shelton, IV et al. |
| 10,045,779 B2 | 8/2018 | Savage et al. |
| 10,045,781 B2 | 8/2018 | Cropper et al. |
| 10,045,813 B2 | 8/2018 | Mueller |
| 10,048,379 B2 | 8/2018 | Markendorf et al. |
| 10,052,044 B2 | 8/2018 | Shelton, IV et al. |
| 10,052,102 B2 | 8/2018 | Baxter, III et al. |
| 10,052,104 B2 | 8/2018 | Shelton, IV et al. |
| 10,054,441 B2 | 8/2018 | Schorr et al. |
| 10,058,393 B2 | 8/2018 | Bonutti et al. |
| 10,069,633 B2 | 9/2018 | Gulati et al. |
| 10,076,326 B2 | 9/2018 | Yates et al. |
| 10,080,618 B2 | 9/2018 | Marshall et al. |
| 10,084,833 B2 | 9/2018 | McDonnell et al. |
| D831,209 S | 10/2018 | Huitema et al. |
| 10,085,748 B2 | 10/2018 | Morgan et al. |
| 10,085,749 B2 | 10/2018 | Cappola et al. |
| 10,095,942 B2 | 10/2018 | Mentese et al. |
| 10,097,578 B2 | 10/2018 | Baldonado et al. |
| 10,098,527 B2 | 10/2018 | Weisenburgh, II et al. |
| 10,098,635 B2 | 10/2018 | Burbank |
| 10,098,642 B2 | 10/2018 | Baxter, III et al. |
| 10,098,705 B2 | 10/2018 | Brisson et al. |
| 10,105,140 B2 | 10/2018 | Malinouskas et al. |
| 10,105,142 B2 | 10/2018 | Baxter, III et al. |
| 10,111,658 B2 | 10/2018 | Chowaniec et al. |
| 10,111,665 B2 | 10/2018 | Aranyi et al. |

(56) References Cited

U.S. PATENT DOCUMENTS

| | | | |
|---|---|---|---|
| 10,111,679 | B2 | 10/2018 | Baber et al. |
| 10,117,649 | B2 | 11/2018 | Baxter et al. |
| 10,117,651 | B2 | 11/2018 | Whitman et al. |
| 10,117,702 | B2 | 11/2018 | Danziger et al. |
| 10,118,119 | B2 | 11/2018 | Sappok et al. |
| 10,130,359 | B2 | 11/2018 | Hess et al. |
| 10,130,360 | B2 | 11/2018 | Olson et al. |
| 10,130,361 | B2 | 11/2018 | Yates et al. |
| 10,130,367 | B2 | 11/2018 | Cappola et al. |
| 10,133,248 | B2 | 11/2018 | Fitzsimmons et al. |
| 10,135,242 | B2 | 11/2018 | Baber et al. |
| 10,136,887 | B2 | 11/2018 | Shelton, IV et al. |
| 10,136,891 | B2 | 11/2018 | Shelton, IV et al. |
| 10,136,949 | B2 | 11/2018 | Felder et al. |
| 10,143,526 | B2 | 12/2018 | Walker et al. |
| 10,143,948 | B2 | 12/2018 | Bonifas et al. |
| 10,149,680 | B2 | 12/2018 | Parihar et al. |
| 10,152,789 | B2 | 12/2018 | Carnes et al. |
| 10,154,841 | B2 | 12/2018 | Weaner et al. |
| 10,159,044 | B2 | 12/2018 | Hrabak |
| 10,159,481 | B2 | 12/2018 | Whitman et al. |
| 10,159,483 | B2 | 12/2018 | Beckman et al. |
| 10,164,466 | B2 | 12/2018 | Calderoni |
| 10,166,025 | B2 | 1/2019 | Leimbach et al. |
| 10,169,862 | B2 | 1/2019 | Andre et al. |
| 10,172,687 | B2 | 1/2019 | Garbus et al. |
| 10,175,096 | B2 | 1/2019 | Dickerson |
| 10,175,127 | B2 | 1/2019 | Collins et al. |
| 10,178,992 | B2 | 1/2019 | Wise et al. |
| 10,179,413 | B2 | 1/2019 | Rockrohr |
| 10,180,463 | B2 | 1/2019 | Beckman et al. |
| 10,182,814 | B2 | 1/2019 | Okoniewski |
| 10,182,816 | B2 | 1/2019 | Shelton, IV et al. |
| 10,182,818 | B2 | 1/2019 | Hensel et al. |
| 10,188,385 | B2 | 1/2019 | Kerr et al. |
| 10,189,157 | B2 | 1/2019 | Schlegel et al. |
| 10,190,888 | B2 | 1/2019 | Hryb et al. |
| 10,194,891 | B2 | 2/2019 | Jeong et al. |
| 10,194,907 | B2 | 2/2019 | Marczyk et al. |
| 10,194,913 | B2 | 2/2019 | Nalagatla et al. |
| 10,194,972 | B2 | 2/2019 | Yates et al. |
| 10,197,803 | B2 | 2/2019 | Badiali et al. |
| 10,198,965 | B2 | 2/2019 | Hart |
| 10,201,311 | B2 | 2/2019 | Chou et al. |
| 10,201,349 | B2 | 2/2019 | Leimbach et al. |
| 10,201,364 | B2 | 2/2019 | Leimbach et al. |
| 10,201,365 | B2 | 2/2019 | Boudreaux et al. |
| 10,205,708 | B1 | 2/2019 | Fletcher et al. |
| 10,206,605 | B2 | 2/2019 | Shelton, IV et al. |
| 10,206,752 | B2 | 2/2019 | Hares et al. |
| 10,213,201 | B2 | 2/2019 | Shelton, IV et al. |
| 10,213,203 | B2 | 2/2019 | Swayze et al. |
| 10,213,266 | B2 | 2/2019 | Zemlok et al. |
| 10,213,268 | B2 | 2/2019 | Dachs, II |
| 10,219,491 | B2 | 3/2019 | Stiles, Jr. et al. |
| 10,220,522 | B2 | 3/2019 | Rockrohr |
| 10,222,750 | B2 | 3/2019 | Bang et al. |
| 10,226,249 | B2 | 3/2019 | Jaworek et al. |
| 10,226,250 | B2 | 3/2019 | Beckman et al. |
| 10,226,302 | B2 | 3/2019 | Lacal et al. |
| 10,231,634 | B2 | 3/2019 | Zand et al. |
| 10,231,733 | B2 | 3/2019 | Ehrenfels et al. |
| 10,231,775 | B2 | 3/2019 | Shelton, IV et al. |
| 10,238,413 | B2 | 3/2019 | Hibner et al. |
| 10,245,027 | B2 | 4/2019 | Shelton, IV et al. |
| 10,245,028 | B2 | 4/2019 | Shelton, IV et al. |
| 10,245,029 | B2 | 4/2019 | Hunter et al. |
| 10,245,030 | B2 | 4/2019 | Hunter et al. |
| 10,245,033 | B2 | 4/2019 | Overmyer et al. |
| 10,245,037 | B2 | 4/2019 | Conklin et al. |
| 10,245,038 | B2 | 4/2019 | Hopkins et al. |
| 10,251,661 | B2 | 4/2019 | Collings et al. |
| 10,251,725 | B2 | 4/2019 | Valentine et al. |
| 10,258,331 | B2 | 4/2019 | Shelton, IV et al. |
| 10,258,359 | B2 | 4/2019 | Kapadia |
| 10,258,362 | B2 | 4/2019 | Conlon |
| 10,258,363 | B2 | 4/2019 | Worrell et al. |
| 10,258,415 | B2 | 4/2019 | Harrah et al. |
| 10,258,418 | B2 | 4/2019 | Shelton, IV et al. |
| 10,258,425 | B2 | 4/2019 | Mustufa et al. |
| 10,263,171 | B2 | 4/2019 | Wiener et al. |
| 10,265,035 | B2 | 4/2019 | Fehre et al. |
| 10,265,068 | B2 | 4/2019 | Harris et al. |
| 10,265,072 | B2 | 4/2019 | Shelton, IV et al. |
| 10,265,090 | B2 | 4/2019 | Ingmanson et al. |
| 10,265,130 | B2 | 4/2019 | Hess et al. |
| 10,271,840 | B2 | 4/2019 | Sapre |
| 10,271,844 | B2 | 4/2019 | Valentine et al. |
| 10,271,850 | B2 | 4/2019 | Williams |
| 10,271,851 | B2 | 4/2019 | Shelton, IV et al. |
| D847,989 | S | 5/2019 | Shelton, IV et al. |
| 10,278,698 | B2 | 5/2019 | Racenet |
| 10,278,778 | B2 | 5/2019 | State et al. |
| 10,283,220 | B2 | 5/2019 | Azizian et al. |
| 10,285,694 | B2 | 5/2019 | Viola et al. |
| 10,285,698 | B2 | 5/2019 | Cappola et al. |
| 10,285,700 | B2 | 5/2019 | Scheib |
| 10,285,705 | B2 | 5/2019 | Shelton, IV et al. |
| 10,292,704 | B2 | 5/2019 | Harris et al. |
| 10,292,707 | B2 | 5/2019 | Shelton, IV et al. |
| 10,292,758 | B2 | 5/2019 | Boudreaux et al. |
| 10,292,771 | B2 | 5/2019 | Wood et al. |
| 10,293,129 | B2 | 5/2019 | Fox et al. |
| 10,299,792 | B2 | 5/2019 | Huitema et al. |
| 10,299,870 | B2 | 5/2019 | Connolly et al. |
| 10,305,926 | B2 | 5/2019 | Mihan et al. |
| D850,617 | S | 6/2019 | Shelton, IV et al. |
| 10,307,159 | B2 | 6/2019 | Harris et al. |
| 10,307,170 | B2 | 6/2019 | Parfett et al. |
| 10,307,199 | B2 | 6/2019 | Farritor et al. |
| 10,311,036 | B1 | 6/2019 | Hussam et al. |
| 10,313,137 | B2 | 6/2019 | Aarnio et al. |
| 10,314,577 | B2 | 6/2019 | Laurent et al. |
| 10,314,582 | B2 | 6/2019 | Shelton, IV et al. |
| 10,321,907 | B2 | 6/2019 | Shelton, IV et al. |
| 10,321,964 | B2 | 6/2019 | Grover et al. |
| 10,327,764 | B2 | 6/2019 | Harris et al. |
| 10,335,147 | B2 | 7/2019 | Rector et al. |
| 10,335,149 | B2 | 7/2019 | Baxter, III et al. |
| 10,335,180 | B2 | 7/2019 | Johnson et al. |
| 10,335,227 | B2 | 7/2019 | Heard |
| 10,342,543 | B2 | 7/2019 | Shelton, IV et al. |
| 10,342,602 | B2 | 7/2019 | Strobl et al. |
| 10,342,623 | B2 | 7/2019 | Huelman et al. |
| 10,343,102 | B2 | 7/2019 | Reasoner et al. |
| 10,349,824 | B2 | 7/2019 | Claude et al. |
| 10,349,941 | B2 | 7/2019 | Marczyk et al. |
| 10,350,016 | B2 | 7/2019 | Burbank et al. |
| 10,357,246 | B2 | 7/2019 | Shelton, IV et al. |
| 10,357,247 | B2 | 7/2019 | Shelton, IV et al. |
| 10,362,179 | B2 | 7/2019 | Harris |
| 10,363,032 | B2 | 7/2019 | Scheib et al. |
| 10,363,037 | B2 | 7/2019 | Aronhalt et al. |
| 10,368,861 | B2 | 8/2019 | Baxter, III et al. |
| 10,368,865 | B2 | 8/2019 | Harris et al. |
| 10,368,867 | B2 | 8/2019 | Harris et al. |
| 10,368,876 | B2 | 8/2019 | Bhatnagar et al. |
| 10,368,894 | B2 | 8/2019 | Madan et al. |
| 10,368,903 | B2 | 8/2019 | Morales et al. |
| 10,376,263 | B2 | 8/2019 | Morgan et al. |
| 10,376,305 | B2 | 8/2019 | Yates et al. |
| 10,376,337 | B2 | 8/2019 | Kilroy et al. |
| 10,376,338 | B2 | 8/2019 | Taylor et al. |
| 10,378,893 | B2 | 8/2019 | Mankovskii |
| 10,383,518 | B2 | 8/2019 | Abu-Tarif et al. |
| 10,383,699 | B2 | 8/2019 | Kilroy et al. |
| 10,384,021 | B2 | 8/2019 | Koeth et al. |
| 10,390,718 | B2 | 8/2019 | Chen et al. |
| 10,390,794 | B2 | 8/2019 | Kuroiwa et al. |
| 10,390,825 | B2 | 8/2019 | Shelton, IV et al. |
| 10,390,831 | B2 | 8/2019 | Holsten et al. |
| 10,390,895 | B2 | 8/2019 | Henderson et al. |
| 10,398,348 | B2 | 9/2019 | Osadchy et al. |
| 10,398,434 | B2 | 9/2019 | Shelton, IV et al. |

(56) References Cited

U.S. PATENT DOCUMENTS

| | | |
|---|---|---|
| 10,398,517 B2 | 9/2019 | Eckert et al. |
| 10,398,521 B2 | 9/2019 | Itkowitz et al. |
| 10,404,521 B2 | 9/2019 | McChord et al. |
| 10,404,801 B2 | 9/2019 | Martch |
| 10,405,857 B2 | 9/2019 | Shelton, IV et al. |
| 10,405,863 B2 | 9/2019 | Wise et al. |
| 10,413,291 B2 | 9/2019 | Worthington et al. |
| 10,413,293 B2 | 9/2019 | Shelton, IV et al. |
| 10,413,297 B2 | 9/2019 | Harris et al. |
| 10,417,446 B2 | 9/2019 | Takeyama |
| 10,420,552 B2 | 9/2019 | Shelton, IV et al. |
| 10,420,558 B2 | 9/2019 | Nalagatla et al. |
| 10,420,559 B2 | 9/2019 | Marczyk et al. |
| 10,420,620 B2 | 9/2019 | Rockrohr |
| 10,420,865 B2 | 9/2019 | Reasoner et al. |
| 10,422,727 B2 | 9/2019 | Pliskin |
| 10,426,466 B2 | 10/2019 | Contini et al. |
| 10,426,467 B2 | 10/2019 | Miller et al. |
| 10,426,468 B2 | 10/2019 | Contini et al. |
| 10,426,471 B2 | 10/2019 | Shelton, IV et al. |
| 10,426,481 B2 | 10/2019 | Aronhalt et al. |
| 10,433,837 B2 | 10/2019 | Worthington et al. |
| 10,433,844 B2 | 10/2019 | Shelton, IV et al. |
| 10,433,849 B2 | 10/2019 | Shelton, IV et al. |
| 10,433,918 B2 | 10/2019 | Shelton, IV et al. |
| 10,441,279 B2 | 10/2019 | Shelton, IV et al. |
| 10,441,345 B2 | 10/2019 | Aldridge et al. |
| 10,448,948 B2 | 10/2019 | Shelton, IV et al. |
| 10,448,950 B2 | 10/2019 | Shelton, IV et al. |
| 10,456,137 B2 | 10/2019 | Vendely et al. |
| 10,456,140 B2 | 10/2019 | Shelton, IV et al. |
| 10,456,193 B2 | 10/2019 | Yates et al. |
| 10,463,365 B2 | 11/2019 | Williams |
| 10,463,367 B2 | 11/2019 | Kostrzewski et al. |
| 10,463,371 B2 | 11/2019 | Kostrzewski |
| 10,463,436 B2 | 11/2019 | Jackson et al. |
| 10,470,762 B2 | 11/2019 | Leimbach et al. |
| 10,470,764 B2 | 11/2019 | Baxter, III et al. |
| 10,470,768 B2 | 11/2019 | Harris et al. |
| 10,470,791 B2 | 11/2019 | Houser |
| 10,471,254 B2 | 11/2019 | Sano et al. |
| 10,478,181 B2 | 11/2019 | Shelton, IV et al. |
| 10,478,185 B2 | 11/2019 | Nicholas |
| 10,478,189 B2 | 11/2019 | Bear et al. |
| 10,478,190 B2 | 11/2019 | Miller et al. |
| 10,478,544 B2 | 11/2019 | Friederichs et al. |
| 10,485,450 B2 | 11/2019 | Gupta et al. |
| 10,485,542 B2 | 11/2019 | Shelton, IV et al. |
| 10,485,543 B2 | 11/2019 | Shelton, IV et al. |
| 10,492,783 B2 | 12/2019 | Shelton, IV et al. |
| 10,492,784 B2 | 12/2019 | Beardsley et al. |
| 10,492,785 B2 | 12/2019 | Overmyer et al. |
| 10,496,788 B2 | 12/2019 | Amarasingham et al. |
| 10,498,269 B2 | 12/2019 | Zemlok et al. |
| 10,499,891 B2 | 12/2019 | Chaplin et al. |
| 10,499,914 B2 | 12/2019 | Huang et al. |
| 10,499,915 B2 | 12/2019 | Aranyi |
| 10,499,994 B2 | 12/2019 | Luks et al. |
| 10,507,068 B2 | 12/2019 | Kopp et al. |
| 10,512,461 B2 | 12/2019 | Gupta et al. |
| 10,512,499 B2 | 12/2019 | McHenry et al. |
| 10,512,514 B2 | 12/2019 | Nowlin et al. |
| 10,517,588 B2 | 12/2019 | Gupta et al. |
| 10,517,595 B2 | 12/2019 | Hunter et al. |
| 10,517,596 B2 | 12/2019 | Hunter et al. |
| 10,517,686 B2 | 12/2019 | Vokrot et al. |
| 10,524,789 B2 | 1/2020 | Swayze et al. |
| 10,531,874 B2 | 1/2020 | Morgan et al. |
| 10,531,929 B2 | 1/2020 | Widenhouse et al. |
| 10,532,330 B2 | 1/2020 | Diallo et al. |
| 10,536,617 B2 | 1/2020 | Liang et al. |
| 10,537,324 B2 | 1/2020 | Shelton, IV et al. |
| 10,537,325 B2 | 1/2020 | Bakos et al. |
| 10,537,351 B2 | 1/2020 | Shelton, IV et al. |
| 10,542,978 B2 | 1/2020 | Chowaniec et al. |
| 10,542,979 B2 | 1/2020 | Shelton, IV et al. |
| 10,542,982 B2 | 1/2020 | Beckman et al. |
| 10,542,991 B2 | 1/2020 | Shelton, IV et al. |
| 10,548,504 B2 | 2/2020 | Shelton, IV et al. |
| 10,548,612 B2 | 2/2020 | Martinez et al. |
| 10,548,673 B2 | 2/2020 | Harris et al. |
| 10,552,574 B2 | 2/2020 | Sweeney |
| 10,555,675 B2 | 2/2020 | Satish et al. |
| 10,555,748 B2 | 2/2020 | Yates et al. |
| 10,555,750 B2 | 2/2020 | Conlon et al. |
| 10,555,769 B2 | 2/2020 | Worrell et al. |
| 10,561,422 B2 | 2/2020 | Schellin et al. |
| 10,561,471 B2 | 2/2020 | Nichogi |
| 10,568,625 B2 | 2/2020 | Harris et al. |
| 10,568,626 B2 | 2/2020 | Shelton, IV et al. |
| 10,568,632 B2 | 2/2020 | Miller et al. |
| 10,568,704 B2 | 2/2020 | Savall et al. |
| 10,575,868 B2 | 3/2020 | Hall et al. |
| 10,582,928 B2 | 3/2020 | Hunter et al. |
| 10,582,931 B2 | 3/2020 | Mujawar |
| 10,586,074 B2 | 3/2020 | Rose et al. |
| 10,588,625 B2 | 3/2020 | Weaner et al. |
| 10,588,629 B2 | 3/2020 | Malinouskas et al. |
| 10,588,630 B2 | 3/2020 | Shelton, IV et al. |
| 10,588,631 B2 | 3/2020 | Shelton, IV et al. |
| 10,588,632 B2 | 3/2020 | Shelton, IV et al. |
| 10,588,711 B2 | 3/2020 | DiCarlo et al. |
| 10,592,067 B2 | 3/2020 | Merdan et al. |
| 10,595,844 B2 | 3/2020 | Nawana et al. |
| 10,595,882 B2 | 3/2020 | Parfett et al. |
| 10,595,887 B2 | 3/2020 | Shelton, IV et al. |
| 10,595,930 B2 | 3/2020 | Scheib et al. |
| 10,595,952 B2 | 3/2020 | Forrest et al. |
| 10,602,848 B2 | 3/2020 | Magana |
| 10,603,036 B2 | 3/2020 | Hunter et al. |
| 10,603,128 B2 | 3/2020 | Zergiebel et al. |
| 10,610,223 B2 | 4/2020 | Wellman et al. |
| 10,610,224 B2 | 4/2020 | Shelton, IV et al. |
| 10,610,286 B2 | 4/2020 | Wiener et al. |
| 10,610,313 B2 | 4/2020 | Bailey et al. |
| 10,617,412 B2 | 4/2020 | Shelton, IV et al. |
| 10,617,414 B2 | 4/2020 | Shelton, IV et al. |
| 10,617,482 B2 | 4/2020 | Houser et al. |
| 10,617,484 B2 | 4/2020 | Kilroy et al. |
| 10,624,635 B2 | 4/2020 | Harris et al. |
| 10,624,691 B2 | 4/2020 | Wiener et al. |
| 10,631,423 B2 | 4/2020 | Collins et al. |
| 10,631,858 B2 | 4/2020 | Burbank |
| 10,631,912 B2 | 4/2020 | McFarlin et al. |
| 10,631,916 B2 | 4/2020 | Horner et al. |
| 10,631,917 B2 | 4/2020 | Ineson |
| 10,631,939 B2 | 4/2020 | Dachs, II et al. |
| 10,639,027 B2 | 5/2020 | Shelton, IV et al. |
| 10,639,034 B2 | 5/2020 | Harris et al. |
| 10,639,035 B2 | 5/2020 | Shelton, IV et al. |
| 10,639,036 B2 | 5/2020 | Yates et al. |
| 10,639,037 B2 | 5/2020 | Shelton, IV et al. |
| 10,639,039 B2 | 5/2020 | Vendely et al. |
| 10,639,098 B2 | 5/2020 | Cosman et al. |
| 10,639,111 B2 | 5/2020 | Kopp |
| 10,639,185 B2 | 5/2020 | Agrawal et al. |
| 10,653,413 B2 | 5/2020 | Worthington et al. |
| 10,653,476 B2 | 5/2020 | Ross |
| 10,653,489 B2 | 5/2020 | Kopp |
| 10,656,720 B1 | 5/2020 | Holz |
| 10,660,705 B2 | 5/2020 | Piron et al. |
| 10,667,809 B2 | 6/2020 | Bakos et al. |
| 10,667,810 B2 | 6/2020 | Shelton, IV et al. |
| 10,667,811 B2 | 6/2020 | Harris et al. |
| 10,667,877 B2 | 6/2020 | Kapadia |
| 10,674,897 B2 | 6/2020 | Levy |
| 10,675,021 B2 | 6/2020 | Harris et al. |
| 10,675,023 B2 | 6/2020 | Cappola |
| 10,675,024 B2 | 6/2020 | Shelton, IV et al. |
| 10,675,025 B2 | 6/2020 | Swayze et al. |
| 10,675,026 B2 | 6/2020 | Harris et al. |
| 10,675,035 B2 | 6/2020 | Zingman |
| 10,675,104 B2 | 6/2020 | Kapadia |
| 10,677,764 B2 | 6/2020 | Ross et al. |

(56) References Cited

U.S. PATENT DOCUMENTS

| | | |
|---|---|---|
| 10,679,758 B2 | 6/2020 | Fox et al. |
| 10,682,136 B2 | 6/2020 | Harris et al. |
| 10,682,138 B2 | 6/2020 | Shelton, IV et al. |
| 10,686,805 B2 | 6/2020 | Reybok, Jr. et al. |
| 10,687,806 B2 | 6/2020 | Shelton, IV et al. |
| 10,687,809 B2 | 6/2020 | Shelton, IV et al. |
| 10,687,810 B2 | 6/2020 | Shelton, IV et al. |
| 10,687,884 B2 | 6/2020 | Wiener et al. |
| 10,687,905 B2 | 6/2020 | Kostrzewski |
| 10,695,055 B2 | 6/2020 | Shelton, IV et al. |
| 10,695,081 B2 | 6/2020 | Shelton, IV et al. |
| 10,695,134 B2 | 6/2020 | Barral et al. |
| 10,702,270 B2 | 7/2020 | Shelton, IV et al. |
| 10,702,271 B2 | 7/2020 | Aranyi et al. |
| 10,709,446 B2 | 7/2020 | Harris et al. |
| 10,716,489 B2 | 7/2020 | Kalvoy et al. |
| 10,716,615 B2 | 7/2020 | Shelton, IV et al. |
| 10,716,639 B2 | 7/2020 | Kapadia et al. |
| 10,717,194 B2 | 7/2020 | Griffiths et al. |
| 10,722,222 B2 | 7/2020 | Aranyi |
| 10,722,233 B2 | 7/2020 | Wellman |
| 10,722,292 B2 | 7/2020 | Arya et al. |
| D893,717 S | 8/2020 | Messerly et al. |
| 10,729,458 B2 | 8/2020 | Stoddard et al. |
| 10,729,509 B2 | 8/2020 | Shelton, IV et al. |
| 10,733,267 B2 | 8/2020 | Pedersen |
| 10,736,219 B2 | 8/2020 | Seow et al. |
| 10,736,616 B2 | 8/2020 | Scheib et al. |
| 10,736,628 B2 | 8/2020 | Yates et al. |
| 10,736,629 B2 | 8/2020 | Shelton, IV et al. |
| 10,736,636 B2 | 8/2020 | Baxter, III et al. |
| 10,736,705 B2 | 8/2020 | Scheib et al. |
| 10,743,872 B2 | 8/2020 | Leimbach et al. |
| 10,748,115 B2 | 8/2020 | Laster et al. |
| 10,751,052 B2 | 8/2020 | Stokes et al. |
| 10,751,136 B2 | 8/2020 | Farritor et al. |
| 10,751,768 B2 | 8/2020 | Hersey et al. |
| 10,755,813 B2 | 8/2020 | Shelton, IV et al. |
| D896,379 S | 9/2020 | Shelton, IV et al. |
| 10,758,229 B2 | 9/2020 | Shelton, IV et al. |
| 10,758,230 B2 | 9/2020 | Shelton, IV et al. |
| 10,758,294 B2 | 9/2020 | Jones |
| 10,758,310 B2 | 9/2020 | Shelton, IV et al. |
| 10,765,376 B2 | 9/2020 | Brown, III et al. |
| 10,765,424 B2 | 9/2020 | Baxter, III et al. |
| 10,765,427 B2 | 9/2020 | Shelton, IV et al. |
| 10,765,470 B2 | 9/2020 | Yates et al. |
| 10,772,630 B2 | 9/2020 | Wixey |
| 10,772,651 B2 | 9/2020 | Shelton, IV et al. |
| 10,772,688 B2 | 9/2020 | Peine et al. |
| 10,779,818 B2 | 9/2020 | Zemlok et al. |
| 10,779,821 B2 | 9/2020 | Harris et al. |
| 10,779,823 B2 | 9/2020 | Shelton, IV et al. |
| 10,779,897 B2 | 9/2020 | Rockrohr |
| 10,779,900 B2 | 9/2020 | Pedros et al. |
| 10,783,634 B2 | 9/2020 | Nye et al. |
| 10,786,298 B2 | 9/2020 | Johnson |
| 10,786,317 B2 | 9/2020 | Zhou et al. |
| 10,786,327 B2 | 9/2020 | Anderson et al. |
| 10,792,118 B2 | 10/2020 | Prpa et al. |
| 10,792,422 B2 | 10/2020 | Douglas et al. |
| 10,799,304 B2 | 10/2020 | Kapadia et al. |
| 10,803,977 B2 | 10/2020 | Sanmugalingham |
| 10,806,445 B2 | 10/2020 | Penna et al. |
| 10,806,453 B2 | 10/2020 | Chen et al. |
| 10,806,454 B2 | 10/2020 | Kopp |
| 10,806,506 B2 | 10/2020 | Gaspredes et al. |
| 10,806,532 B2 | 10/2020 | Grubbs et al. |
| 10,835,247 B2 | 11/2020 | Shelton, IV et al. |
| 10,856,768 B2 | 12/2020 | Osadchy et al. |
| 10,864,037 B2 | 12/2020 | Mun et al. |
| 10,872,684 B2 | 12/2020 | McNutt et al. |
| 10,902,944 B1 | 1/2021 | Casey et al. |
| 10,905,418 B2 | 2/2021 | Shelton, IV et al. |
| 10,905,420 B2 | 2/2021 | Jasemian et al. |
| 10,932,784 B2 | 3/2021 | Mozdzierz et al. |
| 10,959,729 B2 | 3/2021 | Ehrenfels et al. |
| 10,987,102 B2 | 4/2021 | Gonzalez et al. |
| 10,992,698 B2 | 4/2021 | Patel et al. |
| 10,998,098 B2 | 5/2021 | Greene et al. |
| 2002/0049551 A1 | 4/2002 | Friedman et al. |
| 2002/0072746 A1 | 6/2002 | Lingenfelder et al. |
| 2003/0009111 A1 | 1/2003 | Cory et al. |
| 2003/0093503 A1 | 5/2003 | Yamaki et al. |
| 2003/0114851 A1 | 6/2003 | Truckai et al. |
| 2003/0210812 A1 | 11/2003 | Khamene et al. |
| 2003/0223877 A1 | 12/2003 | Anstine et al. |
| 2004/0078236 A1 | 4/2004 | Stoodley et al. |
| 2004/0199180 A1 | 10/2004 | Knodel et al. |
| 2004/0199659 A1 | 10/2004 | Ishikawa et al. |
| 2004/0206365 A1 | 10/2004 | Knowlton |
| 2004/0243148 A1 | 12/2004 | Wasielewski |
| 2004/0243435 A1 | 12/2004 | Williams |
| 2005/0020909 A1 | 1/2005 | Moctezuma de la Barrera et al. |
| 2005/0023324 A1 | 2/2005 | Doll et al. |
| 2005/0063575 A1 | 3/2005 | Ma et al. |
| 2005/0065438 A1 | 3/2005 | Miller |
| 2005/0131390 A1 | 6/2005 | Heinrich et al. |
| 2005/0143759 A1 | 6/2005 | Kelly |
| 2005/0149001 A1 | 7/2005 | Uchikubo et al. |
| 2005/0149356 A1 | 7/2005 | Cyr et al. |
| 2005/0192633 A1 | 9/2005 | Montpetit |
| 2005/0222631 A1 | 10/2005 | Dalal et al. |
| 2005/0236474 A1 | 10/2005 | Onuma et al. |
| 2005/0277913 A1 | 12/2005 | McCary |
| 2006/0020272 A1 | 1/2006 | Gildenberg |
| 2006/0025816 A1 | 2/2006 | Shelton |
| 2006/0059018 A1 | 3/2006 | Shiobara et al. |
| 2006/0079874 A1 | 4/2006 | Faller et al. |
| 2006/0116908 A1 | 6/2006 | Dew et al. |
| 2006/0184160 A1 | 8/2006 | Ozaki et al. |
| 2006/0241399 A1 | 10/2006 | Fabian |
| 2007/0010838 A1 | 1/2007 | Shelton et al. |
| 2007/0016235 A1 | 1/2007 | Tanaka et al. |
| 2007/0027459 A1 | 2/2007 | Horvath et al. |
| 2007/0049947 A1 | 3/2007 | Menn et al. |
| 2007/0078678 A1 | 4/2007 | DiSilvestro et al. |
| 2007/0167702 A1 | 7/2007 | Nasser et al. |
| 2007/0168461 A1 | 7/2007 | Moore |
| 2007/0173803 A1 | 7/2007 | Wham et al. |
| 2007/0175955 A1 | 8/2007 | Shelton et al. |
| 2007/0179482 A1 | 8/2007 | Anderson |
| 2007/0191713 A1 | 8/2007 | Eichmann et al. |
| 2007/0225556 A1 | 9/2007 | Ortiz et al. |
| 2007/0225690 A1 | 9/2007 | Sekiguchi et al. |
| 2007/0244478 A1 | 10/2007 | Bahney |
| 2007/0249990 A1 | 10/2007 | Cosmescu |
| 2007/0270660 A1 | 11/2007 | Caylor et al. |
| 2007/0282333 A1 | 12/2007 | Fortson et al. |
| 2007/0293218 A1 | 12/2007 | Meylan et al. |
| 2008/0013460 A1 | 1/2008 | Allen et al. |
| 2008/0015664 A1 | 1/2008 | Podhajsky |
| 2008/0015912 A1 | 1/2008 | Rosenthal et al. |
| 2008/0033404 A1 | 2/2008 | Romoda et al. |
| 2008/0040151 A1 | 2/2008 | Moore |
| 2008/0059658 A1 | 3/2008 | Williams |
| 2008/0077158 A1 | 3/2008 | Haider et al. |
| 2008/0083414 A1 | 4/2008 | Messerges |
| 2008/0177258 A1 | 7/2008 | Govari et al. |
| 2008/0177362 A1 | 7/2008 | Phillips et al. |
| 2008/0200940 A1 | 8/2008 | Eichmann et al. |
| 2008/0255413 A1 | 10/2008 | Zemlok et al. |
| 2008/0262654 A1 | 10/2008 | Omori et al. |
| 2008/0281301 A1 | 11/2008 | DeBoer et al. |
| 2008/0281678 A1 | 11/2008 | Keuls et al. |
| 2008/0296346 A1 | 12/2008 | Shelton, IV et al. |
| 2008/0306759 A1 | 12/2008 | Ilkin et al. |
| 2008/0312953 A1 | 12/2008 | Claus |
| 2009/0036750 A1 | 2/2009 | Weinstein et al. |
| 2009/0036794 A1 | 2/2009 | Stubhaug et al. |
| 2009/0043253 A1 | 2/2009 | Podaima |
| 2009/0046146 A1 | 2/2009 | Hoyt |
| 2009/0048589 A1 | 2/2009 | Takashino et al. |
| 2009/0076409 A1 | 3/2009 | Wu et al. |

(56) References Cited

U.S. PATENT DOCUMENTS

| | | |
|---|---|---|
| 2009/0090763 A1 | 4/2009 | Zemlok et al. |
| 2009/0099866 A1 | 4/2009 | Newman |
| 2009/0182577 A1 | 7/2009 | Squilla et al. |
| 2009/0206131 A1 | 8/2009 | Weisenburgh, II et al. |
| 2009/0217932 A1 | 9/2009 | Voegele |
| 2009/0234352 A1 | 9/2009 | Behnke et al. |
| 2009/0259149 A1 | 10/2009 | Tahara et al. |
| 2009/0259221 A1 | 10/2009 | Tahara et al. |
| 2009/0307681 A1 | 12/2009 | Armado et al. |
| 2009/0326321 A1 | 12/2009 | Jacobsen et al. |
| 2009/0326336 A1 | 12/2009 | Lemke et al. |
| 2010/0065604 A1 | 3/2010 | Weng |
| 2010/0069942 A1 | 3/2010 | Shelton, IV |
| 2010/0070417 A1 | 3/2010 | Flynn et al. |
| 2010/0132334 A1 | 6/2010 | Duclos et al. |
| 2010/0137845 A1 | 6/2010 | Ramstein et al. |
| 2010/0168561 A1 | 7/2010 | Anderson |
| 2010/0179831 A1 | 7/2010 | Brown et al. |
| 2010/0191100 A1 | 7/2010 | Anderson et al. |
| 2010/0198248 A1 | 8/2010 | Vakharia |
| 2010/0217991 A1 | 8/2010 | Choi |
| 2010/0235689 A1 | 9/2010 | Tian et al. |
| 2010/0250571 A1 | 9/2010 | Pierce et al. |
| 2010/0292535 A1 | 11/2010 | Paskar |
| 2010/0292684 A1 | 11/2010 | Cybulski et al. |
| 2011/0022032 A1 | 1/2011 | Zemlok et al. |
| 2011/0071530 A1 | 3/2011 | Carson |
| 2011/0077512 A1 | 3/2011 | Boswell |
| 2011/0087238 A1 | 4/2011 | Wang et al. |
| 2011/0105895 A1 | 5/2011 | Kornblau et al. |
| 2011/0118708 A1 | 5/2011 | Burbank et al. |
| 2011/0119075 A1 | 5/2011 | Dhoble |
| 2011/0125149 A1 | 5/2011 | El-Galley et al. |
| 2011/0152712 A1 | 6/2011 | Cao et al. |
| 2011/0166883 A1 | 7/2011 | Palmer et al. |
| 2011/0237883 A1 | 9/2011 | Chun |
| 2011/0264000 A1 | 10/2011 | Paul et al. |
| 2011/0306840 A1 | 12/2011 | Allen et al. |
| 2012/0022519 A1 | 1/2012 | Huang et al. |
| 2012/0059684 A1 | 3/2012 | Hampapur et al. |
| 2012/0078247 A1 | 3/2012 | Worrell et al. |
| 2012/0080336 A1 | 4/2012 | Shelton, IV et al. |
| 2012/0116265 A1 | 5/2012 | Houser et al. |
| 2012/0116381 A1 | 5/2012 | Houser et al. |
| 2012/0130217 A1 | 5/2012 | Kauphusman et al. |
| 2012/0145714 A1 | 6/2012 | Farascioni et al. |
| 2012/0172696 A1 | 7/2012 | Kallback et al. |
| 2012/0191091 A1 | 7/2012 | Allen |
| 2012/0203785 A1 | 8/2012 | Awada |
| 2012/0211542 A1 | 8/2012 | Racenet |
| 2012/0245958 A1 | 9/2012 | Lawrence et al. |
| 2012/0265555 A1 | 10/2012 | Cappuzzo et al. |
| 2012/0292367 A1 | 11/2012 | Morgan et al. |
| 2012/0319859 A1 | 12/2012 | Taub et al. |
| 2013/0024213 A1 | 1/2013 | Poon |
| 2013/0046182 A1 | 2/2013 | Hegg et al. |
| 2013/0046279 A1 | 2/2013 | Niklewski et al. |
| 2013/0066647 A1 | 3/2013 | Andrie et al. |
| 2013/0090526 A1 | 4/2013 | Suzuki et al. |
| 2013/0093829 A1 | 4/2013 | Rosenblatt et al. |
| 2013/0105552 A1 | 5/2013 | Weir et al. |
| 2013/0116218 A1 | 5/2013 | Kaplan et al. |
| 2013/0165776 A1 | 6/2013 | Blomqvist |
| 2013/0178853 A1 | 7/2013 | Hyink et al. |
| 2013/0206813 A1 | 8/2013 | Nalagatla |
| 2013/0214025 A1 | 8/2013 | Zemlok et al. |
| 2013/0253480 A1 | 9/2013 | Kimball et al. |
| 2013/0256373 A1 | 10/2013 | Schmid et al. |
| 2013/0267874 A1 | 10/2013 | Marcotte et al. |
| 2013/0277410 A1 | 10/2013 | Fernandez et al. |
| 2013/0317837 A1 | 11/2013 | Ballantyne et al. |
| 2013/0321425 A1 | 12/2013 | Greene et al. |
| 2013/0325809 A1 | 12/2013 | Kim et al. |
| 2013/0331873 A1 | 12/2013 | Ross et al. |
| 2013/0331875 A1 | 12/2013 | Ross et al. |
| 2014/0001231 A1 | 1/2014 | Shelton, IV et al. |
| 2014/0001234 A1 | 1/2014 | Shelton, IV et al. |
| 2014/0005640 A1 | 1/2014 | Shelton, IV et al. |
| 2014/0006132 A1 | 1/2014 | Barker |
| 2014/0006943 A1 | 1/2014 | Robbins et al. |
| 2014/0013565 A1 | 1/2014 | MacDonald et al. |
| 2014/0029411 A1 | 1/2014 | Nayak et al. |
| 2014/0033926 A1 | 2/2014 | Fassel et al. |
| 2014/0035762 A1 | 2/2014 | Shelton, IV et al. |
| 2014/0066700 A1 | 3/2014 | Wilson et al. |
| 2014/0081255 A1 | 3/2014 | Johnson et al. |
| 2014/0081659 A1 | 3/2014 | Nawana et al. |
| 2014/0084949 A1 | 3/2014 | Smith et al. |
| 2014/0087999 A1 | 3/2014 | Kaplan et al. |
| 2014/0092089 A1 | 4/2014 | Kasuya et al. |
| 2014/0107697 A1 | 4/2014 | Patani et al. |
| 2014/0108035 A1 | 4/2014 | Akbay et al. |
| 2014/0108983 A1 | 4/2014 | William R. et al. |
| 2014/0148729 A1 | 5/2014 | Schmitz et al. |
| 2014/0166724 A1 | 6/2014 | Schellin et al. |
| 2014/0187856 A1 | 7/2014 | Holoien et al. |
| 2014/0194864 A1 | 7/2014 | Martin et al. |
| 2014/0204190 A1 | 7/2014 | Rosenblatt, III et al. |
| 2014/0243799 A1 | 8/2014 | Parihar |
| 2014/0243809 A1 | 8/2014 | Gelfand et al. |
| 2014/0246475 A1 | 9/2014 | Hall et al. |
| 2014/0249557 A1 | 9/2014 | Koch et al. |
| 2014/0252064 A1 | 9/2014 | Mozdzierz et al. |
| 2014/0263541 A1 | 9/2014 | Leimbach et al. |
| 2014/0263552 A1 | 9/2014 | Hall et al. |
| 2014/0303660 A1 | 10/2014 | Boyden et al. |
| 2015/0006201 A1 | 1/2015 | Pait et al. |
| 2015/0025549 A1 | 1/2015 | Kilroy et al. |
| 2015/0032150 A1* | 1/2015 | Ishida .............. A61B 17/29 606/205 |
| 2015/0051452 A1 | 2/2015 | Ciaccio |
| 2015/0051617 A1 | 2/2015 | Takemura et al. |
| 2015/0053737 A1 | 2/2015 | Leimbach et al. |
| 2015/0066000 A1 | 3/2015 | An et al. |
| 2015/0070187 A1 | 3/2015 | Wiesner et al. |
| 2015/0108198 A1 | 4/2015 | Estrella |
| 2015/0133945 A1 | 5/2015 | Dushyant et al. |
| 2015/0196295 A1 | 7/2015 | Shelton, IV et al. |
| 2015/0199109 A1 | 7/2015 | Lee |
| 2015/0238355 A1 | 8/2015 | Vezzu et al. |
| 2015/0272557 A1 | 10/2015 | Overmyer et al. |
| 2015/0272571 A1 | 10/2015 | Leimbach et al. |
| 2015/0272580 A1 | 10/2015 | Leimbach et al. |
| 2015/0272582 A1 | 10/2015 | Leimbach et al. |
| 2015/0297200 A1 | 10/2015 | Fitzsimmons et al. |
| 2015/0297222 A1 | 10/2015 | Huitema et al. |
| 2015/0297228 A1 | 10/2015 | Huitema et al. |
| 2015/0297233 A1 | 10/2015 | Huitema et al. |
| 2015/0297311 A1 | 10/2015 | Tesar |
| 2015/0302157 A1 | 10/2015 | Collar et al. |
| 2015/0310174 A1 | 10/2015 | Coudert et al. |
| 2015/0313538 A1 | 11/2015 | Bechtel et al. |
| 2015/0317899 A1 | 11/2015 | Dumbauld et al. |
| 2015/0324114 A1 | 11/2015 | Hurley et al. |
| 2015/0332003 A1 | 11/2015 | Stamm et al. |
| 2015/0332196 A1 | 11/2015 | Stiller et al. |
| 2016/0000437 A1 | 1/2016 | Giordano et al. |
| 2016/0015471 A1 | 1/2016 | Piron et al. |
| 2016/0034648 A1 | 2/2016 | Mohlenbrock et al. |
| 2016/0038253 A1 | 2/2016 | Piron et al. |
| 2016/0066913 A1 | 3/2016 | Swayze et al. |
| 2016/0106516 A1 | 4/2016 | Mesallum |
| 2016/0106934 A1 | 4/2016 | Hiraga et al. |
| 2016/0158468 A1 | 6/2016 | Tang et al. |
| 2016/0174978 A1* | 6/2016 | Overmyer ........ A61B 17/07207 227/178.1 |
| 2016/0180045 A1 | 6/2016 | Syed |
| 2016/0192960 A1 | 7/2016 | Bueno et al. |
| 2016/0206202 A1 | 7/2016 | Frangioni |
| 2016/0224760 A1 | 8/2016 | Petak et al. |
| 2016/0235303 A1 | 8/2016 | Fleming et al. |
| 2016/0249910 A1 | 9/2016 | Shelton, IV et al. |
| 2016/0287912 A1 | 10/2016 | Warnking |
| 2016/0296246 A1 | 10/2016 | Schaller |

(56) References Cited

U.S. PATENT DOCUMENTS

| | | |
|---|---|---|
| 2016/0302210 A1 | 10/2016 | Thornton et al. |
| 2016/0310055 A1 | 10/2016 | Zand et al. |
| 2016/0321400 A1 | 11/2016 | Durrant et al. |
| 2016/0323283 A1 | 11/2016 | Kang et al. |
| 2016/0324537 A1 | 11/2016 | Green et al. |
| 2016/0342753 A1 | 11/2016 | Feazell |
| 2016/0342916 A1 | 11/2016 | Arceneaux et al. |
| 2016/0345857 A1 | 12/2016 | Jensrud et al. |
| 2016/0350490 A1 | 12/2016 | Martinez et al. |
| 2016/0361070 A1 | 12/2016 | Ardel et al. |
| 2016/0374665 A1 | 12/2016 | DiNardo et al. |
| 2016/0374723 A1 | 12/2016 | Frankhouser et al. |
| 2016/0374762 A1 | 12/2016 | Case et al. |
| 2017/0000516 A1 | 1/2017 | Stulen et al. |
| 2017/0000553 A1 | 1/2017 | Wiener et al. |
| 2017/0027603 A1 | 2/2017 | Pandey |
| 2017/0068792 A1 | 3/2017 | Reiner |
| 2017/0079730 A1 | 3/2017 | Azizian et al. |
| 2017/0086829 A1 | 3/2017 | Vendely et al. |
| 2017/0086930 A1 | 3/2017 | Thompson et al. |
| 2017/0105754 A1 | 4/2017 | Boudreaux et al. |
| 2017/0116873 A1 | 4/2017 | Lendvay et al. |
| 2017/0132374 A1 | 5/2017 | Lee et al. |
| 2017/0132785 A1 | 5/2017 | Wshah et al. |
| 2017/0143284 A1 | 5/2017 | Sehnert et al. |
| 2017/0143442 A1 | 5/2017 | Tesar et al. |
| 2017/0151026 A1 | 6/2017 | Panescu et al. |
| 2017/0156076 A1 | 6/2017 | Eom et al. |
| 2017/0164997 A1 | 6/2017 | Johnson et al. |
| 2017/0165012 A1 | 6/2017 | Chaplin et al. |
| 2017/0172565 A1 | 6/2017 | Heneveld |
| 2017/0172614 A1 | 6/2017 | Scheib et al. |
| 2017/0177807 A1 | 6/2017 | Fabian |
| 2017/0196583 A1 | 7/2017 | Sugiyama |
| 2017/0196637 A1 | 7/2017 | Shelton, IV et al. |
| 2017/0202591 A1 | 7/2017 | Shelton, IV et al. |
| 2017/0202605 A1 | 7/2017 | Shelton, IV et al. |
| 2017/0202607 A1 | 7/2017 | Shelton, IV et al. |
| 2017/0224332 A1 | 8/2017 | Hunter et al. |
| 2017/0224334 A1 | 8/2017 | Worthington et al. |
| 2017/0224428 A1 | 8/2017 | Kopp |
| 2017/0231627 A1 | 8/2017 | Shelton, IV et al. |
| 2017/0231628 A1 | 8/2017 | Shelton, IV et al. |
| 2017/0245809 A1 | 8/2017 | Ma et al. |
| 2017/0249432 A1 | 8/2017 | Grantcharov |
| 2017/0262604 A1 | 9/2017 | Francois |
| 2017/0265864 A1 | 9/2017 | Hessler et al. |
| 2017/0273715 A1 | 9/2017 | Piron et al. |
| 2017/0281171 A1 | 10/2017 | Shelton, IV et al. |
| 2017/0281173 A1 | 10/2017 | Shelton, IV et al. |
| 2017/0281186 A1 | 10/2017 | Shelton, IV et al. |
| 2017/0281187 A1 | 10/2017 | Shelton, IV et al. |
| 2017/0281189 A1 | 10/2017 | Nalagatla et al. |
| 2017/0290585 A1 | 10/2017 | Shelton, IV et al. |
| 2017/0296169 A1 | 10/2017 | Yates et al. |
| 2017/0296173 A1 | 10/2017 | Shelton, IV et al. |
| 2017/0296177 A1 | 10/2017 | Harris et al. |
| 2017/0296185 A1 | 10/2017 | Swensgard et al. |
| 2017/0296213 A1 | 10/2017 | Swensgard et al. |
| 2017/0303984 A1 | 10/2017 | Malackowski |
| 2017/0304020 A1 | 10/2017 | Ng et al. |
| 2017/0312456 A1 | 11/2017 | Phillips |
| 2017/0325876 A1 | 11/2017 | Nakadate et al. |
| 2017/0325878 A1 | 11/2017 | Messerly et al. |
| 2017/0360499 A1 | 12/2017 | Greep et al. |
| 2017/0367583 A1 | 12/2017 | Black et al. |
| 2017/0367695 A1 | 12/2017 | Shelton, IV et al. |
| 2017/0367697 A1 | 12/2017 | Shelton, IV et al. |
| 2017/0367754 A1 | 12/2017 | Narisawa |
| 2017/0367771 A1 | 12/2017 | Tako et al. |
| 2017/0367772 A1 | 12/2017 | Gunn et al. |
| 2017/0370710 A1 | 12/2017 | Chen et al. |
| 2018/0008359 A1 | 1/2018 | Randle |
| 2018/0011983 A1 | 1/2018 | Zuhars et al. |
| 2018/0014848 A1 | 1/2018 | Messerly et al. |
| 2018/0049817 A1 | 2/2018 | Swayze et al. |
| 2018/0050196 A1 | 2/2018 | Pawsey et al. |
| 2018/0055529 A1 | 3/2018 | Messerly et al. |
| 2018/0065248 A1 | 3/2018 | Barral et al. |
| 2018/0078170 A1 | 3/2018 | Panescu et al. |
| 2018/0098816 A1 | 4/2018 | Govari et al. |
| 2018/0110523 A1 | 4/2018 | Shelton, IV |
| 2018/0116662 A1 | 5/2018 | Shelton, IV et al. |
| 2018/0116735 A1 | 5/2018 | Tierney et al. |
| 2018/0122506 A1 | 5/2018 | Grantcharov et al. |
| 2018/0125590 A1 | 5/2018 | Giordano et al. |
| 2018/0132895 A1 | 5/2018 | Silver |
| 2018/0144243 A1 | 5/2018 | Hsieh et al. |
| 2018/0153574 A1 | 6/2018 | Faller et al. |
| 2018/0153628 A1 | 6/2018 | Grover et al. |
| 2018/0153632 A1 | 6/2018 | Tokarchuk et al. |
| 2018/0154297 A1 | 6/2018 | Maletich et al. |
| 2018/0161716 A1 | 6/2018 | Li et al. |
| 2018/0168575 A1 | 6/2018 | Simms et al. |
| 2018/0168577 A1 | 6/2018 | Aronhalt et al. |
| 2018/0168578 A1 | 6/2018 | Aronhalt et al. |
| 2018/0168579 A1 | 6/2018 | Aronhalt et al. |
| 2018/0168584 A1 | 6/2018 | Harris et al. |
| 2018/0168586 A1 | 6/2018 | Shelton, IV et al. |
| 2018/0168589 A1 | 6/2018 | Swayze et al. |
| 2018/0168590 A1 | 6/2018 | Overmyer et al. |
| 2018/0168592 A1 | 6/2018 | Overmyer et al. |
| 2018/0168593 A1 | 6/2018 | Overmyer et al. |
| 2018/0168597 A1 | 6/2018 | Fanelli et al. |
| 2018/0168598 A1 | 6/2018 | Shelton, IV et al. |
| 2018/0168601 A1 | 6/2018 | Bakos et al. |
| 2018/0168603 A1 | 6/2018 | Morgan et al. |
| 2018/0168605 A1 | 6/2018 | Baber et al. |
| 2018/0168607 A1 | 6/2018 | Shelton, IV et al. |
| 2018/0168608 A1 | 6/2018 | Shelton, IV et al. |
| 2018/0168609 A1 | 6/2018 | Fanelli et al. |
| 2018/0168610 A1 | 6/2018 | Shelton, IV et al. |
| 2018/0168614 A1 | 6/2018 | Shelton, IV et al. |
| 2018/0168615 A1 | 6/2018 | Shelton, IV et al. |
| 2018/0168617 A1 | 6/2018 | Shelton, IV et al. |
| 2018/0168618 A1 | 6/2018 | Scott et al. |
| 2018/0168619 A1 | 6/2018 | Scott et al. |
| 2018/0168623 A1 | 6/2018 | Simms et al. |
| 2018/0168625 A1 | 6/2018 | Posada et al. |
| 2018/0168627 A1 | 6/2018 | Weaner et al. |
| 2018/0168628 A1 | 6/2018 | Hunter et al. |
| 2018/0168629 A1 | 6/2018 | Shelton, IV et al. |
| 2018/0168632 A1 | 6/2018 | Harris et al. |
| 2018/0168633 A1 | 6/2018 | Shelton, IV et al. |
| 2018/0168639 A1 | 6/2018 | Shelton, IV et al. |
| 2018/0168647 A1 | 6/2018 | Shelton, IV et al. |
| 2018/0168648 A1 | 6/2018 | Shelton, IV et al. |
| 2018/0168649 A1 | 6/2018 | Shelton, IV et al. |
| 2018/0168650 A1 | 6/2018 | Shelton, IV et al. |
| 2018/0168651 A1 | 6/2018 | Shelton, IV et al. |
| 2018/0168715 A1 | 6/2018 | Strobl |
| 2018/0199995 A1 | 7/2018 | Odermatt et al. |
| 2018/0206884 A1 | 7/2018 | Beaupre |
| 2018/0206905 A1 | 7/2018 | Batchelor et al. |
| 2018/0207307 A1 | 7/2018 | Schwartz et al. |
| 2018/0214025 A1 | 8/2018 | Homyk et al. |
| 2018/0221598 A1 | 8/2018 | Silver |
| 2018/0228557 A1 | 8/2018 | Darisse et al. |
| 2018/0233222 A1 | 8/2018 | Daley et al. |
| 2018/0235719 A1 | 8/2018 | Jarc |
| 2018/0242967 A1 | 8/2018 | Meade |
| 2018/0250084 A1 | 9/2018 | Kopp et al. |
| 2018/0263710 A1 | 9/2018 | Sakaguchi et al. |
| 2018/0263717 A1 | 9/2018 | Kopp |
| 2018/0268320 A1 | 9/2018 | Shekhar |
| 2018/0271520 A1 | 9/2018 | Shelton, IV et al. |
| 2018/0271603 A1 | 9/2018 | Nir et al. |
| 2018/0296286 A1 | 10/2018 | Peine et al. |
| 2018/0303552 A1 | 10/2018 | Ryan et al. |
| 2018/0304471 A1 | 10/2018 | Tokuchi |
| 2018/0310935 A1 | 11/2018 | Wixey |
| 2018/0310986 A1 | 11/2018 | Batchelor et al. |
| 2018/0317826 A1 | 11/2018 | Muhsin et al. |
| 2018/0317915 A1 | 11/2018 | McDonald, II |

(56) References Cited

U.S. PATENT DOCUMENTS

| | | |
|---|---|---|
| 2018/0358112 A1 | 12/2018 | Sharifi Sedeh et al. |
| 2018/0360449 A1 | 12/2018 | Shelton, IV et al. |
| 2018/0360452 A1 | 12/2018 | Shelton, IV et al. |
| 2018/0360454 A1 | 12/2018 | Shelton, IV et al. |
| 2018/0360456 A1 | 12/2018 | Shelton, IV et al. |
| 2018/0368930 A1 | 12/2018 | Esterberg et al. |
| 2018/0369511 A1 | 12/2018 | Zergiebel et al. |
| 2019/0000446 A1 | 1/2019 | Shelton, IV et al. |
| 2019/0000448 A1 | 1/2019 | Shelton, IV et al. |
| 2019/0000478 A1 | 1/2019 | Messerly et al. |
| 2019/0000530 A1 | 1/2019 | Yates et al. |
| 2019/0000565 A1 | 1/2019 | Shelton, IV et al. |
| 2019/0000569 A1 | 1/2019 | Crawford et al. |
| 2019/0001079 A1 | 1/2019 | Zergiebel et al. |
| 2019/0005641 A1 | 1/2019 | Yamamoto |
| 2019/0006047 A1 | 1/2019 | Gorek et al. |
| 2019/0025040 A1 | 1/2019 | Andreason et al. |
| 2019/0029712 A1 | 1/2019 | Stoddard et al. |
| 2019/0036688 A1 | 1/2019 | Wasily et al. |
| 2019/0038335 A1 | 2/2019 | Mohr et al. |
| 2019/0038364 A1 | 2/2019 | Enoki |
| 2019/0053801 A1 | 2/2019 | Wixey et al. |
| 2019/0053866 A1 | 2/2019 | Seow et al. |
| 2019/0069949 A1 | 3/2019 | Vrba et al. |
| 2019/0069962 A1 | 3/2019 | Tabandeh et al. |
| 2019/0069964 A1 | 3/2019 | Hagn |
| 2019/0070550 A1 | 3/2019 | Lalomia et al. |
| 2019/0070731 A1 | 3/2019 | Bowling et al. |
| 2019/0087544 A1 | 3/2019 | Peterson |
| 2019/0090969 A1 | 3/2019 | Jarc et al. |
| 2019/0104919 A1 | 4/2019 | Shelton, IV et al. |
| 2019/0125320 A1 | 5/2019 | Shelton, IV et al. |
| 2019/0125321 A1 | 5/2019 | Shelton, IV et al. |
| 2019/0125324 A1 | 5/2019 | Scheib et al. |
| 2019/0125335 A1 | 5/2019 | Shelton, IV et al. |
| 2019/0125336 A1 | 5/2019 | Deck et al. |
| 2019/0125337 A1 | 5/2019 | Shelton, IV et al. |
| 2019/0125338 A1 | 5/2019 | Shelton, IV et al. |
| 2019/0125339 A1 | 5/2019 | Shelton, IV et al. |
| 2019/0125344 A1 | 5/2019 | DiNardo et al. |
| 2019/0125347 A1 | 5/2019 | Stokes et al. |
| 2019/0125348 A1 | 5/2019 | Shelton, IV et al. |
| 2019/0125352 A1 | 5/2019 | Shelton, IV et al. |
| 2019/0125353 A1 | 5/2019 | Shelton, IV et al. |
| 2019/0125354 A1 | 5/2019 | Deck et al. |
| 2019/0125355 A1 | 5/2019 | Shelton, IV et al. |
| 2019/0125356 A1 | 5/2019 | Shelton, IV et al. |
| 2019/0125357 A1 | 5/2019 | Shelton, IV et al. |
| 2019/0125358 A1 | 5/2019 | Shelton, IV et al. |
| 2019/0125359 A1 | 5/2019 | Shelton, IV et al. |
| 2019/0125360 A1 | 5/2019 | Shelton, IV et al. |
| 2019/0125361 A1 | 5/2019 | Shelton, IV et al. |
| 2019/0125377 A1 | 5/2019 | Shelton, IV |
| 2019/0125378 A1 | 5/2019 | Shelton, IV et al. |
| 2019/0125380 A1 | 5/2019 | Hunter et al. |
| 2019/0125381 A1 | 5/2019 | Scheib et al. |
| 2019/0125383 A1 | 5/2019 | Scheib et al. |
| 2019/0125384 A1 | 5/2019 | Scheib et al. |
| 2019/0125385 A1 | 5/2019 | Scheib et al. |
| 2019/0125386 A1 | 5/2019 | Shelton, IV et al. |
| 2019/0125387 A1 | 5/2019 | Parihar et al. |
| 2019/0125388 A1 | 5/2019 | Shelton, IV et al. |
| 2019/0125389 A1 | 5/2019 | Shelton, IV et al. |
| 2019/0125430 A1 | 5/2019 | Shelton, IV et al. |
| 2019/0125431 A1 | 5/2019 | Shelton, IV et al. |
| 2019/0125432 A1 | 5/2019 | Shelton, IV et al. |
| 2019/0125454 A1 | 5/2019 | Stokes et al. |
| 2019/0125455 A1 | 5/2019 | Shelton, IV et al. |
| 2019/0125456 A1 | 5/2019 | Shelton, IV et al. |
| 2019/0125457 A1 | 5/2019 | Parihar et al. |
| 2019/0125458 A1 | 5/2019 | Shelton, IV et al. |
| 2019/0125459 A1 | 5/2019 | Shelton, IV et al. |
| 2019/0125476 A1 | 5/2019 | Shelton, IV et al. |
| 2019/0133703 A1 | 5/2019 | Seow et al. |
| 2019/0142449 A1 | 5/2019 | Shelton, IV et al. |
| 2019/0142535 A1 | 5/2019 | Seow et al. |
| 2019/0145942 A1 | 5/2019 | Dutriez et al. |
| 2019/0150975 A1 | 5/2019 | Kawasaki et al. |
| 2019/0159778 A1 | 5/2019 | Shelton, IV et al. |
| 2019/0162179 A1 | 5/2019 | O'Shea et al. |
| 2019/0192157 A1 | 6/2019 | Scott et al. |
| 2019/0192236 A1 | 6/2019 | Shelton, IV et al. |
| 2019/0200844 A1 | 7/2019 | Shelton, IV et al. |
| 2019/0200863 A1 | 7/2019 | Shelton, IV et al. |
| 2019/0200905 A1 | 7/2019 | Shelton, IV et al. |
| 2019/0200906 A1 | 7/2019 | Shelton, IV et al. |
| 2019/0200977 A1 | 7/2019 | Shelton, IV et al. |
| 2019/0200980 A1 | 7/2019 | Shelton, IV et al. |
| 2019/0200981 A1 | 7/2019 | Harris et al. |
| 2019/0200984 A1 | 7/2019 | Shelton, IV et al. |
| 2019/0200985 A1 | 7/2019 | Shelton, IV et al. |
| 2019/0200986 A1 | 7/2019 | Shelton, IV et al. |
| 2019/0200987 A1 | 7/2019 | Shelton, IV et al. |
| 2019/0200988 A1 | 7/2019 | Shelton, IV |
| 2019/0200996 A1 | 7/2019 | Shelton, IV et al. |
| 2019/0200997 A1 | 7/2019 | Shelton, IV et al. |
| 2019/0200998 A1 | 7/2019 | Shelton, IV et al. |
| 2019/0201020 A1 | 7/2019 | Shelton, IV et al. |
| 2019/0201021 A1 | 7/2019 | Shelton, IV et al. |
| 2019/0201023 A1 | 7/2019 | Shelton, IV et al. |
| 2019/0201024 A1 | 7/2019 | Shelton, IV et al. |
| 2019/0201025 A1 | 7/2019 | Shelton, IV et al. |
| 2019/0201026 A1 | 7/2019 | Shelton, IV et al. |
| 2019/0201027 A1 | 7/2019 | Shelton, IV et al. |
| 2019/0201028 A1 | 7/2019 | Shelton, IV et al. |
| 2019/0201029 A1 | 7/2019 | Shelton, IV et al. |
| 2019/0201030 A1 | 7/2019 | Shelton, IV et al. |
| 2019/0201033 A1 | 7/2019 | Yates et al. |
| 2019/0201034 A1 | 7/2019 | Shelton, IV et al. |
| 2019/0201036 A1 | 7/2019 | Nott et al. |
| 2019/0201037 A1 | 7/2019 | Houser et al. |
| 2019/0201038 A1 | 7/2019 | Yates et al. |
| 2019/0201039 A1 | 7/2019 | Widenhouse et al. |
| 2019/0201040 A1 | 7/2019 | Messerly et al. |
| 2019/0201041 A1 | 7/2019 | Kimball et al. |
| 2019/0201042 A1 | 7/2019 | Nott et al. |
| 2019/0201043 A1 | 7/2019 | Shelton, IV et al. |
| 2019/0201044 A1 | 7/2019 | Shelton, IV et al. |
| 2019/0201045 A1 | 7/2019 | Yates et al. |
| 2019/0201046 A1 | 7/2019 | Shelton, IV et al. |
| 2019/0201047 A1 | 7/2019 | Yates et al. |
| 2019/0201073 A1 | 7/2019 | Nott et al. |
| 2019/0201074 A1 | 7/2019 | Yates et al. |
| 2019/0201075 A1 | 7/2019 | Shelton, IV et al. |
| 2019/0201077 A1 | 7/2019 | Yates et al. |
| 2019/0201079 A1 | 7/2019 | Shelton, IV et al. |
| 2019/0201080 A1 | 7/2019 | Messerly et al. |
| 2019/0201081 A1 | 7/2019 | Shelton, IV et al. |
| 2019/0201082 A1 | 7/2019 | Shelton, IV et al. |
| 2019/0201083 A1 | 7/2019 | Shelton, IV et al. |
| 2019/0201084 A1 | 7/2019 | Shelton, IV et al. |
| 2019/0201085 A1 | 7/2019 | Shelton, IV et al. |
| 2019/0201086 A1 | 7/2019 | Shelton, IV et al. |
| 2019/0201087 A1 | 7/2019 | Shelton, IV et al. |
| 2019/0201088 A1 | 7/2019 | Shelton, IV et al. |
| 2019/0201090 A1 | 7/2019 | Shelton, IV et al. |
| 2019/0201091 A1 | 7/2019 | Yates et al. |
| 2019/0201092 A1 | 7/2019 | Yates et al. |
| 2019/0201102 A1 | 7/2019 | Shelton, IV et al. |
| 2019/0201104 A1 | 7/2019 | Shelton, IV et al. |
| 2019/0201105 A1 | 7/2019 | Shelton, IV et al. |
| 2019/0201111 A1 | 7/2019 | Shelton, IV et al. |
| 2019/0201112 A1 | 7/2019 | Wiener et al. |
| 2019/0201113 A1 | 7/2019 | Shelton, IV et al. |
| 2019/0201114 A1 | 7/2019 | Shelton, IV et al. |
| 2019/0201115 A1 | 7/2019 | Shelton, IV et al. |
| 2019/0201116 A1 | 7/2019 | Shelton, IV et al. |
| 2019/0201117 A1 | 7/2019 | Yates et al. |
| 2019/0201118 A1 | 7/2019 | Shelton, IV et al. |
| 2019/0201119 A1 | 7/2019 | Harris et al. |
| 2019/0201120 A1 | 7/2019 | Shelton, IV et al. |
| 2019/0201123 A1 | 7/2019 | Shelton, IV et al. |
| 2019/0201124 A1 | 7/2019 | Shelton, IV et al. |
| 2019/0201125 A1 | 7/2019 | Shelton, IV et al. |

(56) References Cited

U.S. PATENT DOCUMENTS

| | | |
|---|---|---|
| 2019/0201126 A1 | 7/2019 | Shelton, IV et al. |
| 2019/0201127 A1 | 7/2019 | Shelton, IV et al. |
| 2019/0201128 A1 | 7/2019 | Yates et al. |
| 2019/0201129 A1 | 7/2019 | Shelton, IV et al. |
| 2019/0201130 A1 | 7/2019 | Shelton, IV et al. |
| 2019/0201135 A1 | 7/2019 | Shelton, IV et al. |
| 2019/0201136 A1 | 7/2019 | Shelton, IV et al. |
| 2019/0201137 A1 | 7/2019 | Shelton, IV et al. |
| 2019/0201138 A1 | 7/2019 | Yates et al. |
| 2019/0201139 A1 | 7/2019 | Shelton, IV et al. |
| 2019/0201140 A1 | 7/2019 | Yates et al. |
| 2019/0201141 A1 | 7/2019 | Shelton, IV et al. |
| 2019/0201142 A1 | 7/2019 | Shelton, IV et al. |
| 2019/0201143 A1 | 7/2019 | Shelton, IV et al. |
| 2019/0201144 A1 | 7/2019 | Shelton, IV et al. |
| 2019/0201145 A1 | 7/2019 | Shelton, IV et al. |
| 2019/0201146 A1 | 7/2019 | Shelton, IV et al. |
| 2019/0201158 A1 | 7/2019 | Shelton, IV et al. |
| 2019/0201159 A1 | 7/2019 | Shelton, IV et al. |
| 2019/0201594 A1 | 7/2019 | Shelton, IV et al. |
| 2019/0201597 A1 | 7/2019 | Shelton, IV et al. |
| 2019/0204201 A1 | 7/2019 | Shelton, IV et al. |
| 2019/0205001 A1 | 7/2019 | Messerly et al. |
| 2019/0205441 A1 | 7/2019 | Shelton, IV et al. |
| 2019/0205566 A1 | 7/2019 | Shelton, IV et al. |
| 2019/0205567 A1 | 7/2019 | Shelton, IV et al. |
| 2019/0206003 A1 | 7/2019 | Harris et al. |
| 2019/0206004 A1 | 7/2019 | Shelton, IV et al. |
| 2019/0206050 A1 | 7/2019 | Yates et al. |
| 2019/0206216 A1 | 7/2019 | Shelton, IV et al. |
| 2019/0206542 A1 | 7/2019 | Shelton, IV et al. |
| 2019/0206551 A1 | 7/2019 | Yates et al. |
| 2019/0206555 A1 | 7/2019 | Morgan et al. |
| 2019/0206556 A1 | 7/2019 | Shelton, IV et al. |
| 2019/0206561 A1 | 7/2019 | Shelton, IV et al. |
| 2019/0206562 A1 | 7/2019 | Shelton, IV et al. |
| 2019/0206563 A1 | 7/2019 | Shelton, IV et al. |
| 2019/0206564 A1 | 7/2019 | Shelton, IV et al. |
| 2019/0206565 A1 | 7/2019 | Shelton, IV |
| 2019/0206569 A1 | 7/2019 | Shelton, IV et al. |
| 2019/0206576 A1 | 7/2019 | Shelton, IV et al. |
| 2019/0207773 A1 | 7/2019 | Shelton, IV et al. |
| 2019/0207857 A1 | 7/2019 | Shelton, IV et al. |
| 2019/0207911 A1 | 7/2019 | Wiener et al. |
| 2019/0208641 A1 | 7/2019 | Yates et al. |
| 2019/0254759 A1 | 8/2019 | Azizian |
| 2019/0261984 A1 | 8/2019 | Nelson et al. |
| 2019/0269476 A1 | 9/2019 | Bowling et al. |
| 2019/0272917 A1 | 9/2019 | Couture et al. |
| 2019/0274662 A1 | 9/2019 | Rockman et al. |
| 2019/0274705 A1 | 9/2019 | Sawhney et al. |
| 2019/0274706 A1 | 9/2019 | Nott et al. |
| 2019/0274707 A1 | 9/2019 | Sawhney et al. |
| 2019/0274708 A1 | 9/2019 | Boudreaux |
| 2019/0274709 A1 | 9/2019 | Scoggins |
| 2019/0274710 A1 | 9/2019 | Black |
| 2019/0274711 A1 | 9/2019 | Scoggins et al. |
| 2019/0274712 A1 | 9/2019 | Faller et al. |
| 2019/0274713 A1 | 9/2019 | Scoggins et al. |
| 2019/0274714 A1 | 9/2019 | Cuti et al. |
| 2019/0274716 A1 | 9/2019 | Nott et al. |
| 2019/0274717 A1 | 9/2019 | Nott et al. |
| 2019/0274718 A1 | 9/2019 | Denzinger et al. |
| 2019/0274719 A1 | 9/2019 | Stulen |
| 2019/0274720 A1 | 9/2019 | Gee et al. |
| 2019/0274749 A1 | 9/2019 | Brady et al. |
| 2019/0274750 A1 | 9/2019 | Jayme et al. |
| 2019/0274752 A1 | 9/2019 | Denzinger et al. |
| 2019/0290389 A1 | 9/2019 | Kopp |
| 2019/0298340 A1 | 10/2019 | Shelton, IV et al. |
| 2019/0298341 A1 | 10/2019 | Shelton, IV et al. |
| 2019/0298342 A1 | 10/2019 | Shelton, IV et al. |
| 2019/0298343 A1 | 10/2019 | Shelton, IV et al. |
| 2019/0298346 A1 | 10/2019 | Shelton, IV et al. |
| 2019/0298347 A1 | 10/2019 | Shelton, IV et al. |
| 2019/0298350 A1 | 10/2019 | Shelton, IV et al. |
| 2019/0298351 A1 | 10/2019 | Shelton, IV et al. |
| 2019/0298352 A1 | 10/2019 | Shelton, IV et al. |
| 2019/0298353 A1 | 10/2019 | Shelton, IV et al. |
| 2019/0298354 A1 | 10/2019 | Shelton, IV et al. |
| 2019/0298355 A1 | 10/2019 | Shelton, IV et al. |
| 2019/0298356 A1 | 10/2019 | Shelton, IV et al. |
| 2019/0298357 A1 | 10/2019 | Shelton, IV et al. |
| 2019/0298464 A1 | 10/2019 | Abbott |
| 2019/0298481 A1 | 10/2019 | Rosenberg et al. |
| 2019/0307520 A1 | 10/2019 | Peine et al. |
| 2019/0311802 A1 | 10/2019 | Kokubo et al. |
| 2019/0314015 A1 | 10/2019 | Shelton, IV et al. |
| 2019/0314016 A1 | 10/2019 | Huitema et al. |
| 2019/0321117 A1 | 10/2019 | Itkowitz et al. |
| 2019/0333626 A1 | 10/2019 | Mansi et al. |
| 2019/0343594 A1 | 11/2019 | Garcia Kilroy et al. |
| 2019/0374140 A1 | 12/2019 | Tucker et al. |
| 2020/0000470 A1 | 1/2020 | Du et al. |
| 2020/0046353 A1 | 2/2020 | Deck et al. |
| 2020/0054317 A1 | 2/2020 | Pisarnwongs et al. |
| 2020/0054320 A1 | 2/2020 | Harris et al. |
| 2020/0054321 A1 | 2/2020 | Harris et al. |
| 2020/0054322 A1 | 2/2020 | Harris et al. |
| 2020/0054323 A1 | 2/2020 | Harris et al. |
| 2020/0054326 A1 | 2/2020 | Harris et al. |
| 2020/0054327 A1 | 2/2020 | Harris et al. |
| 2020/0054328 A1 | 2/2020 | Harris et al. |
| 2020/0054329 A1 | 2/2020 | Shelton, IV et al. |
| 2020/0054330 A1 | 2/2020 | Harris et al. |
| 2020/0054331 A1 | 2/2020 | Harris et al. |
| 2020/0078096 A1 | 3/2020 | Barbagli et al. |
| 2020/0100830 A1 | 4/2020 | Henderson et al. |
| 2020/0162896 A1 | 5/2020 | Su et al. |
| 2020/0178971 A1 | 6/2020 | Harris et al. |
| 2020/0261075 A1 | 8/2020 | Boudreaux et al. |
| 2020/0261076 A1 | 8/2020 | Boudreaux et al. |
| 2020/0261077 A1 | 8/2020 | Shelton, IV et al. |
| 2020/0261078 A1 | 8/2020 | Bakos et al. |
| 2020/0261080 A1 | 8/2020 | Bakos et al. |
| 2020/0261081 A1 | 8/2020 | Boudreaux et al. |
| 2020/0261082 A1 | 8/2020 | Boudreaux et al. |
| 2020/0261083 A1 | 8/2020 | Bakos et al. |
| 2020/0261084 A1 | 8/2020 | Bakos et al. |
| 2020/0261085 A1 | 8/2020 | Boudreaux et al. |
| 2020/0261086 A1 | 8/2020 | Zeiner et al. |
| 2020/0261087 A1 | 8/2020 | Timm et al. |
| 2020/0261088 A1 | 8/2020 | Harris et al. |
| 2020/0261089 A1 | 8/2020 | Shelton, IV et al. |
| 2020/0275928 A1 | 9/2020 | Shelton, IV et al. |
| 2020/0275930 A1 | 9/2020 | Harris et al. |
| 2020/0281665 A1 | 9/2020 | Kopp |
| 2020/0405375 A1 | 12/2020 | Shelton, IV et al. |
| 2021/0000555 A1 | 1/2021 | Shelton, IV et al. |
| 2021/0007760 A1 | 1/2021 | Reisin |
| 2021/0015568 A1 | 1/2021 | Liao et al. |
| 2021/0022731 A1 | 1/2021 | Eisinger |
| 2021/0022738 A1 | 1/2021 | Weir et al. |
| 2021/0022809 A1 | 1/2021 | Crawford et al. |
| 2021/0059674 A1 | 3/2021 | Shelton, IV et al. |

FOREIGN PATENT DOCUMENTS

| | | |
|---|---|---|
| CN | 101617950 A | 1/2010 |
| CN | 104490448 B | 3/2017 |
| CN | 206097107 U | 4/2017 |
| CN | 108652695 A | 10/2018 |
| DE | 3824913 A1 | 2/1990 |
| DE | 4002843 C1 | 4/1991 |
| DE | 102005051367 A1 | 4/2007 |
| DE | 102016207666 A1 | 11/2017 |
| EP | 0000756 B1 | 10/1981 |
| EP | 2732772 A1 | 5/2014 |
| EP | 2942023 A2 | 11/2015 |
| EP | 3047806 A1 | 7/2016 |
| EP | 3056923 A1 | 8/2016 |
| EP | 3095399 A2 | 11/2016 |
| EP | 3120781 A2 | 1/2017 |
| EP | 3135225 A2 | 3/2017 |

(56) References Cited

FOREIGN PATENT DOCUMENTS

| | | |
|---|---|---|
| EP | 3141181 A1 | 3/2017 |
| GB | 2037167 A1 | 7/1980 |
| GB | 2509523 A | 7/2014 |
| JP | S5373315 A | 6/1978 |
| JP | 2017513561 A | 6/2017 |
| KR | 20140104587 A | 8/2014 |
| KR | 101587721 B1 | 1/2016 |
| WO | WO-9734533 A1 | 9/1997 |
| WO | WO-0024322 A1 | 5/2000 |
| WO | WO-0108578 A1 | 2/2001 |
| WO | WO-0112089 A1 | 2/2001 |
| WO | WO-0120892 A2 | 3/2001 |
| WO | WO-03079909 A2 | 10/2003 |
| WO | WO-2007137304 A2 | 11/2007 |
| WO | WO-2008056618 A2 | 5/2008 |
| WO | WO-2008069816 A1 | 6/2008 |
| WO | WO-2008147555 A2 | 12/2008 |
| WO | WO-2011112931 A1 | 9/2011 |
| WO | WO-2013143573 A1 | 10/2013 |
| WO | WO-2014134196 A1 | 9/2014 |
| WO | WO-2015129395 A1 | 9/2015 |
| WO | WO-2016100719 A1 | 6/2016 |
| WO | WO-2016206015 A1 | 12/2016 |
| WO | WO-2017011382 A1 | 1/2017 |
| WO | WO-2017011646 A1 | 1/2017 |
| WO | WO-2017058695 A1 | 4/2017 |
| WO | WO-2017151996 A1 | 9/2017 |
| WO | WO-2017189317 A1 | 11/2017 |
| WO | WO-2017205308 A1 | 11/2017 |
| WO | WO-2017210499 A1 | 12/2017 |
| WO | WO-2017210501 A1 | 12/2017 |
| WO | WO-2018152141 A1 | 8/2018 |
| WO | WO-2018176414 A1 | 10/2018 |

OTHER PUBLICATIONS

Flores et al., "Large-scale Offloading in the Internet of Things," 2017 IEEE International Conference on Pervasive Computing and Communications Workshops (Percom Workshops), IEEE, pp. 479-484, Mar. 13, 2017.

Kalantarian et al., "Computation Offloading for Real-Time Health-Monitoring Devices," 2016 38th Annual International Conference of the IEEE Engineering in Medicine and Biology Society (EBMC), IEEE, pp. 4971-4974, Aug. 16, 2016.

Yuyi Mao et al., "A Survey on Mobile Edge Computing: The Communication Perspective," IEEE Communications Surveys & Tutorials, pp. 2322-2358, Jun. 13, 2017.

Khazaei et al., "Health Informatics for Neonatal Intensive Care Units: An Analytical Modeling Perspective," IEEE Journal of Translational Engineering in Health and Medicine, vol. 3, pp. 1-9, Oct. 21, 2015.

Benkmann et al., "Concept of iterative optimization of minimally invasive surgery," 2017 22nd International Conference on Methods and Models in Automation and Robotics (MMAR), IEEE pp. 443-446, Aug. 28, 2017.

Trautman, Peter, "Breaking the Human-Robot Deadlock: Surpassing Shared Control Performance Limits with Sparse Human-Robot Interaction," Robotics: Science and Systems XIII, pp. 1-10, Jul. 12, 2017.

Yang et al., "A dynamic stategy for packet scheduling and bandwidth allocation based on channel quality in IEEE 802.16e OFDMA system," Journal of Network and Computer Applications, vol. 39, pp. 52-60, May 2, 2013.

Takahashi et al., "Automatic smoke evacuation in laparoscopic surgery: a simplified method for objective evaluation," Surgical Endoscopy, vol. 27, No. 8, pp. 2980-2987, Feb. 23, 2013.

Miksch et al., "Utilizing temporal data abstraction for data validation and therapy planning for artificially ventilated newborn infants," Artificial Intelligence in Medicine, vol. 8, No. 6, pp. 543-576 (1996).

Horn et al., "Effective data validation of high-frequency data: Time-point-time-interval-, and trend-based methods," Computers in Biology and Medic, New York, NY, vol. 27, No. 5, pp. 389-409 (1997).

Stacey et al., "Temporal abstraction in intelligent clinical data analysis: A survey," Artificial Intelligence in Medicine, vol. 39, No. 1, pp. 1-24 (2006).

Zoccali, Bruno, "A Method for Approximating Component Temperatures at Altitude Conditions Based on CFD Analysis at Sea Level Conditions," (white paper), www.tdmginc.com, Dec. 6, 2018 (9 pages).

Slocinski et al., "Distance measure for impedance spectra for quantified evaluations," Lecture Notes on Impedance Spectroscopy, vol. 3, Taylor and Francis Group (Jul. 2012)—Book Not Attached.

Engel et al. "A safe robot system for craniofacial surgery", 2013 IEEE International Conference on Robotics and Automation (ICRA); May 6-10, 2013; Karlsruhe, Germany, vol. 2, Jan. 1, 2001, pp. 2020-2024.

Bonaci et al., "To Make a Robot Secure: An Experimental Analysis of Cyber Security Threats Against Teleoperated Surgical Robots," May 13, 2015. Retrieved from the Internet: URL:https://arxiv.org/pdf/1504.04339v2.pdf [retrieved on Aug. 24, 2019].

Homa Alemzadeh et al., "Targeted Attacks on Teleoperated Surgical Robots: Dynamic Model-Based Detection and Mitigation," 2016 46th Annual IEEE/IFIP International Conference on Dependable Systems and Networks (DSN), IEEE, Jun. 28, 2016, pp. 395-406.

Phumzile Malindi, "5. QoS in Telemedicine," "Telemedicine," Jun. 20, 2011, IntechOpen, pp. 119-138.

Staub et al., "Contour-based Surgical Instrument Tracking Supported by Kinematic Prediction," Proceedings of the 2010 3rd IEEE RAS & EMBS International Conference on Biomedical Robotics and Biomechatronics, Sep. 1, 2010, pp. 746-752.

Allan et al., "3-D Pose Estimation of Articulated Instruments in Robotic Minimally Invasive Surgery," IEEE Transactions on Medical Imaging, vol. 37, No. 5, May 1, 2018, pp. 1204-1213.

Kassahun et al., "Surgical Robotics Beyond Enhanced Dexterity Instrumentation: A Survey of the Machine Learning Techniques and their Role in Intelligent and Autonomous Surgical Actions." International Journal of Computer Assisted Radiology and Surgery, vol. 11, No. 4, Oct. 8, 2015, pp. 553-568.

Weede et al. "An Intelligent and Autonomous Endoscopic Guidance System for Minimally Invasive Surgery," 2013 IEEE International Conference on Robotics ad Automation (ICRA), May 6-10, 2013. Karlsruhe, Germany, May 1, 2011, pp. 5762-5768.

Altenberg et al., "Genes of Glycolysis are Ubiquitously Overexpressed in 24 Cancer Classes," Genomics, vol. 84, pp. 1014-1020 (2004).

Harold I. Brandon and V. Leroy Young, Mar. 1997, Surgical Services Management vol. 3 No. 3. retrieved from the internet <https://www.surgimedics.com/Research%20Articles/Electrosurgical%20Plume/Characterization%20And%20Removal%20Of%20Electrosurgical%20Smoke.pdf> (Year: 1997).

Marshall Brain, How Microcontrollers Work, 2006, retrieved from the internet <https://web.archive.org/web/20060221235221/http://electronics.howstuffworks.com/microcontroller.htm/printable> (Year: 2006).

CRC Press, "The Measurement, Instrumentation and Sensors Handbook," 1999, Section VII, Chapter 41, Peter O'Shea, "Phase Measurement," pp. 1303-1321, ISBN 0-8493-2145-X.

Jiang, "'Sound of Silence': a secure indoor wireless ultrasonic communication system," Article, 2014, pp. 46-50, Snapshots of Doctoral Research at University College Cork, School of Engineering—Electrical & Electronic Engineering, UCC, Cork, Ireland.

Li, et al., "Short-range ultrasonic communications in air using quadrature modulation," Journal, Oct. 30, 2009, pp. 2060-2072, IEEE Transactions on Ultrasonics, Ferroelectrics, and Frequency Control, vol. 56, No. 10, IEEE.

Salamon, "AI Detects Polyps Better Than Colonoscopists" Online Article, Jun. 3, 2018, Medscape Medical News, Digestive Disease Week (DDW) 2018: Presentation 133.

Misawa, et al. "Artificial Intelligence-Assisted Polyp Detection for Colonoscopy: Initial Experience," Article, Jun. 2018, pp. 2027-2029, vol. 154, Issue 8, American Gastroenterolgy Association.

(56) References Cited

OTHER PUBLICATIONS

Dottorato, "Analysis and Design of the Rectangular Microstrip Patch Antennas for TM0n0 operating mode,"Article, Oct. 8, 2010, pp. 1-9, Microwave Journal.

Miller, et al., "Impact of Powered and Tissue-Specific Endoscopic Stapling Technology on Clinical and Economic Outcomes of Video-Assisted Thoracic Surgery Lobectomy Procedures: A Retrospective, Observational Study," Article, Apr. 2018, pp. 707-723, vol. 35 (Issue 5), Advances in Therapy.

Hsiao-Wei Tang, "*ARCM*", Video, Sep. 2012, YouTube, 5 screenshots, Retrieved from internet: <https://www.youtube.com/watch?v=UldQaxb3fRw&feature=youtu.be>.

Giannios, et al., "Visible to near-infrared refractive properties of freshly-excised human-liver tissues: marking hepatic malignancies," Article, Jun. 14, 2016, pp. 1-10, Scientific Reports 6, Article No. 27910, Nature.

Vander Heiden, et al., "Understanding the Warburg effect: the metabolic requirements of cell proliferation," Article, May 22, 2009, pp. 1-12, vol. 324, Issue 5930, Science.

Hirayama et al., "Quantitative Metabolome Profiling of Colon and Stomach Cancer Microenvironment by Capillary Electrophoresis Time-of-Flight Mass Spectrometry," Article, Jun. 2009, pp. 4918-4925, vol. 69, Issue 11, Cancer Research.

Cengiz, et al., "A Tale of Two Compartments: Interstitial Versus Blood Glucose Monitoring," Article, Jun. 2009, pp. S11-S16, vol. 11, Supplement 1, Diabetes Technology & Therapeutics.

Shen, et al., "An iridium nanoparticles dispersed carbon based thick film electrochemical biosensor and its application for a single use, disposable glucose biosensor," Article, Feb. 3, 2007, pp. 106-113, vol. 125, Issue 1, Sensors and Actuators B: Chemical, Science Direct.

"ATM-MPLS Network Interworking Version 2.0, af-aic-0178.001" ATM Standard, The ATM Forum Technical Committee, published Aug. 2003.

IEEE Std 802.3-2012 (Revision of IEEE Std 802.3-2008, published Dec. 28, 2012.

IEEE Std No. 177, "Standard Definitions and Methods of Measurement for Piezoelectric Vibrators," published May 1966, The Institute of Electrical and Electronics Engineers, Inc., New York, N.Y.

Shi et al., An intuitive control console for robotic syrgery system, 2014, IEEE, p. 404-407 (Year: 2014).

Choi et al., a haptic augmented reality surgeon console for a laparoscopic surgery robot system, 2013, IEEE, p. 355-357 (Year: 2013).

Xie et al., Development of stereo vision and master-slave controller for a compact surgical robot system, 2015, IEEE, p. 403-407 (Year: 2015).

Sun et al., Innovative effector design for simulation training in robotic surgery, 2010, IEEE, p. 1735-1759 (Year: 2010).

Anonymous, "Internet of Things Powers Connected Surgical Device Infrastructure Case Study", Dec. 31, 2016 (Dec. 31, 2016), Retrieved from the Internet: URL:https://www.cognizant.com/services-resources/150110_IoT_connected_surgical_devices.pdf.

Draijer, Matthijs et al., "Review of laser pseckle contrast techniques for visualizing tissue perfusion," Lasers in Medical Science, Springer-Verlag, LO, vol. 24, No. 4, Dec. 3, 2008, pp. 639-651.

Roy D Cullum, "Handbook of Engineering Design", ISBN: 9780408005586, Jan. 1, 1988 (Jan. 1, 1988), XP055578597, ISBN: 9780408005586, 10-20, Chapter 6, p. 138, right-hand column, paragraph 3.

"Surgical instrumentation: the true cost of instrument trays and a potential strategy for optimization"; Mhlaba et al.; Sep. 23, 2015 (Year: 2015).

Nabil Simaan et al, "Intelligent Surgical Robots with Situational Awareness: From Good to Great Surgeons", DOI: 10.1115/1.2015-Sep-6 external link, Sep. 2015 (Sep. 2015), p. 3-6, Retrieved from the Internet: URL:http://memagazineselect.asmedigitalcollection.asme.org/data/journals/meena/936888/me-2015-sep6.pdf XP055530863.

Anonymous: "Titanium Key Chain Tool 1.1, Ultralight Multipurpose Key Chain Tool, Forward Cutting Can Opener—Vargo Titanium," vargooutdoors.com, Jul. 5, 2014 (Jul. 5, 2014), retrieved from the internet: https://vargooutdoors.com/titanium-key-chain-tool-1-1.html.

Anonymous: "Screwdriver—Wikipedia", en.wikipedia.org, Jun. 23, 2019, XP055725151, Retrieved from the Internet: URL:https://en.wikipedia.org/w/index.php?title=Screwdriver&oldid=903111203 [retrieved on Mar. 20, 2021].

Nordlinger, Christopher, "The Internet of Things and the Operating Room of the Future," May 4, 2015, https://medium.com/@chrisnordlinger/the-internet-of-things-and-the-operating-room-of-the-future-8999a143d7b1, retrieved from the internet on Apr. 27, 2021, 9 pages.

\* cited by examiner

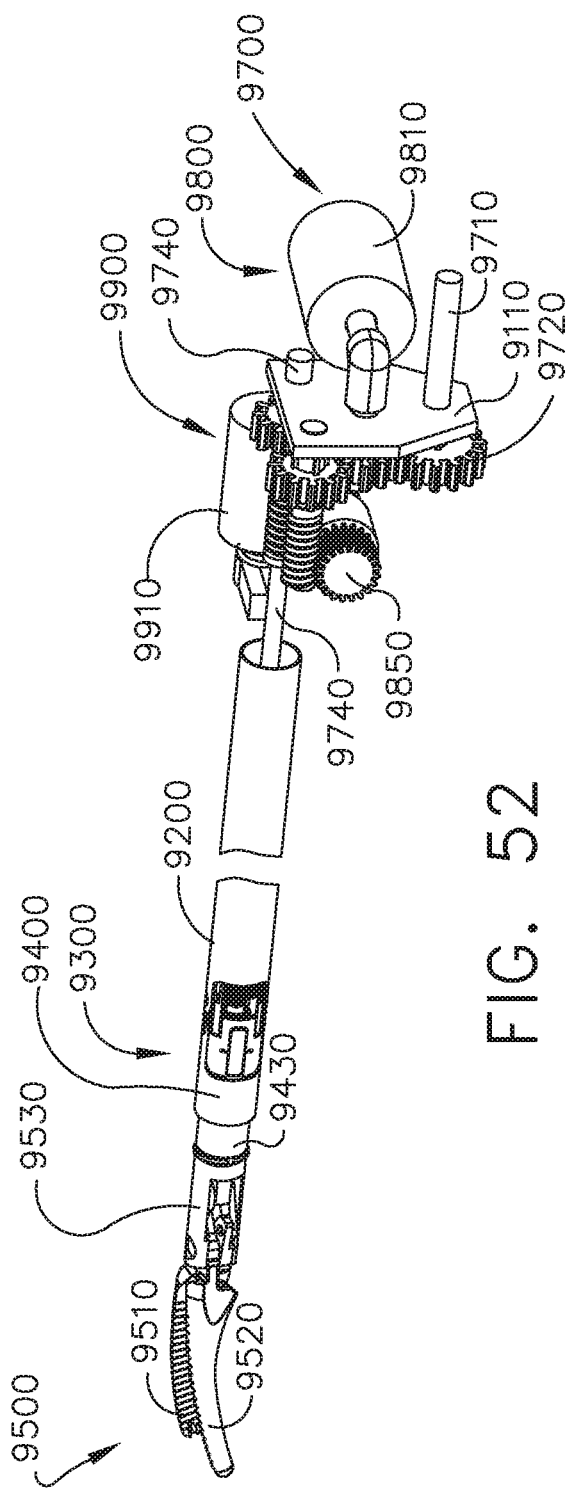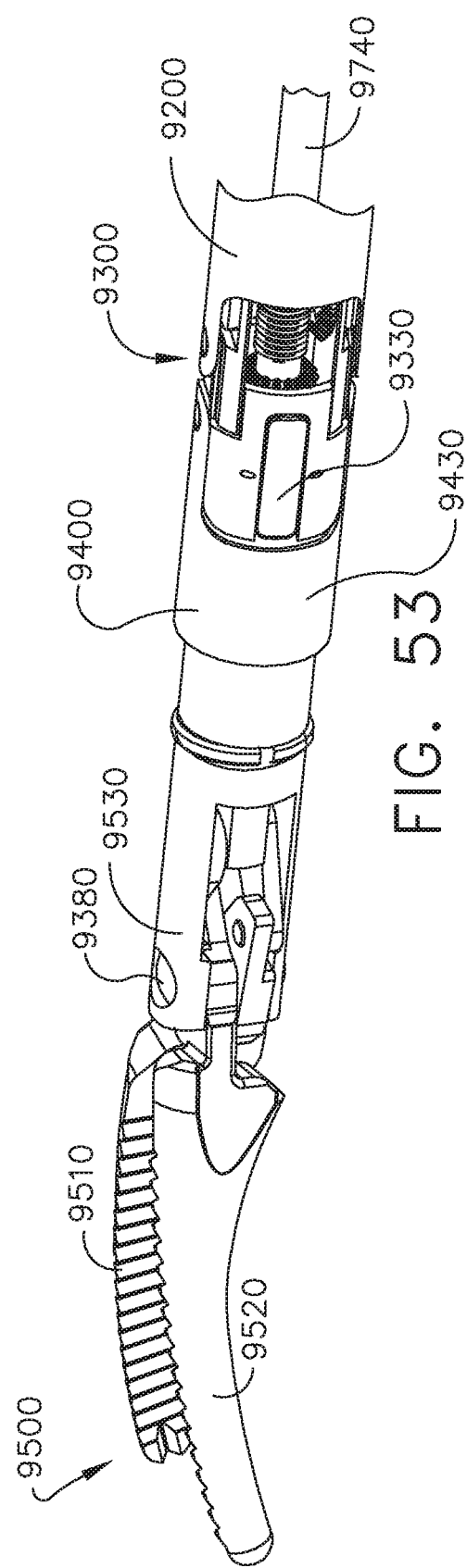

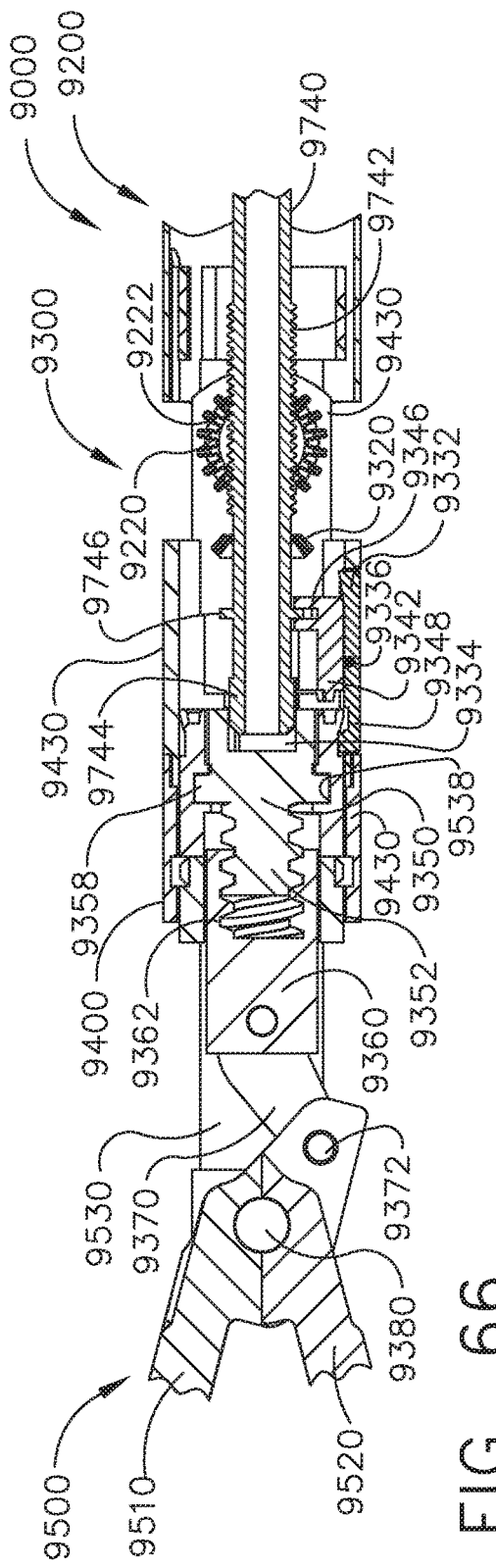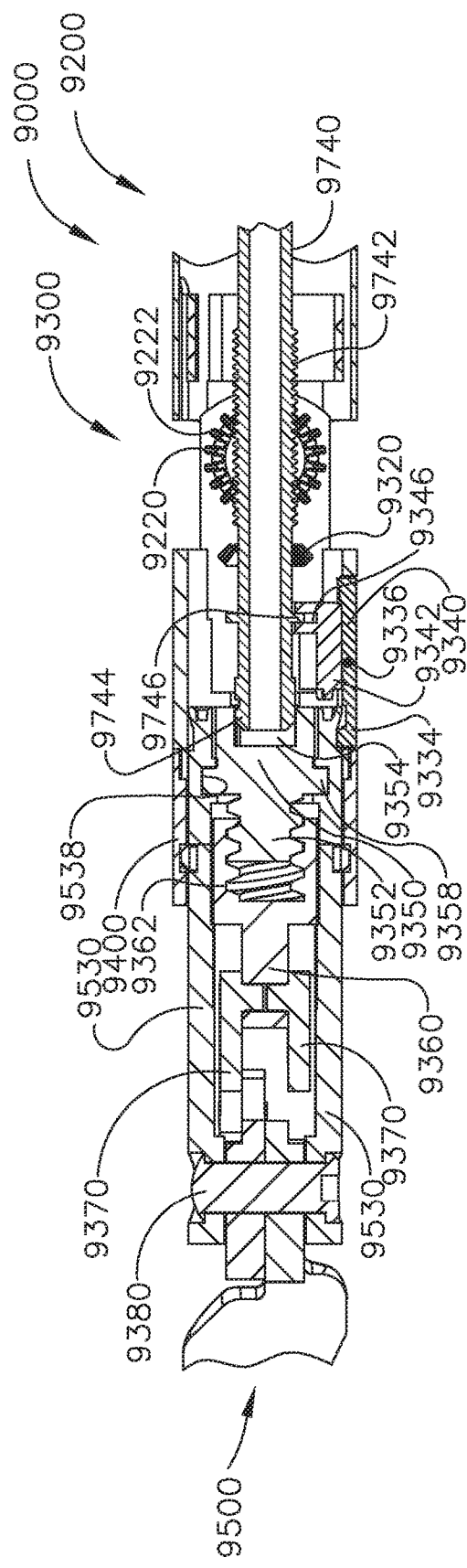

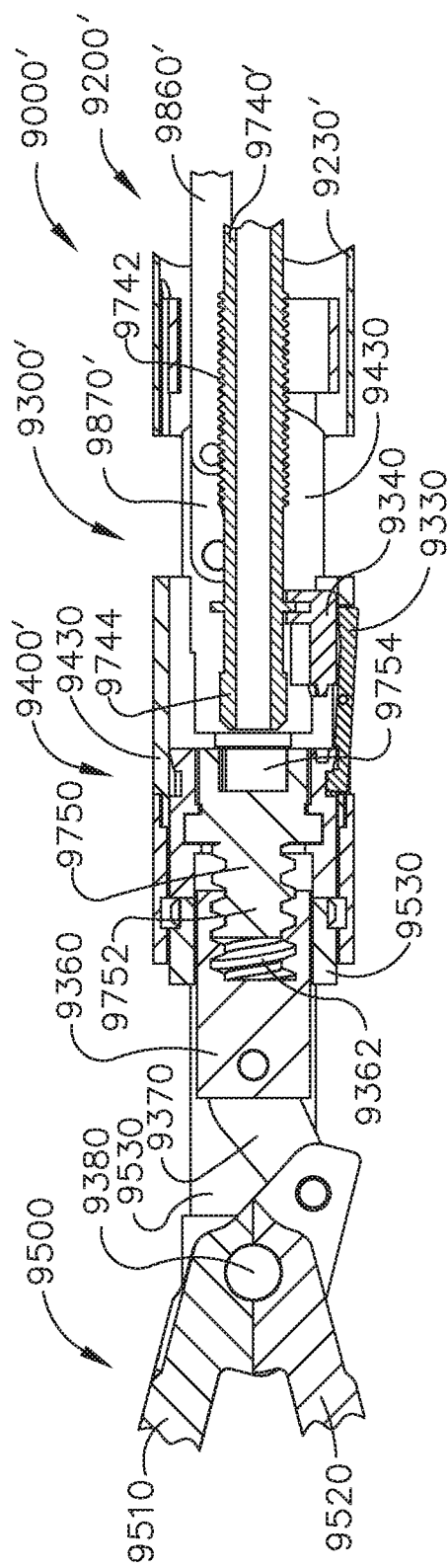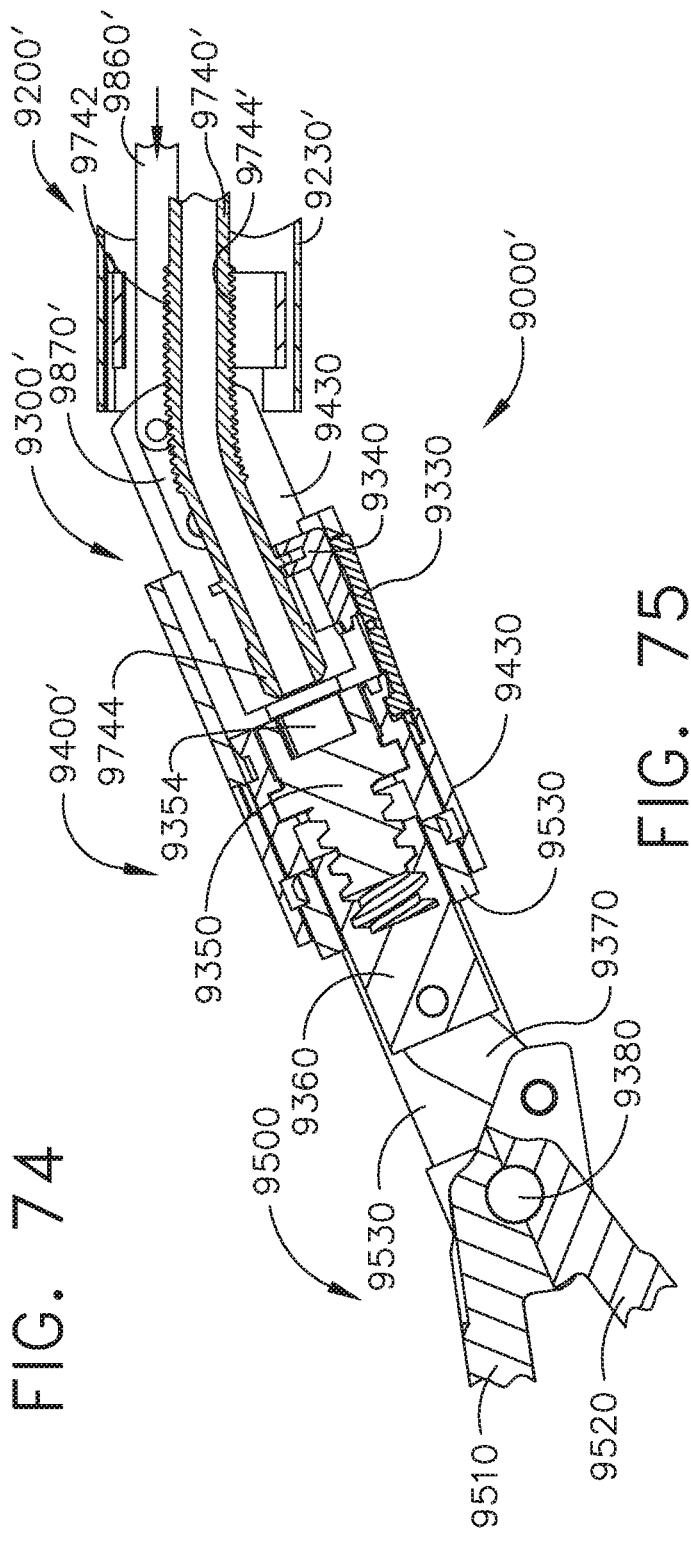
FIG. 74
FIG. 75

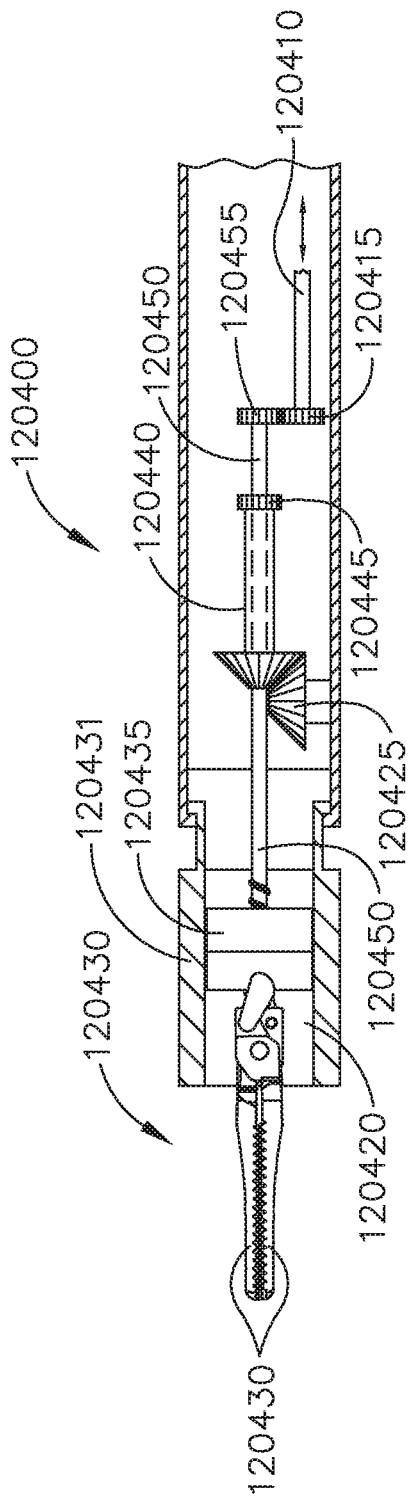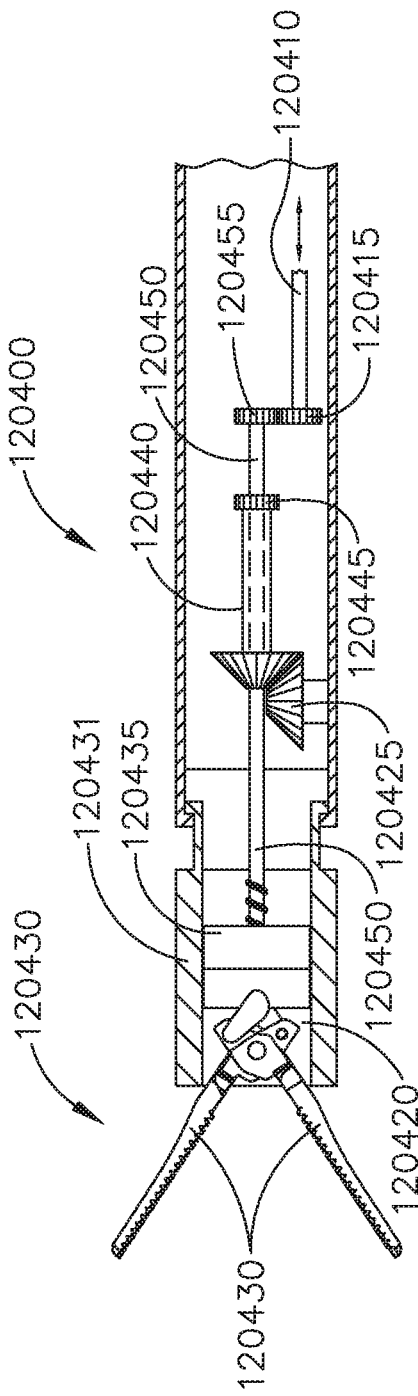

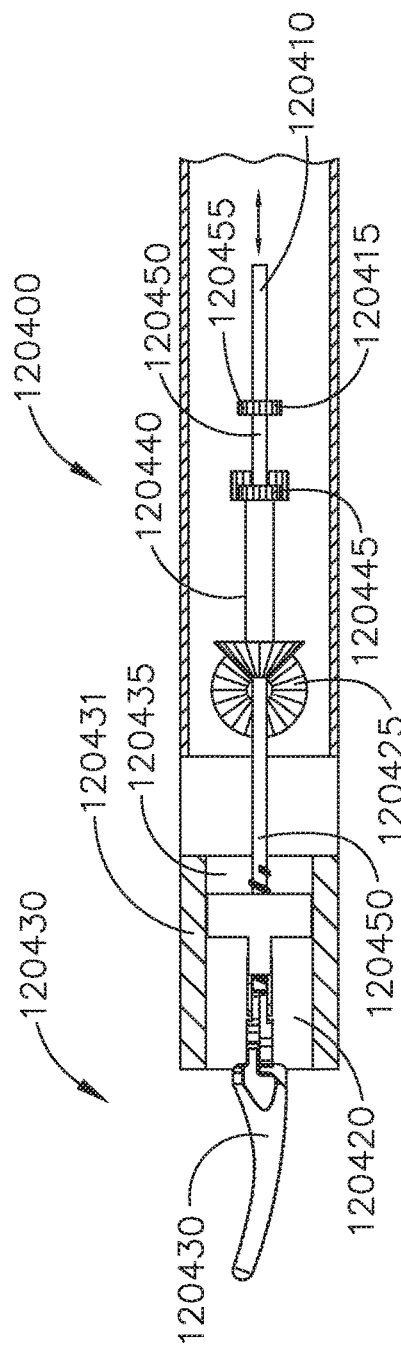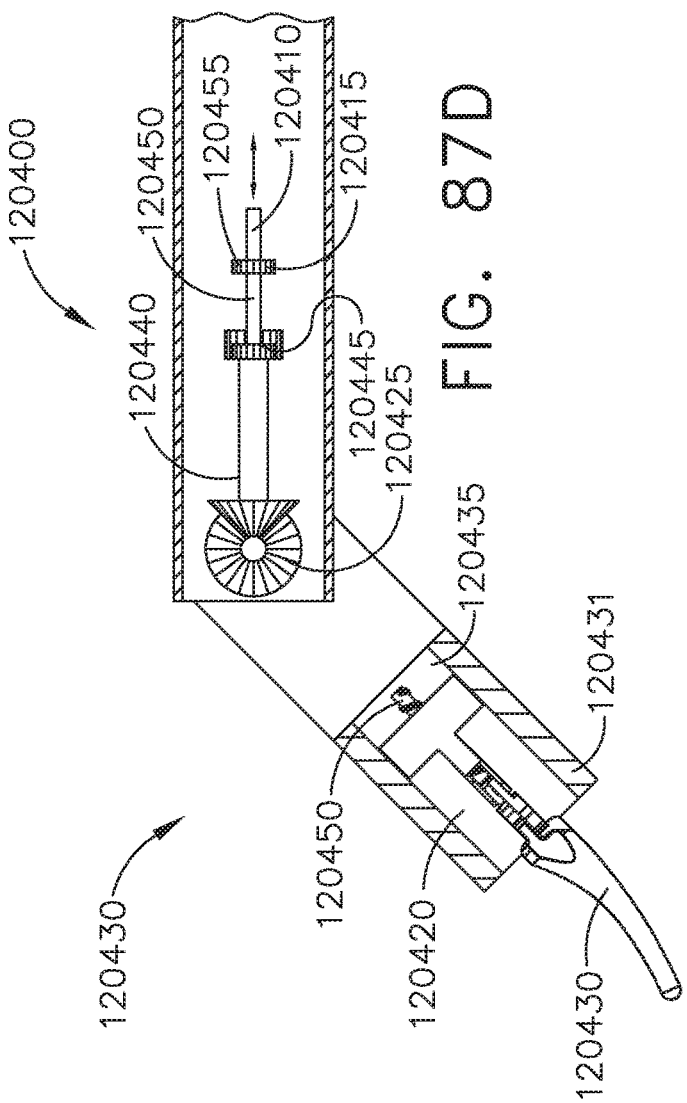

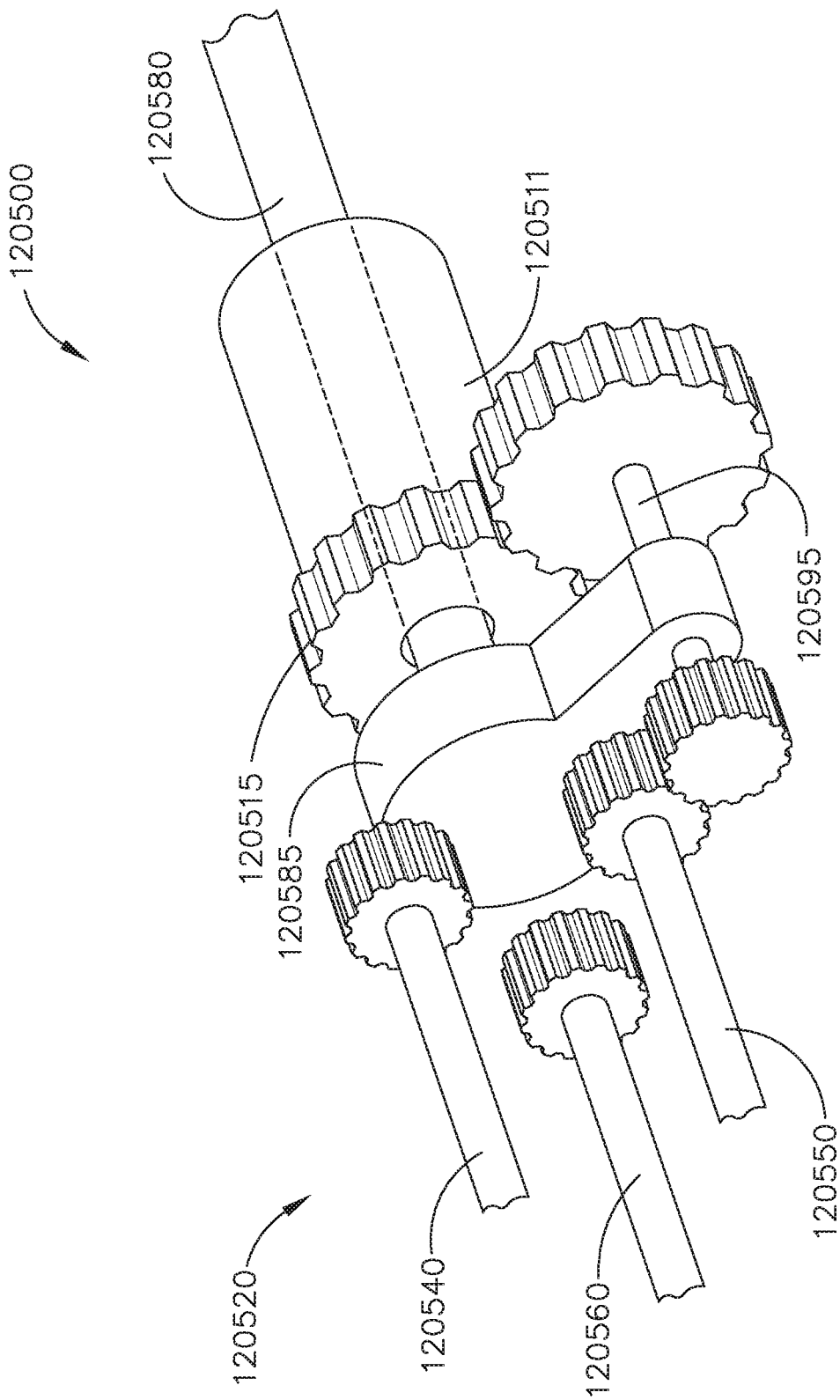

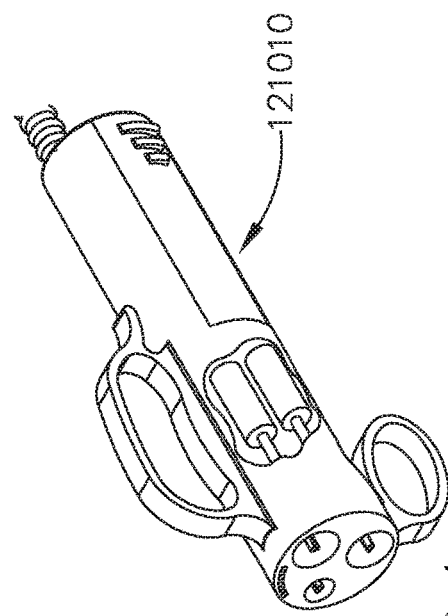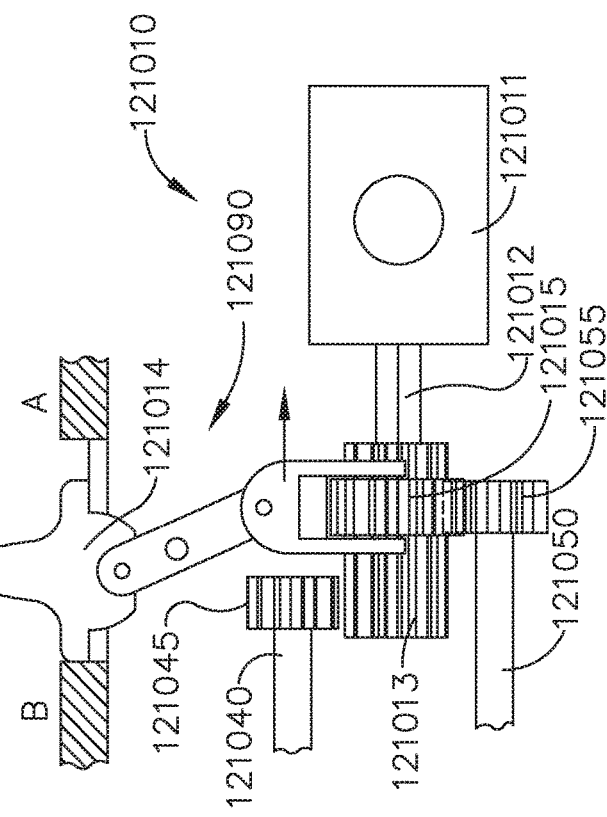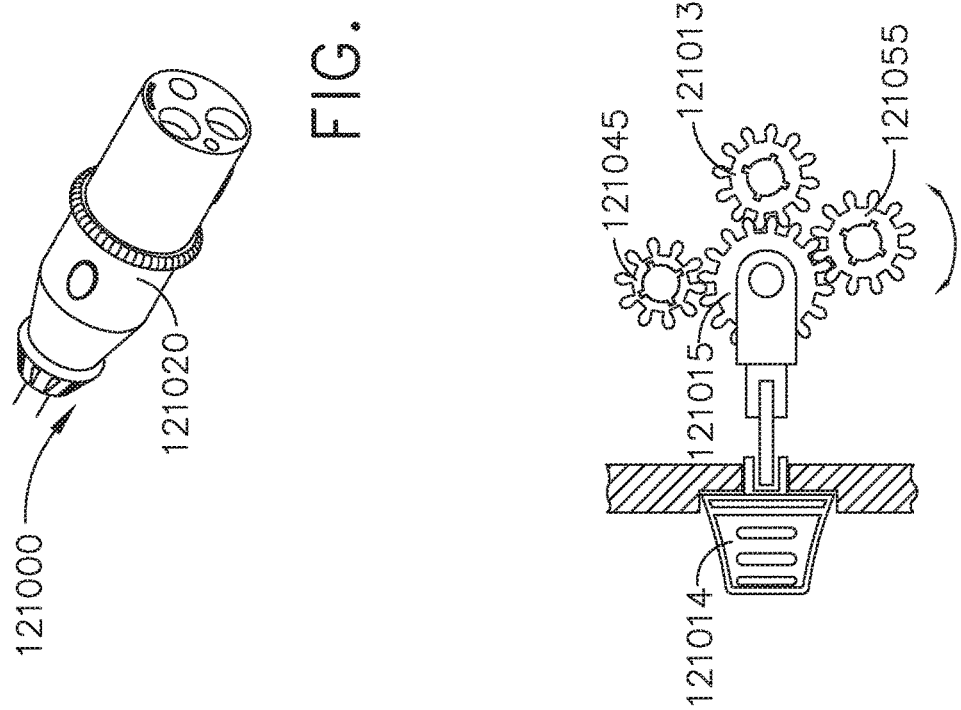

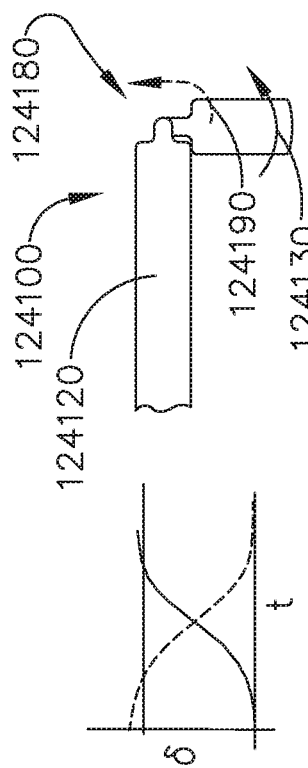
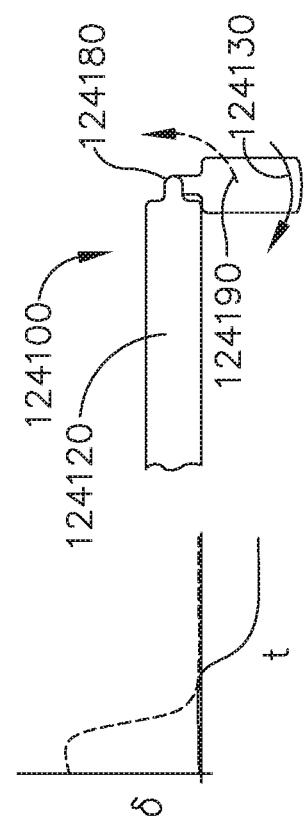
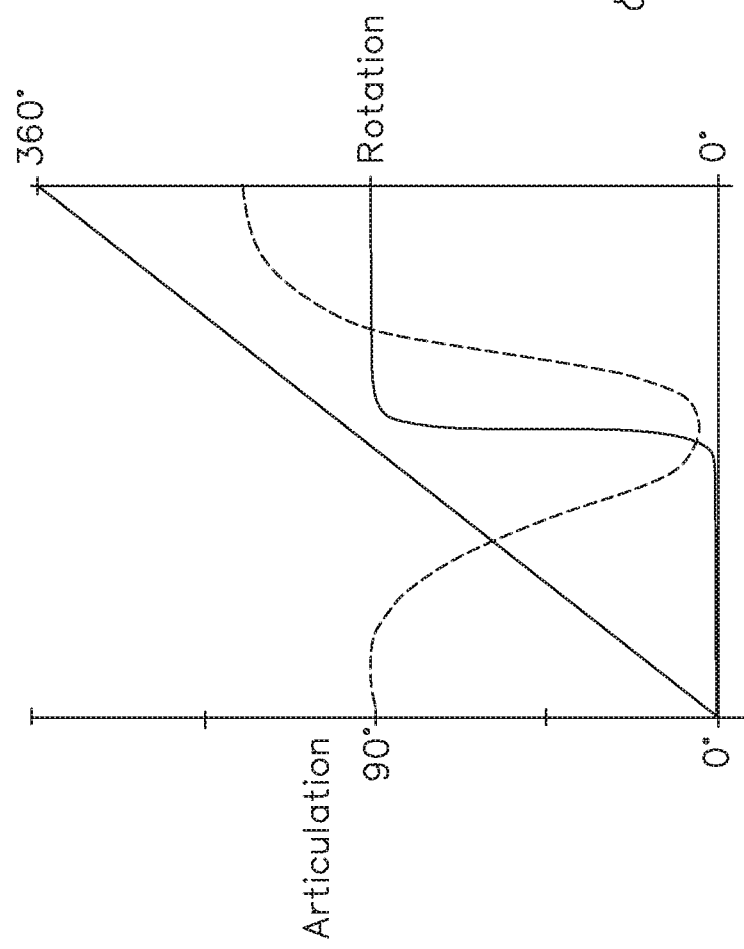
FIG. 105   FIG. 106
FIG. 107   FIG. 108
FIG. 104

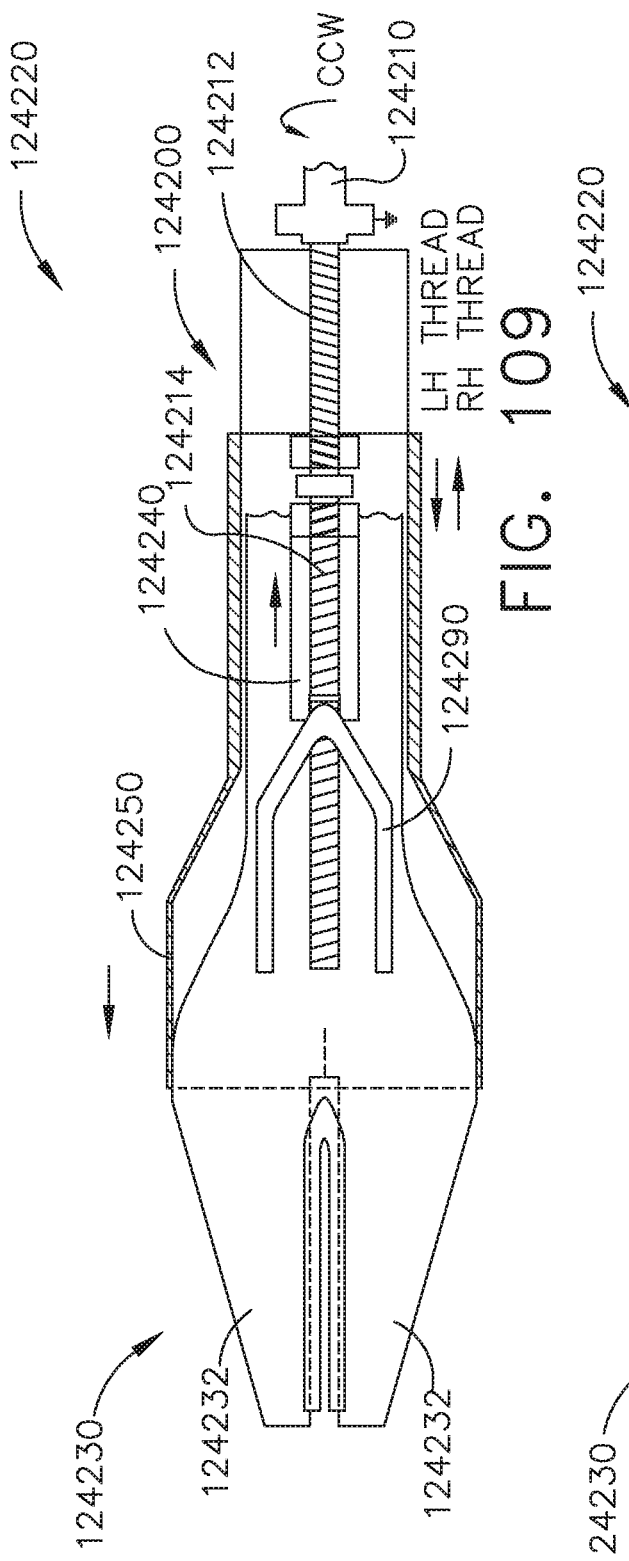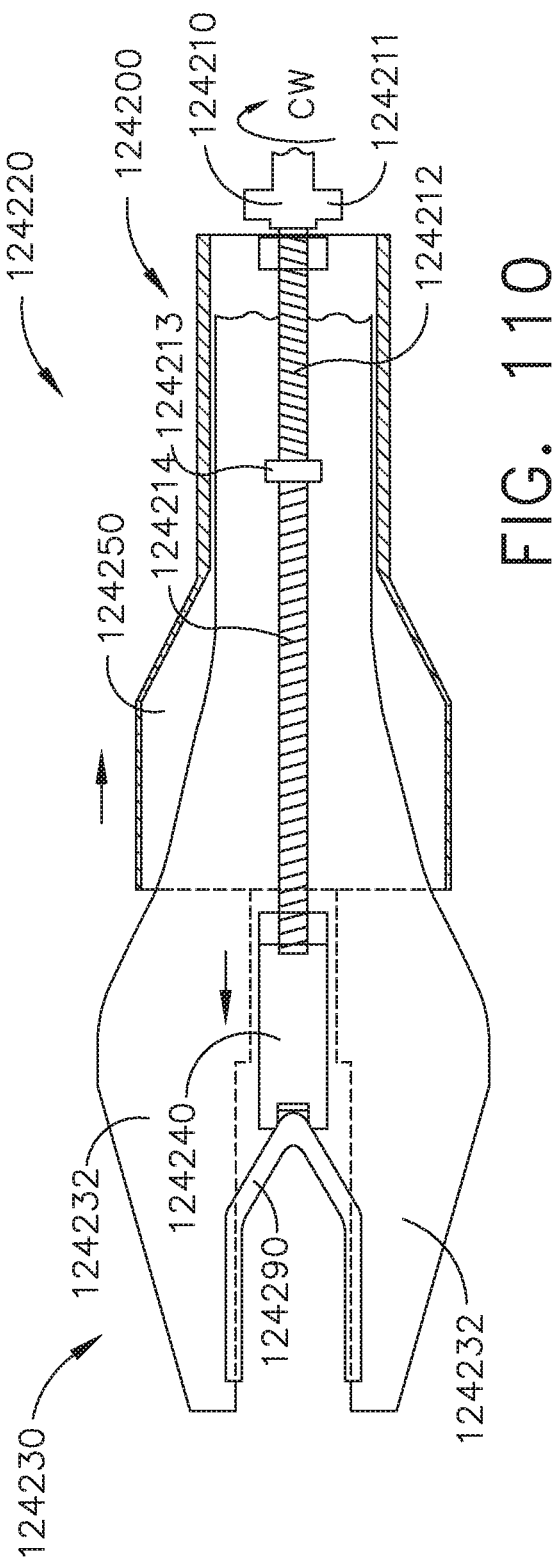

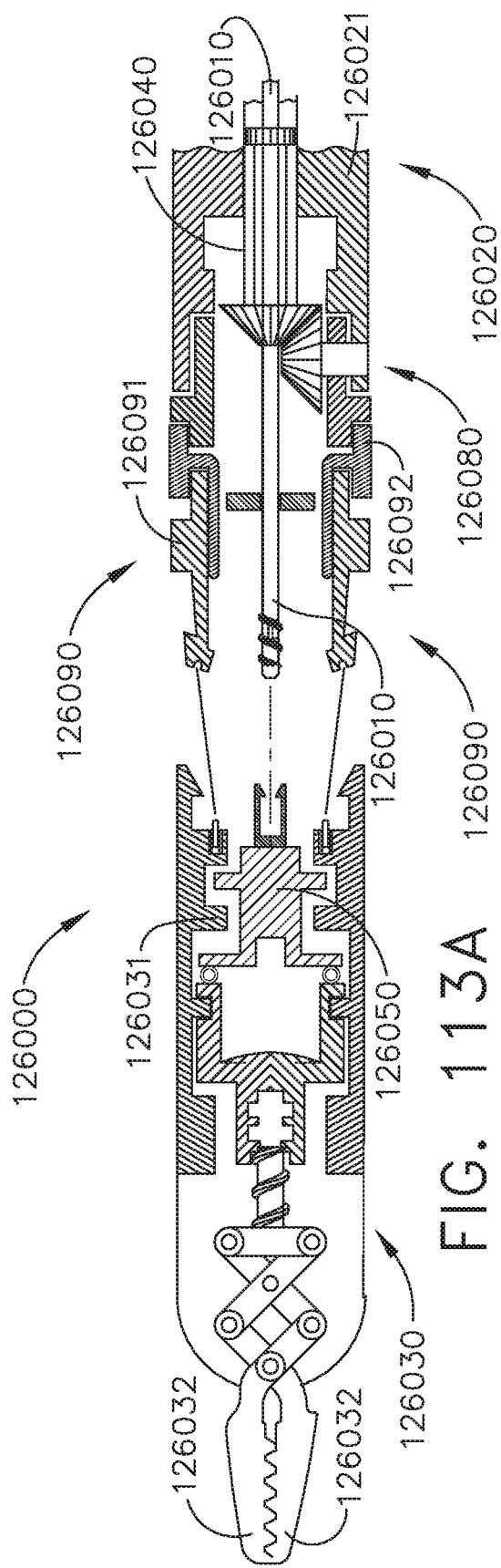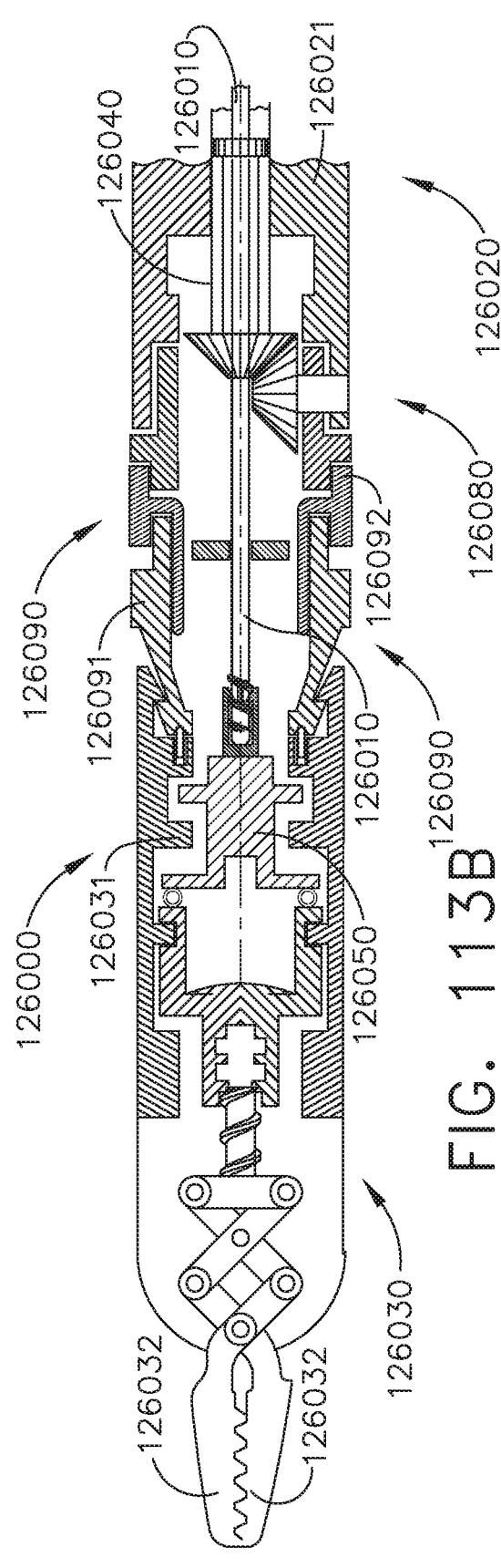

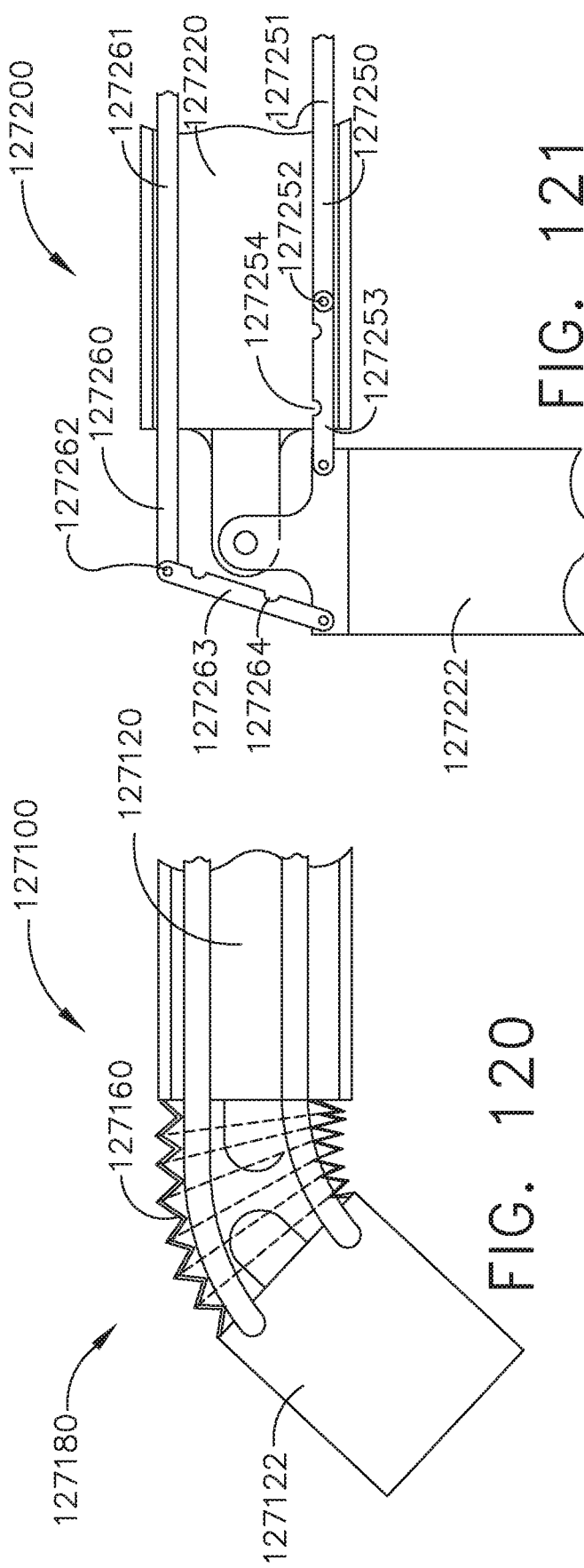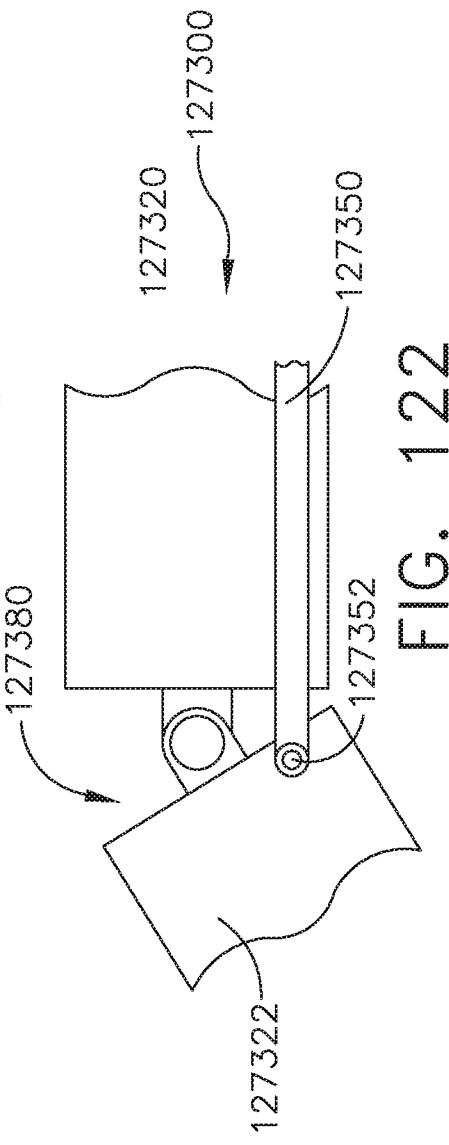

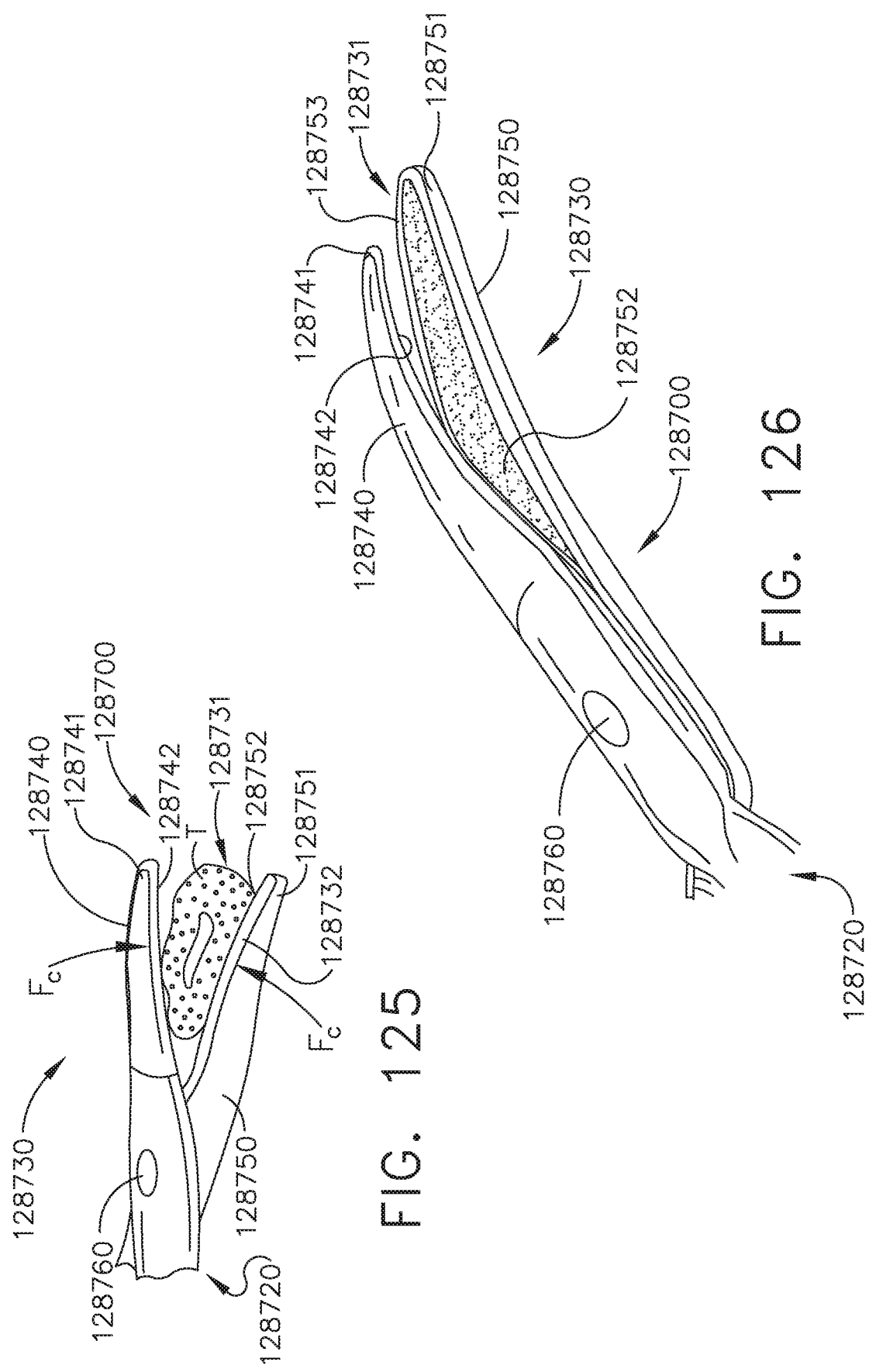

SURGICAL INSTRUMENTS COMPRISING AN ARTICULATION DRIVE THAT PROVIDES FOR HIGH ARTICULATION ANGLES

CROSS-REFERENCE TO RELATED APPLICATIONS

This non-provisional application claims the benefit under 35 U.S.C. § 119(e) of U.S. Provisional Patent Application Ser. No. 62/578,793, entitled SURGICAL INSTRUMENT WITH REMOTE RELEASE, filed Oct. 30, 2017, of U.S. Provisional Patent Application Ser. No. 62/578,804, entitled SURGICAL INSTRUMENT HAVING DUAL ROTATABLE MEMBERS TO EFFECT DIFFERENT TYPES OF END EFFECTOR MOVEMENT, filed Oct. 30, 2017, of U.S. Provisional Patent Application Ser. No. 62/578,817, entitled SURGICAL INSTRUMENT WITH ROTARY DRIVE SELECTIVELY ACTUATING MULTIPLE END EFFECTOR FUNCTIONS, filed Oct. 30, 2017, of U.S. Provisional Patent Application Ser. No. 62/578,835, entitled SURGICAL INSTRUMENT WITH ROTARY DRIVE SELECTIVELY ACTUATING MULTIPLE END EFFECTOR FUNCTIONS, filed Oct. 30, 2017, of U.S. Provisional Patent Application Ser. No. 62/578,844, entitled SURGICAL INSTRUMENT WITH MODULAR POWER SOURCES, filed Oct. 30, 2017, and of U.S. Provisional Patent Application Ser. No. 62/578,855, entitled SURGICAL INSTRUMENT WITH SENSOR AND/OR CONTROL SYSTEMS, filed Oct. 30, 2017, the disclosures of which are incorporated by reference herein in their entirety. This non-provisional application claims the benefit under 35 U.S.C. § 119(e) of U.S. Provisional Patent Application Ser. No. 62/665,129, entitled SURGICAL SUTURING SYSTEMS, filed May 1, 2018, of U.S. Provisional Patent Application Ser. No. 62/665,139, entitled SURGICAL INSTRUMENTS COMPRISING CONTROL SYSTEMS, filed May 1, 2018, of U.S. Provisional Patent Application Ser. No. 62/665,177, entitled SURGICAL INSTRUMENTS COMPRISING HANDLE ARRANGEMENTS, filed May 1, 2018, of U.S. Provisional Patent Application Ser. No. 62/665,128, entitled MODULAR SURGICAL INSTRUMENTS, filed May 1, 2018, of U.S. Provisional Patent Application Ser. No. 62/665,192, entitled SURGICAL DISSECTORS, filed May 1, 2018, and of U.S. Provisional Patent Application Ser. No. 62/665,134, entitled SURGICAL CLIP APPLIER, filed May 1, 2018, the disclosures of which are incorporated by reference herein in their entirety.

BACKGROUND

The present invention relates to surgical systems and, in various arrangements, to grasping instruments that are designed to grasp the tissue of a patient, dissecting instruments configured to manipulate the tissue of a patient, clip appliers configured to clip the tissue of a patient, and suturing instruments configured to suture the tissue of a patient, among others.

BRIEF DESCRIPTION OF THE DRAWINGS

Various features of the embodiments described herein, together with advantages thereof, may be understood in accordance with the following description taken in conjunction with the accompanying drawings as follows:

FIG. 52 is a perspective view of the shaft assembly of FIG. 51 illustrated with some components removed;

FIG. 53 is a perspective view of an end effector of the shaft assembly of FIG. 51.

FIG. 66 is a partial top cross-sectional view of the end effector of FIG. 53 in a rotation drive mode;

FIG. 67 is a partial top cross-sectional view of the end effector of FIG. 53 in a rotated configuration;

FIG. 74 is a partial top cross-sectional view of the end effector of FIG. 71 in an articulation drive mode;

FIG. 75 is a partial top cross-sectional view of the end effector of FIG. 71 in an articulated configuration;

FIG. 87A is a partial cross-sectional view of a drive system of a surgical instrument comprising a shiftable input in accordance with at least one embodiment;

FIG. 87B depicts the surgical instrument of FIG. 87A in an open configuration;

FIG. 87C depicts the surgical instrument of FIG. 87A in an unarticulated configuration;

FIG. 87D depicts the surgical instrument of FIG. 87A in an articulated configuration;

FIG. 88B depicts the transmission in a second configuration;

FIG. 94 is a partial perspective view of a surgical instrument system in accordance with at least one embodiment;

FIG. 95A is a side view of a drive system of the surgical instrument system of FIG. 94;

FIG. 95B is an end view of the drive system of FIG. 95A;

FIG. 104 is a graph depicting the rotation and articulation of an end effector of a surgical instrument;

FIG. 105 is a partial top view of a shaft assembly comprising a rotatable and articulatable end effector;

FIG. 106 is a graph depicting the rotation and articulation of the end effector of FIG. 105 in at least one instance;

FIG. 107 is another partial top view of the shaft assembly of FIG. 105;

FIG. 108 is a graph depicted the rotation and articulation of the end effector of FIG. 105 in at least one instance;

FIG. 109 is a partial cross-sectional view of a surgical instrument in accordance with at least one embodiment;

FIG. 110 is a partial cross-sectional view of the surgical instrument of FIG. 109;

FIG. 111A is a partial cross-sectional view of a surgical instrument comprising a shiftable transmission in accordance with at least one embodiment;

FIG. 111B illustrates the transmission of FIG. 111A in a first configuration;

FIG. 111C illustrates the transmission of FIG. 111B in a second configuration;

FIG. 112 is a partial perspective view of a surgical instrument in accordance with at least one embodiment;

FIG. 113A is a partial cross-sectional view of a surgical instrument comprising a shaft assembly and a detachable end effector in accordance with at least one embodiment;

FIG. 113B depicts the end effector in an attached state;

FIG. 114 is a partial cross-sectional view of a drive shaft interconnection in accordance with at least one embodiment;

FIG. 115 is a partial cross-sectional view of a shaft assembly comprising an end effector and an articulation system in accordance with at least one embodiment;

FIG. 116 is a partial cross-sectional view of the shaft assembly of FIG. 115;

FIG. 117 is a partial exploded view of the articulation system of FIG. 115;

FIG. 118 is a partial cross-sectional view of a surgical instrument comprising an articulation system in accordance with at least one embodiment;

FIG. 119 is a partial cross-sectional view of the surgical instrument of FIG. 118 in an articulated configuration;

Figure 123:
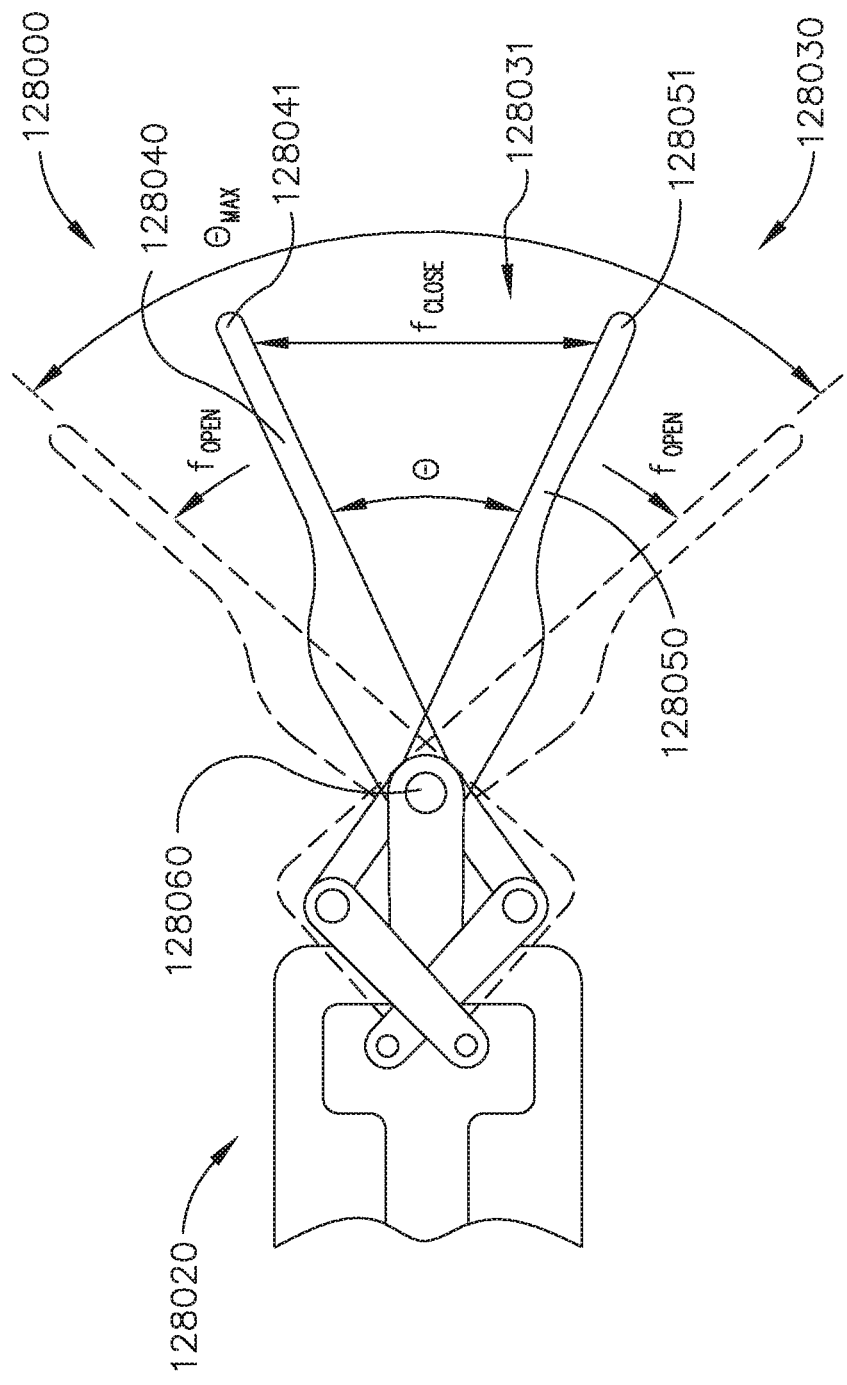
Figure 124:
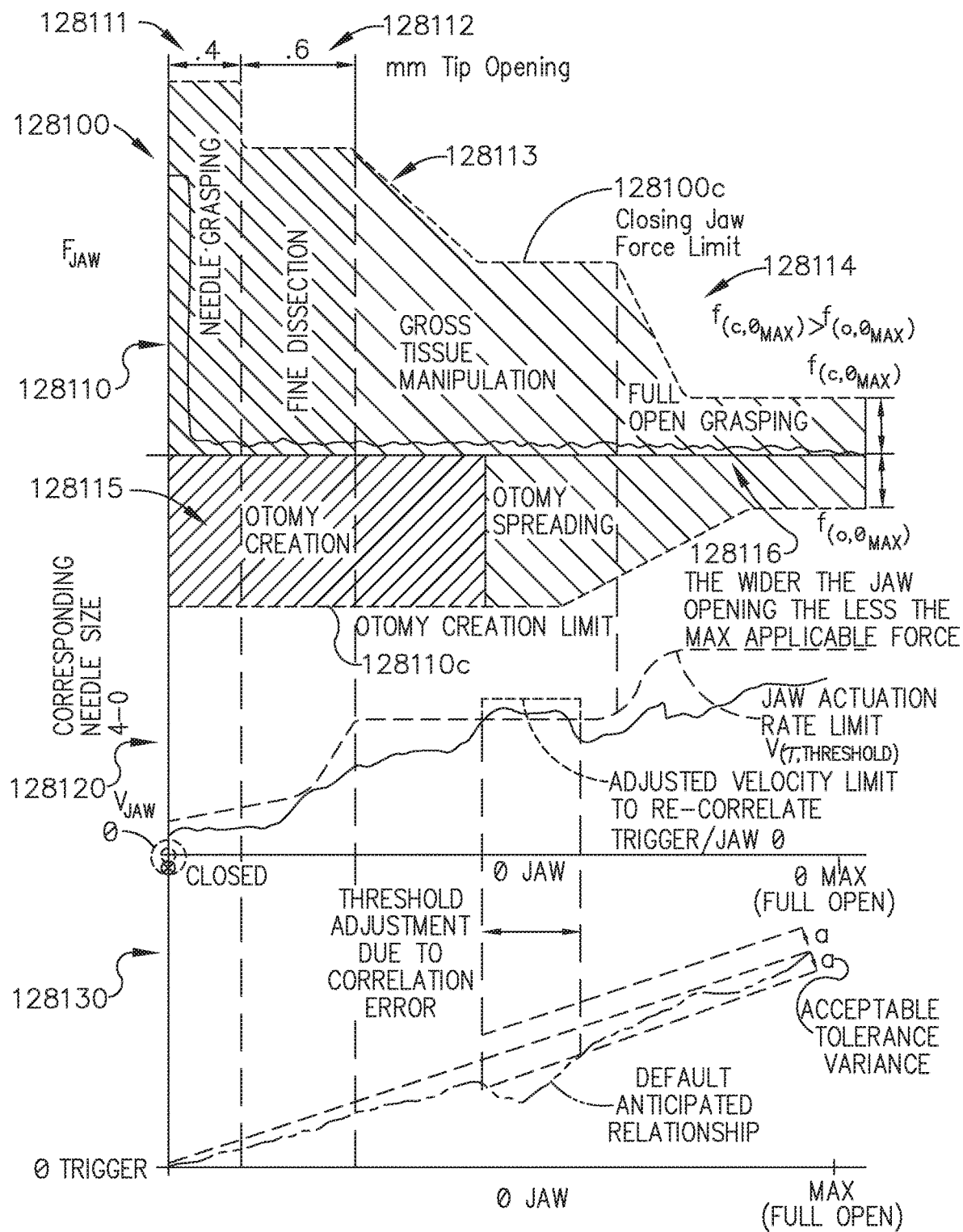
Figure 127:
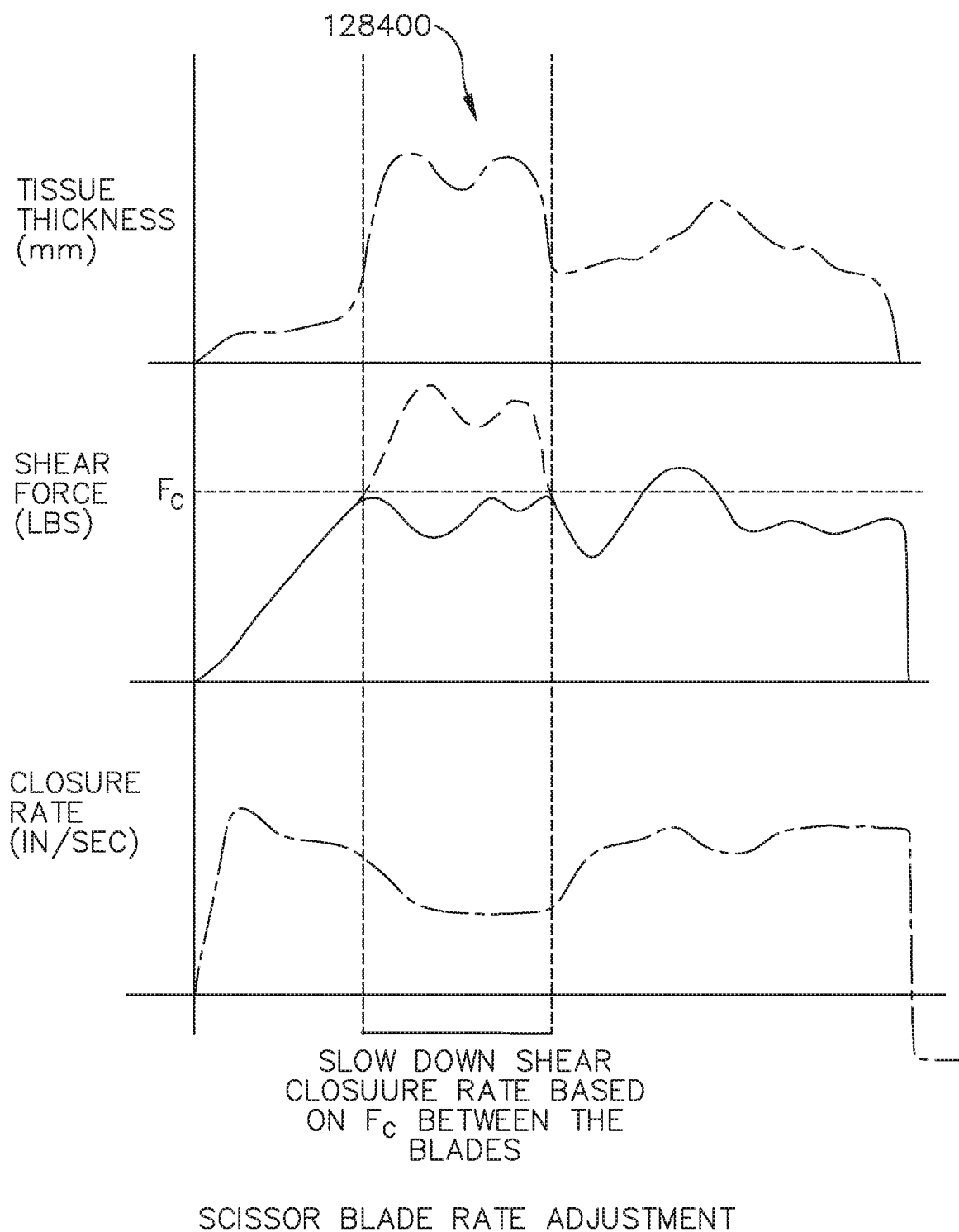
Figure 128:
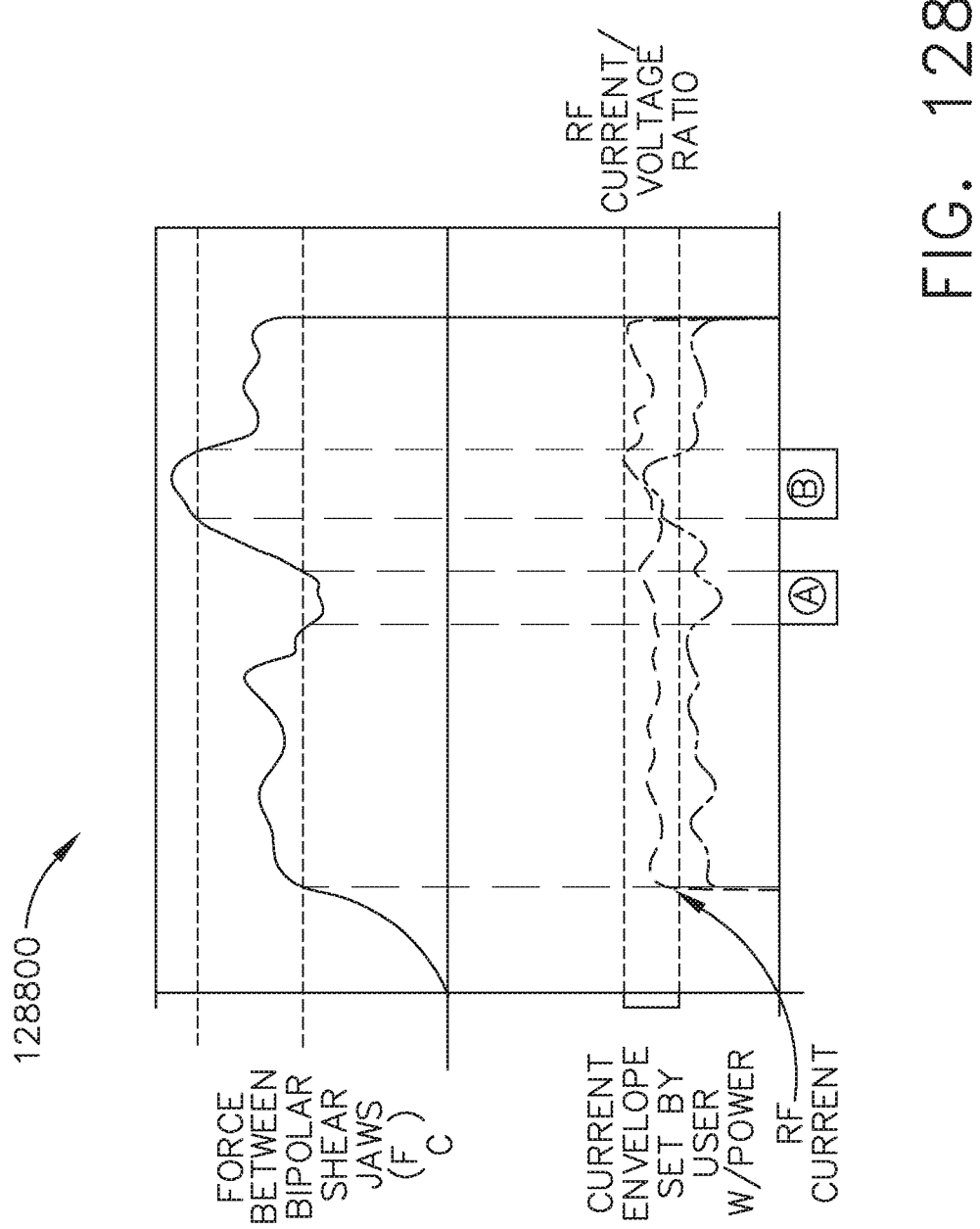

FIG. 120 is a partial plan view of an articulation system of a surgical instrument in accordance with at least one embodiment;

FIG. 121 is a partial plan view of an articulation system of a surgical instrument in accordance with at least one embodiment;

FIG. 122 is a partial plan view of an articulation system of a surgical instrument in accordance with at least one embodiment;

FIG. 123 is a partial cross-sectional view of a surgical instrument including a jaw assembly capable of grasping and dissection in accordance with at least one embodiment;

FIG. 124 is a graph depicting the force, speed, and orientation of the jaw assembly of FIG. 123 in accordance with at least one embodiment;

FIG. 125 is a partial perspective view of bipolar forceps being used to cut tissue;

FIG. 126 is a perspective view of the bipolar forceps of FIG. 125;

FIG. 127 is a graph depicting the force and speed of the jaws of the bipolar forceps of FIG. 125 in accordance with at least one embodiment; and FIG. 128 is another graph depicting the operation of the bipolar forceps of FIG. 125 in accordance with at least one embodiment.

Corresponding reference characters indicate corresponding parts throughout the several views. The exemplifications set out herein illustrate various embodiments of the inven-

DETAILED DESCRIPTION

Applicant of the present application owns the following U.S. patent applications that were filed on Aug. 24, 2018 and which are each herein incorporated by reference in their respective entireties:

U.S. patent application Ser. No. 16/112,129, entitled SURGICAL SUTURING INSTRUMENT CONFIGURED TO MANIPULATE TISSUE USING MECHANICAL AND ELECTRICAL POWER, now U.S. Patent Application Publication No. 2019/0125431;

U.S. patent application Ser. No. 16/112,155, entitled SURGICAL SUTURING INSTRUMENT COMPRISING A CAPTURE WIDTH WHICH IS LARGER THAN TROCAR DIAMETER, now U.S. Patent Application Publication No. 2019/0125335;

U.S. patent application Ser. No. 16/112,168, entitled SURGICAL SUTURING INSTRUMENT COMPRISING A NON-CIRCULAR NEEDLE, now U.S. Patent Application Publication No. 2019/0125336;

U.S. patent application Ser. No. 16/112,180, entitled ELECTRICAL POWER OUTPUT CONTROL BASED ON MECHANICAL FORCES, now U.S. Patent Application Publication No. 2019/0125432;

U.S. patent application Ser. No. 16/112,193, entitled REACTIVE ALGORITHM FOR SURGICAL SYSTEM, now U.S. Pat. No. 10,932,806;

U.S. patent application Ser. No. 16/112,099, entitled SURGICAL INSTRUMENT COMPRISING AN ADAPTIVE ELECTRICAL SYSTEM, now U.S. Patent Application Publication No. 2019/0125378;

U.S. patent application Ser. No. 16/112,112, entitled CONTROL SYSTEM ARRANGEMENTS FOR A MODULAR SURGICAL INSTRUMENT, now U.S. Patent Application Publication No. 2019/0125320;

U.S. patent application Ser. No. 16/116,119, entitled ADAPTIVE CONTROL PROGRAMS FOR A SURGICAL SYSTEM COMPRISING MORE THAN ONE TYPE OF CARTRIDGE, now U.S. Patent Application Publication No. 2019/0125338;

U.S. patent application Ser. No. 16/112,097, entitled SURGICAL INSTRUMENT SYSTEMS COMPRISING BATTERY ARRANGEMENTS, now U.S. Patent Application Publication No. 2019/0125377;

U.S. patent application Ser. No. 16/112,109, entitled SURGICAL INSTRUMENT SYSTEMS COMPRISING HANDLE ARRANGEMENTS, now U.S. Patent Application Publication No. 2019/0125388;

U.S. patent application Ser. No. 16/112,114, entitled SURGICAL INSTRUMENT SYSTEMS COMPRISING FEEDBACK MECHANISMS, now U.S. Pat. No. 10,980,560;

U.S. patent application Ser. No. 16/112,117, entitled SURGICAL INSTRUMENT SYSTEMS COMPRISING LOCKOUT MECHANISMS, now U.S. Patent Application Publication No. 2019/0125476;

U.S. patent application Ser. No. 16/112,095, entitled SURGICAL INSTRUMENTS COMPRISING A LOCKABLE END EFFECTOR SOCKET, now U.S. Patent Application Publication No. 2019/0125387;

U.S. patent application Ser. No. 16/112,121, entitled SURGICAL INSTRUMENTS COMPRISING A SHIFTING MECHANISM, now U.S. Pat. No. 11,026,712;

U.S. patent application Ser. No. 16/112,151, entitled SURGICAL INSTRUMENTS COMPRISING A SYSTEM FOR ARTICULATION AND ROTATION COMPENSATION, now U.S. Pat. No. 10,772,651;

U.S. patent application Ser. No. 16/112,154, entitled SURGICAL INSTRUMENTS COMPRISING A BIASED SHIFTING MECHANISM, now U.S. Patent Application Publication No. 2019/0125321;

U.S. patent application Ser. No. 16/112,062, entitled SURGICAL DISSECTORS AND MANUFACTURING TECHNIQUES, now U.S. Pat. No. 10,959,744;

U.S. patent application Ser. No. 16/112,098, entitled SURGICAL DISSECTORS CONFIGURED TO APPLY MECHANICAL AND ELECTRICAL ENERGY, now U.S. Patent Application Publication No. 2019/0125430;

U.S. patent application Ser. No. 16/112,237, entitled SURGICAL CLIP APPLIER CONFIGURED TO STORE CLIPS IN A STORED STATE, now U.S. Pat. No. 11,026,713;

U.S. patent application Ser. No. 16/112,245, entitled SURGICAL CLIP APPLIER COMPRISING AN EMPTY CLIP CARTRIDGE LOCKOUT, now U.S. Pat. No. 11,051,836;

U.S. patent application Ser. No. 16/112,249, entitled SURGICAL CLIP APPLIER COMPRISING AN AUTOMATIC CLIP FEEDING SYSTEM, now U.S. Patent Application Publication No. 2019/0125353;

U.S. patent application Ser. No. 16/112,253, entitled SURGICAL CLIP APPLIER COMPRISING ADAPTIVE FIRING CONTROL, now U.S. Patent Application Publication No. 2019/0125348; and U.S. patent application Ser. No. 16/112,257, entitled SURGICAL CLIP APPLIER COMPRISING ADAPTIVE CONTROL IN RESPONSE TO A STRAIN GAUGE CIRCUIT, now U.S. Pat. No. 11,071,560.

Applicant of the present application owns the following U.S. patent applications that were filed on May 1, 2018 and which are each herein incorporated by reference in their respective entireties:

U.S. Provisional Patent Application Ser. No. 62/665,129, entitled SURGICAL SUTURING SYSTEMS;

U.S. Provisional Patent Application Ser. No. 62/665,139, entitled SURGICAL INSTRUMENTS COMPRISING CONTROL SYSTEMS;

U.S. Provisional Patent Application Ser. No. 62/665,177, entitled SURGICAL INSTRUMENTS COMPRISING HANDLE ARRANGEMENTS;

U.S. Provisional Patent Application Ser. No. 62/665,128, entitled MODULAR SURGICAL INSTRUMENTS;

U.S. Provisional Patent Application Ser. No. 62/665,192, entitled SURGICAL DISSECTORS; and U.S. Provisional Patent Application Ser. No. 62/665,134, entitled SURGICAL CLIP APPLIER.

Applicant of the present application owns the following U.S. patent applications that were filed on Feb. 28, 2018 and which are each herein incorporated by reference in their respective entireties:

U.S. patent application Ser. No. 15/908,021, entitled SURGICAL INSTRUMENT WITH REMOTE RELEASE;

U.S. patent application Ser. No. 15/908,012, entitled SURGICAL INSTRUMENT HAVING DUAL ROTATABLE MEMBERS TO EFFECT DIFFERENT TYPES OF END EFFECTOR MOVEMENT;

U.S. patent application Ser. No. 15/908,040, entitled SURGICAL INSTRUMENT WITH ROTARY DRIVE SELECTIVELY ACTUATING MULTIPLE END EFFECTOR FUNCTIONS;

U.S. patent application Ser. No. 15/908,057, entitled SURGICAL INSTRUMENT WITH ROTARY DRIVE SELECTIVELY ACTUATING MULTIPLE END EFFECTOR FUNCTIONS;

U.S. patent application Ser. No. 15/908,058, entitled SURGICAL INSTRUMENT WITH MODULAR POWER SOURCES; and U.S. patent application Ser. No. 15/908,143, entitled SURGICAL INSTRUMENT WITH SENSOR AND/OR CONTROL SYSTEMS.

Applicant of the present application owns the following U.S. patent applications that were filed on Oct. 30, 2017 and which are each herein incorporated by reference in their respective entireties:

U.S. Provisional Patent Application Ser. No. 62/578,793, entitled SURGICAL INSTRUMENT WITH REMOTE RELEASE;

U.S. Provisional Patent Application Ser. No. 62/578,804, entitled SURGICAL INSTRUMENT HAVING DUAL ROTATABLE MEMBERS TO EFFECT DIFFERENT TYPES OF END EFFECTOR MOVEMENT;

U.S. Provisional Patent Application Ser. No. 62/578,817, entitled SURGICAL INSTRUMENT WITH ROTARY DRIVE SELECTIVELY ACTUATING MULTIPLE END EFFECTOR FUNCTIONS;

U.S. Provisional Patent Application Ser. No. 62/578,835, entitled SURGICAL INSTRUMENT WITH ROTARY DRIVE SELECTIVELY ACTUATING MULTIPLE END EFFECTOR FUNCTIONS;

U.S. Provisional Patent Application Ser. No. 62/578,844, entitled SURGICAL INSTRUMENT WITH MODULAR POWER SOURCES; and U.S. Provisional Patent Application Ser. No. 62/578,855, entitled SURGICAL INSTRUMENT WITH SENSOR AND/OR CONTROL SYSTEMS.

Applicant of the present application owns the following U.S. Provisional Patent Applications, filed on Dec. 28, 2017, the disclosure of each of which is herein incorporated by reference in its entirety:

U.S. Provisional Patent Application Ser. No. 62/611,341, entitled INTERACTIVE SURGICAL PLATFORM;

U.S. Provisional Patent Application Ser. No. 62/611,340, entitled CLOUD-BASED MEDICAL ANALYTICS; and U.S. Provisional Patent Application Ser. No. 62/611,339, entitled ROBOT ASSISTED SURGICAL PLATFORM.

Applicant of the present application owns the following U.S. Provisional Patent Applications, filed on Mar. 28, 2018, each of which is herein incorporated by reference in its entirety:

U.S. Provisional Patent Application Ser. No. 62/649,302, entitled INTERACTIVE SURGICAL SYSTEMS WITH ENCRYPTED COMMUNICATION CAPABILITIES;

U.S. Provisional Patent Application Ser. No. 62/649,294, entitled DATA STRIPPING METHOD TO INTERROGATE PATIENT RECORDS AND CREATE ANONYMIZED RECORD;

U.S. Provisional Patent Application Ser. No. 62/649,300, entitled SURGICAL HUB SITUATIONAL AWARENESS;

U.S. Provisional Patent Application Ser. No. 62/649,309, entitled SURGICAL HUB SPATIAL AWARENESS TO DETERMINE DEVICES IN OPERATING THEATER;

U.S. Provisional Patent Application Ser. No. 62/649,310, entitled COMPUTER IMPLEMENTED INTERACTIVE SURGICAL SYSTEMS;

U.S. Provisional Patent Application Ser. No. 62/649,291, entitled USE OF LASER LIGHT AND RED-GREEN-BLUE COLORATION TO DETERMINE PROPERTIES OF BACK SCATTERED LIGHT;

U.S. Provisional Patent Application Ser. No. 62/649,296, entitled ADAPTIVE CONTROL PROGRAM UPDATES FOR SURGICAL DEVICES;

U.S. Provisional Patent Application Ser. No. 62/649,333, entitled CLOUD-BASED MEDICAL ANALYTICS FOR CUSTOMIZATION AND RECOMMENDATIONS TO A USER;

U.S. Provisional Patent Application Ser. No. 62/649,327, entitled CLOUD-BASED MEDICAL ANALYTICS FOR SECURITY AND AUTHENTICATION TRENDS AND REACTIVE MEASURES;

U.S. Provisional Patent Application Ser. No. 62/649,315, entitled DATA HANDLING AND PRIORITIZATION IN A CLOUD ANALYTICS NETWORK;

U.S. Provisional Patent Application Ser. No. 62/649,313, entitled CLOUD INTERFACE FOR COUPLED SURGICAL DEVICES;

U.S. Provisional Patent Application Ser. No. 62/649,320, entitled DRIVE ARRANGEMENTS FOR ROBOT-ASSISTED SURGICAL PLATFORMS;

U.S. Provisional Patent Application Ser. No. 62/649,307, entitled AUTOMATIC TOOL ADJUSTMENTS FOR ROBOT-ASSISTED SURGICAL PLATFORMS; and U.S. Provisional Patent Application Ser. No. 62/649,323, entitled SENSING ARRANGEMENTS FOR ROBOT-ASSISTED SURGICAL PLATFORMS.

Applicant of the present application owns the following U.S. patent applications, filed on Mar. 29, 2018, each of which is herein incorporated by reference in its entirety:

U.S. patent application Ser. No. 15/940,641, entitled INTERACTIVE SURGICAL SYSTEMS WITH ENCRYPTED COMMUNICATION CAPABILITIES;

U.S. patent application Ser. No. 15/940,648, entitled INTERACTIVE SURGICAL SYSTEMS WITH CONDITION HANDLING OF DEVICES AND DATA CAPABILITIES;

U.S. patent application Ser. No. 15/940,656, entitled SURGICAL HUB COORDINATION OF CONTROL AND COMMUNICATION OF OPERATING ROOM DEVICES;

U.S. patent application Ser. No. 15/940,666, entitled SPATIAL AWARENESS OF SURGICAL HUBS IN OPERATING ROOMS;

U.S. patent application Ser. No. 15/940,670, entitled COOPERATIVE UTILIZATION OF DATA DERIVED FROM SECONDARY SOURCES BY INTELLIGENT SURGICAL HUBS;

U.S. patent application Ser. No. 15/940,677, entitled SURGICAL HUB CONTROL ARRANGEMENTS;

U.S. patent application Ser. No. 15/940,632, entitled DATA STRIPPING METHOD TO INTERROGATE PATIENT RECORDS AND CREATE ANONYMIZED RECORD;

U.S. patent application Ser. No. 15/940,640, entitled COMMUNICATION HUB AND STORAGE DEVICE FOR STORING PARAMETERS AND STATUS OF A SURGICAL DEVICE TO BE SHARED WITH CLOUD BASED ANALYTICS SYSTEMS;

U.S. patent application Ser. No. 15/940,645, entitled SELF DESCRIBING DATA PACKETS GENERATED AT AN ISSUING INSTRUMENT;

U.S. patent application Ser. No. 15/940,649, entitled DATA PAIRING TO INTERCONNECT A DEVICE MEASURED PARAMETER WITH AN OUTCOME;

U.S. patent application Ser. No. 15/940,654, entitled SURGICAL HUB SITUATIONAL AWARENESS;

U.S. patent application Ser. No. 15/940,663, entitled SURGICAL SYSTEM DISTRIBUTED PROCESSING;

U.S. patent application Ser. No. 15/940,668, entitled AGGREGATION AND REPORTING OF SURGICAL HUB DATA;

U.S. patent application Ser. No. 15/940,671, entitled SURGICAL HUB SPATIAL AWARENESS TO DETERMINE DEVICES IN OPERATING THEATER;

U.S. patent application Ser. No. 15/940,686, entitled DISPLAY OF ALIGNMENT OF STAPLE CARTRIDGE TO PRIOR LINEAR STAPLE LINE;

U.S. patent application Ser. No. 15/940,700, entitled STERILE FIELD INTERACTIVE CONTROL DISPLAYS;

U.S. patent application Ser. No. 15/940,629, entitled COMPUTER IMPLEMENTED INTERACTIVE SURGICAL SYSTEMS;

U.S. patent application Ser. No. 15/940,704, entitled USE OF LASER LIGHT AND RED-GREEN-BLUE COLORATION TO DETERMINE PROPERTIES OF BACK SCATTERED LIGHT;

U.S. patent application Ser. No. 15/940,722, entitled CHARACTERIZATION OF TISSUE IRREGULARITIES THROUGH THE USE OF MONO-CHROMATIC LIGHT REFRACTIVITY; and U.S. patent application Ser. No. 15/940,742, entitled DUAL CMOS ARRAY IMAGING.

Applicant of the present application owns the following U.S. patent applications, filed on Mar. 29, 2018, each of which is herein incorporated by reference in its entirety:

U.S. patent application Ser. No. 15/940,636, entitled ADAPTIVE CONTROL PROGRAM UPDATES FOR SURGICAL DEVICES;

U.S. patent application Ser. No. 15/940,653, entitled ADAPTIVE CONTROL PROGRAM UPDATES FOR SURGICAL HUBS;

U.S. patent application Ser. No. 15/940,660, entitled CLOUD-BASED MEDICAL ANALYTICS FOR CUSTOMIZATION AND RECOMMENDATIONS TO A USER;

U.S. patent application Ser. No. 15/940,679, entitled CLOUD-BASED MEDICAL ANALYTICS FOR LINKING OF LOCAL USAGE TRENDS WITH THE RESOURCE ACQUISITION BEHAVIORS OF LARGER DATA SET;

U.S. patent application Ser. No. 15/940,694, entitled CLOUD-BASED MEDICAL ANALYTICS FOR MEDICAL FACILITY SEGMENTED INDIVIDUALIZATION OF INSTRUMENT FUNCTION;

U.S. patent application Ser. No. 15/940,634, entitled CLOUD-BASED MEDICAL ANALYTICS FOR SECURITY AND AUTHENTICATION TRENDS AND REACTIVE MEASURES;

U.S. patent application Ser. No. 15/940,706, entitled DATA HANDLING AND PRIORITIZATION IN A CLOUD ANALYTICS NETWORK; and U.S. patent application Ser. No. 15/940,675, entitled CLOUD INTERFACE FOR COUPLED SURGICAL DEVICES.

Applicant of the present application owns the following U.S. patent applications, filed on Mar. 29, 2018, each of which is herein incorporated by reference in its entirety:

U.S. patent application Ser. No. 15/940,627, entitled DRIVE ARRANGEMENTS FOR ROBOT-ASSISTED SURGICAL PLATFORMS;

U.S. patent application Ser. No. 15/940,637, entitled COMMUNICATION ARRANGEMENTS FOR ROBOT-ASSISTED SURGICAL PLATFORMS;

U.S. patent application Ser. No. 15/940,642, entitled CONTROLS FOR ROBOT-ASSISTED SURGICAL PLATFORMS;

U.S. patent application Ser. No. 15/940,676, entitled AUTOMATIC TOOL ADJUSTMENTS FOR ROBOT-ASSISTED SURGICAL PLATFORMS;

U.S. patent application Ser. No. 15/940,680, entitled CONTROLLERS FOR ROBOT-ASSISTED SURGICAL PLATFORMS;

U.S. patent application Ser. No. 15/940,683, entitled COOPERATIVE SURGICAL ACTIONS FOR ROBOT-ASSISTED SURGICAL PLATFORMS;

U.S. patent application Ser. No. 15/940,690, entitled DISPLAY ARRANGEMENTS FOR ROBOT-ASSISTED SURGICAL PLATFORMS; and U.S. patent application Ser. No. 15/940,711, entitled SENSING ARRANGEMENTS FOR ROBOT-ASSISTED SURGICAL PLATFORMS.

Applicant of the present application owns the following U.S. Provisional Patent Applications, filed on Mar. 30, 2018, each of which is herein incorporated by reference in its entirety:

U.S. Provisional Patent Application Ser. No. 62/650,887, entitled SURGICAL SYSTEMS WITH OPTIMIZED SENSING CAPABILITIES;

U.S. Provisional Patent Application Ser. No. 62/650,877, entitled SURGICAL SMOKE EVACUATION SENSING AND CONTROLS;

U.S. Provisional Patent Application Ser. No. 62/650,882, entitled SMOKE EVACUATION MODULE FOR INTERACTIVE SURGICAL PLATFORM; and U.S. Provisional Patent Application Ser. No. 62/650,898, entitled CAPACITIVE COUPLED RETURN PATH PAD WITH SEPARABLE ARRAY ELEMENTS.

Applicant of the present application owns the following U.S. Provisional Patent Application, filed on Apr. 19, 2018, which is herein incorporated by reference in its entirety:

U.S. Provisional Patent Application Ser. No. 62/659,900, entitled METHOD OF HUB COMMUNICATION.

Numerous specific details are set forth to provide a thorough understanding of the overall structure, function, manufacture, and use of the embodiments as described in the specification and illustrated in the accompanying drawings. Well-known operations, components, and elements have not been described in detail so as not to obscure the embodiments described in the specification. The reader will understand that the embodiments described and illustrated herein are non-limiting examples, and thus it can be appreciated that the specific structural and functional details disclosed herein may be representative and illustrative. Variations and changes thereto may be made without departing from the scope of the claims.

The terms "comprise" (and any form of comprise, such as "comprises" and "comprising"), "have" (and any form of have, such as "has" and "having"), "include" (and any form of include, such as "includes" and "including"), and "contain" (and any form of contain, such as "contains" and "containing") are open-ended linking verbs. As a result, a surgical system, device, or apparatus that "comprises," "has," "includes", or "contains" one or more elements possesses those one or more elements, but is not limited to possessing only those one or more elements. Likewise, an element of a system, device, or apparatus that "comprises," "has," "includes", or "contains" one or more features possesses those one or more features, but is not limited to possessing only those one or more features.

The terms "proximal" and "distal" are used herein with reference to a clinician manipulating the handle portion of the surgical instrument. The term "proximal" refers to the portion closest to the clinician and the term "distal" refers to the portion located away from the clinician. It will be further appreciated that, for convenience and clarity, spatial terms such as "vertical", "horizontal", "up", and "down" may be used herein with respect to the drawings. However, surgical instruments are used in many orientations and positions, and these terms are not intended to be limiting and/or absolute.

Various exemplary devices and methods are provided for performing laparoscopic and minimally invasive surgical procedures. However, the reader will readily appreciate that the various methods and devices disclosed herein can be used in numerous surgical procedures and applications including, for example, in connection with open surgical procedures. As the present Detailed Description proceeds, the reader will further appreciate that the various instruments disclosed herein can be inserted into a body in any way, such as through a natural orifice, through an incision or puncture hole formed in tissue, etc. The working portions or end effector portions of the instruments can be inserted directly into a patient's body or can be inserted through an access device that has a working channel through which the end effector and elongate shaft of a surgical instrument can be advanced.

A surgical instrument, such as a grasper, for example, can comprise a handle, a shaft extending from the handle, and an end effector extending from the shaft. In various instances, the end effector comprises a first jaw and a second jaw, wherein one or both of the jaws are movable relative to the other to grasp the tissue of a patient. That said, an end effector of a surgical instrument can comprise any suitable arrangement and can perform any suitable function. For instance, an end effector can comprise first and second jaws configured to dissect or separate the tissue of a patient. Also, for instance, an end effector can be configured to suture and/or clip the tissue of a patient. In various instances, the end effector and/or shaft of the surgical instrument are configured to be inserted into a patient through a trocar, or cannula, and can have any suitable diameter, such as approximately 5 mm, 8 mm, and/or 12 mm, for example. U.S. patent application Ser. No. 11/013,924, entitled TROCAR SEAL ASSEMBLY, now U.S. Pat. No. 7,371,227, is incorporated by reference in its entirety. The shaft can define a longitudinal axis and at least a portion of the end effector can be rotatable about the longitudinal axis. Moreover, the surgical instrument can further comprise an articulation joint which can permit at least a portion of the end effector to be articulated relative to the shaft. In use, a clinician can rotate and/or articulate the end effector in order to maneuver the end effector within the patient.

Figure 1:
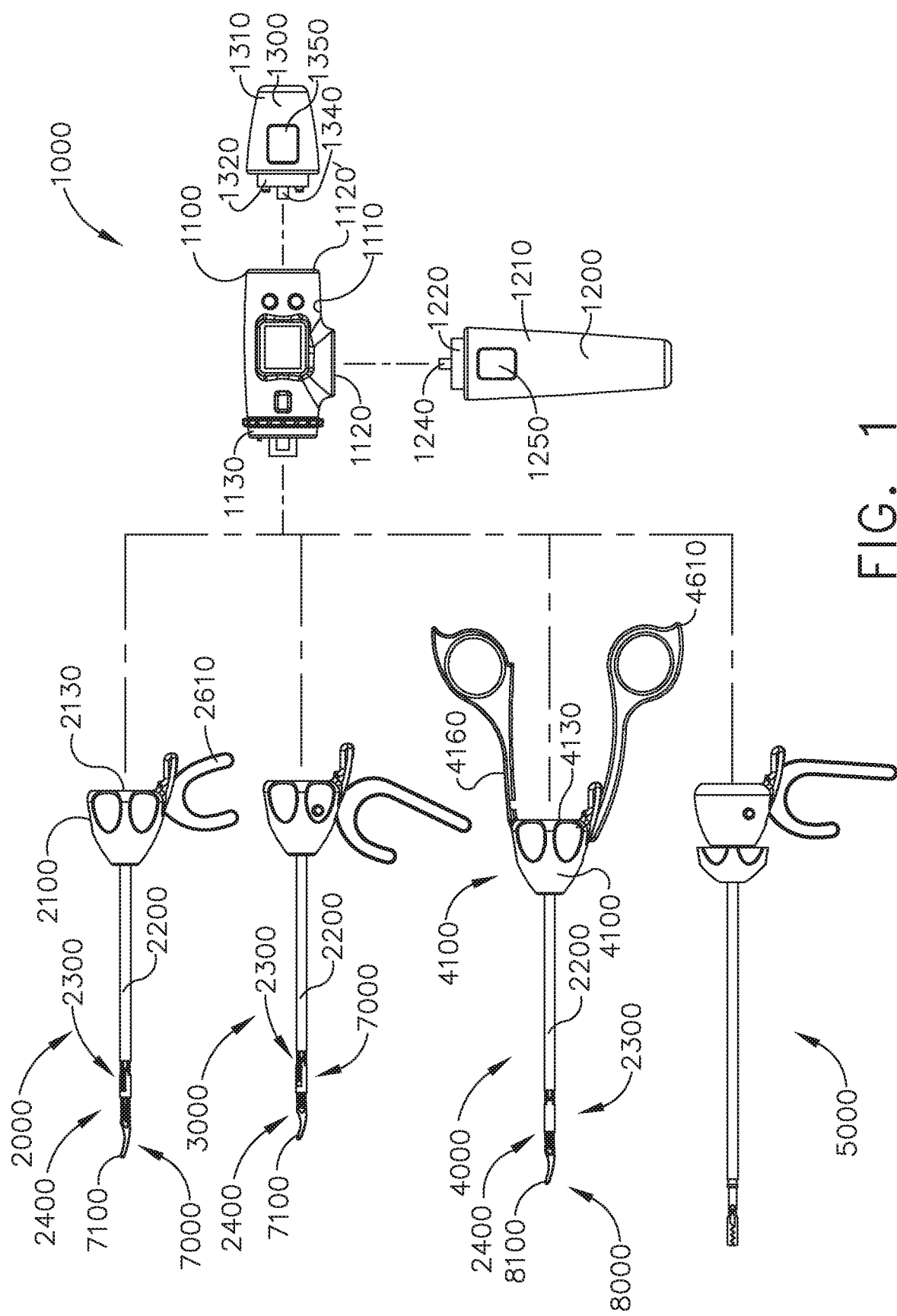
FIG. 1 illustrates a surgical system comprising a handle and several shaft assemblies—each of which are selectively attachable to the handle in accordance with at least one embodiment.
Figure 2:
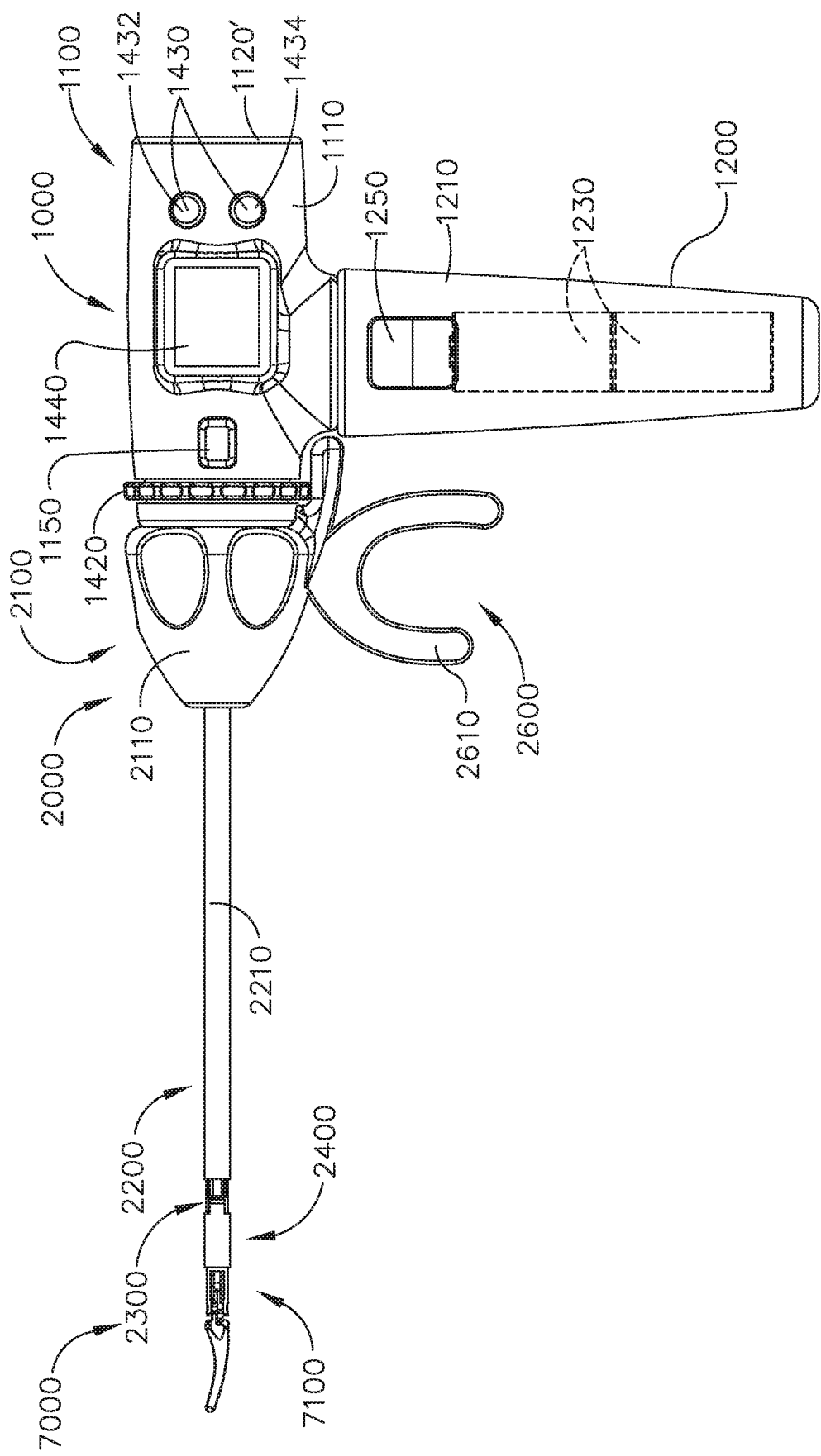
FIG. 2 is an elevational view of the handle and one of the shaft assemblies of the surgical system of FIG. 1.
Figure 3:
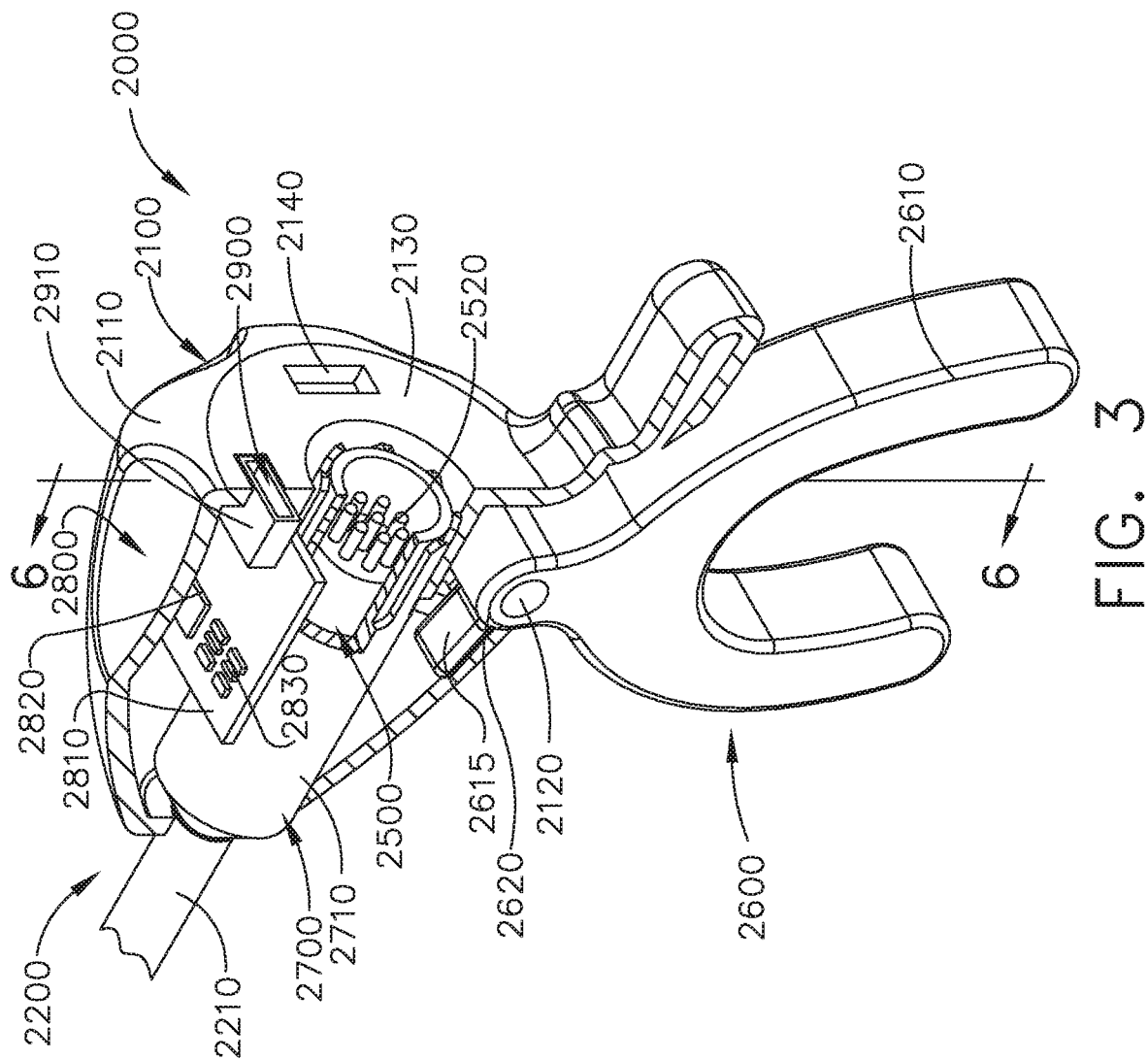
FIG. 3 is a partial cross-sectional perspective view of the shaft assembly of FIG. 2.
Figure 4:
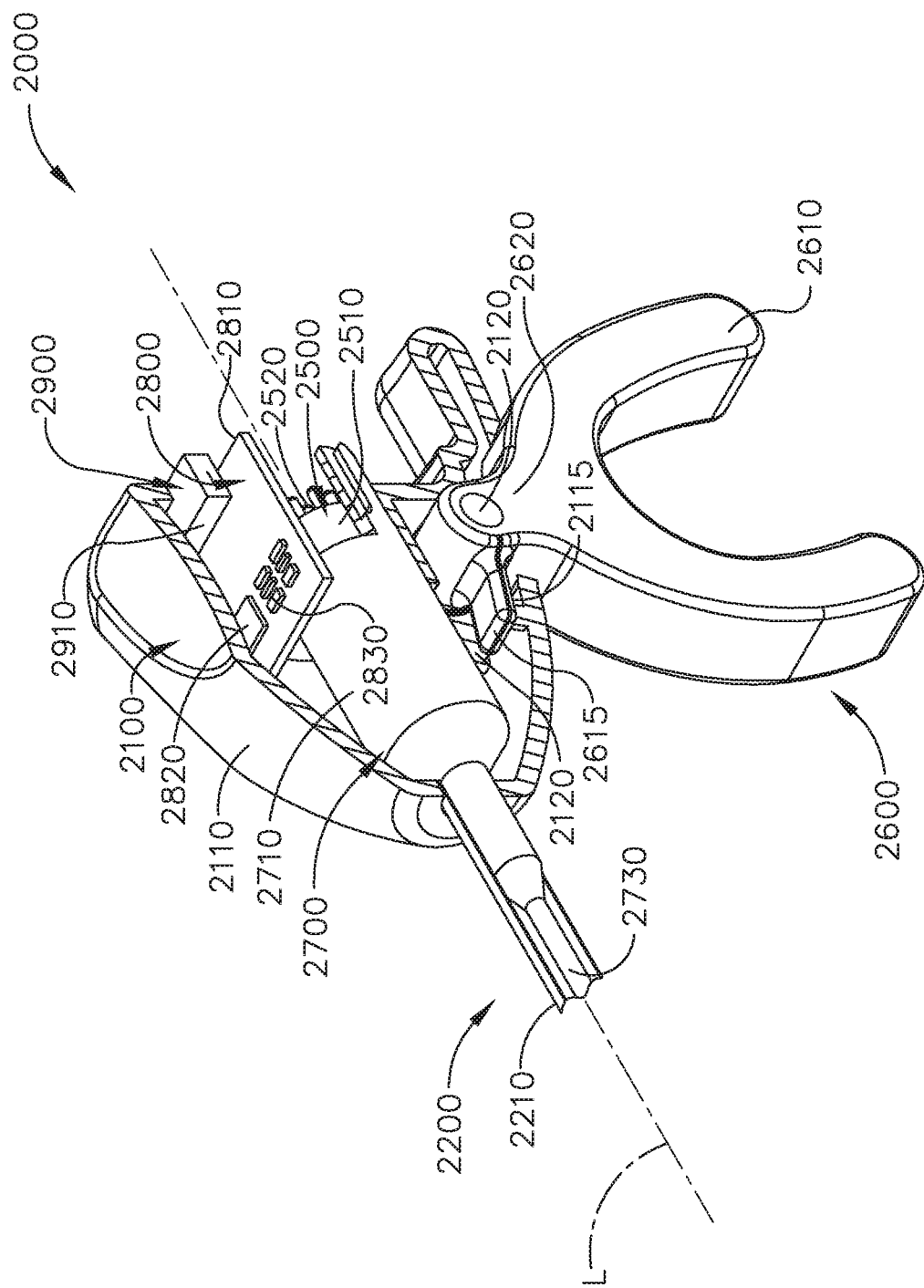
FIG. 4 is another partial cross-sectional perspective view of the shaft assembly of FIG. 2.
Figure 45:
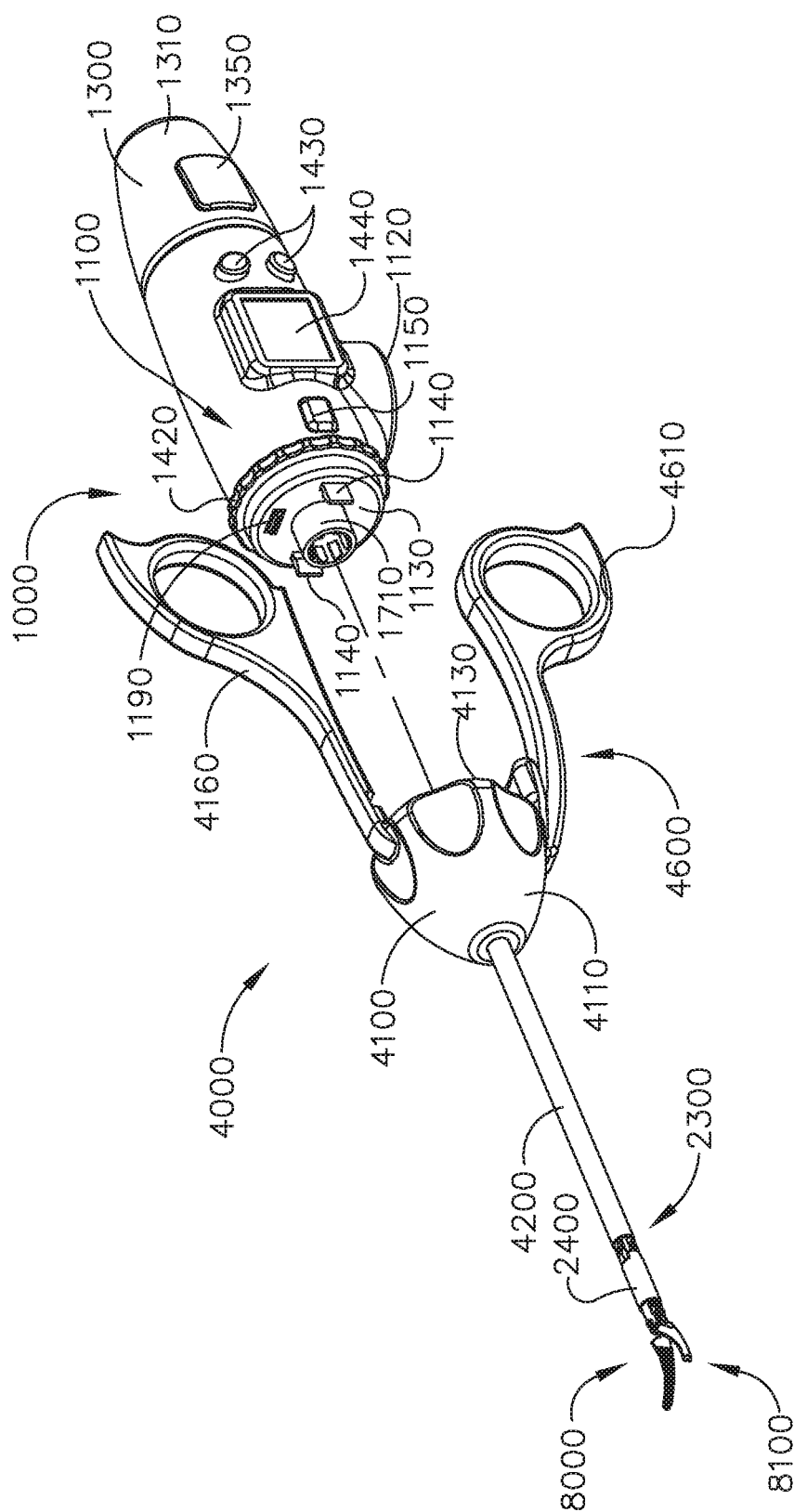
FIG. 45 is a perspective view of the handle drive module of FIG. 7 and one of the shaft assemblies of the surgical system of FIG. 1.
Figure 46:
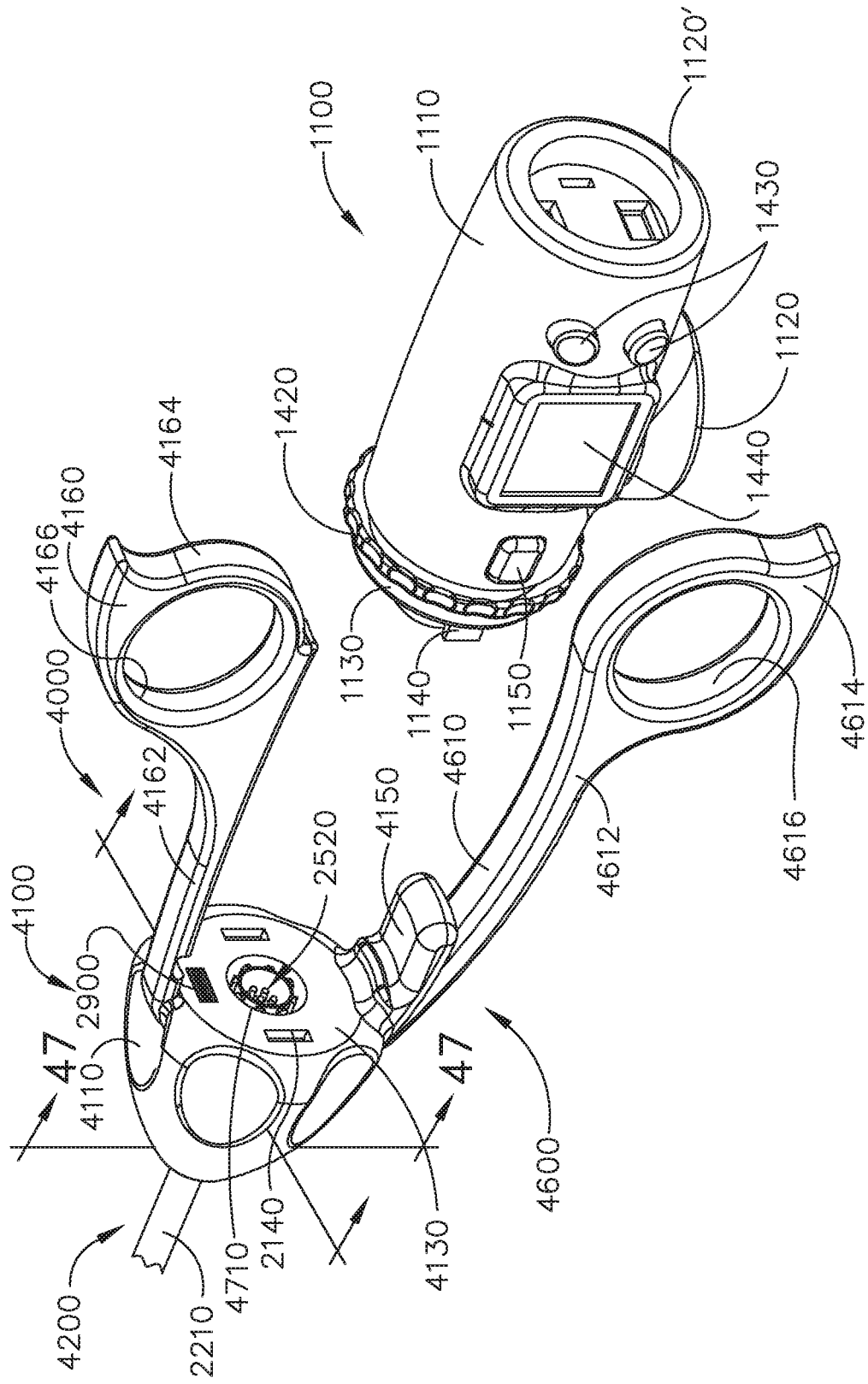
FIG. 46 is another perspective view of the handle drive module of FIG. 7 and the shaft assembly of FIG. 45.

A surgical instrument system is depicted in FIG. 1. The surgical instrument system comprises a handle assembly 1000 which is selectively usable with a shaft assembly 2000, a shaft assembly 3000, a shaft assembly 4000, a shaft assembly 5000, and/or any other suitable shaft assembly. The shaft assembly 2000 is attached to the handle assembly 1000 in FIG. 2 and the shaft assembly 4000 is attached to the handle assembly 1000 in FIG. 45. The shaft assembly 2000 comprises a proximal portion 2100, an elongate shaft 2200 extending from the proximal portion 2100, a distal attachment portion 2400, and an articulation joint 2300 rotatably connecting the distal attachment portion 2400 to the elongate shaft 2200. The shaft assembly 2000 further comprises a replaceable end effector assembly 7000 attached to the distal attachment portion 2400. The replaceable end effector assembly 7000 comprises a jaw assembly 7100 configured to be opened and closed to clamp and/or manipulate the tissue of a patient. In use, the end effector assembly 7000 can be articulated about the articulation joint 2300 and/or rotated relative to the distal attachment portion 2400 about a longitudinal axis to better position the jaw assembly 7100 within the patient, as described in greater detail further below.

Referring again to FIG. 1, the handle assembly 1000 comprises, among other things, a drive module 1100. As described in greater detail below, the drive module 1100 comprises a distal mounting interface which permits a clinician to selectively attach one of the shaft assemblies 2000, 3000, 4000, and 5000, for example, to the drive module 1100. Thus, each of the shaft assemblies 2000, 3000, 4000, and 5000 comprises an identical, or an at least similar, proximal mounting interface which is configured to engage the distal mounting interface of the drive module 1100. As also described in greater detail below, the mounting interface of the drive module 1100 mechanically secures and electrically couples the selected shaft assembly to the drive module 1100. The drive module 1100 further comprises at least one electric motor, one or more controls and/or displays, and a controller configured to operate the electric motor—the rotational output of which is transmitted to a drive system of the shaft assembly attached to the drive module 1100. Moreover, the drive module 1100 is usable with one ore more power modules, such as power modules 1200 and 1300, for example, which are operably attachable to the drive module 1100 to supply power thereto.

Further to the above, referring again to FIGS. 1 and 2, the handle drive module 1100 comprises a housing 1110, a first module connector 1120, and a second module connector 1120'. The power module 1200 comprises a housing 1210, a connector 1220, one or more release latches 1250, and one or more batteries 1230. The connector 1220 is configured to be engaged with the first module connector 1120 of the drive module 1100 in order to attach the power module 1200 to the drive module 1100. The connector 1220 comprises one or more latches 1240 which mechanically couple and fixedly secure the housing 1210 of the power module 1200 to the housing 1110 of the drive module 1100. The latches 1240 are movable into disengaged positions when the release latches 1250 are depressed so that the power module 1200 can be detached from the drive module 1100. The connector 1220 also comprises one or more electrical contacts which place the batteries 1230, and/or an electrical circuit including the batteries 1230, in electrical communication with an electrical circuit in the drive module 1100.

Figure 47:
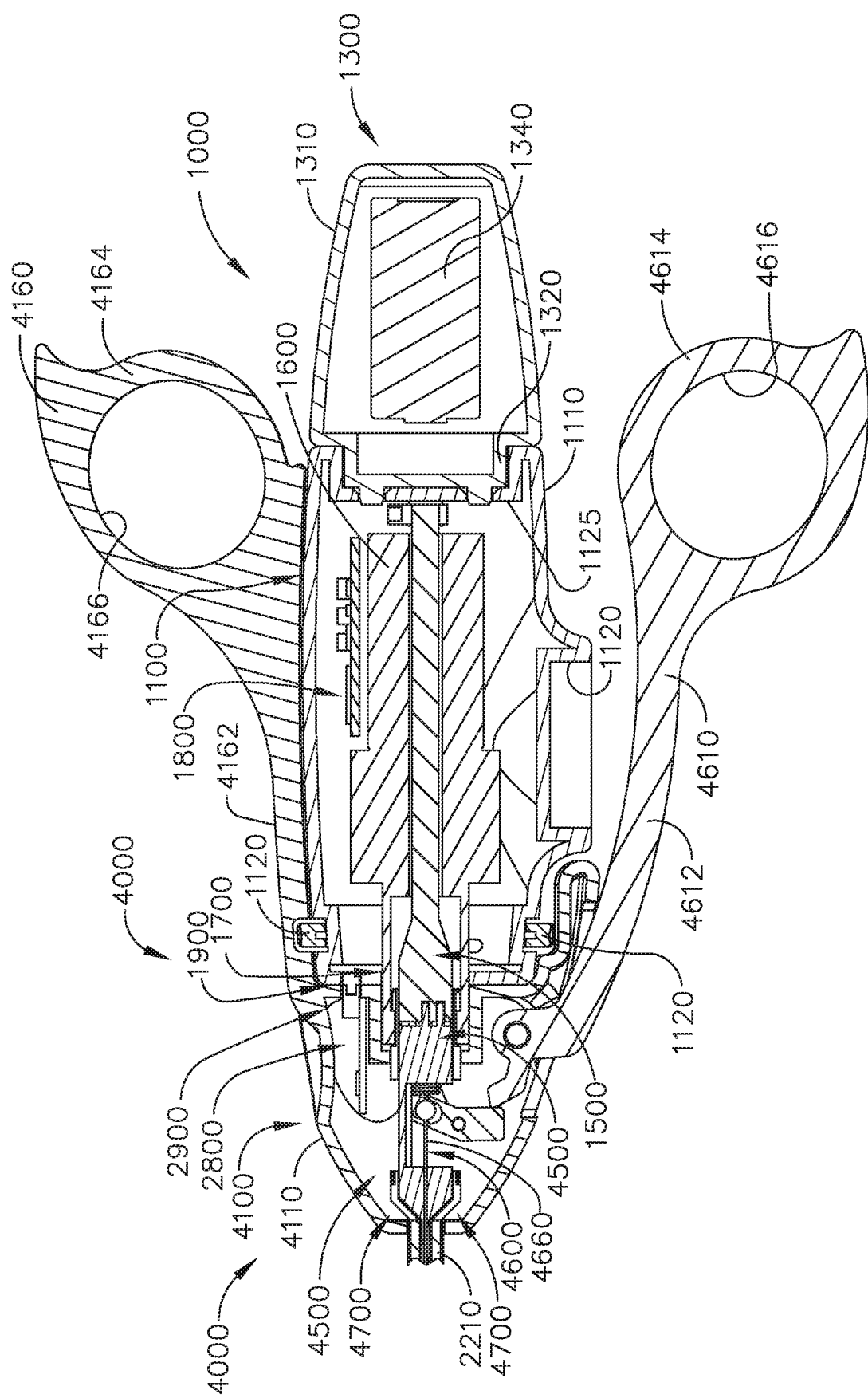
FIG. 47 is a partial cross-sectional view of the shaft assembly of FIG. 45 attached to the handle of FIG. 1.

Further to the above, referring again to FIGS. 1 and 2, the power module 1300 comprises a housing 1310, a connector 1320, one or more release latches 1350, and one or more batteries 1330 (FIG. 47). The connector 1320 is configured to be engaged with the second module connector 1120' of the drive module 1100 to attach the power module 1300 to the drive module 1100. The connector 1320 comprises one or more latches 1340 which mechanically couple and fixedly secure the housing 1310 of the power module 1300 to the housing 1110 of the drive module 1100. The latches 1340 are movable into disengaged positions when the release latches 1350 are depressed so that the power module 1300 can be detached from the drive module 1100. The connector 1320 also comprises one or more electrical contacts which place the batteries 1330 of the power module 1300, and/or an electrical power circuit including the batteries 1330, in electrical communication with an electrical power circuit in the drive module 1100.

Further to the above, the power module 1200, when attached to the drive module 1100, comprises a pistol grip which can allow a clinician to hold the handle 1000 in a manner which places the drive module 1100 on top of the clinician's hand. The power module 1300, when attached to the drive module 1100, comprises an end grip which allows a clinician to hold the handle 1000 like a wand. The power module 1200 is longer than the power module 1300, although the power modules 1200 and 1300 can comprise any suitable length. The power module 1200 has more battery cells than the power module 1300 and can suitably accommodate these additional battery cells owing to its length. In various instances, the power module 1200 can provide more power to the drive module 1100 than the power module 1300 while, in some instances, the power module 1200 can provide power for a longer period of time. In some instances, the housing 1110 of the drive module 1100 comprises keys, and/or any other suitable features, which prevent the power module 1200 from being connected to the second module connector 1120' and, similarly, prevent the power module 1300 from being connected to the first module connector 1120. Such an arrangement can assure that the longer power module 1200 is used in the pistol grip arrangement and that the shorter power module 1300 is used in the wand grip arrangement. In alternative embodiments, the power module 1200 and the power module 1300 can be selectively coupled to the drive module 1100 at either the first module connector 1120 or the second module connector 1120'. Such embodiments provide a clinician with more options to customize the handle 1000 in a manner suitable to them.

In various instances, further to the above, only one of the power modules 1200 and 1300 is coupled to the drive module 1100 at a time. In certain instances, the power module 1200 can be in the way when the shaft assembly 4000, for example, is attached to the drive module 1100. Alternatively, both of the power modules 1200 and 1300 can be operably coupled to the drive module 1100 at the same time. In such instances, the drive module 1100 can have access to power provided by both of the power modules 1200 and 1300. Moreover, a clinician can switch between a pistol grip and a wand grip when both of the power modules 1200 and 1300 are attached to the drive module 1100. Moreover, such an arrangement allows the power module 1300 to act as a counterbalance to a shaft assembly, such as shaft assemblies 2000, 3000, 4000, or 5000, for example, attached to the drive module 1100.

Figure 7:
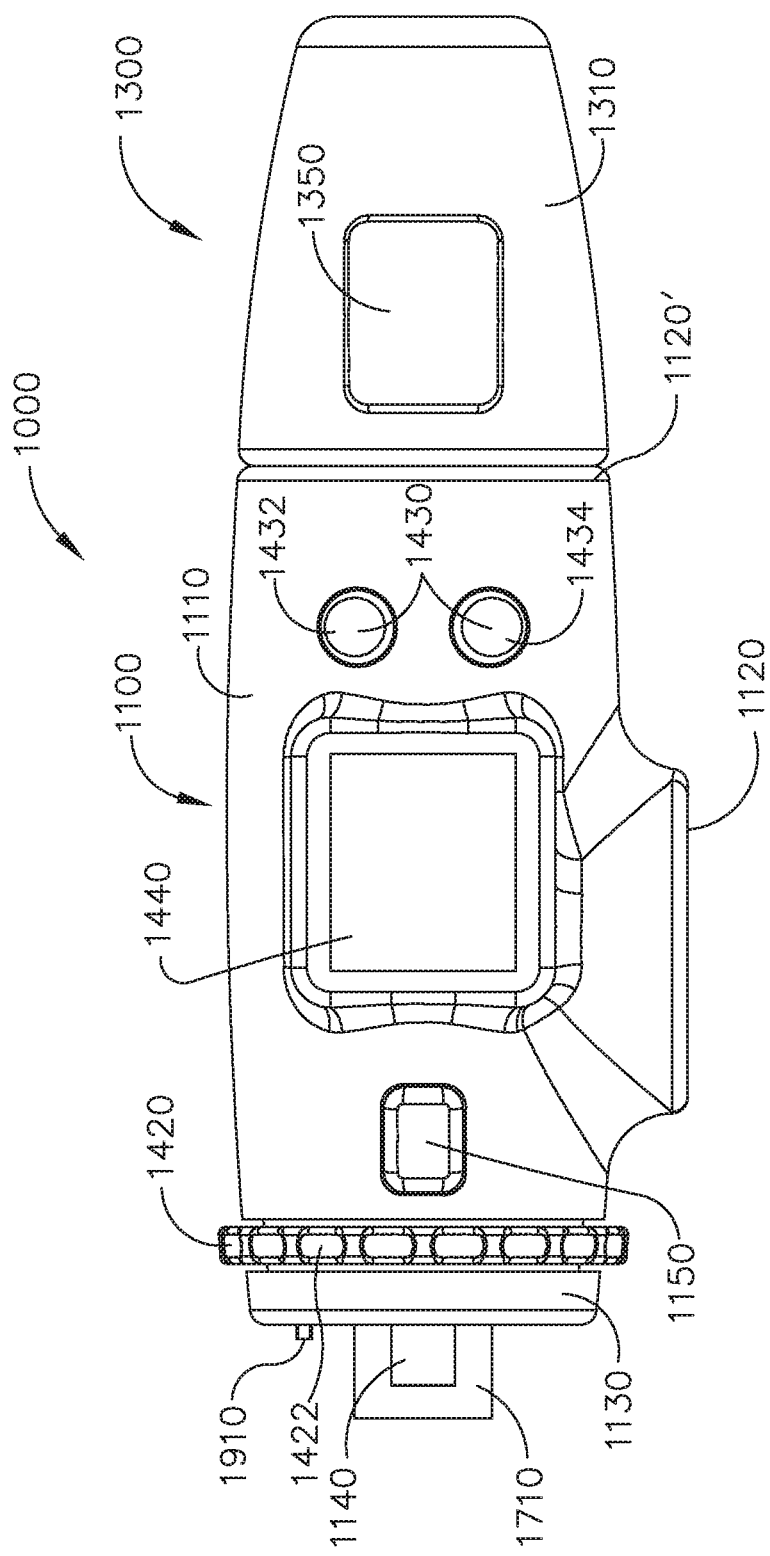
FIG. 7 is an elevational view of a drive module of the handle of FIG. 1.
Figure 8:
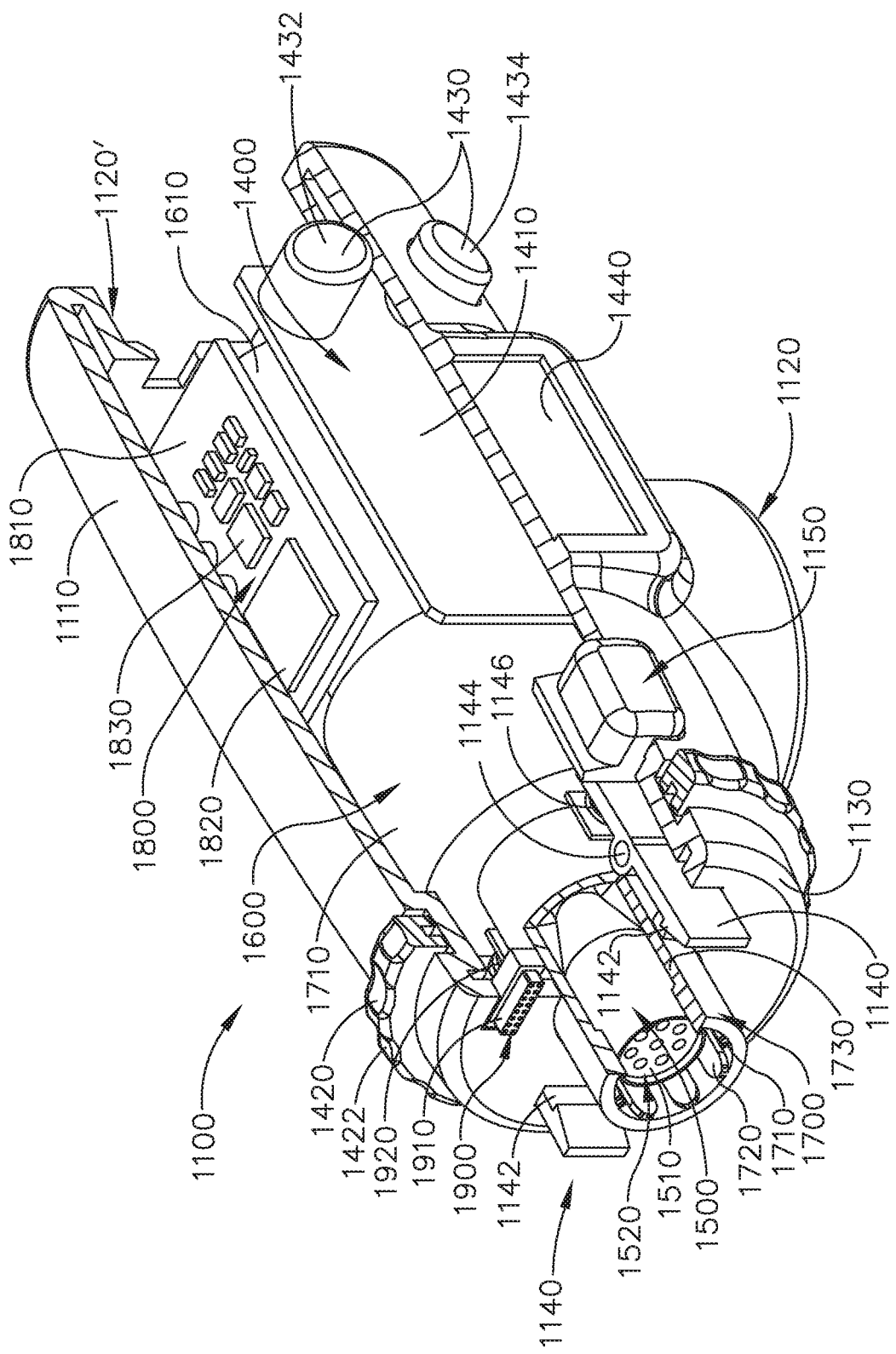
FIG. 8 is a cross-sectional perspective view of the drive module of FIG. 7.
Figure 9:
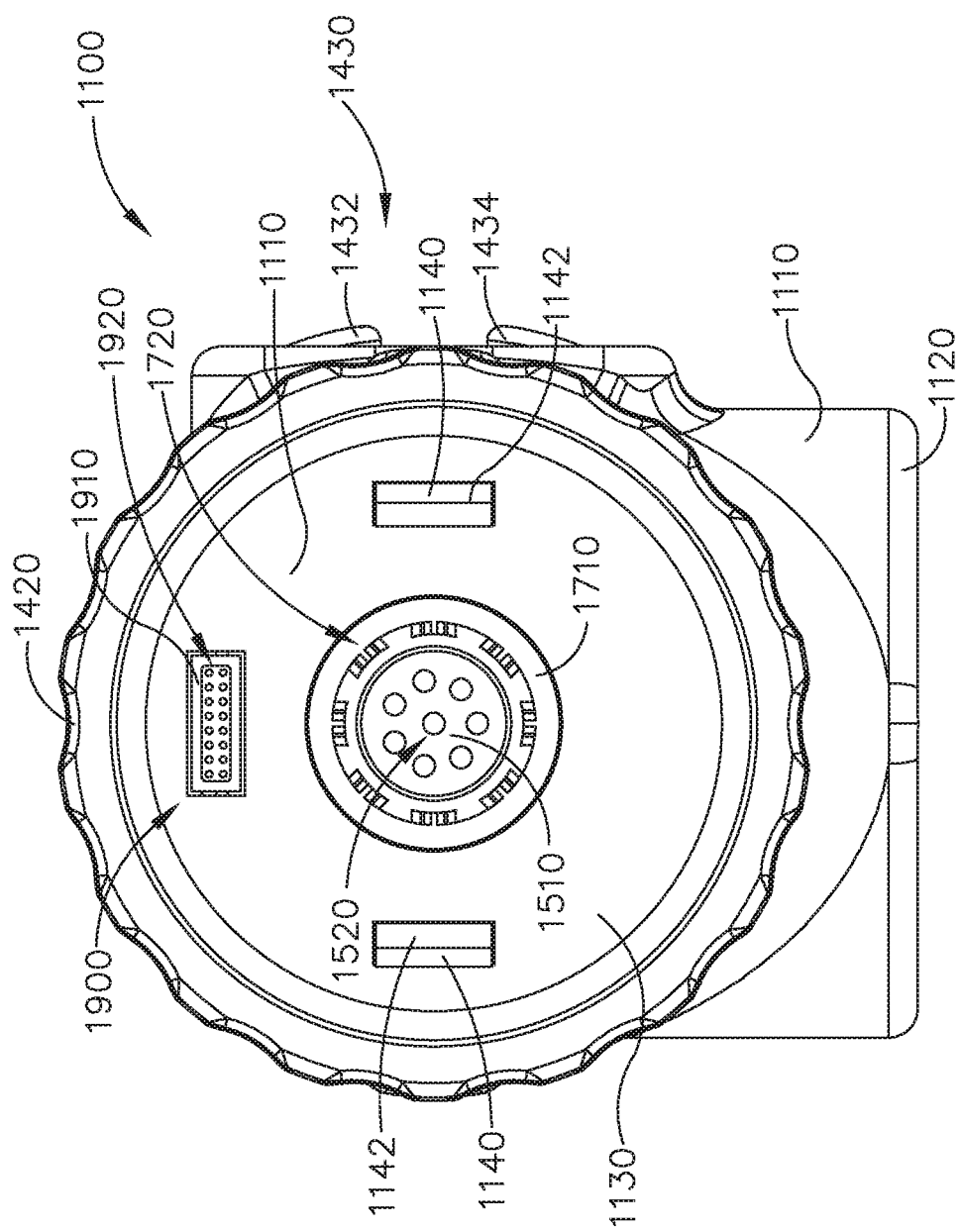
FIG. 9 is an end view of the drive module of FIG. 7.

Referring to FIGS. 7 and 8, the handle drive module 1100 further comprises a frame 1500, a motor assembly 1600, a drive system 1700 operably engaged with the motor assembly 1600, and a control system 1800. The frame 1500 comprises an elongate shaft that extends through the motor assembly 1600. The elongate shaft comprises a distal end 1510 and electrical contacts, or sockets, 1520 defined in the distal end 1510. The electrical contacts 1520 are in electrical communication with the control system 1800 of the drive module 1100 via one or more electrical circuits and are configured to convey signals and/or power between the control system 1800 and the shaft assembly, such as the shaft assembly 2000, 3000, 4000, or 5000, for example, attached to the drive module 1100. The control system 1800 comprises a printed circuit board (PCB) 1810, at least one microprocessor 1820, and at least one memory device 1830. The board 1810 can be rigid and/or flexible and can comprise any suitable number of layers. The microprocessor 1820 and the memory device 1830 are part of a control circuit defined on the board 1810 which controls the operation of the motor assembly 1600, as described in greater detail below.

Figure 12:
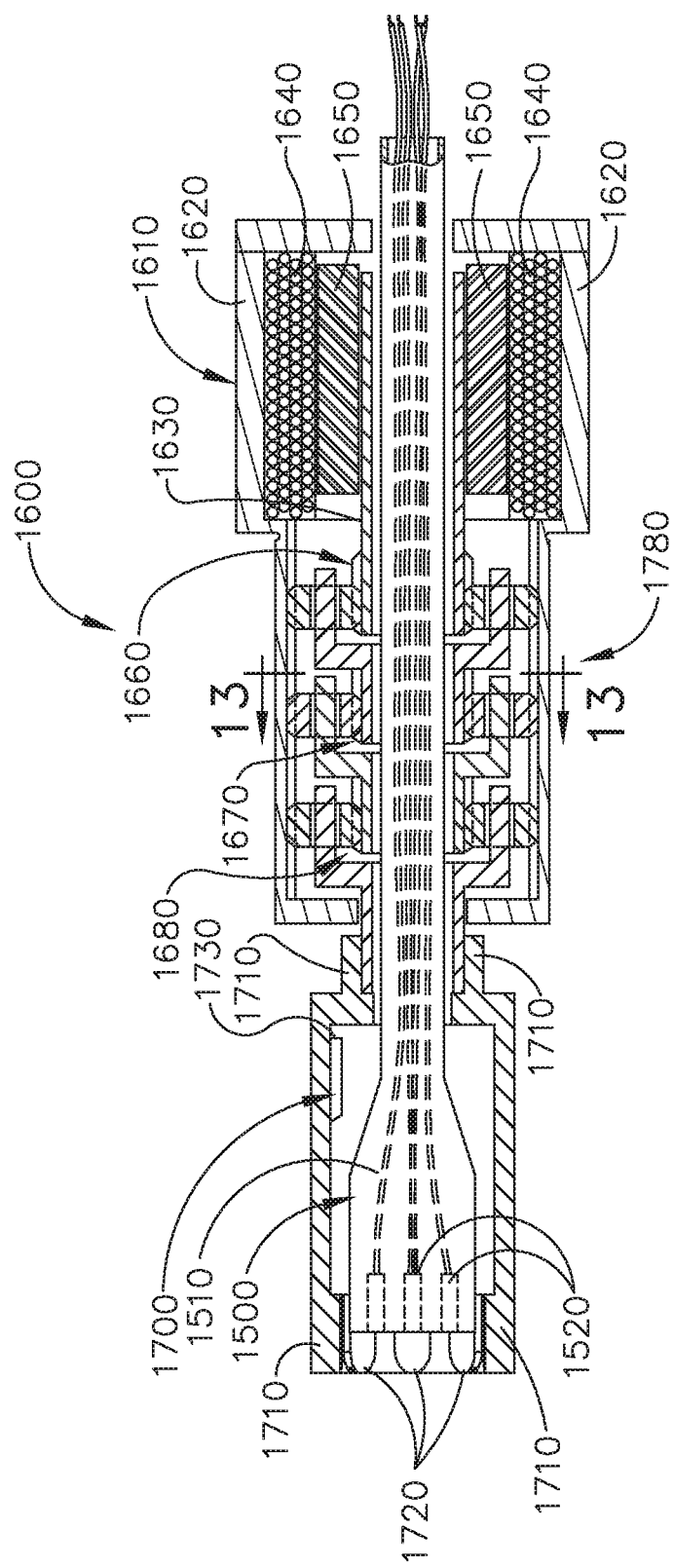
FIG. 12 is a cross-sectional perspective view of a motor and a speed reduction gear assembly of the drive module of FIG. 7.
Figure 13:
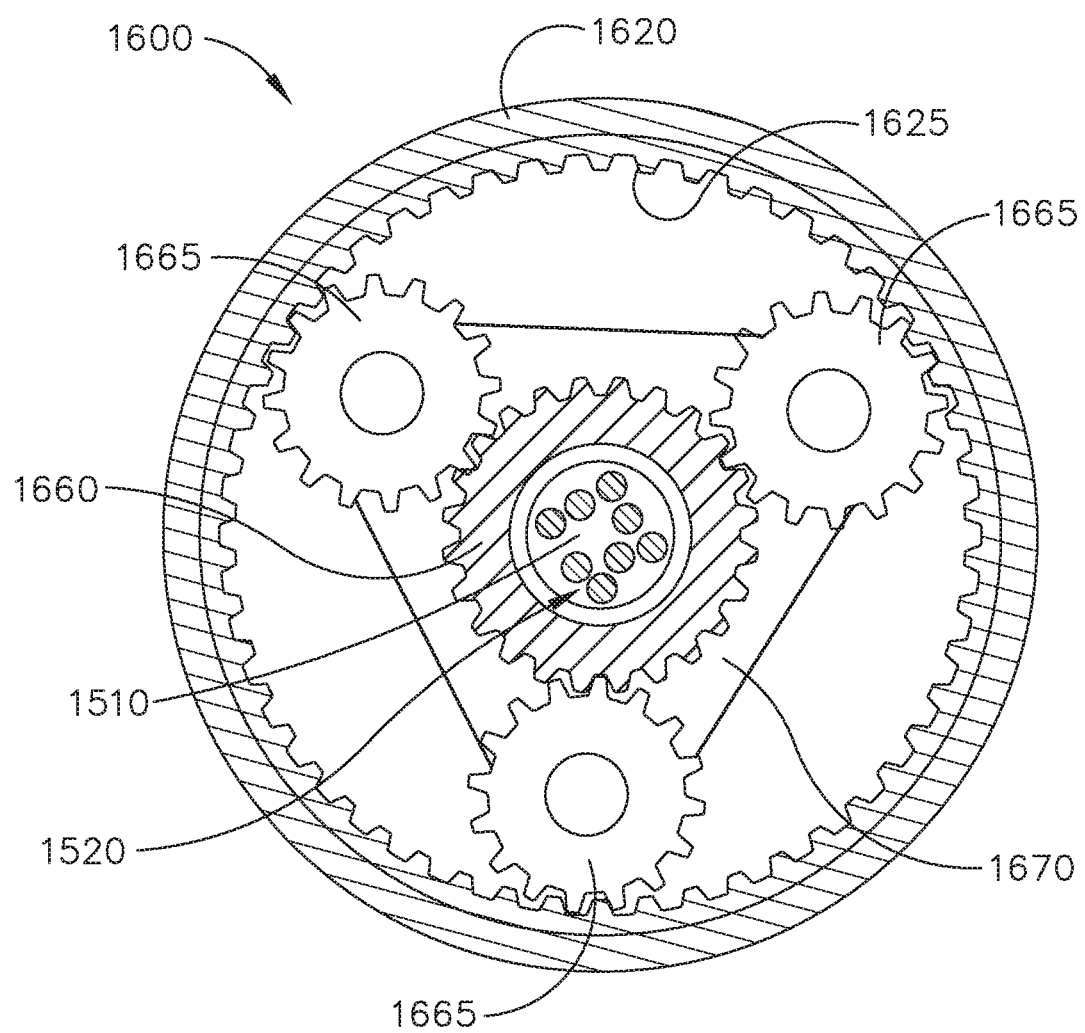
FIG. 13 is an end view of the speed reduction gear assembly of FIG. 12.
Figure 14:
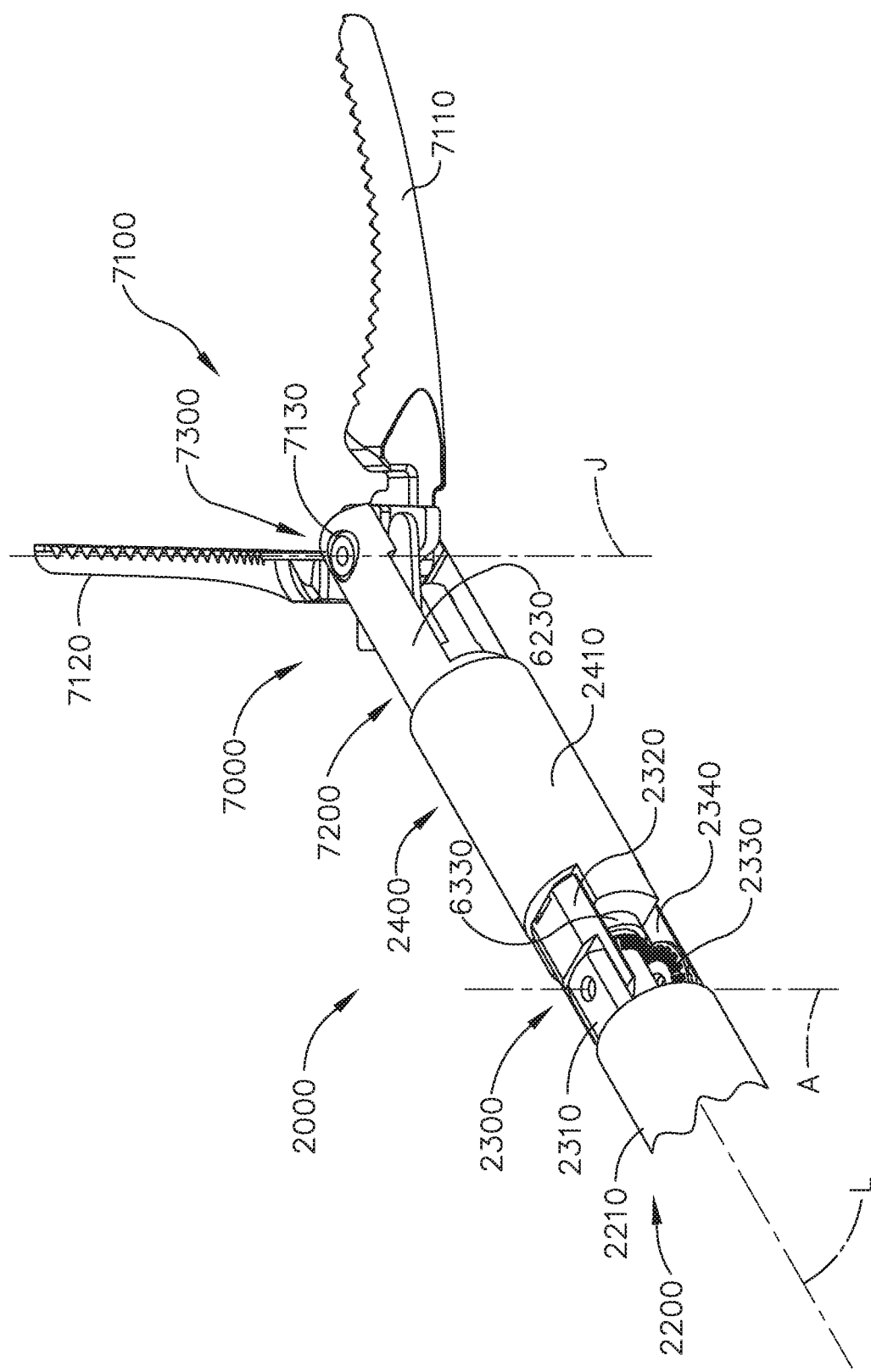
FIG. 14 is a partial perspective view of an end effector of the shaft assembly of FIG. 2 in an open configuration.

Referring to FIGS. 12 and 13, the motor assembly 1600 comprises an electric motor 1610 including a housing 1620, a drive shaft 1630, and a gear reduction system. The electric motor 1610 further comprises a stator including windings 1640 and a rotor including magnetic elements 1650. The stator windings 1640 are supported in the housing 1620 and the rotor magnetic elements 1650 are mounted to the drive shaft 1630. When the stator windings 1640 are energized with an electric current controlled by the control system 1800, the drive shaft 1630 is rotated about a longitudinal axis. The drive shaft 1630 is operably engaged with a first planetary gear system 1660 which includes a central sun gear and several planetary gears operably intermeshed with the sun gear. The sun gear of the first planetary gear system 1660 is fixedly mounted to the drive shaft 1630 such that it rotates with the drive shaft 1630. The planetary gears of the first planetary gear system 1660 are rotatably mounted to the sun gear of a second planetary gear system 1670 and, also, intermeshed with a geared or splined inner surface 1625 of the motor housing 1620. As a result of the above, the rotation of the first sun gear rotates the first planetary gears which rotate the second sun gear. Similar to the above, the second planetary gear system 1670 further comprises planetary gears 1665 (FIG. 13) which drive a third planetary gear system and, ultimately, the drive shaft 1710. The planetary gear systems 1660, 1670, and 1680 co-operate to gear down the speed applied to the drive shaft 1710 by the motor shaft 1620. Various alternative embodiments are envisioned without a speed reduction system. Such embodiments are suitable when it is desirable to drive the end effector functions quickly. Notably, the drive shaft 1630 comprises an aperture, or hollow core, extending therethrough through which wires and/or electrical circuits can extend.

The control system 1800 is in communication with the motor assembly 1600 and the electrical power circuit of the drive module 1100. The control system 1800 is configured to control the power delivered to the motor assembly 1600 from the electrical power circuit. The electrical power circuit is configured to supply a constant, or at least nearly constant, direct current (DC) voltage. In at least one instance, the electrical power circuit supplies 3 VDC to the control system 1800. The control system 1800 comprises a pulse width modulation (PWM) circuit which is configured to deliver voltage pulses to the motor assembly 1600. The duration or width of the voltage pulses, and/or the duration or width between the voltage pulses, supplied by the PWM circuit can be controlled in order to control the power applied to the motor assembly 1600. By controlling the power applied to the motor assembly 1600, the PWM circuit can control the speed of the output shaft of the motor assembly 1600. In addition to or in lieu of a PWM circuit, the control system 1800 can include a frequency modulation (FM) circuit. As discussed in greater detail below, the control system 1800 is operable in more than one operating mode and, depending on the operating mode being used, the control system 1800 can operate the motor assembly 1600 at a speed, or a range of speeds, which is determined to be appropriate for that operating mode.

Further to the above, referring again to FIGS. 7 and 8, the drive system 1700 comprises a rotatable shaft 1710 comprising a splined distal end 1720 and a longitudinal aperture 1730 defined therein. The rotatable shaft 1710 is operably mounted to the output shaft of the motor assembly 1600 such that the rotatable shaft 1710 rotates with the motor output shaft. The handle frame 1510 extends through the longitudinal aperture 1730 and rotatably supports the rotatable shaft 1710. As a result, the handle frame 1510 serves as a bearing for the rotatable shaft 1710. The handle frame 1510 and the rotatable shaft 1710 extend distally from a mounting interface 1130 of the drive module 1110 and are coupled with corresponding components on the shaft assembly 2000 when the shaft assembly 2000 is assembled to the drive module 1100. Referring primarily to FIGS. 3-6, the shaft assembly 2000 further comprises a frame 2500 and a drive system 2700. The frame 2500 comprises a longitudinal shaft 2510 extending through the shaft assembly 2000 and a plurality of electrical contacts, or pins, 2520 extending proximally from the shaft 2510. When the shaft assembly 2000 is attached to the drive module 1100, the electrical contacts 2520 on the shaft frame 2510 engage the electrical contacts 1520 on the handle frame 1510 and create electrical pathways therebetween.

Similar to the above, the drive system 2700 comprises a rotatable drive shaft 2710 which is operably coupled to the rotatable drive shaft 1710 of the handle 1000 when the shaft assembly 2000 is assembled to the drive module 1100 such that the drive shaft 2710 rotates with the drive shaft 1710. To this end, the drive shaft 2710 comprises a splined proximal end 2720 which mates with the splined distal end 1720 of the drive shaft 1710 such that the drive shafts 1710 and 2710 rotate together when the drive shaft 1710 is rotated by the motor assembly 1600. Given the nature of the splined interconnection between the drive shafts 1710 and 2710 and the electrical interconnection between the frames 1510 and 2510, the shaft assembly 2000 is assembled to the handle 1000 along a longitudinal axis; however, the operable interconnection between the drive shafts 1710 and 2710 and the electrical interconnection between the frames 1510 and 2510 can comprise any suitable configuration which can allow a shaft assembly to be assembled to the handle 1000 in any suitable manner.

Figure 10:
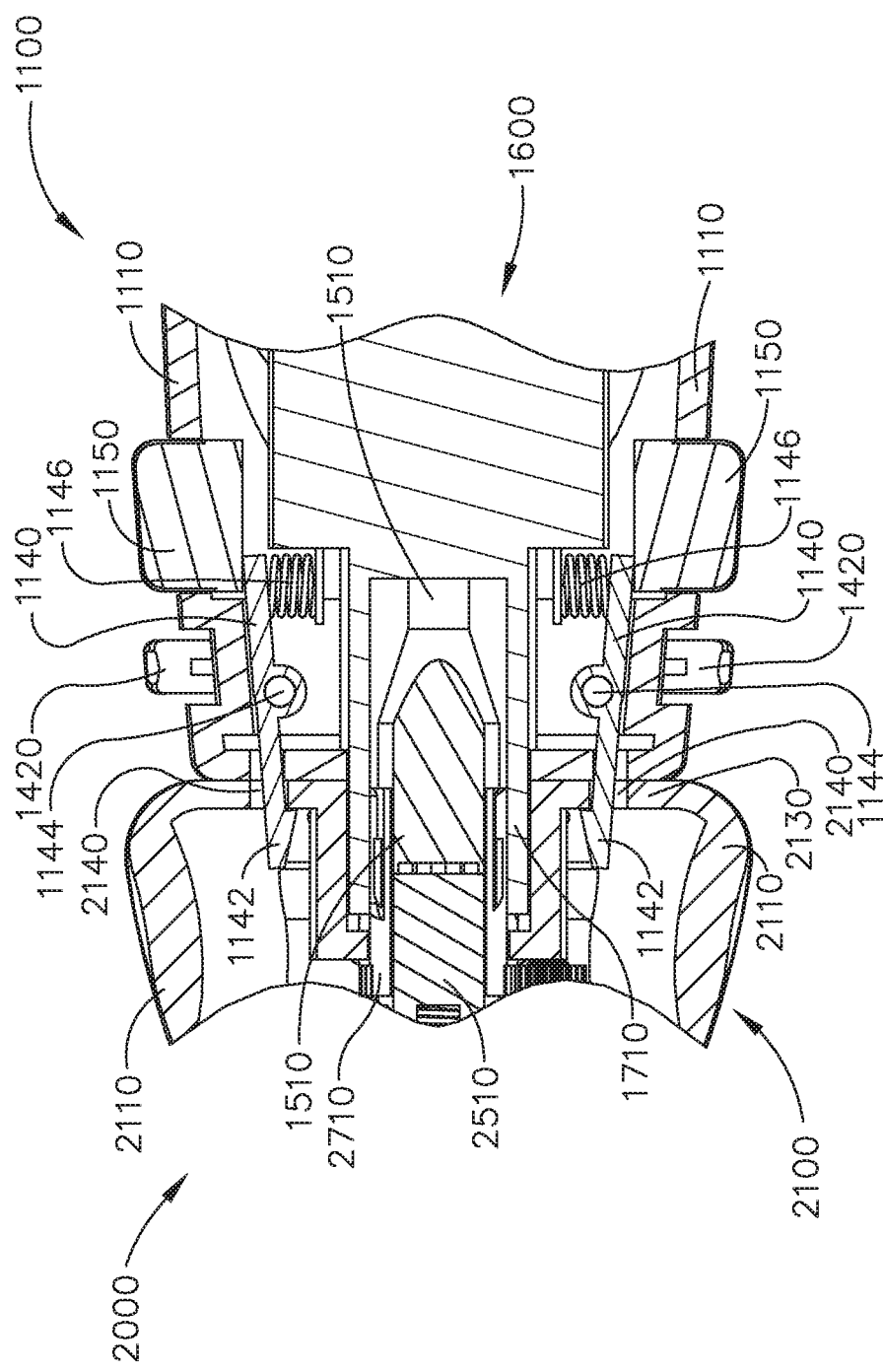
FIG. 10 is a partial cross-sectional view of the interconnection between the handle and shaft assembly of FIG. 2 in a locked configuration.
Figure 11:
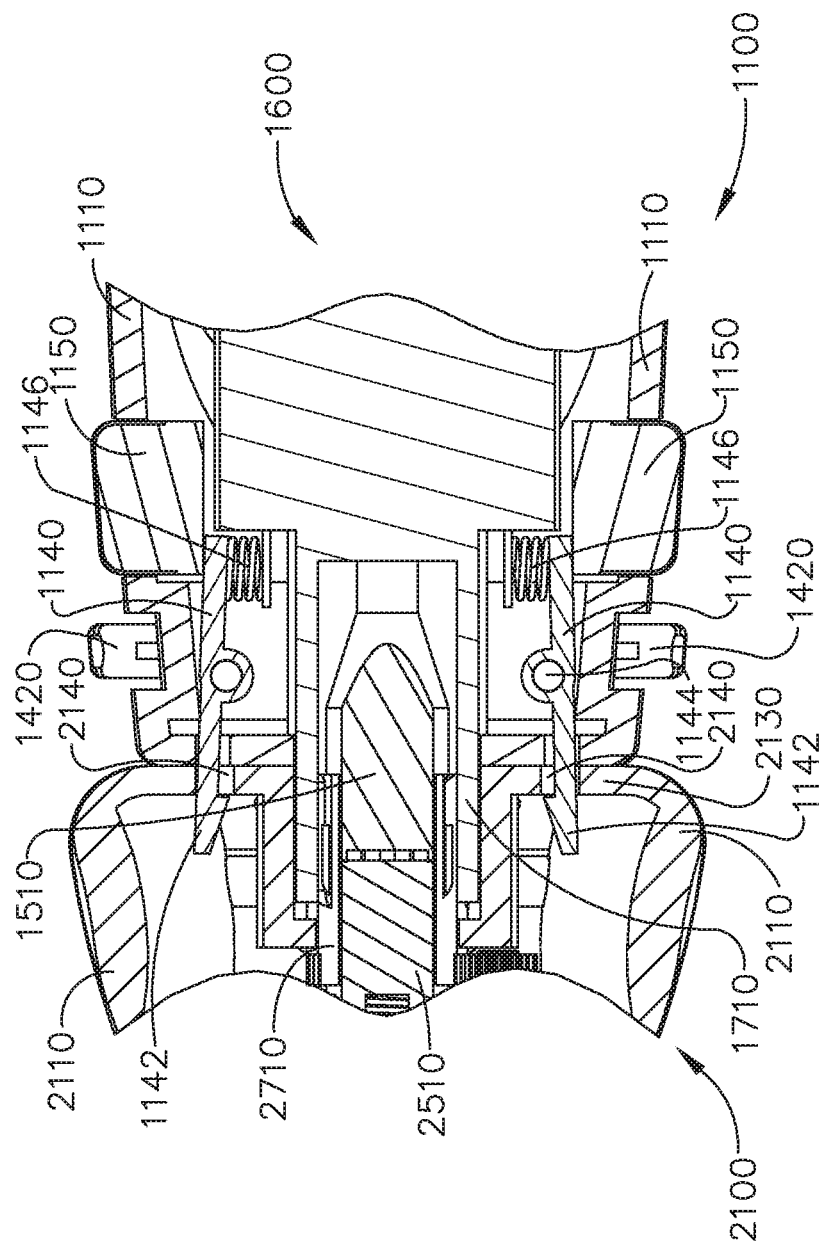
FIG. 11 is a partial cross-sectional view of the interconnection between the handle and shaft assembly of FIG. 2 in an unlocked configuration.

As discussed above, referring to FIGS. 3-8, the mounting interface 1130 of the drive module 1110 is configured to be coupled to a corresponding mounting interface on the shaft assemblies 2000, 3000, 4000, and 5000, for example. For instance, the shaft assembly 2000 comprises a mounting interface 2130 configured to be coupled to the mounting interface 1130 of the drive module 1100. More specifically, the proximal portion 2100 of the shaft assembly 2000 comprises a housing 2110 which defines the mounting interface 2130. Referring primarily to FIG. 8, the drive module 1100 comprises latches 1140 which are configured to releasably hold the mounting interface 2130 of the shaft assembly 2000 against the mounting interface 1130 of the drive module 1100. When the drive module 1100 and the shaft assembly 2000 are brought together along a longitudinal axis, as described above, the latches 1140 contact the mounting interface 2130 and rotate outwardly into an unlocked position. Referring primarily to FIGS. 8, 10, and 11, each latch 1140 comprises a lock end 1142 and a pivot portion 1144. The pivot portion 1144 of each latch 1140 is rotatably coupled to the housing 1110 of the drive module 1100 and, when the latches 1140 are rotated outwardly, as mentioned above, the latches 1140 rotate about the pivot portions 1144. Notably, each latch 1140 further comprises a biasing spring 1146 configured to bias the latches 1140 inwardly into a locked position. Each biasing spring 1146 is compressed between a latch 1140 and the housing 1110 of the drive module 1100 such that the biasing springs 1146 apply biasing forces to the latches 1140; however, such biasing forces are overcome when the latches 1140 are rotated outwardly into their unlocked positions by the shaft assembly 2000. That said, when the latches 1140 rotate outwardly after contacting the mounting interface 2130, the lock ends 1142 of the latches 1140 can enter into latch windows 2140 defined in the mounting interface 2130. Once the lock ends 1142 pass through the latch windows 2140, the springs 1146 can bias the latches 1140 back into their locked positions. Each lock end 1142 comprises a lock shoulder, or surface, which securely holds the shaft assembly 2000 to the drive module 1100.

Further to the above, the biasing springs 1146 hold the latches 1140 in their locked positions. The distal ends 1142 are sized and configured to prevent, or at least inhibit, relative longitudinal movement, i.e., translation along a longitudinal axis, between the shaft assembly 2000 and the drive module 1100 when the latches 1140 are in their locked positions. Moreover, the latches 1140 and the latch windows 1240 are sized and configured to prevent relative lateral movement, i.e., translation transverse to the longitudinal axis, between the shaft assembly 2000 and the drive module 1100. In addition, the latches 1140 and the latch windows 2140 are sized and configured to prevent the shaft assembly 2000 from rotating relative to the drive module 1100. The drive module 1100 further comprises release actuators 1150 which, when depressed by a clinician, move the latches 1140 from their locked positions into their unlocked positions. The drive module 1100 comprises a first release actuator 1150 slideably mounted in an opening defined in the first side of the handle housing 1110 and a second release actuator 1150 slideably mounted in an opening defined in a second, or opposite, side of the handle housing 1110. Although the release actuators 1150 are actuatable separately, both release actuators 1150 typically need to be depressed to completely unlock the shaft assembly 2000 from the drive module 1100 and allow the shaft assembly 2000 to be detached from the drive module 1100. That said, it is possible that the shaft assembly 2000 could be detached from the drive module 1100 by depressing only one release actuator 1150.

Once the shaft assembly 2000 has been secured to the handle 1000 and the end effector 7000, for example, has been assembled to the shaft 2000, the clinician can maneuver the handle 1000 to insert the end effector 7000 into a patient. In at least one instance, the end effector 7000 is inserted into the patient through a trocar and then manipulated in order to position the jaw assembly 7100 of the end effector assembly 7000 relative to the patient's tissue. Oftentimes, the jaw assembly 7100 must be in its closed, or clamped, configuration in order to fit through the trocar. Once through the trocar, the jaw assembly 7100 can be opened so that the patient tissue fit between the jaws of the jaw assembly 7100. At such point, the jaw assembly 7100 can be returned to its closed configuration to clamp the patient tissue between the jaws. The clamping force applied to the patient tissue by the jaw assembly 7100 is sufficient to move or otherwise manipulate the tissue during a surgical procedure. Thereafter, the jaw assembly 7100 can be re-opened to release the patient tissue from the end effector 7000. This process can be repeated until it is desirable to remove the end effector 7000 from the patient. At such point, the jaw assembly 7100 can be returned to its closed configuration and retracted through the trocar. Other surgical techniques are envisioned in which the end effector 7000 is inserted into a patient through an open incision, or without the use of the trocar. In any event, it is envisioned that the jaw assembly 7100 may have to be opened and closed several times throughout a surgical technique.

Referring again to FIGS. 3-6, the shaft assembly 2000 further comprises a clamping trigger system 2600 and a control system 2800. The clamping trigger system 2600 comprises a clamping trigger 2610 rotatably connected to the proximal housing 2110 of the shaft assembly 2000. As discussed below, the clamping trigger 2610 actuates the motor 1610 to operate the jaw drive of the end effector 7000 when the clamping trigger 2610 is actuated. The clamping trigger 2610 comprises an elongate portion which is graspable by the clinician while holding the handle 1000. The clamping trigger 2610 further comprises a mounting portion 2620 which is pivotably connected to a mounting portion 2120 of the proximal housing 2110 such that the clamping trigger 2610 is rotatable about a fixed, or an at least substantially fixed, axis. The closure trigger 2610 is rotatable between a distal position and a proximal position, wherein the proximal position of the closure trigger 2610 is closer to the pistol grip of the handle 1000 than the distal position. The closure trigger 2610 further comprises a tab 2615 extending therefrom which rotates within the proximal housing 2110. When the closure trigger 2610 is in its distal position, the tab 2615 is positioned above, but not in contact with, a switch 2115 mounted on the proximal housing 2110. The switch 2115 is part of an electrical circuit configured to detect the actuation of the closure trigger 2610 which is in an open condition the closure trigger 2610 is in its open position. When the closure trigger 2610 is moved into its proximal position, the tab 2615 comes into contact with the switch 2115 and closes the electrical circuit. In various instances, the switch 2115 can comprise a toggle switch, for example, which is mechanically switched between open and closed states when contacted by the tab 2615 of the closure trigger 2610. In certain instances, the switch 2115 can comprise a proximity sensor, for example, and/or any suitable type of sensor. In at least one instance, the switch 2115 comprises a Hall Effect sensor which can detect the amount in which the closure trigger 2610 has been rotated and, based on the amount of rotation, control the speed in which the motor 1610 is operated. In such instances, larger rotations of the closure trigger 2610 result in faster speeds of the motor 1610 while smaller rotations result in slower speeds, for example. In any event, the electrical circuit is in communication with the control system 2800 of the shaft assembly 2000, which is discussed in greater detail below.

Further to the above, the control system 2800 of the shaft assembly 2000 comprises a printed circuit board (PCB) 2810, at least one microprocessor 2820, and at least one memory device 2830. The board 2810 can be rigid and/or flexible and can comprise any suitable number of layers. The microprocessor 2820 and the memory device 2830 are part of a control circuit defined on the board 2810 which communicates with the control system 1800 of the handle 1000. The shaft assembly 2000 further comprises a signal communication system 2900 and the handle 1000 further comprises a signal communication system 1900 which are configured to convey data between the shaft control system 2800 and the handle control system 1800. The signal communication system 2900 is configured to transmit data to the signal communication system 1900 utilizing any suitable analog and/or digital components. In various instances, the communication systems 2900 and 1900 can communicate using a plurality of discrete channels which allows the input gates of the microprocessor 1820 to be directly controlled, at least in part, by the output gates of the microprocessor 2820. In some instances, the communication systems 2900 and 1900 can utilize multiplexing. In at least one such instance, the control system 2900 includes a multiplexing device that sends multiple signals on a carrier channel at the same time in the form of a single, complex signal to a multiplexing device of the control system 1900 that recovers the separate signals from the complex signal.

The communication system 2900 comprises an electrical connector 2910 mounted to the circuit board 2810. The electrical connector 2910 comprises a connector body and a plurality of electrically-conductive contacts mounted to the connector body. The electrically-conductive contacts comprise male pins, for example, which are soldered to electrical traces defined in the circuit board 2810. In other instances, the male pins can be in communication with circuit board traces through zero-insertion-force (ZIF) sockets, for example. The communication system 1900 comprises an electrical connector 1910 mounted to the circuit board 1810. The electrical connector 1910 comprises a connector body and a plurality of electrically-conductive contacts mounted to the connector body. The electrically-conductive contacts comprise female pins, for example, which are soldered to electrical traces defined in the circuit board 1810. In other instances, the female pins can be in communication with circuit board traces through zero-insertion-force (ZIF) sockets, for example. When the shaft assembly 2000 is assembled to the drive module 1100, the electrical connector 2910 is operably coupled to the electrical connector 1910 such that the electrical contacts form electrical pathways therebetween. The above being said, the connectors 1910 and 2910 can comprise any suitable electrical contacts. Moreover, the communication systems 1900 and 2900 can communicate with one another in any suitable manner. In various instances, the communication systems 1900 and 2900 communicate wirelessly. In at least one such instance, the communication system 2900 comprises a wireless signal transmitter and the communication system 1900 comprises a wireless signal receiver such that the shaft assembly 2000 can wirelessly communicate data to the handle 1000. Likewise, the communication system 1900 can comprise a wireless signal transmitter and the communication system 2900 can comprise a wireless signal receiver such that the handle 1000 can wirelessly communicate data to the shaft assembly 2000.

As discussed above, the control system 1800 of the handle 1000 is in communication with, and is configured to control, the electrical power circuit of the handle 1000. The handle control system 1800 is also powered by the electrical power circuit of the handle 1000. The handle communication system 1900 is in signal communication with the handle control system 1800 and is also powered by the electrical power circuit of the handle 1000. The handle communication system 1900 is powered by the handle electrical power circuit via the handle control system 1800, but could be directly powered by the electrical power circuit. As also discussed above, the handle communication system 1900 is in signal communication with the shaft communication system 2900. That said, the shaft communication system 2900 is also powered by the handle electrical power circuit via the handle communication system 1900. To this end, the electrical connectors 1910 and 2010 connect both one or more signal circuits and one or more power circuits between the handle 1000 and the shaft assembly 2000. Moreover, the shaft communication system 2900 is in signal communication with the shaft control system 2800, as discussed above, and is also configured to supply power to the shaft control system 2800. Thus, the control systems 1800 and 2800 and the communication systems 1900 and 2900 are all powered by the electrical power circuit of the handle 1000; however, alternative embodiments are envisioned in which the shaft assembly 2000 comprises its own power source, such as one or more batteries, for example, an and electrical power circuit configured to supply power from the batteries to the handle systems 2800 and 2900. In at least one such embodiment, the handle control system 1800 and the handle communication system 1900 are powered by the handle electrical power system and the shaft control system 2800 and the handle communication system 2900 are powered by the shaft electrical power system.

Further to the above, the actuation of the clamping trigger 2610 is detected by the shaft control system 2800 and communicated to the handle control system 1800 via the communication systems 2900 and 1900. Upon receiving a signal that the clamping trigger 2610 has been actuated, the handle control system 1800 supplies power to the electric motor 1610 of the motor assembly 1600 to rotate the drive shaft 1710 of the handle drive system 1700, and the drive shaft 2710 of the shaft drive system 2700, in a direction which closes the jaw assembly 7100 of the end effector 7000. The mechanism for converting the rotation of the drive shaft 2710 to a closure motion of the jaw assembly 7100 is discussed in greater detail below. So long as the clamping trigger 2610 is held in its actuated position, the electric motor 1610 will rotate the drive shaft 1710 until the jaw assembly 7100 reaches its fully-clamped position. When the jaw assembly 7100 reaches its fully-clamped position, the handle control system 1800 cuts the electrical power to the electric motor 1610. The handle control system 1800 can determine when the jaw assembly 7100 has reached its fully-clamped position in any suitable manner. For instance, the handle control system 1800 can comprise an encoder system which monitors the rotation of, and counts the rotations of, the output shaft of the electric motor 1610 and, once the number of rotations reaches a predetermined threshold, the handle control system 1800 can discontinue supplying power to the electric motor 1610. In at least one instance, the end effector assembly 7000 can comprise one or more sensors configured to detect when the jaw assembly 7100 has reached its fully-clamped position. In at least one such instance, the sensors in the end effector 7000 are in signal communication with the handle control system 1800 via electrical circuits extending through the shaft assembly 2000 which can include the electrical contacts 1520 and 2520, for example.

When the clamping trigger 2610 is rotated distally out of its proximal position, the switch 2115 is opened which is detected by the shaft control system 2800 and communicated to the handle control system 1800 via the communication systems 2900 and 1900. Upon receiving a signal that the clamping trigger 2610 has been moved out of its actuated position, the handle control system 1800 reverses the polarity of the voltage differential being applied to the electric motor 1610 of the motor assembly 1600 to rotate the drive shaft 1710 of the handle drive system 1700, and the drive shaft 2710 of the shaft drive system 2700, in an opposite direction which, as a result, opens the jaw assembly 7100 of the end effector 7000. When the jaw assembly 7100 reaches its fully-open position, the handle control system 1800 cuts the electrical power to the electric motor 1610. The handle control system 1800 can determine when the jaw assembly 7100 has reached its fully-open position in any suitable manner. For instance, the handle control system 1800 can utilize the encoder system and/or the one or more sensors described above to determine the configuration of the jaw assembly 7100. In view of the above, the clinician needs to be mindful about holding the clamping trigger 2610 in its actuated position in order to maintain the jaw assembly 7100 in its clamped configuration as, otherwise, the control system 1800 will open jaw assembly 7100. With this in mind, the shaft assembly 2000 further comprises an actuator latch 2630 configured to releasably hold the clamping trigger 2610 in its actuated position to prevent the accidental opening of the jaw assembly 7100. The actuator latch 2630 can be manually released, or otherwise defeated, by the clinician to allow the clamping trigger 2610 to be rotated distally and open the jaw assembly 7100.

The clamping trigger system 2600 further comprises a resilient biasing member, such as a torsion spring, for example, configured to resist the closure of the clamping trigger system 2600. The torsion spring can also assist in reducing and/or mitigating sudden movements and/or jitter of the clamping trigger 2610. Such a torsion spring can also automatically return the clamping trigger 2610 to its unactuated position when the clamping trigger 2610 is released. The actuator latch 2630 discussed above can suitably hold the clamping trigger 2610 in its actuated position against the biasing force of the torsion spring.

As discussed above, the control system 1800 operates the electric motor 1610 to open and close the jaw assembly 7100. The control system 1800 is configured to open and close the jaw assembly 7100 at the same speed. In such instances, the control system 1800 applies the same voltage pulses to the electric motor 1610, albeit with different voltage polarities, when opening and closing the jaw assembly 7100. That said, the control system 1800 can be configured to open and close the jaw assembly 7100 at different speeds. For instance, the jaw assembly 7100 can be closed at a first speed and opened at a second speed which is faster than the first speed. In such instances, the slower closing speed affords the clinician an opportunity to better position the jaw assembly 7100 while clamping the tissue. Alternatively, the control system 1800 can open the jaw assembly 7100 at a slower speed. In such instances, the slower opening speed reduces the possibility of the opening jaws colliding with adjacent tissue. In either event, the control system 1800 can decrease the duration of the voltage pulses and/or increase the duration between the voltage pulses to slow down and/or speed up the movement of the jaw assembly 7100.

As discussed above, the control system 1800 is configured to interpret the position of the clamping trigger 2610 as a command to position the jaw assembly 7100 in a specific configuration. For instance, the control system 1800 is configured to interpret the proximal-most position of the clamping trigger 2610 as a command to close the jaw assembly 7100 and any other position of the clamping trigger as a command to open the jaw assembly 7100. That said, the control system 1800 can be configured to interpret the position of the clamping trigger 2610 in a proximal range of positions, instead of a single position, as a command to close the jaw assembly 7100. Such an arrangement can allow the jaw assembly 7000 to be better responsive to the clinician's input. In such instances, the range of motion of the clamping trigger 2610 is divided into ranges—a proximal range which is interpreted as a command to close the jaw assembly 7100 and a distal range which is interpreted as a command to open the jaw assembly 7100. In at least one instance, the range of motion of the clamping trigger 2610 can have an intermediate range between the proximal range and the distal range. When the clamping trigger 2610 is in the intermediate range, the control system 1800 can interpret the position of the clamping trigger 2610 as a command to neither open nor close the jaw assembly 7100. Such an intermediate range can prevent, or reduce the possibility of, jitter between the opening and closing ranges. In the instances described above, the control system 1800 can be configured to ignore cumulative commands to open or close the jaw assembly 7100. For instance, if the closure trigger 2610 has already been fully retracted into its proximal-most position, the control assembly 1800 can ignore the motion of the clamping trigger 2610 in the proximal, or clamping, range until the clamping trigger 2610 enters into the distal, or opening, range wherein, at such point, the control system 1800 can then actuate the electric motor 1610 to open the jaw assembly 7100.

In certain instances, further to the above, the position of the clamping trigger 2610 within the clamping trigger range, or at least a portion of the clamping trigger range, can allow the clinician to control the speed of the electric motor 1610 and, thus, the speed in which the jaw assembly 7100 is being opened or closed by the control assembly 1800. In at least one instance, the sensor 2115 comprises a Hall Effect sensor, and/or any other suitable sensor, configured to detect the position of the clamping trigger 2610 between its distal, unactuated position and its proximal, fully-actuated position. The Hall Effect sensor is configured to transmit a signal to the handle control system 1800 via the shaft control system 2800 such that the handle control system 1800 can control the speed of the electric motor 1610 in response to the position of the clamping trigger 2610. In at least one instance, the handle control system 1800 controls the speed of the electric motor 1610 proportionately, or in a linear manner, to the position of the clamping trigger 2610. For example, if the clamping trigger 2610 is moved half way through its range, then the handle control system 1800 will operate the electric motor 1610 at half of the speed in which the electric motor 1610 is operated when the clamping trigger 2610 is fully-retracted. Similarly, if the clamping trigger 2610 is moved a quarter way through its range, then the handle control system 1800 will operate the electric motor 1610 at a quarter of the speed in which the electric motor 1610 is operated when the clamping trigger 2610 is fully-retracted. Other embodiments are envisioned in which the handle control system 1800 controls the speed of the electric motor 1610 in a non-linear manner to the position of the clamping trigger 2610. In at least one instance, the control system 1800 operates the electric motor 1610 slowly in the distal portion of the clamping trigger range while quickly accelerating the speed of the electric motor 1610 in the proximal portion of the clamping trigger range.

As described above, the clamping trigger 2610 is movable to operate the electric motor 1610 to open or close the jaw assembly 7100 of the end effector 7000. The electric motor 1610 is also operable to rotate the end effector 7000 about a longitudinal axis and articulate the end effector 7000 relative to the elongate shaft 2200 about the articulation joint 2300 of the shaft assembly 2000. Referring primarily to FIGS. 7 and 8, the drive module 1100 comprises an input system 1400 including a rotation actuator 1420 and an articulation actuator 1430. The input system 1400 further comprises a printed circuit board (PCB) 1410 which is in signal communication with the printed circuit board (PCB) 1810 of the control system 1800. The drive module 1100 comprises an electrical circuit, such as a flexible wiring harness or ribbon, for example, which permits the input system 1400 to communicate with the control system 1800. The rotation actuator 1420 is rotatably supported on the housing 1110 and is in signal communication with the input board 1410 and/or control board 1810, as described in greater detail below. The articulation actuator 1430 is supported by and in signal communication with the input board 1410 and/or control board 1810, as also described in greater detail below.

Referring primarily to FIGS. 8, 10, and 11, further to the above, the handle housing 1110 comprises an annular groove or slot defined therein adjacent the distal mounting interface 1130. The rotation actuator 1420 comprises an annular ring 1422 rotatably supported within the annular groove and, owing to the configuration of the sidewalls of the annular groove, the annular ring 1422 is constrained from translating longitudinally and/or laterally with respect to the handle housing 1110. The annular ring 1422 is rotatable in a first, or clockwise, direction and a second, or counter-clockwise, direction, about a longitudinal axis extending through the frame 1500 of the drive module 1100. The rotation actuator 1420 comprises one or more sensors configured to detect the rotation of the annular ring 1422. In at least one instance, the rotation actuator 1420 comprises a first sensor positioned on a first side of the drive module 1100 and a second sensor positioned on a second, or opposite, side of the drive module 1100 and the annular ring 1422 comprises a detectable element which is detectable by the first and second sensors. The first sensor is configured to detect when the annular ring 1422 is rotated in the first direction and the second sensor is configured to detect when the annular ring 1422 is rotated in the second direction. When the first sensor detects that the annular ring 1422 is rotated in the first direction, the handle control system 1800 rotates the handle drive shaft 1710, the drive shaft 2710, and the end effector 7000 in the first direction, as described in greater detail below. Similarly, the handle control system 1800 rotates the handle drive shaft 1710, the drive shaft 2710, and the end effector 7000 in the second direction when the second sensor detects that the annular ring 1422 is rotated in the second direction. In view of the above, the reader should appreciate that the clamping trigger 2610 and the rotation actuator 1420 are both operable to rotate the drive shaft 2710.

In various embodiments, further to the above, the first and second sensors comprise switches which are mechanically closable by the detectable element of the annular ring 1422. When the annular ring 1422 is rotated in the first direction from a center position, the detectable element closes the switch of the first sensor. When the switch of the first sensor is closed, the control system 1800 operates the electric motor 1610 to rotate the end effector 7000 in the first direction. When the annular ring 1422 is rotated in the second direction toward the center position, the detectable element is disengaged from the first switch and the first switch is re-opened. Once the first switch is re-opened, the control system 1800 cuts the power to the electric motor 1610 to stop the rotation of the end effector 7000. Similarly, the detectable element closes the switch of the second sensor when the annular ring 1422 is rotated in the second direction from the center position. When the switch of the second sensor is closed, the control system 1800 operates the electric motor 1610 to rotate the end effector 7000 in the second direction. When the annular ring 1422 is rotated in the first direction toward the center position, the detectable element is disengaged from the second switch and the second switch is re-opened. Once the second switch is re-opened, the control system 1800 cuts the power to the electric motor 1610 to stop the rotation of the end effector 7000.

In various embodiments, further to the above, the first and second sensors of the rotation actuator 1420 comprise proximity sensors, for example. In certain embodiments, the first and second sensors of the rotation actuator 1420 comprise Hall Effect sensors, and/or any suitable sensors, configured to detect the distance between the detectable element of the annular ring 1422 and the first and second sensors. If the first Hall Effect sensor detects that the annular ring 1422 has been rotated in the first direction, then, as discussed above, the control system 1800 will rotate the end effector 7000 in the first direction. In addition, the control system 1800 can rotate the end effector 7000 at a faster speed when the detectable element is closer to the first Hall Effect sensor than when the detectable element is further away from the first Hall Effect sensor. If the second Hall Effect sensor detects that the annular ring 1422 has been rotated in the second direction, then, as discussed above, the control system 1800 will rotate the end effector 7000 in the second direction. In addition, the control system 1800 can rotate the end effector 7000 at a faster speed when the detectable element is closer to the second Hall Effect sensor than when the detectable element is further away from the second Hall Effect sensor. As a result, the speed in which the end effector 7000 is rotated is a function of the amount, or degree, in which the annular ring 1422 is rotated. The control system 1800 is further configured to evaluate the inputs from both the first and second Hall Effect sensors when determining the direction and speed in which to rotate the end effector 7000. In various instances, the control system 1800 can use the closest Hall Effect sensor to the detectable element of the annular ring 1422 as a primary source of data and the Hall Effect sensor furthest away from the detectable element as a conformational source of data to double-check the data provided by the primary source of data. The control system 1800 can further comprise a data integrity protocol to resolve situations in which the control system 1800 is provided with conflicting data. In any event, the handle control system 1800 can enter into a neutral state in which the handle control system 1800 does not rotate the end effector 7000 when the Hall Effect sensors detect that the detectable element is in its center position, or in a position which is equidistant between the first Hall Effect sensor and the second Hall Effect sensor. In at least one such instance, the control system 1800 can enter into its neutral state when the detectable element is in a central range of positions. Such an arrangement would prevent, or at least reduce the possibility of, rotational jitter when the clinician is not intending to rotate the end effector 7000.

Further to the above, the rotation actuator 1420 can comprise one or more springs configured to center, or at least substantially center, the rotation actuator 1420 when it is released by the clinician. In such instances, the springs can act to shut off the electric motor 1610 and stop the rotation of the end effector 7000. In at least one instance, the rotation actuator 1420 comprises a first torsion spring configured to rotate the rotation actuator 1420 in the first direction and a second torsion spring configured to rotate the rotation actuator 1420 in the second direction. The first and second torsion springs can have the same, or at least substantially the same, spring constant such that the forces and/or torques applied by the first and second torsion springs balance, or at least substantially balance, the rotation actuator 1420 in its center position.

In view of the above, the reader should appreciate that the clamping trigger 2610 and the rotation actuator 1420 are both operable to rotate the drive shaft 2710 and either, respectively, operate the jaw assembly 7100 or rotate the end effector 7000. The system that uses the rotation of the drive shaft 2710 to selectively perform these functions is described in greater detail below.

Referring to FIGS. 7 and 8, the articulation actuator 1430 comprises a first push button 1432 and a second push button 1434. The first push button 1432 is part of a first articulation control circuit and the second push button 1434 is part of a second articulation circuit of the input system 1400. The first push button 1432 comprises a first switch that is closed when the first push button 1432 is depressed. The handle control system 1800 is configured to sense the closure of the first switch and, moreover, the closure of the first articulation control circuit. When the handle control system 1800 detects that the first articulation control circuit has been closed, the handle control system 1800 operates the electric motor 1610 to articulate the end effector 7000 in a first articulation direction about the articulation joint 2300. When the first push button 1432 is released by the clinician, the first articulation control circuit is opened which, once detected by the control system 1800, causes the control system 1800 to cut the power to the electric motor 1610 to stop the articulation of the end effector 7000.

In various instances, further to the above, the articulation range of the end effector 7000 is limited and the control system 1800 can utilize the encoder system discussed above for monitoring the rotational output of the electric motor 1610, for example, to monitor the amount, or degree, in which the end effector 7000 is rotated in the first direction. In addition to or in lieu of the encoder system, the shaft assembly 2000 can comprise a first sensor configured to detect when the end effector 7000 has reached the limit of its articulation in the first direction. In any event, when the control system 1800 determines that the end effector 7000 has reached the limit of articulation in the first direction, the control system 1800 can cut the power to the electric motor 1610 to stop the articulation of the end effector 7000.

Similar to the above, the second push button 1434 comprises a second switch that is closed when the second push button 1434 is depressed. The handle control system 1800 is configured to sense the closure of the second switch and, moreover, the closure of the second articulation control circuit. When the handle control system 1800 detects that the second articulation control circuit has been closed, the handle control system 1800 operates the electric motor 1610 to articulate the end effector 7000 in a second direction about the articulation joint 2300. When the second push button 1434 is released by the clinician, the second articulation control circuit is opened which, once detected by the control system 1800, causes the control system 1800 to cut the power to the electric motor 1610 to stop the articulation of the end effector 7000.

In various instances, the articulation range of the end effector 7000 is limited and the control system 1800 can utilize the encoder system discussed above for monitoring the rotational output of the electric motor 1610, for example, to monitor the amount, or degree, in which the end effector 7000 is rotated in the second direction. In addition to or in lieu of the encoder system, the shaft assembly 2000 can comprise a second sensor configured to detect when the end effector 7000 has reached the limit of its articulation in the second direction. In any event, when the control system 1800 determines that the end effector 7000 has reached the limit of articulation in the second direction, the control system 1800 can cut the power to the electric motor 1610 to stop the articulation of the end effector 7000.

Figure 15:
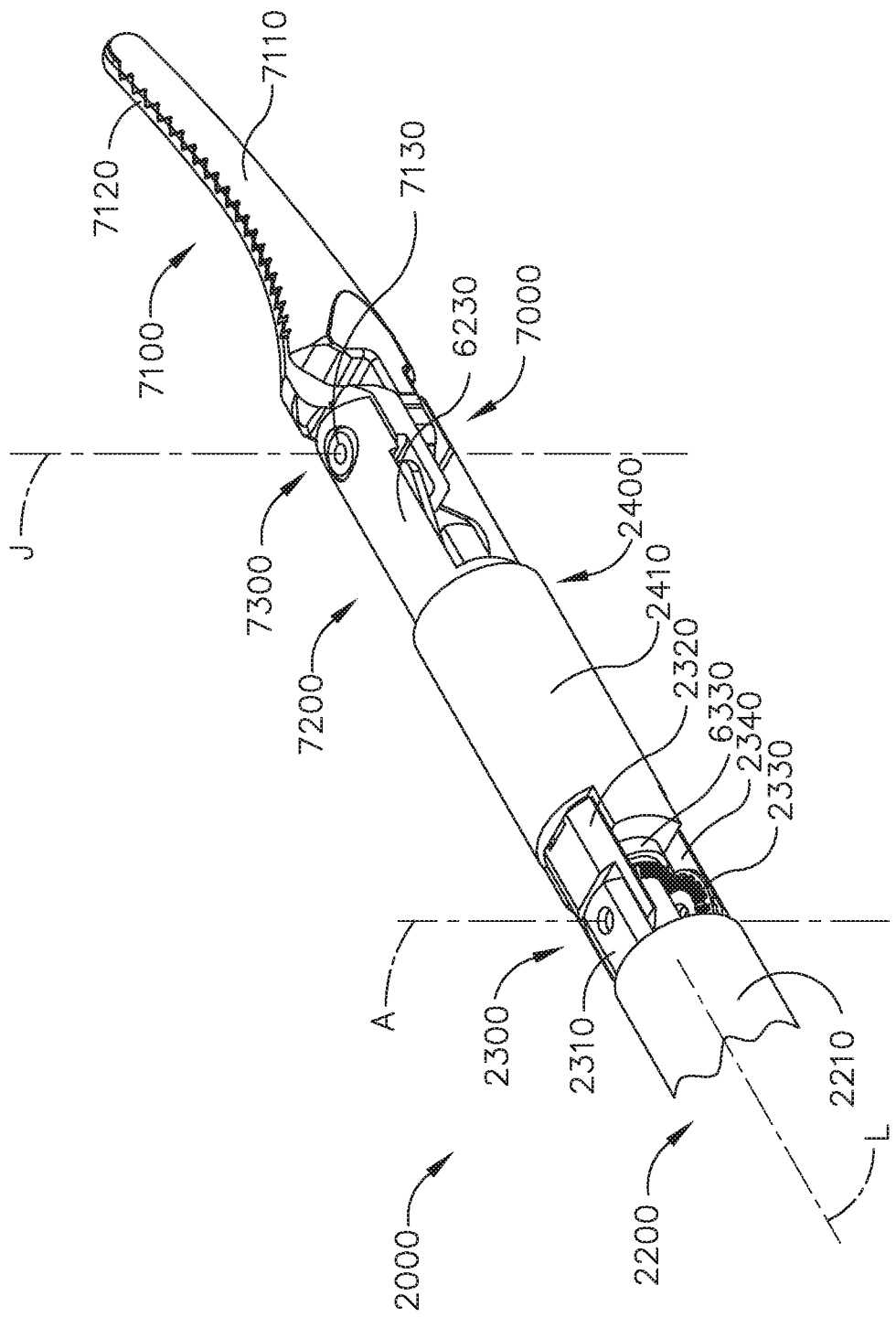
FIG. 15 is a partial perspective view of the end effector of FIG. 14 in a closed configuration.

As described above, the end effector 7000 is articulatable in a first direction (FIG. 16) and/or a second direction (FIG. 17) from a center, or unarticulated, position (FIG. 15). Once the end effector 7000 has been articulated, the clinician can attempt to re-center the end effector 7000 by using the first and second articulation push buttons 1432 and 1434. As the reader can appreciate, the clinician may struggle to re-center the end effector 7000 as, for instance, the end effector 7000 may not be entirely visible once it is positioned in the patient. In some instances, the end effector 7000 may not fit back through a trocar if the end effector 7000 is not re-centered, or at least substantially re-centered. With that in mind, the control system 1800 is configured to provide feedback to the clinician when the end effector 7000 is moved into its unarticulated, or centered, position. In at least one instance, the feedback comprises audio feedback and the handle control system 1800 can comprise a speaker which emits a sound, such as a beep, for example, when the end effector 7000 is centered. In certain instances, the feedback comprises visual feedback and the handle control system 1800 can comprise a light emitting diode (LED), for example, positioned on the handle housing 1110 which flashes when the end effector 7000 is centered. In various instances, the feedback comprises haptic feedback and the handle control system 1800 can comprise an electric motor comprising an eccentric element which vibrates the handle 1000 when the end effector 7000 is centered. Manually re-centering the end effector 7000 in this way can be facilitated by the control system 1800 slowing the motor 1610 when the end effector 7000 is approaching its centered position. In at least one instance, the control system 1800 slows the articulation of the end effector 7000 when the end effector 7000 is within approximately 5 degrees of center in either direction, for example.

In addition to or in lieu of the above, the handle control system 1800 can be configured to re-center the end effector 7000. In at least one such instance, the handle control system 1800 can re-center the end effector 7000 when both of the articulation buttons 1432 and 1434 of the articulation actuator 1430 are depressed at the same time. When the handle control system 1800 comprises an encoder system configured to monitor the rotational output of the electric motor 1610, for example, the handle control system 1800 can determine the amount and direction of articulation needed to re-center, or at least substantially re-center, the end effector 7000. In various instances, the input system 1400 can comprise a home button, for example, which, when depressed, automatically centers the end effector 7000.

Figure 5:
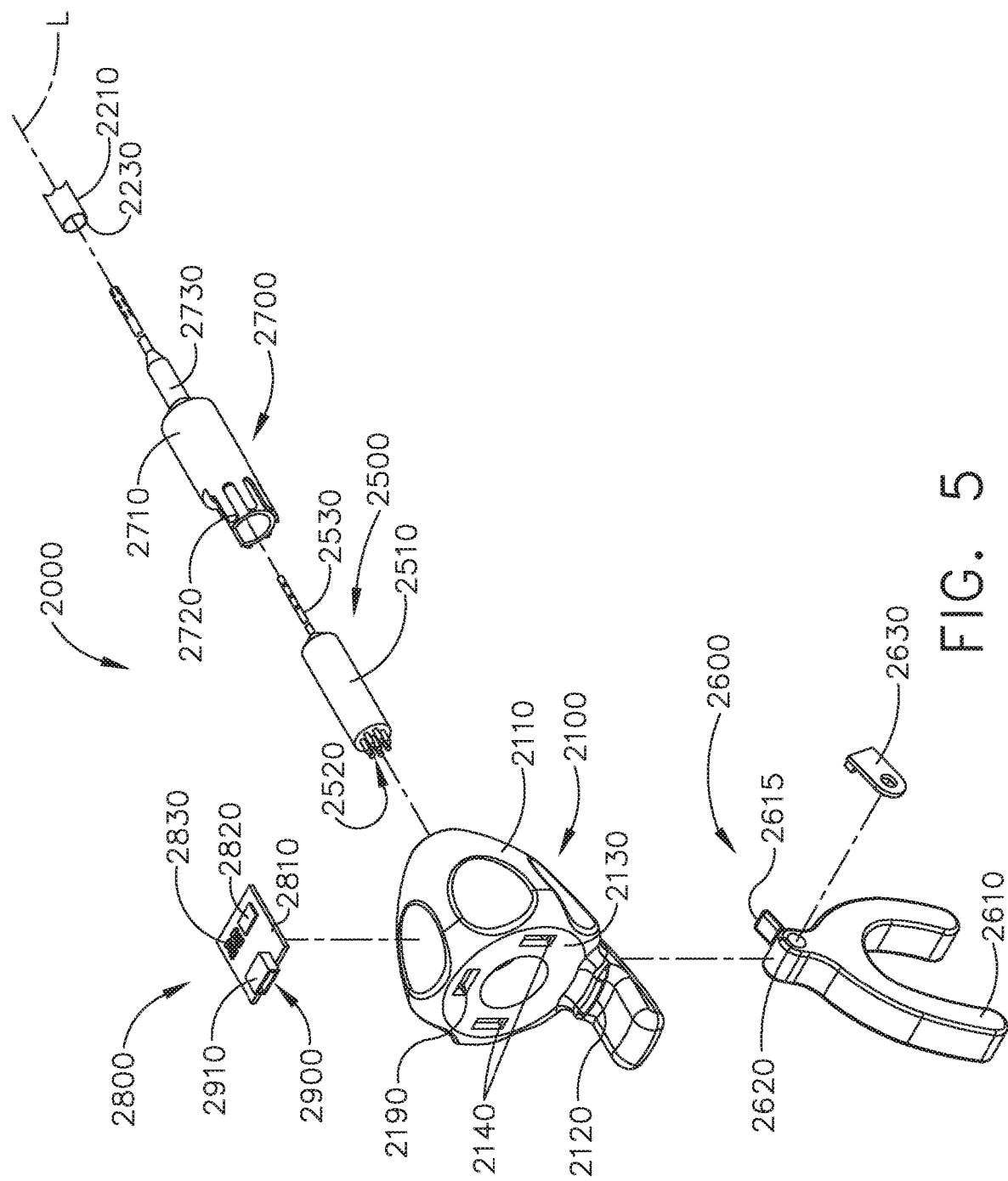
FIG. 5 is a partial exploded view of the shaft assembly of FIG. 2.
Figure 6:
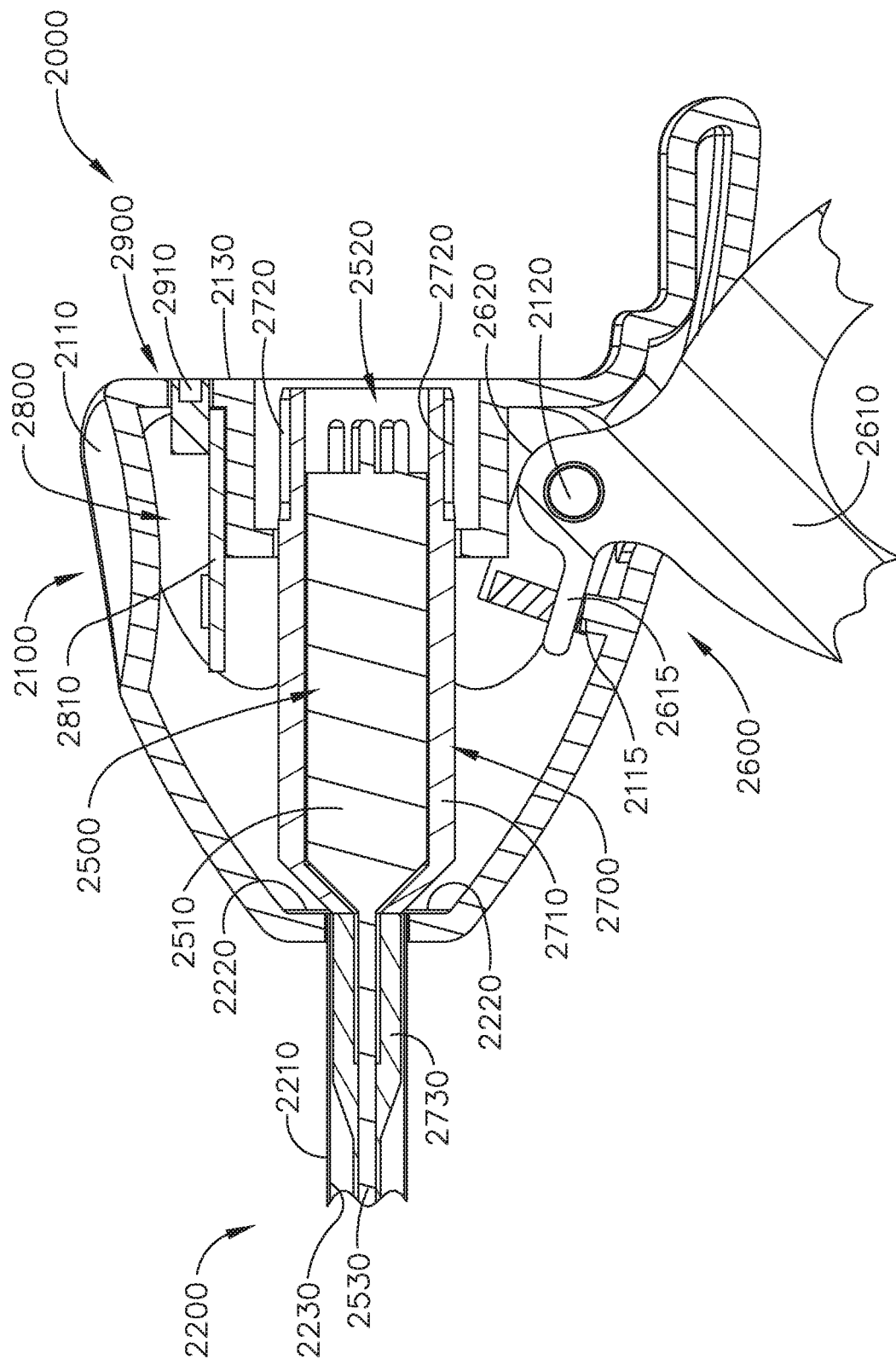
FIG. 6 is a partial cross-sectional elevational view of the shaft assembly of FIG. 2.

Referring primarily to FIGS. 5 and 6, the elongate shaft 2200 of the shaft assembly 2000 comprises an outer housing, or tube, 2210 mounted to the proximal housing 2110 of the proximal portion 2100. The outer housing 2210 comprises a longitudinal aperture 2230 extending therethrough and a proximal flange 2220 which secures the outer housing 2210 to the proximal housing 2110. The frame 2500 of the shaft assembly 2000 extends through the longitudinal aperture 2230 of the elongate shaft 2200. More specifically, the shaft 2510 of the shaft frame 2500 necks down into a smaller shaft 2530 which extends through the longitudinal aperture 2230. That said, the shaft frame 2500 can comprise any suitable arrangement. The drive system 2700 of the shaft assembly 2000 also extends through the longitudinal aperture 2230 of the elongate shaft 2200. More specifically, the drive shaft 2710 of the shaft drive system 2700 necks down into a smaller drive shaft 2730 which extends through the longitudinal aperture 2230. That said, the shaft drive system 2700 can comprise any suitable arrangement.

Figure 20:
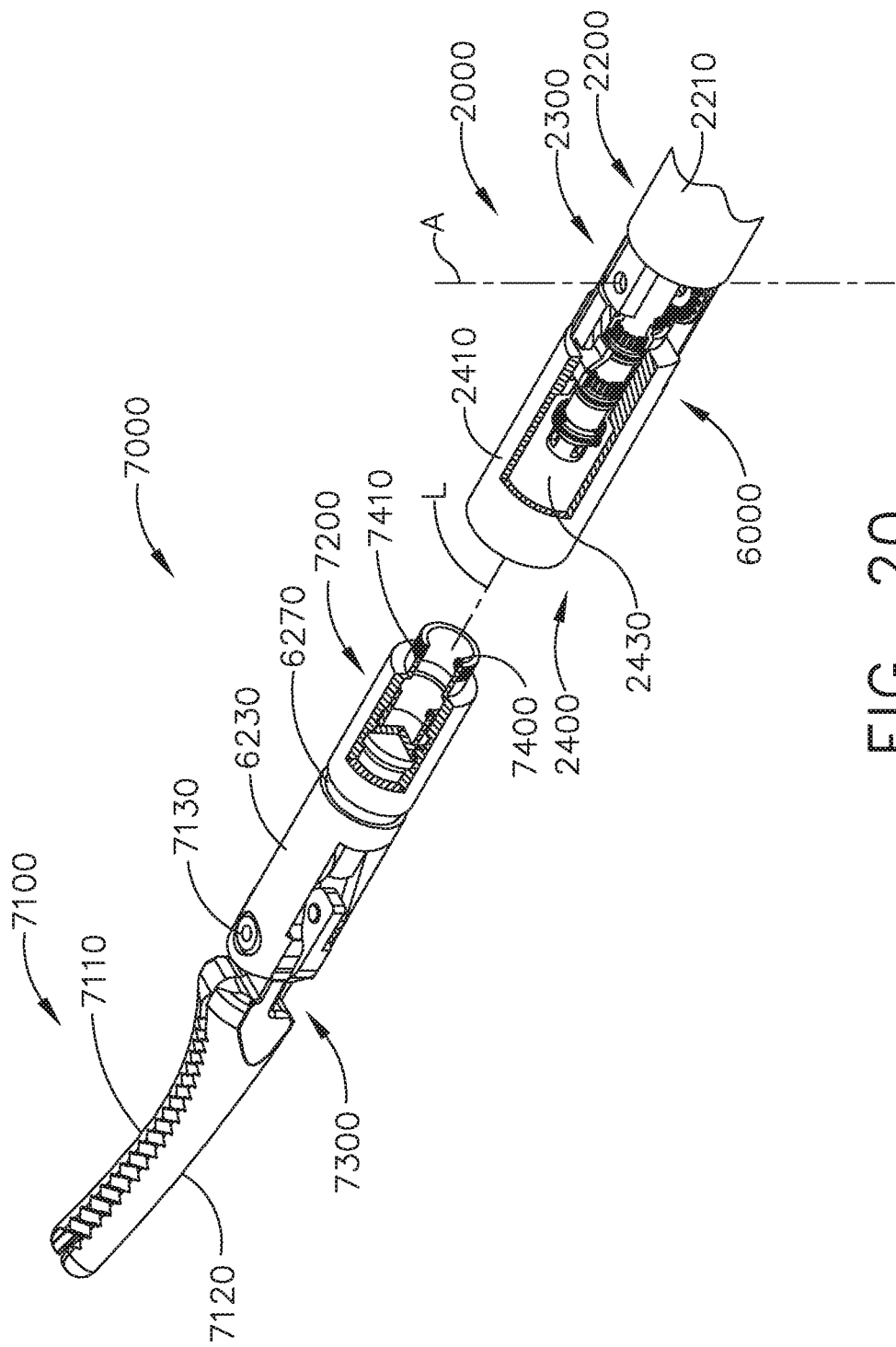
FIG. 20 is a partial cross-sectional perspective view of the end effector of FIG. 14 detached from the shaft assembly of FIG. 2.
Figure 22:
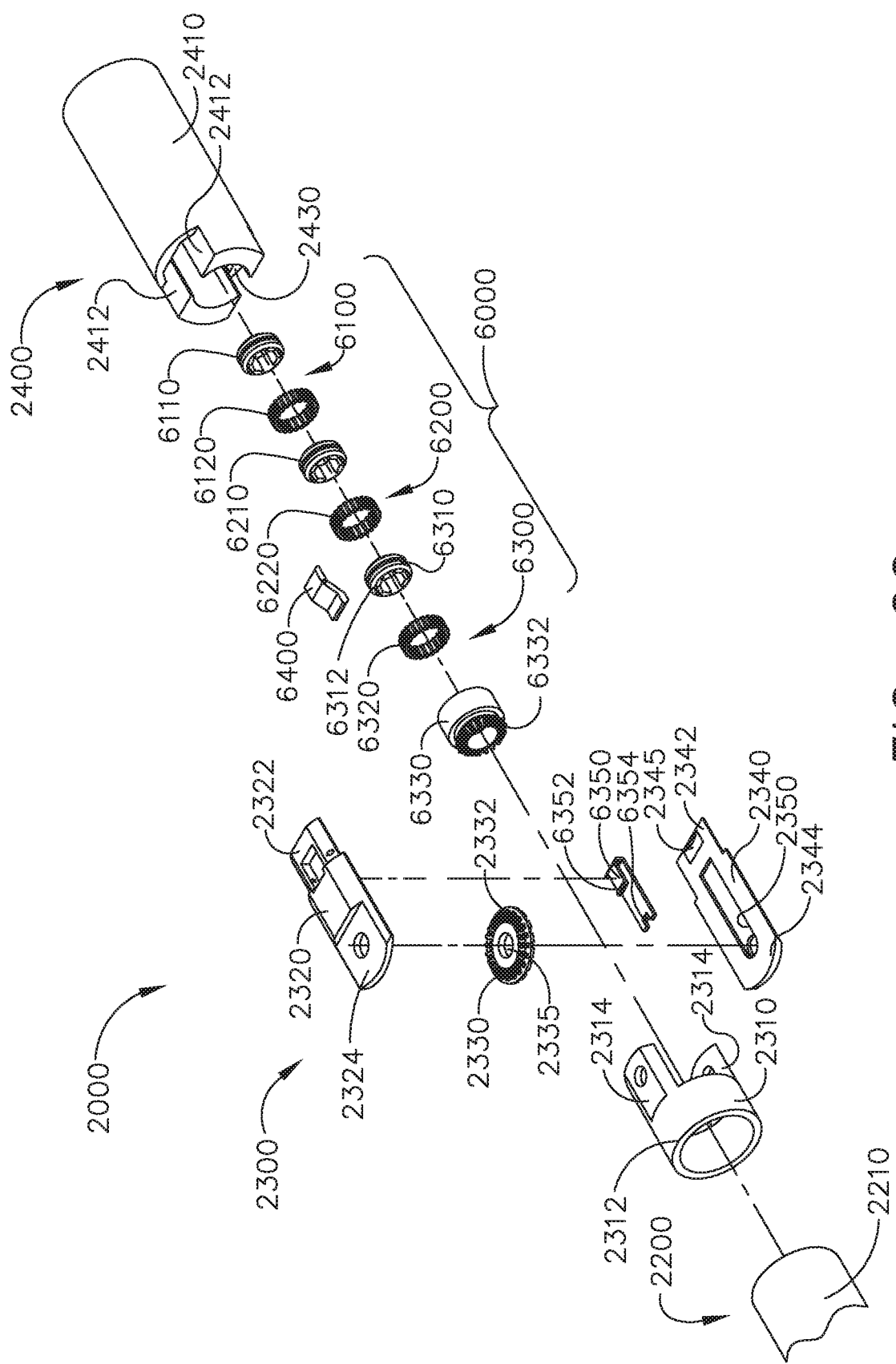
FIG. 22 is an exploded view of a distal attachment portion of the shaft assembly of FIG. 2.
Figure 23:
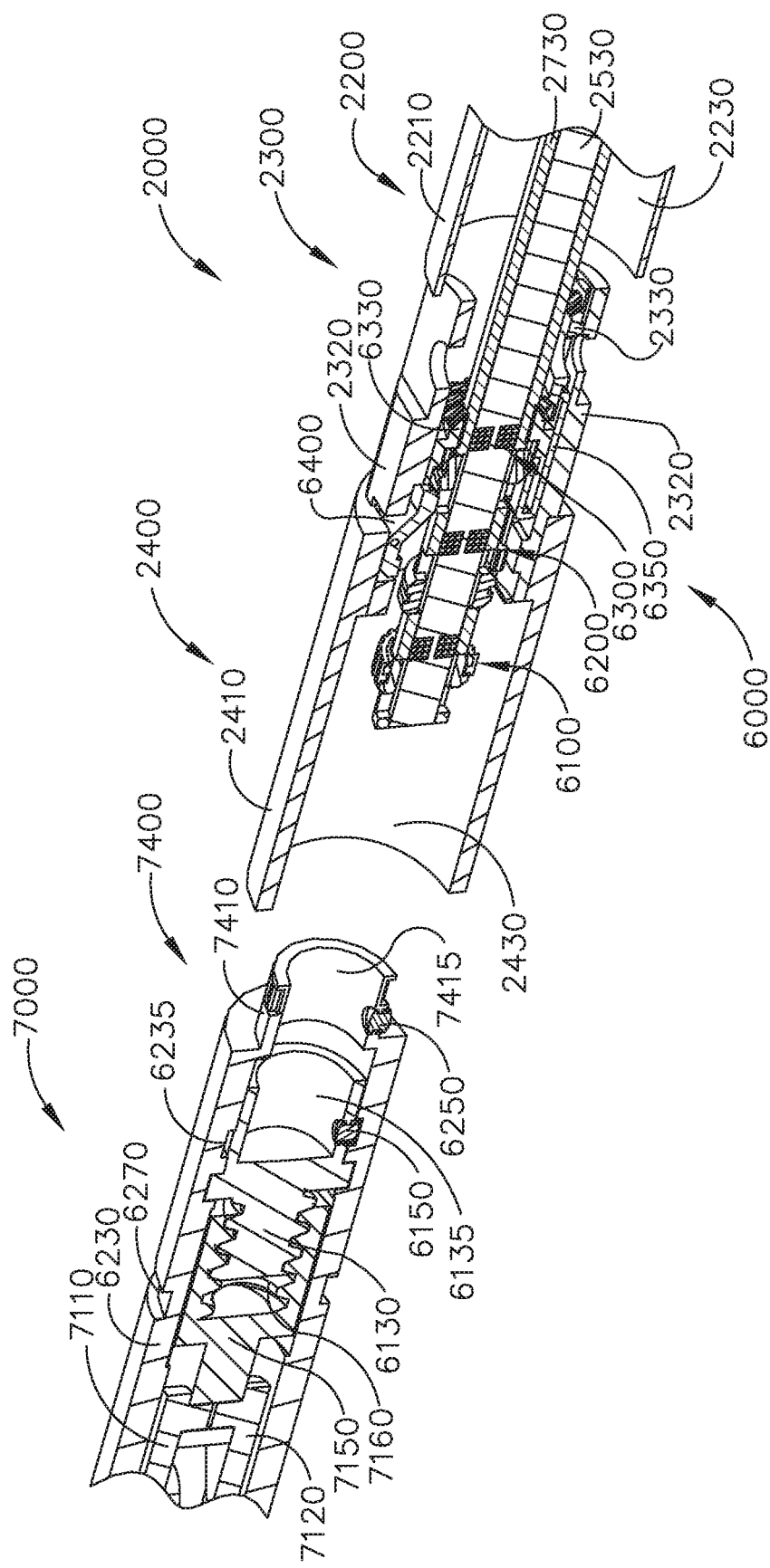
FIG. 23 is another partial cross-sectional perspective view of the end effector of FIG. 14 detached from the shaft assembly of FIG. 2.
Figure 24:
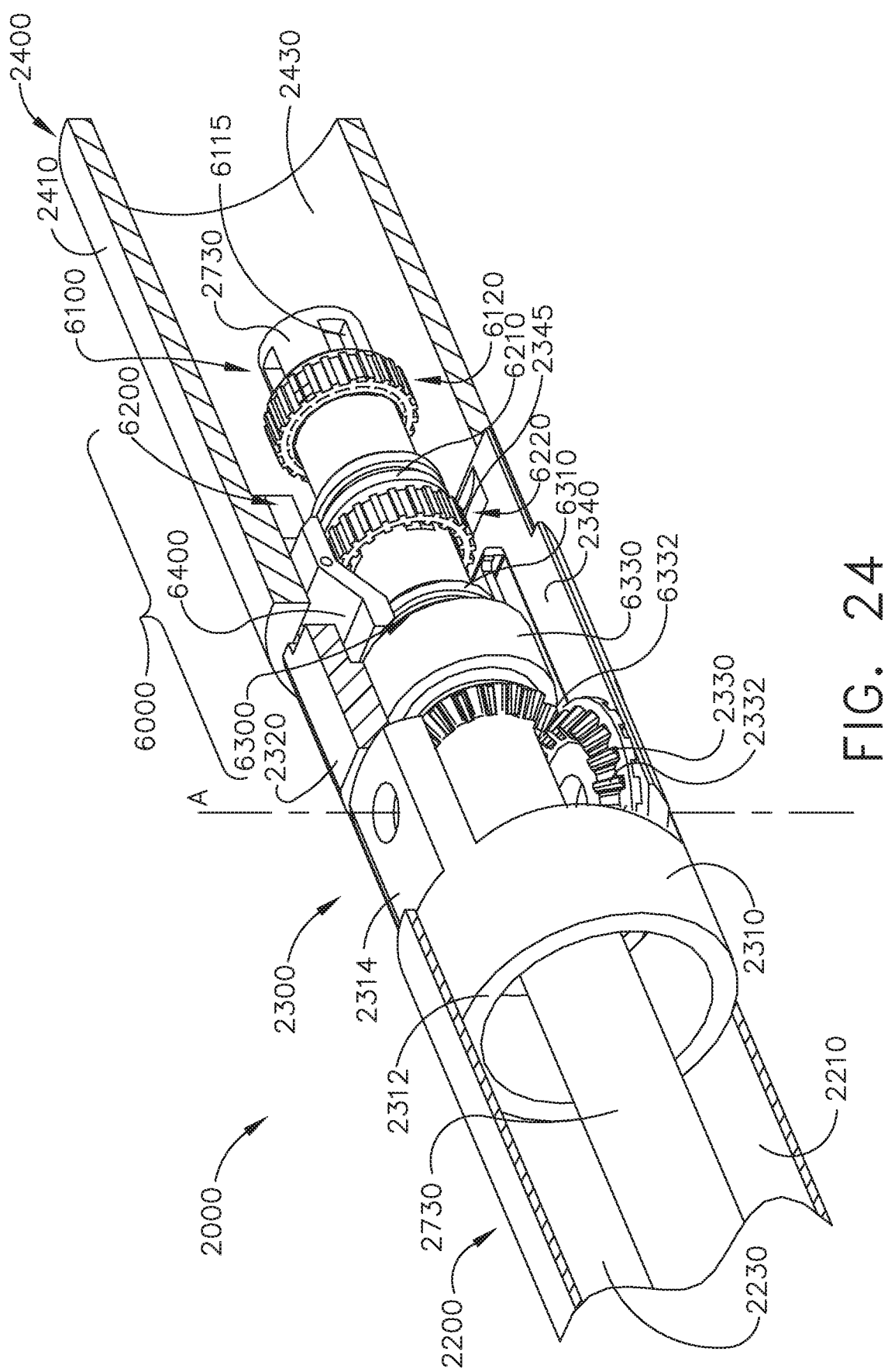
FIG. 24 is a partial cross-sectional perspective view of the end effector of FIG. 14 attached to the shaft assembly of FIG. 2.

Referring primarily to FIGS. 20, 23, and 24, the outer housing 2210 of the elongate shaft 2200 extends to the articulation joint 2300. The articulation joint 2300 comprises a proximal frame 2310 mounted to the outer housing 2210 such that there is little, if any, relative translation and/or rotation between the proximal frame 2310 and the outer housing 2210. Referring primarily to FIG. 22, the proximal frame 2310 comprises an annular portion 2312 mounted to the sidewall of the outer housing 2210 and tabs 2314 extending distally from the annular portion 2312. The articulation joint 2300 further comprises links 2320 and 2340 which are rotatably mounted to the frame 2310 and mounted to an outer housing 2410 of the distal attachment portion 2400. The link 2320 comprises a distal end 2322 mounted to the outer housing 2410. More specifically, the distal end 2322 of the link 2320 is received and fixedly secured within a mounting slot 2412 defined in the outer housing 2410. Similarly, the link 2340 comprises a distal end 2342 mounted to the outer housing 2410. More specifically, the distal end 2342 of the link 2340 is received and fixedly secured within a mounting slot defined in the outer housing 2410. The link 2320 comprises a proximal end 2324 rotatably coupled to a tab 2314 of the proximal articulation frame 2310. Although not illustrated in FIG. 22, a pin extends through apertures defined in the proximal end 2324 and the tab 2314 to define a pivot axis therebetween. Similarly, the link 2340 comprises a proximal end 2344 rotatably coupled to a tab 2314 of the proximal articulation frame 2310. Although not illustrated in FIG. 22, a pin extends through apertures defined in the proximal end 2344 and the tab 2314 to define a pivot axis therebetween. These pivot axes are collinear, or at least substantially collinear, and define an articulation axis A of the articulation joint 2300.

Referring primarily to FIGS. 20, 23, and 24, the outer housing 2410 of the distal attachment portion 2400 comprises a longitudinal aperture 2430 extending therethrough. The longitudinal aperture 2430 is configured to receive a proximal attachment portion 7400 of the end effector 7000. The end effector 7000 comprises an outer housing 6230 which is closely received within the longitudinal aperture 2430 of the distal attachment portion 2400 such that there is little, if any, relative radial movement between the proximal attachment portion 7400 of the end effector 7000 and the distal attachment portion 2400 of the shaft assembly 2000. The proximal attachment portion 7400 further comprises an annular array of lock notches 7410 defined on the outer housing 6230 which is releasably engaged by an end effector lock 6400 in the distal attachment portion 2400 of the shaft assembly 2000. When the end effector lock 6400 is engaged with the array of lock notches 7410, the end effector lock 6400 prevents, or at least inhibits, relative longitudinal movement between the proximal attachment portion 7400 of the end effector 7000 and the distal attachment portion 2400 of the shaft assembly 2000. As a result of the above, only relative rotation between the proximal attachment portion 7400 of the end effector 7000 and the distal attachment portion 2400 of the shaft assembly 2000 is permitted. To this end, the outer housing 6230 of the end effector 7000 is closely received within the longitudinal aperture 2430 defined in the distal attachment portion 2400 of the shaft assembly 2000.

Figure 21:
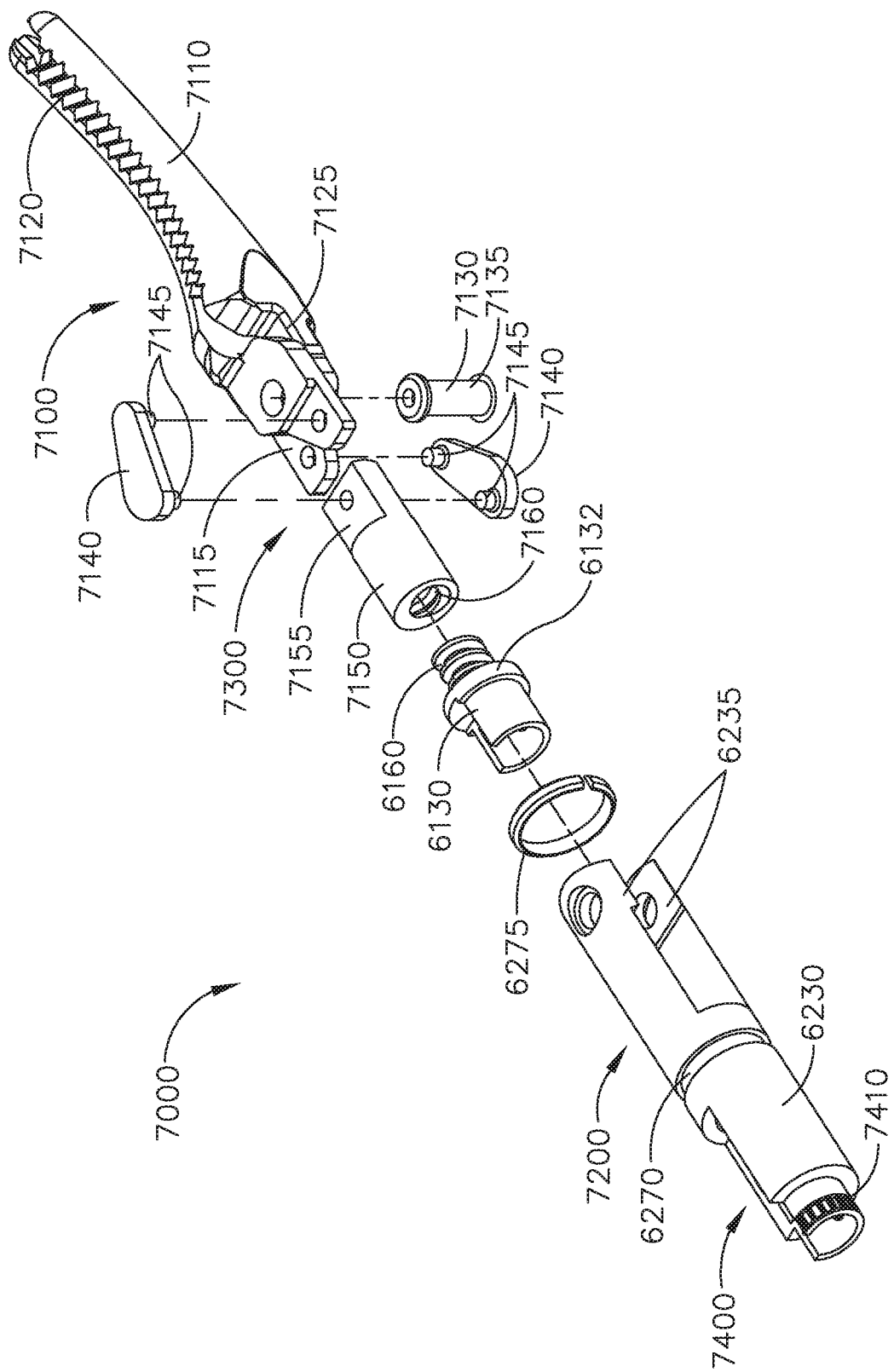
FIG. 21 is an exploded view of the end effector of FIG. 14 illustrated with some components removed.

Further to the above, referring to FIG. 21, the outer housing 6230 further comprises an annular slot, or recess, 6270 defined therein which is configured to receive an O-ring 6275 therein. The O-ring 6275 is compressed between the outer housing 6230 and the sidewall of the longitudinal aperture 2430 when the end effector 7000 is inserted into the distal attachment portion 2400. The O-ring 6275 is configured to resist, but permit, relative rotation between the end effector 7000 and the distal attachment portion 2400 such that the O-ring 6275 can prevent, or reduce the possibility of, unintentional relative rotation between the end effector 7000 and the distal attachment portion 2400. In various instances, the O-ring 6275 can provide a seal between the end effector 7000 and the distal attachment portion 2400 to prevent, or at least reduce the possibility of, fluid ingress into the shaft assembly 2000, for example.

Referring to FIGS. 14-21, the jaw assembly 7100 of the end effector 7000 comprises a first jaw 7110 and a second jaw 7120. Each jaw 7110, 7120 comprises a distal end which is configured to assist a clinician in dissecting tissue with the end effector 7000. Each jaw 7110, 7120 further comprises a plurality of teeth which are configured to assist a clinician in grasping and holding onto tissue with the end effector 7000. Moreover, referring primarily to FIG. 21, each jaw 7110, 7120 comprises a proximal end, i.e., proximal ends 7115, 7125, respectively, which rotatably connect the jaws 7110, 7120 together. Each proximal end 7115, 7125 comprises an aperture extending therethrough which is configured to closely receive a pin 7130 therein. The pin 7130 comprises a central body 7135 closely received within the apertures defined in the proximal ends 7115, 7125 of the jaws 7110, 7120 such that there is little, if any, relative translation between the jaws 7110, 7120 and the pin 7130. The pin 7130 defines a jaw axis J about which the jaws 7110, 7120 can be rotated and, also, rotatably mounts the jaws 7110, 7120 to the outer housing 6230 of the end effector 7000. More specifically, the outer housing 6230 comprises distally-extending tabs 6235 having apertures defined therein which are also configured to closely receive the pin 7130 such that the jaw assembly 7100 does not translate relative to a shaft portion 7200 of the end effector 7000. The pin 7130 further comprises enlarged ends which prevent the jaws 7110, 7120 from becoming detached from the pin 7130 and also prevents the jaw assembly 7100 from becoming detached from the shaft portion 7200. This arrangement defines a rotation joint 7300.

Referring primarily to FIGS. 21 and 23, the jaws 7110 and 7120 are rotatable between their open and closed positions by a jaw assembly drive including drive links 7140, a drive nut 7150, and a drive screw 6130. As described in greater detail below, the drive screw 6130 is selectively rotatable by the drive shaft 2730 of the shaft drive system 2700. The drive screw 6130 comprises an annular flange 6132 which is closely received within a slot, or groove, 6232 (FIG. 25) defined in the outer housing 6230 of the end effector 7000. The sidewalls of the slot 6232 are configured to prevent, or at least inhibit, longitudinal and/or radial translation between the drive screw 6130 and the outer housing 6230, but yet permit relative rotational motion between the drive screw 6130 and the outer housing 6230. The drive screw 6130 further comprises a threaded end 6160 which is threadably engaged with a threaded aperture 7160 defined in the drive nut 7150. The drive nut 7150 is constrained from rotating with the drive screw 6130 and, as a result, the drive nut 7150 is translated when the drive screw 6130 is rotated. In use, the drive screw 6130 is rotated in a first direction to displace the drive nut 7150 proximally and in a second, or opposite, direction to displace the drive nut 7150 distally. The drive nut 7150 further comprises a distal end 7155 comprising an aperture defined therein which is configured to closely receive pins 7145 extending from the drive links 7140. Referring primarily to FIG. 21, a first drive link 7140 is attached to one side of the distal end 7155 and a second drive link 7140 is attached to the opposite side of the distal end 7155. The first drive link 7140 comprises another pin 7145 extending therefrom which is closely received in an aperture defined in the proximal end 7115 of the first jaw 7110 and, similarly, the second drive link 7140 comprises another pin extending therefrom which is closely received in an aperture defined in the proximal end 7125 of the second jaw 7120. As a result of the above, the drive links 7140 operably connect the jaws 7110 and 7120 to the drive nut 7150. When the drive nut 7150 is driven proximally by the drive screw 6130, as described above, the jaws 7110, 7120 are rotated into the closed, or clamped, configuration. Correspondingly, the jaws 7110, 7120 are rotated into their open configuration when the drive nut 7150 is driven distally by the drive screw 6130.

Figure 16:
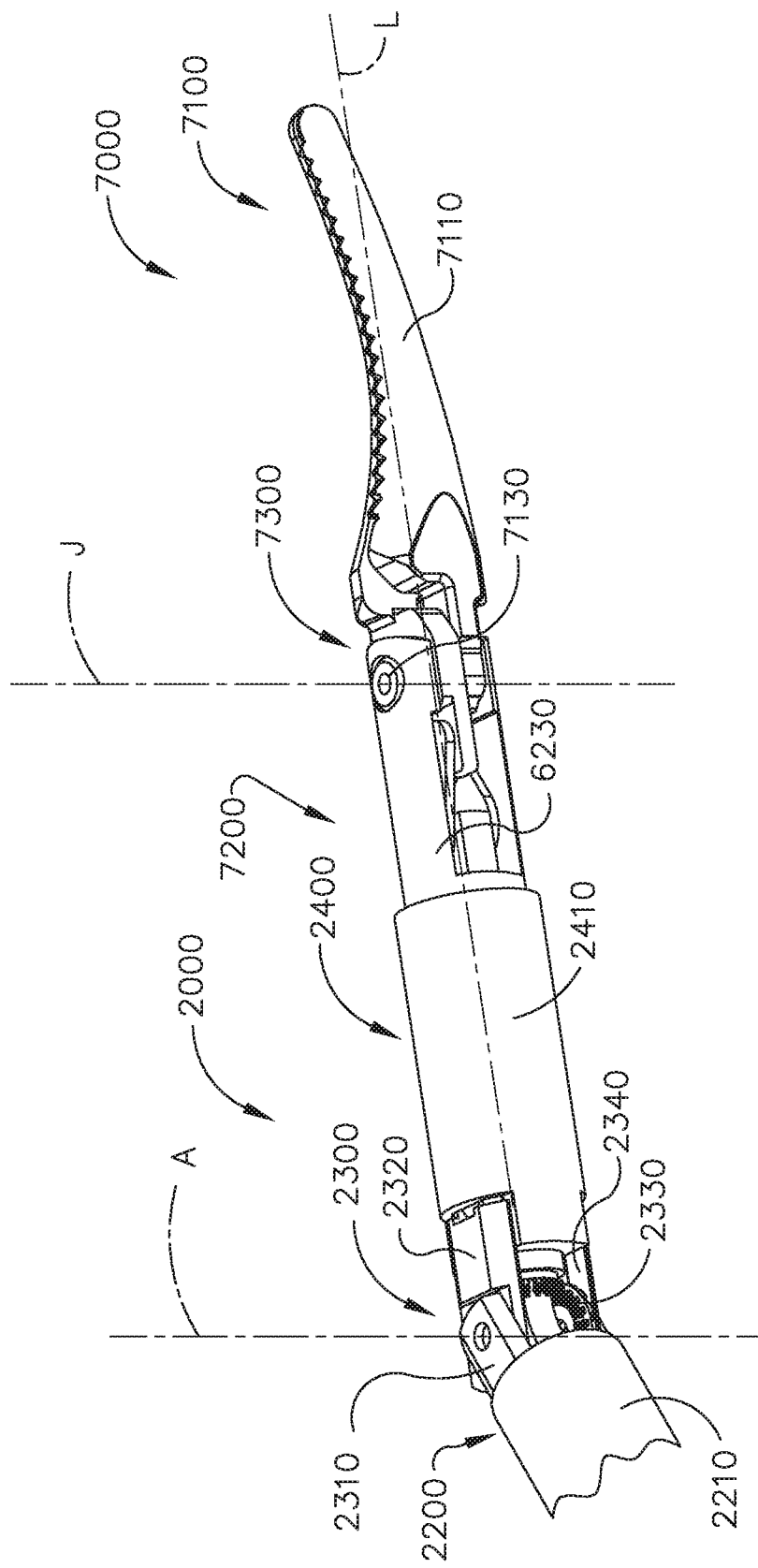
FIG. 16 is a partial perspective view of the end effector of FIG. 14 articulated in a first direction.
Figure 17:
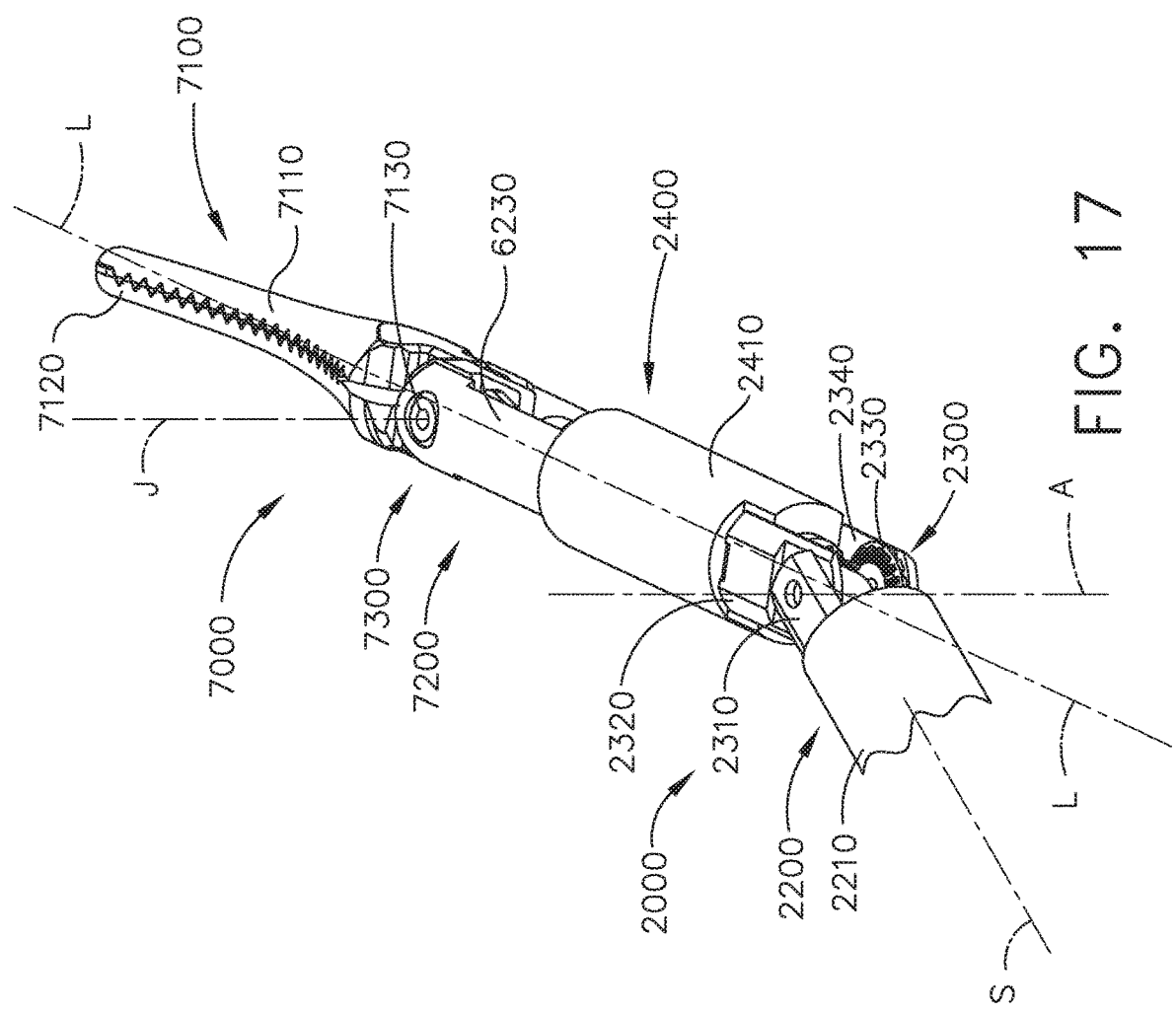
FIG. 17 is a partial perspective view of the end effector of FIG. 14 articulated in a second direction.
Figure 18:
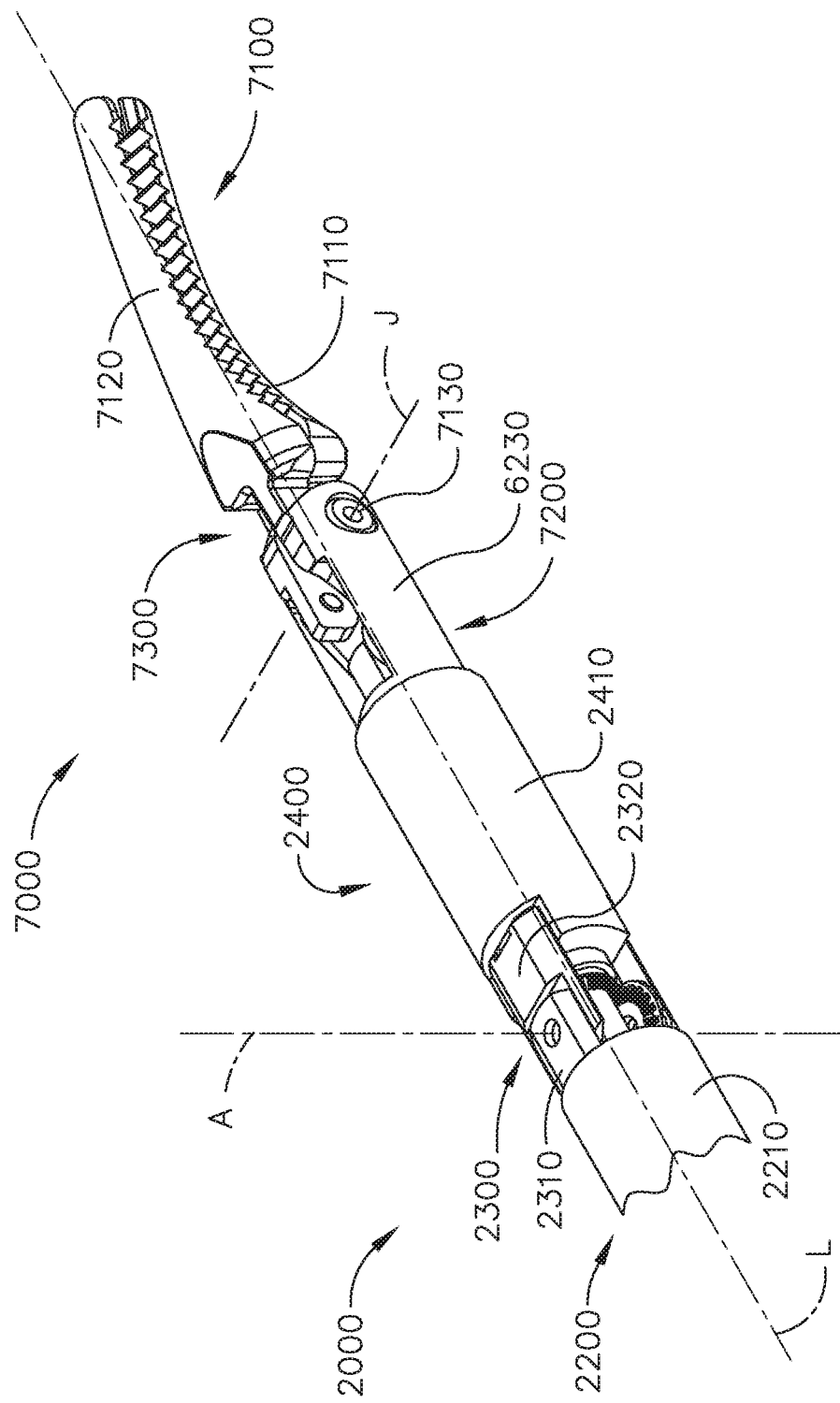
FIG. 18 is a partial perspective view of the end effector of FIG. 14 rotated in a first direction.
Figure 19:
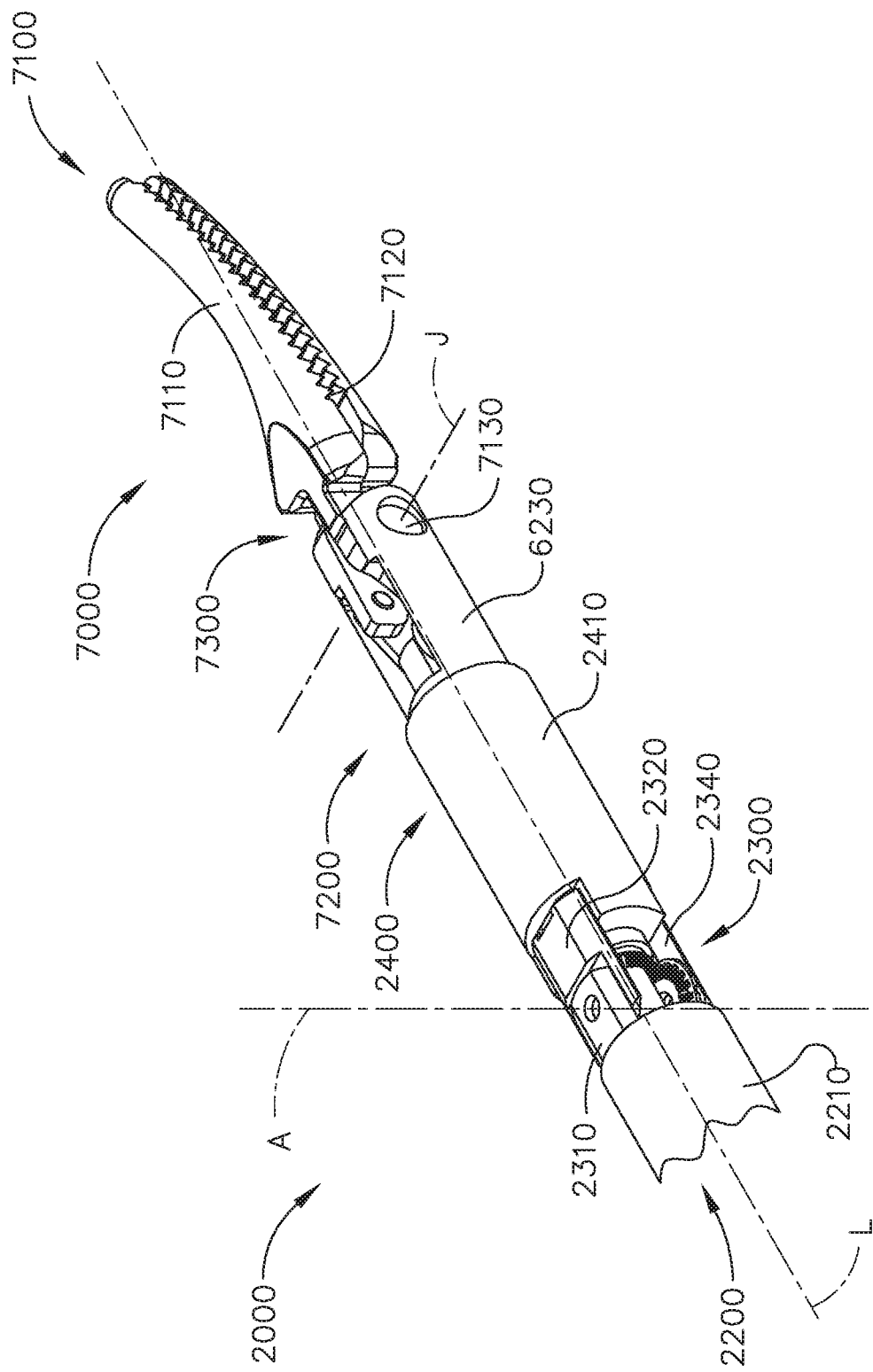
FIG. 19 is a partial perspective view of the end effector of FIG. 14 rotated in a second direction.
Figure 26:
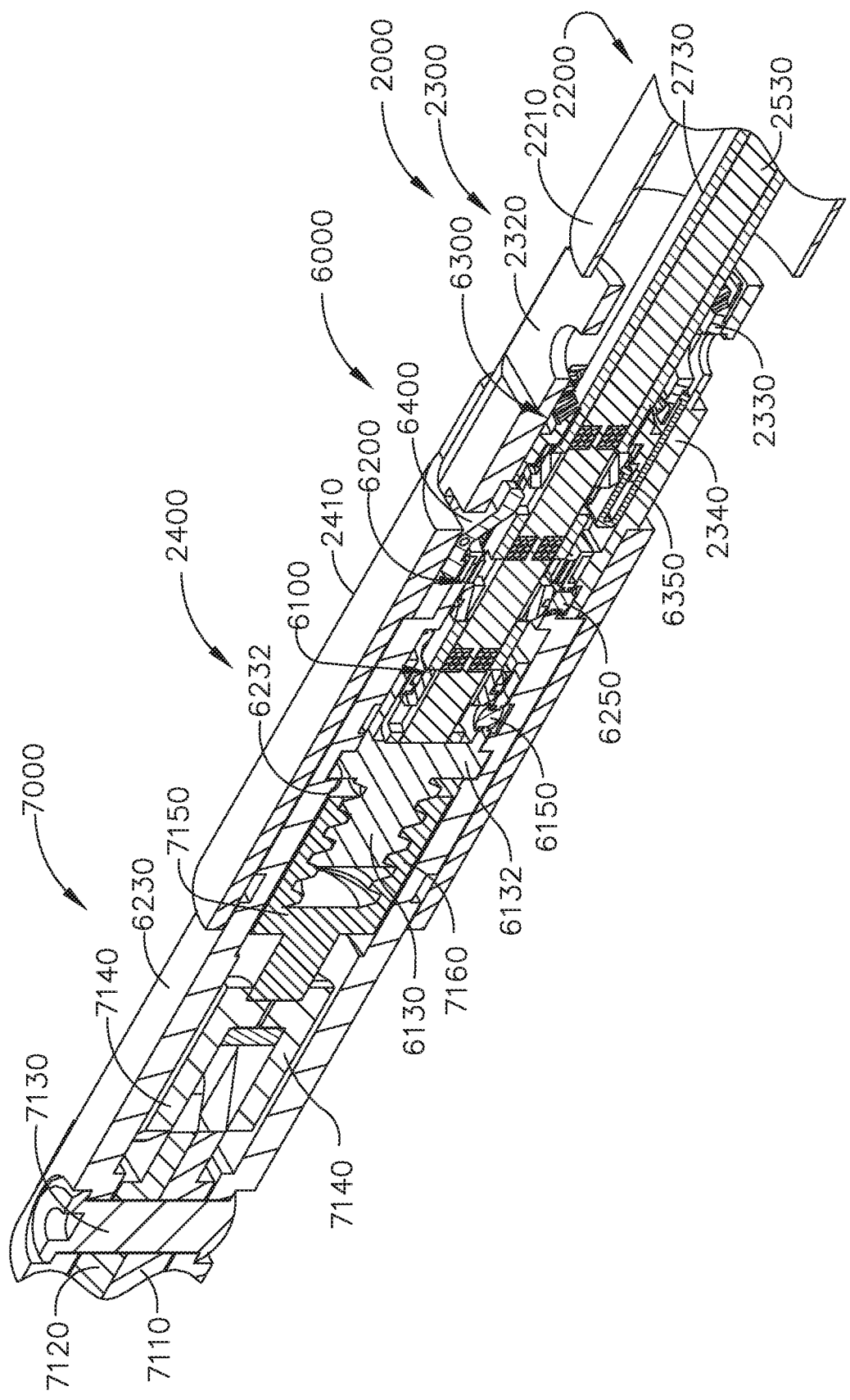
FIG. 26 is another partial cross-sectional perspective view of the end effector of FIG. 14 attached to the shaft assembly of FIG. 2.
Figure 27:
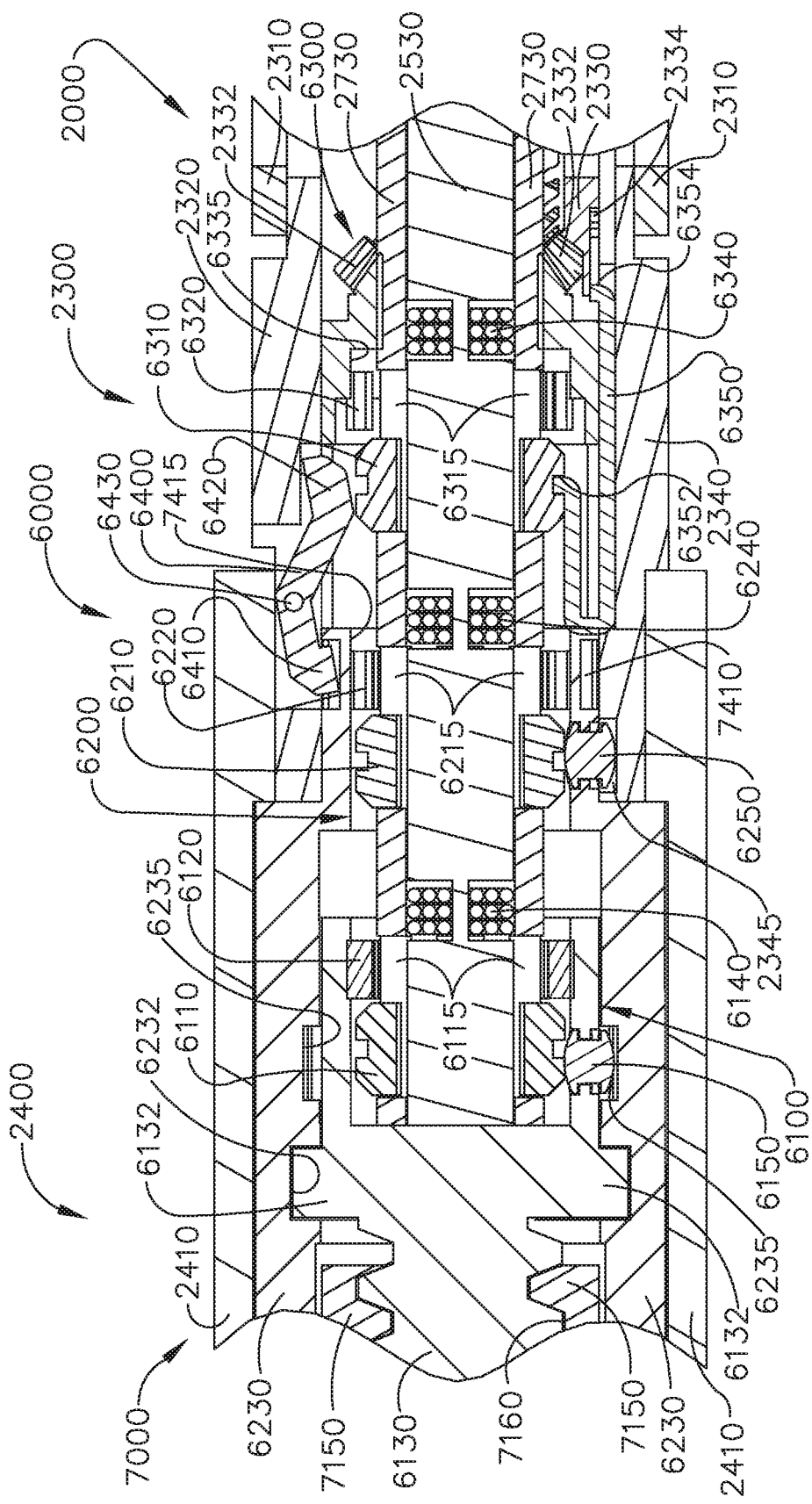
FIG. 27 is a partial cross-sectional view of the end effector of FIG. 14 attached to the shaft assembly of FIG. 2 depicting a first, second, and third clutch of the end effector.

As discussed above, the control system 1800 is configured to actuate the electric motor 1610 to perform three different end effector functions—clamping/opening the jaw assembly 7100 (FIGS. 14 and 15), rotating the end effector 7000 about a longitudinal axis (FIGS. 18 and 19), and articulating the end effector 7000 about an articulation axis (FIGS. 16 and 17). Referring primarily to FIGS. 26 and 27, the control system 1800 is configured to operate a transmission 6000 to selectively perform these three end effector functions. The transmission 6000 comprises a first clutch system 6100 configured to selectively transmit the rotation of the drive shaft 2730 to the drive screw 6130 of the end effector 7000 to open or close the jaw assembly 7100, depending on the direction in which the drive shaft 2730 is rotated. The transmission 6000 further comprises a second clutch system 6200 configured to selectively transmit the rotation of the drive shaft 2730 to the outer housing 6230 of the end effector 7000 to rotate the end effector 7000 about the longitudinal axis L. The transmission 6000 also comprises a third clutch system 6300 configured to selectively transmit the rotation of the drive shaft 2730 to the articulation joint 2300 to articulate the distal attachment portion 2400 and the end effector 7000 about the articulation axis A. The clutch systems 6100, 6200, and 6300 are in electrical communication with the control system 1800 via electrical circuits extending through the shaft 2510, the connector pins 2520, the connector pins 1520, and the shaft 1510, for example. In at least one instance, each of these clutch control circuits comprises two connector pins 2520 and two connector pins 1520, for example.

In various instances, further to the above, the shaft 2510 and/or the shaft 1510 comprise a flexible circuit including electrical traces which form part of the clutch control circuits. The flexible circuit can comprise a ribbon, or substrate, with conductive pathways defined therein and/or thereon. The flexible circuit can also comprise sensors and/or any solid state component, such as signal smoothing capacitors, for example, mounted thereto. In at least one instance, each of the conductive pathways can comprise one or more signal smoothing capacitors which can, among other things, even out fluctuations in signals transmitted through the conductive pathways. In various instances, the flexible circuit can be coated with at least one material, such as an elastomer, for example, which can seal the flexible circuit against fluid ingress.

Figure 22A:
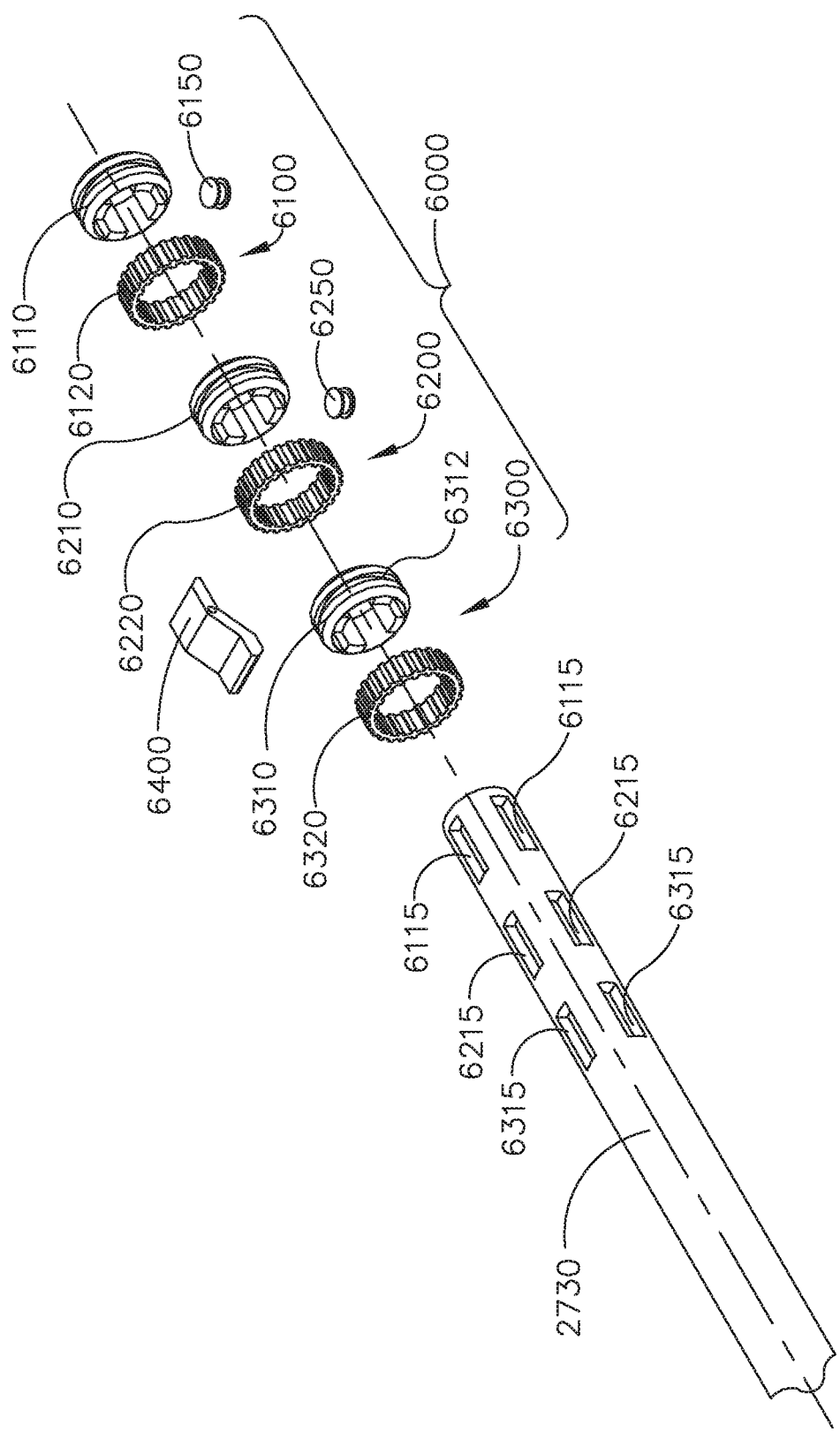
FIG. 22A is an exploded view of the distal portion of the shaft assembly of FIG. 2 illustrated with some components removed.
Figure 28:
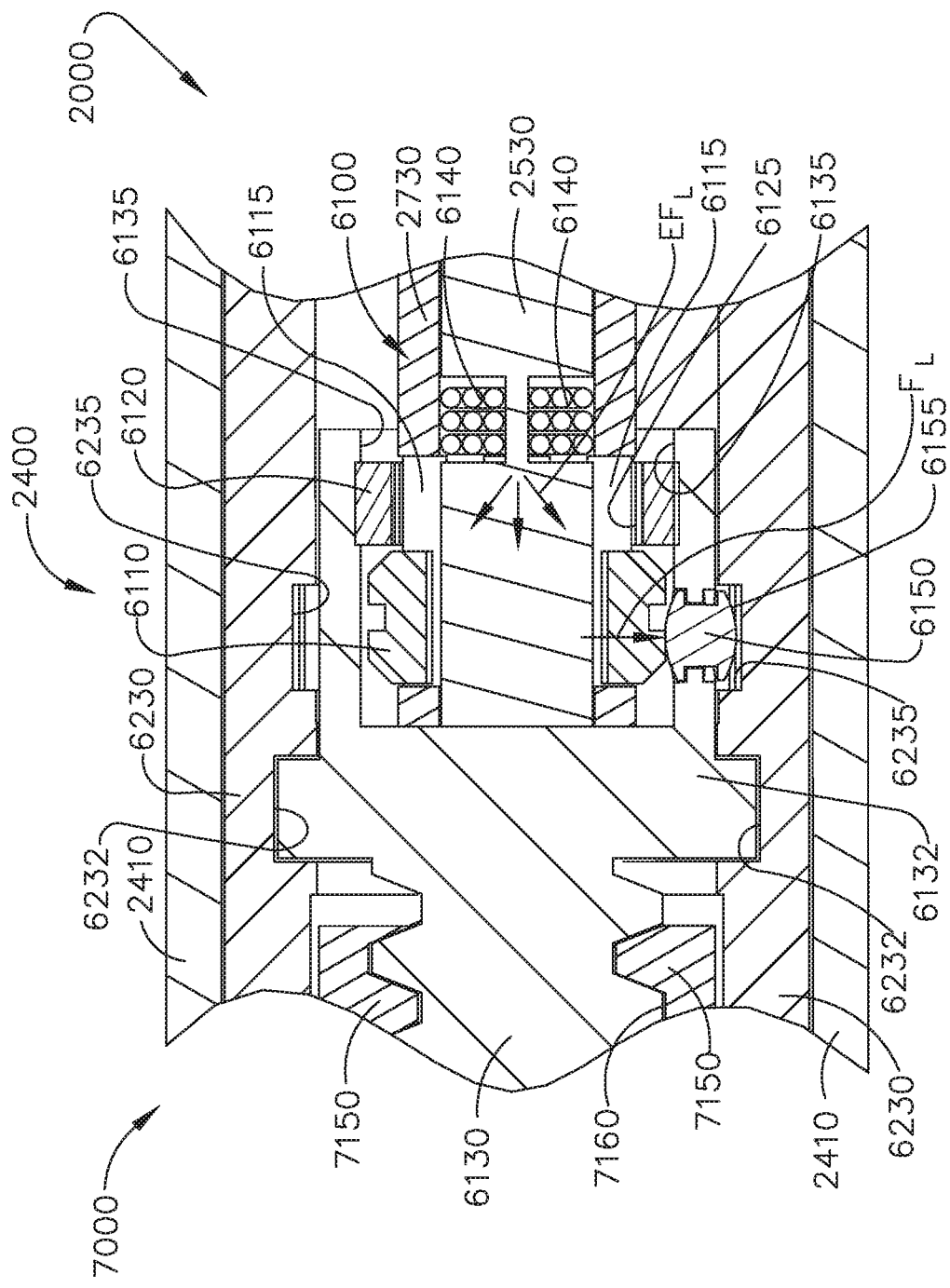
FIG. 28 depicts the first clutch of FIG. 27 in an unactuated condition.

Referring primarily to FIG. 28, the first clutch system 6100 comprises a first clutch 6110, an expandable first drive ring 6120, and a first electromagnetic actuator 6140. The first clutch 6110 comprises an annular ring and is slideably disposed on the drive shaft 2730. The first clutch 6110 is comprised of a magnetic material and is movable between a disengaged, or unactuated, position (FIG. 28) and an engaged, or actuated, position (FIG. 29) by electromagnetic fields EF generated by the first electromagnetic actuator 6140. In various instances, the first clutch 6110 is at least partially comprised of iron and/or nickel, for example. In at least one instance, the first clutch 6110 comprises a permanent magnet. As illustrated in FIG. 22A, the drive shaft 2730 comprises one or more longitudinal key slots 6115 defined therein which are configured to constrain the longitudinal movement of the clutch 6110 relative to the drive shaft 2730. More specifically, the clutch 6110 comprises one or more keys extending into the key slots 6115 such that the distal ends of the key slots 6115 stop the distal movement of the clutch 6110 and the proximal ends of the key slots 6115 stop the proximal movement of the clutch 6110.

Figure 29:
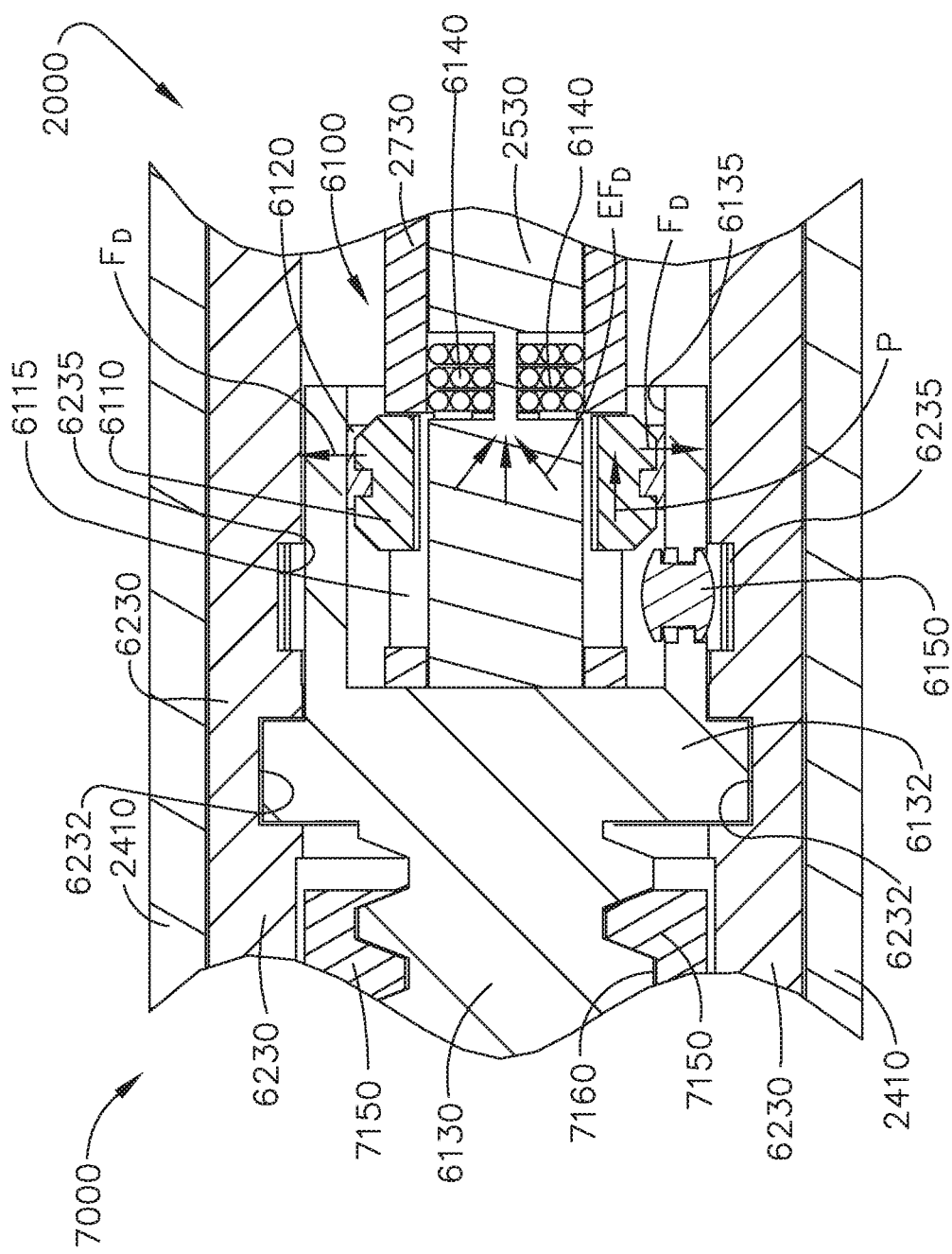
FIG. 29 depicts the first clutch of FIG. 27 in an actuated condition.

When the first clutch 6110 is in its disengaged position (FIG. 28), the first clutch 6110 rotates with the drive shaft 2130 but does not transmit rotational motion to the first drive ring 6120. As can be seen in FIG. 28, the first clutch 6110 is separated from, or not in contact with, the first drive ring 6120. As a result, the rotation of the drive shaft 2730 and the first clutch 6110 is not transmitted to the drive screw 6130 when the first clutch assembly 6100 is in its disengaged state. When the first clutch 6110 is in its engaged position (FIG. 29), the first clutch 6110 is engaged with the first drive ring 6120 such that the first drive ring 6120 is expanded, or stretched, radially outwardly into contact with the drive screw 6130. In at least one instance, the first drive ring 6120 comprises an elastomeric band, for example. As can be seen in FIG. 29, the first drive ring 6120 is compressed against an annular inner sidewall 6135 of the drive screw 6130. As a result, the rotation of the drive shaft 2730 and the first clutch 6110 is transmitted to the drive screw 6130 when the first clutch assembly 6100 is in its engaged state. Depending on the direction in which the drive shaft 2730 is rotated, the first clutch assembly 6100 can move the jaw assembly 7100 into its open and closed configurations when the first clutch assembly 6100 is in its engaged state.

As described above, the first electromagnetic actuator 6140 is configured to generate magnetic fields to move the first clutch 6110 between its disengaged (FIG. 28) and engaged (FIG. 29) positions. For instance, referring to FIG. 28, the first electromagnetic actuator 6140 is configured to emit a magnetic field $EF_L$ which repulses, or drives, the first clutch 6110 away from the first drive ring 6120 when the first clutch assembly 6100 is in its disengaged state. The first electromagnetic actuator 6140 comprises one or more wound coils in a cavity defined in the shaft frame 2530 which generate the magnetic field $EF_L$ when current flows in a first direction through a first electrical clutch circuit including the wound coils. The control system 1800 is configured to apply a first voltage polarity to the first electrical clutch circuit to create the current flowing in the first direction. The control system 1800 can continuously apply the first voltage polarity to the first electric shaft circuit to continuously hold the first clutch 6110 in its disengaged position. While such an arrangement can prevent the first clutch 6110 from unintentionally engaging the first drive ring 6120, such an arrangement can also consume a lot of power. Alternatively, the control system 1800 can apply the first voltage polarity to the first electrical clutch circuit for a sufficient period of time to position the first clutch 6110 in its disengaged position and then discontinue applying the first voltage polarity to the first electric clutch circuit, thereby resulting in a lower consumption of power. That being said, the first clutch assembly 6100 further comprises a first clutch lock 6150 mounted in the drive screw 6130 which is configured to releasably hold the first clutch 6110 in its disengaged position. The first clutch lock 6150 is configured to prevent, or at least reduce the possibility of, the first clutch 6110 from becoming unintentionally engaged with the first drive ring 6120. When the first clutch 6110 is in its disengaged position, as illustrated in FIG. 28, the first clutch lock 6150 interferes with the free movement of the first clutch 6110 and holds the first clutch 6110 in position via a friction force and/or an interference force therebetween. In at least one instance, the first clutch lock 6150 comprises an elastomeric plug, seat, or detent, comprised of rubber, for example. In certain instances, the first clutch lock 6150 comprises a permanent magnet which holds the first clutch 6110 in its disengaged position by an electromagnetic force. In any event, the first electromagnetic actuator 6140 can apply an electromagnetic pulling force to the first clutch 6110 that overcomes these forces, as described in greater detail below.

Further to the above, referring to FIG. 29, the first electromagnetic actuator 6140 is configured to emit a magnetic field $EF_D$ which pulls, or drives, the first clutch 6110 toward the first drive ring 6120 when the first clutch assembly 6100 is in its engaged state. The coils of the first electromagnetic actuator 6140 generate the magnetic field $EF_D$ when current flows in a second, or opposite, direction through the first electrical clutch circuit. The control system 1800 is configured to apply an opposite voltage polarity to the first electrical clutch circuit to create the current flowing in the opposite direction. The control system 1800 can continuously apply the opposite voltage polarity to the first electrical clutch circuit to continuously hold the first clutch 6110 in its engaged position and maintain the operable engagement between the first drive ring 6120 and the drive screw 6130. Alternatively, the first clutch 6110 can be configured to become wedged within the first drive ring 6120 when the first clutch 6110 is in its engaged position and, in such instances, the control system 1800 may not need to continuously apply a voltage polarity to the first electrical clutch circuit to hold the first clutch assembly 6100 in its engaged state. In such instances, the control system 1800 can discontinue applying the voltage polarity once the first clutch 6110 has been sufficiently wedged in the first drive ring 6120.

Notably, further to the above, the first clutch lock 6150 is also configured to lockout the jaw assembly drive when the first clutch 6110 is in its disengaged position. More specifically, referring again to FIG. 28, the first clutch 6110 pushes the first clutch lock 6150 in the drive screw 6130 into engagement with the outer housing 6230 of the end effector 7000 when the first clutch 6110 is in its disengaged position such that the drive screw 6130 does not rotate, or at least substantially rotate, relative to the outer housing 6230. The outer housing 6230 comprises a slot 6235 defined therein which is configured to receive the first clutch lock 6150. When the first clutch 6110 is moved into its engaged position, referring to FIG. 29, the first clutch 6110 is no longer engaged with the first clutch lock 6150 and, as a result, the first clutch lock 6150 is no longer biased into engagement with the outer housing 6230 and the drive screw 6130 can rotate freely with respect to the outer housing 6230. As a result of the above, the first clutch 6110 can do at least two things—operate the jaw drive when the first clutch 6110 is in its engaged position and lock out the jaw drive when the first clutch 6110 is in its disengaged position.

Moreover, further to the above, the threads of the threaded portions 6160 and 7160 can be configured to prevent, or at least resist, backdriving of the jaw drive. In at least one instance, the thread pitch and/or angle of the threaded portions 6160 and 7160, for example, can be selected to prevent the backdriving, or unintentional opening, of the jaw assembly 7100. As a result of the above, the possibility of the jaw assembly 7100 unintentionally opening or closing is prevented, or at least reduced.

Figure 30:
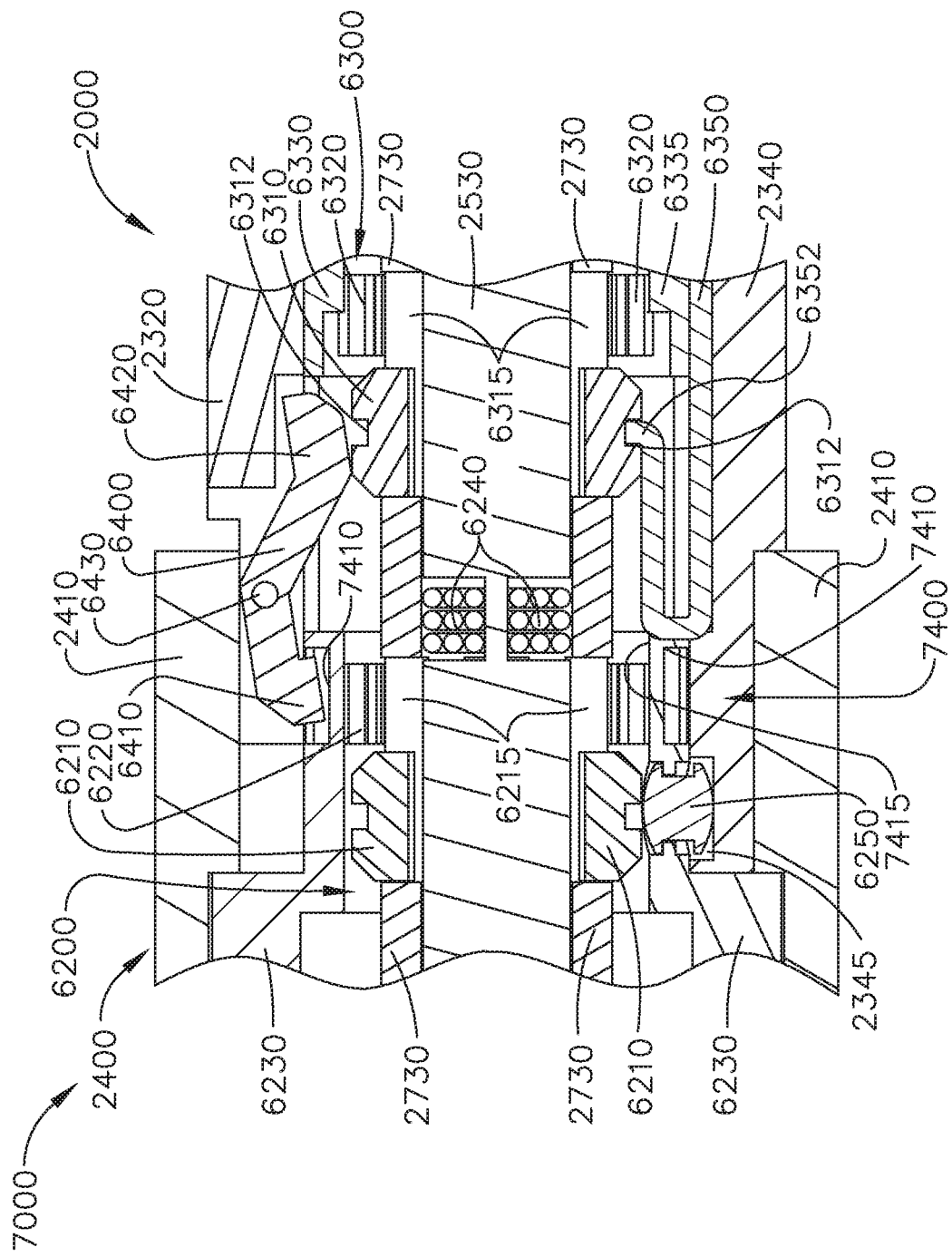
FIG. 30 depicts the second clutch of FIG. 27 in an unactuated condition.

Referring primarily to FIG. 30, the second clutch system 6200 comprises a second clutch 6210, an expandable second drive ring 6220, and a second electromagnetic actuator 6240. The second clutch 6210 comprises an annular ring and is slideably disposed on the drive shaft 2730. The second clutch 6210 is comprised of a magnetic material and is movable between a disengaged, or unactuated, position (FIG. 30) and an engaged, or actuated, position (FIG. 31) by electromagnetic fields EF generated by the second electromagnetic actuator 6240. In various instances, the second clutch 6210 is at least partially comprised of iron and/or nickel, for example. In at least one instance, the second clutch 6210 comprises a permanent magnet. As illustrated in FIG. 22A, the drive shaft 2730 comprises one or more longitudinal key slots 6215 defined therein which are configured to constrain the longitudinal movement of the second clutch 6210 relative to the drive shaft 2730. More specifically, the second clutch 6210 comprises one or more keys extending into the key slots 6215 such that the distal ends of the key slots 6215 stop the distal movement of the second clutch 6210 and the proximal ends of the key slots 6215 stop the proximal movement of the second clutch 6210.

Figure 31:
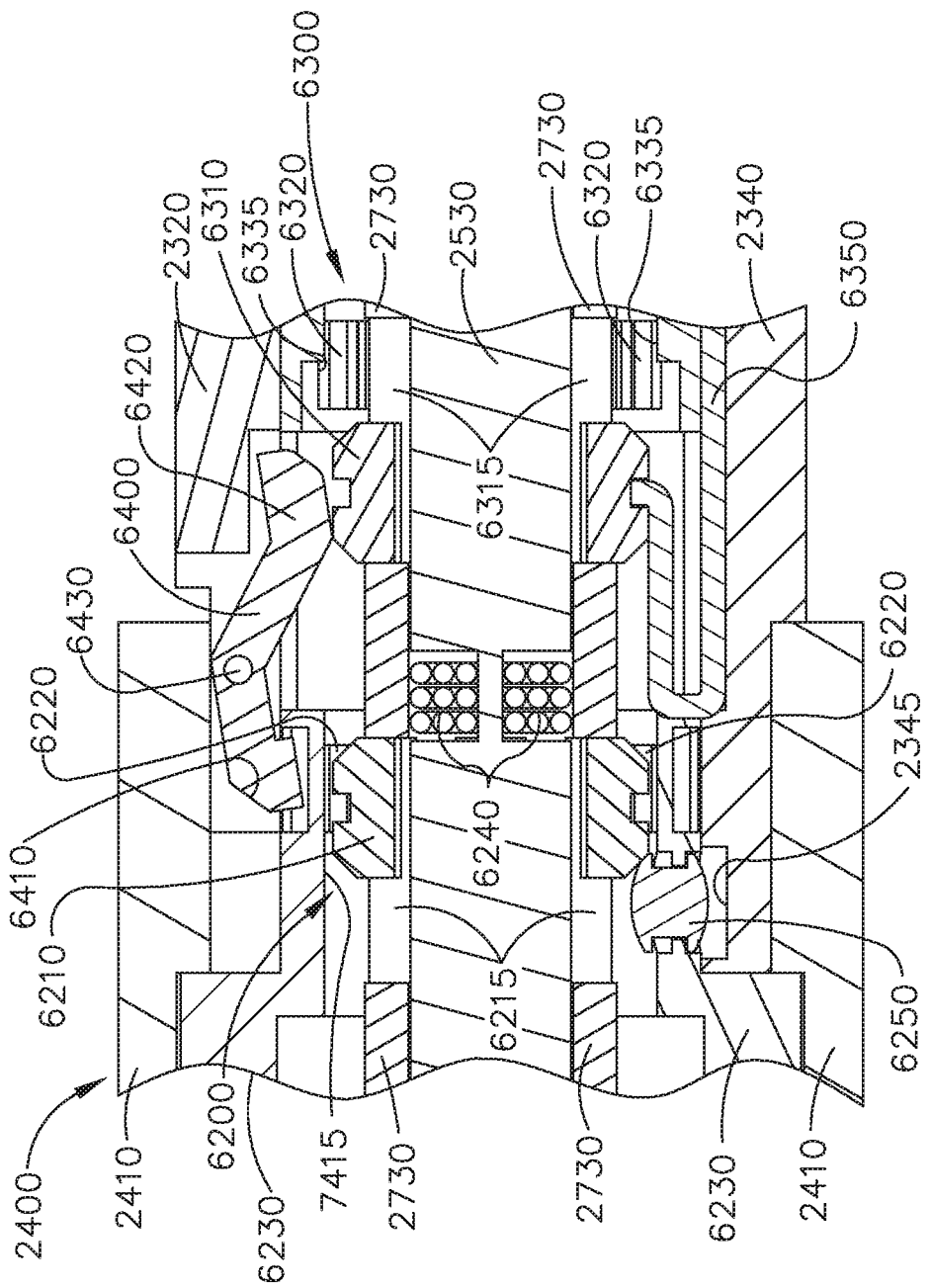
FIG. 31 depicts the second clutch of FIG. 27 in an actuated condition.

When the second clutch 6210 is in its disengaged position, referring to FIG. 30, the second clutch 6210 rotates with the drive shaft 2730 but does not transmit rotational motion to the second drive ring 6220. As can be seen in FIG. 30, the second clutch 6210 is separated from, or not in contact with, the second drive ring 6220. As a result, the rotation of the drive shaft 2730 and the second clutch 6210 is not transmitted to the outer housing 6230 of the end effector 7000 when the second clutch assembly 6200 is in its disengaged state. When the second clutch 6210 is in its engaged position (FIG. 31), the second clutch 6210 is engaged with the second drive ring 6220 such that the second drive ring 6220 is expanded, or stretched, radially outwardly into contact with the outer housing 6230. In at least one instance, the second drive ring 6220 comprises an elastomeric band, for example. As can be seen in FIG. 31, the second drive ring 6220 is compressed against an annular inner sidewall 7415 of the outer housing 6230. As a result, the rotation of the drive shaft 2730 and the second clutch 6210 is transmitted to the outer housing 6230 when the second clutch assembly 6200 is in its engaged state. Depending on the direction in which the drive shaft 2730 is rotated, the second clutch assembly 6200 can rotate the end effector 7000 in a first direction or a second direction about the longitudinal axis L when the second clutch assembly 6200 is in its engaged state.

As described above, the second electromagnetic actuator 6240 is configured to generate magnetic fields to move the second clutch 6210 between its disengaged (FIG. 30) and engaged (FIG. 31) positions. For instance, the second electromagnetic actuator 6240 is configured to emit a magnetic field $EF_L$ which repulses, or drives, the second clutch 6210 away from the second drive ring 6220 when the second clutch assembly 6200 is in its disengaged state. The second electromagnetic actuator 6240 comprises one or more wound coils in a cavity defined in the shaft frame 2530 which generate the magnetic field $EF_L$ when current flows in a first direction through a second electrical clutch circuit including the wound coils. The control system 1800 is configured to apply a first voltage polarity to the second electrical clutch circuit to create the current flowing in the first direction. The control system 1800 can continuously apply the first voltage polarity to the second electric clutch circuit to continuously hold the second clutch 6120 in its disengaged position. While such an arrangement can prevent the second clutch 6210 from unintentionally engaging the second drive ring 6220, such an arrangement can also consume a lot of power. Alternatively, the control system 1800 can apply the first voltage polarity to the second electrical clutch circuit for a sufficient period of time to position the second clutch 6210 in its disengaged position and then discontinue applying the first voltage polarity to the second electric clutch circuit, thereby resulting in a lower consumption of power. That being said, the second clutch assembly 6200 further comprises a second clutch lock 6250 mounted in the outer housing 6230 which is configured to releasably hold the second clutch 6210 in its disengaged position. Similar to the above, the second clutch lock 6250 can prevent, or at least reduce the possibility of, the second clutch 6210 from becoming unintentionally engaged with the second drive ring 6220. When the second clutch 6210 is in its disengaged position, as illustrated in FIG. 30, the second clutch lock 6250 interferes with the free movement of the second clutch 6210 and holds the second clutch 6210 in position via a friction and/or interference force therebetween. In at least one instance, the second clutch lock 6250 comprises an elastomeric plug, seat, or detent, comprised of rubber, for example. In certain instances, the second clutch lock 6250 comprises a permanent magnet which holds the second clutch 6210 in its disengaged position by an electromagnetic force. That said, the second electromagnetic actuator 6240 can apply an electromagnetic pulling force to the second clutch 6210 that overcomes these forces, as described in greater detail below.

Further to the above, referring to FIG. 31, the second electromagnetic actuator 6240 is configured to emit a magnetic field $EF_D$ which pulls, or drives, the second clutch 6210 toward the second drive ring 6220 when the second clutch assembly 6200 is in its engaged state. The coils of the second electromagnetic actuator 6240 generate the magnetic field $EF_D$ when current flows in a second, or opposite, direction through the second electrical shaft circuit. The control system 1800 is configured to apply an opposite voltage polarity to the second electrical shaft circuit to create the current flowing in the opposite direction. The control system 1800 can continuously apply the opposite voltage polarity to the second electric shaft circuit to continuously hold the second clutch 6210 in its engaged position and maintain the operable engagement between the second drive ring 6220 and the outer housing 6230. Alternatively, the second clutch 6210 can be configured to become wedged within the second drive ring 6220 when the second clutch 6210 is in its engaged position and, in such instances, the control system 1800 may not need to continuously apply a voltage polarity to the second shaft electrical circuit to hold the second clutch assembly 6200 in its engaged state. In such instances, the control system 1800 can discontinue applying the voltage polarity once the second clutch 6210 has been sufficiently wedged in the second drive ring 6220.

Notably, further to the above, the second clutch lock 6250 is also configured to lockout the rotation of the end effector 7000 when the second clutch 6210 is in its disengaged position. More specifically, referring again to FIG. 30, the second clutch 6210 pushes the second clutch lock 6250 in the outer shaft 6230 into engagement with the articulation link 2340 when the second clutch 6210 is in its disengaged position such that the end effector 7000 does not rotate, or at least substantially rotate, relative to the distal attachment portion 2400 of the shaft assembly 2000. As illustrated in FIG. 27, the second clutch lock 6250 is positioned or wedged within a slot, or channel, 2345 defined in the articulation link 2340 when the second clutch 6210 is in its disengaged position. As a result of the above, the possibility of the end effector 7000 unintentionally rotating is prevented, or at least reduced. Moreover, as a result of the above, the second clutch 6210 can do at least two things—operate the end effector rotation drive when the second clutch 6210 is in its engaged position and lock out the end effector rotation drive when the second clutch 6210 is in its disengaged position.

Figure 25:
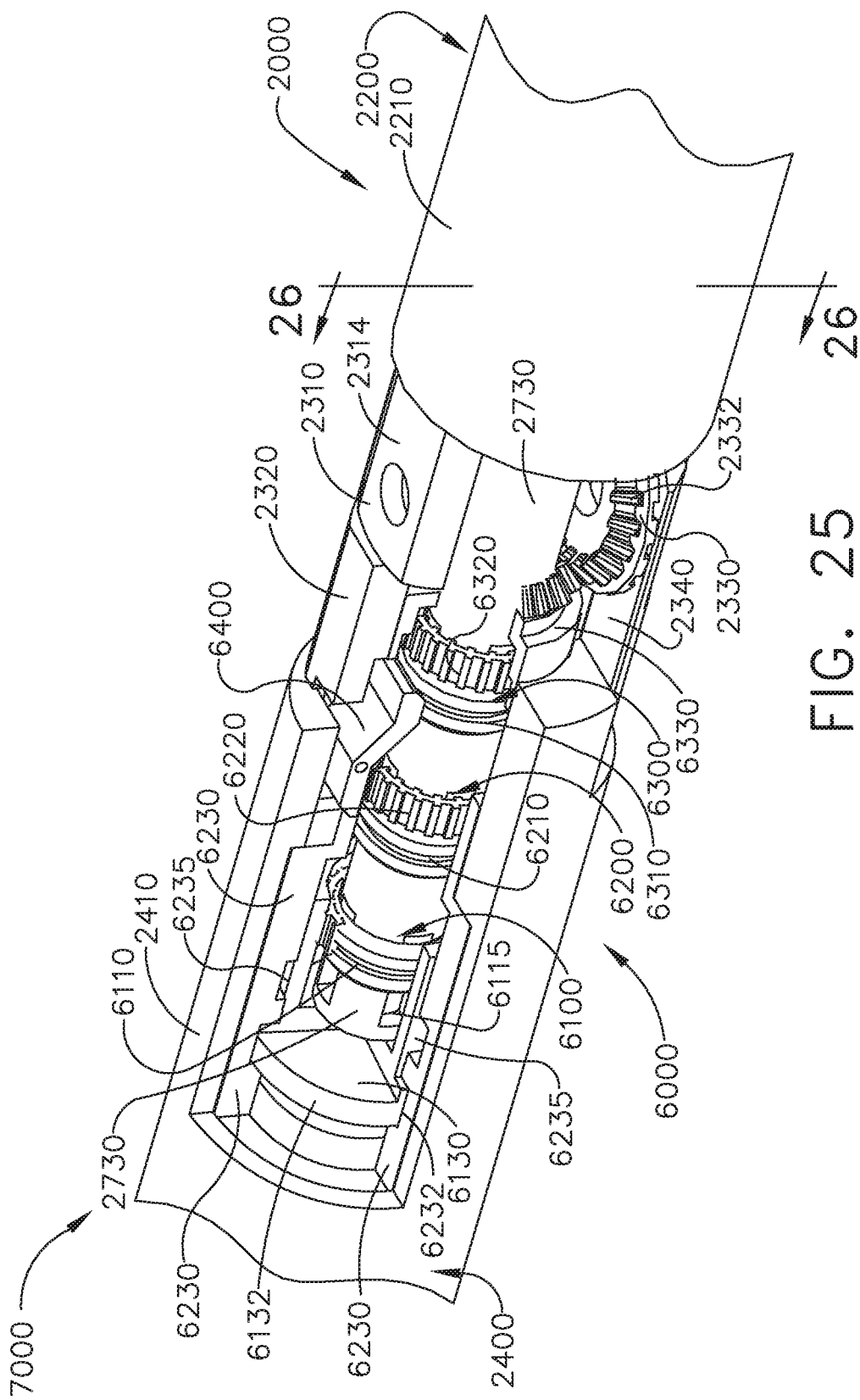
FIG. 25 is a partial cross-sectional perspective view of the end effector of FIG. 14 attached to the shaft assembly of FIG. 2.

Referring primarily to FIGS. 22, 24, and 25, the shaft assembly 2000 further comprises an articulation drive system configured to articulate the distal attachment portion 2400 and the end effector 7000 about the articulation joint 2300. The articulation drive system comprises an articulation drive 6330 rotatably supported within the distal attachment portion 2400. That said, the articulation drive 6330 is closely received within the distal attachment portion 2400 such that the articulation drive 6330 does not translate, or at least substantially translate, relative to the distal attachment portion 2400. The articulation drive system of the shaft assembly 2000 further comprises a stationary gear 2330 fixedly mounted to the articulation frame 2310. More specifically, the stationary gear 2330 is fixedly mounted to a pin connecting a tab 2314 of the articulation frame 2310 and the articulation link 2340 such that the stationary gear 2330 does not rotate relative to the articulation frame 2310. The stationary gear 2330 comprises a central body 2335 and an annular array of stationary teeth 2332 extending around the perimeter of the central body 2335. The articulation drive 6330 comprises an annular array of drive teeth 6332 which is meshingly engaged with the stationary teeth 2332. When the articulation drive 6330 is rotated, the articulation drive 6330 pushes against the stationary gear 2330 and articulates the distal attachment portion 2400 of the shaft assembly 2000 and the end effector 7000 about the articulation joint 2300.

Figure 32:
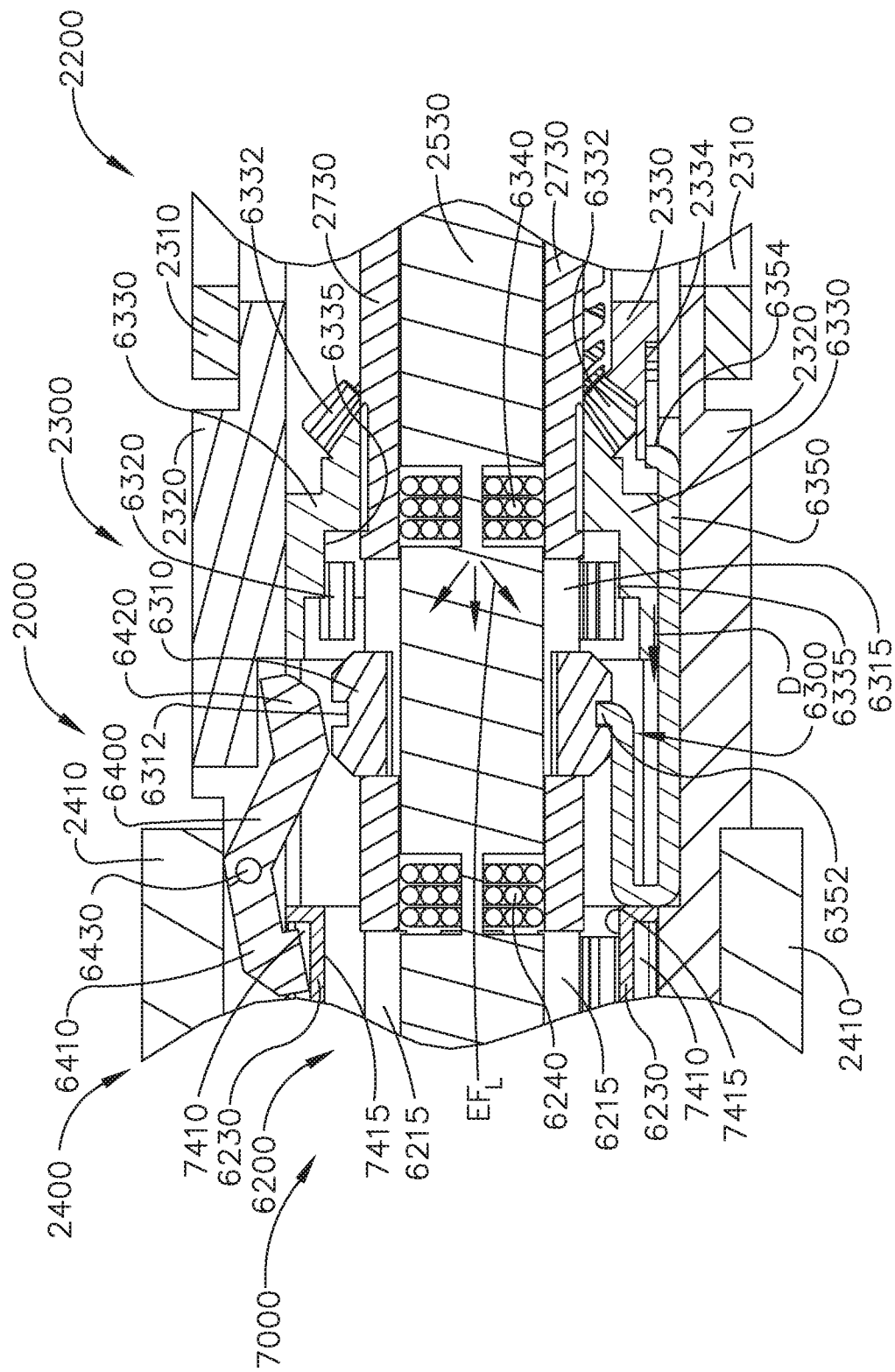
FIG. 32 depicts the third clutch of FIG. 27 in an unactuated condition.

Referring primarily to FIG. 32, the third clutch system 6300 comprises a third clutch 6310, an expandable third drive ring 6320, and a third electromagnetic actuator 6340. The third clutch 6310 comprises an annular ring and is slideably disposed on the drive shaft 2730. The third clutch 6310 is comprised of a magnetic material and is movable between a disengaged, or unactuated, position (FIG. 32) and an engaged, or actuated, position (FIG. 33) by electromagnetic fields EF generated by the third electromagnetic actuator 6340. In various instances, the third clutch 6310 is at least partially comprised of iron and/or nickel, for example. In at least one instance, the third clutch 6310 comprises a permanent magnet. As illustrated in FIG. 22A, the drive shaft 2730 comprises one or more longitudinal key slots 6315 defined therein which are configured to constrain the longitudinal movement of the third clutch 6310 relative to the drive shaft 2730. More specifically, the third clutch 6310 comprises one or more keys extending into the key slots 6315 such that the distal ends of the key slots 6315 stop the distal movement of the third clutch 6310 and the proximal ends of the key slots 6315 stop the proximal movement of the third clutch 6310.

Figure 33:
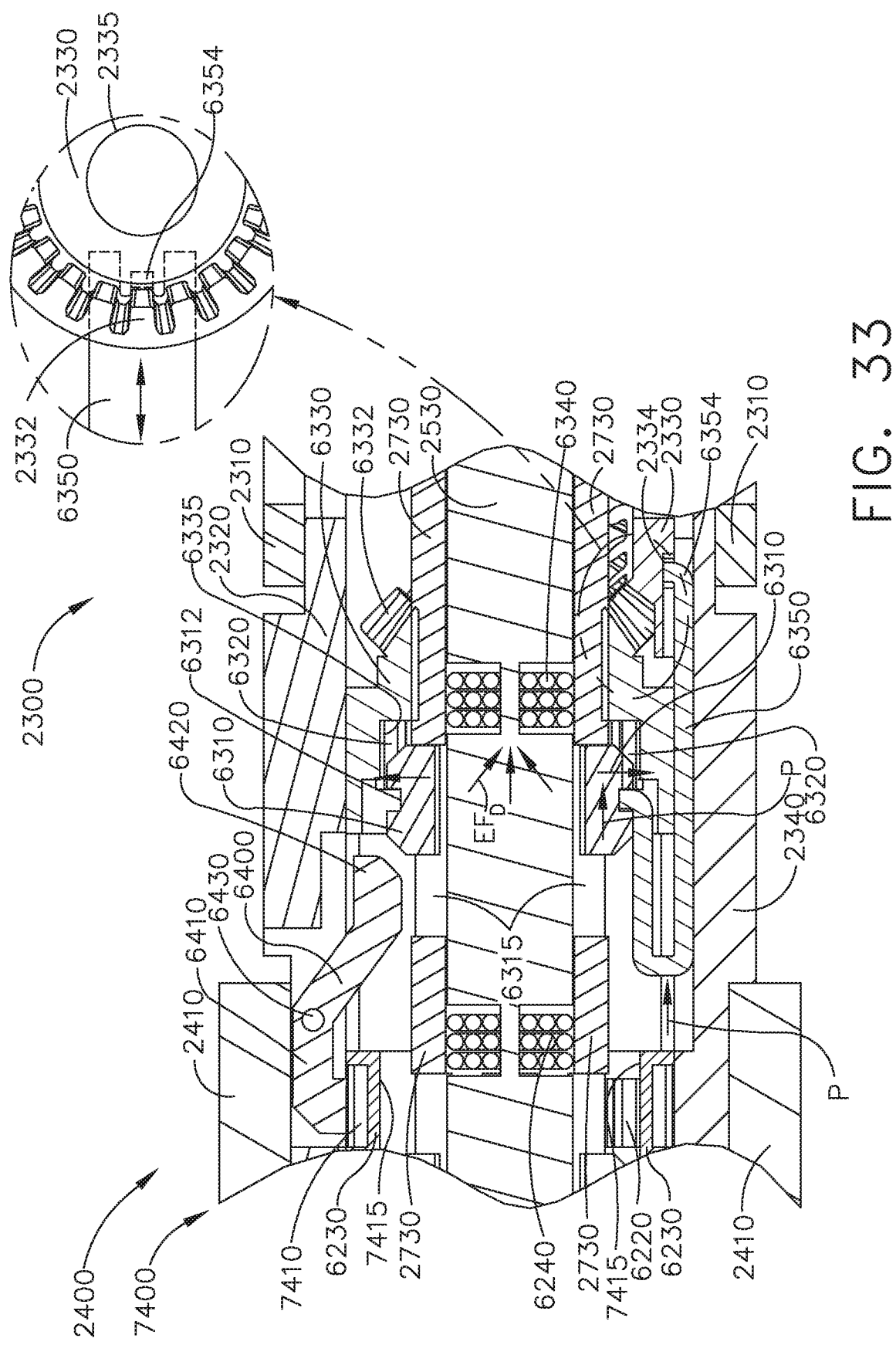
FIG. 33 depicts the third clutch of FIG. 27 in an actuated condition.

When the third clutch 6310 is in its disengaged position, referring to FIG. 32, the third clutch 6310 rotates with the drive shaft 2730 but does not transmit rotational motion to the third drive ring 6320. As can be seen in FIG. 32, the third clutch 6310 is separated from, or not in contact with, the third drive ring 6320. As a result, the rotation of the drive shaft 2730 and the third clutch 6310 is not transmitted to the articulation drive 6330 when the third clutch assembly 6300 is in its disengaged state. When the third clutch 6310 is in its engaged position, referring to FIG. 33, the third clutch 6310 is engaged with the third drive ring 6320 such that the third drive ring 6320 is expanded, or stretched, radially outwardly into contact with the articulation drive 6330. In at least one instance, the third drive ring 6320 comprises an elastomeric band, for example. As can be seen in FIG. 33, the third drive ring 6320 is compressed against an annular inner sidewall 6335 of the articulation drive 6330. As a result, the rotation of the drive shaft 2730 and the third clutch 6310 is transmitted to the articulation drive 6330 when the third clutch assembly 6300 is in its engaged state. Depending on the direction in which the drive shaft 2730 is rotated, the third clutch assembly 6300 can articulate the distal attachment portion 2400 of the shaft assembly 2000 and the end effector 7000 in a first or second direction about the articulation joint 2300.

As described above, the third electromagnetic actuator 6340 is configured to generate magnetic fields to move the third clutch 6310 between its disengaged (FIG. 32) and engaged (FIG. 33) positions. For instance, referring to FIG. 32, the third electromagnetic actuator 6340 is configured to emit a magnetic field $EF_L$ which repulses, or drives, the third clutch 6310 away from the third drive ring 6320 when the third clutch assembly 6300 is in its disengaged state. The third electromagnetic actuator 6340 comprises one or more wound coils in a cavity defined in the shaft frame 2530 which generate the magnetic field $EF_L$ when current flows in a first direction through a third electrical clutch circuit including the wound coils. The control system 1800 is configured to apply a first voltage polarity to the third electrical clutch circuit to create the current flowing in the first direction. The control system 1800 can continuously apply the first voltage polarity to the third electric clutch circuit to continuously hold the third clutch 6310 in its disengaged position. While such an arrangement can prevent the third clutch 6310 from unintentionally engaging the third drive ring 6320, such an arrangement can also consume a lot of power. Alternatively, the control system 1800 can apply the first voltage polarity to the third electrical clutch circuit for a sufficient period of time to position the third clutch 6310 in its disengaged position and then discontinue applying the first voltage polarity to the third electric clutch circuit, thereby resulting in a lower consumption of power.

Further to the above, the third electromagnetic actuator 6340 is configured to emit a magnetic field $EF_D$ which pulls, or drives, the third clutch 6310 toward the third drive ring 6320 when the third clutch assembly 6300 is in its engaged state. The coils of the third electromagnetic actuator 6340 generate the magnetic field $EF_D$ when current flows in a second, or opposite, direction through the third electrical clutch circuit. The control system 1800 is configured to apply an opposite voltage polarity to the third electrical shaft circuit to create the current flowing in the opposite direction. The control system 1800 can continuously apply the opposite voltage polarity to the third electric shaft circuit to continuously hold the third clutch 6310 in its engaged position and maintain the operable engagement between the third drive ring 6320 and the articulation drive 6330. Alternatively, the third clutch 6210 can be configured to become wedged within the third drive ring 6320 when the third clutch 6310 is in its engaged position and, in such instances, the control system 1800 may not need to continuously apply a voltage polarity to the third shaft electrical circuit to hold the third clutch assembly 6300 in its engaged state. In such instances, the control system 1800 can discontinue applying the voltage polarity once the third clutch 6310 has been sufficiently wedged in the third drive ring 6320. In any event, the end effector 7000 is articulatable in a first direction or a second direction, depending on the direction in which the drive shaft 2730 is rotated, when the third clutch assembly 6300 is in its engaged state.

Further to the above, referring to FIGS. 22, 32, and 33, the articulation drive system further comprises a lockout 6350 which prevents, or at least inhibits, the articulation of the distal attachment portion 2400 of the shaft assembly 2000 and the end effector 7000 about the articulation joint 2300 when the third clutch 6310 is in its disengaged position (FIG. 32). Referring primarily to FIG. 22, the articulation link 2340 comprises a slot, or groove, 2350 defined therein wherein the lockout 6350 is slideably positioned in the slot 2350 and extends at least partially under the stationary articulation gear 2330. The lockout 6350 comprises at attachment hook 6352 engaged with the third clutch 6310. More specifically, the third clutch 6310 comprises an annular slot, or groove, 6312 defined therein and the attachment hook 6352 is positioned in the annular slot 6312 such that the lockout 6350 translates with the third clutch 6310. Notably, however, the lockout 6350 does not rotate, or at least substantially rotate, with the third clutch 6310. Instead, the annular groove 6312 in the third clutch 6310 permits the third clutch 6310 to rotate relative to the lockout 6350. The lockout 6350 further comprises a lockout hook 6354 slideably positioned in a radially-extending lockout slot 2334 defined in the bottom of the stationary gear 2330. When the third clutch 6310 is in its disengaged position, as illustrated in FIG. 32, the lockout 6350 is in a locked position in which the lockout hook 6354 prevents the end effector 7000 from rotating about the articulation joint 2300. When the third clutch 6310 is in its engaged position, as illustrated in FIG. 33, the lockout 6350 is in an unlocked position in which the lockout hook 6354 is no longer positioned in the lockout slot 2334. Instead, the lockout hook 6354 is positioned in a clearance slot defined in the middle or body 2335 of the stationary gear 2330. In such instances, the lockout hook 6354 can rotate within the clearance slot when the end effector 7000 rotates about the articulation joint 2300.

Further to the above, the radially-extending lockout slot 2334 depicted in FIGS. 32 and 33 extends longitudinally, i.e., along an axis which is parallel to the longitudinal axis of the elongate shaft 2200. Once the end effector 7000 has been articulated, however, the lockout hook 6354 is no longer aligned with the longitudinal lockout slot 2334. With this in mind, the stationary gear 2330 comprises a plurality, or an array, of radially-extending lockout slots 2334 defined in the bottom of the stationary gear 2330 such that, when the third clutch 6310 is deactuated and the lockout 6350 is pulled distally after the end effector 7000 has been articulated, the lockout hook 6354 can enter one of the lockout slots 2334 and lock the end effector 7000 in its articulated position. Thus, as a result, the end effector 7000 can be locked in an unarticulated and an articulated position. In various instances, the lockout slots 2334 can define discrete articulated positions for the end effector 7000. For instance, the lockout slots 2334 can be defined at 10 degree intervals, for example, which can define discrete articulation orientations for the end effector 7000 at 10 degree intervals. In other instances, these orientations can be at 5 degree intervals, for example. In alternative embodiments, the lockout 6350 comprises a brake that engages a circumferential shoulder defined in the stationary gear 2330 when the third clutch 6310 is disengaged from the third drive ring 6320. In such an embodiment, the end effector 7000 can be locked in any suitable orientation. In any event, the lockout 6350 prevents, or at least reduces the possibility of, the end effector 7000 unintentionally articulating. As a result of the above, the third clutch 6310 can do things—operate the articulation drive when it is in its engaged position and lock out the articulation drive when it is in its disengaged position.

Referring primarily to FIGS. 24 and 25, the shaft frame 2530 and the drive shaft 2730 extend through the articulation joint 2300 into the distal attachment portion 2400. When the end effector 7000 is articulated, as illustrated in FIGS. 16 and 17, the shaft frame 2530 and the drive shaft 2730 bend to accommodate the articulation of the end effector 7000. Thus, the shaft frame 2530 and the drive shaft 2730 are comprised of any suitable material which accommodates the articulation of the end effector 7000. Moreover, as discussed above, the shaft frame 2530 houses the first, second, and third electromagnetic actuators 6140, 6240, and 6340. In various instances, the first, second, and third electromagnetic actuators 6140, 6240, and 6340 each comprise wound wire coils, such as copper wire coils, for example, and the shaft frame 2530 is comprised of an insulative material to prevent, or at least reduce the possibility of, short circuits between the first, second, and third electromagnetic actuators 6140, 6240, and 6340. In various instances, the first, second, and third electrical clutch circuits extending through the shaft frame 2530 are comprised of insulated electrical wires, for example. Further to the above, the first, second, and third electrical clutch circuits place the electromagnetic actuators 6140, 6240, and 6340 in communication with the control system 1800 in the drive module 1100.

As described above, the clutches 6110, 6210, and/or 6310 can be held in their disengaged positions so that they do not unintentionally move into their engaged positions. In various arrangements, the clutch system 6000 comprises a first biasing member, such as a spring, for example, configured to bias the first clutch 6110 into its disengaged position, a second biasing member, such as a spring, for example, configured to bias the second clutch 6210 into its disengaged position, and/or a third biasing member, such as a spring, for example, configured to bias the third clutch 6110 into its disengaged position. In such arrangements, the biasing forces of the springs can be selectively overcome by the electromagnetic forces generated by the electromagnetic actuators when energized by an electrical current. Further to the above, the clutches 6110, 6210, and/or 6310 can be retained in their engaged positions by the drive rings 6120, 6220, and/or 6320, respectively. More specifically, in at least one instance, the drive rings 6120, 6220, and/or 6320 are comprised of an elastic material which grips or frictionally holds the clutches 6110, 6210, and/or 6310, respectively, in their engaged positions. In various alternative embodiments, the clutch system 6000 comprises a first biasing member, such as a spring, for example, configured to bias the first clutch 6110 into its engaged position, a second biasing member, such as a spring, for example, configured to bias the second clutch 6210 into its engaged position, and/or a third biasing member, such as a spring, for example, configured to bias the third clutch 6110 into its engaged position. In such arrangements, the biasing forces of the springs can be overcome by the electromagnetic forces applied by the electromagnetic actuators 6140, 6240, and/or 6340, respectively, as needed to selectively hold the clutches 6110, 6210, and 6310 in their disengaged positions. In any one operational mode of the surgical system, the control assembly 1800 can energize one of the electromagnetic actuators to engage one of the clutches while energizing the other two electromagnetic actuators to disengage the other two clutches.

Although the clutch system 6000 comprises three clutches to control three drive systems of the surgical system, a clutch system can comprise any suitable number of clutches to control any suitable number of systems. Moreover, although the clutches of the clutch system 6000 slide proximally and distally between their engaged and disengaged positions, the clutches of a clutch system can move in any suitable manner. In addition, although the clutches of the clutch system 6000 are engaged one at a time to control one drive motion at a time, various instances are envisioned in which more than one clutch can be engaged to control more than one drive motion at a time.

In view of the above, the reader should appreciate that the control system 1800 is configured to, one, operate the motor system 1600 to rotate the drive shaft system 2700 in an appropriate direction and, two, operate the clutch system 6000 to transfer the rotation of the drive shaft system 2700 to the appropriate function of the end effector 7000. Moreover, as discussed above, the control system 1800 is responsive to inputs from the clamping trigger system 2600 of the shaft assembly 2000 and the input system 1400 of the handle 1000. When the clamping trigger system 2600 is actuated, as discussed above, the control system 1800 activates the first clutch assembly 6100 and deactivates the second clutch assembly 6200 and the third clutch assembly 6300. In such instances, the control system 1800 also supplies power to the motor system 1600 to rotate the drive shaft system 2700 in a first direction to clamp the jaw assembly 7100 of the end effector 7000. When the control system 1800 detects that the jaw assembly 7100 is in its clamped configuration, the control system 1800 stops the motor assembly 1600 and deactivates the first clutch assembly 6100. When the control system 1800 detects that the clamping trigger system 2600 has been moved to, or is being moved to, its unactuated position, the control system 1800 activates, or maintains the activation of, the first clutch assembly 6100 and deactivates, or maintains the deactivation of, the second clutch assembly 6200 and the third clutch assembly 6300. In such instances, the control system 1800 also supplies power to the motor system 1600 to rotate the drive shaft system 2700 in a second direction to open the jaw assembly 7100 of the end effector 7000.

When the rotation actuator 1420 is actuated in a first direction, further to the above, the control system 1800 activates the second clutch assembly 6200 and deactivates the first clutch assembly 6100 and the third clutch assembly 6300. In such instances, the control system 1800 also supplies power to the motor system 1600 to rotate the drive shaft system 2700 in a first direction to rotate the end effector 7000 in a first direction. When the control system 1800 detects that the rotation actuator 1420 has been actuated in a second direction, the control system 1800 activates, or maintains the activation of, the second clutch assembly 6200 and deactivates, or maintains the deactivation of, the first clutch assembly 6100 and the third clutch assembly 6300. In such instances, the control system 1800 also supplies power to the motor system 1600 to rotate the drive shaft system 2700 in a second direction to rotate the drive shaft system 2700 in a second direction to rotate the end effector 7000 in a second direction. When the control system 1800 detects that the rotation actuator 1420 is not actuated, the control system 1800 deactivates the second clutch assembly 6200.

When the first articulation actuator 1432 is depressed, further to the above, the control system 1800 activates the third clutch assembly 6300 and deactivates the first clutch assembly 6100 and the second clutch assembly 6200. In such instances, the control system 1800 also supplies power to the motor system 1600 to rotate the drive shaft system 2700 in a first direction to articulate the end effector 7000 in a first direction. When the control system 1800 detects that the second articulation actuator 1434 is depressed, the control system 1800 activates, or maintains the activation of, the third clutch assembly 6200 and deactivates, or maintains the deactivation of, the first clutch assembly 6100 and the second clutch assembly 6200. In such instances, the control system 1800 also supplies power to the motor system 1600 to rotate the drive shaft system 2700 in a second direction to articulate the end effector 7000 in a second direction. When the control system 1800 detects that neither the first articulation actuator 1432 nor the second articulation actuator 1434 are actuated, the control system 1800 deactivates the third clutch assembly 6200.

Further to the above, the control system 1800 is configured to change the operating mode of the stapling system based on the inputs it receives from the clamping trigger system 2600 of the shaft assembly 2000 and the input system 1400 of the handle 1000. The control system 1800 is configured to shift the clutch system 6000 before rotating the shaft drive system 2700 to perform the corresponding end effector function. Moreover, the control system 1800 is configured to stop the rotation of the shaft drive system 2700 before shifting the clutch system 6000. Such an arrangement can prevent the sudden movements in the end effector 7000. Alternatively, the control system 1800 can shift the clutch system 600 while the shaft drive system 2700 is rotating. Such an arrangement can allow the control system 1800 to shift quickly between operating modes.

Figure 34:
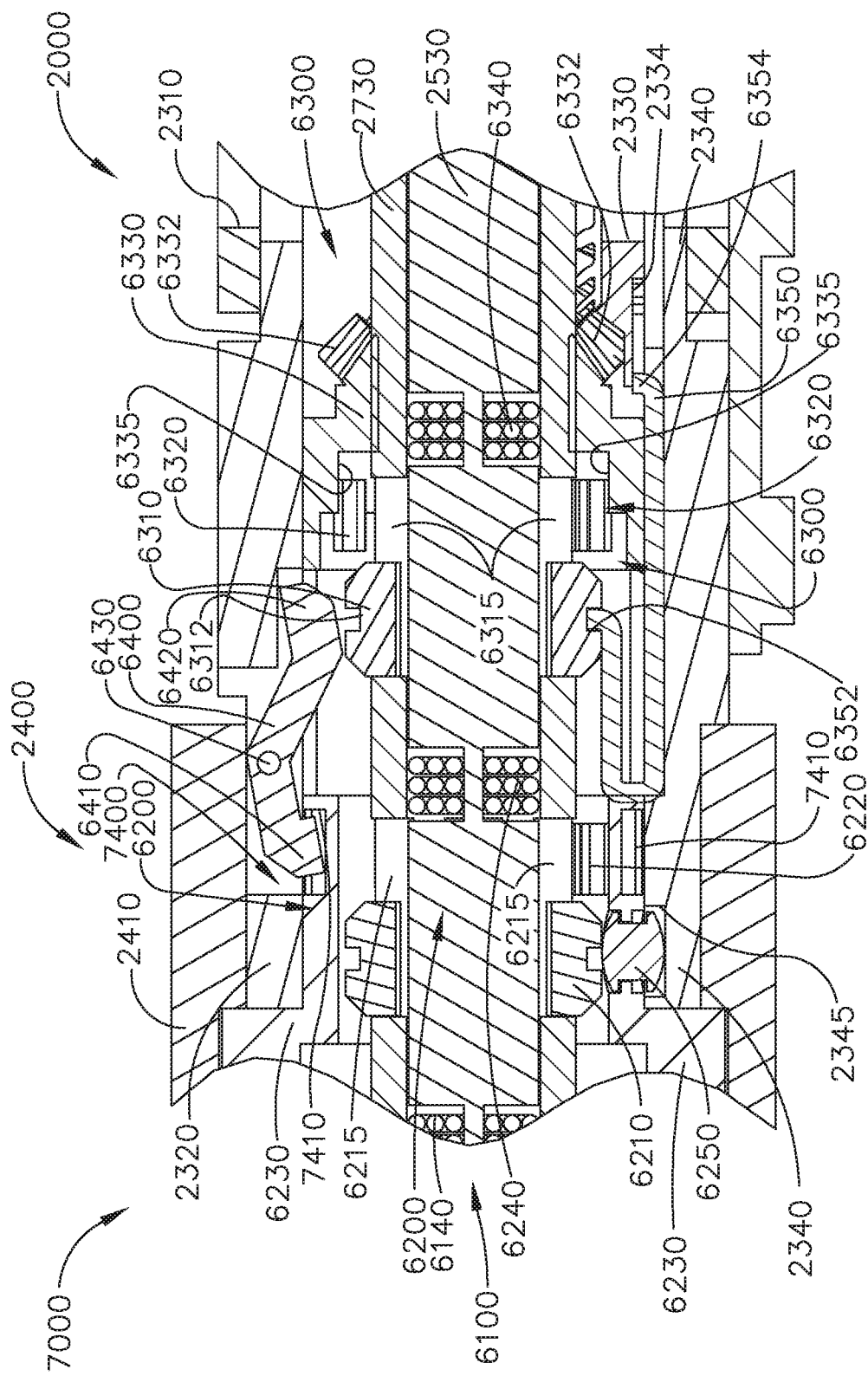
FIG. 34 depicts the second and third clutches of FIG. 27 in their unactuated conditions and the end effector of FIG. 14 locked to the shaft assembly of FIG. 2.
Figure 35:
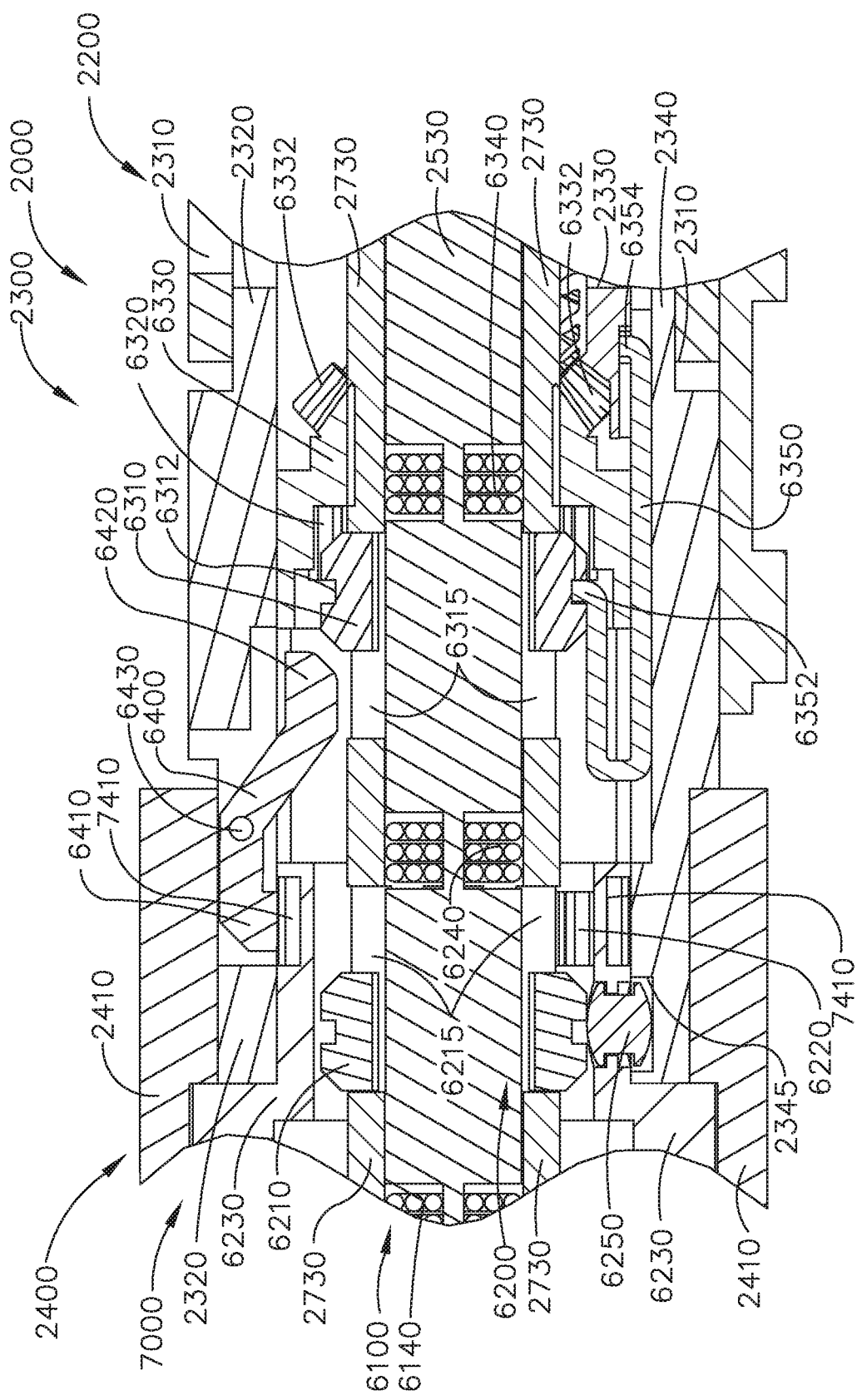
FIG. 35 depicts the second clutch of FIG. 27 in its unactuated condition and the third clutch of FIG. 27 in its actuated condition.
Figure 36:
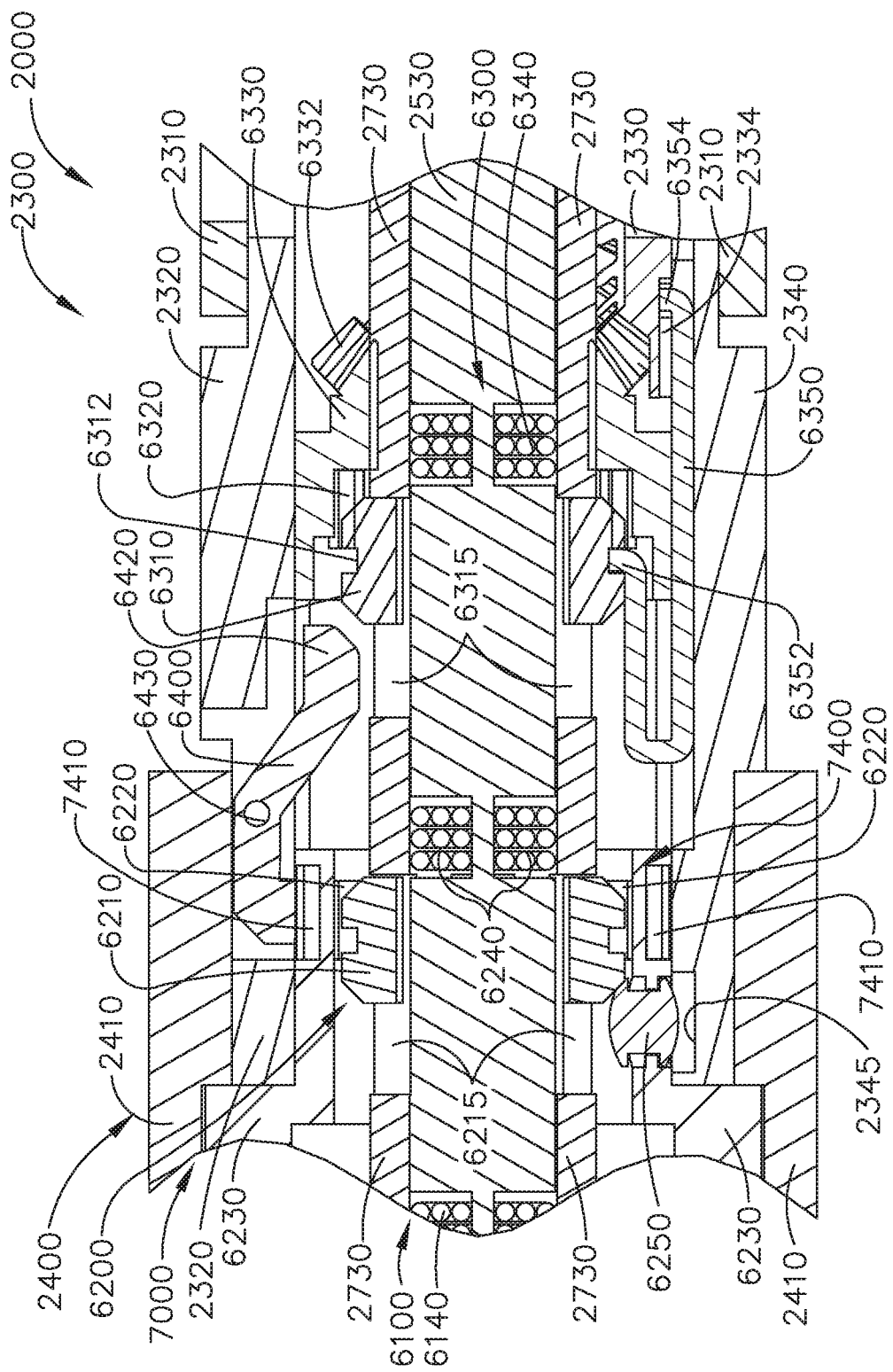
FIG. 36 depicts the second and third clutches of FIG. 27 in their actuated conditions and the end effector of FIG. 14 unlocked from the shaft assembly of FIG. 2.

As discussed above, referring to FIG. 34, the distal attachment portion 2400 of the shaft assembly 2000 comprises an end effector lock 6400 configured to prevent the end effector 7000 from being unintentionally decoupled from the shaft assembly 2000. The end effector lock 6400 comprises a lock end 6410 selectively engageable with the annular array of lock notches 7410 defined on the proximal attachment portion 7400 of the end effector 7000, a proximal end 6420, and a pivot 6430 rotatably connecting the end effector lock 6400 to the articulation link 2320. When the third clutch 6310 of the third clutch assembly 6300 is in its disengaged position, as illustrated in FIG. 34, the third clutch 6310 is contact with the proximal end 6420 of the end effector lock 6400 such that the lock end 6410 of the end effector lock 6400 is engaged with the array of lock notches 7410. In such instances, the end effector 7000 can rotate relative to the end effector lock 6400 but cannot translate relative to the distal attachment portion 2400. When the third clutch 6310 is moved into its engaged position, as illustrated in FIG. 35, the third clutch 6310 is no longer engaged with the proximal end 6420 of the end effector lock 6400. In such instances, the end effector lock 6400 is free to pivot upwardly and permit the end effector 7000 to be detached from the shaft assembly 2000.

The above being said, referring again to FIG. 34, it is possible that the second clutch 6210 of the second clutch assembly 6200 is in its disengaged position when the clinician detaches, or attempts to detach, the end effector 7000 from the shaft assembly 2000. As discussed above, the second clutch 6210 is engaged with the second clutch lock 6250 when the second clutch 6210 is in its disengaged position and, in such instances, the second clutch lock 6250 is pushed into engagement with the articulation link 2340. More specifically, the second clutch lock 6250 is positioned in the channel 2345 defined in the articulation 2340 when the second clutch 6210 is engaged with the second clutch lock 6250 which may prevent, or at least impede, the end effector 7000 from being detached from the shaft assembly 2000. To facilitate the release of the end effector 7000 from the shaft assembly 2000, the control system 1800 can move the second clutch 6210 into its engaged position in addition to moving the third clutch 6310 into its engaged position. In such instances, the end effector 7000 can clear both the end effector lock 6400 and the second clutch lock 6250 when the end effector 7000 is removed.

In at least one instance, further to the above, the drive module 1100 comprises an input switch and/or sensor in communication with the control system 1800 via the input system 1400, and/or the control system 1800 directly, which, when actuated, causes the control system 1800 to unlock the end effector 7000. In various instances, the drive module 1100 comprises an input screen 1440 in communication with the board 1410 of the input system 1400 which is configured to receive an unlock input from the clinician. In response to the unlock input, the control system 1800 can stop the motor system 1600, if it is running, and unlock the end effector 7000 as described above. The input screen 1440 is also configured to receive a lock input from the clinician in which the input system 1800 moves the second clutch assembly 6200 and/or the third clutch assembly 6300 into their unactuated states to lock the end effector 7000 to the shaft assembly 2000.

Figure 37:
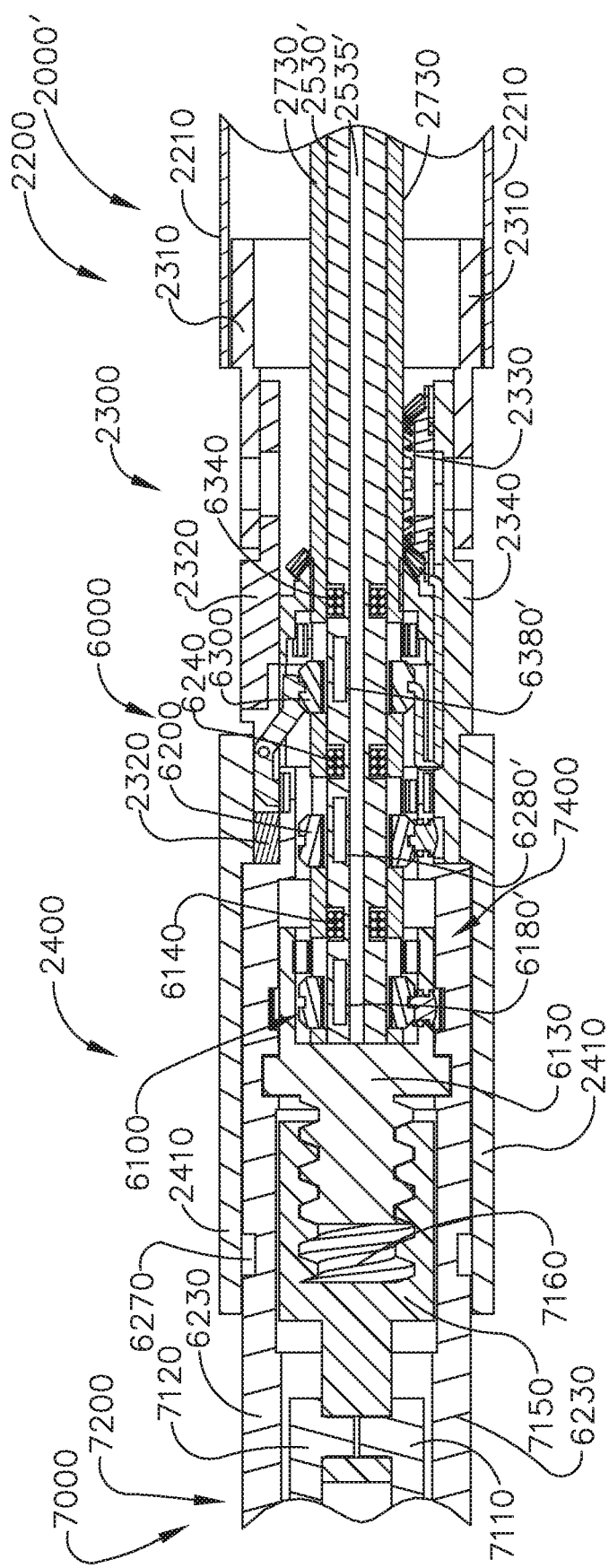
FIG. 37 is a partial cross-sectional view of a shaft assembly in accordance with at least one alternative embodiment comprising sensors configured to detect the conditions of the first, second, and third clutches of FIG. 27.

FIG. 37 depicts a shaft assembly 2000' in accordance with at least one alternative embodiment. The shaft assembly 2000' is similar to the shaft assembly 2000 in many respects, most of which will not be repeated herein for the sake of brevity. Similar to the shaft assembly 2000, the shaft assembly 2000' comprises a shaft frame, i.e., shaft frame 2530'. The shaft frame 2530' comprises a longitudinal passage 2535' and, in addition, a plurality of clutch position sensors, i.e., a first sensor 6180', a second sensor 6280', and a third sensor 6380' positioned in the shaft frame 2530'. The first sensor 6180' is in signal communication with the control system 1800 as part of a first sensing circuit. The first sensing circuit comprises signal wires extending through the longitudinal passage 2535'; however, the first sensing circuit can comprise a wireless signal transmitter and receiver to place the first sensor 6180' in signal communication with the control system 1800. The first sensor 6180' is positioned and arranged to detect the position of the first clutch 6110 of the first clutch assembly 6100. Based on data received from the first sensor 6180', the control system 1800 can determine whether the first clutch 6110 is in its engaged position, its disengaged position, or somewhere in-between. With this information, the control system 1800 can assess whether or not the first clutch 6110 is in the correct position given the operating state of the surgical instrument. For instance, if the surgical instrument is in its jaw clamping/opening operating state, the control system 1800 can verify whether the first clutch 6110 is properly positioned in its engaged position. In such instances, further to the below, the control system 1800 can also verify that the second clutch 6210 is in its disengaged position via the second sensor 6280' and that the third clutch 6310 is in its disengaged position via the third sensor 6380'. Correspondingly, the control system 1800 can verify whether the first clutch 6110 is properly positioned in its disengaged position if the surgical instrument is not in its jaw clamping/opening state. To the extent that the first clutch 6110 is not in its proper position, the control system 1800 can actuate the first electromagnetic actuator 6140 in an attempt to properly position the first clutch 6110. Likewise, the control system 1800 can actuate the electromagnetic actuators 6240 and/or 6340 to properly position the clutches 6210 and/or 6310, if necessary.

The second sensor 6280' is in signal communication with the control system 1800 as part of a second sensing circuit. The second sensing circuit comprises signal wires extending through the longitudinal passage 2535'; however, the second sensing circuit can comprise a wireless signal transmitter and receiver to place the second sensor 6280' in signal communication with the control system 1800. The second sensor 6280' is positioned and arranged to detect the position of the second clutch 6210 of the first clutch assembly 6200. Based on data received from the second sensor 6280', the control system 1800 can determine whether the second clutch 6210 is in its engaged position, its disengaged position, or somewhere in-between. With this information, the control system 1800 can assess whether or not the second clutch 6210 is in the correct position given the operating state of the surgical instrument. For instance, if the surgical instrument is in its end effector rotation operating state, the control system 1800 can verify whether the second clutch 6210 is properly positioned in its engaged position. In such instances, the control system 1800 can also verify that the first clutch 6110 is in its disengaged position via the first sensor 6180' and, further to the below, the control system 1800 can also verify that the third clutch 6310 is in its disengaged position via the third sensor 6380'. Correspondingly, the control system 1800 can verify whether the second clutch 6110 is properly positioned in its disengaged position if the surgical instrument is not in its end effector rotation state. To the extent that the second clutch 6210 is not in its proper position, the control system 1800 can actuate the second electromagnetic actuator 6240 in an attempt to properly position the second clutch 6210. Likewise, the control system 1800 can actuate the electromagnetic actuators 6140 and/or 6340 to properly position the clutches 6110 and/or 6310, if necessary.

The third sensor 6380' is in signal communication with the control system 1800 as part of a third sensing circuit. The third sensing circuit comprises signal wires extending through the longitudinal passage 2535'; however, the third sensing circuit can comprise a wireless signal transmitter and receiver to place the third sensor 6380' in signal communication with the control system 1800. The third sensor 6380' is positioned and arranged to detect the position of the third clutch 6310 of the third clutch assembly 6300. Based on data received from the third sensor 6380', the control system 1800 can determine whether the third clutch 6310 is in its engaged position, its disengaged position, or somewhere in-between. With this information, the control system 1800 can assess whether or not the third clutch 6310 is in the correct position given the operating state of the surgical instrument. For instance, if the surgical instrument is in its end effector articulation operating state, the control system 1800 can verify whether the third clutch 6310 is properly positioned in its engaged position. In such instances, the control system 1800 can also verify that the first clutch 6110 is in its disengaged position via the first sensor 6180' and that the second clutch 6210 is in its disengaged position via the second sensor 6280'. Correspondingly, the control system 1800 can verify whether the third clutch 6310 is properly positioned in its disengaged position if the surgical instrument is not in its end effector articulation state. To the extent that the third clutch 6310 is not in its proper position, the control system 1800 can actuate the third electromagnetic actuator 6340 in an attempt to properly position the third clutch 6310. Likewise, the control system 1800 can actuate the electromagnetic actuators 6140 and/or 6240 to properly position the clutches 6110 and/or 6210, if necessary.

Further to the above, the clutch position sensors, i.e., the first sensor 6180', the second sensor 6280', and the third sensor 6380' can comprise any suitable type of sensor. In various instances, the first sensor 6180', the second sensor 6280', and the third sensor 6380' each comprise a proximity sensor. In such an arrangement, the sensors 6180', 6280', and 6380' are configured to detect whether or not the clutches 6110, 6210, and 6310, respectively, are in their engaged positions. In various instances, the first sensor 6180', the second sensor 6280', and the third sensor 6380' each comprise a Hall Effect sensor, for example. In such an arrangement, the sensors 6180', 6280', and 6380' can not only detect whether or not the clutches 6110, 6210, and 6310, respectively, are in their engaged positions but the sensors 6180', 6280', and 6380' can also detect how close the clutches 6110, 6210, and 6310 are with respect to their engaged or disengaged positions.

Figure 38:
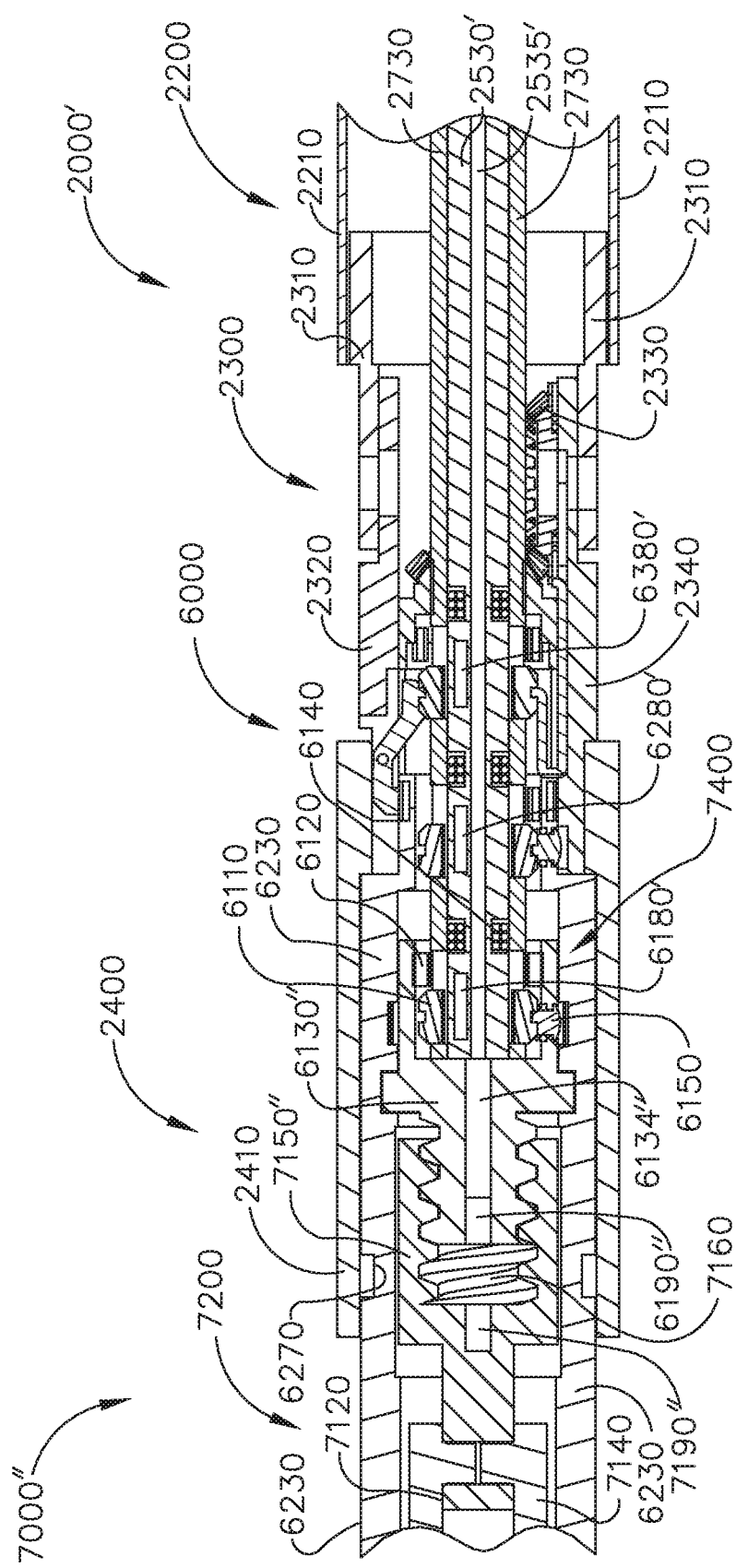
FIG. 38 is a partial cross-sectional view of a shaft assembly in accordance with at least one alternative embodiment comprising sensors configured to detect the conditions of the first, second, and third clutches of FIG. 27.

FIG. 38 depicts the shaft assembly 2000' and an end effector 7000" in accordance with at least one alternative embodiment. The end effector 7000" is similar to the end effector 7000 in many respects, most of which will not be repeated herein for the sake of brevity. Similar to the end effector 7000, the shaft assembly 7000" comprises a jaw assembly 7100 and a jaw assembly drive configured to move the jaw assembly 7100 between its open and closed configurations. The jaw assembly drive comprises drive links 7140, a drive nut 7150", and a drive screw 6130". The drive nut 7150" comprises a sensor 7190" positioned therein which is configured to detect the position of a magnetic element 6190" positioned in the drive screw 6130". The magnetic element 6190" is positioned in an elongate aperture 6134" defined in the drive screw 6130" and can comprise a permanent magnet and/or can be comprised of iron, nickel, and/or any suitable metal, for example. In various instances, the sensor 7190" comprises a proximity sensor, for example, which is in signal communication with the control system 1800. In certain instances, the sensor 7190" comprises a Hall Effect sensor, for example, in signal communication with the control system 1800. In certain instances, the sensor 7190" comprises an optical sensor, for example, and the detectable element 6190" comprises an optically detectable element, such as a reflective element, for example. In either event, the sensor 7190" is configured to communicate wirelessly with the control system 1800 via a wireless signal transmitter and receiver and/or via a wired connection extending through the shaft frame passage 2532', for example.

The sensor 7190", further to the above, is configured to detect when the magnetic element 6190" is adjacent to the sensor 7190" such that the control system 1800 can use this data to determine that the jaw assembly 7100 has reached the end of its clamping stroke. At such point, the control system 1800 can stop the motor assembly 1600. The sensor 7190" and the control system 1800 are also configured to determine the distance between where the drive screw 6130" is currently positioned and where the drive screw 6130" should be positioned at the end of its closure stroke in order to calculate the amount of closure stroke of the drive screw 6130" that is still needed to close the jaw assembly 7100. Moreover, such information can be used by the control system 1800 to assess the current configuration of the jaw assembly 7100, i.e., whether the jaw assembly 7100 is in its open configuration, its closed configuration, or a partially closed configuration. The sensor system could be used to determine when the jaw assembly 7100 has reached its fully open position and stop the motor assembly 1600 at that point. In various instances, the control system 1800 could use this sensor system to confirm that the first clutch assembly 6100 is in its actuated state by confirming that the jaw assembly 7100 is moving while the motor assembly 1600 is turning. Similarly, the control system 1800 could use this sensor system to confirm that the first clutch assembly 6100 is in its unactuated state by confirming that the jaw assembly 7100 is not moving while the motor assembly 1600 is turning.

Figure 39:
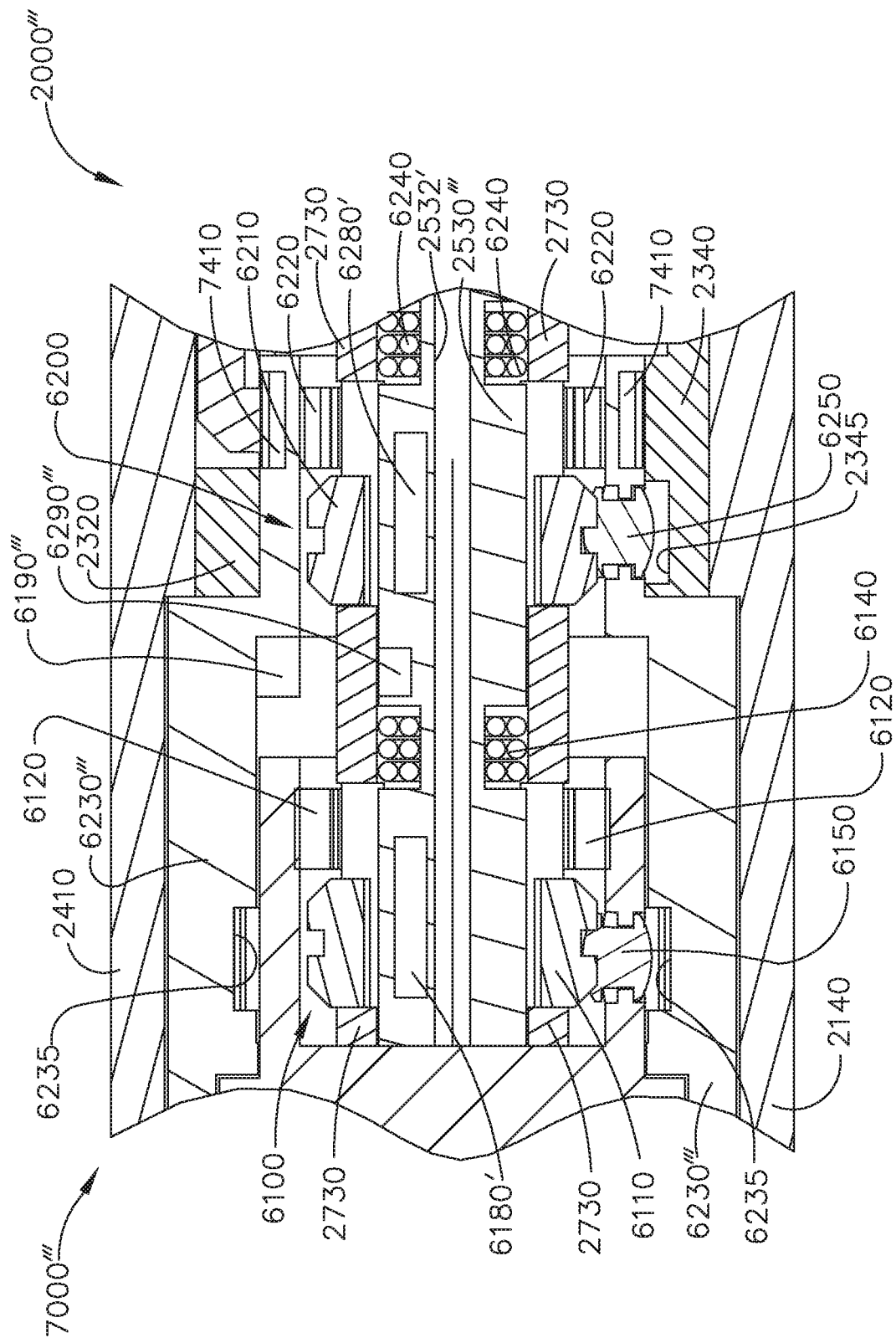
FIG. 39 depicts the first and second clutches of FIG. 38 in their unactuated conditions and a sensor in accordance with at least one alternative embodiment.

FIG. 39 depicts a shaft assembly 2000''' and an end effector 7000''' in accordance with at least one alternative embodiment. The shaft assembly 2000''' is similar to the shaft assemblies 2000 and 2000' in many respects, most of which will not be repeated herein for the sake of brevity. The end effector 7000''' is similar to the end effectors 7000 and 7000" in many respects, most of which will not be repeated herein for the sake of brevity. Similar to the end effector 7000, the end effector 7000''' comprises a jaw assembly 7100 and a jaw assembly drive configured to move the jaw assembly 7100 between its open and closed configurations and, in addition, an end effector rotation drive that rotates the end effector 7000''' relative to the distal attachment portion 2400 of the shaft assembly 2000'. The end effector rotation drive comprises an outer housing 6230''' that is rotated relative to a shaft frame 2530''' of the end effector 7000''' by the second clutch assembly 6200. The shaft frame 2530''' comprises a sensor 6290''' positioned therein which is configured to detect the position of a magnetic element 6190''' positioned in and/or on the outer housing 6230'''. The magnetic element 6190''' can comprise a permanent magnet and/or can be comprised of iron, nickel, and/or any suitable metal, for example. In various instances, the sensor 6290''' comprises a proximity sensor, for example, in signal communication with the control system 1800. In certain instances, the sensor 6290''' comprises a Hall Effect sensor, for example, in signal communication with the control system 1800. In either event, the sensor 6290''' is configured to communicate wirelessly with the control system 1800 via a wireless signal transmitter and receiver and/or via a wired connection extending through the shaft frame passage 2532', for example. In various instances, the control system 1800 can use the sensor 6290''' to confirm whether the magnetic element 6190''' is rotating and, thus, confirm that the second clutch assembly 6200 is in its actuated state. Similarly, the control system 1800 can use the sensor 6290''' to confirm whether the magnetic element 6190''' is not rotating and, thus, confirm that the second clutch assembly 6200 is in its unactuated state. The control system 1800 can also use the sensor 6290''' to confirm that the second clutch assembly 6200 is in its unactuated state by confirming that the second clutch 6210 is positioned adjacent the sensor 6290'''.

Figure 40:
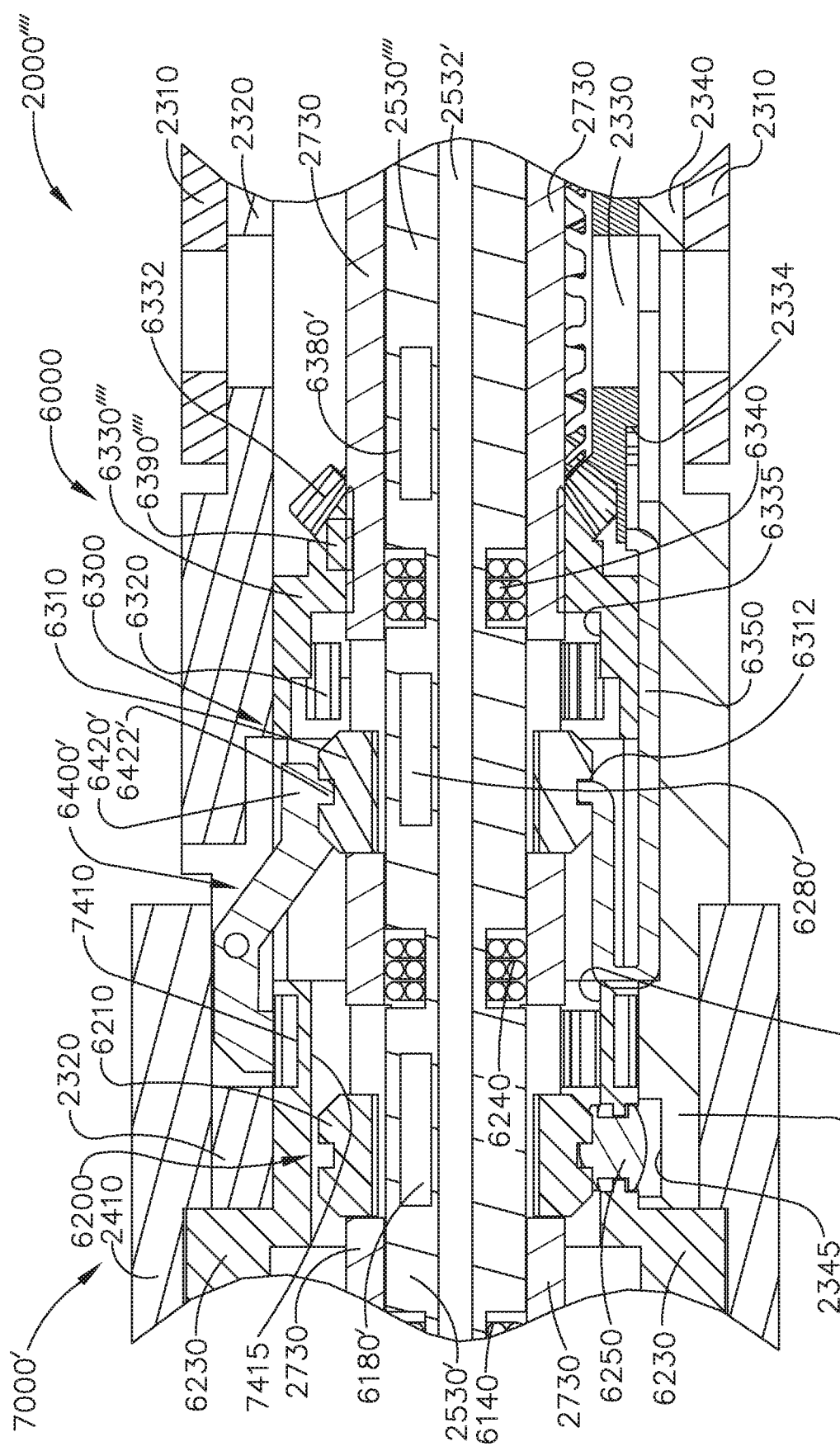
FIG. 40 depicts the second and third clutches of FIG. 38 in their unactuated conditions and a sensor in accordance with at least one alternative embodiment.

FIG. 40 depicts a shaft assembly 2000'''' in accordance with at least one alternative embodiment. The shaft assembly 2000'''' is similar to the shaft assemblies 2000, 2000', and 2000''' in many respects, most of which will not be repeated herein for the sake of brevity. Similar to the shaft assembly 2000, the shaft assembly 2000'''' comprises, among other things, an elongate shaft 2200, an articulation joint 2300, and a distal attachment portion 2400 configured to receive an end effector, such as end effector 7000', for example. Similar to the shaft assembly 2000, the shaft assembly 2000'''' comprises an articulation drive, i.e., articulation drive 6330'''' configured to rotate the distal attachment portion 2400 and the end effector 7000' about the articulation joint 2300. Similar to the above, a shaft frame 2530'''' comprises a sensor positioned therein configured to detect the position, and/or rotation, of a magnetic element 6390'''' positioned in and/or on the articulation drive 6330''''. The magnetic element 6390"" can comprise a permanent magnet and/or can be comprised of iron, nickel, and/or any suitable metal, for example. In various instances, the sensor comprises a proximity sensor, for example, in signal communication with the control system 1800. In certain instances, the sensor comprises a Hall Effect sensor, for example, in signal communication with the control system 1800. In either event, the sensor is configured to communicate wirelessly with the control system 1800 via a wireless signal transmitter and receiver and/or via a wired connection extending through the shaft frame passage 2532', for example. In various instances, the control system 1800 can use the sensor to confirm whether the magnetic element 6390"" is rotating and, thus, confirm that the third clutch assembly 6300 is in its actuated state. Similarly, the control system 1800 can use the sensor to confirm whether the magnetic element 6390"" is not rotating and, thus, confirm that the third clutch assembly 6300 is in its unactuated state. In certain instances, the control system 1800 can use the sensor to confirm that the third clutch assembly 6300 is in its unactuated state by confirming that the third clutch 6310 is positioned adjacent the sensor.

Referring to FIG. 40 once again, the shaft assembly 2000"" comprises an end effector lock 6400' configured to releasably lock the end effector 7000', for example, to the shaft assembly 2000"". The end effector lock 6400' is similar to the end effector lock 6400 in many respects, most of which will not be discussed herein for the sake of brevity. Notably, though, a proximal end 6420' of the lock 6400' comprises a tooth 6422' configured to engage the annular slot 6312 of the third clutch 6310 and releasably hold the third clutch 6310 in its disengaged position. That said, the actuation of the third electromagnetic assembly 6340 can disengage the third clutch 6310 from the end effector lock 6400'. Moreover, in such instances, the proximal movement of the third clutch 6310 into its engaged position rotates the end effector lock 6400' into a locked position and into engagement with the lock notches 7410 to lock the end effector 7000' to the shaft assembly 2000"". Correspondingly, the distal movement of the third clutch 6310 into its disengaged position unlocks the end effector 7000' and allows the end effector 7000' to be disassembled from the shaft assembly 2000"".

Further to the above, an instrument system including a handle and a shaft assembly attached thereto can be configured to perform a diagnostic check to assess the state of the clutch assemblies 6100, 6200, and 6300. In at least one instance, the control system 1800 sequentially actuates the electromagnetic actuators 6140, 6240, and/or 6340—in any suitable order—to verify the positions of the clutches 6110, 6210, and/or 6310, respectively, and/or verify that the clutches are responsive to the electromagnetic actuators and, thus, not stuck. The control system 1800 can use sensors, including any of the sensors disclosed herein, to verify the movement of the clutches 6110, 6120, and 6130 in response to the electromagnetic fields created by the electromagnetic actuators 6140, 6240, and/or 6340. In addition, the diagnostic check can also include verifying the motions of the drive systems. In at least one instance, the control system 1800 sequentially actuates the electromagnetic actuators 6140, 6240, and/or 6340—in any suitable order—to verify that the jaw drive opens and/or closes the jaw assembly 7100, the rotation drive rotates the end effector 7000, and/or the articulation drive articulates the end effector 7000, for example. The control system 1800 can use sensors to verify the motions of the jaw assembly 7100 and end effector 7000.

The control system 1800 can perform the diagnostic test at any suitable time, such as when a shaft assembly is attached to the handle and/or when the handle is powered on, for example. If the control system 1800 determines that the instrument system passed the diagnostic test, the control system 1800 can permit the ordinary operation of the instrument system. In at least one instance, the handle can comprise an indicator, such as a green LED, for example, which indicates that the diagnostic check has been passed. If the control system 1800 determines that the instrument system failed the diagnostic test, the control system 1800 can prevent and/or modify the operation of the instrument system. In at least one instance, the control system 1800 can limit the functionality of the instrument system to only the functions necessary to remove the instrument system from the patient, such as straightening the end effector 7000 and/or opening and closing the jaw assembly 7100, for example. In at least one respect, the control system 1800 enters into a limp mode. The limp mode of the control system 1800 can reduce a current rotational speed of the motor 1610 by any percentage selected from a range of about 75% to about 25%, for example. In one example, the limp mode reduces a current rotational speed of the motor 1610 by 50%. In one example, the limp mode reduces a current rotational speed of the motor 1610 by 75%. The limp mode may cause a current torque of the motor 1610 to be reduced by any percentage selected from a range of about 75% to about 25%, for example. In one example, the limp mode reduces a current torque of the motor 1610 by 50%. The handle can comprise an indicator, such as a red LED, for example, which indicates that the instrument system failed the diagnostic check and/or that the instrument system has entered into a limp mode. The above being said, any suitable feedback can be used to warn the clinician that the instrument system is not operating properly such as, for example, an audible warning and/or a tactile or vibratory warning, for example.

Figure 41:
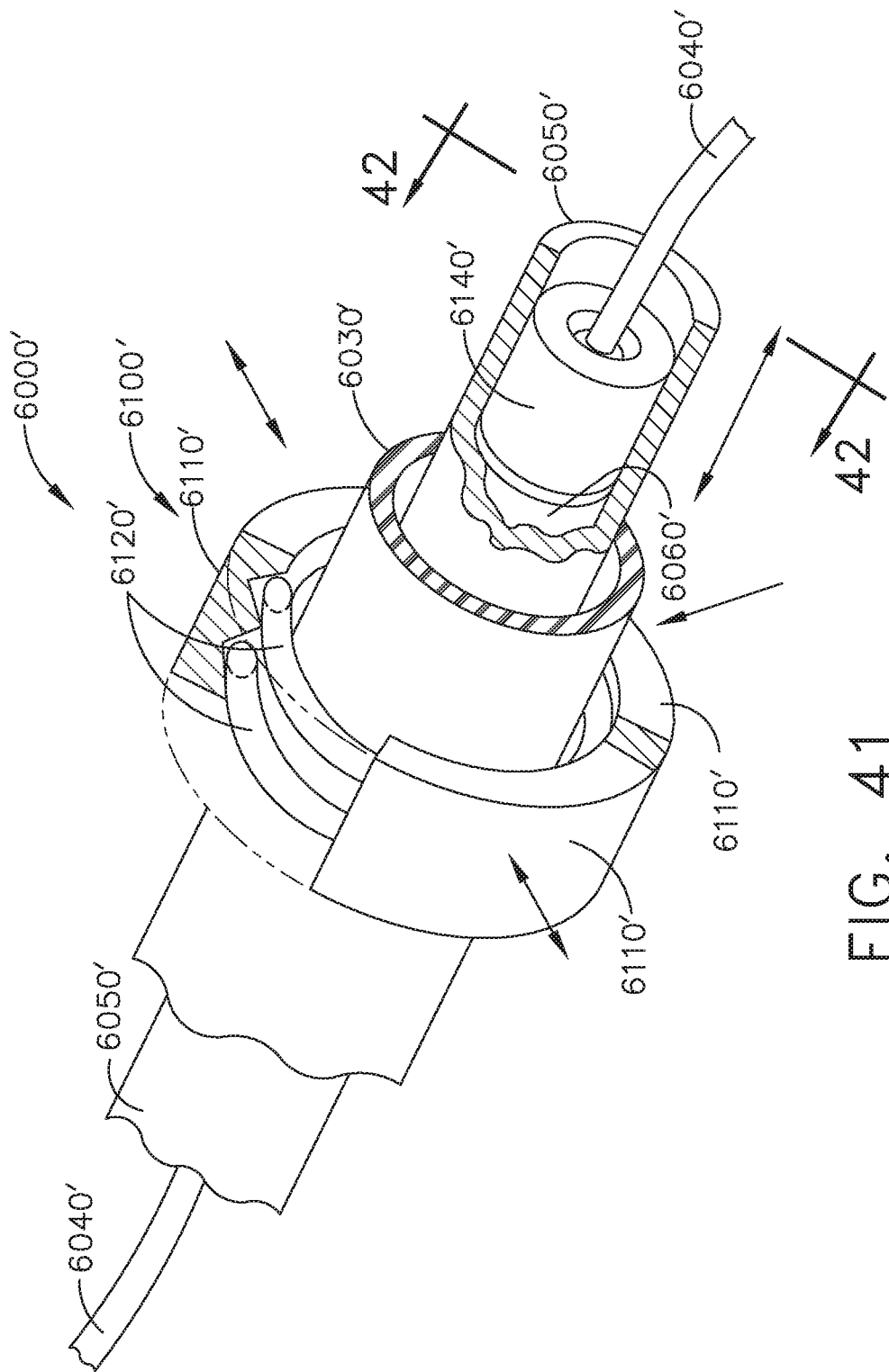
FIG. 41 is a partial cross-sectional view of a shaft assembly in accordance with at least one embodiment.
Figure 42:
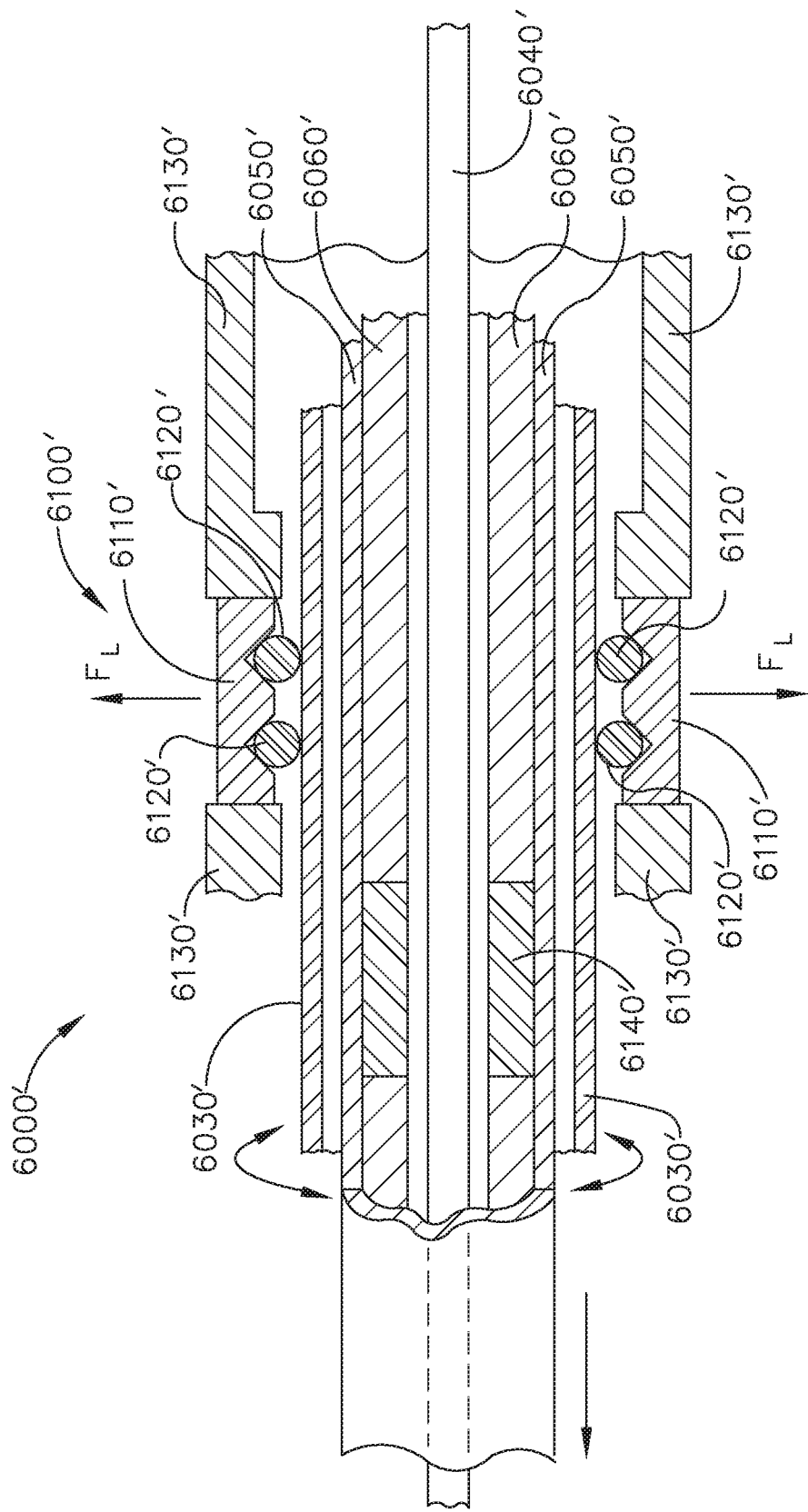
FIG. 42 is a partial cross-sectional view of the shaft assembly of FIG. 41 comprising a clutch illustrated in an unactuated condition.
Figure 43:
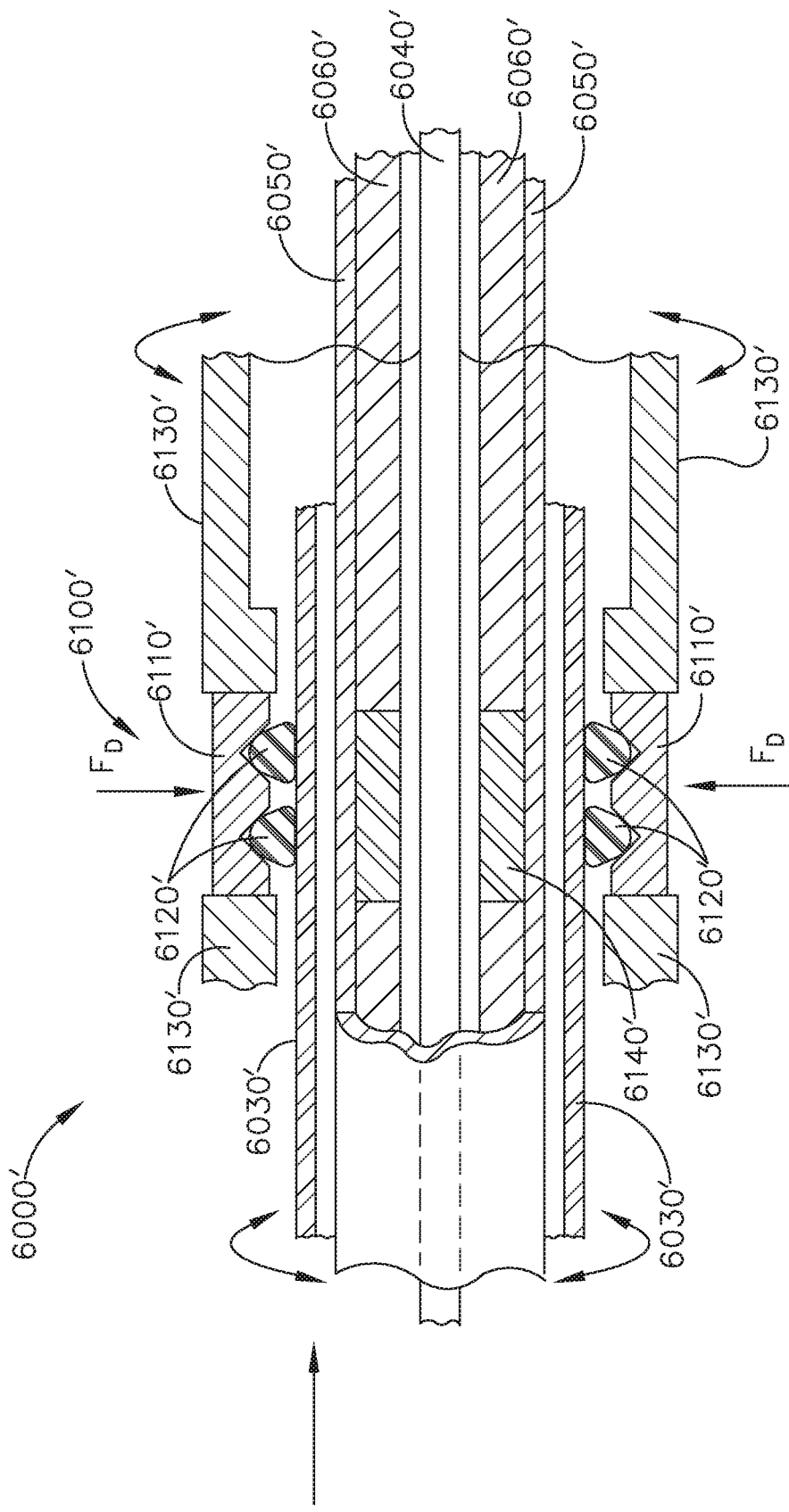
FIG. 43 is a partial cross-sectional view of the shaft assembly of FIG. 41 illustrating the clutch in an actuated condition.

FIGS. 41-43 depict a clutch system 6000' in accordance with at least one alternative embodiment. The clutch system 6000' is similar to the clutch system 6000 in many respects, most of which will not be repeated herein for the sake of brevity. Similar to the clutch system 6000, the clutch system 6000' comprises a clutch assembly 6100' which is actuatable to selectively couple a rotatable drive input 6030' with a rotatable drive output 6130'. The clutch assembly 6100' comprises clutch plates 6110' and drive rings 6120'. The clutch plates 6110' are comprised of a magnetic material, such as iron and/or nickel, for example, and can comprise a permanent magnet. As described in greater detail below, the clutch plates 6110' are movable between unactuated positions (FIG. 42) and actuated positions (FIG. 43) within the drive output 6130'. The clutch plates 6110' are slideably positioned in apertures defined in the drive output 6130' such that the clutch plates 6110' rotate with the drive output 6130' regardless of whether the clutch plates 6110' are in their unactuated or actuated positions.

When the clutch plates 6110' are in their unactuated positions, as illustrated in FIG. 42, the rotation of the drive input 6030' is not transferred to the drive output 6130'. More specifically, when the drive input 6030' is rotated, in such instances, the drive input 6030' slides past and rotates relative to the drive rings 6120' and, as a result, the drive rings 6120' do not drive the clutch plates 6110' and the drive output 6130'. When the clutch plates 6110' are in their actuated positions, as illustrated in FIG. 43, the clutch plates 6110' resiliently compress the drive rings 6120' against the drive input 6030'. The drive rings 6120' are comprised of any suitable compressible material, such as rubber, for example. In any event, in such instances, the rotation of the drive input 6030' is transferred to the drive output 6130' via the drive rings 6120' and the clutch plates 6110'. The clutch system 6000' comprises a clutch actuator 6140' configured to move the clutch plates 6110' into their actuated positions. The clutch actuator 6140' is comprised of a magnetic material such as iron and/or nickel, for example, and can comprise a permanent magnet. The clutch actuator 6140' is slideably positioned in a longitudinal shaft frame 6050' extending through the drive input 6030' and can be moved between an unactuated position (FIG. 42) and an actuated position (FIG. 43) by a clutch shaft 6060'. In at least one instance, the clutch shaft 6060' comprises a polymer cable, for example. When the clutch actuator 6140' is in its actuated position, as illustrated in FIG. 43, the clutch actuator 6140' pulls the clutch plates 6110' inwardly to compress the drive rings 6120', as discussed above. When the clutch actuator 6140' is moved into its unactuated position, as illustrated in FIG. 42, the drive rings 6120' resiliently expand and push the clutch plates 6110' away from the drive input 6030'. In various alternative embodiments, the clutch actuator 6140' can comprise an electromagnet. In such an arrangement, the clutch actuator 6140' can be actuated by an electrical circuit extending through a longitudinal aperture defined in the clutch shaft 6060', for example. In various instances, the clutch system 6000' further comprises electrical wires 6040', for example, extending through the longitudinal aperture.

Figure 44:
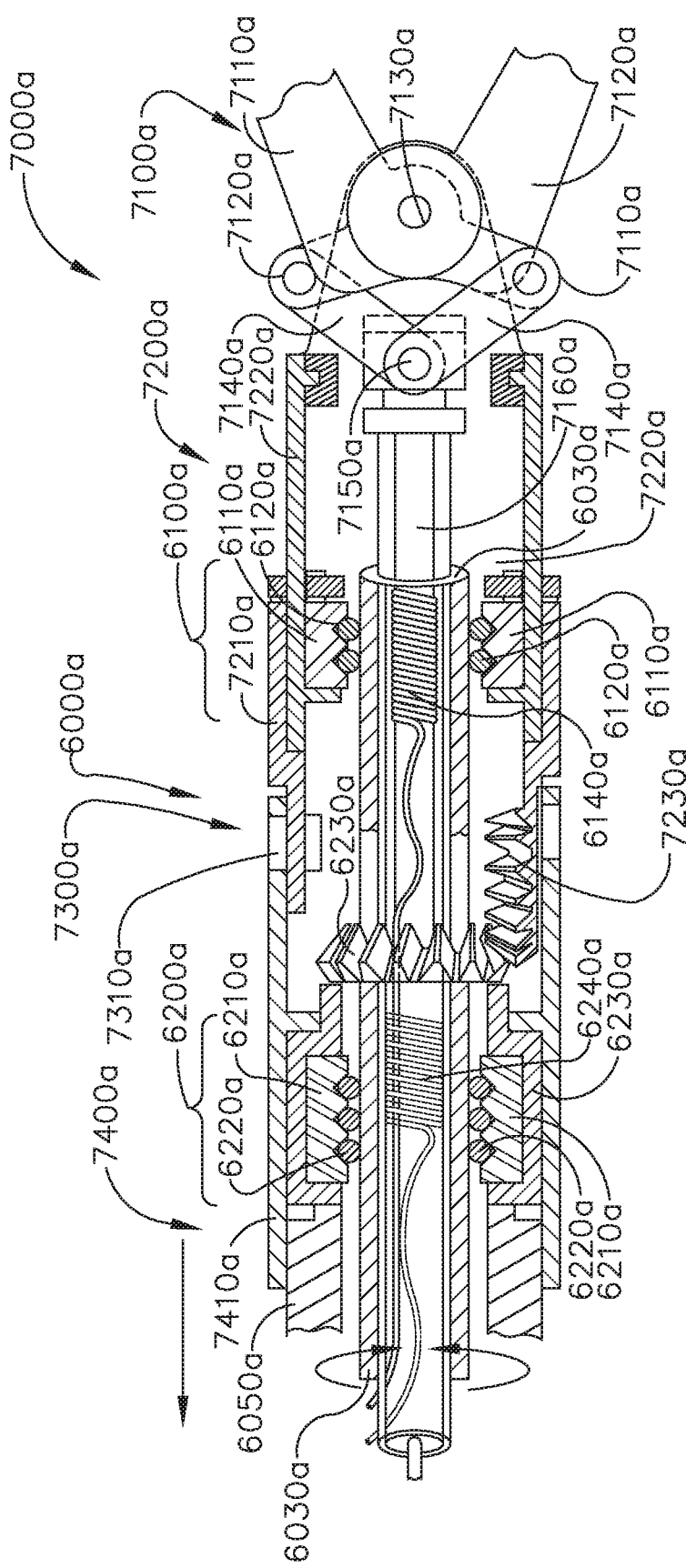
FIG. 44 is a partial cross-sectional view of a shaft assembly in accordance with at least one embodiment comprising first and second clutches illustrated in an unactuated condition.

FIG. 44 depicts an end effector 7000a including a jaw assembly 7100a, a jaw assembly drive, and a clutch system 6000a in accordance with at least one alternative embodiment. The jaw assembly 7100a comprises a first jaw 7110a and a second jaw 7120a which are selectively rotatable about a pivot 7130a. The jaw assembly drive comprises a translatable actuator rod 7160a and drive links 7140a which are pivotably coupled to the actuator rod 7160a about a pivot 7150a. The drive links 7140a are also pivotably coupled to the jaws 7110a and 7120a such that the jaws 7110a and 7120a are rotated closed when the actuator rod 7160a is pulled proximally and rotated open when the actuator rod 7160a is pushed distally. The clutch system 6000a is similar to the clutch systems 6000 and 6000' in many respects, most of which will not be repeated herein for the sake of brevity. The clutch system 6000a comprises a first clutch assembly 6100a and a second clutch assembly 6200a which are configured to selectively transmit the rotation of a drive input 6030a to rotate the jaw assembly 7100a about a longitudinal axis and articulate the jaw assembly 7100a about an articulation joint 7300a, respectively, as described in greater detail below.

The first clutch assembly 6100a comprises clutch plates 6110a and drive rings 6120a and work in a manner similar to the clutch plates 6110' and drive rings 6120' discussed above. When the clutch plates 6110a are actuated by an electromagnetic actuator 6140a, the rotation of the drive input 6030a is transferred to an outer shaft housing 7200a. More specifically, the outer shaft housing 7200a comprises a proximal outer housing 7210a and a distal outer housing 7220a which is rotatably supported by the proximal outer housing 7210a and is rotated relative to the proximal outer housing 7210a by the drive input 6030a when the clutch plates 6110a are in their actuated position. The rotation of the distal outer housing 7220a rotates the jaw assembly 7100a about the longitudinal axis owing to fact that the pivot 7130a of the jaw assembly 7100a is mounted to the distal outer housing 7220a. As a result, the outer shaft housing 7200a rotates the jaw assembly 7100a in a first direction when the outer shaft housing 7200a is rotated in a first direction by the drive input 6030a. Similarly, the outer shaft housing 7200a rotates the jaw assembly 7100a in a second direction when the outer shaft housing 7200a is rotated in a second direction by the drive input 6030a. When the electromagnetic actuator 6140a is de-energized, the drive rings 6120a expand and the clutch plates 6110a are moved into their unactuated positions, thereby decoupling the end effector rotation drive from the drive input 6030a.

The second clutch assembly 6200a comprises clutch plates 6210a and drive rings 6220a and work in a manner similar to the clutch plates 6110' and drive rings 6120' discussed above. When the clutch plates 6210a are actuated by an electromagnetic actuator 6240a, the rotation of the drive input 6030a is transferred to an articulation drive 6230a. The articulation drive 6230a is rotatably supported within an outer shaft housing 7410a of an end effector attachment portion 7400a and is rotatably supported by a shaft frame 6050a extending through the outer shaft housing 7410a. The articulation drive 6230a comprises a gear face defined thereon which is operably intermeshed with a stationary gear face 7230a defined on the proximal outer housing 7210a of the outer shaft housing 7200a. As a result, the articulation drive 6230a articulates the outer shaft housing 7200a and the jaw assembly 7100a in a first direction when the articulation drive 6230a is rotated in a first direction by the drive input 6030a. Similarly, the articulation drive 6230a articulates the outer shaft housing 7200a and the jaw assembly 7100a in a second direction when the articulation drive 6230a is rotated in a second direction by the drive input 6030a. When the electromagnetic actuator 6240a is de-energized, the drive rings 6220a expand and the clutch plates 6210a are moved into their unactuated positions, thereby decoupling the end effector articulation drive from the drive input 6030a.

Further to the above, the shaft assembly 4000 is illustrated in FIGS. 45-49. The shaft assembly 4000 is similar to the shaft assemblies 2000, 2000', 2000''', and 2000'''' in many respects, most of which will not be repeated herein for the sake of brevity. The shaft assembly 4000 comprises a proximal portion 4100, an elongate shaft 4200, a distal attachment portion 2400, and an articulate joint 2300 which rotatably connects the distal attachment portion 2040 to the elongate shaft 4200. The proximal portion 4100, similar to the proximal portion 2100, is operably attachable to the drive module 1100 of the handle 1000. The proximal portion 4100 comprises a housing 4110 including an attachment interface 4130 configured to mount the shaft assembly 4000 to the attachment interface 1130 of the handle 1000. The shaft assembly 4000 further comprises a frame 4500 including a shaft 4510 configured to be coupled to the shaft 1510 of the handle frame 1500 when the shaft assembly 4000 is attached to the handle 1000. The shaft assembly 4000 also comprises a drive system 4700 including a rotatable drive shaft 4710 configured to be operably coupled to the drive shaft 1710 of the handle drive system 1700 when the shaft assembly 4000 is attached to the handle 1000. The distal attachment portion 2400 is configured to receive an end effector, such as end effector 8000, for example. The end effector 8000 is similar to the end effector 7000 in many respects, most of which will not be repeated herein for the sake of brevity. That said, the end effector 8000 comprises a jaw assembly 8100 configured to, among other things, grasp tissue.

Figure 48:
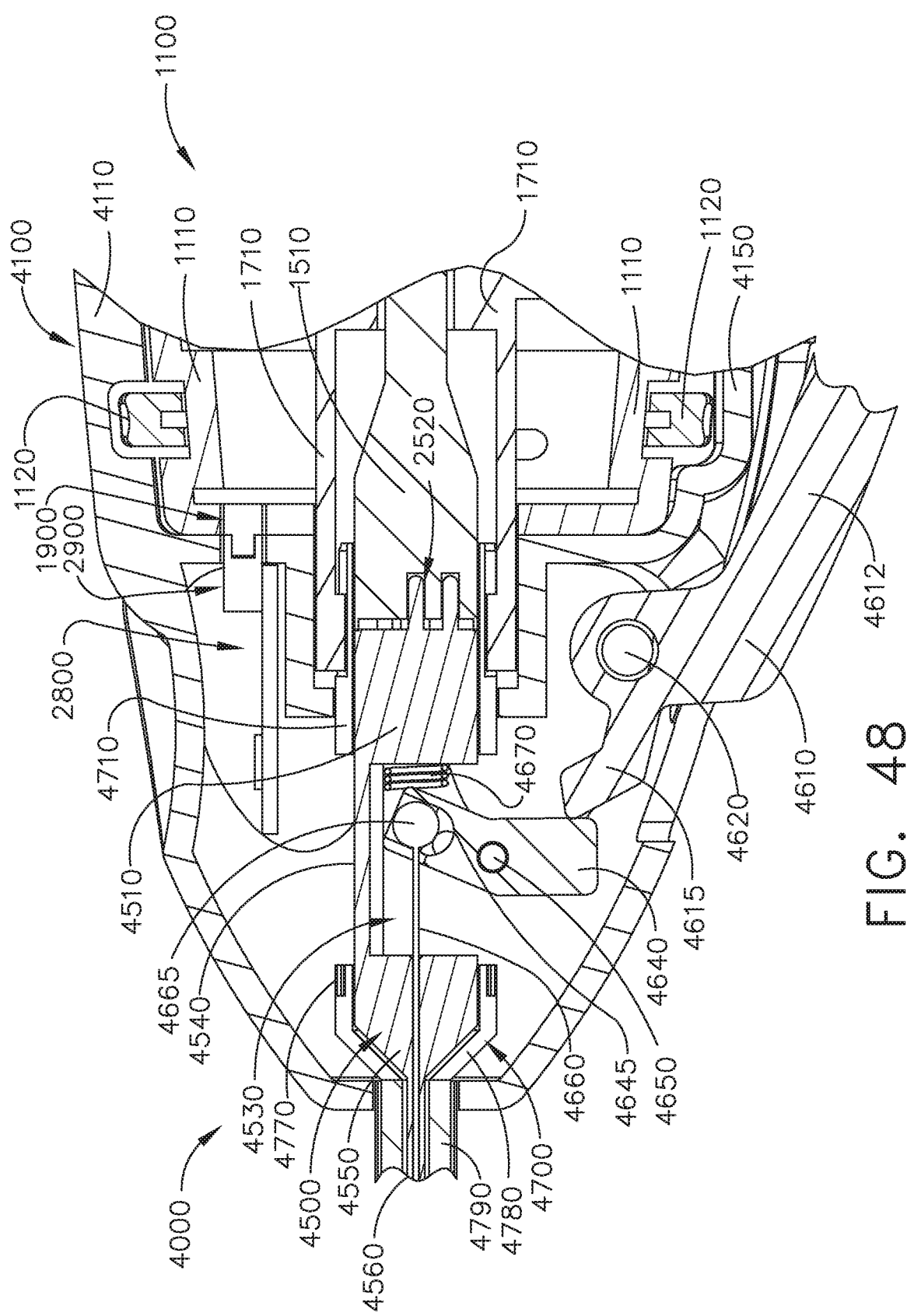
FIG. 48 is another partial cross-sectional view of the shaft assembly of FIG. 45 attached to the handle of FIG. 1.
Figure 49:
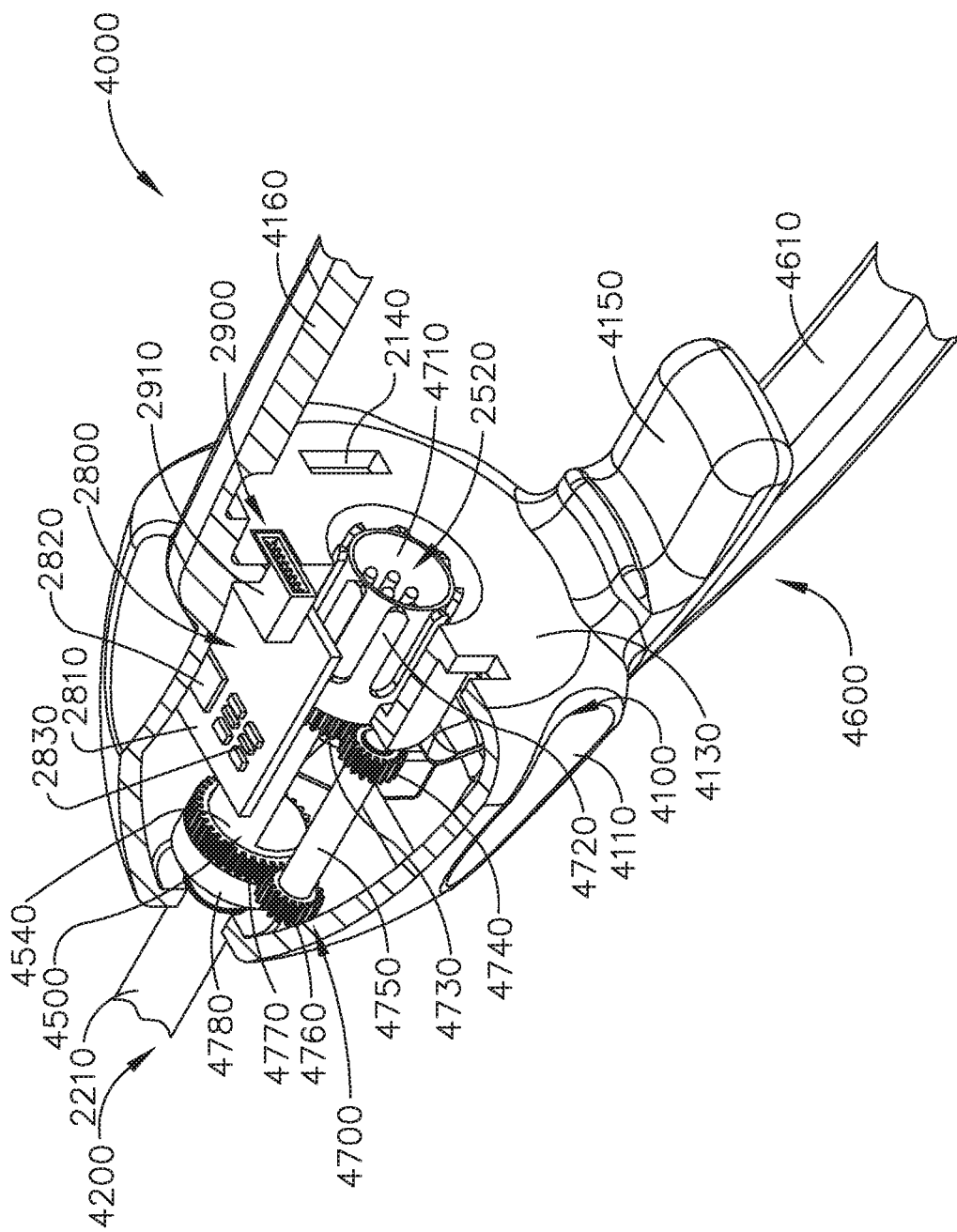
FIG. 49 is a partial cross-sectional perspective view of the shaft assembly of FIG. 45.

As discussed above, referring primarily to FIGS. 47-49, the frame 4500 of the shaft assembly 4000 comprises a frame shaft 4510. The frame shaft 4510 comprises a notch, or cut-out, 4530 defined therein. As discussed in greater detail below, the cut-out 4530 is configured to provide clearance for a jaw closure actuation system 4600. The frame 4500 further comprises a distal portion 4550 and a bridge 4540 connecting the distal portion 4550 to the frame shaft 4510. The frame 4500 further comprises a longitudinal portion 4560 extending through the elongate shaft 4200 to the distal attachment portion 2400. Similar to the above, the frame shaft 4510 comprises one or more electrical traces defined thereon and/or therein. The electrical traces extend through the longitudinal portion 4560, the distal portion 4550, the bridge 4540, and/or any suitable portion of the frame shaft 4510 to the electrical contacts 2520. Referring primarily to FIG. 48, the distal portion 4550 and longitudinal portion 4560 comprise a longitudinal aperture defined therein which is configured to receive a rod 4660 of the jaw closure actuation system 4600, as described in greater detail below.

As also discussed above, referring primarily to FIGS. 48 and 49, the drive system 4700 of the shaft assembly 4000 comprises a drive shaft 4710. The drive shaft 4710 is rotatably supported within the proximal shaft housing 4110 by the frame shaft 4510 and is rotatable about a longitudinal axis extending through the frame shaft 4510. The drive system 4700 further comprises a transfer shaft 4750 and an output shaft 4780. The transfer shaft 4750 is also rotatably supported within the proximal shaft housing 4110 and is rotatable about a longitudinal axis extending parallel to, or at least substantially parallel to, the frame shaft 4510 and the longitudinal axis defined therethrough. The transfer shaft 4750 comprises a proximal spur gear 4740 fixedly mounted thereto such that the proximal spur gear 4740 rotates with the transfer shaft 4750. The proximal spur gear 4740 is operably intermeshed with an annular gear face 4730 defined around the outer circumference of the drive shaft 4710 such that the rotation of the drive shaft 4710 is transferred to the transfer shaft 4750. The transfer shaft 4750 further comprises a distal spur gear 4760 fixedly mounted thereto such that the distal spur gear 4760 rotates with the transfer shaft 4750. The distal spur gear 4760 is operably intermeshed with an annular gear 4770 defined around the outer circumference of the output shaft 4780 such that the rotation of the transfer shaft 4750 is transferred to the output shaft 4780. Similar to the above, the output shaft 4780 is rotatably supported within the proximal shaft housing 4110 by the distal portion 4550 of the shaft frame 4500 such that the output shaft 4780 rotates about the longitudinal shaft axis. Notably, the output shaft 4780 is not directly coupled to the input shaft 4710; rather, the output shaft 4780 is operably coupled to the input shaft 4710 by the transfer shaft 4750. Such an arrangement provides room for the manually-actuated jaw closure actuation system 4600 discussed below.

Further to the above, referring primarily to FIGS. 47 and 48, the jaw closure actuation system 4600 comprises an actuation, or scissors, trigger 4610 rotatably coupled to the proximal shaft housing 4110 about a pivot 4620. The actuation trigger 4610 comprises an elongate portion 4612, a proximal end 4614, and a grip ring aperture 4616 defined in the proximal end 4614 which is configured to be gripped by the clinician. The shaft assembly 4000 further comprises a stationary grip 4160 extending from the proximal housing 4110. The stationary grip 4160 comprises an elongate portion 4162, a proximal end 4164, and a grip ring aperture 4166 defined in the proximal end 4164 which is configured to be gripped by the clinician. In use, as described in greater detail below, the actuation trigger 4610 is rotatable between an unactuated position and an actuated position (FIG. 48), i.e., toward the stationary grip 4160, to close the jaw assembly 8100 of the end effector 8000.

Referring primarily to FIG. 48, the jaw closure actuation system 4600 further comprises a drive link 4640 rotatably coupled to the proximal shaft housing 4110 about a pivot 4650 and, in addition, an actuation rod 4660 operably coupled to the drive link 4640. The actuation rod 4660 extends through an aperture defined in the longitudinal frame portion 4560 and is translatable along the longitudinal axis of the shaft frame 4500. The actuation rod 4660 comprises a distal end operably coupled to the jaw assembly 8100 and a proximal end 4665 positioned in a drive slot 4645 defined in the drive link 4640 such that the actuation rod 4660 is translated longitudinally when the drive link 4640 is rotated about the pivot 4650. Notably, the proximal end 4665 is rotatably supported within the drive slot 4645 such that the actuation rod 4660 can rotate with the end effector 8000.

Further to the above, the actuation trigger 4610 further comprises a drive arm 4615 configured to engage and rotate the drive link 4640 proximally, and translate the actuation rod 4660 proximally, when the actuation trigger 4610 is actuated, i.e., moved closer to the proximal shaft housing 4110. In such instances, the proximal rotation of the drive link 4640 resiliently compresses a biasing member, such as a coil spring 4670, for example, positioned intermediate the drive link 4640 and the frame shaft 4510. When the actuation trigger 4610 is released, the compressed coil spring 4670 re-expands and pushes the drive link 4640 and the actuation rod 4660 distally to open the jaw assembly 8100 of the end effector 8000. Moreover, the distal rotation of the drive link 4640 drives, and automatically rotates, the actuation trigger 4610 back into its unactuated position. That being said, the clinician could manually return the actuation trigger 4610 back into its unactuated position. In such instances, the actuation trigger 4610 could be opened slowly. In either event, the shaft assembly 4000 further comprises a lock configured to releasably hold the actuation trigger 4610 in its actuated position such that the clinician can use their hand to perform another task without the jaw assembly 8100 opening unintentionally.

In various alternative embodiments, further to the above, the actuation rod 4660 can be pushed distally to close the jaw assembly 8100. In at least one such instance, the actuation rod 4660 is mounted directly to the actuation trigger 4610 such that, when the actuation trigger 4610 is actuated, the actuation trigger 4610 drives the actuation rod 4660 distally. Similar to the above, the actuation trigger 4610 can compress a spring when the actuation trigger 4610 is closed such that, when the actuation trigger 4610 is released, the actuation rod 4660 is pushed proximally.

Further to the above, the shaft assembly 4000 has three functions—opening/closing the jaw assembly of an end effector, rotating the end effector about a longitudinal axis, and articulating the end effector about an articulation axis. The end effector rotation and articulation functions of the shaft assembly 4000 are driven by the motor assembly 1600 and the control system 1800 of the drive module 1100 while the jaw actuation function is manually-driven by the jaw closure actuation system 4600. The jaw closure actuation system 4600 could be a motor-driven system but, instead, the jaw closure actuation system 4600 has been kept a manually-driven system such that the clinician can have a better feel for the tissue being clamped within the end effector. While motorizing the end effector rotation and actuation systems provides certain advantages for controlling the position of the end effector, motorizing the jaw closure actuation system 4600 may cause the clinician to lose a tactile sense of the force being applied to the tissue and may not be able to assess whether the force is insufficient or excessive. Thus, the jaw closure actuation system 4600 is manually-driven even though the end effector rotation and articulation systems are motor-driven.

Figure 50:
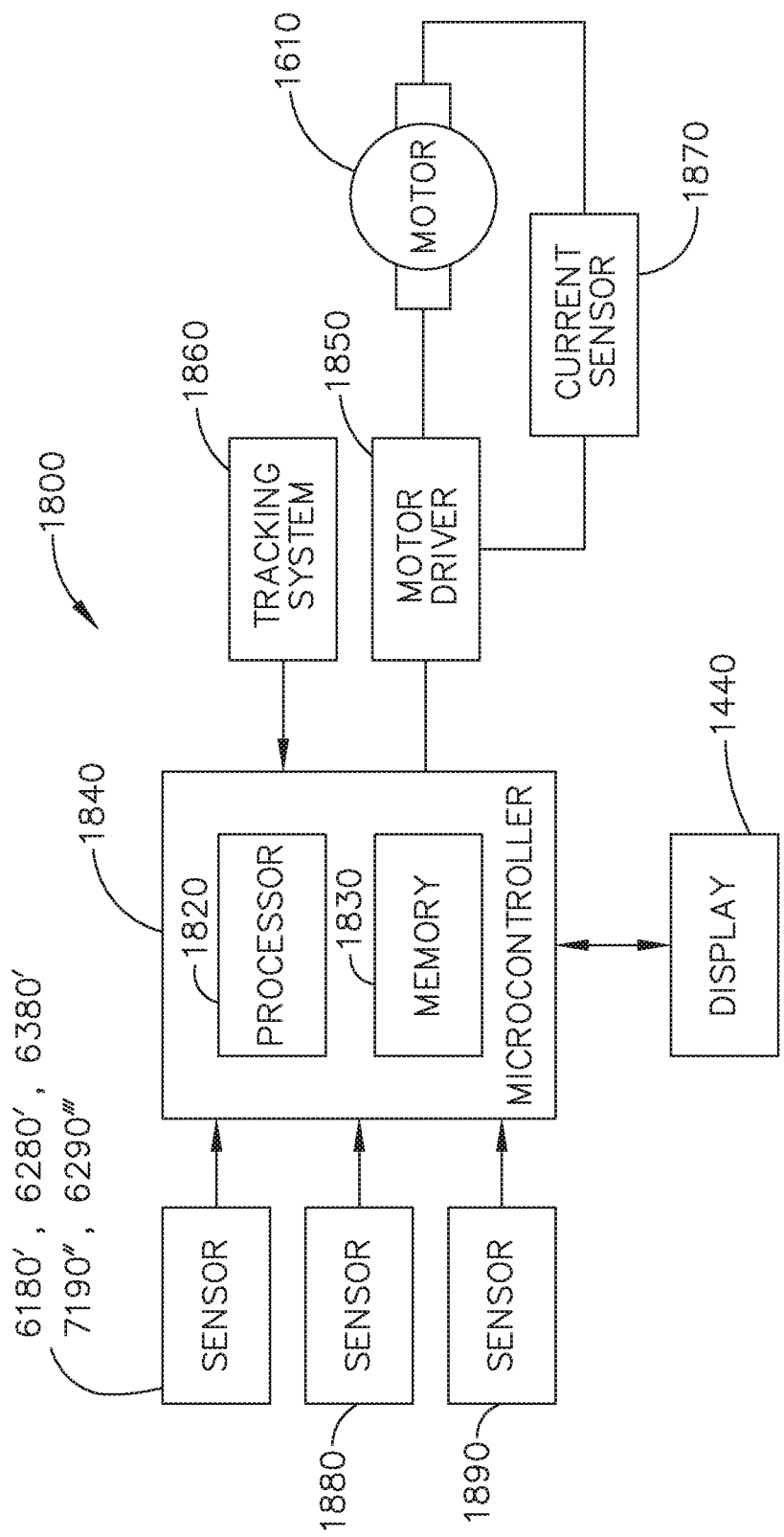
FIG. 50 is a schematic of the control system of the surgical system of FIG. 1.

FIG. 50 is a logic diagram of the control system 1800 of the surgical system depicted in FIG. 1 in accordance with at least one embodiment. The control system 1800 comprises a control circuit. The control circuit includes a microcontroller 1840 comprising a processor 1820 and a memory 1830. One or more sensors, such as sensors 1880, 1890, 6180', 6280', 6380', 7190", and/or 6290'", for example, provide real time feedback to the processor 1820. The control system 1800 further comprises a motor driver 1850 configured to control the electric motor 1610 and a tracking system 1860 configured to determine the position of one or more longitudinally movable components in the surgical instrument, such as the clutches 6110, 6120, and 6130 and/or the longitudinally-movable drive nut 7150 of the jaw assembly drive, for example. The tracking system 1860 is also configured to determine the position of one or more rotational components in the surgical instrument, such as the drive shaft 2530, the outer shaft 6230, and/or the articulation drive 6330, for example. The tracking system 1860 provides position information to the processor 1820, which can be programmed or configured to, among other things, determine the position of the clutches 6110, 6120, and 6130 and the drive nut 7150 as well as the orientation of the jaws 7110 and 7120. The motor driver 1850 may be an A3941 available from Allegro Microsystems, Inc., for example; however, other motor drivers may be readily substituted for use in the tracking system 1860. A detailed description of an absolute positioning system is described in U.S. Patent Application Publication No. 2017/0296213, entitled SYSTEMS AND METHODS FOR CONTROLLING A SURGICAL STAPLING AND CUTTING INSTRUMENT, the entire disclosure of which is hereby incorporated herein by reference.

The microcontroller 1840 may be any single core or multicore processor such as those known under the trade name ARM Cortex by Texas Instruments, for example. In at least one instance, the microcontroller 1840 is a LM4F230H5QR ARM Cortex-M4F Processor Core, available from Texas Instruments, for example, comprising on-chip memory of 256 KB single-cycle flash memory, or other non-volatile memory, up to 40 MHz, a prefetch buffer to improve performance above 40 MHz, a 32 KB single-cycle serial random access memory (SRAM), internal read-only memory (ROM) loaded with StellarisWare® software, 2 KB electrically erasable programmable read-only memory (EEPROM), one or more pulse width modulation (PWM) modules and/or frequency modulation (FM) modules, one or more quadrature encoder inputs (QEI) analog, one or more 12-bit Analog-to-Digital Converters (ADC) with 12 analog input channels, for example, details of which are available from the product datasheet.

In various instances, the microcontroller 1840 comprises a safety controller comprising two controller-based families such as TMS570 and RM4x known under the trade name Hercules ARM Cortex R4, also by Texas Instruments. The safety controller may be configured specifically for IEC 61508 and ISO 26262 safety critical applications, among others, to provide advanced integrated safety features while delivering scalable performance, connectivity, and memory options.

The microcontroller 1840 is programmed to perform various functions such as precisely controlling the speed and/or position of the drive nut 7150 of the jaw closure assembly, for example. The microcontroller 1840 is also programmed to precisely control the rotational speed and position of the end effector 7000 and the articulation speed and position of the end effector 7000. In various instances, the microcontroller 1840 computes a response in the software of the microcontroller 1840. The computed response is compared to a measured response of the actual system to obtain an "observed" response, which is used for actual feedback decisions. The observed response is a favorable, tuned, value that balances the smooth, continuous nature of the simulated response with the measured response, which can detect outside influences on the system.

The motor 1610 is controlled by the motor driver 1850. In various forms, the motor 1610 is a DC brushed driving motor having a maximum rotational speed of approximately 25,000 RPM, for example. In other arrangements, the motor 1610 includes a brushless motor, a cordless motor, a synchronous motor, a stepper motor, or any other suitable electric motor. The motor driver 1850 may comprise an H-bridge driver comprising field-effect transistors (FETs), for example. The motor driver 1850 may be an A3941 available from Allegro Microsystems, Inc., for example. The A3941 driver 1850 is a full-bridge controller for use with external N-channel power metal oxide semiconductor field effect transistors (MOSFETs) specifically designed for inductive loads, such as brush DC motors. In various instances, the driver 1850 comprises a unique charge pump regulator provides full (>10 V) gate drive for battery voltages down to 7 V and allows the A3941 to operate with a reduced gate drive, down to 5.5 V. A bootstrap capacitor may be employed to provide the above-battery supply voltage required for N-channel MOSFETs. An internal charge pump for the high-side drive allows DC (100% duty cycle) operation. The full bridge can be driven in fast or slow decay modes using diode or synchronous rectification. In the slow decay mode, current recirculation can be through the high-side or the lowside FETs. The power FETs are protected from shoot-through by resistor adjustable dead time. Integrated diagnostics provide indication of undervoltage, over-temperature, and power bridge faults, and can be configured to protect the power MOSFETs under most short circuit conditions. Other motor drivers may be readily substituted.

The tracking system 1860 comprises a controlled motor drive circuit arrangement comprising one or more position sensors, such as sensors 1880, 1890, 6180', 6280', 6380', 7190", and/or 6290'", for example. The position sensors for an absolute positioning system provide a unique position signal corresponding to the location of a displacement member. As used herein, the term displacement member is used generically to refer to any movable member of the surgical system. In various instances, the displacement member may be coupled to any position sensor suitable for measuring linear displacement. Linear displacement sensors may include contact or non-contact displacement sensors. Linear displacement sensors may comprise linear variable differential transformers (LVDT), differential variable reluctance transducers (DVRT), a slide potentiometer, a magnetic sensing system comprising a movable magnet and a series of linearly arranged Hall Effect sensors, a magnetic sensing system comprising a fixed magnet and a series of movable linearly arranged Hall Effect sensors, an optical sensing system comprising a movable light source and a series of linearly arranged photo diodes or photo detectors, or an optical sensing system comprising a fixed light source and a series of movable linearly arranged photo diodes or photo detectors, or any combination thereof.

The position sensors 1880, 1890, 6180', 6280', 6380', 7190", and/or 6290'", for example, may comprise any number of magnetic sensing elements, such as, for example, magnetic sensors classified according to whether they measure the total magnetic field or the vector components of the magnetic field. The techniques used to produce both types of magnetic sensors encompass many aspects of physics and electronics. The technologies used for magnetic field sensing include search coil, fluxgate, optically pumped, nuclear precession, SQUID, Hall-Effect, anisotropic magnetoresistance, giant magnetoresistance, magnetic tunnel junctions, giant magnetoimpedance, magnetostrictive/piezoelectric composites, magnetodiode, magnetotransistor, fiber optic, magnetooptic, and microelectromechanical systems-based magnetic sensors, among others.

In various instances, one or more of the position sensors of the tracking system 1860 comprise a magnetic rotary absolute positioning system. Such position sensors may be implemented as an AS5055EQFT single-chip magnetic rotary position sensor available from Austria Microsystems, AG and can be interfaced with the controller 1840 to provide an absolute positioning system. In certain instances, a position sensor comprises a low-voltage and low-power component and includes four Hall-Effect elements in an area of the position sensor that is located adjacent a magnet. A high resolution ADC and a smart power management controller are also provided on the chip. A CORDIC processor (for Coordinate Rotation Digital Computer), also known as the digit-by-digit method and Volder's algorithm, is provided to implement a simple and efficient algorithm to calculate hyperbolic and trigonometric functions that require only addition, subtraction, bitshift, and table lookup operations. The angle position, alarm bits, and magnetic field information are transmitted over a standard serial communication interface such as an SPI interface to the controller 1840. The position sensors can provide 12 or 14 bits of resolution, for example. The position sensors can be an AS5055 chip provided in a small QFN 16-pin 4×4×0.85 mm package, for example.

The tracking system 1860 may comprise and/or be programmed to implement a feedback controller, such as a PID, state feedback, and adaptive controller. A power source converts the signal from the feedback controller into a physical input to the system, in this case voltage. Other examples include pulse width modulation (PWM) and/or frequency modulation (FM) of the voltage, current, and force. Other sensor(s) may be provided to measure physical parameters of the physical system in addition to position. In various instances, the other sensor(s) can include sensor arrangements such as those described in U.S. Pat. No. 9,345,481, entitled STAPLE CARTRIDGE TISSUE THICKNESS SENSOR SYSTEM, which is hereby incorporated herein by reference in its entirety; U.S. Patent Application Publication No. 2014/0263552, entitled STAPLE CARTRIDGE TISSUE THICKNESS SENSOR SYSTEM, which is hereby incorporated herein by reference in its entirety; and U.S. patent application Ser. No. 15/628,175, entitled TECHNIQUES FOR ADAPTIVE CONTROL OF MOTOR VELOCITY OF A SURGICAL STAPLING AND CUTTING INSTRUMENT, which is hereby incorporated herein by reference in its entirety. In a digital signal processing system, absolute positioning system is coupled to a digital data acquisition system where the output of the absolute positioning system will have finite resolution and sampling frequency. The absolute positioning system may comprise a compare and combine circuit to combine a computed response with a measured response using algorithms such as weighted average and theoretical control loop that drives the computed response towards the measured response. The computed response of the physical system takes into account properties like mass, inertial, viscous friction, inductance resistance, etc., to predict what the states and outputs of the physical system will be by knowing the input.

The absolute positioning system provides an absolute position of the displacement member upon power up of the instrument without retracting or advancing the displacement member to a reset (zero or home) position as may be required with conventional rotary encoders that merely count the number of steps forwards or backwards that the motor 1610 has taken to infer the position of a device actuator, drive bar, knife, and the like.

A sensor 1880 comprising a strain gauge or a micro-strain gauge, for example, is configured to measure one or more parameters of the end effector, such as, for example, the strain experienced by the jaws 7110 and 7120 during a clamping operation. The measured strain is converted to a digital signal and provided to the processor 1820. In addition to or in lieu of the sensor 1880, a sensor 1890 comprising a load sensor, for example, can measure the closure force applied by the closure drive system to the jaws 7110 and 7120. In various instances, a current sensor 1870 can be employed to measure the current drawn by the motor 1610. The force required to clamp the jaw assembly 7100 can correspond to the current drawn by the motor 1610, for example. The measured force is converted to a digital signal and provided to the processor 1820. A magnetic field sensor can be employed to measure the thickness of the captured tissue. The measurement of the magnetic field sensor can also be converted to a digital signal and provided to the processor 1820.

The measurements of the tissue compression, the tissue thickness, and/or the force required to close the end effector on the tissue as measured by the sensors can be used by the controller 1840 to characterize the position and/or speed of the movable member being tracked. In at least one instance, a memory 1830 may store a technique, an equation, and/or a look-up table which can be employed by the controller 1840 in the assessment. In various instances, the controller 1840 can provide the user of the surgical instrument with a choice as to the manner in which the surgical instrument should be operated. To this end, the display 1440 can display a variety of operating conditions of the instrument and can include touch screen functionality for data input. Moreover, information displayed on the display 1440 may be overlaid with images acquired via the imaging modules of one or more endoscopes and/or one or more additional surgical instruments used during the surgical procedure.

As discussed above, the drive module 1100 of the handle 1000 and/or the shaft assemblies 2000, 3000, 4000, and/or 5000, for example, attachable thereto comprise control systems. Each of the control systems can comprise a circuit board having one or more processors and/or memory devices. Among other things, the control systems are configured to store sensor data, for example. They are also configured to store data which identifies the shaft assembly to the handle 1000. Moreover, they are also configured to store data including whether or not the shaft assembly has been previously used and/or how many times the shaft assembly has been used. This information can be obtained by the handle 1000 to assess whether or not the shaft assembly is suitable for use and/or has been used less than a predetermined number of times, for example.

Figure 51:
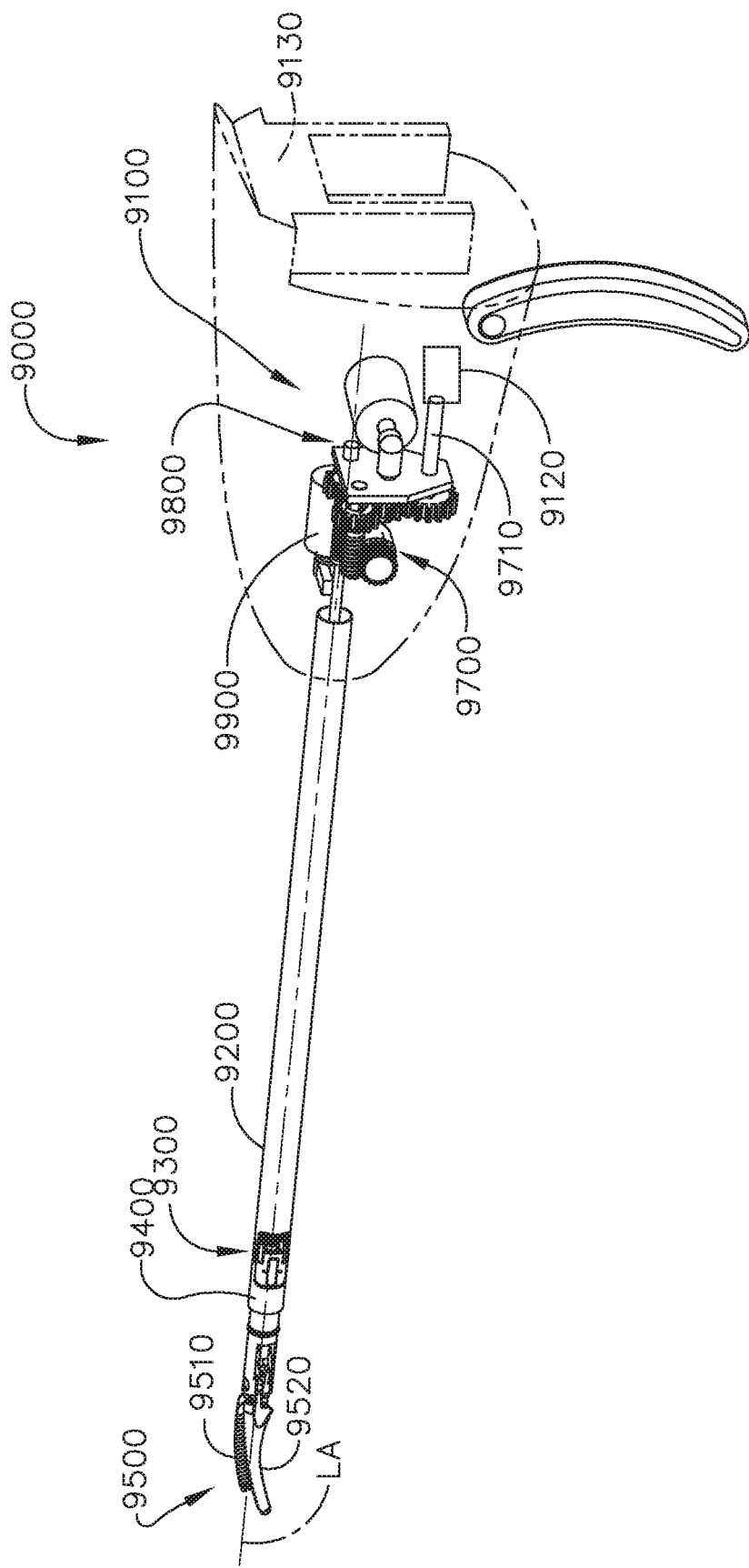
FIG. 51 is a perspective view of a shaft assembly in accordance with at least one embodiment.

A shaft assembly 9000 is illustrated in FIGS. 51-69. The shaft assembly 9000 is similar to the shaft assemblies 2000, 3000, 4000, and 5000 in many respects, most of which will not be discussed herein for the sake of brevity. As illustrated in FIG. 51, the shaft assembly 9000 comprises a proximal portion 9100, an elongate shaft 9200 extending from the proximal portion 9100, a distal attachment portion 9400, and an articulation joint 9300. The proximal portion 9100 comprises an interface 9130 configured to be attached to a handle, such as the handle 1000, for example. The articulation joint 9300 rotatably connects the distal attachment portion 9400 to the elongate shaft 9200. The shaft assembly 9000 further comprises an end effector assembly 9500 attached to the distal attachment portion 9400. The end effector assembly 9500 comprises a first jaw 9510 and a second jaw 9520 configured to be opened and closed to clamp and/or manipulate the tissue of a patient. In use, the end effector assembly 9500 can be articulated about the articulation joint 9300 and/or rotated relative to the distal attachment portion 9400 about a longitudinal axis LA to better situate the jaws 9510 and 9520 within a patient in order to perform various end effector functions, as will be described in greater detail below.

Figure 54:
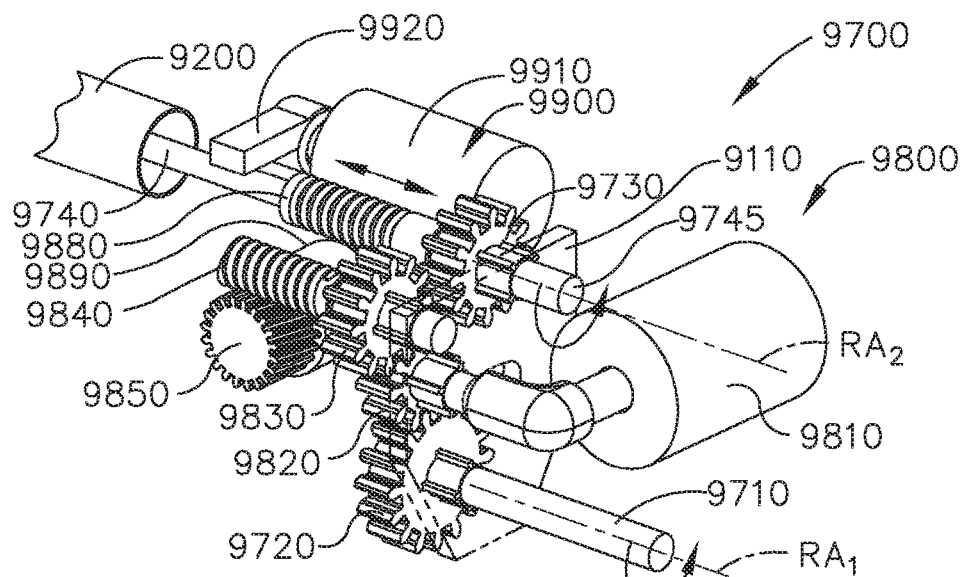
FIG. 54 is a perspective view of a drive assembly of the shaft assembly of FIG. 51.
Figure 55:
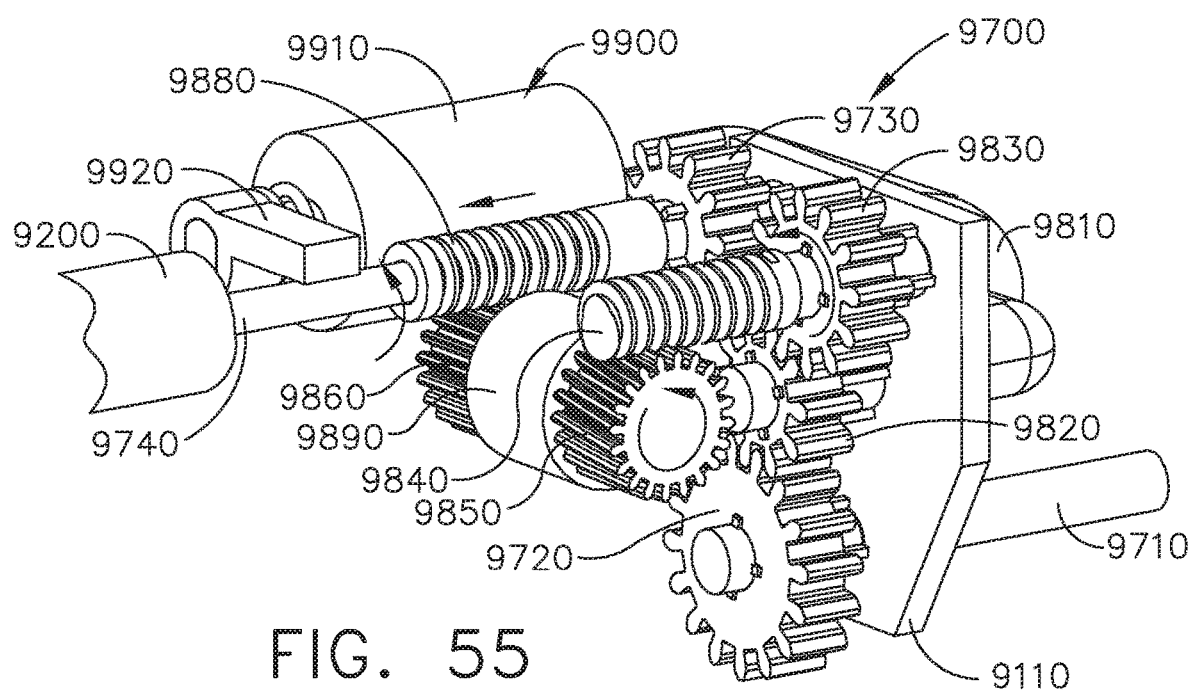
FIG. 55 is another perspective view of the drive assembly of FIG. 54.

Referring to FIG. 52, the shaft assembly 9000 comprises a drive assembly 9700 supported on a frame 9110 in the proximal shaft portion 9100. The drive assembly 9700 is capable of being operated in two configurations—a shifting configuration and a drive configuration. Moreover, as discussed in greater detail below, the drive assembly 9700 is configured to provide three end effector functions by way of one rotary input. The drive assembly 9700 comprises a first, or input, rotatable drive shaft 9710 configured to transfer rotational motions from a drive motor 9120 (illustrated in FIG. 51) to a main gear 9720 of the drive assembly 9700. Referring to FIGS. 54 and 55, the input drive shaft 9710 is rotatable about a first rotation axis $RA_1$ and is rotatably supported by the frame 9110. The main gear 9720 is mounted to the input drive shaft 9710 such that the main gear 9720 rotates with the input drive shaft 9710. The drive assembly 9700 further comprises a second, or output, rotatable drive shaft 9740. The output drive shaft 9740 is rotatable about a second rotation axis $RA_2$ and is also rotatably supported by the frame 9110. As described in greater detail below, the drive assembly 9700 also comprises a first rotatable gear 9730 and a second rotatable gear 9830 which are selectively engageable with the main gear 9720.

Figures 58, 59:
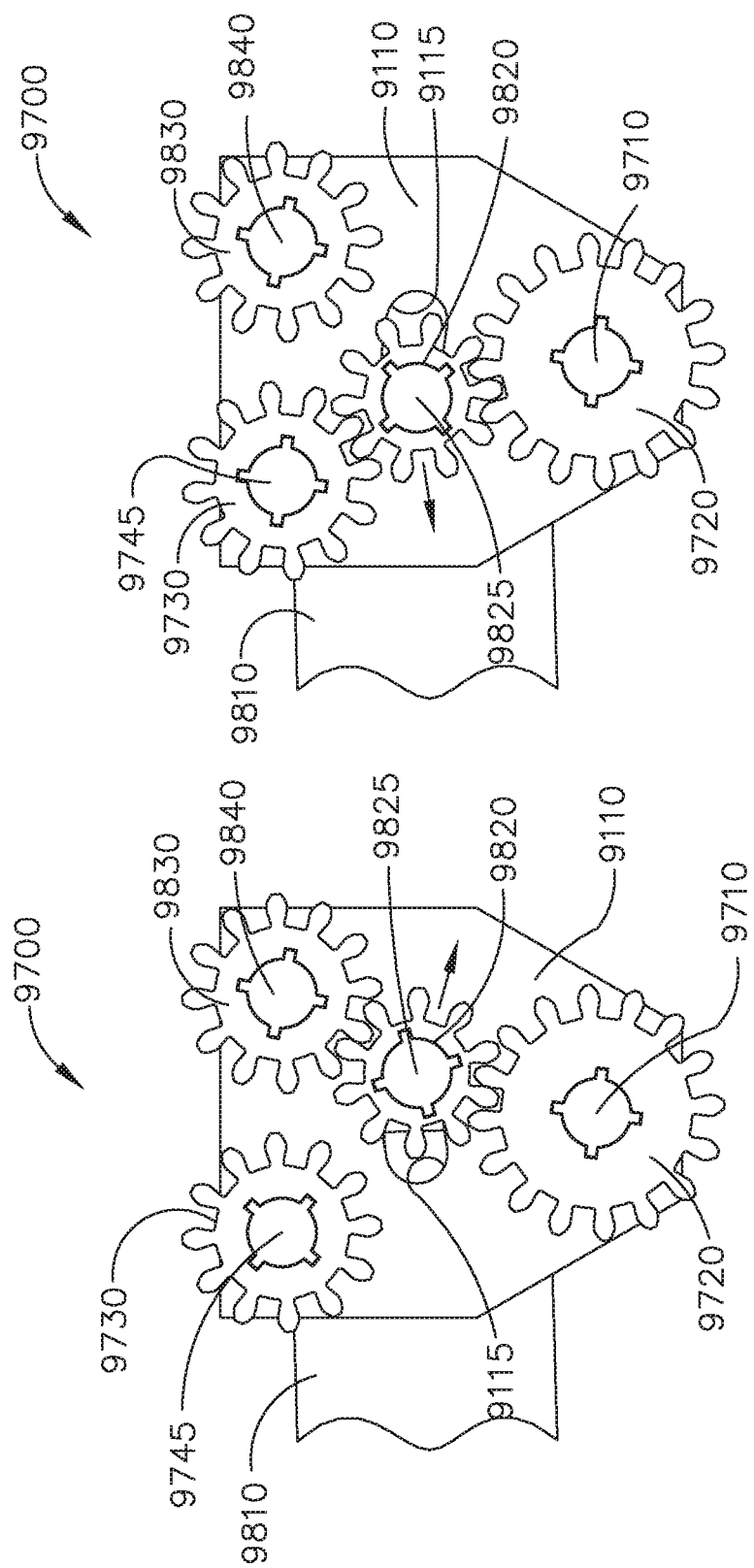
FIG. 58 is an elevational view of the drive assembly of FIG. 54 illustrated in a shifting configuration with some components removed.
FIG. 59 is an elevational view of the drive assembly of FIG. 54 illustrated in a drive configuration with some components removed.

Referring to FIG. 52, the shaft assembly 9000 further comprises a shifting assembly 9800 configured to shift the drive assembly 9700. The shifting assembly 9800 comprises a solenoid 9810 which translates a shifter gear 9820 to place the drive assembly 9700 in its shifting configuration or its drive configuration. Referring to FIGS. 58 and 59, the shifter gear 9820 is operably intermeshed with the main gear 9720 of the drive assembly 9700 when the shifter gear 9820 is in its shifting configuration (FIG. 58) and, also, its drive configuration (FIG. 59). That being said, the shifter gear 9820 rotatably drives either the first rotatable gear 9730 or the second rotatable gear 9830 depending on whether the drive assembly 9700 is in its shifting configuration (FIG. 58) or its drive configuration (FIG. 59). Ultimately, the first and second rotatable gears 9730 and 9830 both drive the output drive shaft 9740, but in different ways. More specifically, the output drive shaft 9740 is rotated by the shifter gear 9820 via the first rotatable gear 9730 when the drive assembly 9700 is in its drive configuration and, on the other hand, the output drive shaft 9740 is translated by the shifter gear 9820 via the second rotatable gear 9830 when the drive assembly 9700 is in its shifting configuration.

Referring primarily to FIGS. 58 and 59, the frame 9110 comprises a slot 9115 defined therein which is configured to guide and/or constrain the movement of the shifter gear 9820. The slot 9115 comprises a first end configured to stop the shifter gear 9820 in its first position and a second end configured to stop the shifter gear 9820 in its second position. More specifically, the shifter gear 9820 is rotatably mounted to a shifter shaft 9825 extending through the slot 9115 which slides within the slot 9115 and moves the shifter gear 9820 between its first and second positions when the solenoid 9810 is actuated. The slot 9115 comprises arcuate sidewalls extending between the first and second ends thereof which define an arcuate path for the shifter gear 9820. The arcuate path is centered about the axis $RA_1$ extending through the input shaft 9710. That said, the slot 9115 can comprise any suitable configuration and define any suitable path for the shifter gear 9820. In at least one instance, the slot 9115 is straight and defines a straight path for the shifter gear 9820.

Figure 56:
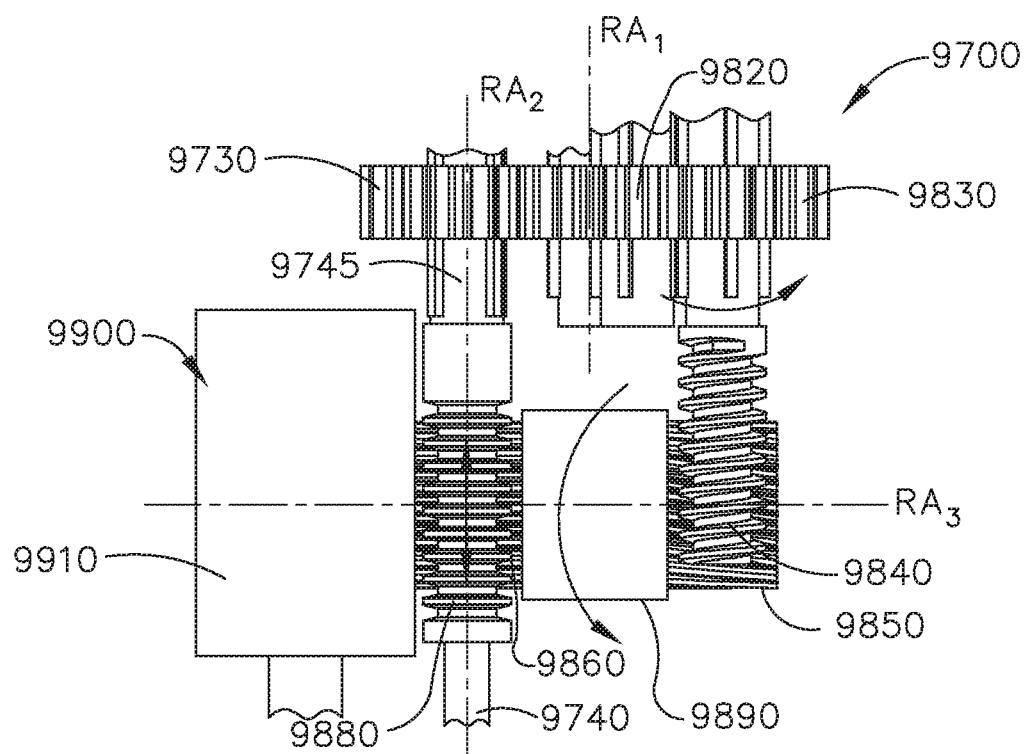
FIG. 56 is a partial plan view of the drive assembly of FIG. 54.

Referring to FIGS. 55 and 56, the shifting assembly 9800 further comprises a threaded transfer shaft 9840 mounted to the second rotatable gear 9830 such that the transfer shaft 9840 turns with the second rotatable gear 9830. Similar to the input shaft 9710, the transfer shaft 9840 is rotatably supported by the frame 9110. The shifting assembly 9800 further comprises a lateral shaft 9890 rotatably supported within the proximal portion 9100 which comprises a pinion gear 9850 operably intermeshed with the transfer shaft 9840 such that the rotation of the transfer shaft 9840 is transferred to the lateral shaft 9890. The lateral shaft 9890 further comprises a rack gear 9860 defined thereon which is meshingly engaged with a rack 9880 defined on the output drive shaft 9740. The lateral shaft 9890 is rotatable about a third rotation axis $RA_3$. As illustrated in FIG. 56, the first rotation axis $RA_1$ and the second rotation axis $RA_2$ are parallel, or at least substantially parallel, to one another, and the third rotation axis $RA_3$ is perpendicular, or at least substantially perpendicular, to the first rotation axis $RA_1$ and the second rotation axis $RA_2$.

Figure 60:
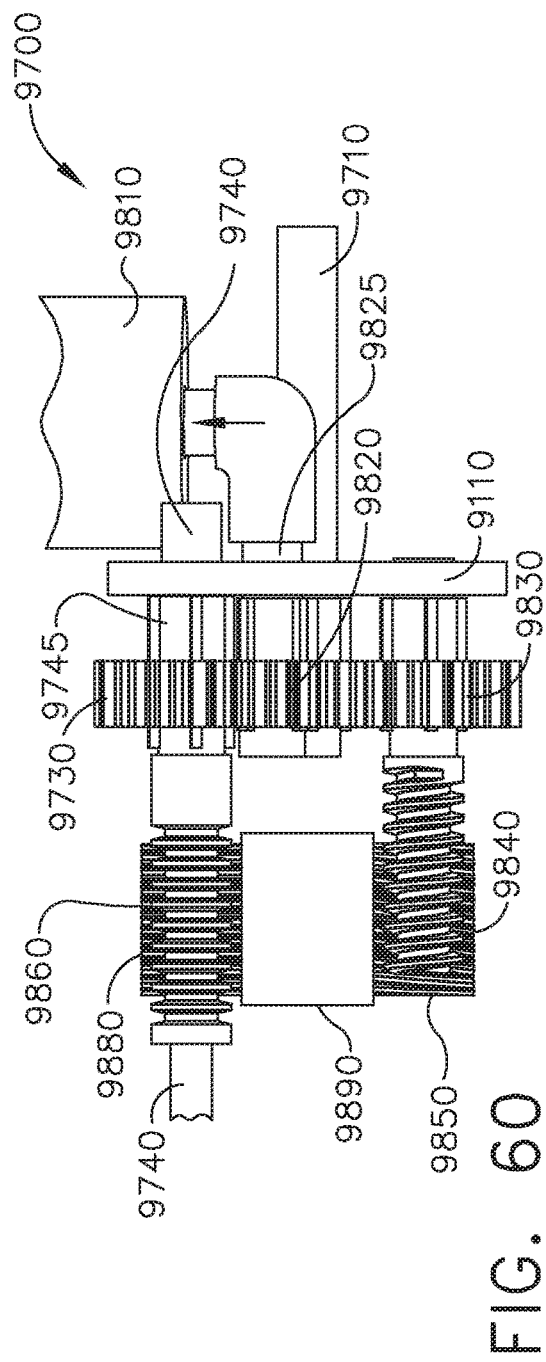
FIG. 60 is a top view of the drive assembly of FIG. 54 in the drive configuration.
Figure 61:
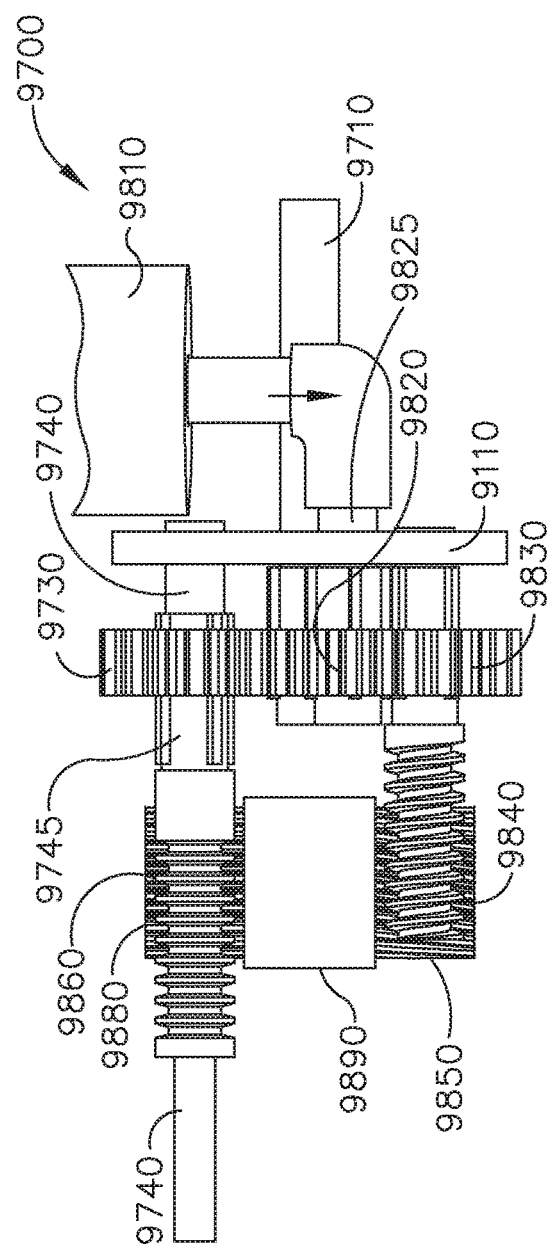
FIG. 61 is a top view of the drive assembly of FIG. 54 in the shifting configuration.

As outlined above, referring to FIG. 56, the shifter gear 9820 is intermeshed with the rotatable gear 9830 when the drive assembly 9700 is in its shifting configuration. As the motor 9120 powers the input shaft 9710 to rotate the main gear 9720, the shifter gear 9820 also rotates. As the shifter gear 9820 rotates while engaged with the rotatable gear 9830, the transfer shaft 9840 rotates in the same direction as the rotatable gear 9830 and the lateral shaft 9890 rotates about the axis $RA_3$. When the main gear 9720 is rotated in a first direction, in this configuration, the rack gear 9860 drives the drive shaft 9740 distally via the rack 9880, as illustrated in FIG. 61. When the main gear 9720 is rotated in a second, or opposite, direction, the rack gear 9860 drives the drive shaft 9740 proximally, as illustrated in FIG. 60. As discussed in greater detail below, the drive shaft 9740 is shiftable proximally and distally to place the drive shaft 9740 in a first, or proximal, drive configuration, a second, or intermediate, drive configuration, and a third, or distal, drive configuration.

Further to the above, the shaft assembly 9000 and/or handle 1000, for example, comprise a control system configured to operate the drive motor 9120 and the solenoid 9810. The control system of the shaft assembly 9000 is similar to the control system 1800 and/or 2800 in many respects, most of which will not be discussed herein for the sake of brevity. The control system is configured to receive inputs from the clinician and, in response to those inputs, shift the shaft assembly 9000 into a first, or articulation, operating mode, a second, or rotation, operating mode, or a third, or jaw drive, operating mode. The first, second, and third operating modes of the shaft assembly 9000 correspond to the first, second, and third positions of the output shaft 9740. When the shaft assembly 9000 is instructed to switch between operating modes, the solenoid 9810 moves the shifter gear 9820 into its second position and then rotates the input shaft 9710 to translate the output shaft 9740. The control system is configured to correlate the amount in which the input shaft 9710 is rotated to the amount in which the output shaft 9740 is translated. The control system is configured to monitor the rotations of the drive motor 9120 and then stop the drive motor 9120 once the drive motor 9120 has been rotated the appropriate number of rotations to shift the output shaft 9740. The control system comprises a memory device which stores the number of rotations needed to translate the output shaft 9740 between its first, second, and third positions. For instance, the memory device stores the number of rotations of the drive motor 9120 to translate the output shaft 9740 between the first position and the second position, the first position and the third position, and the second position and the third position. The control system is also configured to know what position the output shaft 9740 is currently in before operating the drive motor 9120. In various instances, the control system can comprise a sensor system configured to detect the current position of the output shaft 9740 and then determine the number of rotations, and the direction of those rotations, in which the drive motor 9120 should be operated.

Once the output shaft 9740 has been positioned in the first, second, or third position, as described above, the control system operates the solenoid 9810 to place the shifter gear 9820 in the drive configuration. In such instances, the shifter gear 9820 is disengaged from the second gear 9830 and then engaged with the first gear 9730. The first gear 9730 is mounted to the output shaft 9740 such that the rotation of the first gear 9730 is transmitted to the output shaft 9740. More specifically, the first gear 9730 is disposed on the splined proximal end 9745 of the output shaft 9740 such that the first gear 9730 and the output shaft 9740 rotate together. That said, the output shaft 9740 can translate relative to the first gear 9730 owing to the splined proximal end 9745 such that the first gear 9730 remains aligned with the shifter gear 9820 when the output shaft 9740 is being translated as described above. As discussed in greater detail below, the input shaft 9710 is rotatable in a first direction to rotate the output shaft 9740 in a first direction and a second direction to rotate the output shaft 9740 in a second direction.

FIGS. 58 and 61 illustrate the drive assembly 9700 in the shifting configuration. The main gear 9720 is rotatably engaged with the shifter gear 9820 in the shifting configuration to transfer motion from the input drive shaft 9710 to the second rotatable gear 9830. FIGS. 59 and 60 illustrate the drive assembly 9700 in the drive configuration. In the drive configuration, the main gear 9720 is rotatably engaged with the shifter gear 9820 to transfer motion from the input drive shaft 9710 to the first rotatable gear 9730. As discussed above, the output drive shaft 9740 is translatable. In fact, the output drive shaft 9740 is translatable between three different operational positions—a first, or proximal, position in which the output drive shaft 9740 drives an articulation system, a second, or intermediate, position in which the output drive shaft 9740 drives an end effector rotation system, and a third, or distal, position in which the output shaft 9740 drives a jaw drive system.

Figure 62:
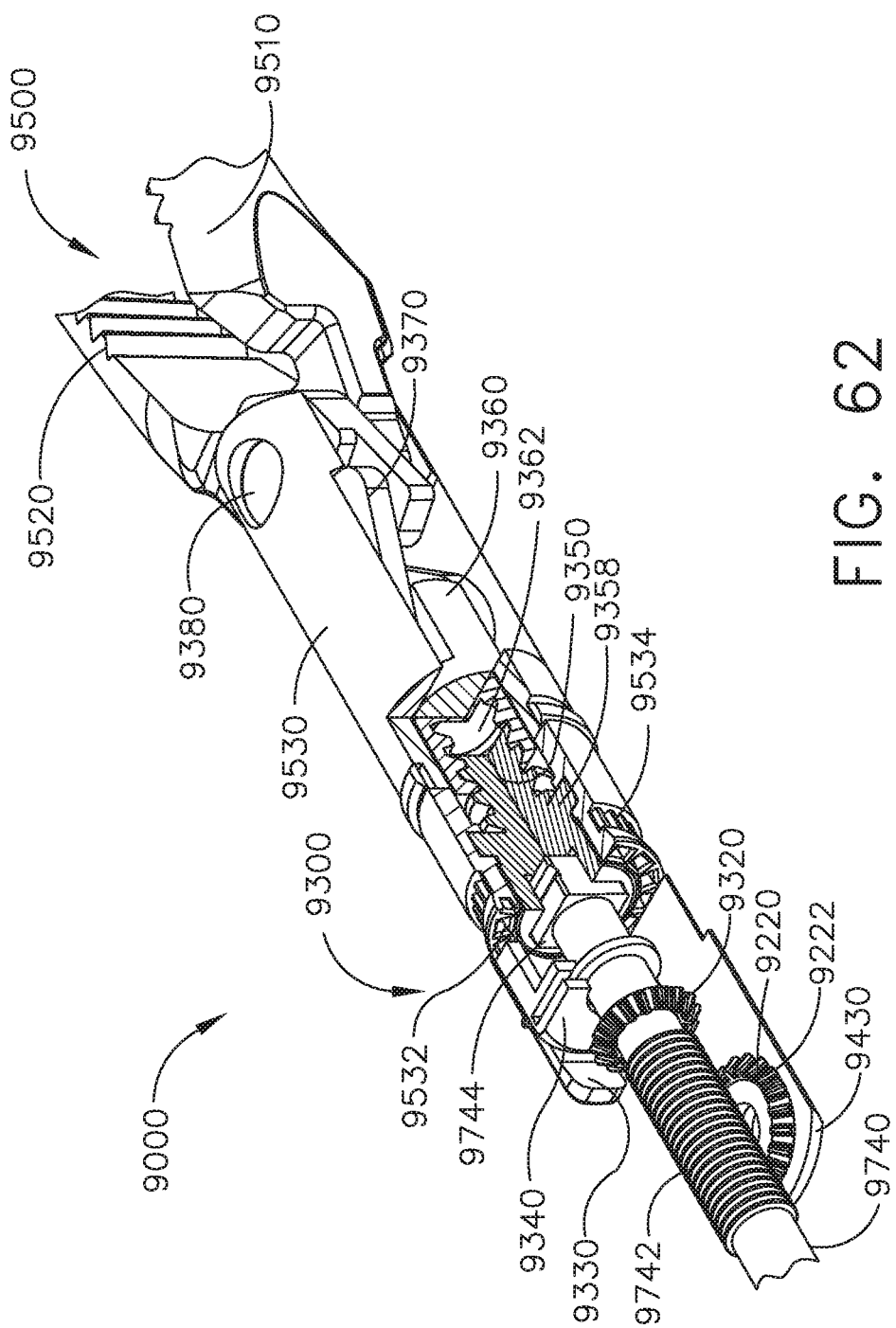
FIG. 62 is a partial perspective cross-sectional view of the end effector of FIG. 53.
Figure 63:
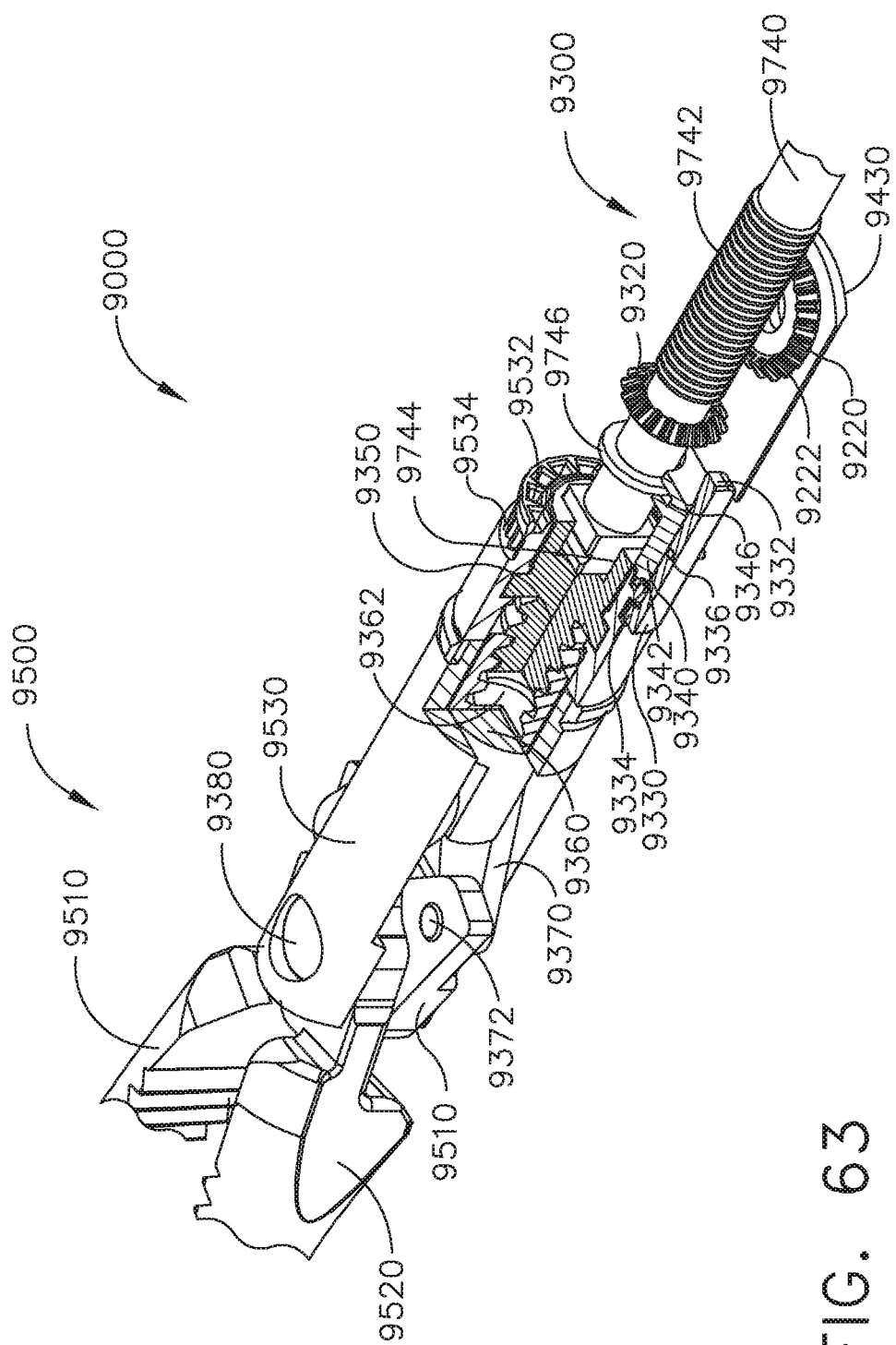
FIG. 63 is a partial perspective cross-sectional view of the end effector of FIG. 53.
Figure 64:
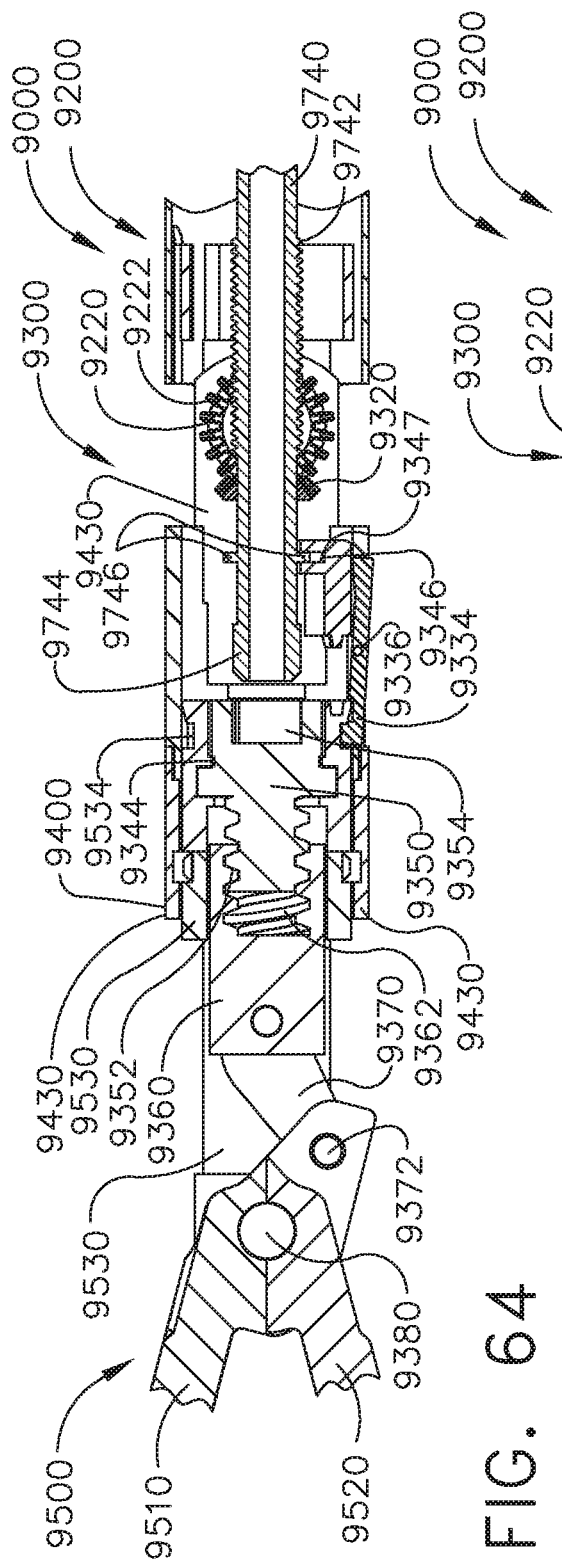
FIG. 64 is a partial top cross-sectional view of the end effector of FIG. 53 in an articulation drive mode.
Figure 65:
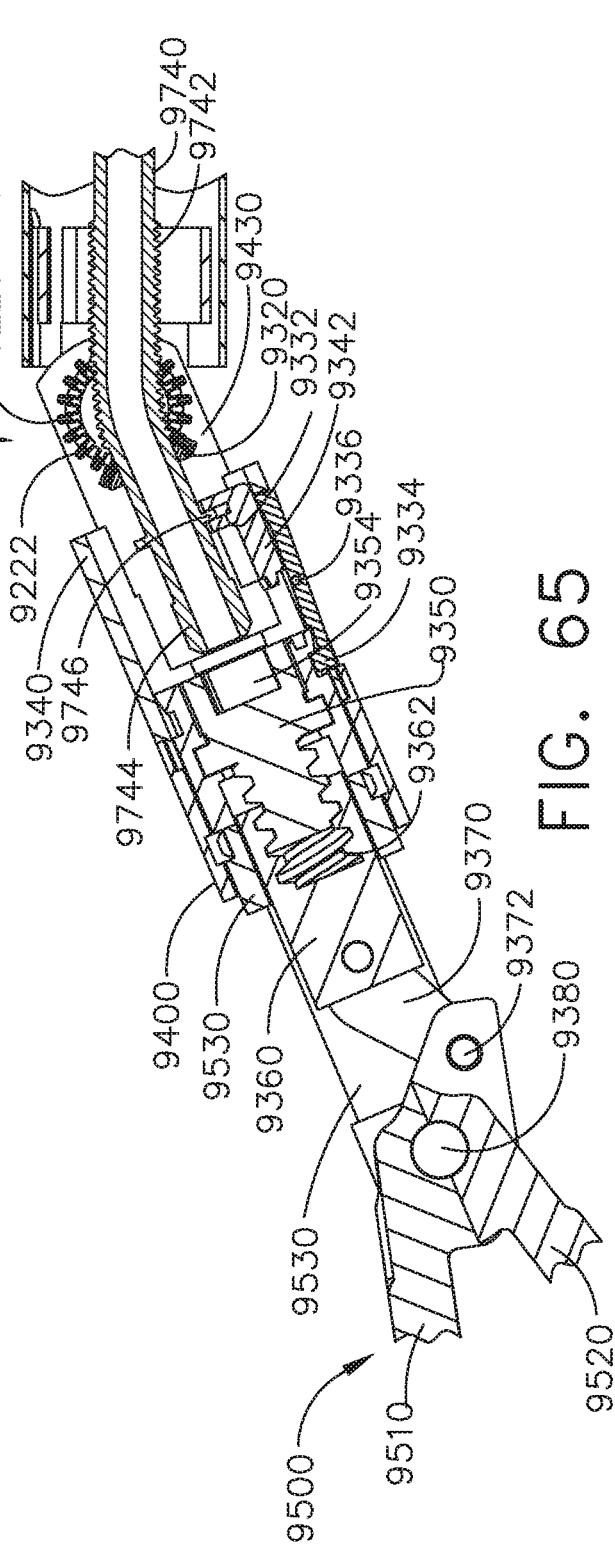
FIG. 65 is a partial top cross-sectional view of the end effector of FIG. 53 in an articulated configuration.

Turning now to FIGS. 62 and 63, the articulation joint 9300 comprises an articulation system configured to articulate the distal attachment portion 9400 and the end effector 9500 in a first direction and a second direction. The articulation system comprises a fixed gear 9220 mounted on an outer housing 9530 of the end effector 9500 and, also, an articulation drive gear 9320 fixedly mounted to the output shaft 9740 such that the articulation drive gear 9320 rotates with the output shaft 9740. When the output shaft 9740 is in its first, or proximal position, as illustrated in FIGS. 64 and 65, the articulation drive gear 9320 is operably intermeshed with the fixed gear 9220. As the output drive shaft 9740 is rotated in the first direction, in such instances, the articulation drive gear 9320 rotates in conjunction with the output shaft 9740 which articulates the end effector 9500 in a first articulation direction due to the meshing engagement of the articulation drive gear 9320 and the fixed gear 9220. As the output shaft 9740 is rotated in the second direction, the articulation drive gear 9320 rotates in conjunction with the output drive shaft 9740 which articulates the end effector 9500 in a second, or opposite, articulation direction, also due to the meshing engagement of the articulation drive gear 9320 and the fixed gear 9220. When the end effector 9500 is articulated, the output drive shaft 9740 is configured to bend in order to accommodate the articulation motion of the end effector 9500. Thus, the output drive shaft 9740 is comprised of suitable materials which compliment the bending movement of the output shaft 9740 during an articulation motion, as illustrated in FIG. 65.

As discussed above, referring again to FIGS. 64 and 65, the end effector 9500 is in its articulation mode when the output shaft 9740 is in its first, or proximal, position. In such instances, as also discussed above, the rotation of the output shaft 9740 articulates the end effector 9500. That said, in such instances, the rotation of the output shaft 9740 does not rotate the end effector 9500 about the longitudinal axis and/or operate the jaw drive to open and close the jaws 9510 and 9520. Stated another way, the jaw opening/closure mode and the end effector rotation mode are inactive when the end effector 9500 is in the articulation mode. As illustrated in FIGS. 64 and 65, the distal end 9744 of the output shaft 9740 is not engaged with a drive screw 9350 of the jaw drive when the end effector 9500 is in the articulation mode and, as such, the output shaft 9740 cannot drive the drive screw 9350 until the output shaft 9740 has been shifted distally, as described in greater detail below. Moreover, the end effector 9500 can't be rotated about the longitudinal axis because the end effector 9500 is locked to the distal attachment portion 9400 of the shaft assembly 9000 by a rotation lock 9330 when the end effector 9500 is in the articulation mode. In such instances, the housing 9530 of the end effector 9500 is locked to a housing 9430 of the distal attachment portion 9400 by the rotation lock 9330 such that the end effector 9500 cannot rotate relative to the shaft assembly 9000 until the output shaft 9740 has been shifted distally, as described in greater detail below.

Further to the above, referring again to FIGS. 64 and 65, the rotation lock 9330 is pivotably coupled to the housing 9430 of the distal attachment portion 9400 about a center attachment portion 9336. The rotation lock 9330 further comprises a proximal end 9332 and a distal lock end 9334. When the output shaft 9740 is in its first, or proximal, drive position, and the end effector 9500 is in its articulation mode, the distal lock end 9334 of the rotation lock 9330 is wedged into engagement with an annular array of lock apertures 9534 defined around the outer housing 9530 of the end effector 9500. More specifically, the proximal end 9332 of the rotation lock 9330 is wedged outwardly by a drive lock 9340 coupled to the output shaft 9740 which, in turn, wedges the distal lock end 9334 inwardly. The drive lock 9340, which is described in greater detail below, comprises a slot 9346 defined therein and is translated proximally and distally with the output shaft 9740 by a flange 9746 extending into the slot 9346. When the output shaft 9740 is moved distally out of its first, or proximal, drive position, the drive lock 9340 is moved out of engagement with the proximal end 9332 of the rotation lock 9330, as illustrated in FIGS. 66-69.

When the output shaft 9740 is not in its first, or proximal, drive position, the articulation drive gear 9320 is not operably intermeshed with the fixed gear 9220. In such instances, the rotation of the output shaft 9740 does not articulate the end effector 9500. That said, the end effector 9500 is held in its articulated position by the drive shaft 9740 when the drive shaft 9740 is translated distally from its first position. More specifically, the drive shaft 9740 comprises articulation lock teeth 9742 defined thereon which engage, or mesh with, the teeth 9222 of the fixed gear 9220 when the drive shaft 9740 is advanced distally and, owing to the engagement between the teeth 9742 and 9222, the end effector 9500 is locked in position. This articulation lock works when the end effector 9500 is articulated in the first direction, articulated in the second direction, and when the end effector 9500 is unarticulated. Moreover, this articulation lock is engaged as soon as the drive shaft 9740 is displaced distally from its first position. Thus, the articulation lock is engaged when the drive shaft 9740 is in its second position and third position. In order to unlock the articulation lock, the drive shaft 9740 is moved back into its first position to disengage the teeth 9742 from the teeth 9222. At such point, the end effector 9500 can be articulated once again.

When the output drive shaft 9740 is in its second, or intermediate, position, referring to FIGS. 66 and 67, the end effector 9500 is in its rotation drive mode. In such instances, the articulation drive gear 9320 mounted to the output shaft 9740 is not engaged with the fixed gear 9220 and, as a result, the rotation of the output shaft 9740 does not articulate the distal attachment portion 9400 and the end effector 9500. That said, the distal end 9744 of the output shaft 9740 is positioned within the drive socket 9354 of the drive screw 9350 when the output shaft 9740 is in its second position. Notably, though, the distal end 9744 is not fully seated in the drive socket 9354—this happens when the output shaft 9740 is translated distally into its third, or distal, position (FIGS. 68 and 69), as discussed in greater detail below. That being said, the rotation of the output shaft 9740 is transferred to the drive screw 9350 when the output shaft 9740 is in its second, or intermediate, position. Owing to a close, or friction, fit between the drive screw 9350 and the outer housing 9530 of the end effector 9500, however, the rotation of the drive screw 9350 is transferred to the outer housing 9350. More specifically, the drive screw 9350 comprises a flange 9358 closely received within a slot 9538 defined in the outer housing 9530 and, as such, the drive screw 9350 and the outer housing 9530 rotate together when the end effector 9500 is in its rotation drive mode. Moreover, the entire end effector 9500, including the jaws 9510 and 9520 rotatably coupled to the outer housing 9530 by a pivot pin 9380, is rotated about a longitudinal axis when the end effector 9500 is in its rotation drive mode and the output shaft 9740 is rotated.

When the output shaft 9740 is rotated in a first direction when the end effector 9500 is in its rotation drive mode, further to the above, the end effector 9500 is rotated relative to the distal attachment portion 9400 of the shaft assembly 9000 in the first direction. Correspondingly, the end effector 9500 is rotated relative to the distal attachment portion 9400 in a second, or opposite, direction when the output shaft 9740 is rotated in the second, or opposite, direction. Notably, the rotation of the drive screw 9350 does not open and/or close the jaws 9510 and 9520 in such instances as the drive screw 9350 does not rotate relative to the outer housing 9530 and/or jaws 9510 and 9520. Also, notably, the outer housing 9530 of the end effector 9500 rotates relative to the outer housing 9430 of the distal attachment portion 9400 when the end effector 9500 is in its rotation drive mode. This is due to the distal displacement of the drive lock 9340 away from the proximal end 9332 of the rotation lock 9330 when the drive shaft 9740 is moved into its second position such that, as a result, the outer housing 9530 of the end effector 9500 can rotate relative to the outer housing 9430 of the distal attachment portion 9400.

Figure 68:
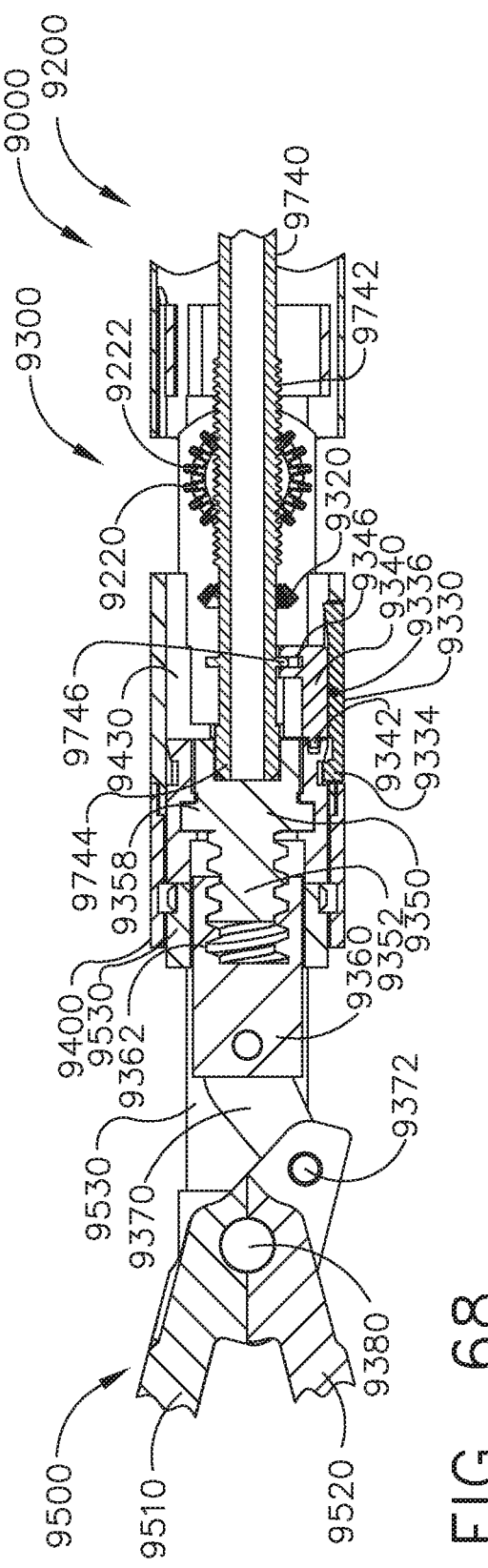
FIG. 68 is a partial top cross-sectional view of the end effector of FIG. 53 in a jaw open/closure drive mode.
Figure 69:
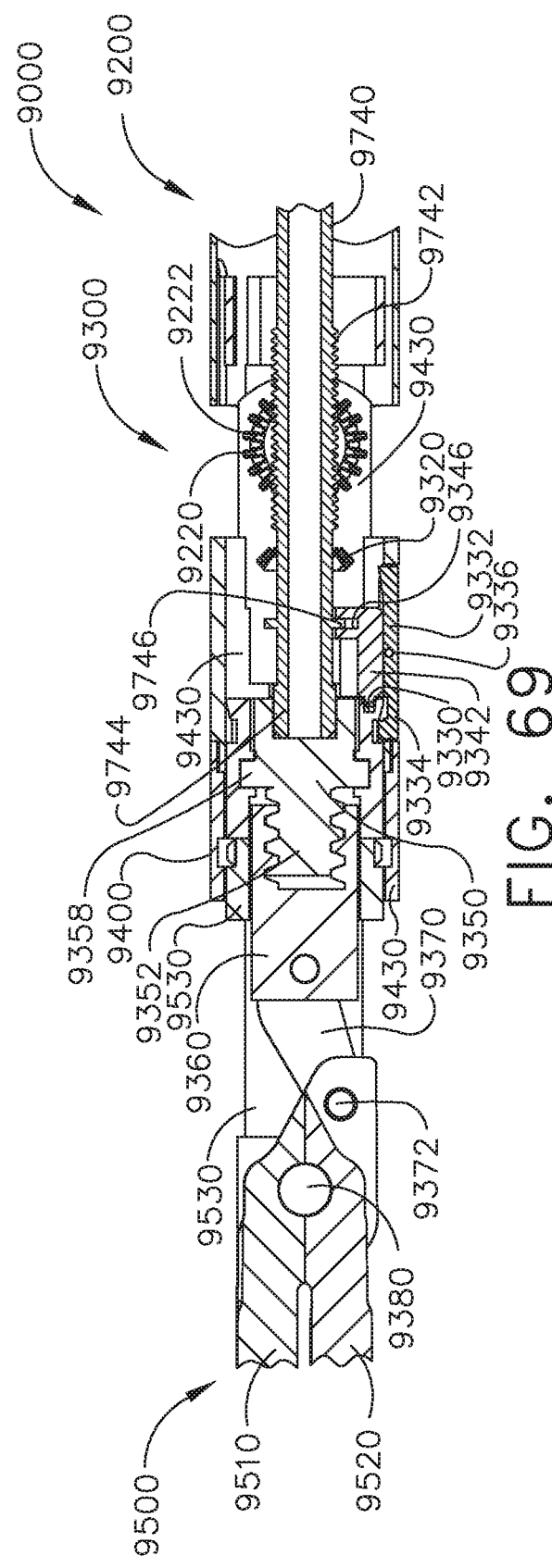
FIG. 69 is a partial top cross-sectional view of the end effector of FIG. 53 in a closed configuration.

When the output drive shaft 9740 is in its third, or distal, position, referring to FIGS. 68 and 69, the end effector 9500 is in its jaw drive mode. In such instances, the articulation drive gear 9320 mounted to the output shaft 9740 is not engaged with the fixed gear 9220 and, as a result, the rotation of the output shaft 9740 does not articulate the distal attachment portion 9400 and the end effector 9500. That said, further to the above, the distal end 9744 of the drive shaft 9740 is fully seated in the drive socket 9354 of the drive screw 9350 when the end effector 9500 is in its distal position. As a result, the drive screw 9350 rotates with the output shaft 9740. Moreover, the drive screw 9350 rotates relative to the outer housing 9530 when the end effector 9500 is in its jaw drive mode. This is because the drive lock 9340 coupled to the drive shaft 9740 is driven distally into engagement with the outer housing 9530 when the drive shaft 9740 is moved into its third, or distal, drive position and, as a result, prevents the outer housing 9530 from rotating with the drive screw 9350. More specifically, referring to FIG. 63, the drive lock 9340 comprises a distal lock end 9342 configured to engage an annular array of lock apertures 9532 defined in the proximal end of the outer housing 9530 and, once the distal lock end 9342 is engaged with the apertures 9532, the outer housing 9530 is held in position by the drive lock 9340.

Further to the above, the end effector 9500 further comprises a drive nut 9360 threadably engaged with the drive screw 9350 and, in addition, two drive links 9370 pivotably coupled to the drive nut 9360—each of which is also pivotably coupled to a jaw 9510 and 9520. The drive nut 9360 comprises a threaded aperture 9362 defined therein threadably engaged with a threaded end 9352 of the drive shaft 9350. The drive nut 9360 is constrained from rotating relative to the outer housing 9530 and, as a result, the drive nut 9360 is translated proximally or distally when the drive screw 9350 is rotated, depending on the direction in which the drive screw 9350 is rotated. When the drive screw 9350 is rotated in a first direction by the drive shaft 9740, the drive screw 9350 pushes the drive nut 9360 and the drive links 9370 distally to open the jaws 9510 and 9520. When the drive screw 9350 is rotated in a second direction by the drive shaft 9740, the drive screw 9350 pulls the drive nut and the drive links 9370 proximally to close the jaws 9510 and 9520. That being said, a different thread could be used to reverse these motions.

In view of the above, the end effector 9500 cannot be rotated about its longitudinal axis and the jaws 9510 and 9520 cannot be opened and closed during the articulation mode. Moreover, the end effector 9500 cannot be articulated about the articulation joint 9300 and the jaws 9510 and 9520 cannot be opened and closed during the end effector rotation mode. Similarly, the end effector 9500 cannot be rotated or articulated during the jaw drive mode.

Further to the above, the shaft assembly 9000 comprises a braking system 9900 configured to hold the drive shaft 9740 in its first, or articulation, drive position, its second, or rotation, drive position, and/or its third, or jaw drive, position. The braking system 9900 comprises a solenoid 9910, a brake arm 9920 operably connected to a rotatable output shaft of the solenoid 9910, and a biasing member. The brake arm 9920 is rotatable between a first position in which the brake arm 9920 is engaged with the drive shaft 9740 and a second position in which the brake arm 9920 is disengaged from the drive shaft 9740. The biasing member biases the brake arm 9920 into its first position, but this bias is overcome when the solenoid 9910 is actuated. When the brake arm 9920 is in its first position, the brake arm 9920 opposes, through friction, the movement of the drive shaft 9740. In such instances, the brake arm 9920 can reduce the possibility of the drive shaft 9740 being accidentally pushed longitudinally out of position. When the brake arm 9920 is in its second position, the brake arm 9920 does not oppose the motion of the drive shaft 9740. In various instances, the solenoid 9910 can be actuated to lift the brake arm 9920 when the shaft assembly 9000 has been shifted into its drive configuration by the solenoid 9810, as discussed above. In at least one such instance, the solenoid 9910 can be actuated to lift the brake arm 9920 when the shaft assembly 9000 is in its drive configuration and the input motor 9120 is being operated. The shifting solenoid 9810 and the brake solenoid 9910 are in communication with the control system of the shaft assembly 9000 and/or the control system of the handle 1000, for example, and can be selectively actuated by the control system. The control system can actuate the solenoid 9910 to inhibit the movement of the drive shaft 9740 at any suitable time. In at least one instance, the control system is configured to always apply a braking force to the drive shaft 9740 except when the shaft assembly 9000 and/or handle are in a limp mode, for example. In certain alternative embodiments, a static friction member, for example, can be used to inhibit unintended displacement of the drive shaft 9740.

The shaft assembly 9000 further comprises a sensor system configured to detect the longitudinal position of the drive shaft 9740. In at least one instance, the drive shaft 9740 comprises a magnetic element, such as a permanent magnet, iron, and/or nickel, for example, which is detectable by one or more sensors of the sensor system. In at least one instance, a sensor of the sensor system comprises a Hall Effect sensor, for example. The sensor system is in communication with the control system of the shaft assembly 9000 and/or the handle 1000, for example, and is configured to confirm whether the drive shaft 9740 is in its proximal drive position, its intermediate drive position, its distal drive position, or somewhere in-between. With this information, the control system can monitor the position of the drive shaft 9740 in real-time and adjust the longitudinal position of the drive shaft 9740, if necessary.

Figure 70:
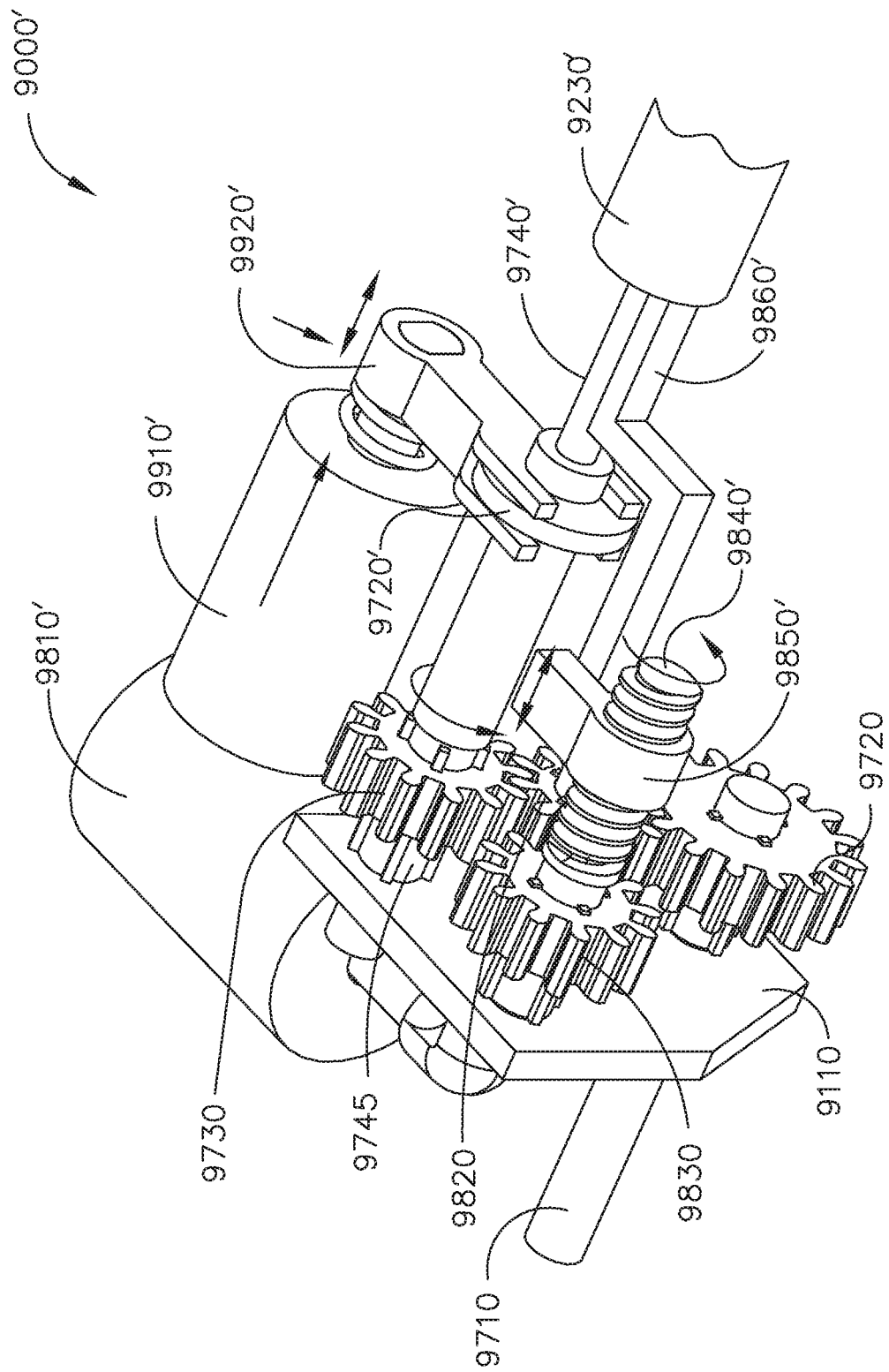
FIG. 70 is a perspective view of a drive assembly of a shaft assembly in accordance with at least one embodiment.
Figure 71:
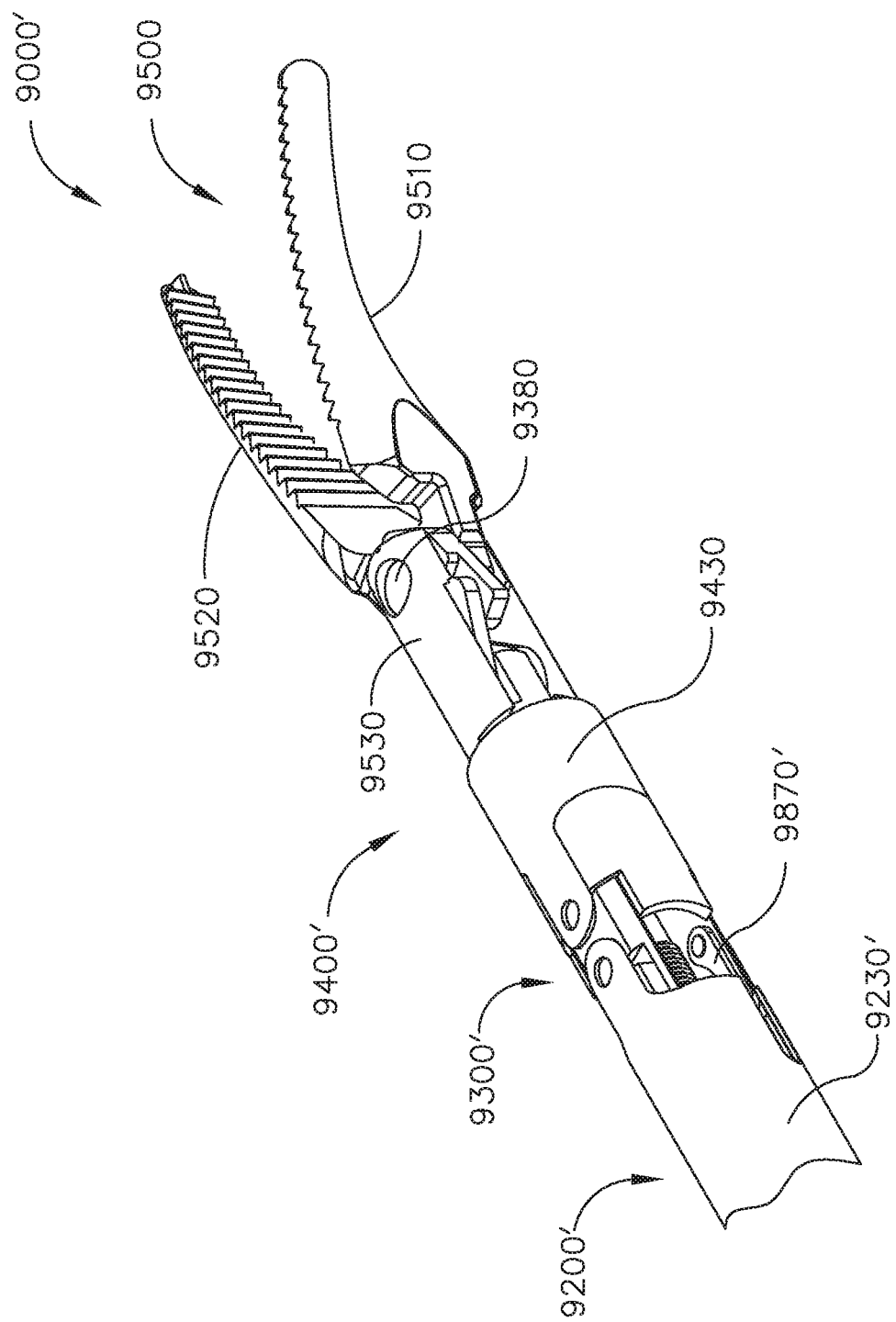
FIG. 71 is a perspective view of an end effector of the shaft assembly of FIG. 70 in an open configuration.
Figure 72:
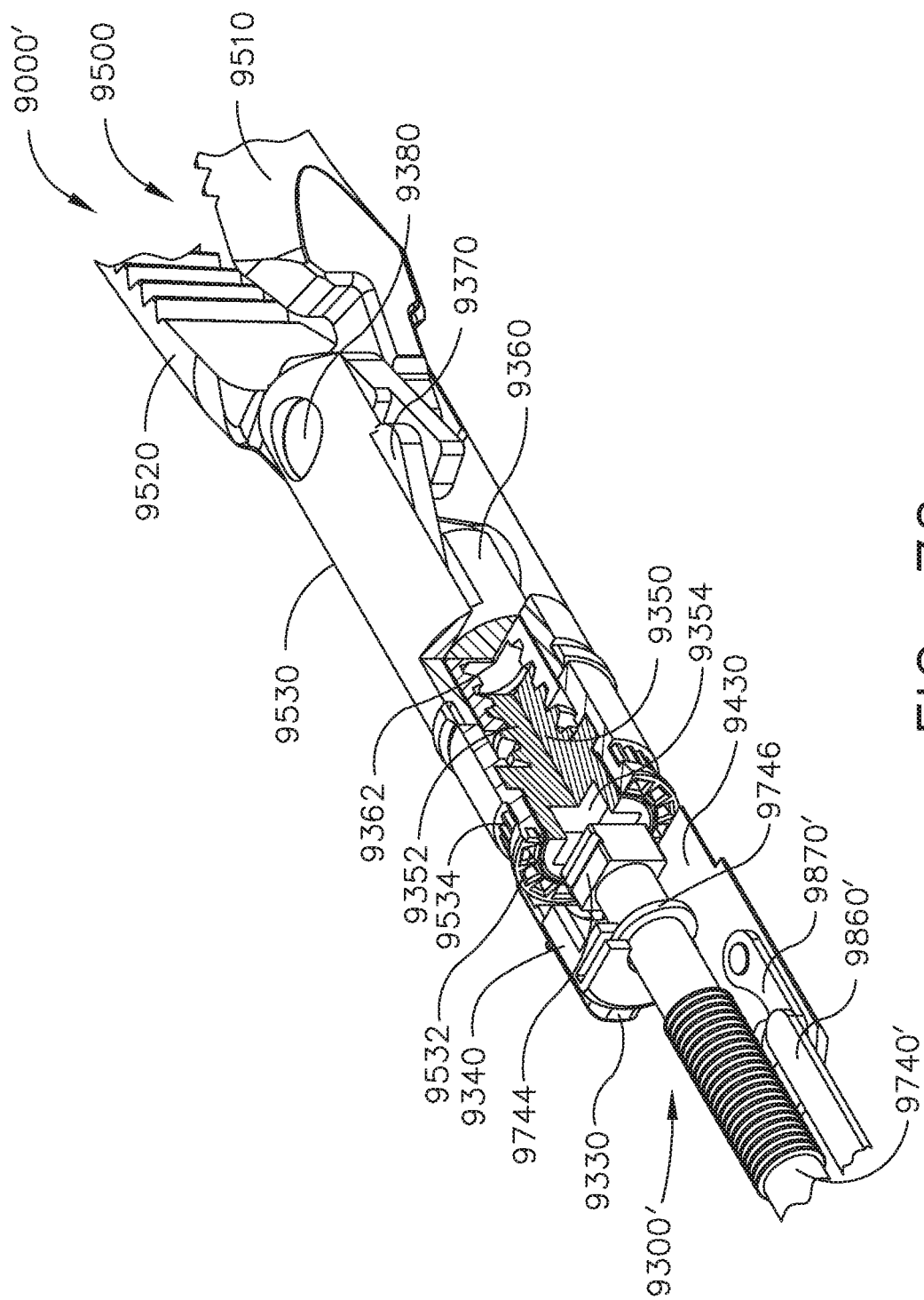
FIG. 72 is a partial perspective cross-sectional view of the end effector of FIG. 71.
Figure 73:
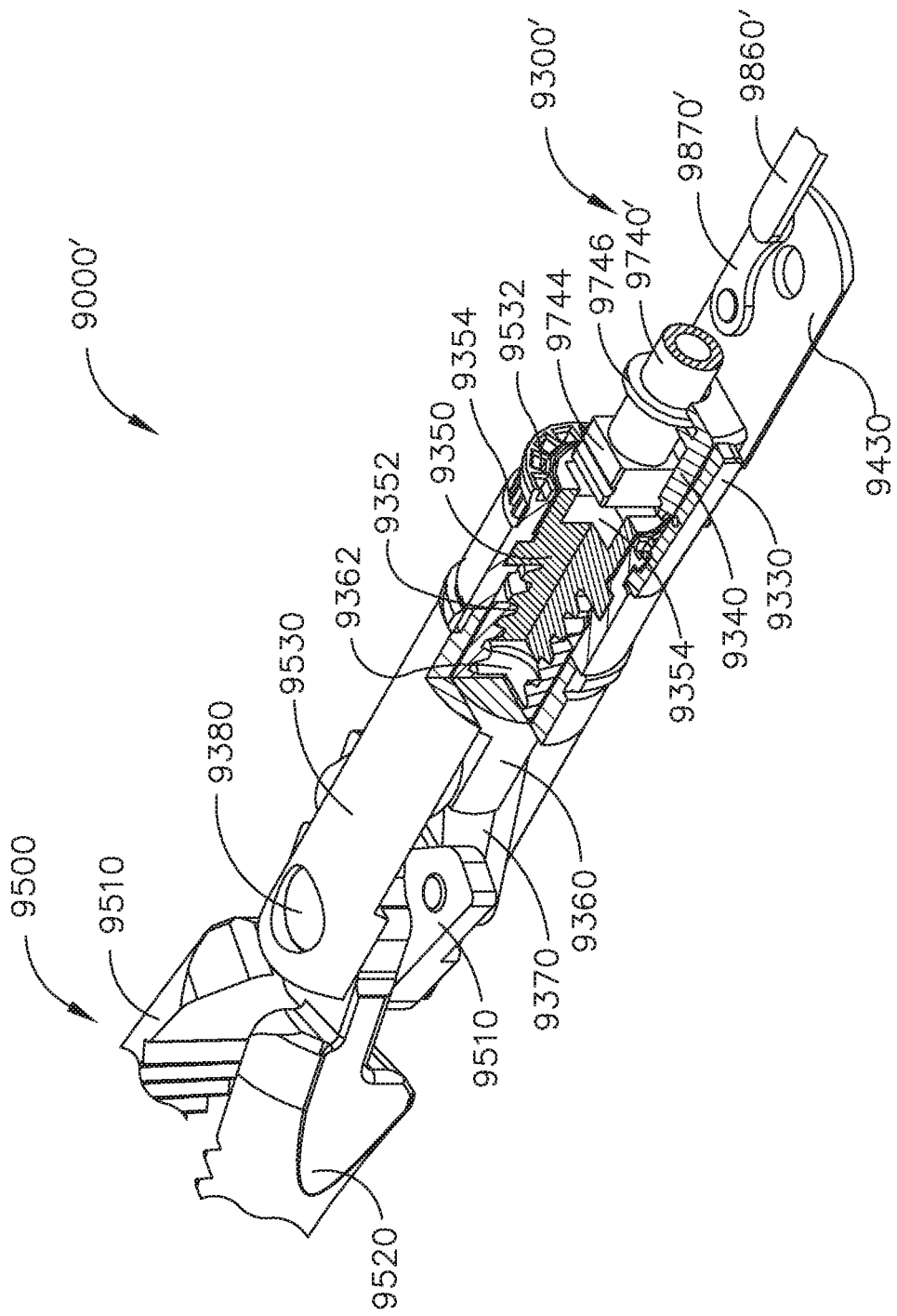
FIG. 73 is another partial perspective cross-sectional view of the end effector of FIG. 71.

A shaft assembly 9000' is depicted tin FIGS. 70-79 which is similar to the shaft assembly 9000 in many respects, most of which will not be discussed herein for the sake of brevity. Referring primarily to FIG. 71, the shaft assembly 9000' comprises an elongate shaft 9200', a distal attachment portion 9400', and an articulation joint 9300' rotatably connecting the distal attachment portion 9400' to the elongate shaft 9200'. The shaft assembly 9000' further comprises an end effector 9500 rotatably supported within an outer housing 9430 of the distal attachment portion 9400'. The shaft assembly 9000' also comprises a drive system configured to rotate the end effector 9500 about a longitudinal axis, articulate the end effector 9500 about the articulation joint 9300', and open and close the jaws 9510 and 9520 of the end effector 9500.

Figure 77:
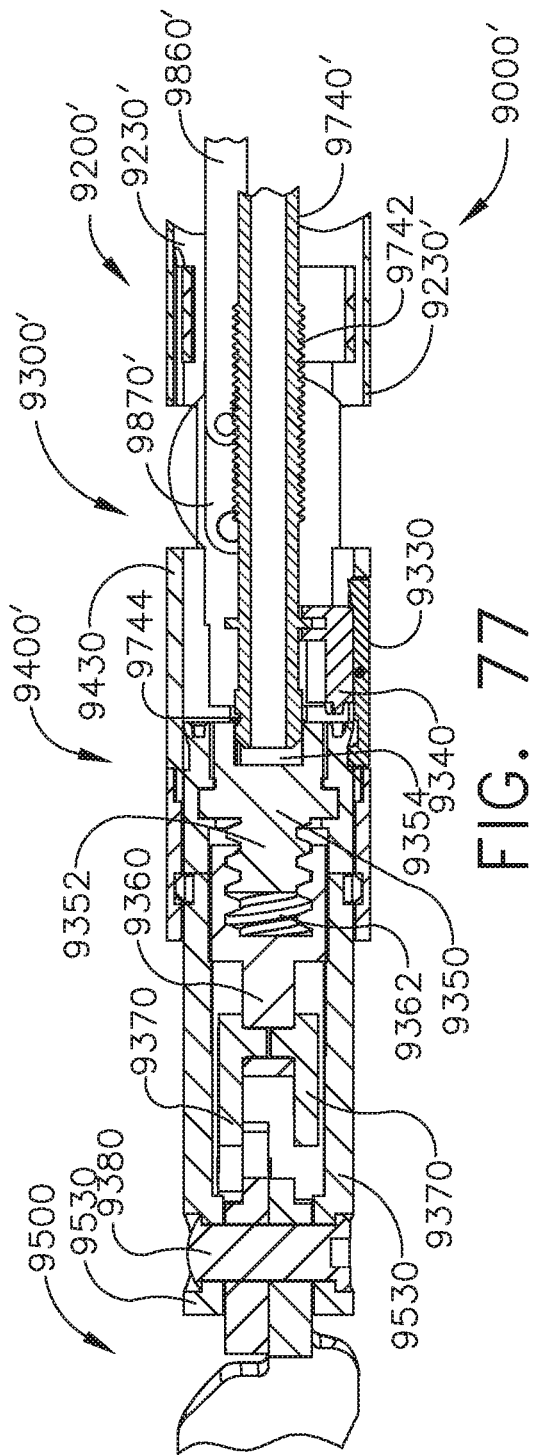
FIG. 77 is a partial top cross-sectional view of the end effector of FIG. 71 in a rotated configuration.
Figure 78:
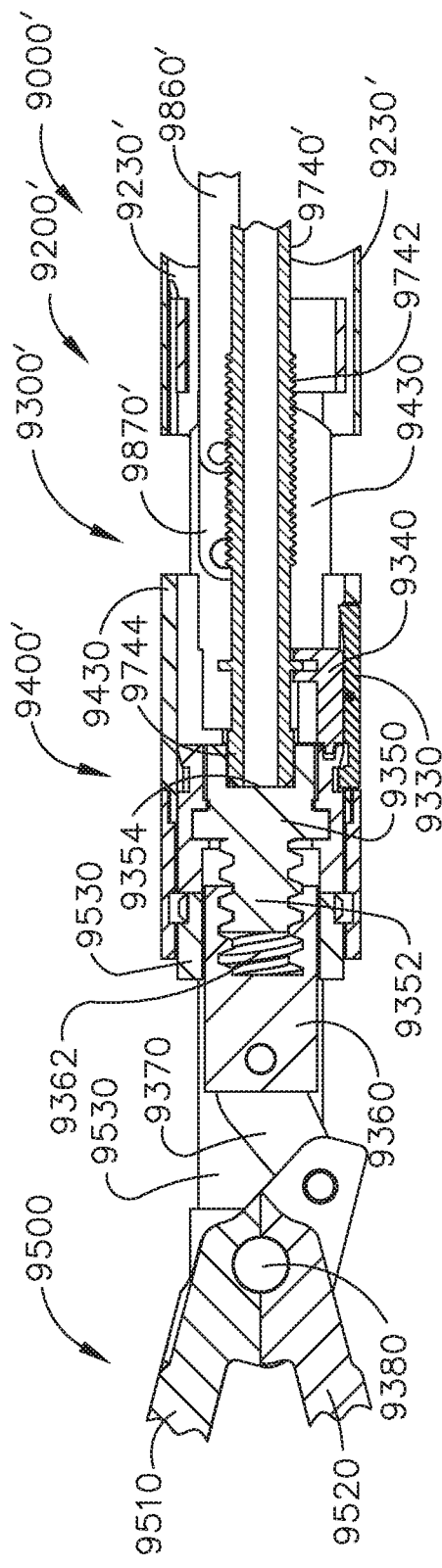
FIG. 78 is a partial top cross-sectional view of the end effector of FIG. 71 in a jaw open/closure drive mode.
Figure 79:
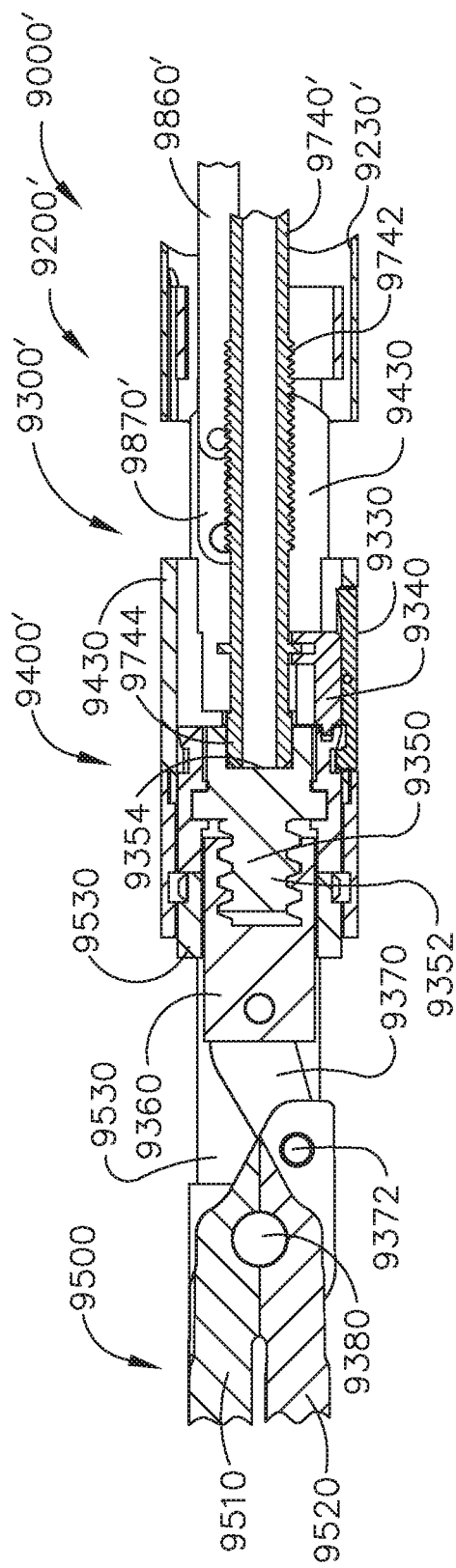
FIG. 79 is a partial top cross-sectional view of the end effector of FIG. 71 in a closed configuration.

Referring primarily to FIG. 70, the drive system comprises, among other things, a rotatable input shaft 9710, a first output shaft 9740', and a second output shaft 9860'. The drive system further comprises a shifter solenoid 9810' configured to selectively couple the input shaft 9710 with the first output shaft 9740' in a first drive configuration and the second output shaft 9860' in a second drive configuration. In the first drive configuration, the rotatable input shaft 9710 rotates the main gear 9720 which, in turn, rotates the shifter gear 9820. In such instances, the shifter gear 9820 rotates the first drive gear 9730 which, in turn, rotates the first output shaft 9740'. Similar to the output shaft 9740, the first drive gear 9730 is engaged with a splined proximal end 9745 of the first output shaft 9740' such that the first output shaft 9740' rotates with, but can translate relative to, the first drive gear 9730. The drive system of the shaft assembly 9000' further comprises a second shifter solenoid 9910' configured to translate the first output shaft 9740' between a disengaged position (FIGS. 74 and 75), a first drive position (FIGS. 76 and 77), and a second drive position (FIGS. 78 and 79). The second shifter solenoid 9910' comprises a shift arm 9920' engaged with a flange 9720' defined on the first output shaft 9740' which is configured to push the first output shaft 9740' between its disengaged position, first drive position, and second drive position.

In the second drive configuration, further to the above, the rotatable input shaft 9710 rotates the main gear 9720 which, in turn, rotates the shifter gear 9820. In such instances, the shifter gear 9820 rotates the second drive gear 9830 which, in turn, rotates a threaded shaft 9840'. The drive system further comprises a drive nut 9850' threadably engaged with the threaded shaft 9840' such that, when the threaded shaft 9840' is rotated in a first direction by the input shaft 9710, the drive nut 9850' is translated proximally and, when the threaded shaft 9840' is rotated in a second, or opposite, direction by the input shaft 9710, the drive nut 9850' is translated distally. The second output shaft 9860' comprises a bar fixedly mounted to the drive nut 9850' such that the second output shaft 9860' translates with the drive nut 9850'. Thus, the rotation of the rotatable input shaft 9710 translates the second output shaft 9860'. The translatable second output shaft 9860' extends through an outer housing 9230' of the elongate shaft 9200' alongside the rotatable/translatable first output shaft 9740'. As described in greater detail below, the first output shaft 9740' drives a first end effector function and a second end effector function while the second output shaft 9860' drives a third end effector function.

Further to the above, referring to FIGS. 72-75, the drive system further comprises a drive link 9870' pivotably coupled to the second output shaft 9860'. The drive link 9870' extends across the articulation joint 9300' and is pivotably coupled to the outer housing 9430 of the distal attachment portion 9400'. When the input shaft 9710 is rotated in the first direction and the drive link 9870' is pulled proximally by the drive nut 9850', the distal attachment portion 9400' and the end effector 9500 are articulated in a first articulation direction. When the input shaft 9710 is rotated in the second direction and the drive link 9870' is pushed distally by the drive nut 9850', referring to FIG. 75, the distal attachment portion 9400' and the end effector 9500 are articulated in a second, or opposite, articulation direction. The threaded interface between the threaded shaft 9840' and the drive nut 9850' prevents, or at least inhibits, the articulation drive from being back-driven, or unintentionally articulated. As a result, the end effector 9500 is held in position when the shifter gear 9820 is shifted out of engagement with the second gear 9830 and into engagement with the first gear 9730. Notably, the first output shaft 9740' is not involved in the articulation of the end effector 9500. In fact, the first output shaft 9740' is in its disengaged position such that the distal end 9744 of the first output shaft 9740' is not engaged with the drive screw 9750 when the end effector 9500 is being articulated.

Figure 76:
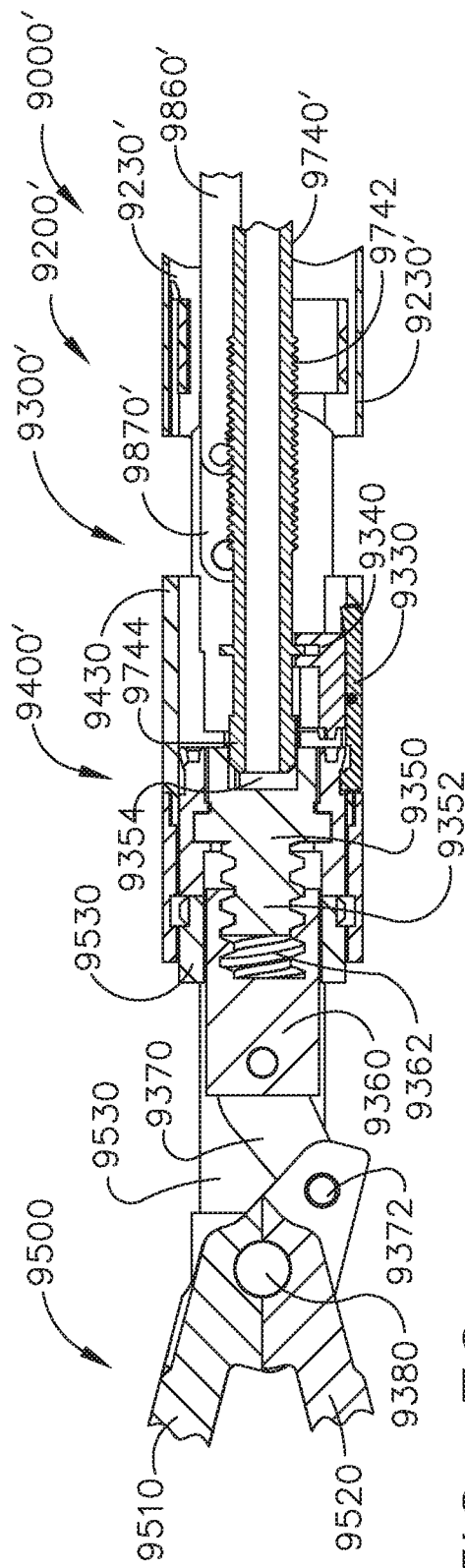
FIG. 76 is a partial top cross-sectional view of the end effector of FIG. 71 in a rotation drive mode.

Further to the above, the first output shaft 9740' is used to selectively rotate the end effector 9500 about a longitudinal axis. The first output shaft 9740' is also used to selectively operate the jaw drive to open and close the end effector 9500. The first drive position of the first rotatable output shaft 9740' is used to rotate the end effector 9500 of the shaft assembly 9000' about a longitudinal axis. As illustrated in FIGS. 76 and 77, the distal end 9744 of the first output shaft 9740' is seated, but not completely seated, within the drive socket 9354 defined in the drive screw 9350 when the first output shaft 9740' is in its first drive position. Notably, however, the drive lock 9340 is not engaged with the outer housing 9530 of the end effector 9500 and, as a result, the outer housing 9530 rotates with the drive screw 9350. In such instances, the rotation of the first output shaft 9740' is transferred to the drive screw 9350 to rotate the entire end effector 9500, as described above. The second drive position of the first rotatable output shaft 9740' is used to open and close the jaws 9510 and 9520. As illustrated in FIGS. 78 and 79, the distal end 9744 of the first output shaft 9740' is completely seated within the drive socket 9354 defined in the drive screw 9350 when the first output shaft 9740' is in its second drive position. Notably, the drive lock 9340 is engaged with the outer housing 9530 of the end effector 9500 and, as a result, the drive screw 9350 rotates relative to the outer housing 9530. In such instances, the rotation of the first output shaft 9740' opens and closes the jaws 9510 and 9520—depending on the direction in which the first output shaft 9740' is rotated.

The reader should appreciate that the proximal, intermediate, and distal drive positions of the output shaft 9740 of the shaft assembly 9000 are analogous to the proximal, intermediate, and distal drive positions of the first output shaft 9740'. More specifically, the output shaft 9740 is operable to articulate the end effector 9500 when the output shaft 9740 is in its proximal position, while the end effector 9500 is articulated, by the second output shaft 9860', when the first output shaft 9740' is in its proximal position. Moreover, the output shaft 9740 is operable to rotate the end effector 9500 when the output shaft 9740 is in its intermediate position while, likewise, the first output shaft 9740' is operable to rotate the end effector 9500 when the first output shaft 9740' is in its intermediate position. Similarly, the output shaft 9740 is operable to open and close the end effector 9500 when the output shaft 9740 is in its distal position while, likewise, the first output shaft 9740' is operable to open and close the end effector 9500 when the first output shaft 9740' is in its distal position.

Figure 80:
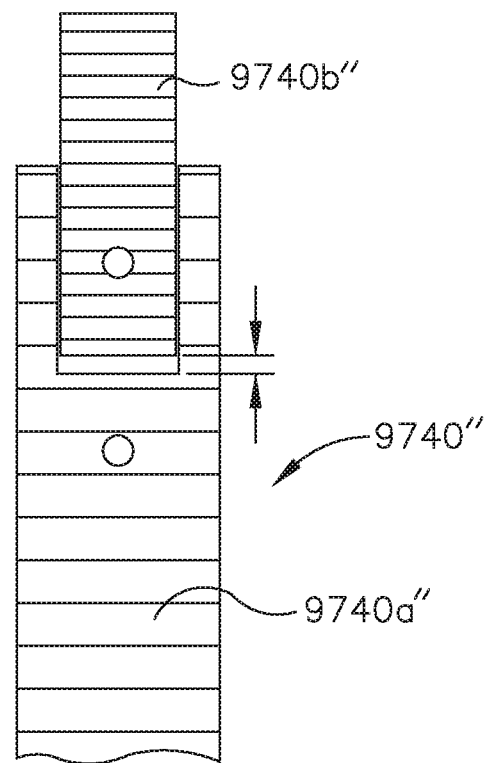
FIG. 80 is a partial top cross-sectional view of a drive shaft in accordance with at least one embodiment.
Figure 81:
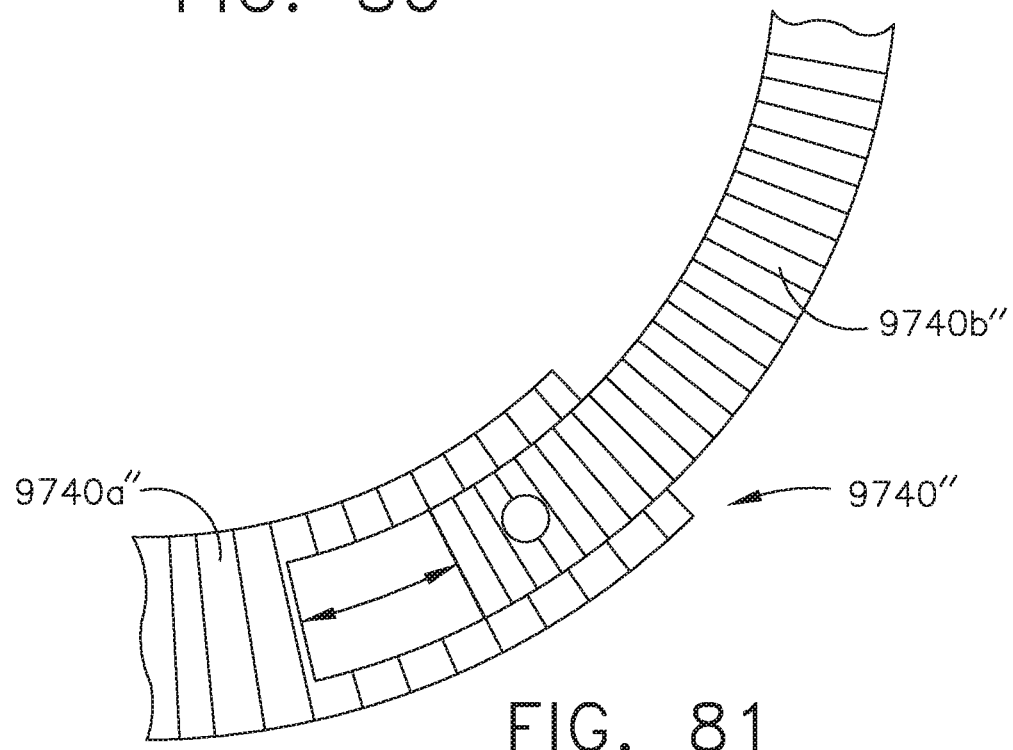
FIG. 81 is a partial top cross-sectional view of the drive shaft of FIG. 80 in an articulated configuration.

The output shaft 9740 of the shaft assembly 9000 and/or the first output shaft 9740' of the shaft assembly 9000' are comprised of a unitary piece of material. Such an arrangement reduces the possibility of the output shafts 9740 and 9740' failing under load. That said, alternative embodiments are envisioned in which the output shafts 9740 and/or 9740' are comprised of two or more components. Referring to FIGS. 80 and 81, a drive shaft 9740" comprises a first shaft component 9740a" and a second shaft component 9740b". The first shaft component 9740a" comprises a drive aperture defined therein and the second shaft component 9740b" is positioned in the drive aperture. The drive aperture comprises a configuration which is configured to transmit torque between the first shaft component 9740a" and the second shaft component 9740b", yet permit relative translational movement between the first shaft component 9740a" and the second shaft component 9740b". Such an arrangement is useful to accommodate the articulation of an end effector when the drive shaft 9740" extends through an articulation joint, for example. In such instances, the interconnection between the first shaft component 9740a" and the second shaft component 9740b" can comprise an extension joint which allows the drive shaft 9740" to extend in length when the end effector is articulated.

Figure 57:
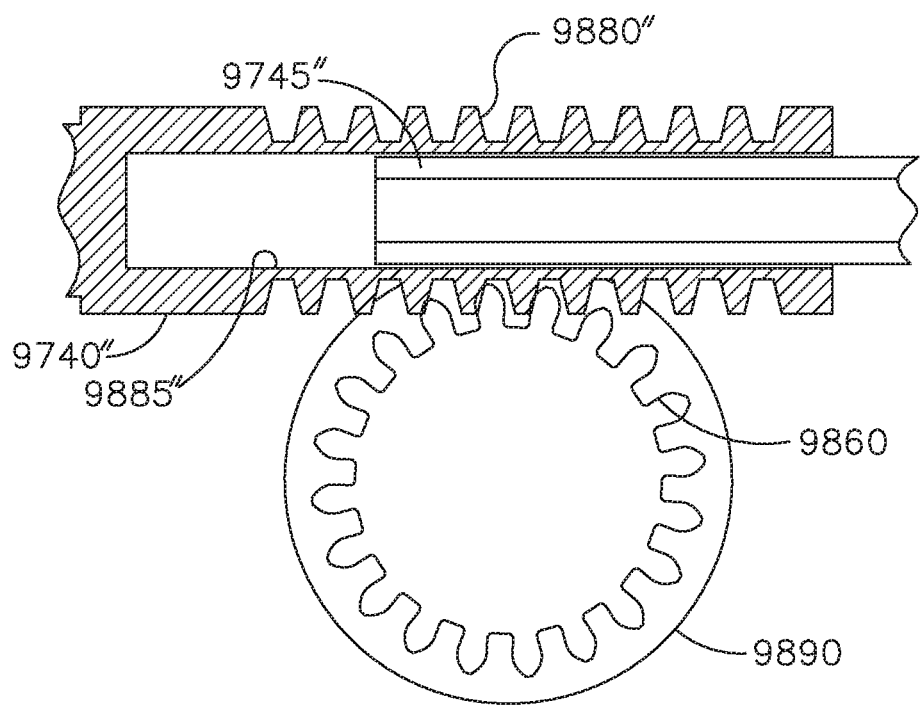
FIG. 57 is a partial cross-sectional view of a drive assembly in accordance with at least one alternative embodiment.

Referring to FIG. 57, the drive shaft 9740" is similar to the drive shaft 9740 in many respects, most of which will not be discussed herein for the sake of brevity. Similar to the drive shaft 9740, the drive shaft 9740" is translated proximally and distally to shift an end effector between drive modes and then rotated to drive the end effector in the selected drive mode. That said, the drive shaft 9740" comprises an extension joint in the proximal drive system which facilitates the translation and rotation of the drive shaft 9740". This extension joint of the drive shaft 9740" comprises a drive aperture 9885" defined in a proximal rack portion 9880" of the drive shaft 9740" and, in addition, a proximal splined portion 9745" slideably positioned in the drive aperture 9885". Similar to the above, the drive aperture 9885" comprises a configuration configured to transmit torque between the proximal splined portion 9745" and the distal portion of the shaft 9740" yet permit relative translation therebetween. In such an arrangement, the proximal splined portion 9745" does not need to move relative to the gear 9730 in order to accommodate the distal displacement of the shaft 9740". Such an arrangement reduces the possibility that the gear 9730 may be pulled out of engagement with the shifter gear 9820, for example.

Further to the above, the rotation lock 9330, which is configured to engage the end effector 9500 to prevent the end effector 9500 from rotating about its longitudinal axis as described above, is also configured to releasably attach the end effector 9500 to the shaft assembly 9000 and/or shaft assembly 9000'. When the end effector 9500 is assembled to the shaft assembly 9000, for example, the rotation lock 9330 engages the annular array of teeth 9534 defined around the perimeter of the end effector housing 9530 to releasably hold the end effector 9500 in position. When the drive shaft 9740 is in its first position, the drive lock 9340 blocks the rotation lock 9330 from being rotated to release the end effector 9500. In order to release the end effector 9500 from the shaft assembly 9000, the drive shaft 9740 can be advanced distally to move the drive lock 9340 distally and allow the rotation lock 9330 to rotate so that the end effector 9500 can be pulled longitudinally away from the shaft assembly 9000. In at least one instance, the drive shaft 9740 must be moved into its third, or distal, drive position in order to release the end effector 9500.

Figure 82:
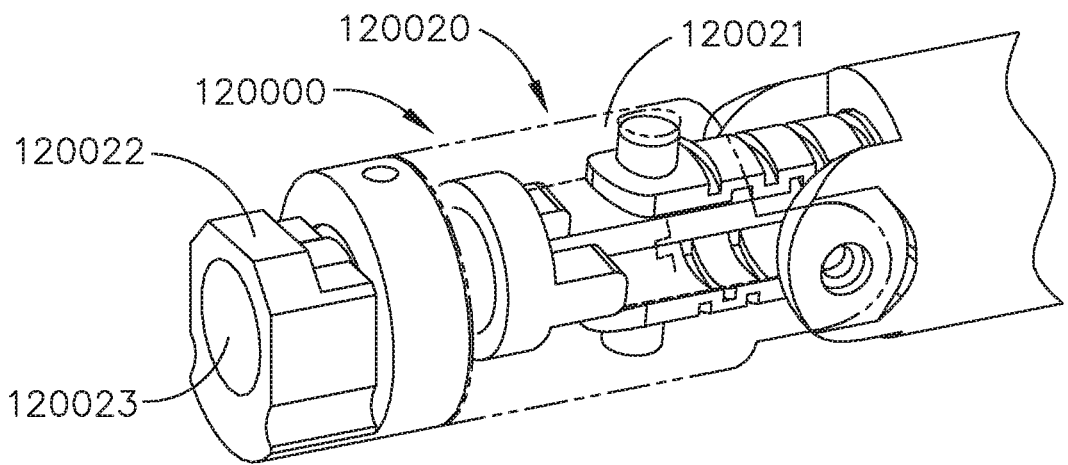
FIG. 82 is a partial perspective view of a distal end of a shaft assembly of a surgical instrument in accordance with at least one embodiment.
Figure 83:
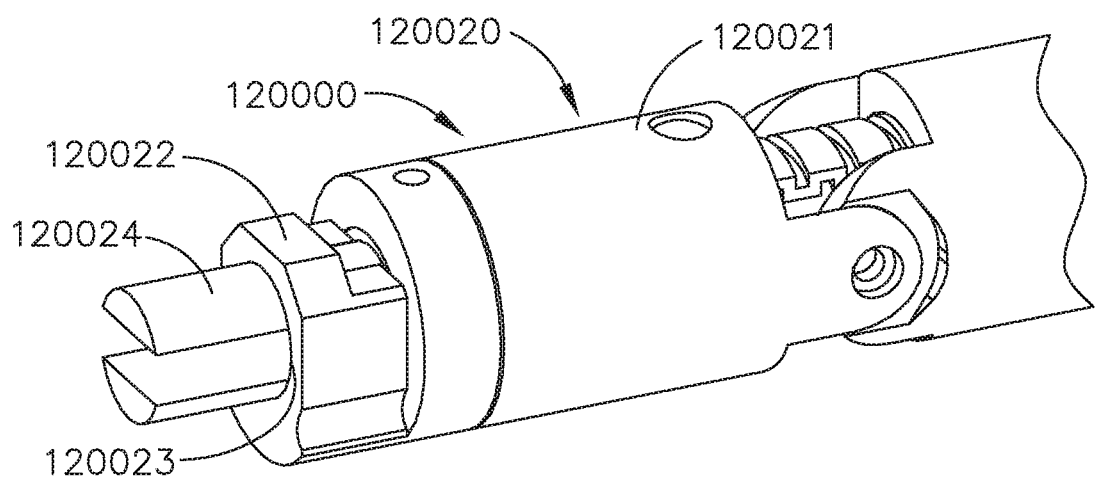
FIG. 83 is a partial perspective view of the distal end of FIG. 82 illustrating an extended lock element.

A surgical system 120000 is illustrated in FIGS. 82 and 83. The surgical system 120000 comprises a handle, a shaft assembly 120020 extending from the handle, and an end effector releasably attachable to the shaft assembly 120020. The shaft assembly 120020 comprises an elongate shaft 120021 including a distal end 120022 and a longitudinal aperture 120023 extending therethrough. The shaft assembly 120020 further comprises a drive member movably positioned in the longitudinal aperture 120023 which is movable longitudinally by a drive system in the handle. The end effector comprises a frame that is mounted to a frame of the elongate shaft 120021 when the end effector is attached to the shaft assembly 120020. The end effector further comprises a drive member that is operably connected to the drive member of the shaft assembly 120020 when the end effector is attached to the shaft assembly 120020. The distal end of the shaft drive member comprises a cradle, or connector, configured to receive the proximal end of the end effector drive member. The cradle is configured to constrain the relative movement between the shaft drive member and the end effector drive member except for the direction, or degree of freedom, in which the end effector drive member was attached to the shaft drive member. In at least one instance, the shaft drive member comprises a longitudinal axis and the end effector drive member is loaded into the cradle in a direction which is transverse to the longitudinal axis.

Further to the above, referring again to FIGS. 82 and 83, the shaft assembly 120020 further comprises a lock configured to constrain the degree of freedom in the loading direction between the shaft drive member and the end effector drive member. In at least one instance, the shaft assembly 120020 comprises a lock 120024 which is slid longitudinally to constrain the movement of the end effector drive member such that it cannot be detached from the shaft drive member. The lock 120024 is slid distally to lock the drive members together and proximally to unlock the drive members so that the drive members can be detached. In various instances, the handle comprises a control which, when actuated, can cause the control system of the surgical system 120000 to lock or unlock the lock 120024. The lock 120024 is not biased into either its locked or unlocked position; however, alternative embodiments are envisioned in which the lock 120024 is biased into its locked position. In such embodiments, the shaft assembly 120020 comprises a biasing member, such as a spring, for example, configured to push the lock 120024 distally toward its locked position. That said, the biasing member can be overcome by the clinician and/or by an actuator, such as a solenoid, for example, which pushes the lock 120024 proximally to unlock the coupling between the shaft drive member and the end effector drive member. In either event, the shaft assembly 120020 can comprise a release mechanism at the distal end thereof, i.e., at the interconnection between the shaft assembly 120020 and the end effector, which can unlock the lock 120024. In addition to or in lieu of the above, the handle can comprise a release mechanism which can unlock the lock 120024.

Figure 84:
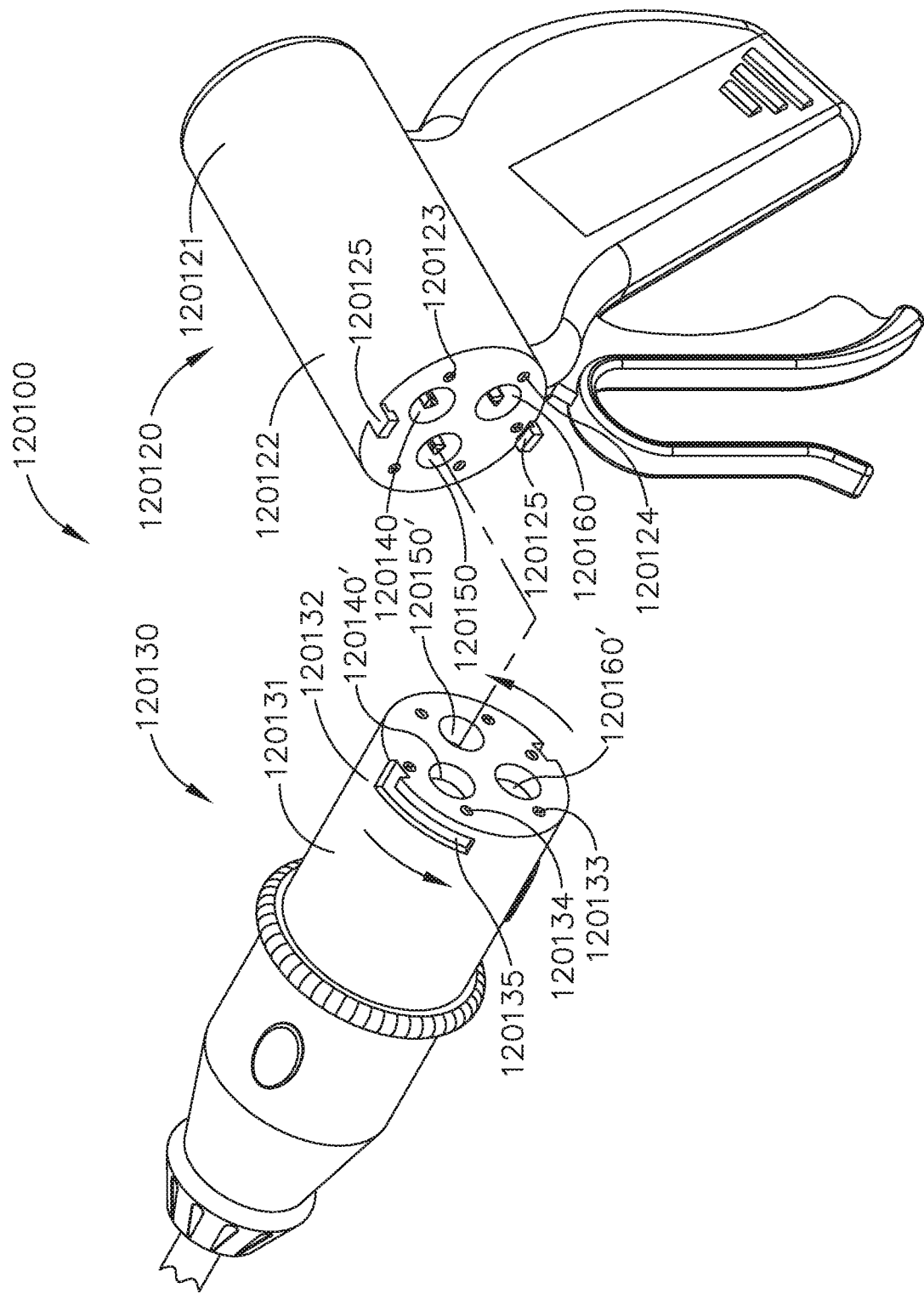
FIG. 84 is a partial perspective view of an interconnection between a shaft and a handle of a surgical instrument in accordance with at least one embodiment.

A surgical system 120100 is illustrated in FIG. 84. The surgical system 120100 comprises a handle, a shaft assembly 120120 extending from the handle, and an end effector 120130 releasably attachable to the shaft assembly 120120. The shaft assembly 120120 comprises an elongate shaft 120121 including a distal end 120122. The shaft assembly 120120 further comprises a first rotatable drive shaft 120140 driven by a first electric motor, a second rotatable drive shaft 120150 driven by a second electric motor, and a third rotatable drive shaft 120160 driven by a third electric motor. The first, second, and third electric motors are positioned in the shaft assembly 120120 and/or the handle. The end effector 120130 comprises an elongate shaft 120131 attachable to the elongate shaft 120121 of the shaft assembly 120120. The end effector 120130 includes a first drive shaft 120130' operably couplable to the first drive shaft 120130, a second drive shaft 120140' operably couplable to the second drive shaft 120140, and a third drive shaft 120160' operably couplable to the third drive shaft 120160 when the end effector 120130 is assembled to the shaft assembly 120120.

Further to the above, the shaft assembly 120120 and the end effector 120130 comprise co-operating features which properly align the three sets of drive shafts when the end effector 120130 is assembled to the shaft assembly 120120. For instance, the shaft assembly 120120 comprises alignment pins 120125 which are configured to be received within alignment slots 120135 defined in the end effector shaft 120131 which are configured to lock the end effector 120130 to the shaft assembly 120120 as the end effector 120130 is rotated relative to the shaft assembly 120120. In various instances, such a connection can comprise a bayonet connection. In addition to or in lieu of these alignment features, the shaft assembly 120120 and the end effector 120130 can comprise magnetic alignment features which align the end effector 120130 relative to the shaft assembly 120120. The distal end 120122 of the shaft assembly 120120 comprises a first group of permanent magnets 120123 and a second group of permanent magnets 120124 embedded therein. The permanent magnets 120123 have positive poles facing distally and the second permanent magnets 120124 have negative poles facing distally. Similarly, the proximal end 120132 of the end effector shaft 120131 comprises a first group of permanent magnets 120133 and a second group of permanent magnets 120134 embedded therein. The first permanent magnets 120133 have positive poles facing proximally and the second permanent magnets 120134 have negative poles facing proximally. When the proximal end 120132 of the end effector 120130 is brought into proximity with the distal end 120122 of the shaft assembly 120120, the magnets prevent the end effector 120130 from being attached from the shaft assembly 120120 in a misaligned manner.

In various instances, further to the above, a first handle comprises three electric motors to drive the first, second, and third drive shafts 120140, 120150, and 120160. In at least one instance, the first drive shaft 120140 of the shaft assembly 120120 articulates the distal end of the end effector 120130' about an articulation joint, the second drive shaft 120150 of the shaft assembly 120120 opens and closes the jaws of the end effector 120130, and the third drive shaft 120160 rotates the distal end of the end effector 120130 about a longitudinal axis. That said, other handles can comprise less than three electric motors and do not drive all of the first, second, and third drive shafts 120140, 120150, and 120160. In at least one such instance, a second handle comprises two electric motors which drive two of the shaft assembly drive shafts. The second handle is configured such that the shaft assembly 120120 is attached to the second handle in a manner in which the first drive shaft 120140 and the second drive shaft 120150 of the shaft assembly 120120 are operably coupled with the electric motors of the second handle. The third drive shaft 120160 is not operably coupled with an electric motor in such instances. As a result, the rotation of the distal end of the end effector 120130 would have to be performed manually by the clinician by rotating the entire surgical system 120100 about the longitudinal axis. In at least one instance, the first handle comprises a pistol grip configuration and the second handle comprises a scissors grip configuration. A third handle may have only one electric motor for driving only one of the shaft assembly drives. In at least one such instance, the third handle comprises a pencil grip configuration and the shaft assembly 120120 is attached to the third handle in a manner in which the first drive shaft 120140, the articulation drive shaft, is operably coupled to the only drive motor. Other arrangements are possible.

Figure 85:
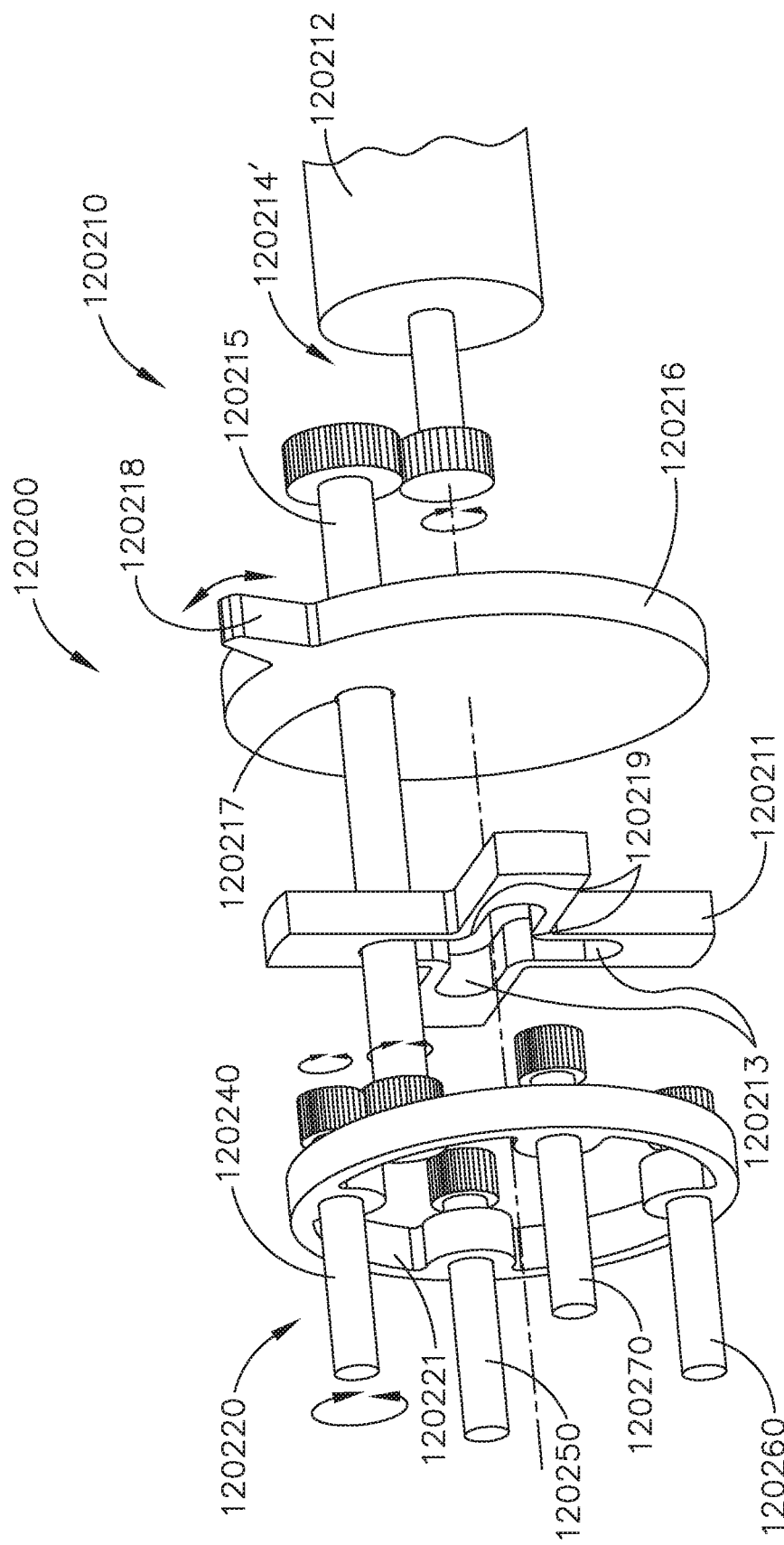
FIG. 85 is a partial perspective view of a drive system of a surgical instrument comprising an electric motor input and a shiftable transmission.

A surgical system 120200 is illustrated in FIG. 85. The surgical system 120200 comprises a handle 120210 and a shaft assembly 120220 attached to the handle 120210. The shaft assembly 120220 comprises a frame 120221 and four rotatable drive shafts—a first drive shaft 120240, a second drive shaft 120250, a third drive shaft 120260, and a fourth drive shaft 120270. The four drive shafts are rotatable independently of one another to perform different functions of the surgical system 120200. The handle 120210 comprises an electric motor 120212 comprising a rotatable output and a rotatable drive shaft 120215 which are operably connected by a gear train 120214. The rotatable drive shaft 120215 is selectively engageable with the four drive shafts of the shaft assembly 120220 to selectively drive one of the four drive shafts at a time. The handle 120210 further comprises a rotatable shifter 120216 configured to place the drive shaft 120215 in one of four distinct and discrete drive positions in which the drive shaft 120215 is operably engaged with one of the four drive shafts 120240, 120250, 120260, and 120270. The rotatable shifter 120216 comprises a throughhole 120217 defined therein through which the drive shaft 120215 extends. The throughhole 120217 comprises sidewalls configured to push the drive shaft 120215 between the four drive positions when the shifter 120216 is rotated. The shifter 120216 comprises a lever, or protrusion, 120218 extending therefrom which a clinician can use to rotate the shifter 120216. That said, the handle 120210 can comprise an electric motor and actuator for shifting the shifter 120216 between its four drive positions.

Further to the above, the shifting system of the handle 120210 comprises a frame, or shift block, 120211 configured to releasably hold the drive shaft 120215 in its four drive positions. The shift block 120211 comprises four drive slots 120213 defined therein which correspond to the four drive positions of the drive shaft 120215. The sidewalls of each drive slot 120213 are configured to prevent, or at least inhibit, lateral movement and/or deflection of the drive shaft 120215 until the drive shaft 120215 is moved into a different position by the shifter 120216. In various instances, the sidewalls of two adjacent drive slots 120213 form a peak 120219 therebetween which prevents, or at least inhibits, the drive shaft 120215 from unintentionally hopping out of a drive slot 120213. As a result of the four peaks 120219 distinctly defining the four drive positions of the drive shaft 120215, the shift block 120211 comprises a quad-stable compliant system. The apex of each peak 120219 is rounded such that the drive shaft 120215 does not get stuck intermediate one of the four stable drive positions, or drive slots 120213. The reader should appreciate that the drive shaft 120215 may flex inwardly when moving between drive slots 120213 and that the resilient inward bending of the drive shaft 120215 stores energy in the drive shaft 120215 which seeks to reactively seat the drive shaft 120215 in the nearest drive slot 120213.

Figure 86:
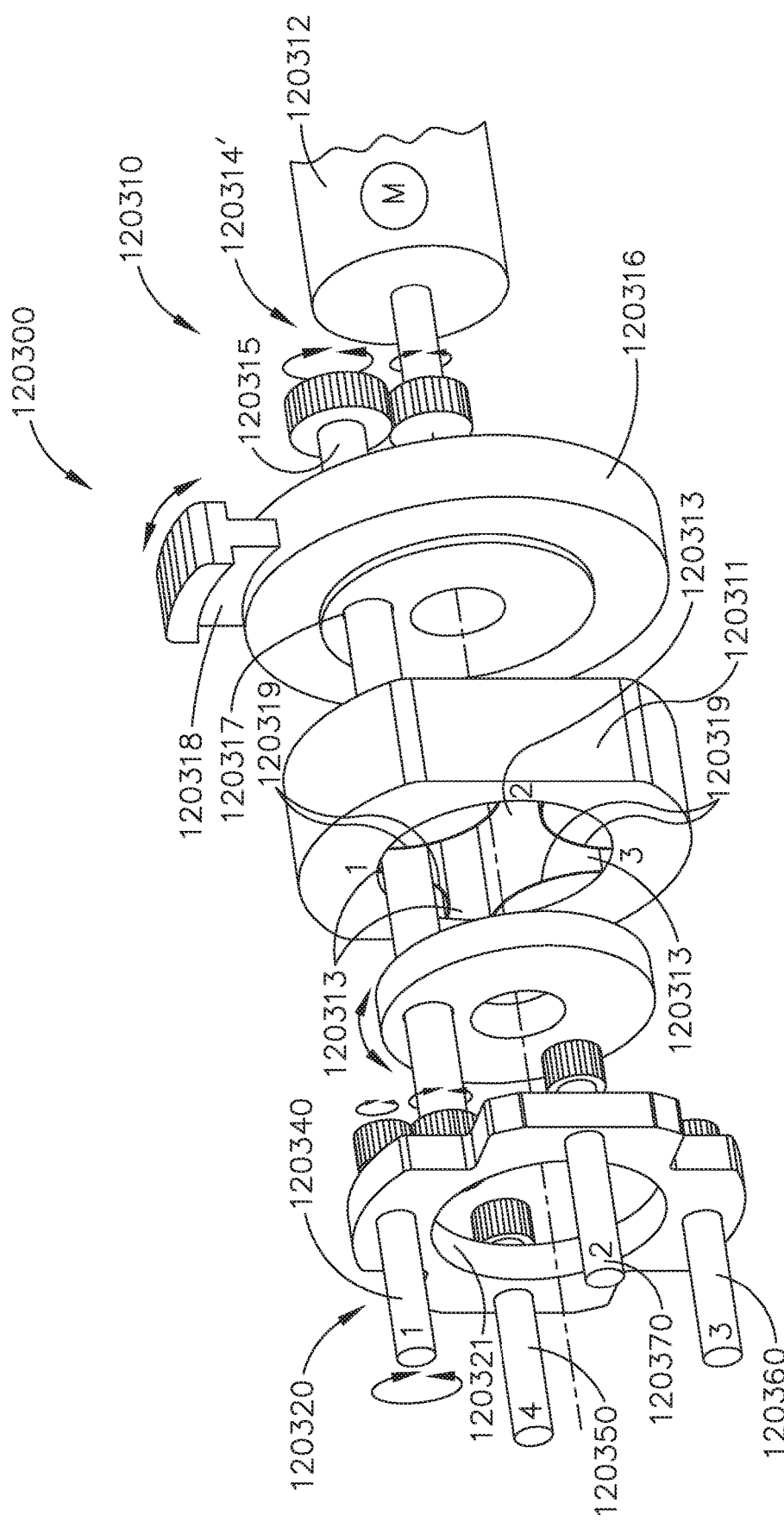
FIG. 86 is a partial perspective view of a drive system of a surgical instrument comprising an electric motor input and a shiftable transmission.
Figure 86A:
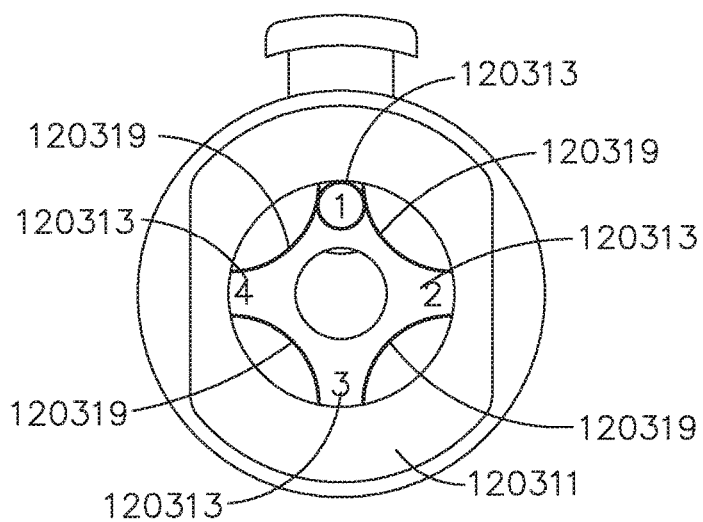
FIG. 86A depicts the transmission of FIG. 86 in a first configuration.
Figure 86B:
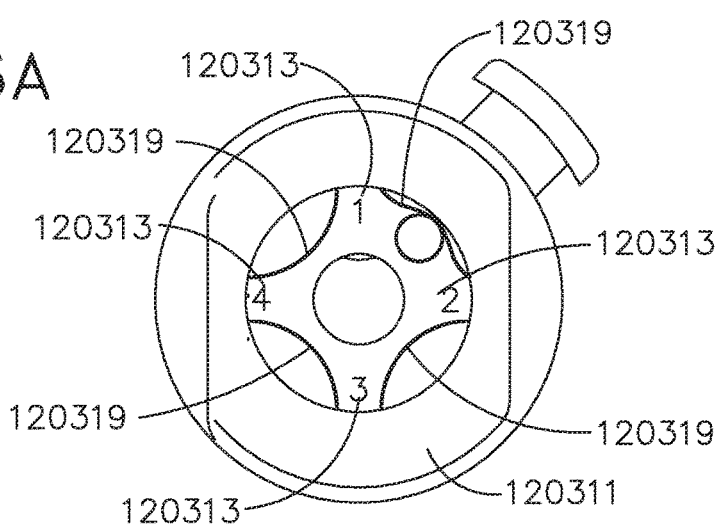
FIG. 86B depicts the transmission of FIG. 86 being shifted into a second configuration.
Figure 86C:
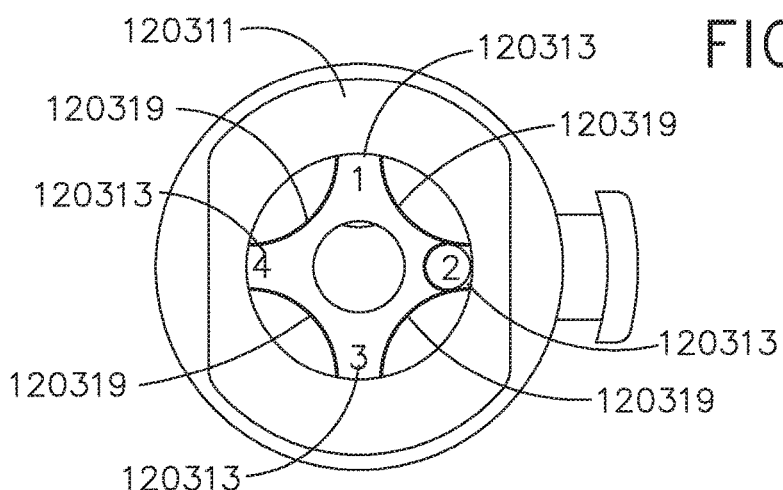
FIG. 86C depicts the transmission of FIG. 86 in the second configuration.

A surgical system 120300 is depicted in FIGS. 86-86C. The surgical system 120300 is similar to the surgical system 120200 in many respects. Referring primarily to FIG. 86A, the shift block 120311 of the surgical system 120300 comprises peaks 120319 positioned intermediate drive slots 120313. The peaks 120219 of the shift block 120211 are comprised of solid material while each of the peaks 120319 of the shift block 120311 is comprised of a leaf spring. Similar to the above, the leaf springs of the peaks 120319 prevent, or at least inhibit, the unintentional shifting of the drive shaft out of a drive slot 120313. Referring primarily to FIG. 86B, the leaf springs are configured to deflect as the drive shaft is being shifted between drive positions, or drive slots, 120313 and then resiliently return to their undeflected configurations once the drive shaft has passed thereby. This resiliency of the leaf springs also prevents, or inhibits, the drive shaft from becoming stuck in an intermediate, or unstable, position as the leaf springs act to resiliently undeflect and push the drive shaft into one of the drive slots 120313. The four stable positions of the shift blocks 120211 and 120311 are 90 degrees, or approximately 90 degrees, apart. That said, a shaft assembly having three drive shafts has three drive positions and a corresponding shift block comprises three drive slots spaced 120 degrees, or approximately 120 degrees, apart. In any event, a shaft assembly can comprise any suitable number of drive shafts and the corresponding shift block can comprise a corresponding number of drive slots that are evenly spaced apart.

Figure 88A:
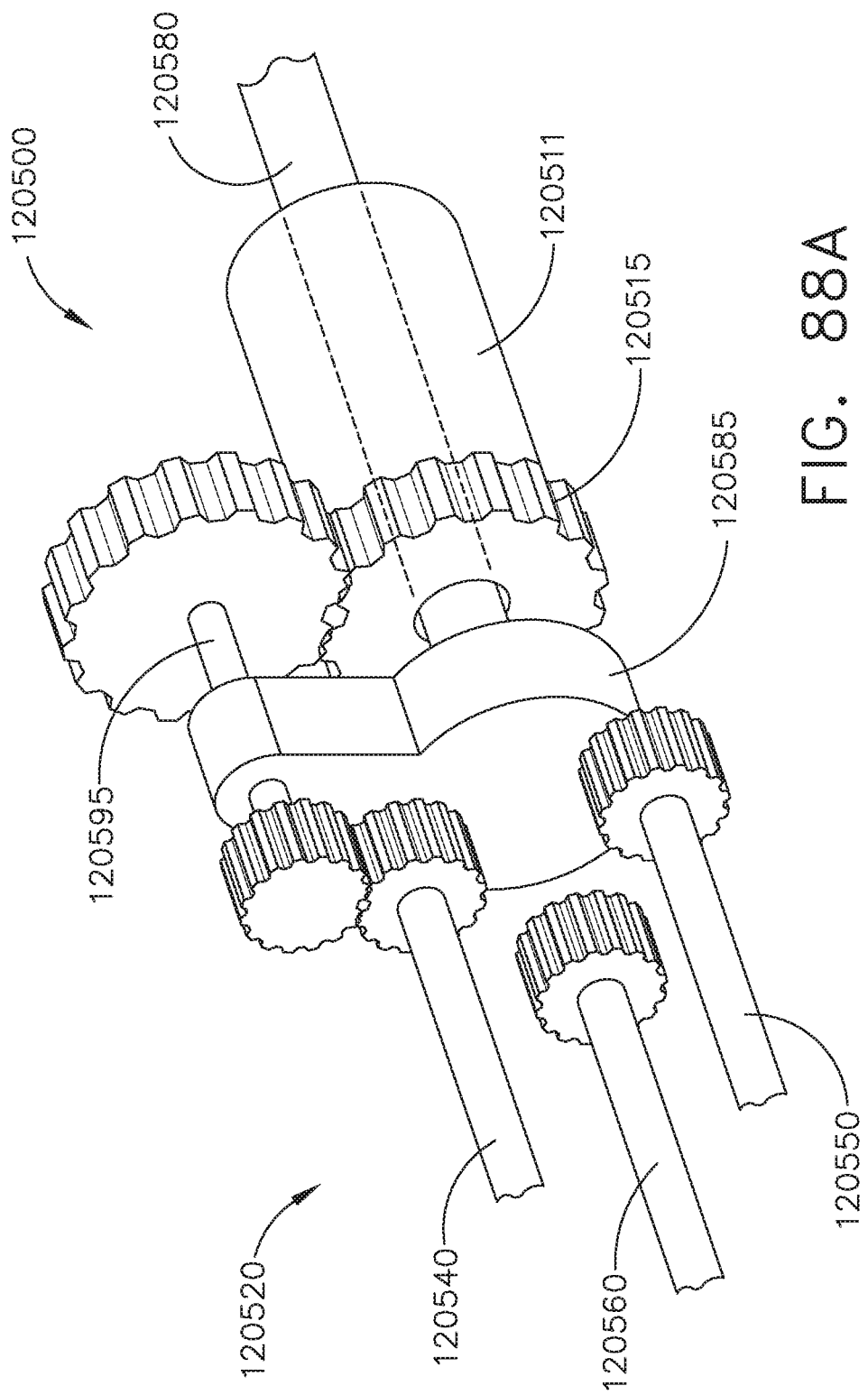
FIG. 88A is a partial cross-sectional view of a drive system of a surgical instrument comprising a transmission in accordance with at least one embodiment.

A surgical system 120500 is depicted in FIGS. 88A and 88B. The surgical system 120500 comprises a handle, a shaft 120520 extending from the handle, and an end effector extending from the shaft 120520. The handle comprises a single rotatable drive shaft 120510 configured to selectively drive a first drive shaft 120540, a second drive shaft 120550, and a third drive shaft 120560 via a shiftable transmission 120590. The drive shaft 120510 comprises a pinion gear 120515 mounted to the distal end thereof which is operably engaged with a transmission shaft 120595 such that the rotation of the drive shaft 120510 is transferred to the transmission shaft 120595. The transmission shaft 120595 is shiftable between three drive positions—a first drive position in which the transmission shaft 120595 is operably engaged with the first drive shaft 120540 (FIG. 88A), a second drive position in which the transmission shaft 120595 is operably engaged with the second drive shaft 120550 (FIG. 88B), and a third drive position in which the transmission shaft 120595 is operably engaged with the third drive shaft 120560. The transmission 120590 is rotated between its first, second, and third drive positions by a rotatable shifter 120580. The shifter 120580 comprises a shift arm 120585 fixedly mounted thereto which comprises a bearing aperture defined therein—the sidewalls of which rotatably support the transmission shaft 120595 when the transmission shaft 120595 is operably engaged with one of the three drive shafts 120540, 120550, and 120560. The three drive positions comprise a middle, or top-dead-center, position in which the transmission shaft 120595 is engaged with the first drive shaft 120540 (FIG. 88A), a lateral position approximately 120 degrees to one side of the top-dead-center position in which the transmission shaft 120595 is engaged with the second drive shaft 120550 (FIG. 88B), and another lateral position approximately 120 degrees to the other side of the top-dead-center position in which the transmission shaft 120595 is engaged with the third drive shaft 120560.

A surgical system 120400 is depicted in FIGS. 87A-87D. The surgical system 120400 comprises a handle, a shaft 120420 extending from the handle, and an end effector 120430 connected to the shaft 120420 about an articulation joint. The handle comprises a rotatable input shaft 120410 shiftable longitudinally between a distal position (FIGS. 87C and 87D) in which the input shaft 120410 is operably engaged with an articulation drive shaft 120440 and a proximal position (FIGS. 87A and 87B) in which the input shaft 120410 is operably engaged with a jaw drive shaft 120450. The input shaft 120410 comprises a pinion gear 120415 defined on the distal thereof that is operably meshed with a pinion gear 120445 defined on the articulation drive shaft 120440 when the input shaft 120140 is in its distal position and operably meshed within a pinion gear 120455 defined on the jaw drive shaft 120450 when the input shaft 120140 is in its proximal position. The articulation drive shaft 120440 comprises a bevel gear fixedly mounted thereto which is operably meshed with a bevel gear fixedly mounted to a frame 120431 of the end effector 120430 such that, when the input shaft 120410 is operably engaged with the articulation drive shaft 120440 and the articulation drive shaft 120440 is rotated in a first direction, the end effector 120430 is articulated in a first direction. Similarly, the articulation drive shaft 120440 is rotated in a second, or opposite, direction, to articulate the end effector 120430 in a second, or opposite, direction.

The jaw drive shaft 120450 comprises a threaded distal end which is threadably engaged with a drive nut 120435 which is translated distally when the jaw drive shaft 120450 is rotated in a first direction and translated proximally when the jaw drive shaft 120450 is rotated in a second, or opposite, direction. The end effector 120430 further comprises a first jaw 120432 and a second jaw 120434 pivotably coupled to one another and pivotably coupled to the drive nut 120435 such that the jaws 120432 and 120434 are opened when the drive nut 120435 is pushed distally and closed when the drive nut 120435 is pulled proximally. Notably, the entire drive shaft 120450 is depicted in FIGS. 87A-87C, but not in FIG. 87D. The drive shaft 120450 has been truncated in FIG. 87D to better show the articulation joint, but the reader should understand that the drive shaft 120450 bends to accommodate the articulation motion. Other embodiments are envisioned in which the drive shaft 120450 comprises at least one universal joint, for example, to accommodate the articulation motion.

As described above, referring again to FIGS. 87A-87D, the input shaft 120410 is translatable to selectively engage the articulation drive system and the jaw drive system and then rotatable to drive the system that it is engaged with. That said, the input shaft 120410 may not be able to drive, or at least properly drive, the articulation drive system or the jaw drive system if the input shaft 120410 is in a position intermediate the proximal drive position and the distal drive position. To this end, the surgical system 120400 comprises a biasing member configured to push the input shaft 120410 into its distal position in which the input shaft 120410 is operably engaged with the articulation drive system. In order to move the input shaft 120410 into its proximal position, an electric actuator must overcome this biasing force. Alternatively, the biasing member is configured to push the input shaft 120410 into its proximal position in which the input shaft 120410 is operably engaged with the jaw drive system.

Further to the above, the frame of the shaft 120420 comprises a rotatable portion 120431 which permits the jaws 120430 to rotate about a longitudinal shaft axis (FIGS. 87A and 87C). In various instances, the surgical system comprises a drive system configured to rotate the jaws 120430 about the longitudinal axis.

Figure 89:
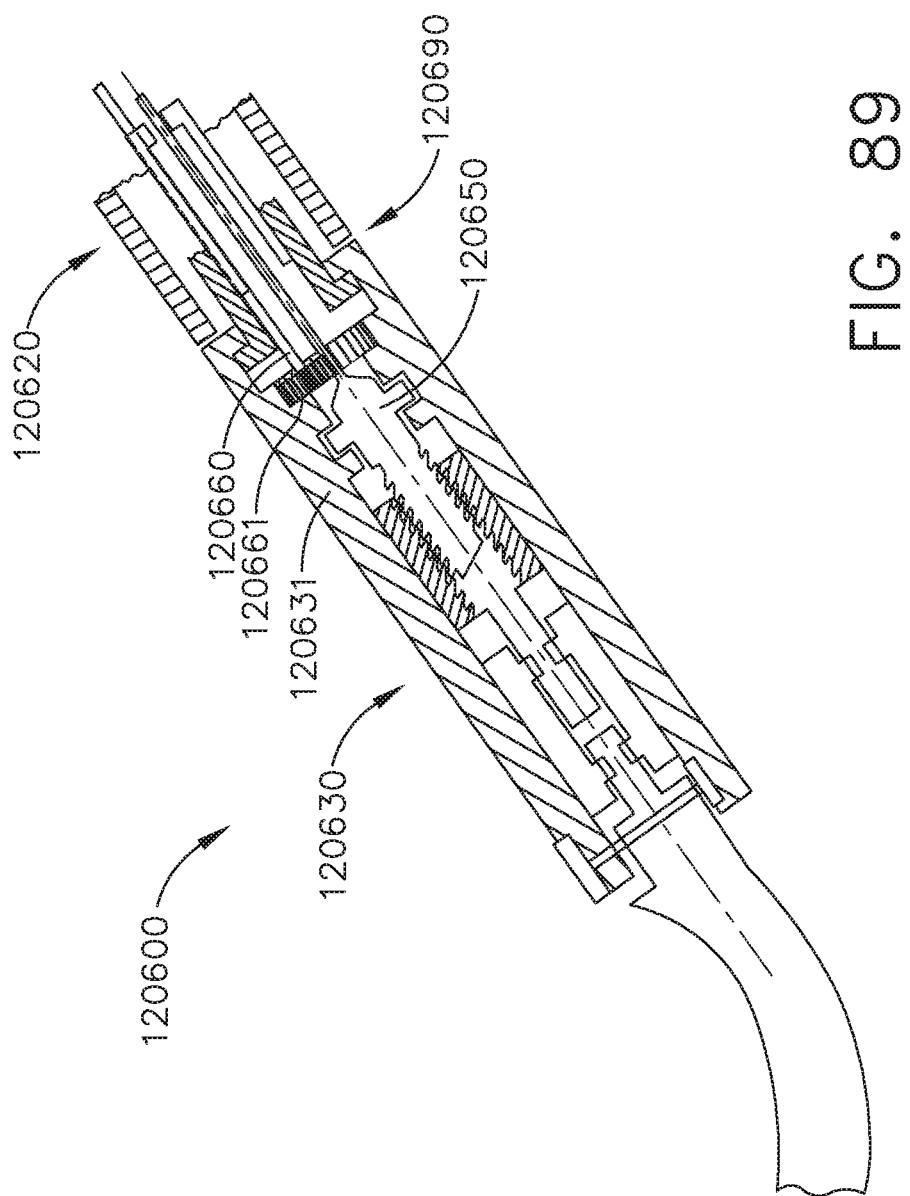
FIG. 89 is a partial cross-sectional view of a drive system of a surgical instrument in accordance with at least one embodiment.
Figure 90:
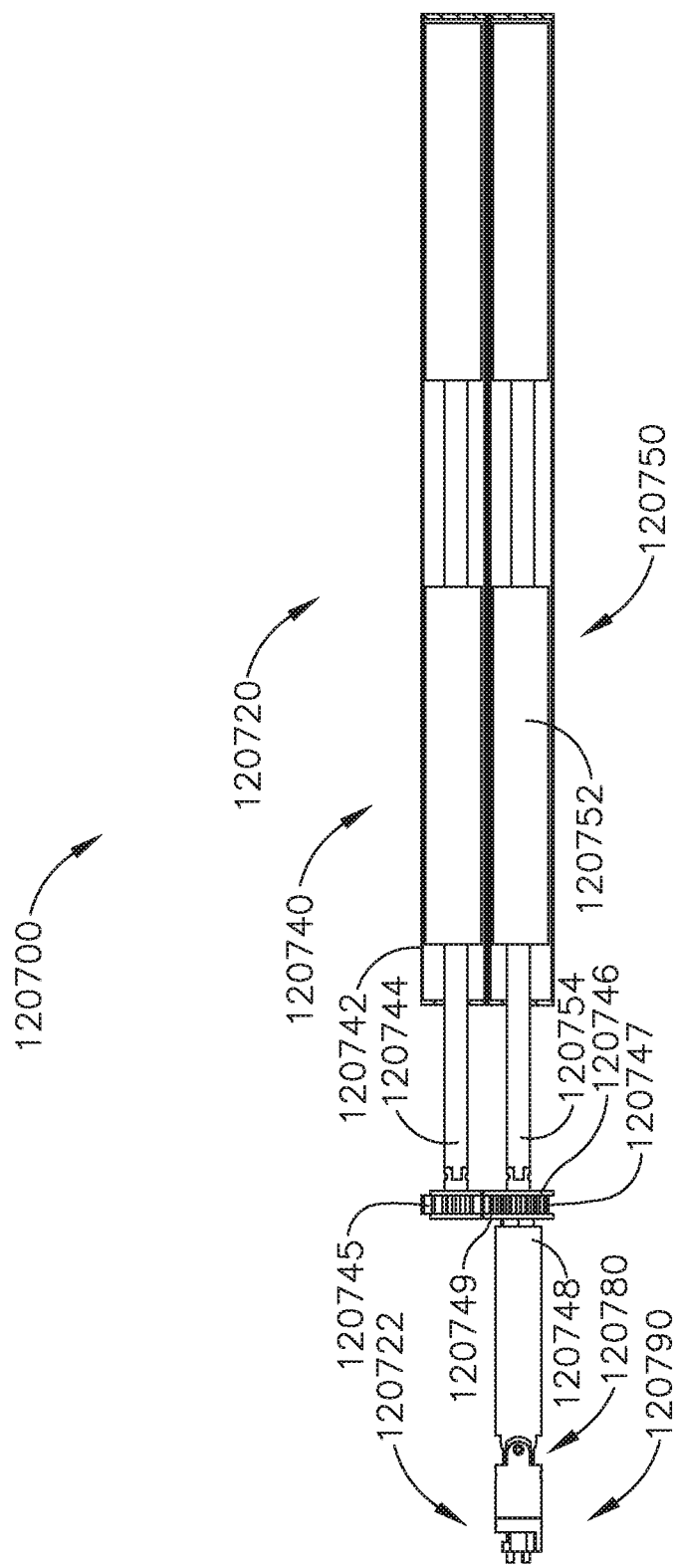
FIG. 90 is a partial perspective view of a drive system of a surgical instrument in accordance with at least one embodiment.
Figure 91:
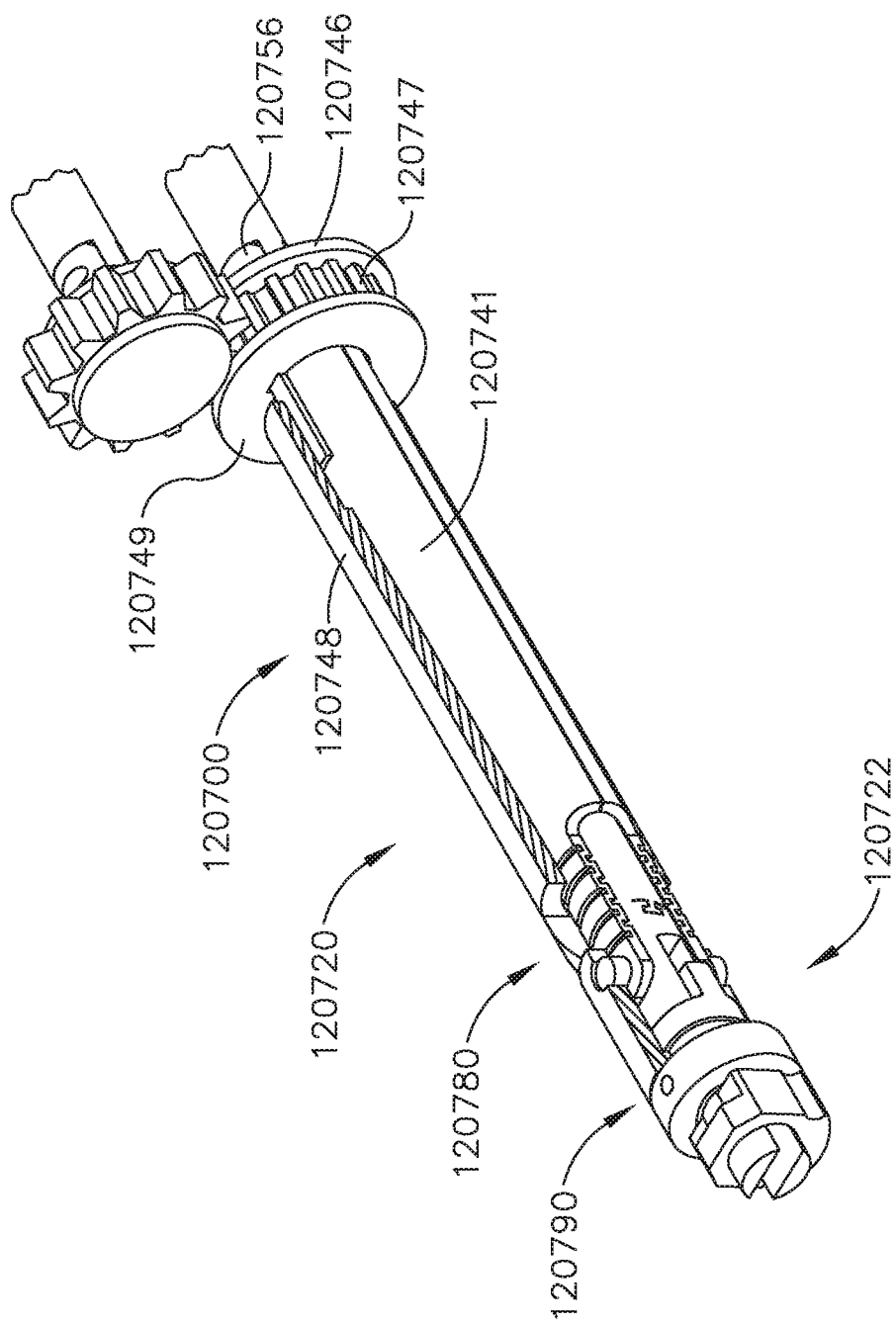
FIG. 91 is a detail view of the drive system of FIG. 90.

In various instances, an input shaft is shiftable between two or more positions to drive two or more functions of a surgical system. A surgical system 120600 is depicted in FIG. 89 which comprises a handle, a shaft assembly 120620 extending from the handle, and an end effector 120630 extending from the shaft assembly 120620. The end effector 120630 is rotatably coupled to the shaft assembly 120620 about a rotation joint 120690 configured to permit the end effector 120630 to be rotated about a longitudinal axis. The surgical system 120600 further comprises a jaw drive shaft 120650 configured to open and close the jaws of the end effector 120630 and, also, a rotation drive shaft 120660 configured to rotate the end effector 120630 about the longitudinal shaft axis. The rotation drive shaft 120660 comprises a pinion gear 120661 mounted to the distal end thereof which is operably intermeshed with a ring of gear teeth defined in the interior of the end effector housing 120631 such that the rotation of the rotation drive shaft 120660 is transferred to the end effector 120630. Similar to the above, the handle comprises an input shaft which is shiftable between a first position in which the input shaft is operably coupled to the jaw drive shaft 120650 and a second position in which the input shaft is operably coupled to the rotation drive shaft 120660. Also, similar to the above, the input shaft can be biased into the first or second position by a biasing member. In at least one embodiment, the input drive is shiftable into a third position to engage an articulation drive shaft of an articulation drive system.

A surgical system 120700 is depicted in FIGS. 90-93. The surgical system 120700 comprises a handle, a shaft assembly 120720 extending from the handle, and an end effector releasably attachable to the shaft assembly 120720. Similar to the above, the end effector comprises first and second jaws that are movable between open and closed positions. The surgical system 120700 further comprises an articulation joint 120780 about which the end effector can be rotated relative to the shaft assembly 120720. Moreover, the surgical system 120700 further comprises a rotation joint 120790 which permits the end effector to be rotated relative to the shaft assembly 120720 about a longitudinal end effector axis. As described in greater detail below, the surgical system 120700 comprises a first drive system 120740 to rotate the shaft assembly 120720 about a longitudinal shaft axis and articulate the end effector and, also, a second drive system 120750 to rotate the end effector relative to the shaft assembly 120720 about the longitudinal end effector axis and drive the jaws between their open and closed positions.

The first drive system 120740 of the surgical system 120700 comprises an electric actuator 120742 and an input shaft 120744. The electric actuator 120742 is configured to rotate and translate the input shaft 120744. The input shaft 120744 comprises a spur gear 120745 fixedly mounted to the distal end thereof such that the spur gear 120745 rotates and translates with the input shaft 120744. The spur gear 120745 is operably meshed with a spur gear 120747 fixedly mounted to an articulation actuator 120741 which is keyed (FIG. 91) to a shaft housing 120748 such that the rotation of the input shaft 120744 is transferred to the shaft housing 120748. The shaft housing 120748 is sufficiently coupled to the frame of the shaft assembly 120720 such that, when the electric actuator 120742 rotates the input shaft 120744, the input shaft 120744 rotates the shaft assembly 120720. Notably, the articulation actuator 120741 comprises a proximal flange 120746 positioned proximally with respect to the spur gear 120747 and a distal flange 120749 positioned distally with respect to the spur gear 120747. The proximal flange 120746 and the distal flange 120749 are configured to prevent the spur gears 120745 and 120747 from translating and becoming operably demeshed from one another. Moreover, the proximal flange 120746 and the distal flange 120749 are configured to be driven proximally and distally by the spur gear 120745 as discussed in greater detail below.

Further to the above, the electric actuator 120742 is configured to translate the drive shaft 120744 proximally and distally to articulate the end effector about the articulation joint 120780. When the drive shaft 120744 is pushed distally by the electric actuator 120742, the spur gear 120745 pushes distally on the distal flange 120749 extending from the articulation actuator 120741. Correspondingly, the spur gear 120745 pulls proximally on the proximal flange 120746 extending from the articulation actuator 120741 when the drive shaft 120744 is pulled proximally by the electric actuator 120742. The articulation actuator 120741 is coupled to a distal end 120722 of the shaft assembly 120720 such that the distal translation of the articulation actuator 120741 articulates the distal shaft end 120722, and the end effector mounted thereto, in a first direction and such that the proximal translation of the articulation actuator 120741 articulates the distal shaft end 120722 and the end effector in a second, or opposite, direction.

Figure 92:
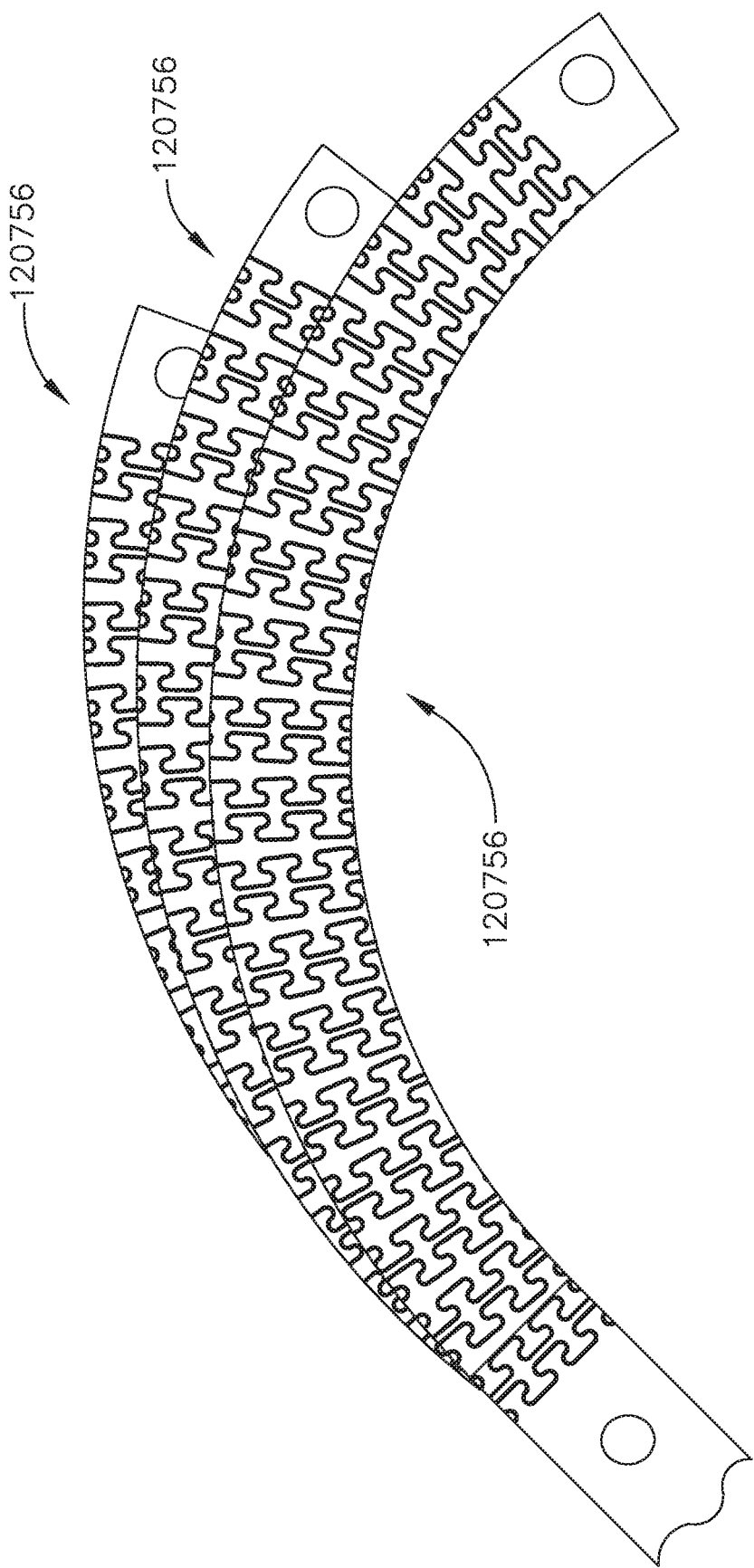
FIG. 92 is a perspective view of flexible drive shafts in accordance with at least one embodiment.

The second drive system 120750 of the surgical system 120700 comprises an electric actuator 120752 and a drive shaft 120754. The electric actuator 120752 is configured to rotate and translate the drive shaft 120754. Referring primarily to FIG. 92, a flexible drive shaft 120756 is mounted to the drive shaft 120754 such that the flexible drive shaft 120756 rotates and translates with the drive shaft 120754. The flexible drive shaft 120756 comprises a laser-cut steel tube, for example, but could comprise any suitable configuration. The flexible drive shaft 120756 extends through the articulation joint 120780 and at least part of the distal shaft end 120722 and is configured to accommodate the articulation of the distal shaft end 120722. The flexible drive shaft 120756 is coupled to the end effector such that, when the flexible drive shaft 120756 is rotated by the electric actuator 120752, the flexible drive shaft 120756 rotates the end effector about the rotation joint 120790. Moreover, the flexible drive shaft 120756 is coupled to the jaw drive of the end effector such that the longitudinal translation of the flexible drive shaft 120756 opens and closes the jaws of the end effector.

As discussed above, the surgical system 120700 is configured to drive four independent motions—end effector rotation, shaft rotation, end effector articulation, and end effector actuation. These functions can be performed at the same time and/or at different times. In at least one instance, it is beneficial to rotate the end effector and the shaft at the same time so that their rotation is synchronized. Otherwise, a clinician may be surprised to discover that the end effector is not turning with the shaft when what they wanted in the first place was to reorient the end effector. That said, the end effector can be rotated independently of the shaft.

Figure 93:
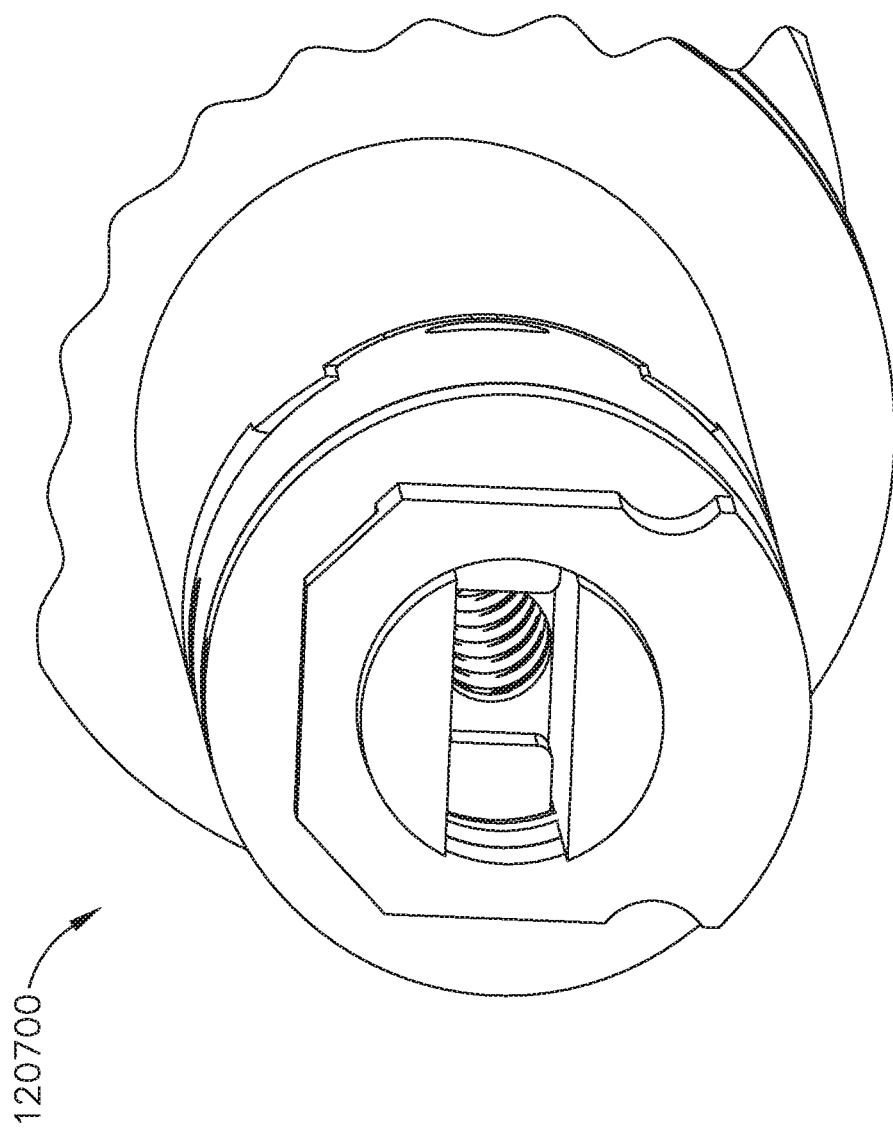
FIG. 93 is a partial perspective view of the surgical instrument of FIG. 90.

FIG. 93 depicts a longitudinal passage extending through the shaft assembly 120720 which is configured for signal and/or power conductors to extend there through.

Further to the above, the rotation of the end effector, the actuation of the end effector, the rotation of the shaft, and the articulation of the end effector can occur sequentially in any suitable order. That said, referring to FIGS. 104-108, two or more of these functions can occur at the same time. A surgical system 124100 is depicted in FIG. 105. The surgical system 124100 comprises a shaft assembly 124120 and an end effector 124130 rotatably connected to the shaft assembly 124120 about an articulation joint 124180. Moreover, the end effector 124130 is rotatable relative to the shaft assembly 124120 about a rotation joint 124190. When the surgical system 124100 is attached to a handle having a sufficient number of drive systems, referring to FIGS. 105 and 106, the end effector 124130 can be rotated and articulated at the same time, for example. Such an arrangement can provide a smooth motion of the end effector 124130. When the surgical system 124100 is not attached to a handle having a sufficient number of drive systems, referring to FIGS. 107 and 108, the end effector 124130 would have to be rotated and articulated sequentially using a shiftable drive.

A surgical system 121000 is illustrated in FIGS. 94-95B. The surgical system 121000 comprises a handle 121010 and a shaft assembly 121020 releasably attachable to the handle 121010. The shaft assembly 121020 comprises three drive systems and the handle 121010 comprises three drive outputs, but only two motors to drive the three drive outputs. One of the motors in the handle 121010 can be dedicated to driving one of the drives of the shaft assembly 121020. The other motor in the handle 121010, i.e. motor 121011, is configured to selectively drive the other two drives of the shaft assembly 121020. The motor 121011 comprises a rotatable output shaft 121012 and an elongate spur gear 121013 fixedly mounted to the output shaft 121012. The output shaft 121012 is selectively couplable with a first drive shaft 121040 and a second drive shaft 121050 by a transmission 121090. The transmission 120190 comprises a transfer gear 121015 slideably engaged with the elongate gear 121013. The transfer gear 121015 is slideable between a first position in which the transfer gear 121015 is operably intermeshed with the elongate spur gear 121013 and a first spur gear 121045 fixedly mounted to the first drive shaft 121040 and a second position in which the transfer gear 121015 is operably intermeshed with the elongate spur gear 121013 and a second spur gear 121055 fixedly mounted to the second drive shaft 121050. The transmission 121090 further comprises a shifting mechanism 121014 configured to move the transfer gear 121015 between its first and second positions. Such an arrangement allows the handle 121010 to be used to drive all three drive systems of the shaft assembly 121020, although the drive systems driven by the first drive shaft 121040 and the second drive shaft 121050 cannot be driven at the same time as the spur gears 121045 and 121055 are separated such that the transfer gear 121015 cannot drive spur gears 121045 and 121055 at the same time.

Figure 96:
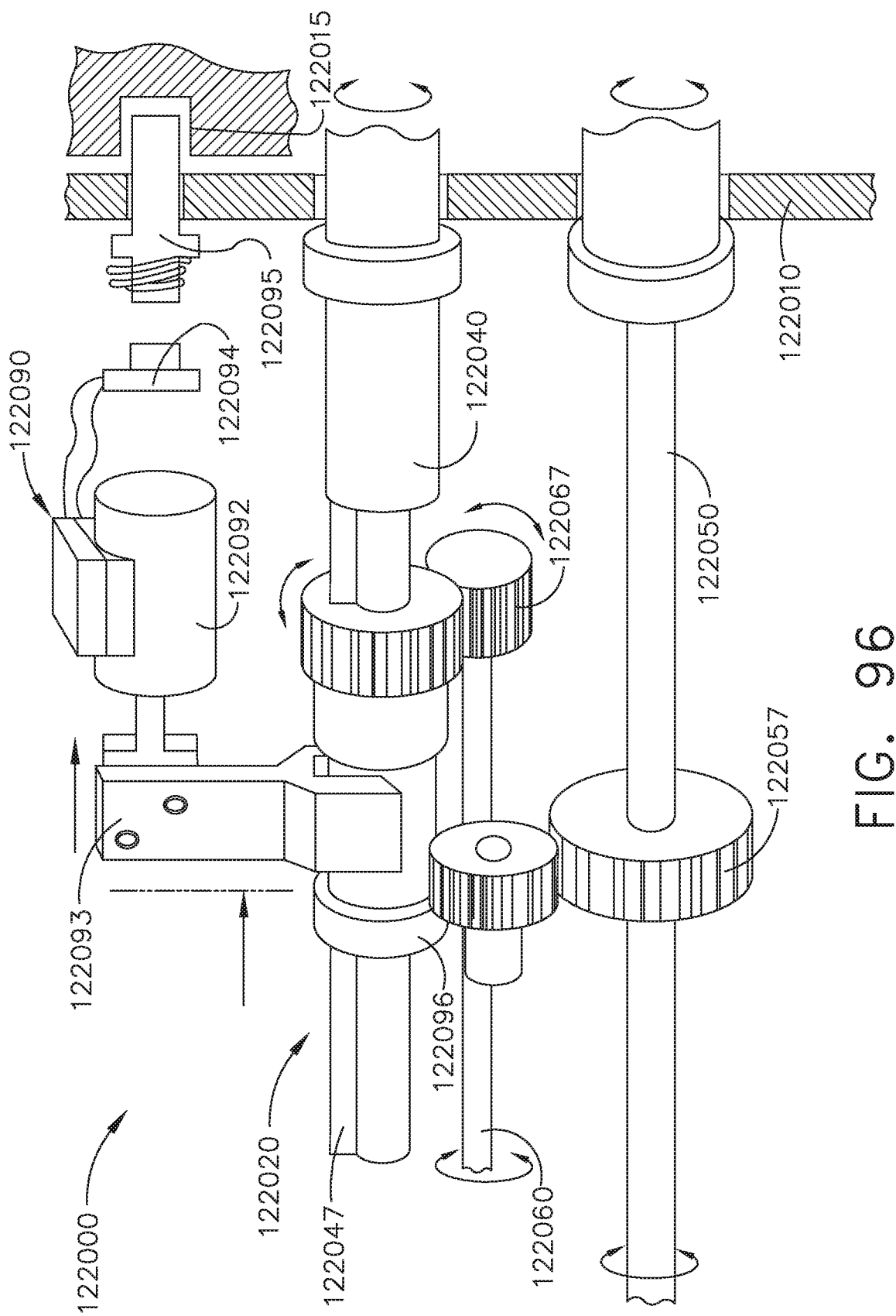
FIG. 96 is a partial perspective view of a drive system of a surgical instrument in accordance with at least one embodiment attached to a first handle.
Figure 97:
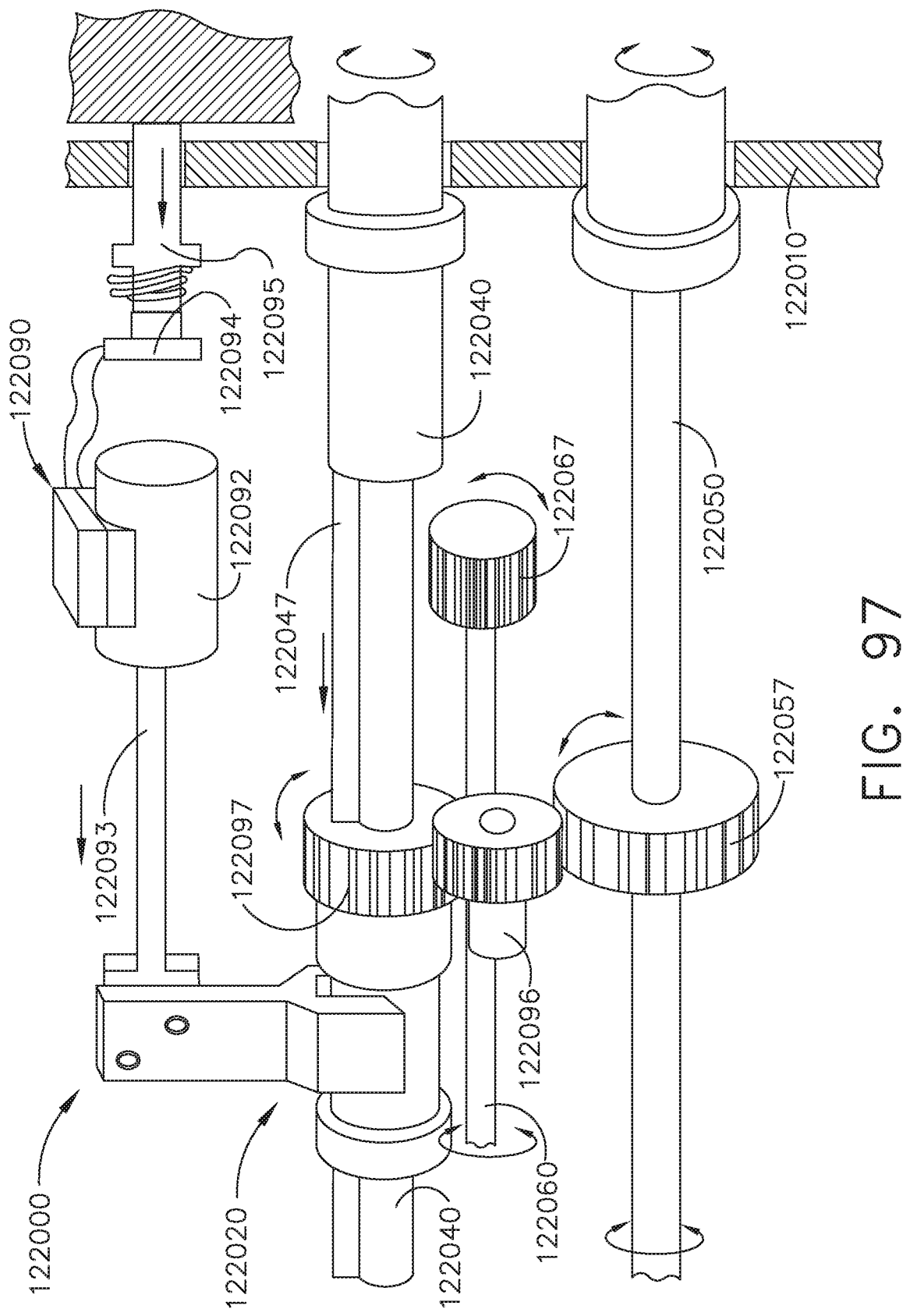
FIG. 97 is a partial perspective view of the drive system of FIG. 96 attached to a second handle.

A surgical system 122000 is illustrated in FIGS. 96 and 97. The surgical system 122000 comprises a handle 122010, a handle 122010', and a shaft assembly 122020 selectively attachable to the handle 122010 (FIG. 96) and the handle 122010' (FIG. 97). Referring to FIG. 96, the handle 122010 comprises two rotatable drive outputs which are operably coupleable with two drive systems of the shaft assembly 122020. The handle 122010 comprises a first drive output which is operably engaged with a first rotatable drive shaft 122040 and a second drive output which is operably engaged with a second rotatable drive shaft 122050 when the shaft assembly 122020 is attached to the handle 122010. The first drive shaft 122040 comprises a longitudinal splined portion 122047 and a spur gear 122097 slideably supported on the splined portion 122047 such that the rotation of the first drive shaft 122040 is transferred to the spur gear 122097 and, as described in greater detail below, the spur gear 122097 is slideable into another, or second position, when the shaft assembly 122020 is attached to the handle 122010' instead. While the shaft assembly 122020 is attached to the handle 122010, however, the spur gear 122097 is in its first position illustrated in FIG. 96 and is operably intermeshed with a spur gear 122067 fixedly mounted to a rotatable drive shaft 122060. In such instances, as a result, the rotation of the first drive shaft 122040 is transferred to the drive shaft 122060 which can drive a function of the surgical system 122000. Also, in such instances, the second drive shaft 122050 is rotatable to drive a second function of the surgical system 122000 independently of the first drive shaft 122040.

Notably, further to the above, the shaft assembly 122020 further comprises a handle detection system 122090 configured to detect whether the shaft assembly 122020 is attached to the handle 122010 or the handle 122010'. The handle detection system 122090 comprises a switch element 122095 extending proximally from the proximal end of the shaft assembly 122020. When the shaft assembly 122020 is attached to the handle 122010 (FIG. 96), the switch element 122095 extends into a clearance aperture 122015 defined in the housing of the handle 122010. The switch element 122095 is biased proximally by a biasing element, such as a spring, for example, such that the switch element 122095 does not contact, or close, a switch contact 122094 in the shaft assembly 122020 unless the switch element 122095 is driven distally—which does not happen when the shaft assembly 122020 is attached to the handle 122010 because of the clearance aperture 122015. When the shaft assembly 122020 is attached to the handle 122010' (FIG. 97), however, the switch element 122095 contacts the housing of the handle 122010' and is driven distally into engagement with the switch contact 122094. The closure of the switch element 122095 actuates a solenoid 122092 of the handle detection system 122090 which drives the transfer gear 122097 from its first position (FIG. 96) into its second position (FIG. 97) via a link arm 122093 and a shuttle 122096. When the transfer gear 122097 is in its second position, as illustrated in FIG. 97, the transfer gear 122097 is no longer operably intermeshed with the spur gear 122067 of the drive shaft 122060 and is, instead, operably intermeshed with a spur gear 122057 fixedly mounted to the second drive shaft 122050. In such instances, the rotation of the first drive shaft 122040 is transferred to the second drive shaft 122050 instead of the drive shaft 122060. Such an arrangement allows the second drive shaft 122050 to always be driven by a motor-driven drive regardless of whether the shaft assembly 122020 is attached to the handle 122010, which has a second independently drivable output, or the handle 122010' which does not have a second independently drivable output. When the shaft assembly 122020 is detached from the handle 122010', the biasing member pushes the switch element 122095 distally once again which opens the switch contact 122094. As a result, the solenoid 122092, or a return spring of the solenoid 122092, returns the transfer gear 122097 back into its first position. In various embodiments, the shaft assembly 122020 comprises a power source, such as a battery, for example, configured to operate the solenoid 122092.

FIGS. 98-103 illustrate a surgical system 123000. The surgical system 123000 comprises a handle 123010 and a shaft assembly 123020 extending from the handle 123010. The handle 123010 comprises a first drive output, a second drive output, and a third drive output. The first drive output is manually-driven, which means that it is powered by the clinician's hand to drive a first function of the surgical system 123000. In at least one instance, the first drive output rotates the shaft assembly 123020 about a longitudinal axis. The second drive output is driven by an electric motor and the third drive output is driven by another electric motor. The second drive output drives a second function of the surgical system 123000 and the third drive output drives a third function of the surgical system 123000. In various instances, the operation of the first drive output can affect the second function and/or the third function of the surgical system 123000. To this end, the handle 123010 comprises a system configured to monitor the manually-driven first drive system and automatically adjust the condition of the second and/or third drive system based on the movement of the first drive system. In at least one instance, the handle 123010 comprises an encoder, for example, configured to monitor the rotation of a rotational member of the first drive system. The encoder is in signal communication with the control system of the surgical system 123000 which is also in signal communication with the electric motors of the second and third drive systems. In various instances, the control system can operate the electric motors of the second and/or third drive systems when the control system detects the motion of the first drive system via the encoder, for example. In at least one instance, the second drive system rotates the end effector, or distal head, of the shaft assembly 123020 about a longitudinal axis and, when the shaft assembly 123020 is rotated manually, the control system can operate the electric motor of the second drive system to maintain, or at least substantially maintain, the alignment between the distal head and the shaft assembly 123020 when the shaft assembly 123020 is rotated.

Figure 98:
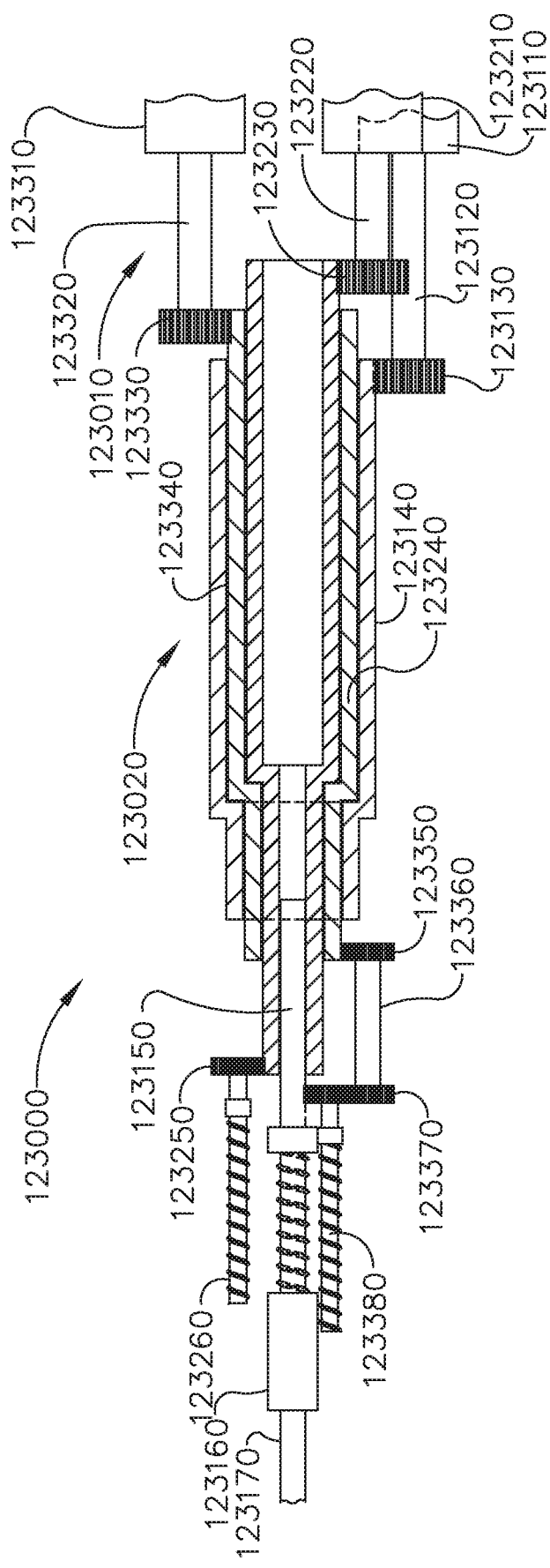
FIG. 98 is a partial cross-sectional view of a drive system of a surgical instrument in accordance with at least one embodiment.
Figure 99:
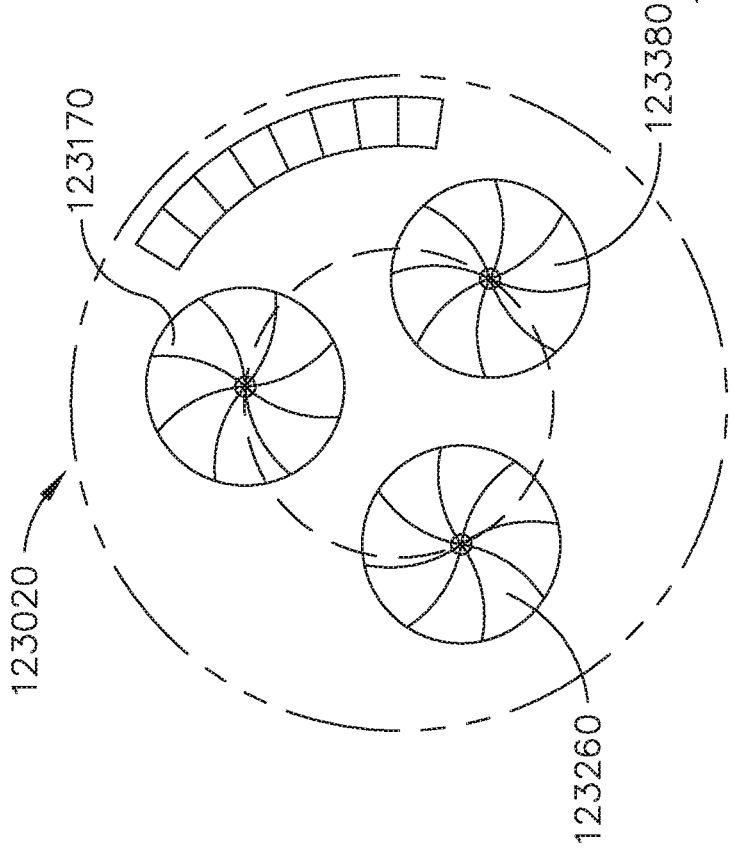
FIG. 99 is an end view of a portion of the surgical instrument of FIG. 98.
Figure 101:
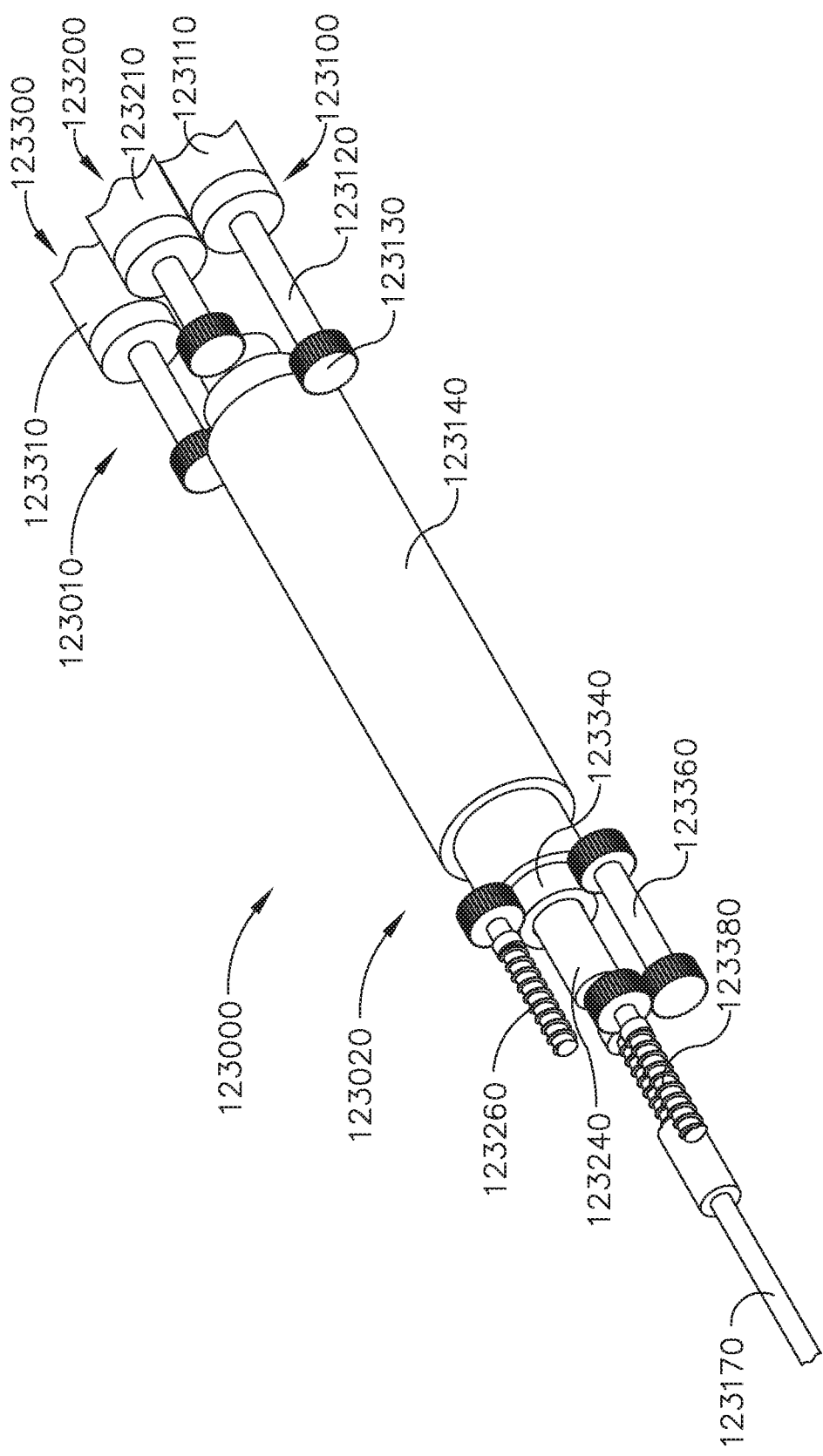
FIG. 101 is a perspective view of the drive system of FIG. 98.

Referring to FIGS. 98, 99, and 101, the handle 123010 comprises a first drive system including a first electric drive motor 123110, a second drive system including a second electric drive motor 123210, and a third drive system including a third electric drive motor 123310. The first drive system is configured to drive a first function of the shaft assembly 123020. The second drive system is configured to drive a second function of the shaft assembly 123020, and the third drive system is configured to drive a third function of the shaft assembly 123020. The first electric drive motor 123110 comprises a rotatable drive shaft 123120 and an output gear 123130 fixedly mounted to the drive shaft 123120. The output gear 123130 is meshingly engaged with a ring of gear teeth surrounding a tubular drive shaft 123140 of the first drive system such that the drive shaft 123140 is rotated when the output gear 123130 is rotated by the electric drive motor 123110. The drive shaft 123140 is operably coupled, via a geared transmission (not shown), with a threaded output shaft 123150 rotatably supported in the shaft assembly 123030. The first drive system further comprises a drive nut 123160 threadably coupled to the threaded output shaft 123150 such that, when the threaded output shaft 123150 is rotated by the tubular drive shaft 123140, the drive nut 123160 is driven proximally or distally, depending on the direction in which the threaded output shaft 123150 is rotated. The first drive system further comprises a drive rod extending from the drive nut 123160 which, in use, is configured to drive one or more end effector functions.

The second electric drive motor 123210 comprises a rotatable drive shaft 123220 and an output gear 123230 fixedly mounted to the drive shaft 123220. The output gear 123230 is meshingly engaged with a ring of gear teeth surrounding a tubular drive shaft 123240 of the second drive system such that the drive shaft 123240 is rotated when the output gear 123230 is rotated by the electric drive motor 123210. The drive shaft 123240 is operably coupled with a spur gear 123250 meshingly engaged with a ring of gear teeth defined on the drive shaft 123240 such that the spur gear 123250 is rotated when the drive shaft 123240 is rotated. The second drive system further comprises a threaded output shaft 123260 that is rotatably supported in the shaft assembly 123030 and fixedly mounted to the spur gear 123250. The second drive system further comprises a drive nut threadably coupled to the threaded output shaft 123260 such that, when the threaded output shaft 123260 is rotated by the tubular drive shaft 123240, the drive nut is driven proximally or distally, depending on the direction in which the threaded output shaft 123260 is rotated.

The third electric drive motor 123310 comprises a rotatable drive shaft 123320 and an output gear 123330 fixedly mounted to the drive shaft 123320. The output gear 123330 is meshingly engaged with a ring of gear teeth surrounding a tubular drive shaft 123340 of the third drive system such that the drive shaft 123340 is rotated when the output gear 123330 is rotated by the electric drive motor 123310. The drive shaft 123340 is operably coupled with a spur gear 123350 meshingly engaged with a ring of gear teeth defined on the drive shaft 123340 such that the spur gear 123350 is rotated when the drive shaft 123340 is rotated. The second drive system further comprises a transfer shaft 123360 that is rotatably supported in the shaft assembly 123030 and fixedly mounted to the spur gear 123350 and, in addition, another spur gear 123370. The spur gear 123370 is operably intermeshed with a threaded output shaft 123380 which is rotatably supported in the shaft assembly 123020. Similar to the above, the third drive system further comprises a drive nut threadably coupled to the threaded output shaft 123380 such that, when the threaded output shaft 123380 is rotated by the transfer shaft 123360, the drive nut is driven proximally or distally, depending on the direction in which the transfer shaft 123360 is rotated.

Figure 100:
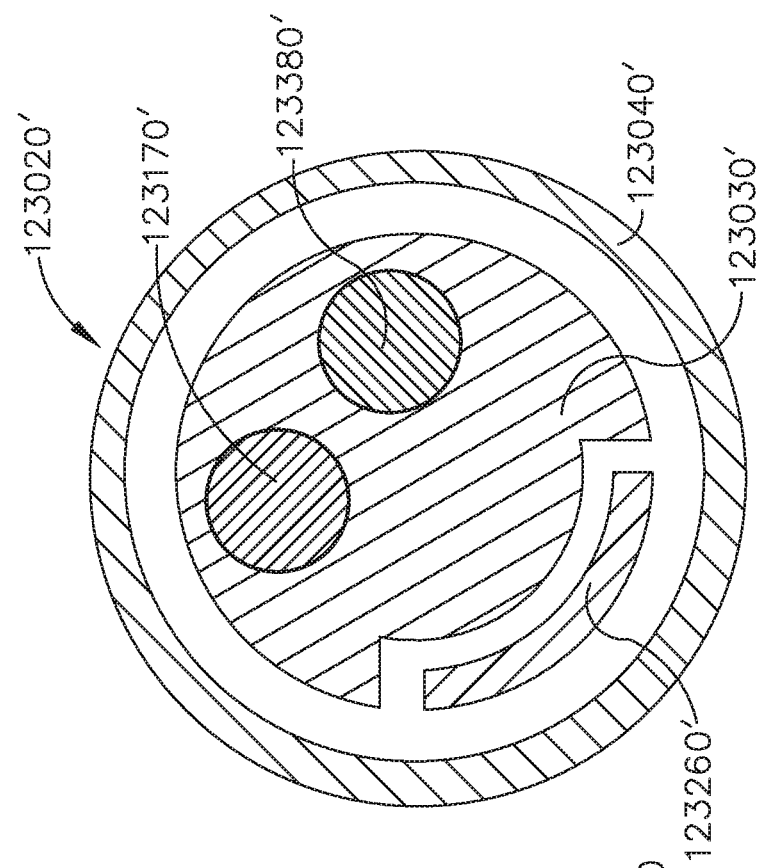
FIG. 100 is a cross-sectional end view of a portion of a surgical instrument in accordance with at least one embodiment.
Figure 103:
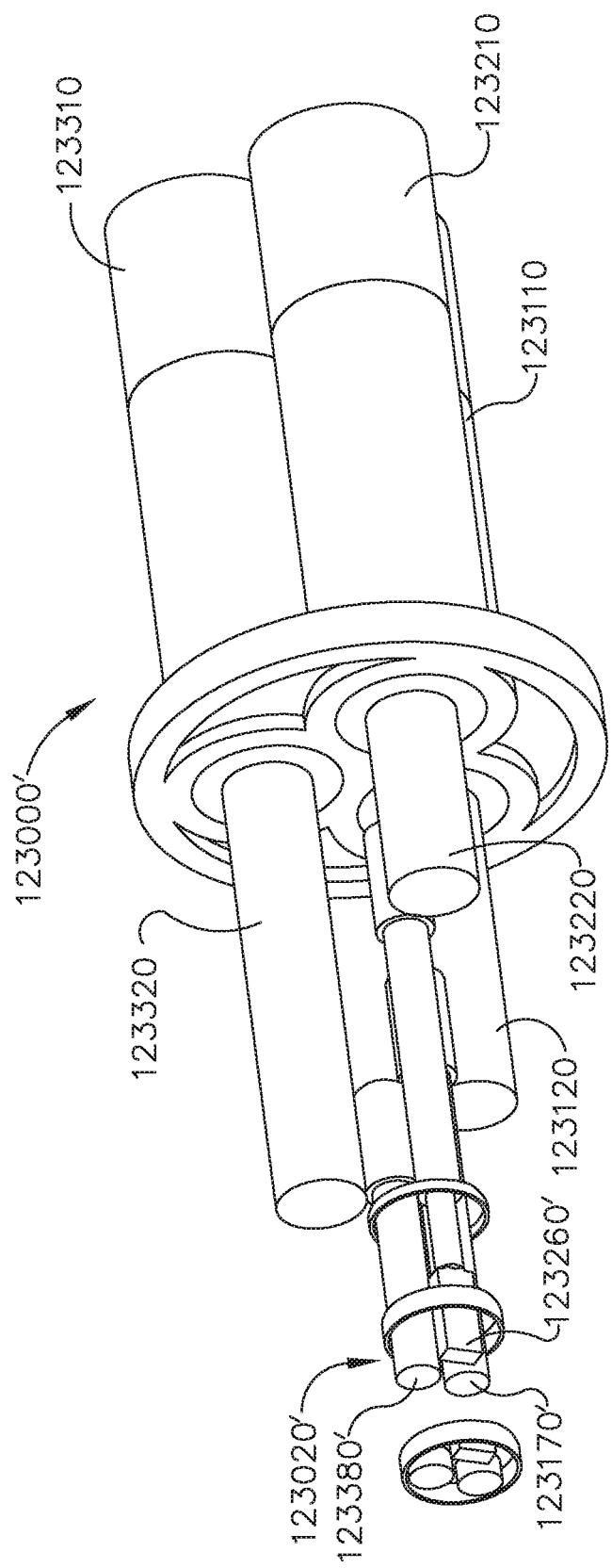
FIG. 103 is a partial perspective view of the surgical instrument of FIG. 100.

A surgical system 123000' is illustrated in FIGS. 100 and 103. The surgical system 123000' is similar to the surgical system 123000 in many respects. For instance, the surgical system 123000' comprises three drive motors, 123110, 123210, and 123310. The first electric drive motor 123110 drives a first drive system of a shaft assembly 123020' including a rotatable output 123170'. The second electric drive motor 123210 drives a second drive system of the shaft assembly 123020' including a translatable output 123260', and the third electric drive motor 123310 drives a third drive system of the shaft assembly 123020' including a rotatable output 123380'. Referring to FIG. 100, the shaft assembly 123020 comprises a housing 123040' and a frame 123030' which rotatably supports the rotatable outputs 123170' and 123380' and slideably supports the translatable output 123260'. Having a translatable output alongside one or more rotatable outputs provides a compact design.

Figure 102:
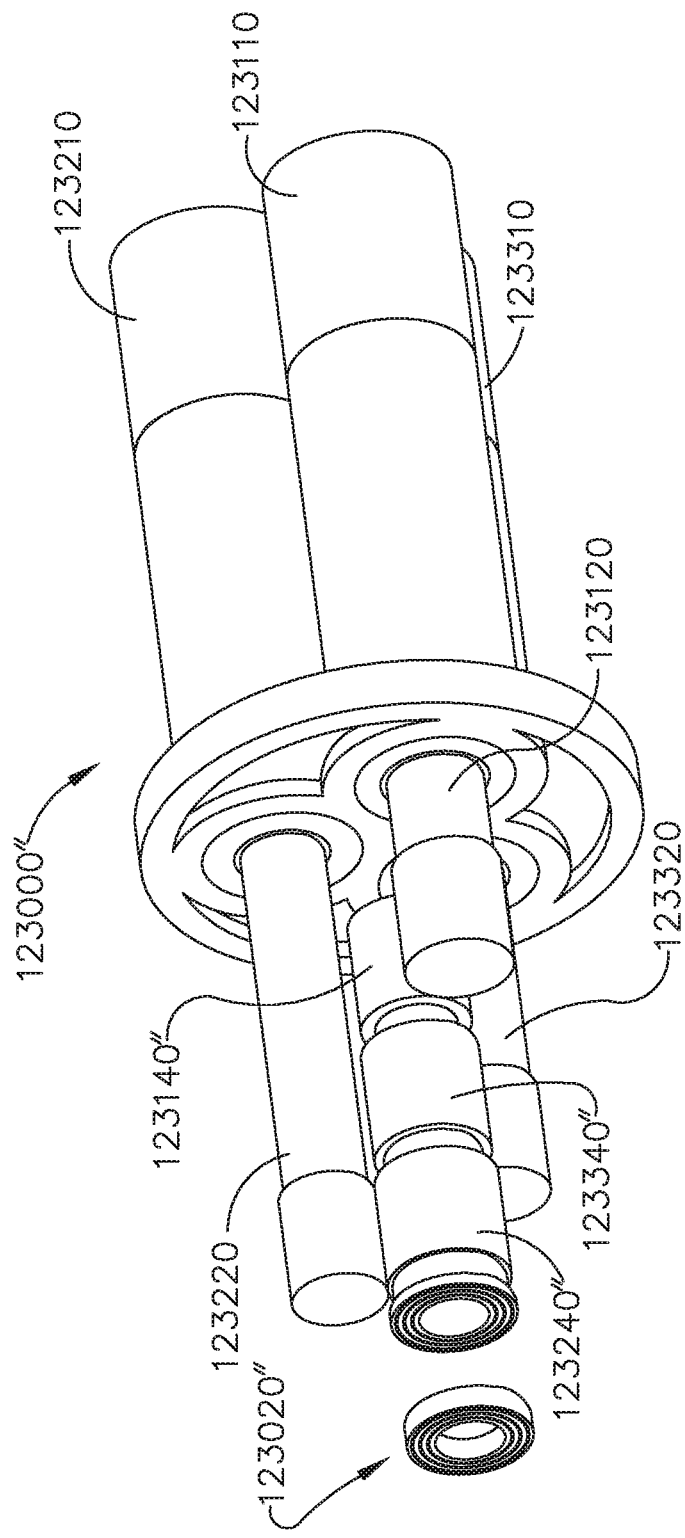
FIG. 102 is a partial perspective view of a drive system in accordance with at least one embodiment illustrated with some components removed.

A surgical system 123000" is illustrated in FIG. 102. The surgical system 123000" is similar to the surgical system 123000 in many respects. For instance, the surgical system 123000" comprises three drive motors, 123110, 123210, and 123310. The first electric drive motor 123110 drives a first drive system of a shaft assembly 123020" including a first rotatable output 123140". The second electric drive motor 123210 drives a second drive system of the shaft assembly 123020" including a second rotatable output 123240", and the third electric drive motor 123310 drives a third drive system of the shaft assembly 123020" including a third rotatable output 123340". The first rotatable outputs 123140", 123240", and 123340" are concentrically nested. Such an arrangement provides a compact design such that the nested outputs provide bearing support to one another.

A surgical system 124200 is illustrated in FIGS. 109 and 110. The surgical system 124200 comprises a handle, a shaft assembly 124200 extending from the handle, and an end effector 124230. The shaft assembly 124220 comprises an input shaft 124210 configured to perform two functions of the surgical system 124200 at the same time. More specifically, the input shaft 124210 is configured to simultaneously drive a clip feeding drive 124240 configured to advance a clip 124290 into the jaws 124232 of the end effector 124230 during a feeding stroke and a crimping drive 124250 configured to deform the clip 124290 during a crimping stroke. The input shaft 124210 comprises a first threaded section 124212 and a second threaded section 124214. The first threaded section 124212 and the second threaded section 124214 have opposite threads, i.e., one has left-hand threads and the other has right-hand threads. Referring to FIG. 109, the clip feeding drive 124240 is threadably engaged with the second threaded section 124214 of the drive shaft 124210 and is advanced distally to perform the clip feeding stroke when the drive shaft 124210 is rotated in a first direction. Referring again to FIG. 109, the clip crimping drive 124250 is threadably engaged with the first threaded section 124212 of the drive shaft 124210 and is retracted proximally when the drive shaft 124210 is rotated in the first direction. Correspondingly, referring to FIG. 110, the clip feeding drive 124240 is retracted proximally and the clip crimping drive 124250 is advanced distally to perform the clip crimping stroke when the drive shaft 124210 is rotated in a second, or opposite, direction. As a result, the clip feeding stroke and the crimping stroke are not performed at the same time; rather, they are performed in an alternating manner. Further to the above, the drive shaft 124210 comprises flanges 124211 and 124213 extending therefrom configured to keep the clip feeding drive 124240 and the clip crimping drive 124250 from becoming decoupled from their respective threaded portions of the drive shaft 124210.

As discussed above, the first threaded section 124212 and the second threaded section 124214 have opposite threads, i.e., one has left-hand threads and the other has right-hand threads, which means that the clip feeding drive and the clip crimping drive move in opposite directions. In various instances, the threads of the first threaded section 124212, or first threads, have a first pitch and the threads of the second threaded section 124214, or second threads, have a second pitch which is the same as the first pitch. Such an arrangement would cause the clip feeding drive and the clip crimping drive to move at the same speed and would be useful when the stroke of the clip feeding drive and the stroke of the clip crimping drive have the same length. Alternatively, the first pitch and the second pitch are different. Such an arrangement would cause the clip feeding drive and the clip crimping drive to move at different speeds and would be useful when the stroke of the clip feeding drive and the stroke of the clip crimping drive have different lengths. Embodiments in which the clip feeding system and the clip crimping system are operated by different drive shafts could be operated at different speeds, operated at different or overlapping times, and/or operated to provide different stroke lengths.

As discussed above, the first threaded section 124212 and the second threaded section 124214 drive different functions of the surgical system 124200. In at least one instance, the first threaded section 124212 can be adapted to perform a first function of a surgical system and the second threaded section 124214 can be adapted to lock out the first function in certain instances.

As discussed above, the drive shaft 124210 is rotatable to translate two different drive members. That said, the drive shaft 124210, itself, is not translatable; however, alternative embodiments are envisioned in which the drive shaft 124210 is both rotatable and translatable. In at least one instance, one of the drives driven by the drive shaft 124210 can be fixed to a frame of the shaft assembly such that the rotation of the drive shaft 124210 displaces the drive shaft 124210 longitudinally. The rotation of the drive shaft 124210 would also drive the second drive system longitudinally at the same time. Such an arrangement can amplify, or double, the drive motion created by the rotation of the drive shaft 124210.

Figure 111A:
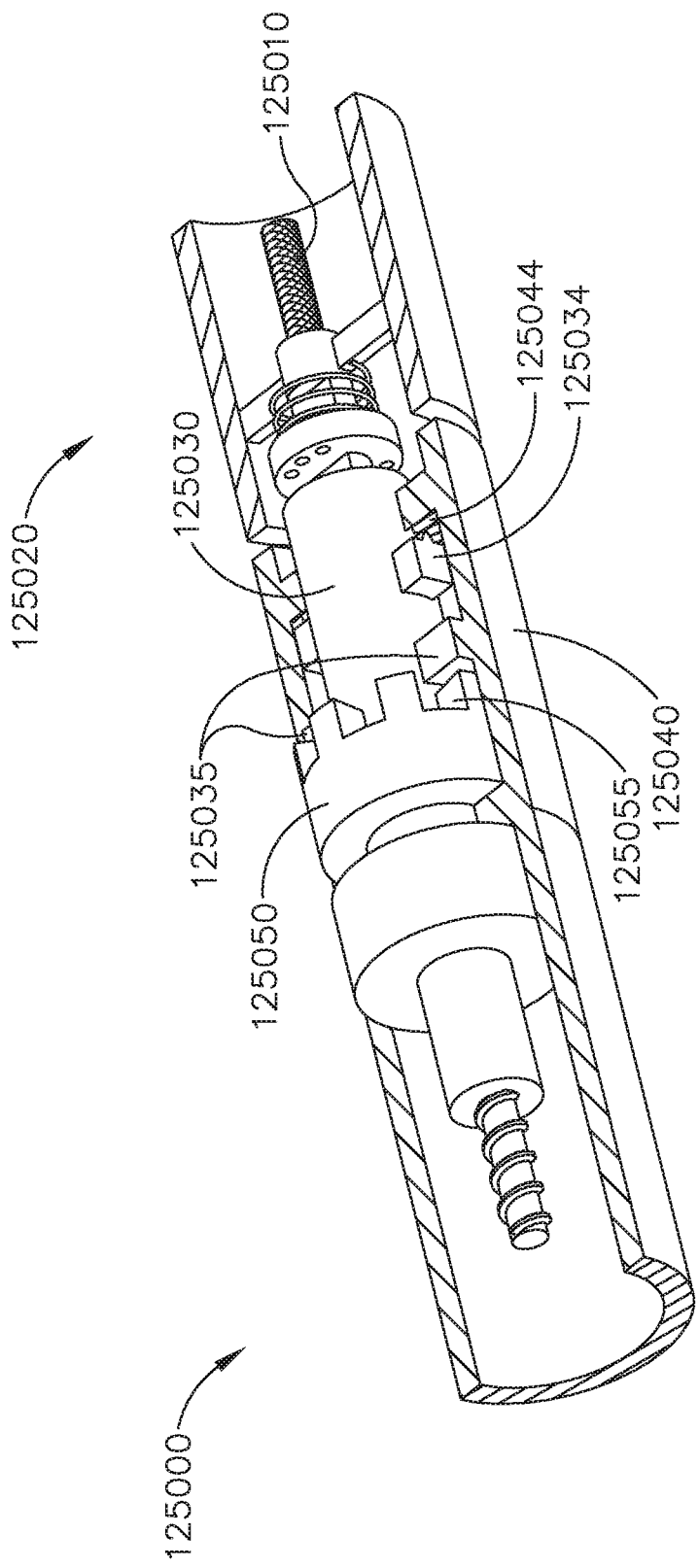
Figure 111B:
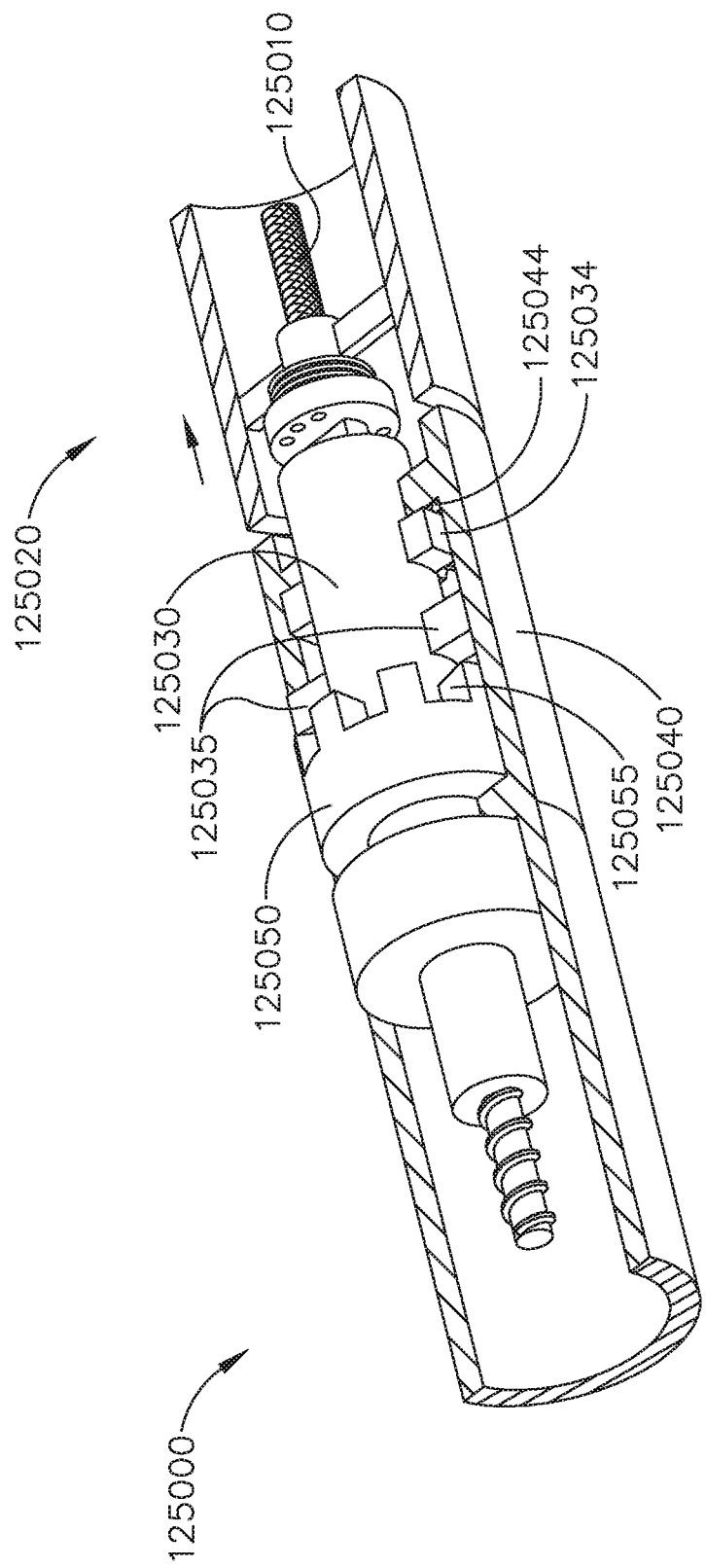
Figure 111C:
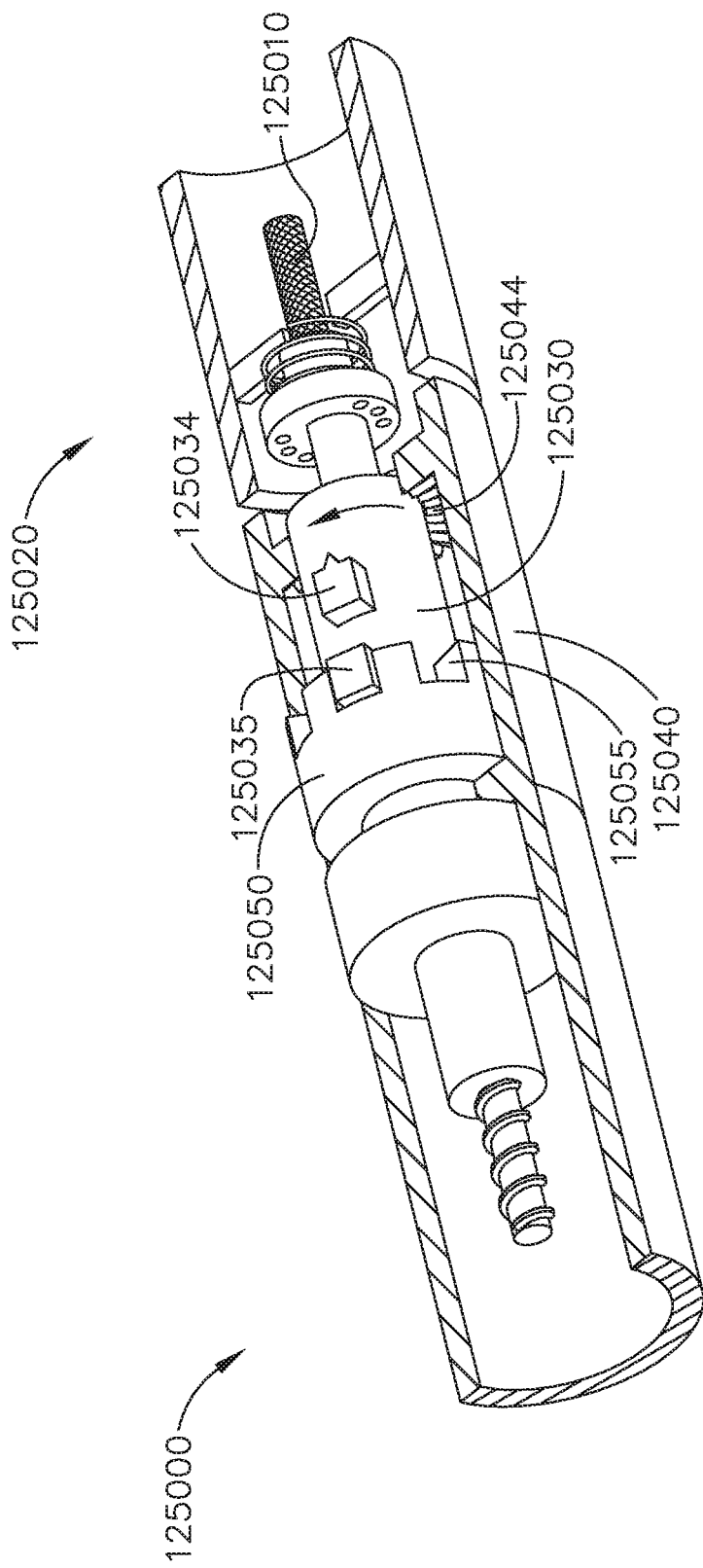

A surgical system 125000 is illustrated in FIGS. 111A-111C. The surgical system 125000 comprises a handle, a shaft assembly 125020 extending from the handle, and an end effector extending from the shaft assembly 125020. The shaft assembly 125020 comprises a rotatable drive shaft 125010 and a drive nut 125030 mounted thereto which is configured to translate longitudinally between a first, or proximal, position and a second, or distal, position to shift the shaft assembly 125020 between a first operating configuration and a second operating configuration. The drive nut 125030 comprises a first set of drive projections 125034 and a second set of drive projections 125035 extending therefrom. When the drive nut 125030 is in its first, or proximal, position, as illustrated in FIG. 111B, the first drive projections 125034 are operably engaged with a first drive gear 125044 mounted to a frame 125040 of the end effector such that the rotation of the drive shaft 125010 is transferred to the frame 125040 and the end effector rotates about a longitudinal axis. When the drive nut 125030 is in its second, or distal, position, as illustrated in FIG. 111C, the second drive projections 125035 are operably engaged with a second drive gear 125055 of a jaw drive system 125050 of the end effector such that the rotation of the drive shaft 125010 opens and closes the jaws of the end effector, depending on the direction in which the drive shaft 125010 is turned. Notably, the first drive gear 125044 and the second drive gear 125055 are spaced apart sufficiently such that the drive nut 125030 is not operably engaged with the end effector rotation drive and the jaw drive at the same time. Moreover, the shaft assembly 125020 further comprises a biasing member, such as a spring, for example, configured to bias the drive nut 125044 into one of the first and second positions such that the drive nut 125044 does not get stuck in an intermediate position. In at least one instance, the shaft assembly 125020 comprises a bi-stable compliant mechanism configured to bias the drive nut 125044 toward the closest position of the first and second positions.

Figure 112:
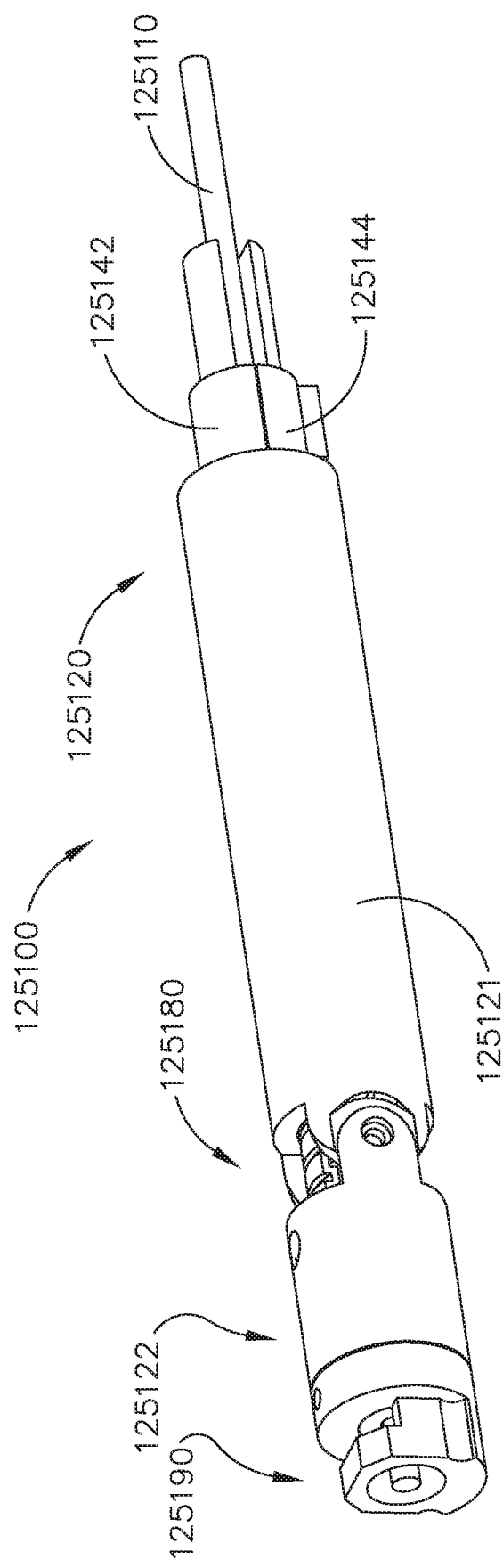

A surgical system 125100 is illustrated in FIG. 112. The surgical system 125100 comprises a handle, a shaft assembly 125120 extending from the handle, and an end effector releasably attachable to the shaft assembly 125120. The shaft assembly 125120 comprises an elongate portion 125121 and a distal portion 125122 rotatably connected to the elongate portion 125121 about an articulation joint 125180. The distal portion 125122 of the shaft assembly 125120 comprises a rotation joint 125190 configured to permit the end effector to rotate relative to the shaft assembly 125120 about a longitudinal axis. The shaft assembly 125120 further comprises a drive shaft 125110 configured to be rotated to rotate the end effector about its longitudinal axis and, also, translated proximally and distally to open and close the jaws of the end effector. The shaft assembly 125120 also comprises push-pull articulation actuators 125412 and 125414 which are moved proximally and distally at the same time, but in different directions, to articulate the distal shaft end 125122 and the end effector about the articulation joint 125180. The articulation actuators 125412 and 125414 are driven longitudinally by a rotatable input drive 125140 threadably engaged with the proximal ends of the articulation actuators 125412 and 125414.

Notably, further to the above, the drive shaft 125110, which extends through the articulation joint 125180, is sufficiently flexible to accommodate the articulation of the end effector. Moreover, the drive shaft 125110 comprises an expansion joint which accommodates the expansion and contraction of the drive shaft 125110 that may occur when the drive shaft 125110 flexes to accommodate the articulation of the end effector. The drive shafts depicted in FIG. 92, for example, can provide such expansion and contraction.

A surgical system 126000 is illustrated in FIGS. 113A and 113B. The surgical system 126000 comprises a handle, a shaft assembly 126020 extending from the handle, and an end effector 126030 releasably attachable to the shaft assembly 126020. The shaft assembly 126020 comprises a frame 126021 and a distal end, wherein the distal end is rotatably connected to the frame 126021 about an articulation joint 126080. The shaft assembly 126020 further comprises a rotatable drive shaft 126040 configured to articulate the distal shaft end—and the end effector 126030 attached thereto—about the articulation joint 126080. When the drive shaft 126040 is rotated in a first direction, the end effector 126030 is articulated in a first direction and, when the drive shaft 126040 is rotated in a second direction, the end effector 126030 is articulated in a second, or opposite, direction. The end effector 126030 comprises a frame 126031 rotatably connected to the distal end of the shaft assembly 126020 about a rotation joint 126090 such that the end effector 126030 can rotate relative to the shaft assembly 126020 about a longitudinal axis. The end effector 126030 further comprises jaws 126032 which are drivable into an open position to dissect the tissue of a patient and/or a closed position to grasp the tissue of a patient, for example. The shaft assembly 126020 comprises a rotatable drive shaft 126010 which, as described in greater detail below, is shiftable between first and second positions to selectively rotate the end effector 126030 about the rotation joint 126090 and to drive the jaws 126032 between their open and closed positions.

Further to the above, the drive shaft 126010 of the shaft assembly 126020 comprises a distal end which is engaged with a drive element 126050 positioned in the end effector 126030 when the end effector 126030 is assembled to the shaft assembly 126020. The drive element 126050 comprises a socket configured to releasably engage the distal end of the drive shaft 126010 such that the drive element 126050 rotates and translates with the drive shaft 126010. The drive shaft 126010 and the drive element 126050 are positionable in a first, or proximal, position in which the drive element 126050 is engaged with a geared face of the end effector frame 126031. In such instances, the end effector 126030 rotates with the drive shaft 126010. More specifically, the end effector 126030 rotates in a first direction when the drive shaft 126010 is rotated in a first direction and in a second, or opposite, direction when the drive shaft 126010 is rotated in a second, or opposite, direction. The drive shaft 126010 and the drive element 126050 are also positionable in a second, or distal, position in which the drive element 126050 is engaged with the jaw drive such that jaws 126032 are moved into their closed position when the drive shaft 126010 is rotated in a first direction and into their open position when the drive shaft 126010 is rotated in a second, or opposite, direction.

Referring to FIG. 113A, the end effector 126030 is releasably attachable to the shaft assembly 126020. To assemble the end effector 126030 to the shaft assembly 126020, referring to FIG. 113B, the end effector 126030 and the shaft assembly 126020 are moved toward one another along a longitudinal axis until the frame 126031 of the end effector 126030 couples to the rotation joint 126090. The rotation joint 126090 comprises flexible locks 126091 which deflect inwardly as the end effector 126030 is being attached to the shaft assembly 126020 and then resiliently deflect outwardly to lock behind lock shoulders defined in the end effector frame 126031. At the same time that the end effector frame 126031 is being coupled to the rotation joint 126090, the drive shaft 126010 is being coupled to the end effector drive element 126050 as described above. The shaft assembly 126020 further comprises lock supports 126092 configured to hold the flexible locks 126091 in their locked configuration to prevent the end effector 126030 from becoming unintentionally decoupled from the shaft assembly 126020. The lock supports 126092 are retractable by the clinician to permit the flexible locks 126091 to deflect and allow the end effector 126030 to be detached from the shaft assembly 126020.

As discussed above, the distal end of the drive shaft 126010 is configured to be releasably engaged with a socket defined in the drive element 126050 such that the drive element 126050 is retained to the drive shaft 126010. This can be accomplished by the interconnection depicted in FIG. 114, for example, discussed below.

Figure 114:
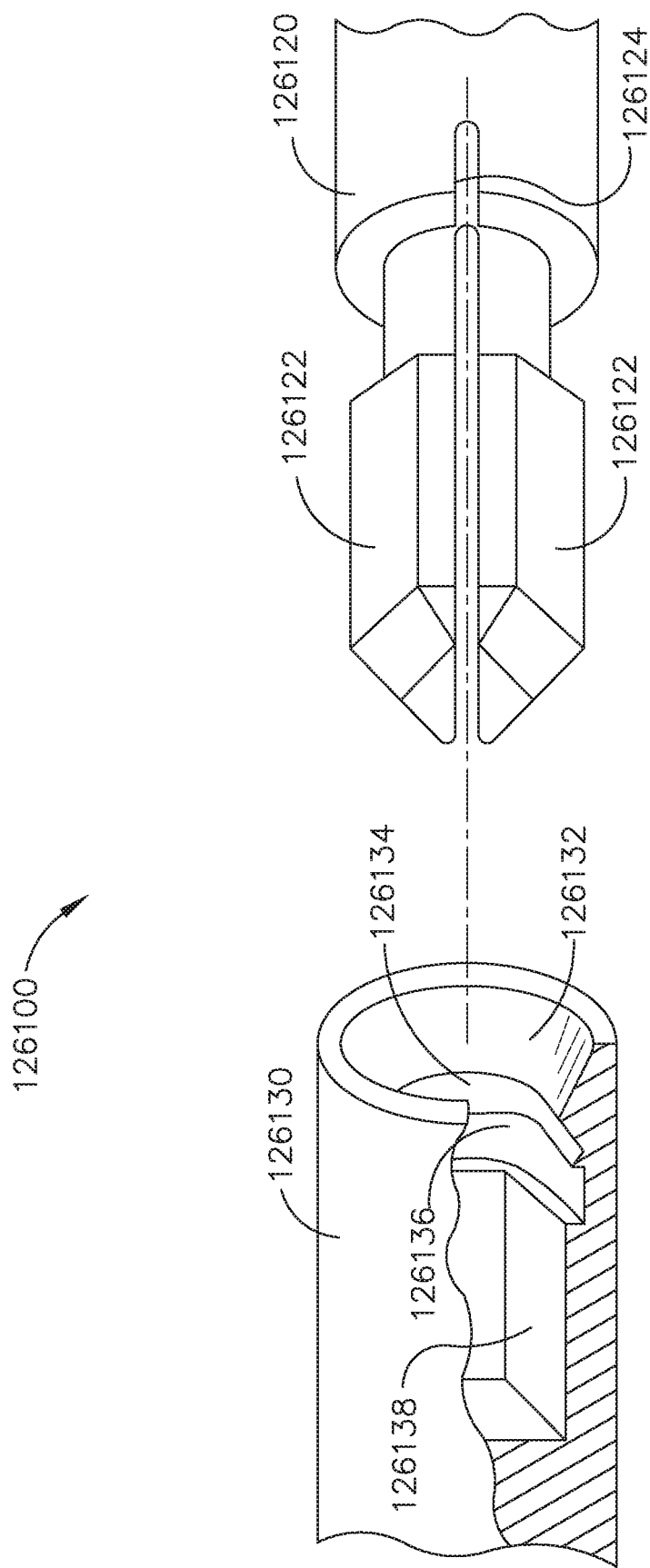

A surgical system 126100 is illustrated in FIG. 114. The surgical system 126100 comprises a handle, a shaft assembly extending from the handle, and an end effector releasably attachable to the shaft assembly. The shaft assembly comprises a rotatable drive shaft 126120 which is engaged with a rotatable drive shaft 126130 of the end effector when the end effector is assembled to the shaft assembly. The distal end of the drive shaft 126020 comprises a hex head configuration, for example, comprising a plurality of flexible lock arms 126122 separated by one or more clearance slots 126124 defined in the drive shaft 126020. The clearance slots 126124 permit the lock arms 126122 to deflect inwardly when the distal end of the drive shaft 126020 is inserted into a hexagonal drive socket, for example, defined in the proximal end of the end effector drive shaft 126130. The drive socket comprises a lead-in, or ramp, 126132 configured to receive the distal end of the drive shaft 126120. In such instances, the lock arms 126122 of the drive shaft 126120 engage the ramp 126132 and deflect inwardly. As the drive shaft 126010 is pushed deeper into the drive socket, the lock arms 126122 clear the apex of the ramp 126132 and resiliently deflect outwardly behind a back ramp 126134. At such point, the lock arms 126122 are substantially constrained by the sidewalls 126138 of the drive socket and the rotation of the drive shaft 16120 is transferable to the end effector drive shaft 126130. The back ramp 126134 inhibits the drive shaft 126120 from becoming decoupled from the end effector shaft 126130; however, the drive shaft 126120 can be detached from the end effector 126130 if a sufficient relative pulling force is applied thereto. In such instances, the lock arms 126122 would deflect inwardly once again to cross over the apex between the ramp 126132 and the back ramp 126134. The drive socket further comprises a slot or groove 126136 configured to provide clearance for the lock arms 126122 to deflect.

Figure 115:
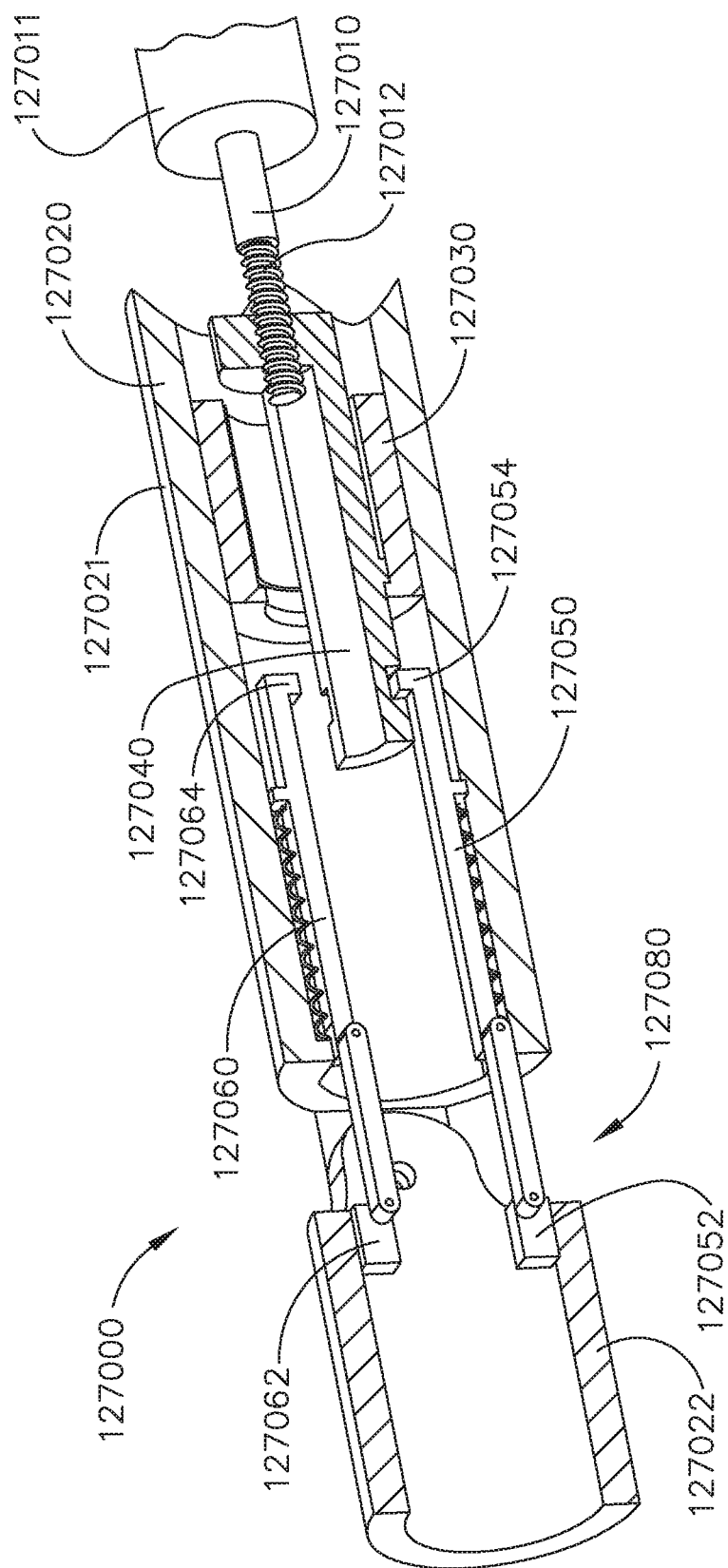
Figure 116:
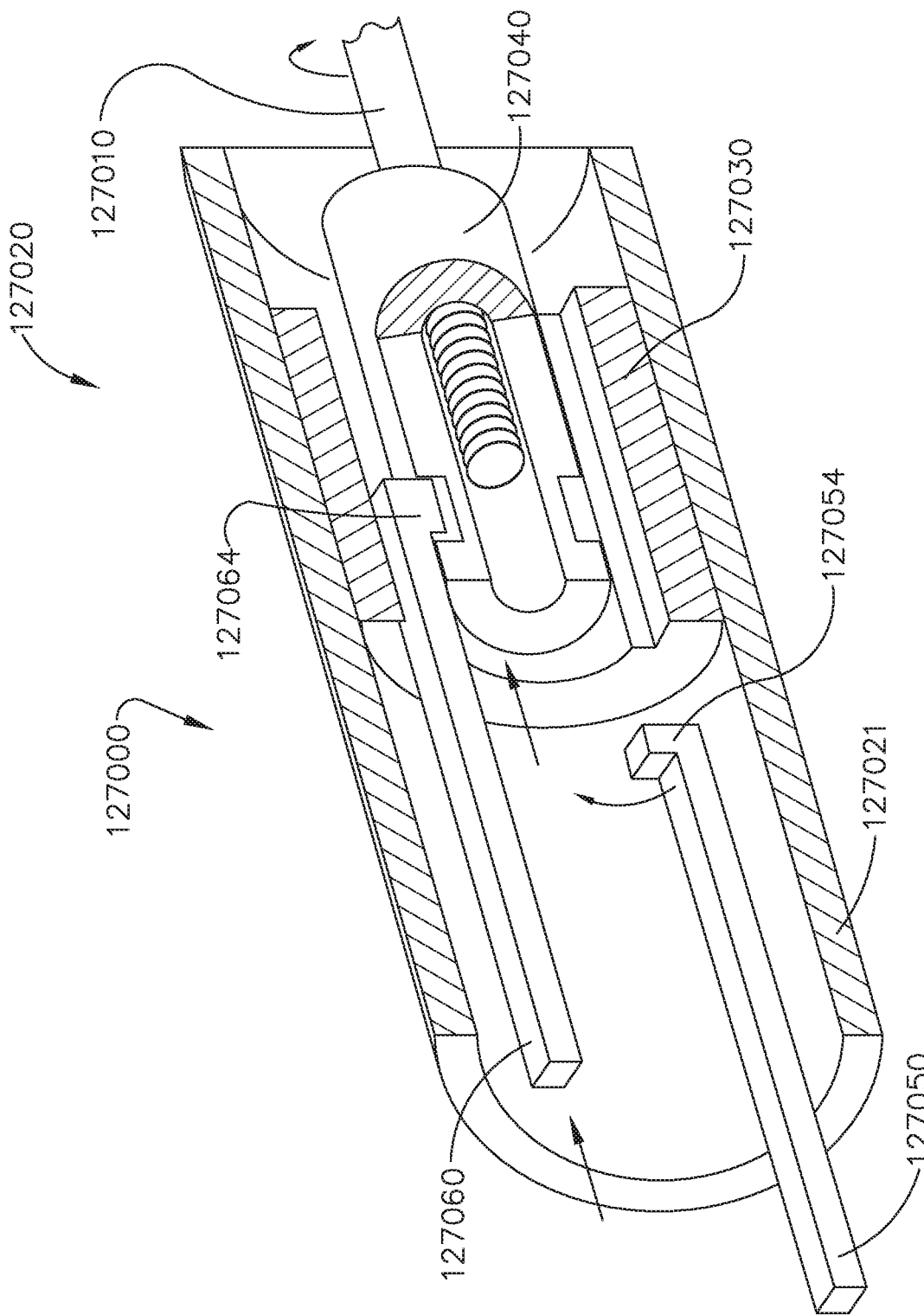
Figure 117:
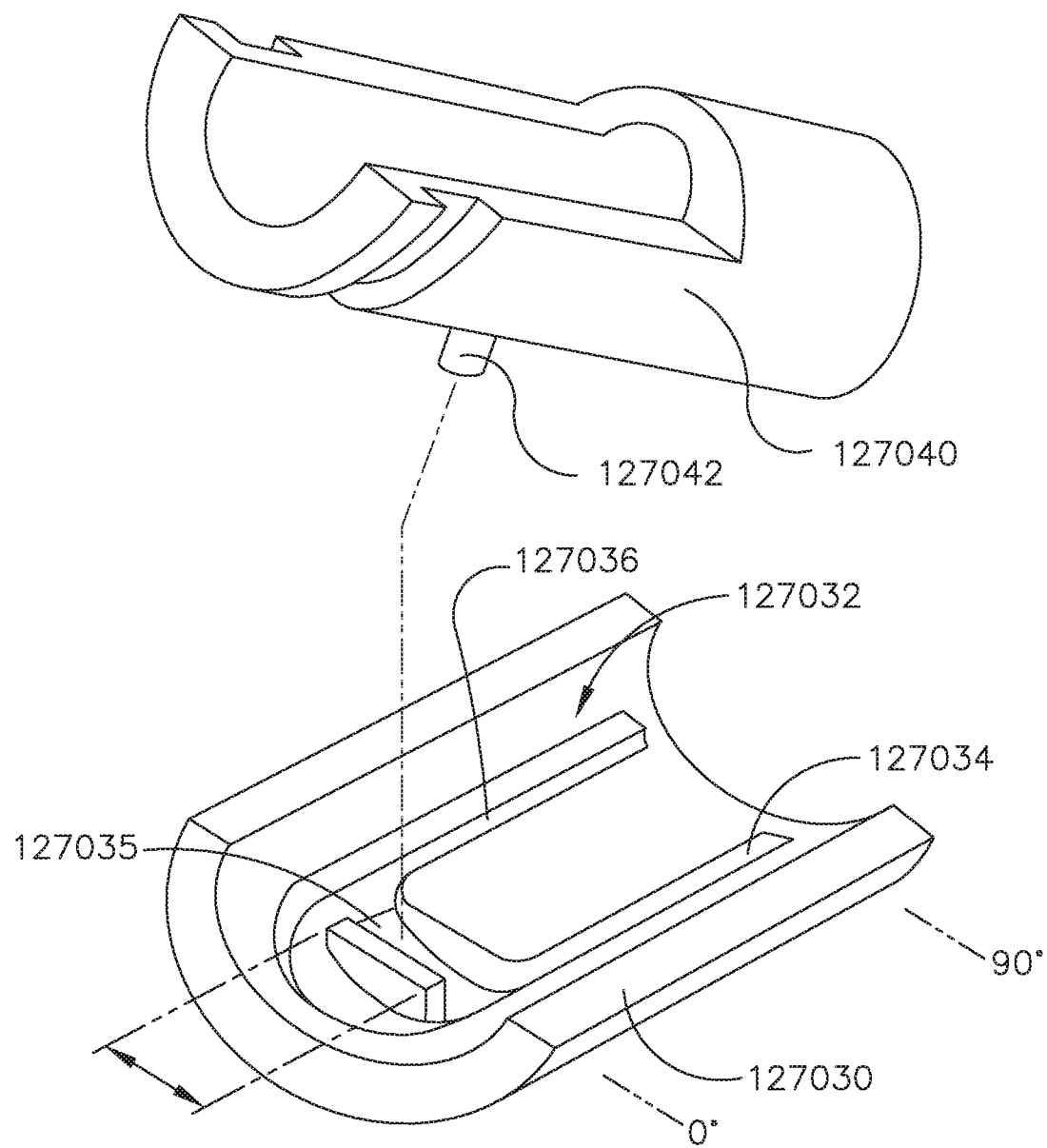

A surgical system 127000 is illustrated in FIGS. 115-117. The surgical system 127000 comprises a handle, a shaft assembly 127020 extending from the handle, and an end effector attachable to the shaft assembly 127020. The shaft assembly 127020 comprises an elongate portion 127021 and a distal end portion 127022 rotatably connected to the elongate portion 127021 about an articulation joint 127080. The shaft assembly 127020 further comprises an articulation drive system 127010 configured to articulate the distal end portion 127022 of the shaft assembly 127020 about the articulation joint 127080. The articulation drive system 127010 comprises an electric drive motor 127011 and a rotatable drive shaft 127012 including a threaded end which is rotated by the drive motor 127011. The threaded end of the drive shaft 127012 is threadably engaged with a shifter 127040 configured to be selectively engaged with a first, or left, articulation bar 127050 and a second, or right, articulation bar 127060 of the articulation drive system 127010. When the shifter 127040 is engaged with the left articulation bar 127050, as illustrated in FIG. 115, the drive shaft 127012 can be rotated to pull the left articulation bar 127050 proximally and articulate the distal end portion 127022, and the end effector attached thereto, to the left. The drive shaft 127012 can be rotated in the opposite direction to return the distal end portion 127022 back to its unarticulated position using the left articulation bar 127050. Notably, the shifter 127040 is not operably engaged with the right articulation bar 127060 when the shifter 127040 is operably engaged with the left articulation bar 127050.

Further to the above, the left articulation bar 127050 comprises an inwardly-extending arm 127054 which is grabbed by the shifter 127040 to push and pull the left articulation bar 127050. The left articulation bar 127050 also comprises a distal end coupled to the distal end portion 127022 at a pin joint 127052 configured to transfer the translational motion of the left articulation bar 127050 to the distal end portion 127022 and articulate the end effector. When the shifter 127040 is engaged with the right articulation bar 127060, as illustrated in FIG. 116, the drive shaft 127012 can be rotated to pull the right articulation bar 127060 proximally and articulate the distal end portion 127022 and the end effector to the right. The drive shaft 127012 can be rotated in the opposite direction to return the distal end portion 127022 back to its unarticulated position using the right articulation bar 127060. The right articulation bar 127060 comprises an inwardly-extending arm 127064 which is grabbed by the shifter 127040 to push and pull the right articulation bar 127050. The right articulation bar 127060 also comprises a distal end coupled to the distal end portion 127022 at a pin joint 127052 configured to transfer the translational motion of the right articulation bar 127060 to the distal end portion 127022 to articulate the end effector. Notably, the shifter 127040 is not operably engaged with the left articulation bar 127050 when the shifter 127040 is operably engaged with the left articulation bar 127060.

Referring primarily to FIG. 117, the shaft assembly 127020 comprises a shift block 127030 fixedly mounted to the elongate portion 127021 of the shaft assembly 127020. The shift block 127030 is configured to confine the motion of the shifter 127040 such that the shifter 127040 moves longitudinally to push and pull the left articulation bar 127050 when the shifter 127040 is rotated to the left and push and pull the right articulation bar 127050 when the shifter 127050 is rotated to the right, as described above. The shift block 127030 comprises a guide track 127032 defined therein which defines the motion path for the shifter 127040. The shifter 127040 comprises a projection 127042 extending therefrom which is positioned in the guide track 127032 and is configured to follow the path defined by the guide track 127032. The guide track 127032 comprises a left longitudinal slot 127034, a right longitudinal slot 127036, and a central slot 127035 extending between and connecting the left longitudinal slot 127034 and the right longitudinal slot 127036. When the shifter 127040 is rotated to the left, the projection 127042 is positioned in the left longitudinal slot 127034 which constrains the shifter 127040 from rotating and limits the motion of the shifter 127040 to longitudinal motion within the left longitudinal slot 127034. When the drive shaft 127012 is rotated in a first direction in such instances, the shifter 127040 moves proximally within the left longitudinal slot 127034 and, when the drive shaft 127012 is rotated in a second, or opposite, direction, the shifter 127040 moves distally within the left longitudinal slot 127034. When the shifter 127040 is rotated to the right, the projection 127042 is positioned in the right longitudinal slot 127036 which constrains the shifter 127040 from rotating and limits the motion of the shifter 127040 to longitudinal motion within the right longitudinal slot 127036. When the drive shaft 127012 is rotated in a first direction in such instances, the shifter 127040 moves proximally within the right longitudinal slot 127036 and, when the drive shaft 127012 is rotated in a second, or opposite, direction, the shifter 127040 moves distally within the right longitudinal slot 127036. The central slot 127035 permits the shifter 127040 to be rotated by the drive shaft 127012 between the left and right longitudinal slots 127034 and 127036 as mentioned above.

Figure 118:
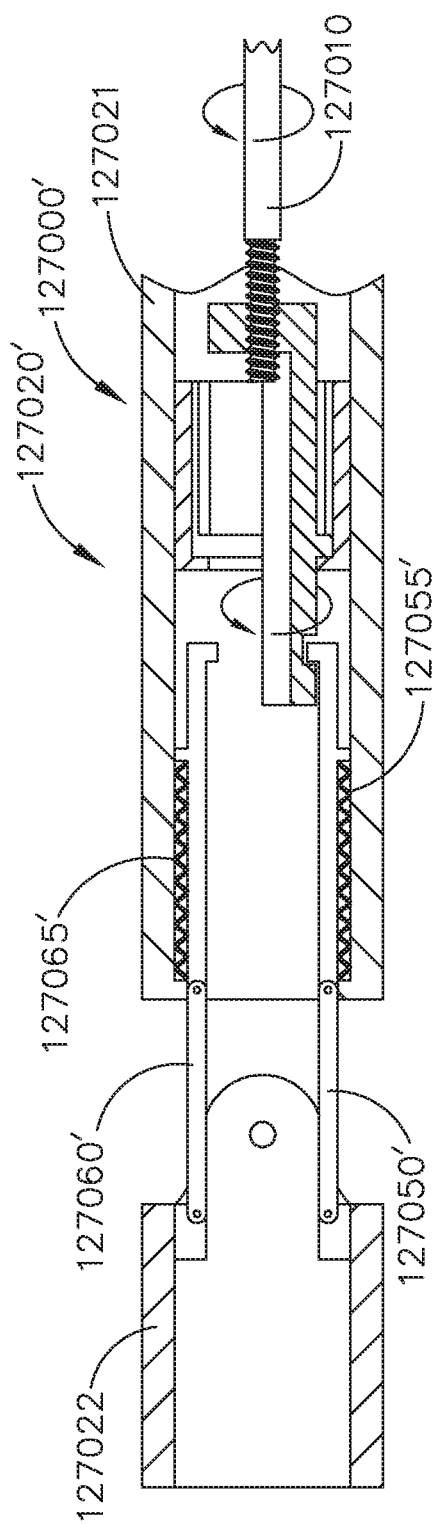
Figure 119:
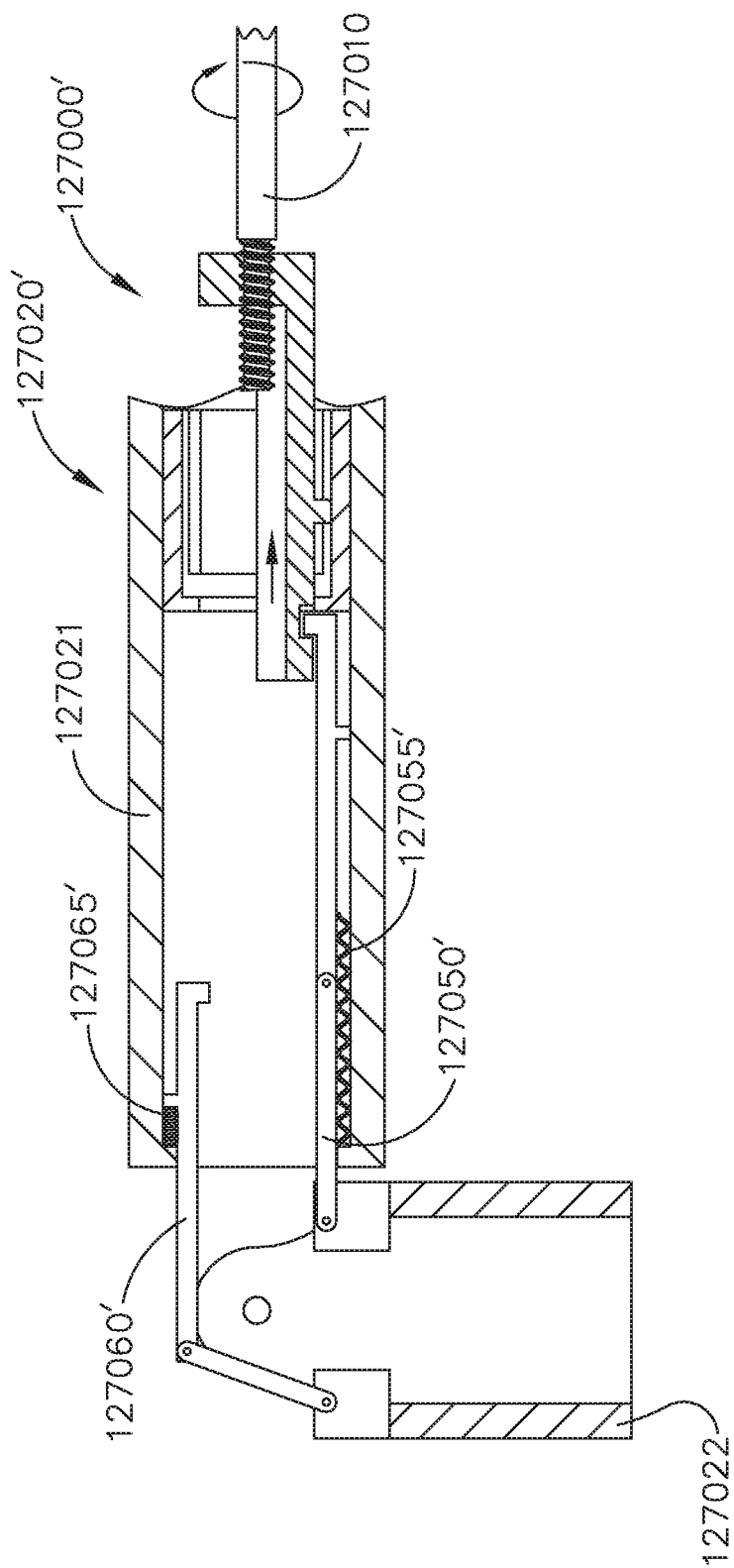

A shaft assembly 127020' of a surgical system 127000' is illustrated in FIGS. 118 and 119 and is similar to the shaft assembly 127020 in many respects. That said, the shaft assembly 127020' further comprises a left articulation bar 127050' that comprises two portions connected by a pivot. Similarly, the shaft assembly 127020' comprises a right articulation bar 127060' that also comprises two portions connected by a pivot. Such articulation bars can permit larger articulations, such as 90 degrees to the left and right, for example, of the distal end portion 127022 and the end effector attached thereto. The shaft assembly 127020' further comprises a left biasing member 127055' configured to apply a biasing force to the left articulation bar 127050' and a right biasing member 127065' configured to apply a biasing force to the right articulation bar 127050' which co-operate to bias the distal end portion 127022, and the end effector attached thereto, to an unarticulated position, as illustrated in FIG. 118.

A surgical system 127100 is illustrated in FIG. 120. The surgical system 127100 comprises a handle, a shaft assembly 127120 extending from the handle, and an end effector releasably attachable to the shaft assembly 127120. The shaft assembly 127120 includes a distal end portion 127122 rotatable about an articulation joint 127180. The end effector is releasably attachable to the distal end portion 127122 such that the end effector articulates with the distal end portion 127122. The shaft assembly 127120 further comprises a first, or left, articulation actuator 127150 configured to pull the distal end portion 127122 to the left and a second, or right, articulation actuator 127160 configured to pull the distal end portion 127122 to the right. The left articulation actuator 127150 and the right articulation actuator 127160 are flexible to accommodate the articulation of the distal end portion 127122. In various instances, such an arrangement can accommodate approximately 60 degrees of articulation to the left and approximately 60 degrees of articulation to the right.

A surgical system 127200 is illustrated in FIG. 121. The surgical system 127200 comprises a handle, a shaft assembly 127220 extending from the handle, and an end effector releasably attachable to the shaft assembly 127220. The shaft assembly 127220 includes a distal end portion 127222 rotatable about an articulation joint. The end effector is releasably attachable to the distal end portion 127222 such that the end effector articulates with the distal end portion 127222. The shaft assembly 127220 further comprises a first, or left, articulation actuator 127250 configured to pull the distal end portion 127222 to the left and a second, or right, articulation actuator 127260 configured to pull the distal end portion 127222 to the right. The left articulation actuator 127250 comprises a first link 127251 and a second link 127253 rotatably connected at a pin joint 127252. The second link 127253 is flexible, or at least more flexible than the first link 127251. To this end, the second link 127253 comprises notches 127254 defined therein to make the second link 127253 flexible. Similarly, the right articulation actuator 127260 comprises a first link 127261 and a second link 127263 rotatably connected at a pin joint 127262. The second link 127263 is flexible, or at least more flexible than the first link 127261. To this end, the second link 127263 comprises notches 127264 defined therein to make the second link 127263 flexible. In various instances, such an arrangement can accommodate approximately 90 degrees of articulation to the left and approximately 90 degrees of articulation to the right.

A surgical system 127300 is illustrated in FIG. 122. The surgical system 127300 comprises a handle, a shaft assembly 127320 extending from the handle, and an end effector releasably attachable to the shaft assembly 127320. The shaft assembly 127320 includes a distal end portion 127322 rotatable about an articulation joint. The end effector is releasably attachable to the distal end portion 127322 such that the end effector articulates with the distal end portion 127322. The shaft assembly 127320 further comprises a first, or left, articulation actuator 127350 configured to pull the distal end portion 127322 to the left, but it does not comprise a second, or right, articulation actuator configured to pull the distal end portion 127322 to the right. The left articulation actuator 127350 is flexible to accommodate the articulation of the distal end portion 127322. In various instances, such an arrangement can provide more articulation in the left direction than the right direction.

A surgical system 128000 is illustrated in FIG. 123. The surgical system 128000 comprises a handle, a shaft 128020 extending from the handle, and an end effector 128030 extending from the shaft 128020. In alternative embodiments, the surgical system 128000 comprises a housing configured to be mounted to a robotic surgical system. In at least one such embodiment, the shaft 128020 extends from the robotic housing mount instead of the handle. In either event, the end effector 128030 comprises jaws 128040 and 128050 which are closeable to grasp a target, such as the tissue T of a patient and/or a suture needle, for example, as discussed in greater detail below. The jaws 128040 and 128050 are also openable to dissect the tissue of a patient, for example. In at least one instance, the jaws 128040 and 128050 are insertable into the patient tissue to create an otomy therein and then spread to open the otomy, as discussed in greater detail below.

Referring again to FIG. 123, the jaws 128040 and 128050 are pivotably coupled to the shaft 128020 about a pivot joint 128060. The pivot joint 128060 defines a fixed axis of rotation, although any suitable arrangement could be used. The jaw 128040 comprises a distal end, or tip, 128041 and an elongate profile which narrows from its proximal end to its distal end 128041. Similarly, the jaw 128050 comprises a distal end, or tip, 128051 and an elongate profile which narrows from its proximal end to its distal end 128051. The distance between the tips 128041 and 128051 define the mouth width, or opening, 128032 of the end effector 128030. When the tips 128041 and 128051 are close to one another, or in contact with one another, the mouth 128032 is small, or closed, and the mouth angle θ is small, or zero. When the tips 128041 and 128051 are far apart, the mouth 128032 is large and the mouth angle θ is large.

Further to the above, the jaws of the end effector 128030 are driven by a jaw drive system including an electric motor. In use, a voltage potential is applied to the electric motor to rotate the drive shaft of the electric motor and drive the jaw drive system. The surgical system 128000 comprises a motor control system configured to apply the voltage potential to the electric motor. In at least one instance, the motor control system is configured to apply a constant DC voltage potential to the electric motor. In such instances, the electric motor will run at a constant speed, or an at least substantially constant speed. In various instances, the motor control system comprises a pulse width modulation (PWM) circuit and/or a frequency modulation (FM) circuit which can apply voltage pulses to the electric motor. The PWM and/or FM circuits can control the speed of the electric motor by controlling the frequency of the voltage pulses supplied to the electric motor, the duration of the voltage pulses supplied to the electric motor, and/or the duration between the voltage pulses supplied to the electric motor.

The motor control system is also configured to monitor the current drawn by the electric motor as a means for monitoring the force being applied by the jaws of the end effector 128030. When the current being drawn by the electric motor is low, the loading force on the jaws is low. Correspondingly, the loading force on the jaws is high when the current being drawn by the electric motor is high. In various instances, the voltage being applied to the electric motor is fixed, or held constant, and the motor current is permitted to fluctuate as a function of the force loading at the jaws. In certain instances, the motor control system is configured to limit the current drawn by the electric motor to limit the force that can be applied by the jaws. In at least one embodiment, the motor control system can include a current regulation circuit that holds constant, or at least substantially constant, the current drawn by the electric motor to maintain a constant loading force at the jaws.

The force generated between the jaws of the end effector 128030, and/or on the jaws of the end effector 128030, may be different depending on the task that the jaws are being used to perform. For instance, the force needed to hold a suture needle may be high as suture needles are typically small and it is possible that a suture needle may slip during use. As such, the jaws of the end effector 128030 are often used to generate large forces when the jaws are close together. On the other hand, the jaws of the end effector 128030 are often used to apply smaller forces when the jaws are positioned further apart to perform larger, or gross, tissue manipulation, for example.

Referring to the upper portion 128110 of the graph 128100 illustrated in FIG. 124, the loading force, f, experienced by the jaws of the end effector 128030 can be limited by a force profile stored in the motor control system. The force limit profile 128110*o* for opening the jaws 128040 and 128050 is different than the force limit profile 128110*c* for closing the jaws 128040 and 128050. This is because the procedures performed when forcing the jaws 128040 and 128050 open are typically different than the procedures performed when forcing the jaws 128040 and 128050 closed. That said, the opening and closing force limit profiles could be the same. While it is likely that the jaws 128040 and 128050 will experience some force loading regardless of whether the jaws 128050 are being opened or closed, the force limit profiles typically come into play when the jaws 128040 and 128050 are being used to perform a particular procedure within the patient. For instance, the jaws 128040 and 128050 are forced open to create and expand an otomy in the tissue of a patient, as represented by graph sections 128115 and 128116, respectively, of graph 128100, while the jaws 128040 and 128050 are forced closed to grasp a needle and/or the patient tissue, as represented by graph sections 128111 and 128112, respectively, of graph 128100.

Referring again to FIG. 124, the opening and closing jaw force limit profiles 128110*o* and 128110*c*, respectively, are depicted on the opposite sides of a zero force line depicted in the graph 128100. As can be seen in the upper section 128110 of graph 128100, the jaw force limit threshold is higher—for both force limit profiles 128110*o* and 128110*c*—when the jaws 128040 and 128050 are just being opened from their fully-closed position. As can also be seen in the upper section 128110 of graph 128100, the jaw force limit threshold is lower—for both force limit profiles 128110*o* and 128110*c*—when the jaws 128040 and 128050 are reaching their fully-opened position. Such an arrangement can reduce the possibility of the jaws 128040 and 128050 damaging adjacent tissue when the being fully opened, for example. In any event, the force that the jaws 128040 and 128050 are allowed to apply is a function of the mouth opening size between the jaws and/or the direction in which the jaws are being moved. For instance, when the jaws 128040 and 128050 are opened widely, or at their maximum, to grasp large objects, referring to graph section 128114 of upper graph section 128110, the jaw force f limit is very low as compared to when the jaws 128040 and 128050 are more closed to perform gross tissue manipulation, referring to graph section 128113 of upper graph section 128110. Moreover, different jaw force limit profiles can be used for different jaw configurations. For instance, Maryland dissectors, which have narrow and pointy jaws, may have a different jaw force limit profile than a grasper having blunt jaws, for example.

In addition to or in lieu of the above, the speed of the jaws 128040 and 128050 can be controlled and/or limited by the motor control system as a function of the mouth opening size between the jaws 128040 and 128050 and/or the direction the jaws are being moved. Referring to the middle portion 128120 and lower portion 128130 of the graph 128100 in FIG. 124, the rate limit profile for moving the jaws 128040 and 128050 permits the jaws to be moved slowly when the jaws are near their closed position and moved quickly when the jaws are near their open position. In such instances, the jaws 128040 and 128050 are accelerated as the jaws are opened. Such an arrangement can provide fine control over the jaws 128040 and 128050 when they are close together to facilitate the fine dissection of tissue, for example. Notably, the rate limit profile for opening and closing the jaws 128040 and 128050 is the same, but they could be different in other embodiments. In alternative embodiments, the rate limit profile for moving the jaws 128040 and 128050 permits the jaws to be moved quickly when the jaws are near their closed position and slowly when the jaws are near their open position. In such instances, the jaws 128040 and 128050 are decelerated as the jaws are opened. Such an arrangement can provide fine control over the jaws 128040 and 128050 when the jaws are being used to stretch an otomy, for example. The above being said, the speed of the jaws 128040 and 128050 can be adjusted once the jaws experience loading resistance from the patient tissue, for example. In at least one such instance, the jaw opening rate and/or the jaw closing rate can be reduced once the jaws 128040 and 128050 begin to experience force resistance above a threshold, for example.

In various instances, further to the above, the handle of the surgical system 128000 comprises an actuator, the motion of which tracks, or is supposed to track, the motion of the jaws 128040 and 128050 of the end effector 128030. For instance, the actuator can comprise a scissors-grip configuration which is openable and closable to mimic the opening and closing of the end effector jaws 128040 and 128050. The control system of the surgical system 128000 can comprise one or more sensor systems configured to monitor the state of the end effector jaws 128040 and 128050 and the state of the handle actuator and, if there is a discrepancy between the two states, the control system can take a corrective action once the discrepancy exceeds a threshold and/or threshold range. In at least one instance, the control system can provide feedback, such as audio, tactile, and/or haptic feedback, for example, to the clinician that the discrepancy exists and/or provide the degree of discrepancy to the clinician. In such instances, the clinician can make mental compensations for this discrepancy. In addition to or in lieu of the above, the control system can adapt its control program of the jaws 128040 and 128050 to match the motion of the actuator. In at least one instance, the control system can monitor the loading force being applied to the jaws and align the closed position of the actuator with the position of the jaws when the jaws experience the peak force loading condition when grasping tissue. Similarly, the control system can align the open position of the actuator with the position of the jaws when the jaws experience the minimum force loading condition when grasping tissue. In various instances, the control system is configured to provide the clinician with a control to override these adjustments and allow the clinician to use their own discretion in using the surgical system 128000 in an appropriate manner.

A surgical system 128700 is illustrated in FIGS. 125 and 126. The surgical system 128700 comprises a handle, a shaft assembly 128720 extending from the handle, and an end effector 128730 extending from the shaft assembly 128720. In alternative embodiments, the surgical system 128700 comprises a housing configured to be mounted to a robotic surgical system. In at least one such embodiment, the shaft 128720 extends from the robotic housing mount instead of the handle. In either event, the end effector 128730 comprises shears configured to transect the tissue of a patient. The shears comprise two jaws 128740 and 128750 configured to transect the patient tissue positioned between the jaws 128740 and 128750 as the jaws 128740 and 128750 are being closed. Each of the jaws 128740 and 128750 comprises a sharp edge configured to cut the tissue and is pivotably mounted to the shaft 128720 about a pivot joint 128760. Such an arrangement can comprise bypassing scissors shears. Other embodiments are envisioned in which one of the jaws 128740 and 128750 comprises a knife edge and the other comprises a mandrel against the tissue is supported and transected. Such an arrangement can comprise a knife wedge in which the knife wedge is moved toward the mandrel. In at least one embodiment, the jaw comprising the knife edge is movable and the jaw comprising the mandrel is stationary. The above being said, embodiments are envisioned in which the tissue-engaging edges of one or both of the jaws 128740 and 128750 are not necessarily sharp.

As discussed above, the end effector 128730 comprises two scissor jaws 128740 and 128750 movable between an open position and a closed position to cut the tissue of a patient. The jaw 128740 comprises a sharp distal end 128741 and the jaw 128750 comprises a sharp distal end 128751 which are configured to snip the tissue of the patient at the mouth 128731 of the end effector 128730, for example. That said, other embodiments are envisioned in which the distal ends 128741 and 128751 are blunt and can be used to dissect tissue, for example. In any event, the jaws are driven by a jaw drive system including an electric drive motor, the speed of which is adjustable to adjust the closure rate and/or opening rate of the jaws. Referring to the graph 128400 of FIG. 127, the control system of the surgical system is configured to monitor the loading, or shear, force on the jaws 128740 and 128750 as the jaws 128740 and 128750 are being closed and adaptively slow down the drive motor when large forces, or forces above a threshold Fc, are experienced by the jaws 128740 and 128750. Such large forces often occur when the tissue T being cut by the jaws 128740 and 128750 is thick, for example. Similar to the above, the control system can monitor the current drawn by the drive motor as a proxy for the loading force being experienced by the jaws 128740 and 128750. In addition to or in lieu of this approach, the control system can be configured to measure the jaw loading force directly by one or more load cells and/or strain gauges, for example. Once the loading force experienced by the jaws 128740 and 128750 drops below the force threshold Fc, the control system can adaptively speed up the jaw closure rate. Alternatively, the control system can maintain the lower closure rate of the jaws 128740 and 128750 even though the force threshold is no longer being exceeded.

The above-provided discussion with respect to the surgical system 128700 can provide mechanical energy or a mechanical cutting force to the tissue of a patient. That said, the surgical system 128700 is also configured to provide electrosurgical energy or an electrosurgical cutting force to the tissue of a patient. In various instances, the electrosurgical energy comprises RF energy, for example; however, electrosurgical energy could be supplied to the patient tissue at any suitable frequency. In addition to or in lieu of AC power, the surgical system 128700 can be configured to supply DC power to the patient tissue. The surgical system 128700 comprises a generator in electrical communication with one or more electrical pathways defined in the instrument shaft 128720 which can supply electrical power to the jaws 128740 and 128750 and also provide a return path for the current. In at least one instance, the jaw 128740 comprises an electrode 128742 in electrical communication with a first electrical pathway in the shaft 128720 and the jaw 128750 comprises an electrode 128752 in electrical communication with a second electrical pathway in the shaft 128720. The first and second electrical pathways are electrically insulated, or at least substantially insulated, from one another and the surrounding shaft structure such that the first and second electrical pathways, the electrodes 128742 and 128752, and the tissue positioned between the electrodes 128742 and 128752 forms a circuit. Such an arrangement provides a bipolar arrangement between the electrodes 128742 and 128752. That said, embodiments are envisioned in which a monopolar arrangement could be used. In such an arrangement, the return path for the current goes through the patient and into a return electrode positioned on or under the patient, for example.

As discussed above, the tissue of a patient can be cut by using a mechanical force and/or an electrical force. Such mechanical and electrical forces can be applied simultaneously and/or sequentially. For instance, both forces can be applied at the beginning of a tissue cutting actuation and then the mechanical force can be discontinued in favor of the electrosurgical force finishing the tissue cutting actuation. Such an approach can apply an energy-created hemostatic seal to the tissue after the mechanical cutting has been completed. In such arrangements, the electrosurgical force is applied throughout the duration of the tissue cutting actuation. In other instances, the mechanical cutting force, without the electrosurgical cutting force, can be used to start a tissue cutting actuation which is then followed by the electrosurgical cutting force after the mechanical cutting force has been stopped. In such arrangements, the mechanical and electrosurgical forces are not overlapping or co-extensive. In various instances, both the mechanical and electrosurgical forces are overlapping and co-extensive throughout the entire tissue cutting actuation. In at least one instance, both forces are overlapping and co-extensive throughout the entire tissue cutting actuation but in magnitudes or intensities that change during the tissue cutting actuation. The above being said, any suitable combination, pattern, and/or sequence of mechanical and electrosurgical cutting forces and energies could be used.

Further to the above, the surgical system 128700 comprises a control system configured to co-ordinate the application of the mechanical force and electrosurgical energy to the patient tissue. In various instances, the control system is in communication with the motor controller which drives the jaws 128740 and 128750 and, also, the electrical generator and comprises one or more sensing systems for monitoring the mechanical force and electrosurgical energy being applied to the tissue. Systems for monitoring the forces within a mechanical drive system are disclosed elsewhere herein. Systems for monitoring the electrosurgical energy being applied to the patient tissue include monitoring the impedance, or changes in the impedance, of the patient tissue via the electrical pathways of the electrosurgical circuit. In at least one instance, referring to the graph 128800 in FIG. 128, the RF current/voltage ratio of the electrosurgical power being applied to the patient tissue by the generator is evaluated by monitoring the current and voltage of the power being supplied by the generator. The impedance of the tissue and the RF current/voltage ratio of the electrosurgical power are a function of many variables such as the temperature of the tissue, the density of the tissue, the thickness of the tissue, the type of tissue between the jaws 128740 and 128750, the duration in which the power is applied to the tissue, among others, which change throughout the application of the electrosurgical energy.

Further to the above, the control system and/or generator of the surgical system 128700 comprises one or more ammeter circuits and/or voltmeter circuits configured to monitor the electrosurgical current and/or voltage, respectively, being applied to the patient tissue. Referring again to FIG. 128, a minimum amplitude limit and/or a maximum amplitude limit on the current being applied to the patient tissue can be preset in the control system and/or can be controllable by the user of the surgical instrument system through one or more input controls. The minimum and maximum amplitude limits can define a current envelope within which the electrosurgical portion of the surgical system 128700 is operated.

In various instances, the control system of the surgical system 128700 is configured to adaptively increase the electrosurgical energy applied to the patient tissue when the drive motor slows. The motor slowing can be a reaction to an increase in the tissue cutting load and/or an adaptation of the control system. Similarly, the control system of the surgical system 128700 is configured to adaptively increase the electrosurgical energy applied to the patient tissue when the drive motor stops. Again, the motor stopping can be a reaction to an increase in the tissue cutting load and/or an adaptation of the control system. Increasing the electrosurgical energy when the electric motor slows and/or stops can compensate for a reduction in mechanical cutting energy. In alternative embodiments, the electrosurgical energy can be reduced and/or stopped when the electric motor slows and/or stops. Such embodiments can afford the clinician to evaluate the situation in a low-energy environment.

In various instances, the control system of the surgical system 128700 is configured to adaptively decrease the electrosurgical energy applied to the patient tissue when the drive motor speeds up. The motor speeding up can be a reaction to a decrease in the cutting load and/or an adaptation of the control system. Decreasing the electrosurgical energy when the electric motor slows and/or stops can compensate for, or balance out, an increase in mechanical cutting energy. In alternative embodiments, the electrosurgical energy can be increased when the electric motor speeds up. Such embodiments can accelerate the closure of the jaws and provide a clean, quick cutting motion.

In various instances, the control system of the surgical system 128700 is configured to adaptively increase the speed of the drive motor when the electrosurgical energy applied to the patient tissue decreases. The electrosurgical energy decreasing can be a reaction to a change in tissue properties and/or an adaptation of the control system. Similarly, the control system of the surgical system 128700 is configured to adaptively increase the speed of the drive motor when electrosurgical energy applied to the patient tissue stops in response to an adaptation of the control system. Increasing the speed of the drive motor when the electrosurgical energy decreases or is stopped can compensate for a reduction in electrosurgical cutting energy. In alternative embodiments, the speed of the drive motor can be reduced and/or stopped when the electrosurgical energy decreases and/or is stopped. Such embodiments can afford the clinician to evaluate the situation in a low-energy and/or static environment.

In various instances, the control system of the surgical system 128700 is configured to adaptively decrease the speed of the electric motor when the electrosurgical energy applied to the patient tissue increases. The electrosurgical energy increasing can be a reaction to a change in tissue properties and/or an adaptation of the control system. Decreasing the drive motor speed when the electrosurgical energy increases can compensate for, or balance out, an increase in electrosurgical cutting energy. In alternative embodiments, the drive motor speed can be increased when the electrosurgical energy increases. Such embodiments can accelerate the closure of the jaws and provide a clean, quick cutting motion.

In various instances, the surgical system 128700 comprises controls, such as on the handle of the surgical system 128700, for example, that a clinician can use to control when the mechanical and/or electrosurgical forces are applied. In addition to or in lieu of manual controls, the control system of the surgical system 128700 is configured to monitor the mechanical force and electrical energy being applied to the tissue and adjust one or the other, if needed, to cut the tissue in a desirable manner according to one or more predetermined force-energy curves and/or matrices. In at least one instance, the control system can increase the electrical energy being delivered to the tissue once the mechanical force being applied reaches a threshold limit. Moreover, the control system is configured to consider other parameters, such as the impedance of the tissue being cut, when making adjustments to the mechanical force and/or electrical energy being applied to the tissue.

The surgical instrument systems described herein are motivated by an electric motor; however, the surgical instrument systems described herein can be motivated in any suitable manner. In certain instances, the motors disclosed herein may comprise a portion or portions of a robotically controlled system. U.S. patent application Ser. No. 13/118, 241, entitled SURGICAL STAPLING INSTRUMENTS WITH ROTATABLE STAPLE DEPLOYMENT ARRANGEMENTS, now U.S. Pat. No. 9,072,535, for example, discloses several examples of a robotic surgical instrument system in greater detail, the entire disclosure of which is incorporated by reference herein.

The surgical instrument systems described herein can be used in connection with the deployment and deformation of staples. Various embodiments are envisioned which deploy fasteners other than staples, such as clamps or tacks, for example. Moreover, various embodiments are envisioned which utilize any suitable means for sealing tissue. For instance, an end effector in accordance with various embodiments can comprise electrodes configured to heat and seal the tissue. Also, for instance, an end effector in accordance with certain embodiments can apply vibrational energy to seal the tissue. In addition, various embodiments are envisioned which utilize a suitable cutting means to cut the tissue.

EXAMPLES

Example 1

A surgical instrument comprising a handle, a shaft comprising a longitudinal shaft axis, an end effector comprising a jaw assembly movable between an open configuration and a clamped configuration, and an articulation joint. The articulation joint is distal with respect to the shaft. The articulation joint rotatably connects the end effector to the shaft. The surgical instrument further comprises an articulation drive including a rotatable articulation drive shaft operably engaged with the end effector. The end effector is rotatable about an articulation axis by the articulation drive shaft. The surgical instrument further comprises a jaw drive including a translatable jaw actuation shaft operably engaged with the jaw assembly. The jaw assembly is movable between the open configuration and the clamped configuration by the translatable jaw actuation shaft.

Example 2

The surgical instrument of Example 1, wherein the end effector is selectively attachable to the shaft, wherein the translatable jaw actuation shaft comprises a distal end, and wherein the jaw assembly comprises a translatable member operably couplable with the distal end of the translatable jaw actuation shaft in a snap-fit manner when the end effector is attached to the shaft.

Example 3

The surgical instrument of Example 2, wherein the translatable member comprises a socket, and wherein the distal end comprises arms configured to flex when entering into the socket and resiliently return toward their unflexed configurations once seated in the socket.

Example 4

The surgical instrument of Example 3, wherein the end effector comprises a longitudinal axis, and wherein the distal end is loaded into the socket along the longitudinal axis when the end effector is attached to the shaft.

Example 5

The surgical instrument of Examples 2, 3, or 4, wherein the end effector comprises at least two locks configured to releasably engage the shaft when the end effector is attached to the shaft to hold the end effector to the shaft.

Example 6

A surgical instrument comprising a handle and a shaft assembly extending from the handle. The shaft assembly comprises a drive shaft including a distal connector. The distal connector comprises a drive socket. The surgical instrument further comprises an end effector selectively attachable to the shaft assembly. The end effector comprises a drive element that is inserted into the drive socket to connect the drive element to the drive shaft when the end effector is attached to the shaft assembly. The surgical instrument further comprises a lock movable between an unlocked position and a locked position to lock the drive element in the drive socket.

Example 7

The surgical instrument of Example 6, wherein the drive socket comprises a flexible portion, wherein the lock constrains the flexible portion when the lock is in the locked position, and wherein the lock does not constrain the flexible portion when the lock is in the unlocked position.

Example 8

The surgical instrument of Examples 6 or 7, further comprising a biasing member configured to position the lock in the locked position.

Example 9

The surgical instrument of Examples 6, 7 or 8, wherein the lock must be moved into the unlocked position to detach the end effector from the shaft assembly.

Example 10

The surgical instrument of Examples 6, 7, 8, or 9, wherein the drive shaft comprises a longitudinal shaft axis and the drive socket comprises a lateral opening facing away from the longitudinal shaft axis.

Example 11

A surgical instrument comprising a handle and a shaft assembly extending from the handle. The shaft assembly comprises a drive shaft including a longitudinal axis and a distal connector. The distal connector comprises a drive socket. The drive socket comprises a lateral opening facing away from the longitudinal shaft axis. The surgical instrument further comprises an end effector selectively attachable to the shaft. The end effector comprises a drive element that is inserted into the drive socket to connect the drive element to the drive shaft when the end effector is attached to the shaft assembly. The surgical instrument further comprises a socket opening cover movable between an unlocked position and a locked position to trap the drive element in the drive socket and lock the drive element to the drive shaft.

Example 12

The surgical instrument of Example 11, further comprising a biasing member configured to position the socket opening cover in the locked position.

Example 13

The surgical instrument of Examples 11 or 12, wherein the socket opening cover must be moved into the unlocked position to detach the end effector from the shaft assembly.

Example 14

A surgical instrument comprising a handle and a shaft assembly extending from the handle. The shaft assembly comprises a drive shaft including a distal connector. The surgical instrument further comprises an end effector selectively attachable to the shaft assembly. The end effector comprises a drive element that is inserted into the distal connector to connect the drive element to the drive shaft when the end effector is attached to the shaft assembly. The surgical instrument further comprises a lock movable between an unlocked position and a locked position to lock the drive element in the drive socket. The lock is biased into the locked position such that the end effector is automatically locked to the shaft assembly when the end effector is attached to the shaft assembly.

Example 15

The surgical instrument of Example 14, wherein the shaft assembly extends distally from the handle, wherein the lock is retracted proximally to release the end effector from the shaft assembly.

Example 16

The surgical instrument of Examples 14 or 15, further comprising a biasing member configured to bias the lock into the locked position.

Example 17

The surgical instrument of Example 16, wherein the biasing member comprises a spring.

Example 18

The surgical instrument of Example 16, wherein the biasing member comprises an electrical lock actuator.

Example 19

The surgical instrument of Examples 14, 15, 16, 17, or 18, wherein the shaft assembly comprises a shaft frame, wherein the end effector comprises an end effector frame, and wherein the surgical instrument further comprises a frame lock configured to releasably lock the end effector frame to the shaft frame.

Example 20

A surgical instrument comprising a handle comprising a first electric motor and a second electric motor. The surgical instrument further comprises a shaft assembly extending from the handle. The shaft assembly comprises a rotatable input shaft operably coupled to the first electric motor, a rotatable shifting shaft operably coupled to the second electric motor, a first rotatable drive shaft, and a second rotatable drive shaft. The surgical instrument further comprises an end effector extending from the shaft assembly. The end effector is configured to perform a first end effector function in response to the rotation of the first rotatable drive shaft. The end effector is configured to perform a second end effector function in response to the rotation of the second rotatable drive shaft. The rotatable shifting shaft is rotatable between a first position and a second position. The rotatable input shaft is operably coupled to the first rotatable drive shaft when the rotatable shifting shaft is in the first position. The rotatable input shaft is operably coupled to the second rotatable drive shaft when the rotatable shifting shaft is in the second position.

Example 21

The surgical instrument of Example 20, wherein the end effector comprises a longitudinal axis, a jaw assembly, and a rotation joint. The jaw assembly is movable between an open configuration and a closed configuration. The rotation of the first rotatable drive shaft in a first direction moves the jaw assembly toward the closed configuration. The rotation of the first rotatable drive shaft in a second direction moves the jaw assembly toward the open configuration. The jaw assembly is rotatable about the longitudinal axis by the rotation of the second rotatable drive shaft.

Example 22

The surgical instrument of Examples 20 or 21, wherein the rotatable input shaft is rotatably supported by the rotatable shifting shaft.

Example 23

The surgical instrument of Examples 20, 21, or 22, wherein the shaft assembly comprises a first stop configured to stop the rotation of the rotatable shifting shaft in the first position and a second stop configured to stop the rotation of the rotatable shifting shaft in the second position.

Example 24

The surgical instrument of Examples 20, 21, 22, or 23, wherein the rotatable input shaft and the rotatable shifting shaft are rotatable about a common longitudinal shaft axis.

Example 25

The surgical instrument of Examples 20, 21, 22, 23, or 24, wherein the shaft assembly further comprises a third rotatable drive shaft, wherein the end effector is configured to perform a third end effector function in response to the rotation of the third rotatable drive shaft, and wherein the rotatable shifting shaft is rotatable into a third position to operably couple the rotatable input shaft with the third rotatable drive shaft.

Example 26

The surgical instrument of Examples 20, 21, 22, 23, 24, or 25, further comprising a control system, wherein the first electric motor and the second electric motor are in communication with the control system, and wherein the control system is configured to control the operation of the first electric motor and the second electric motor.

Example 27

The surgical instrument of Example 26, wherein the control system comprises a first input control and a second input control, wherein the control system operates the second electric motor to rotate the rotatable shifting shaft into the first position when the first input control is actuated, and wherein the control system operates the second electric motor to rotate the rotatable shifting shaft into the second position when the second input control is actuated.

Example 28

The surgical instrument of Examples 26 or 27, wherein the control system does not operate the first electric motor while operating the second electric motor.

Example 29

The surgical instrument of Example 27, wherein the control system is configured to operate the first electric motor before the rotatable shifting shaft is placed in the first position and the second position by the second electric motor.

Example 30

A surgical assembly comprising a housing comprising a first electric motor and a second electric motor. The surgical assembly further comprises a shaft assembly extending from the housing. The shaft assembly comprises a rotatable input shaft operably coupled to the first electric motor, a rotatable shifting shaft operably coupled to the second electric motor, a first rotatable drive shaft, and a second rotatable drive shaft. The surgical assembly further comprises an end effector extending from the shaft assembly. The end effector is configured to perform a first end effector function in response to the rotation of the first rotatable drive shaft. The end effector is configured to perform a second end effector function in response to the rotation of the second rotatable drive shaft. The rotatable shifting shaft is rotatable between a first position and a second position. The rotatable input shaft is operably coupled to the first rotatable drive shaft when the rotatable shifting shaft is in the first position. The rotatable input shaft is operably coupled to the second rotatable drive shaft when the rotatable shifting shaft is in the second position.

Example 31

The surgical assembly of Example 30, wherein the end effector comprises a longitudinal axis, a jaw assembly, and a rotation joint. The jaw assembly is movable between an open configuration and a closed configuration. The rotation of the first rotatable drive shaft in a first direction moves the jaw assembly toward the closed configuration. The rotation of the first rotatable drive shaft in a second direction moves the jaw assembly toward the open configuration. The jaw assembly is rotatable about the longitudinal axis by the rotation of the second rotatable drive shaft.

Example 32

The surgical assembly of Examples 30 or 31, wherein the rotatable input shaft is rotatably supported by the rotatable shifting shaft.

Example 33

The surgical assembly of Examples 30, 31, or 32, wherein the shaft assembly comprises a first stop configured to stop the rotation of the rotatable shifting shaft in the first position and a second stop configured to stop the rotation of the rotatable shifting shaft in the second position.

Example 34

The surgical assembly of Examples 30, 31, 32, or 33, wherein the rotatable input shaft and the rotatable shifting shaft are rotatable about a common longitudinal shaft axis.

Example 35

The surgical assembly of Examples 30, 31, 32, 33, or 34, wherein the shaft assembly further comprises a third rotatable drive shaft, wherein the end effector is configured to perform a third end effector function in response to the rotation of the third rotatable drive shaft, and wherein the rotatable shifting shaft is rotatable into a third position to operably couple the rotatable input shaft with the third rotatable drive shaft.

Example 36

The surgical assembly of Examples 30, 31, 32, 33, 34, or 35, further comprising a control system, wherein the first electric motor and the second electric motor are in communication with the control system, and wherein the control system is configured to control the operation of the first electric motor and the second electric motor.

Example 37

The surgical assembly of Example 36, wherein the control system comprises a first input control and a second input control, wherein the control system operates the second electric motor to rotate the rotatable shifting shaft into the first position when first input control is actuated, and wherein the control system operates the second electric motor to rotate the rotatable shifting shaft into the second position when the second input control is actuated.

Example 38

The surgical assembly of Examples 36 or 37, wherein the control system does not operate the first electric motor while operating the second electric motor.

Example 39

The surgical assembly of Examples 36, 37, or 38, wherein the control system is configured to operate the first electric motor before the rotatable shifting shaft is placed in the first position and the second position by the second electric motor.

Example 40

The surgical assembly of Examples 30, 31, 32, 33, 34, 35, 36, 37, 38, or 39, wherein the housing is configured to be mounted to a robotic surgical system.

Example 41

A surgical instrument comprising a handle and a shaft assembly extending from the handle. The handle comprises a first electric motor and a second electric motor. The shaft assembly comprises a rotatable input shaft operably coupled to the first electric motor, a rotatable shifting shaft operably coupled to the second electric motor, a first rotatable drive shaft, and a second rotatable drive shaft. The surgical instrument further comprises an end effector extending from the shaft assembly. The end effector is configured to perform a first end effector function in response to the rotation of the first rotatable drive shaft. The end effector is configured to perform a second end effector function in response to the rotation of the second rotatable drive shaft. The rotatable shifting shaft is rotatable between a first engaged orientation and a second engaged orientation. The rotatable input shaft is operably coupled to the first rotatable drive shaft when the rotatable shifting shaft is in the first engaged orientation. The rotatable input shaft is operably coupled to the second rotatable drive shaft when the rotatable shifting shaft is in the second engaged orientation. The rotatable input shaft is not operably engaged with the first rotatable drive shaft when the rotatable shifting shaft is not in the first orientation. The rotatable input shaft is not operably engaged with the second rotatable drive shaft when the rotatable shifting shaft is not in the second orientation.

Example 42

A surgical instrument comprising a handle, a shaft comprising a longitudinal shaft axis, and a shaft rotation joint configured to permit the shaft to rotate relative to the handle. The shaft is rotatable about the longitudinal shaft axis. The surgical instrument further comprises an end effector comprising a proximal end effector portion and a distal end effector portion. The surgical instrument further comprises an articulation joint. The articulation joint is distal with respect to the shaft rotation joint. The articulation joint rotatably connects the proximal end effector portion to the shaft. The end effector is rotatable about an articulation axis. The surgical instrument further comprises an end effector rotation joint. The end effector rotation joint is distal with respect to the articulation joint. The distal end effector portion is rotatable relative to the proximal end effector portion about the end effector rotation joint.

Example 43

The surgical instrument of Example 42, further comprising a control system configured to rotate the end effector about the end effector rotation joint while the end effector is being rotated about the articulation joint.

Example 44

The surgical instrument of Example 43, wherein the control system comprises a first electric motor configured to rotate the end effector about the end effector rotation joint and a second electric motor configured to rotate the end effector about the articulation joint.

Example 45

A surgical instrument comprising a handle. The handle comprises a shaft rotation electric motor, an articulation drive electric motor, an end effector rotation electric motor, and a jaw drive electric motor. The surgical instrument further comprises a shaft, a shaft rotation joint, an end effector, an articulation joint, and an end effector rotation joint. The shaft comprises a longitudinal shaft axis. The shaft rotation joint is configured to permit the shaft to rotate relative to the handle. The shaft is rotatable about the longitudinal shaft axis by the shaft rotation electric motor. The end effector comprises a proximal end effector portion and a distal end effector portion. The proximal end effector portion comprises a jaw assembly movable between an open configuration and a clamped configuration by the jaw drive electric motor. The articulation joint is distal with respect to the shaft rotation joint. The articulation joint rotatably connects the proximal end effector portion to the shaft. The end effector is rotatable about an articulation axis by the articulation drive motor. The end effector rotation joint is distal with respect to the articulation joint. The distal end effector portion is rotatable relative to the proximal end effector portion about the end effector rotation joint by the end effector rotation motor.

Example 46

The surgical instrument of Example 45, further comprising a control system configured to operate the end effector rotation electric motor to rotate the end effector about the end effector rotation joint while operating the articulation drive electric motor.

Example 47

A surgical instrument comprising a handle, a shaft comprising a longitudinal shaft axis, an end effector comprising a proximal end effector portion and a distal end effector portion, and an articulation joint. The articulation joint is distal with respect to the shaft. The articulation joint rotatably connects the proximal end effector portion to the shaft. The surgical instrument further comprises a rotatable articulation drive shaft, an end effector rotation joint, and a rotatable end effector drive shaft. The end effector is rotatable about an articulation axis by the articulation drive shaft. The end effector rotation joint is distal with respect to the articulation joint. The distal end effector portion is rotatable relative to the proximal end effector portion about the end effector rotation joint by the rotatable end effector drive shaft. The rotatable articulation drive shaft and the rotatable end effector drive shaft are concentric.

Example 48

The surgical instrument of Example 47, wherein the end effector further comprises a jaw assembly movable between an open configuration and a clamped configuration, and wherein the end effector drive shaft is selectively operable to move the jaw assembly between the open configuration and the clamped configuration.

Example 49

The surgical instrument of Example 48, wherein the end effector drive shaft is translatable to move the jaw assembly between the open configuration and the clamped configuration.

Example 50

The surgical instrument of Examples 47, 48, or 49, further comprising a control system configured to rotate the end effector about the end effector rotation joint while the end effector is being rotated about the articulation joint.

Example 51

The surgical instrument of Example 50, wherein the control system comprises a first electric motor configured to rotate the end effector about the end effector rotation joint and a second electric motor configured to rotate the end effector about the articulation joint.

Example 52

A surgical instrument comprising a handle, a shaft comprising a longitudinal shaft axis, a shaft rotation joint configured to permit the shaft to rotate relative to the handle about the longitudinal shaft axis, an end effector comprising a longitudinal end effector axis, an articulation joint rotatably connecting the end effector to the shaft, an end effector rotation joint configured to permit the end effector to rotate relative to the shaft about the longitudinal end effector axis, a first electric motor configured to rotate the shaft about the longitudinal shaft axis, a first actuator configured to receive a first input from the user of the surgical instrument, a second electric motor configured to rotate the end effector about the longitudinal end effector axis, a second actuator configured to receive a second input from the user of the surgical instrument, and a motor control system. The motor control system is configured to rotate the first electric motor in response to the first input, rotate the second electric motor in response to the second input, and rotate the second electric motor in response to the first input to maintain a rotational alignment between the shaft and the end effector.

Example 53

The surgical instrument of Example 52, wherein the motor control system is configured to rotate the first electric motor in response to the second input to maintain a rotational alignment between the shaft and the end effector.

Example 54

The surgical instrument of Examples 52 or 53, wherein the motor control system comprises a control circuit including a microprocessor.

Example 55

A surgical instrument comprising a handle, a shaft comprising a longitudinal shaft axis, a shaft rotation joint configured to permit the shaft to rotate relative to the handle about the longitudinal shaft axis, an end effector comprising a longitudinal end effector axis, an articulation joint rotatably connecting the end effector to the shaft, an end effector rotation joint configured to permit the end effector to rotate relative to the shaft about the longitudinal end effector axis, a first electric motor configured to rotate the shaft about the longitudinal shaft axis, a first actuator configured to receive a first input from the user of the surgical instrument, a second electric motor configured to rotate the end effector about the longitudinal end effector axis, a second actuator configured to receive a second input from the user of the surgical instrument, and a gear assembly configured to synchronize the rotation of the end effector and the shaft.

Example 56

A surgical instrument comprising a handle, a shaft comprising a longitudinal shaft axis, a shaft rotation joint configured to permit the shaft to rotate relative to the handle about the longitudinal shaft axis, an end effector comprising a longitudinal end effector axis, an articulation joint rotatably connecting the end effector to the shaft, an end effector rotation joint configured to permit the end effector to rotate relative to the shaft about the longitudinal end effector axis, a first electric motor configured to rotate the shaft about the longitudinal shaft axis, a first actuator configured to receive a first input from the user of the surgical instrument, a second electric motor configured to rotate the end effector about the longitudinal end effector axis, a second actuator configured to receive a second input from the user of the surgical instrument, and a motor control system configured to synchronize the rotation of the end effector and the shaft.

Example 57

A surgical assembly comprising a housing, a shaft comprising a longitudinal shaft axis, a shaft rotation joint configured to permit the shaft to rotate relative to the housing about the longitudinal shaft axis, an end effector comprising a longitudinal end effector axis, an articulation joint rotatably connecting the end effector to the shaft, an end effector rotation joint configured to permit the end effector to rotate relative to the shaft about the longitudinal end effector axis, a first electric motor configured to rotate the shaft about the longitudinal shaft axis, a first actuator configured to receive a first input from the user of the surgical assembly, a second electric motor configured to rotate the end effector about the longitudinal end effector axis, a second actuator configured to receive a second input from the user of the surgical instrument, and a motor control system. The motor control system is configured to rotate the first electric motor in response to the first input, rotate the second electric motor in response to the second input, and rotate the second electric motor in response to the first input to maintain a rotational alignment between the shaft and the end effector.

Example 58

The surgical assembly of Example 57, wherein the housing is configured to be mounted to a robotic surgical system.

Example 59

A surgical instrument comprising a shaft, an end effector extending from the shaft, an input shaft, a first output shaft configured to drive a first function of the surgical instrument, a second output shaft configured to drive a second function of the surgical instrument, and a clutch. The clutch is configured to selectively couple the input shaft with the first output shaft when the clutch is in a first configuration and the second output shaft when the clutch is in a second configuration. The clutch comprises a bi-stable compliant mechanism configured to assure that the clutch is always in one of the first configuration and the second configuration.

Example 60

The surgical instrument of Example 59, wherein the clutch comprises a translatable clutch element slideable between a proximal position in the first configuration and a distal position in the second configuration.

Example 61

The surgical instrument of Example 60, wherein the bi-stable compliant mechanism comprises at least one spring configured to position the translatable clutch element in the proximal position and the distal position.

Example 62

The surgical instrument of Examples 60 or 61, wherein the translatable clutch element is movable proximally and distally by a linear clutch drive.

Example 63

The surgical instrument of Examples 59, 60, 61, or 62, further comprising a lock configured to releasably hold the clutch in the first configuration.

Example 64

The surgical instrument of Examples 59, 60, 61, or 62, further comprising a lock configured to releasably hold the clutch in the second configuration.

Example 65

A surgical instrument comprising a shaft, an end effector extending from the shaft, an input shaft, a first output shaft configured to drive a first function of the surgical instrument, a second output shaft configured to drive a second function of the surgical instrument, and a clutch. The clutch is configured to selectively couple the input shaft with the first output shaft when the clutch is in a first configuration and the second output shaft when the clutch is in a second configuration. The clutch comprises a biasing member configured to assure that the clutch is always in one of the first configuration and the second configuration.

Example 66

The surgical instrument of Example 65, wherein the clutch comprises a translatable clutch element slideable between a proximal position in the first configuration and a distal position in the second configuration.

Example 67

The surgical instrument of Example 66, wherein the biasing member comprises at least one spring configured to position the translatable clutch element in the proximal position and the distal position.

Example 68

The surgical instrument of Examples 66 or 67, wherein the translatable clutch element is movable proximally and distally by a linear clutch drive.

Example 69

The surgical instrument of Examples 65, 66, 67, or 68, further comprising a lock configured to releasably hold the clutch in the first configuration.

Example 70

The surgical instrument of Examples 65, 66, 67, or 68, further comprising a lock configured to releasably hold the clutch in the second configuration.

Example 71

A surgical instrument comprising a shaft, an end effector extending from the shaft, an input shaft, a first output shaft configured to drive a first function of the surgical instrument, a second output shaft configured to drive a second function of the surgical instrument, and a clutch. The clutch is configured to selectively couple the input shaft with the first output shaft when the clutch is in a first configuration and the second output shaft when the clutch is in a second configuration. The clutch comprises a biasing member configured to bias the clutch into the first configuration unless the clutch is in the second configuration.

Example 72

The surgical instrument of Example 71, wherein the clutch comprises a translatable clutch element slideable between a proximal position in the first configuration and a distal position in the second configuration.

Example 73

The surgical instrument of Example 72, wherein the biasing member comprises at least one spring configured to position the translatable clutch element in the proximal position and the distal position.

Example 74

The surgical instrument of Examples 72 or 73, wherein the translatable clutch element is movable proximally and distally by a linear clutch drive.

Example 75

The surgical instrument of Examples 71, 72, 73, or 74, further comprising a lock configured to releasably hold the clutch in the first configuration.

Example 76

The surgical instrument of Examples 71, 72, 73, or 74, further comprising a lock configured to releasably hold the clutch in the second configuration.

Example 77

A surgical instrument comprising a shaft, an end effector extending from the shaft, an input shaft, and a plurality of output shafts. Each output shaft is configured to drive an end effector function. The surgical instrument further comprises a clutch configurable in a plurality of clutch positions. The clutch selectively couples the input shaft with an output shaft in each clutch position. The clutch comprises a biasing member configured to bias the clutch into the closest clutch position when the clutch is not positioned in a clutch position.

Example 78

A surgical instrument comprising a handle, a shaft comprising a longitudinal shaft axis, and a shaft rotation joint configured to permit the shaft to rotate relative to the handle. The shaft is rotatable about the longitudinal shaft axis. The surgical instrument further comprises an end effector comprising a proximal end effector portion and a distal end effector portion. The surgical instrument further comprises an articulation joint. The articulation joint is distal with respect to the shaft rotation joint. The articulation joint rotatably connects the proximal end effector portion to the shaft. The end effector is rotatable about an articulation axis. The surgical instrument further comprises an end effector rotation joint. The end effector rotation joint is distal with respect to the articulation joint. The distal end effector portion is rotatable relative to the proximal end effector portion about the end effector rotation joint. The surgical instrument further comprises an articulation drive. The articulation drive comprises a first articulation driver configured to drive the end effector when the articulation drive is in a first state. The articulation drive further comprises a second articulation driver configured to drive the end effector when the articulation drive is in a second state. The first articulation driver is not operably engaged with the end effector when the articulation drive is in the second state. The second articulation driver is not operably engaged with the end effector when the articulation drive is in the first state.

Example 79

The surgical instrument of Example 78, wherein the first articulation driver and the second articulation driver extend through the articulation joint but do not extend through the end effector rotation joint.

Example 80

The surgical instrument of Examples 78 or 79, wherein the shaft has a first portion having a first diameter and a second portion having a second diameter smaller than the first diameter, and wherein the first articulation driver and the second articulation driver extend through the second portion of the shaft.

Example 81

A surgical instrument comprising a handle, a shaft extending from the handle, an end effector extending from the shaft, and an articulation joint. The articulation joint rotatably connects the end effector to the shaft about an articulation axis. The surgical instrument further comprises an articulation drive comprising an articulation actuator, a first articulation driver configured to drive the end effector when the articulation drive is in a first state, and a second articulation driver configured to drive the end effector when the articulation drive is in a second state. The first articulation driver is operably engaged with the articulation actuator when the articulation drive is in the first state. The second articulation driver is not operably engaged with the articulation actuator when the articulation drive is in the first state. The second articulation driver is operably engaged with the articulation actuator when the articulation drive is in the second state. The first articulation driver is not operably engaged with the articulation actuator when the articulation drive is in the second state.

Example 82

The surgical instrument of Example 81, wherein the first articulation driver and the second articulation driver extend through the articulation joint.

Example 83

The surgical instrument of Examples 81 or 82, wherein the shaft has a first portion having a first diameter and a second portion having a second diameter smaller than the first diameter, and wherein the first articulation driver and the second articulation driver extend through the second portion of the shaft.

Example 84

A surgical instrument comprising a handle, a shaft, an end effector, an articulation joint, and an articulation drive. The end effector is rotatable relative to the shaft about the articulation joint. The articulation drive comprises a first articulation driver configured to drive the end effector when the articulation drive is in a first state, and a second articulation driver configured to drive the end effector when the articulation drive is in a second state. The first articulation driver is not operably engaged with the end effector when the articulation drive is in the second state. The second articulation driver is not operably engaged with the end effector when the articulation drive is in the first state.

Example 85

The surgical instrument of Example 84, wherein the articulation drive further comprises an articulation drive shaft and a drive coupler, wherein the drive coupler is rotatable between a first position and a second position, wherein the drive coupler operably couples the first articulation driver to the articulation drive shaft when the drive coupler is in the first position, and wherein the drive coupler operably couples the second articulation driver to the articulation drive shaft when the drive coupler is in the second position.

Example 86

The surgical instrument of Examples 84 or 85, wherein the end effector is rotatable within a range of positions including a first fully-articulated position, an unarticulated position, and a second fully-articulated position, wherein the first articulation driver is configured to move the end effector within a first range including the first fully-articulated position and the unarticulated position, and wherein the second articulation driver is configured to move the end effector within a second range including the second fully-articulated position and the unarticulated position.

Example 87

The surgical instrument of Example 86, wherein the first fully-articulated position is not in the second range, and wherein the second fully-articulated position is not in the first range.

Example 88

The surgical instrument of Examples 84, 85, 86, or 87, wherein the shaft has a first portion having a first diameter and a second portion having a second diameter smaller than the first diameter, and wherein the first articulation driver and the second articulation driver extend through the second portion of the shaft.

Example 89

A surgical instrument comprising a handle, a shaft, an end effector, an articulation joint, and an articulation drive. The end effector is rotatable relative to the shaft about the articulation joint. The articulation drive comprises a first articulation driver configured to drive the end effector when the articulation drive is in a first state, and a second articulation driver configured to drive the end effector when the articulation drive is in a second state. The articulation drive further comprises an articulation drive shaft and a drive coupler. The drive coupler is rotatable between a first position in the first state and a second position in the second state. The drive coupler operably couples the first articulation driver to the articulation drive shaft when the drive coupler is in the first position. The drive coupler operably couples the second articulation driver to the articulation drive shaft when the drive coupler is in the second position.

Example 90

The surgical instrument Example 89, wherein the second articulation driver is uncoupled from the drive coupler when the drive coupler is in the first position, and wherein the first articulation driver is uncoupled from the drive coupler when the drive coupler is in the second position.

Example 91

The surgical instrument of Examples 89 or 90, wherein the end effector is rotatable within a range of positions including a first fully-articulated position, an unarticulated position, and a second fully-articulated position, wherein the first articulation driver is configured to move the end effector within a first range including the first fully-articulated position and the unarticulated position, and wherein the second articulation driver is configured to move the end effector within a second range including the second fully-articulated position and the unarticulated position.

Example 92

The surgical instrument of Example 91, wherein the first fully-articulated position is not in the second range, and wherein the second fully-articulated position is not in the first range.

Example 93

The surgical instrument of Examples 89, 90, 91, or 92, wherein the shaft has a first portion having a first diameter and a second portion having a second diameter smaller than the first diameter, and wherein the first articulation driver and the second articulation driver extend through the second portion of the shaft.

Example 94

A surgical instrument comprising a handle, a shaft, an end effector, an articulation joint, and an articulation drive. The end effector is rotatable relative to the shaft about the articulation joint. The articulation drive comprises a first articulation driver configured to drive the end effector when the articulation drive is in a first state, and a second articulation driver configured to drive the end effector when the articulation drive is in a second state. The end effector is rotatable within a range of positions including a first fully-articulated position, an unarticulated position, and a second fully-articulated position. The first articulation driver is configured to move the end effector within a first range including the first fully-articulated position and the unarticulated position. The second articulation driver is configured to move the end effector within a second range including the second fully-articulated position and the unarticulated position.

Example 95

The surgical instrument of Example 94, wherein the first fully-articulated position is not in the second range, and wherein the second fully-articulated position is not in the first range.

Example 96

The surgical instrument of Examples 94 or 95, wherein the shaft has a first portion having a first diameter and a second portion having a second diameter smaller than the first diameter, and wherein the first articulation driver and the second articulation driver extend through the second portion of the shaft.

Example 97

A surgical instrument comprising a handle, a shaft comprising a longitudinal shaft axis, an end effector comprising a proximal end effector portion and a distal end effector portion, and an articulation joint. The articulation joint is distal with respect to the shaft. The articulation joint rotatably connects the proximal end effector portion to the shaft. The surgical instrument further comprises a rotatable articulation drive shaft. The end effector is rotatable about an articulation axis by the articulation drive shaft. The surgical instrument further comprises an end effector rotation joint. The end effector rotation joint is distal with respect to the articulation joint. The surgical instrument further comprises a rotatable end effector drive shaft. The distal end effector portion is rotatable relative to the proximal end effector portion about the end effector rotation joint by the rotatable end effector drive shaft. The rotatable end effector drive shaft extends through the rotatable articulation drive shaft.

Example 98

The surgical instrument of Example 97, wherein the end effector further comprises a jaw assembly movable between an open configuration and a clamped configuration, and wherein the end effector drive shaft is selectively operable to move the jaw assembly between the open configuration and the clamped configuration.

Example 99

The surgical instrument of Example 98, wherein the end effector drive shaft is translatable to move the jaw assembly between the open configuration and the clamped configuration.

Example 100

A surgical instrument comprising a shaft, an end effector extending from the shaft, an input shaft configured to transmit an input motion, a first output shaft configured to drive a first function of the surgical instrument, a second output shaft configured to drive a second function of the surgical instrument, and a transmission configured to simultaneously drive the first output shaft in a first direction and the second output shaft in a second direction in response to the input motion from the input shaft.

Example 101

The surgical instrument of Example 100, wherein the first output shaft and the second output shaft are configured to translate in response to the input motion.

Example 102

The surgical instrument of Examples 100 or 101, wherein the first output shaft translates further than the second output shaft in response to the input motion.

Example 103

The surgical instrument of Examples 100, 101, or 102, wherein the transmission comprises a first thread and a second thread defined on the input shaft, wherein the first output shaft is threadably engaged with the first thread and the second output shaft is threadably engaged with the second thread, and wherein the first thread and the second thread are different.

Example 104

The surgical instrument of Example 103, wherein the first thread comprises a left-hand thread and the second thread comprises a right-hand thread.

Example 105

The surgical instrument of Examples 100, 101, 102, 103, or 104, wherein the first function comprises unlocking an end effector motion and the second function comprises moving the end effector through the end effector motion.

Example 106

The surgical instrument of Examples 100, 101, 102, 103, or 104, wherein the first function comprises moving the end effector through an end effector motion and the second function comprises locking the end effector to prevent the end effector from performing the end effector motion.

Example 107

The surgical instrument of Examples 100, 101, 102, 103, or 104, wherein the first function comprises moving the end effector between an open configuration and a clamped configuration to clamp tissue within the end effector, and wherein the second function comprises fastening the tissue.

Example 108

The surgical instrument of Example 107, wherein the second function comprises at least one of suturing the tissue, stapling the tissue, and clipping the tissue.

Example 109

A surgical instrument comprising a shaft. The shaft comprises a frame. The surgical instrument further comprises an end effector extending from the shaft, an input shaft configured to transmit an input motion, a first output member coupled to the end effector, a second output member coupled to the frame, and a transmission. The transmission is configured to simultaneously translate the input shaft relative to the second output member and first output member relative to the input shaft.

Example 110

A surgical instrument comprising a shaft, an end effector, and a drive system. The drive system comprises a first rotary electric motor, a first linear electric motor, a second rotary electric motor, and a second linear electric motor. The first rotary electric motor comprises a rotatable output shaft. The first rotary electric motor is configured to drive a first end effector function. The first linear electric motor is configured to translate the first rotary electric motor to perform a second end effector function. The second rotary electric motor comprises a rotatable output shaft. The second rotary electric motor is configured to drive a third end effector function. The second linear electric motor is configured to translate the second rotary electric motor to perform a fourth end effector function.

Example 111

A surgical instrument comprising a shaft, an end effector, and a drive system. The drive system comprises a first output shaft, a second output shaft, a first rotary electric motor configured to rotate the first output shaft to perform a first end effector function, a first linear electric motor configured to translate the first output shaft to perform a second end effector function, a second rotary electric motor configured to rotate the second output shaft to perform a third end effector function, and a second linear electric motor configured to translate the second output shaft to perform a fourth end effector function.

Example 112

The surgical instrument of Example 111, wherein the first output shaft extends through an aperture defined in the second output shaft.

Example 113

The surgical instrument of Examples 111 or 112, further comprising an articulation joint rotatably connecting the end effector to the shaft, wherein the first output shaft comprises a first flexible portion extending through the articulation joint and the second output shaft comprises a second flexible portion extending through the articulation joint.

Example 114

The surgical instrument of Example 113, wherein the first flexible portion comprises a first laser-cut steel tube and the second flexible portion comprises a second laser-cut steel tube.

Example 115

The surgical instrument of Example 114, wherein the first laser-cut steel tube extends through the second laser-cut steel tube.

Example 116

A surgical instrument comprising a shaft, an end effector, and a drive system. The drive system comprises an output shaft, a first electric motor configured to rotate the output shaft to perform a first end effector function, a second electric motor configured to translate the output shaft to perform a second end effector function, a conductor extending with the shaft, and a slip joint in electrical communication with the conductor. The slip joint is configured to translate with the output shaft.

Example 117

A surgical instrument system comprising a first handle and a second handle. The first handle comprises two independently-operable drive inputs. The second handle comprises two synchronously-operated drive inputs. The surgical instrument system further comprises a shaft assembly selectively, and separately, attachable to the first handle and the second handle. The shaft assembly comprises two drive outputs and a clutch system. The two drive inputs are selectively, and separately, engageable with the two independently-operable drive inputs and the two synchronously-operated drive inputs. The clutch system is configured to selectively deactivate one of the two drive outputs when the shaft assembly is attached to the second handle. The two drive outputs are independently drivable by the two independently-operable drive inputs when the shaft assembly is attached to the first handle.

Example 118

The surgical instrument system of Example 117, wherein the two drive outputs comprise a first drive output and a second drive output, wherein the clutch system comprises a clutch element shiftable between a first position and a second position, wherein the first drive output is drivable to perform a function of the shaft assembly and the second drive output is not drivable to perform a function of the shaft assembly when the clutch element is in the first position, and wherein the second drive output is drivable to perform a function of the shaft assembly and the first drive output is not drivable to perform a function of the shaft assembly when the clutch element is in the second position.

Example 119

The surgical instrument system of Examples 117 or 118, wherein the clutch system comprises at least one solenoid-driven clutch element configured to clutch out one of the two drive outputs of the shaft assembly.

Example 120

A surgical instrument handle comprising a housing, a manually-driven actuator, an electric motor, a first output, a second output, and a control circuit. The first output is operably coupled to the manually-driven actuator. The first output is responsive to an actuation of the manually-driven actuator. The second output is operably coupled to the electric motor. The control circuit is configured to operate the electric motor in response to the actuation of the manually-driven actuator.

Example 121

The surgical instrument handle of Example 120, wherein the first output comprises a first rotatable output and the second output comprises a second rotatable output.

Example 122

The surgical instrument handle of Example 121, wherein the rotation of the second rotatable output is synchronized to the rotation of the first rotatable output.

Example 123

The surgical instrument handle of Example 121, wherein the first rotatable output and the second rotatable output are rotated at the same speed.

Example 124

The surgical instrument handle of Example 121, wherein the first rotatable output and the second rotatable output are rotatable at different speeds.

Example 125

The surgical instrument handle of Examples 120, 121, 122, 123, or 124, wherein the control circuit comprises a sensor configured to detect the actuation of the manually-driven actuator.

Example 126

A surgical instrument system comprising a handle, an end effector, a manually-operated actuator, an electric motor, a first output, a second output, and a control circuit. The first output is operably coupled to the manually-operated actuator. The first output is responsive to an actuation of the manually-operated actuator to drive a first end effector function. The second output is operably coupled to the electric motor. The control circuit is configured to operate the electric motor in response to the actuation of the manually-operated actuator to drive the second output at the same time as the first output to perform a second end effector function which is different than the first end effector function.

Example 127

A surgical instrument system comprising a handle, an end effector configured to perform a first end effector function and a second end effector function, a first drive system comprising a first actuator and a first electric motor, a second drive system comprising a second actuator and a second electric motor, and a control system. The control system is operable in a first operating mode in which the first electric motor is responsive to an actuation of the first actuator and the second electric motor is not responsive to an actuation of the first actuator. The control system is further operable in a second operating mode in which the second electric motor is responsive to an actuation of the second actuator and the first electric motor is not responsive to an actuation of the second actuator. The control system is further operable in a third operating mode in which the first electric motor and the second electric motor are responsive to an actuation of the first actuator.

Example 128

The surgical instrument system of Example 127, wherein the control system is operable in a fourth operating mode in which the first electric motor and the second electric motor are responsive to an actuation of the second actuator.

Example 129

The surgical instrument system of Examples 127 or 128, wherein the first end effector function comprises articulating the end effector about an articulation joint and the second end effector function comprises rotating the end effector about a rotation joint.

Example 130

The surgical instrument system of Examples 127 or 128, further comprising a shaft, wherein the end effector extends from the shaft, wherein the first end effector function comprises rotating the shaft about a shaft rotation joint and the second end effector function comprises rotating the end effector about an end effector rotation joint.

Example 131

The surgical instrument system of Example 130, further comprising an articulation joint connecting the end effector to the shaft.

Example 132

A surgical instrument system comprising a first handle, a second handle, and a shaft assembly. The first handle comprises a first output driven by an electric motor. The second handle comprises a second output driven by a manual input provided by the user of the surgical instrument system. The shaft assembly is selectively, and separately, attachable to the first handle and the second handle. The shaft assembly comprises an end effector drive comprising a shaft input. The shaft input is operably coupled to the motor-driven first output when the shaft assembly is attached to the first handle. The shaft input is operably coupled to the manually-driven second output when the shaft assembly is attached to the second handle.

Example 133

The surgical instrument system of Example 132, wherein the first handle comprises a first housing and a first array of magnetic elements mounted to the first housing, wherein the second handle comprises a second housing and a second array of magnetic elements mounted to the second housing, wherein the shaft assembly comprises a shaft housing and a shaft array of magnetic elements, wherein the shaft array of magnetic elements interact with the first array of magnetic elements to orient the shaft assembly relative to the first handle in a first orientation, and wherein the shaft array of magnetic elements interact with the second array of magnetic elements to orient the shaft assembly relative to the second handle in a second orientation which is different than the first orientation.

Example 134

A surgical instrument system comprising a first handle, a second handle, and a shaft assembly. The first handle comprises a first housing, a first output, and a first array of magnetic elements. The second handle comprises a second housing, a second output, and a second array of magnetic elements. The shaft assembly is selectively, and separately, attachable to the first handle and the second handle. The shaft assembly comprises a shaft housing, an end effector drive, and a shaft array of magnetic elements. The end effector drive comprises a shaft input. The shaft input is operably coupled to the first output when the shaft assembly is attached to the first handle. The shaft input is operably coupled to the second output when the shaft assembly is attached to the second handle. The shaft array of magnetic elements interact with the first array of magnetic elements to orient the shaft assembly relative to the first handle in a first orientation. The shaft array of magnetic elements interact with the second array of magnetic elements to orient the shaft assembly relative to the second handle in a second orientation which is different than the first orientation.

The devices, systems, and methods disclosed in the Subject Application can be used with the devices, systems, and methods disclosed in U.S. Provisional Patent Application No. 62/659,900, entitled METHOD OF HUB COMMUNICATION, filed on Apr. 19, 2018, U.S. Provisional Patent Application No. 62/611,341, entitled INTERACTIVE SURGICAL PLATFORM, filed on Dec. 28, 2017, U.S. Provisional Patent Application No. 62/611,340, entitled CLOUD-BASED MEDICAL ANALYTICS, filed on Dec. 28, 2017, and U.S. Provisional Patent Application No. 62/611,339, entitled ROBOT ASSISTED SURGICAL PLATFORM, filed on Dec. 28, 2017, which are incorporated in their entireties herein. The devices, systems, and methods disclosed in the Subject Application can also be used with the devices, systems, and methods disclosed in U.S. patent application Ser. No. 15/908,021, entitled SURGICAL INSTRUMENT WITH REMOTE RELEASE, filed on Feb. 28, 2018, U.S. patent application Ser. No. 15/908,012, entitled SURGICAL INSTRUMENT HAVING DUAL ROTATABLE MEMBERS TO EFFECT DIFFERENT TYPES OF END EFFECTOR MOVEMENT, filed on Feb. 28, 2018, U.S. patent application Ser. No. 15/908,040, entitled SURGICAL INSTRUMENT WITH ROTARY DRIVE SELECTIVELY ACTUATING MULTIPLE END EFFECTOR FUNCTIONS, filed on Feb. 28, 2018, U.S. patent application Ser. No. 15/908,057, entitled SURGICAL INSTRUMENT WITH ROTARY DRIVE SELECTIVELY ACTUATING MULTIPLE END EFFECTOR FUNCTIONS, filed on Feb. 28, 2018, U.S. patent application Ser. No. 15/908,058, entitled SURGICAL INSTRUMENT WITH MODULAR POWER SOURCES, filed on Feb. 28, 2018, and U.S. patent application Ser. No. 15/908,143, entitled SURGICAL INSTRUMENT WITH SENSOR AND/OR CONTROL SYSTEMS, filed on Feb. 28, 2018, which are incorporated in their entireties herein. The devices, systems, and methods disclosed in the Subject Application can also be used with the devices, systems, and methods disclosed in U.S. patent application Ser. No. 14/226,133, now U.S. Patent Application Publication No. 2015/0272557, entitled MODULAR SURGICAL INSTRUMENT SYSTEM, filed on Mar. 26, 2014, which is incorporated in its entirety herein.

The entire disclosures of:

U.S. patent application Ser. No. 11/013,924, entitled TROCAR SEAL ASSEMBLY, now U.S. Pat. No. 7,371,227;

U.S. patent application Ser. No. 11/162,991, entitled ELECTROACTIVE POLYMER-BASED ARTICULATION MECHANISM FOR GRASPER, now U.S. Pat. No. 7,862,579;

U.S. patent application Ser. No. 12/364,256, entitled SURGICAL DISSECTOR, now U.S. Patent Application Publication No. 2010/0198248;

U.S. patent application Ser. No. 13/536,386, entitled EMPTY CLIP CARTRIDGE LOCKOUT, now U.S. Pat. No. 9,282,974;

U.S. patent application Ser. No. 13/832,786, entitled CIRCULAR NEEDLE APPLIER WITH OFFSET NEEDLE AND CARRIER TRACKS, now U.S. Pat. No. 9,398,905;

U.S. patent application Ser. No. 12/592,174, entitled APPARATUS AND METHOD FOR MINIMALLY INVASIVE SUTURING, now U.S. Pat. No. 8,123,764;

U.S. patent application Ser. No. 12/482,049, entitled ENDOSCOPIC STITCHING DEVICES, now U.S. Pat. No. 8,628,545;

U.S. patent application Ser. No. 13/118,241, entitled SURGICAL STAPLING INSTRUMENTS WITH ROTATABLE STAPLE DEPLOYMENT ARRANGEMENTS, now U.S. Pat. No. 9,072,535;

U.S. patent application Ser. No. 11/343,803, entitled SURGICAL INSTRUMENT HAVING RECORDING CAPABILITIES, now U.S. Pat. No. 7,845,537;

U.S. patent application Ser. No. 14/200,111, entitled CONTROL SYSTEMS FOR SURGICAL INSTRUMENTS, now U.S. Pat. No. 9,629,629;

U.S. patent application Ser. No. 14/248,590, entitled MOTOR DRIVEN SURGICAL INSTRUMENTS WITH LOCKABLE DUAL DRIVE SHAFTS, now U.S. Pat. No. 9,826,976;

U.S. patent application Ser. No. 14/813,242, entitled SURGICAL INSTRUMENT COMPRISING SYSTEMS FOR ASSURING THE PROPER SEQUENTIAL OPERATION OF THE SURGICAL INSTRUMENT, now U.S. Patent Application Publication No. 2017/0027571;

U.S. patent application Ser. No. 14/248,587, entitled POWERED SURGICAL STAPLER, now U.S. Pat. No. 9,867,612;

U.S. patent application Ser. No. 12/945,748, entitled SURGICAL TOOL WITH A TWO DEGREE OF FREEDOM WRIST, now U.S. Pat. No. 8,852,174;

U.S. patent application Ser. No. 13/297,158, entitled METHOD FOR PASSIVELY DECOUPLING TORQUE APPLIED BY A REMOTE ACTUATOR INTO AN INDEPENDENTLY ROTATING MEMBER, now U.S. Pat. No. 9,095,362;

International Application No. PCT/US2015/023636, entitled SURGICAL INSTRUMENT WITH SHIFTABLE TRANSMISSION, now International Patent Publication No. WO 2015/153642 A1;

International Application No. PCT/US2015/051837, entitled HANDHELD ELECTROMECHANICAL SURGICAL SYSTEM, now International Patent Publication No. WO 2016/057225 A1;

U.S. patent application Ser. No. 14/657,876, entitled SURGICAL GENERATOR FOR ULTRASONIC AND ELECTROSURGICAL DEVICES, U.S. Patent Application Publication No. 2015/0182277;

U.S. patent application Ser. No. 15/382,515, entitled MODULAR BATTERY POWERED HANDHELD SURGICAL INSTRUMENT AND METHODS THEREFOR, U.S. Patent Application Publication No. 2017/0202605;

U.S. patent application Ser. No. 14/683,358, entitled SURGICAL GENERATOR SYSTEMS AND RELATED METHODS, U.S. Patent Application Publication No. 2016/0296271;

U.S. patent application Ser. No. 14/149,294, entitled HARVESTING ENERGY FROM A SURGICAL GENERATOR, U.S. Pat. No. 9,795,436;

U.S. patent application Ser. No. 15/265,293, entitled TECHNIQUES FOR CIRCUIT TOPOLOGIES FOR COMBINED GENERATOR, U.S. Patent Application Publication No. 2017/0086910; and U.S. patent application Ser. No. 15/265,279, entitled TECHNIQUES FOR OPERATING GENERATOR FOR DIGITALLY GENERATING ELECTRICAL SIGNAL WAVEFORMS AND SURGICAL INSTRUMENTS, U.S. Patent Application Publication No. 2017/0086914, are hereby incorporated by reference herein.

Although various devices have been described herein in connection with certain embodiments, modifications and variations to those embodiments may be implemented. Particular features, structures, or characteristics may be combined in any suitable manner in one or more embodiments. Thus, the particular features, structures, or characteristics illustrated or described in connection with one embodiment may be combined in whole or in part, with the features, structures or characteristics of one ore more other embodiments without limitation. Also, where materials are disclosed for certain components, other materials may be used. Furthermore, according to various embodiments, a single component may be replaced by multiple components, and multiple components may be replaced by a single component, to perform a given function or functions. The foregoing description and following claims are intended to cover all such modification and variations.

The devices disclosed herein can be designed to be disposed of after a single use, or they can be designed to be used multiple times. In either case, however, a device can be reconditioned for reuse after at least one use. Reconditioning can include any combination of the steps including, but not limited to, the disassembly of the device, followed by cleaning or replacement of particular pieces of the device, and subsequent reassembly of the device. In particular, a reconditioning facility and/or surgical team can disassemble a device and, after cleaning and/or replacing particular parts of the device, the device can be reassembled for subsequent use. Those skilled in the art will appreciate that reconditioning of a device can utilize a variety of techniques for disassembly, cleaning/replacement, and reassembly. Use of such techniques, and the resulting reconditioned device, are all within the scope of the present application.

The devices disclosed herein may be processed before surgery. First, a new or used instrument may be obtained and, when necessary, cleaned. The instrument may then be sterilized. In one sterilization technique, the instrument is placed in a closed and sealed container, such as a plastic or TYVEK bag. The container and instrument may then be placed in a field of radiation that can penetrate the container, such as gamma radiation, x-rays, and/or high-energy electrons. The radiation may kill bacteria on the instrument and in the container. The sterilized instrument may then be stored in the sterile container. The sealed container may keep the instrument sterile until it is opened in a medical facility. A device may also be sterilized using any other technique known in the art, including but not limited to beta radiation, gamma radiation, ethylene oxide, plasma peroxide, and/or steam.

While this invention has been described as having exemplary designs, the present invention may be further modified within the spirit and scope of the disclosure. This application is therefore intended to cover any variations, uses, or adaptations of the invention using its general principles.

Any patent, publication, or other disclosure material, in whole or in part, that is said to be incorporated by reference herein is incorporated herein only to the extent that the incorporated materials do not conflict with existing definitions, statements, or other disclosure material set forth in this disclosure. As such, and to the extent necessary, the disclosure as explicitly set forth herein supersedes any conflicting material incorporated herein by reference. Any material, or portion thereof, that is said to be incorporated by reference herein, but which conflicts with existing definitions, statements, or other disclosure material set forth herein will only be incorporated to the extent that no conflict arises between that incorporated material and the existing disclosure material.

What is claimed is:

1. A surgical instrument, comprising:
   a handle;
   a shaft comprising a longitudinal shaft axis;
   a shaft rotation joint configured to permit said shaft to rotate relative to said handle, wherein said shaft is rotatable about said longitudinal shaft axis;
   an end effector comprising a proximal end effector portion and a distal end effector portion;
   an articulation joint, wherein said articulation joint is distal with respect to said shaft rotation joint, wherein said articulation joint rotatably connects said proximal end effector portion to said shaft, and wherein said end effector is rotatable about an articulation axis;
   an end effector rotation joint, wherein said end effector rotation joint is distal with respect to said articulation joint, and wherein said distal end effector portion is rotatable relative to said proximal end effector portion about said end effector rotation joint; and
   an articulation drive, comprising:
      a first articulation driver configured to drive said end effector when said articulation drive is in a first state; and
      a second articulation driver configured to drive said end effector when said articulation drive is in a second state, wherein said first articulation driver is not operably engaged with said end effector when said articulation drive is in said second state, and wherein said second articulation driver is not operably engaged with said end effector when said articulation drive is in said first state.

2. A surgical instrument, comprising:
   a handle;
   a shaft comprising a longitudinal shaft axis;
   a shaft rotation joint configured to permit said shaft to rotate relative to said handle, wherein said shaft is rotatable about said longitudinal shaft axis;
   an end effector comprising a proximal end effector portion and a distal end effector portion;
   an articulation joint, wherein said articulation joint is distal with respect to said shaft rotation joint, wherein said articulation joint rotatably connects said proximal end effector portion to said shaft, and wherein said end effector is rotatable about an articulation axis;
   an end effector rotation joint, wherein said end effector rotation joint is distal with respect to said articulation joint, and wherein said distal end effector portion is rotatable relative to said proximal end effector portion about said end effector rotation joint; and
   an articulation drive, comprising:
      a first articulation driver configured to drive said end effector when said articulation drive is in a first state; and
      a second articulation driver configured to drive said end effector when said articulation drive is in a second state, wherein said first articulation driver is not operably engaged with said end effector when said articulation drive is in said second state, wherein said second articulation driver is not operably engaged with said end effector when said articulation drive is in said first state, and wherein said first articulation driver and said second articulation driver extend through said articulation joint but do not extend through said end effector rotation joint.

3. The surgical instrument of claim 2, wherein said shaft has a first portion having a first diameter and a second portion having a second diameter smaller than said first diameter, and wherein said first articulation driver and said second articulation driver extend through said second portion of said shaft.

4. A surgical instrument, comprising:
   a handle;
   a shaft extending from said handle;
   an end effector extending from said shaft;
   an articulation joint, wherein said articulation joint rotatably connects said end effector to said shaft about an articulation axis;
   an end effector rotation joint configured to enable rotation of said end effector distal to said articulation joint, wherein rotation of said end effector occurs relative to said end effector rotation joint; and
   an articulation drive, comprising:
      an articulation actuator;
      a first articulation driver configured to drive said end effector when said articulation drive is in a first state; and
      a second articulation driver configured to drive said end effector when said articulation drive is in a second state, wherein said first articulation driver is operably engaged with said articulation actuator when said articulation drive is in said first state, wherein said second articulation driver is not operably engaged with said articulation actuator when said articulation drive is in said first state, wherein said second articulation driver is operably engaged with said articulation actuator when said articulation drive is in said second state, and wherein said first articulation driver is not operably engaged with said articulation actuator when said articulation drive is in said second state.

5. The surgical instrument of claim 4, wherein said first articulation driver and said second articulation driver extend through said articulation joint.

6. A surgical instrument, comprising:
   a handle;
   a shaft extending from said handle;
   an end effector extending from said shaft;
   an articulation joint, wherein said articulation joint rotatably connects said end effector to said shaft about an articulation axis; and
   an articulation drive, comprising:
      an articulation actuator;
      a first articulation driver configured to drive said end effector when said articulation drive is in a first state; and
      a second articulation driver configured to drive said end effector when said articulation drive is in a second state, wherein said first articulation driver is operably engaged with said articulation actuator when said articulation drive is in said first state, wherein said second articulation driver is not operably engaged with said articulation actuator when said articulation drive is in said first state, wherein said second articulation driver is operably engaged with said articulation actuator when said articulation drive is in said second state, wherein said first articulation driver is not operably engaged with said articulation actuator when said articulation drive is in said second state, and wherein said shaft has a first portion having a first diameter and a second portion having a second diameter smaller than said first diameter, and wherein said first articulation driver and said second articulation driver extend through said second portion of said shaft.

7. A surgical instrument, comprising:
a handle;
a shaft;
an end effector;
an articulation joint, wherein said end effector is rotatable relative to said shaft about said articulation joint;
an end effector rotation joint, wherein said end effector rotation joint permits rotation of said end effector distally with respect to said articulation joint, wherein rotation of said end effector occurs independently from an articulation motion of said end effector; and
an articulation drive, comprising:
a first articulation driver configured to drive said end effector when said articulation drive is in a first state; and
a second articulation driver configured to drive said end effector when said articulation drive is in a second state, wherein said first articulation driver is not operably engaged with said end effector when said articulation drive is in said second state, and wherein said second articulation driver is not operably engaged with said end effector when said articulation drive is in said first state.

8. A surgical instrument, comprising:
a handle;
a shaft;
an end effector;
an articulation joint, wherein said end effector is rotatable relative to said shaft about said articulation joint; and
an articulation drive, comprising:
a first articulation driver configured to drive said end effector when said articulation drive is in a first state; and
a second articulation driver configured to drive said end effector when said articulation drive is in a second state, wherein said first articulation driver is not operably engaged with said end effector when said articulation drive is in said second state, wherein said second articulation driver is not operably engaged with said end effector when said articulation drive is in said first state, wherein said articulation drive further comprises an articulation drive shaft and a drive coupler, wherein said drive coupler is rotatable between a first position and a second position, wherein said drive coupler operably couples said first articulation driver to said articulation drive shaft when said drive coupler is in said first position, and wherein said drive coupler operably couples said second articulation driver to said articulation drive shaft when said drive coupler is in said second position.

9. The surgical instrument of claim 8, wherein said end effector is rotatable within a range of positions including a first fully-articulated position, an unarticulated position, and a second fully-articulated position, wherein said first articulation driver is configured to move said end effector within a first range including said first fully-articulated position and said unarticulated position, and wherein said second articulation driver is configured to move said end effector within a second range including said second fully-articulated position and said unarticulated position.

10. The surgical instrument of claim 9, wherein said first fully-articulated position is not in said second range, and wherein said second fully-articulated position is not in said first range.

11. The surgical instrument of claim 8, wherein said shaft has a first portion having a first diameter and a second portion having a second diameter smaller than said first diameter, and wherein said first articulation driver and said second articulation driver extend through said second portion of said shaft.

12. A surgical instrument, comprising:
a handle;
a shaft;
an end effector;
an articulation joint, wherein said end effector is rotatable relative to said shaft about said articulation joint;
an end effector rotation joint distal to said articulation joint, wherein said end effector rotation joint is configured to enable independent rotation motions of said end effector distally relative to said articulation joint; and
an articulation drive, comprising:
a first articulation driver configured to drive said end effector when said articulation drive is in a first state;
a second articulation driver configured to drive said end effector when said articulation drive is in a second state;
an articulation drive shaft; and
a drive coupler, wherein said drive coupler is rotatable between a first position in said first state and a second position in said second state, wherein said drive coupler operably couples said first articulation driver to said articulation drive shaft when said drive coupler is in said first position, and wherein said drive coupler operably couples said second articulation driver to said articulation drive shaft when said drive coupler is in said second position.

13. A surgical instrument, comprising:
a handle;
a shaft;
an end effector;
an articulation joint, wherein said end effector is rotatable relative to said shaft about said articulation joint; and
an articulation drive, comprising:
a first articulation driver configured to drive said end effector when said articulation drive is in a first state;
a second articulation driver configured to drive said end effector when said articulation drive is in a second state;
an articulation drive shaft; and
a drive coupler, wherein said drive coupler is rotatable between a first position in said first state and a second position in said second state, wherein said drive coupler operably couples said first articulation driver to said articulation drive shaft when said drive coupler is in said first position, wherein said drive coupler operably couples said second articulation driver to said articulation drive shaft when said drive coupler is in said second position, wherein said second articulation driver is uncoupled from said drive coupler when said drive coupler is in said first position, and wherein said first articulation driver is uncoupled from said drive coupler when said drive coupler is in said second position.

14. The surgical instrument of claim 13, wherein said end effector is rotatable within a range of positions including a first fully-articulated position, an unarticulated position, and a second fully-articulated position, wherein said first articulation driver is configured to move said end effector within a first range including said first fully-articulated position and said unarticulated position, and wherein said second articulation driver is configured to move said end effector within a second range including said second fully-articulated position and said unarticulated position.

15. The surgical instrument of claim 14, wherein said first fully-articulated position is not in said second range, and wherein said second fully-articulated position is not in said first range.

16. The surgical instrument of claim 13, wherein said shaft has a first portion having a first diameter and a second portion having a second diameter smaller than said first diameter, and wherein said first articulation driver and said second articulation driver extend through said second portion of said shaft.

17. A surgical instrument, comprising:
a handle;
a shaft;
an end effector;
an articulation joint, wherein said end effector is rotatable relative to said shaft about said articulation joint;
an end effector rotation joint configured to enable independent rotation of the end effector distal with respect to said articulation joint; and
an articulation drive, comprising:
a first articulation driver configured to drive said end effector when said articulation drive is in a first state; and
a second articulation driver configured to drive said end effector when said articulation drive is in a second state, wherein said end effector is rotatable within a range of positions including a first fully-articulated position, an unarticulated position, and a second fully-articulated position, wherein said first articulation driver is configured to move said end effector within a first range including said first fully-articulated position and said unarticulated position, and wherein said second articulation driver is configured to move said end effector within a second range including said second fully-articulated position and said unarticulated position.

18. The surgical instrument of claim 17, wherein said first fully-articulated position is not in said second range, and wherein said second fully-articulated position is not in said first range.

19. A surgical instrument, comprising:
a handle;
a shaft;
an end effector;
an articulation joint, wherein said end effector is rotatable relative to said shaft about said articulation joint; and
an articulation drive, comprising:
a first articulation driver configured to drive said end effector when said articulation drive is in a first state; and
a second articulation driver configured to drive said end effector when said articulation drive is in a second state, wherein said end effector is rotatable within a range of positions including a first fully-articulated position, an unarticulated position, and a second fully-articulated position, wherein said first articulation driver is configured to move said end effector within a first range including said first fully-articulated position and said unarticulated position, wherein said second articulation driver is configured to move said end effector within a second range including said second fully-articulated position and said unarticulated position, wherein said shaft has a first portion having a first diameter and a second portion having a second diameter smaller than said first diameter, and wherein said first articulation driver and said second articulation driver extend through said second portion of said shaft.

* * * * *